US012569566B2

(12) United States Patent
Moon et al.

(10) Patent No.: US 12,569,566 B2
(45) Date of Patent: Mar. 10, 2026

(54) COMPOSITIONS CONTAINING, METHODS AND USES OF ANTIBODY-TLR AGONIST CONJUGATES

(71) Applicant: Ambrx, Inc., La Jolla, CA (US)

(72) Inventors: Sung-Ju Moon, La Jolla, CA (US); Brian Leon, La Jolla, CA (US); Mingchao Kang, La Jolla, CA (US); Nickolas Knudsen, La Jolla, CA (US); Jianing Wang, La Jolla, CA (US); Sukumar Sakamuri, La Jolla, CA (US); Feng Tian, La Jolla, CA (US)

(73) Assignee: AMBRX, INC., La Jolla, CA (US)

( * ) Notice: Subject to any disclaimer, the term of this patent is extended or adjusted under 35 U.S.C. 154(b) by 1170 days.

(21) Appl. No.: 17/429,911

(22) PCT Filed: Feb. 12, 2020

(86) PCT No.: PCT/US2020/018015

§ 371 (c)(1),
(2) Date: Aug. 10, 2021

(87) PCT Pub. No.: WO2020/168017

PCT Pub. Date: Aug. 20, 2020

(65) Prior Publication Data

US 2022/0226488 A1 Jul. 21, 2022

Related U.S. Application Data

(60) Provisional application No. 62/804,742, filed on Feb. 12, 2019.

(51) Int. Cl.

| | |
|---|---|
| ***A61K 47/68*** | (2017.01) |
| ***A61P 35/00*** | (2006.01) |
| ***A61P 37/04*** | (2006.01) |
| ***C07D 471/04*** | (2006.01) |
| ***C07D 471/14*** | (2006.01) |
| ***C07D 473/18*** | (2006.01) |
| ***C07D 473/34*** | (2006.01) |
| ***C07D 487/04*** | (2006.01) |
| ***C07D 487/14*** | (2006.01) |
| ***C07D 519/00*** | (2006.01) |

(52) U.S. Cl.

CPC ...... *A61K 47/6803* (2017.08); *A61K 47/6855* (2017.08); *A61P 35/00* (2018.01); *A61P 37/04* (2018.01); *C07D 471/04* (2013.01); *C07D 471/14* (2013.01); *C07D 473/18* (2013.01); *C07D 473/34* (2013.01); *C07D 487/04* (2013.01); *C07D 487/14* (2013.01); *C07D 519/00* (2013.01)

(58) Field of Classification Search

CPC ............ A61K 47/6803; A61K 47/6855; A61K 47/6811; A61P 35/00; A61P 37/04; C07D 471/04; C07D 471/14; C07D 473/18; C07D 473/34; C07D 487/04; C07D 487/14; C07D 519/00; C07K 16/32

See application file for complete search history.

(56) References Cited

U.S. PATENT DOCUMENTS

| | | | |
|---|---|---|---|
| 628,121 | A | 7/1899 | Seymour |
| 3,773,919 | A | 11/1973 | Boswell et al. |
| 4,289,872 | A | 9/1981 | Denkewalter et al. |
| 4,414,148 | A | 11/1983 | Jansen et al. |
| 4,485,045 | A | 11/1984 | Regen |
| 4,511,502 | A | 4/1985 | Builder et al. |
| 4,511,503 | A | 4/1985 | Olson et al. |
| 4,512,922 | A | 4/1985 | Jones et al. |
| 4,542,225 | A | 9/1985 | Blattler et al. |
| 4,544,545 | A | 10/1985 | Ryan et al. |
| 4,569,789 | A | 2/1986 | Blattler et al. |
| 4,618,492 | A | 10/1986 | Blattler et al. |
| 4,619,794 | A | 10/1986 | Hauser |
| 4,625,014 | A | 11/1986 | Senter et al. |
| 4,659,839 | A | 4/1987 | Nicolotti et al. |
| 4,670,417 | A | 6/1987 | Iwasaki et al. |
| 4,671,958 | A | 6/1987 | Rodwell et al. |

(Continued)

FOREIGN PATENT DOCUMENTS

| | | | |
|---|---|---|---|
| CA | 3176626 | A1 | 11/2021 |
| CN | 101341118 | A | 1/2009 |

(Continued)

OTHER PUBLICATIONS

Biggadike, K et. al. “Discovery of 6-Amino-2-{[(1S)-1-methylbutyl]oxy}-9-[5-(1-piperidinyl)pentyl]-7,9-dihydro-8H-purin-8-one (GSK2245035), a Highly Potent and Selective Intranasal Toll-Like Receptor 7 Agonist for the Treatment of Asthma”, 2016, J. Med. Chem., 59, 1711-1726. (Year: 2016).*

(Continued)

*Primary Examiner* — Nelson B Moseley, II
*Assistant Examiner* — Alyssa Rae Stonebraker
(74) *Attorney, Agent, or Firm* — BakerHostetler

(57) ABSTRACT

Disclosed herein are TLR-agonists and antibody-drug conjugates thereof. TLR agonist-antibody-drug conjugates of the disclosure comprise an antibody or an antibody fragment that can bind to HER2, and contain at least one non-natural amino acid. The TLR-agonist may be conjugated to a non-natural amino acid of the antibody via an oxime linkage. Further disclosed are methods for making and using such non-natural amino acid-containing TLR-agonists-antibody-drug conjugates, including therapeutic, diagnostic, and other biotechnology uses.

22 Claims, 15 Drawing Sheets

Specification includes a Sequence Listing.

(56) References Cited

U.S. PATENT DOCUMENTS 4,680,338 A 7/1987 Sundoro
4,699,784 A 10/1987 Shih et al.
4,820,352 A 4/1989 Riedhammer et al.
4,870,008 A 9/1989 Brake
4,902,502 A 2/1990 Nitecki et al.
5,021,234 A 6/1991 Ehrenfeld
5,047,335 A 9/1991 Paulson et al.
5,122,614 A 6/1992 Zalipsky
5,219,564 A 6/1993 Zalipsky et al.
5,229,490 A 7/1993 Tam
5,252,714 A 10/1993 Harris et al.
5,281,698 A 1/1994 Nitecki
5,324,844 A 6/1994 Zalipsky
5,382,657 A 1/1995 Karasiewicz et al.
5,446,090 A 8/1995 Harris
5,468,478 A 11/1995 Saifer et al.
5,473,034 A 12/1995 Yasui et al.
5,476,653 A 12/1995 Pitt et al.
5,516,673 A 5/1996 Margel et al.
5,559,213 A 9/1996 Hakimi et al.
5,612,460 A 3/1997 Zalipsky
5,629,384 A 5/1997 Veronese et al.
5,643,575 A 7/1997 Martinez et al.
5,650,234 A 7/1997 Dolence et al.
5,672,662 A 9/1997 Harris et al.
5,736,625 A 4/1998 Callstrom et al.
5,739,208 A 4/1998 Harris
5,747,646 A 5/1998 Hakimi et al.
5,808,096 A 9/1998 Zalipsky
5,824,778 A 10/1998 Ishikawa et al.
5,824,784 A 10/1998 Kinstler et al.
5,834,594 A 11/1998 Hakimi et al.
5,849,860 A 12/1998 Hakimi et al.
5,900,461 A 5/1999 Harris
5,932,462 A 8/1999 Harris et al.
5,980,948 A 11/1999 Goedemoed et al.
5,990,237 A 11/1999 Bentley et al.
6,001,800 A 12/1999 Mehta et al.
6,004,573 A 12/1999 Rathi et al.
6,129,912 A 10/2000 Hortin et al.
6,150,508 A 11/2000 Murphy et al.
6,201,072 B1 3/2001 Rathi et al.
6,214,966 B1 4/2001 Harris
6,235,710 B1 5/2001 Mehta et al.
6,281,211 B1 8/2001 Cai et al.
6,306,821 B1 10/2001 Mikos et al.
6,387,888 B1 5/2002 Mincheff et al.
6,420,339 B1 7/2002 Gegg et al.
6,423,685 B1 7/2002 Drummond et al.
6,436,386 B1 8/2002 Roberts et al.
6,451,346 B1 9/2002 Shah et al.
6,451,810 B1 9/2002 Coleman et al.
6,461,603 B2 10/2002 Bentley et al.
6,515,100 B2 2/2003 Harris
6,521,427 B1 2/2003 Evans
6,552,167 B1 4/2003 Rose
6,608,183 B1 8/2003 Cox, III
6,610,281 B2 8/2003 Harris
6,646,110 B2 11/2003 Nissen et al.
6,656,389 B2 12/2003 Iruvanti et al.
6,656,398 B2 12/2003 Birch et al.
6,667,312 B2 12/2003 Bonk et al.
6,677,347 B2 1/2004 Crooks et al.
6,683,088 B2 1/2004 Crooks et al.
6,756,382 B2 6/2004 Coleman et al.
6,825,350 B2 11/2004 Crooks et al.
6,962,981 B1 11/2005 Murphy et al.
7,045,337 B2 5/2006 Schultz et al.
7,045,605 B2 5/2006 Bander et al.
7,083,970 B2 8/2006 Schultz et al.
7,144,574 B2 12/2006 Rasmussen et al.
7,192,586 B2 3/2007 Bander
7,201,900 B2 4/2007 Murphy et al.
7,381,407 B1 6/2008 Murphy et al.
7,476,513 B2 1/2009 Murphy et al.
7,514,078 B2 4/2009 Bander et al.
7,598,382 B2 10/2009 Hays et al.
7,666,425 B1 2/2010 Bander
7,807,619 B2 10/2010 Bertozzi et al.
7,850,971 B2 12/2010 Maddon et al.
7,910,693 B2 3/2011 Cuello et al.
8,114,965 B2 2/2012 Maddon et al.
8,673,932 B2 3/2014 Kshirsagar et al.
2001/0021763 A1 9/2001 Harris
2001/0044526 A1 11/2001 Shen
2001/0056171 A1 12/2001 Kozlowski
2002/0002250 A1 1/2002 Bentley et al.
2002/0037949 A1 3/2002 Harris et al.
2002/0040076 A1 4/2002 Harris et al.
2002/0052009 A1 5/2002 Hornauer et al.
2002/0052430 A1 5/2002 Harris et al.
2002/0072573 A1 6/2002 Bentley et al.
2002/0082345 A1 6/2002 Kozlowski et al.
2002/0086939 A1 7/2002 Kozlowski
2002/0099133 A1 7/2002 Kozlowski
2002/0156047 A1 10/2002 Zhao
2003/0023023 A1 1/2003 Harris et al.
2003/0055002 A1 3/2003 Fujii et al.
2003/0105224 A1 6/2003 Roberts et al.
2003/0105275 A1 6/2003 Bentley et al.
2003/0114647 A1 6/2003 Harris et al.
2003/0118592 A1 6/2003 Ledbetter et al.
2003/0133939 A1 7/2003 Ledbetter et al.
2003/0143596 A1 7/2003 Bentley et al.
2003/0158333 A1 8/2003 Roberts et al.
2003/0162949 A1 8/2003 Cox, III
2003/0220447 A1 11/2003 Harris
2003/0228274 A1 12/2003 Rose
2003/0228593 A1 12/2003 Suga et al.
2004/0001838 A1 1/2004 Zhao et al.
2004/0013637 A1 1/2004 Bentley et al.
2004/0198637 A1 10/2004 Schultz et al.
2006/0194256 A1 8/2006 Miao et al.
2006/0217289 A1 9/2006 Miao et al.
2006/0217532 A1 9/2006 Miao et al.
2007/0160617 A1 7/2007 Ma et al.
2009/0030031 A1 1/2009 Kshirsagar et al.
2009/0111756 A1 4/2009 Doronina et al.
2009/0118263 A1 5/2009 Hashimoto et al.
2011/0288279 A1 11/2011 Miao et al.
2012/0231023 A1 9/2012 Zurawski et al.
2012/0295847 A1 11/2012 Lau et al.
2015/0284445 A1 10/2015 Jin et al.
2017/0121421 A1* 5/2017 Cortez ............... C07K 16/2863
2017/0182181 A1 6/2017 Garbaccio et al.
2017/0362334 A1 12/2017 Thanos et al.
2021/0038605 A1 2/2021 Jin et al.
2023/0293716 A1 9/2023 Dornan et al.

FOREIGN PATENT DOCUMENTS

CN 101679433 A 3/2010
CN 104583235 A 4/2015
CN 108379591 A 8/2018
DE 3218121 A1 11/1983
EP 0102324 A2 3/1984
EP 0133988 A2 3/1985
EP 0143949 A1 6/1985
EP 0154316 A2 9/1985
EP 0188256 A2 7/1986
EP 0143949 B1 10/1988
EP 0229108 B1 12/1990
EP 0188256 B1 8/1991
EP 0183503 B1 7/1992
EP 0402378 B1 3/1994
EP 0605963 A2 7/1994
EP 0400472 B1 4/1996
EP 0439508 B1 4/1998
EP 0510356 B1 1/1999
EP 0809996 B1 4/2003
EP 1939202 A1 7/2008
EP 0921131 B1 5/2010
EP 2918596 A1 9/2015
JP 2018-534297 A 11/2018

(56) References Cited

FOREIGN PATENT DOCUMENTS

| | | | | |
|---|---|---|---|---|
| WO | WO-8702670 A1 | | 5/1987 | |
| WO | WO-8705330 A1 | | 9/1987 | |
| WO | WO-198705330 | | 9/1987 | |
| WO | WO-9216555 A1 | | 10/1992 | |
| WO | WO-9321259 A1 | | 10/1993 | |
| WO | WO-9404193 A1 | | 3/1994 | |
| WO | WO-9414758 A1 | | 7/1994 | |
| WO | WO-9417039 A1 | | 8/1994 | |
| WO | WO-9418247 A1 | | 8/1994 | |
| WO | WO-9428024 A1 | | 12/1994 | |
| WO | WO-9500162 A1 | | 1/1995 | |
| WO | WO-9506058 A1 | | 3/1995 | |
| WO | WO-9511924 A1 | | 5/1995 | |
| WO | WO-9513090 A1 | | 5/1995 | |
| WO | WO-9513312 A1 | | 5/1995 | |
| WO | WO-9533490 A1 | | 12/1995 | |
| WO | WO-9600080 A1 | | 1/1996 | |
| WO | WO-9607670 A1 | | 3/1996 | |
| WO | WO-9621469 A1 | | 7/1996 | |
| WO | WO-9640791 A1 | | 12/1996 | |
| WO | WO-9641813 A2 | | 12/1996 | |
| WO | WO-9703106 A1 | | 1/1997 | |
| WO | WO-9718832 A1 | | 5/1997 | |
| WO | WO-9732607 A2 | | 9/1997 | |
| WO | WO-9805363 A2 | | 2/1998 | |
| WO | WO-9832466 A1 | | 7/1998 | |
| WO | WO-9841562 A1 | | 9/1998 | |
| WO | WO-9848837 A1 | | 11/1998 | |
| WO | WO-9932134 A1 | | 7/1999 | |
| WO | WO-9932139 A1 | | 7/1999 | |
| WO | WO-9932140 A1 | | 7/1999 | |
| WO | WO-02085923 A2 | | 10/2002 | |
| WO | WO-03101972 A1 | | 12/2003 | |
| WO | WO-2006069246 A2 | | 6/2006 | |
| WO | WO-2006116423 A2 | | 11/2006 | |
| WO | WO-2007002222 A2 | | 1/2007 | |
| WO | WO-2007070659 A2 | | 6/2007 | |
| WO | WO-2007079130 A2 | | 7/2007 | |
| WO | WO-2008077079 A1 | | 6/2008 | |
| WO | WO-2008114817 A1 | * | 9/2008 | ........... A61K 31/522 |
| WO | WO-2010027513 A2 | | 3/2010 | |
| WO | 2010/037395 A2 | | 4/2010 | |
| WO | 2010/044074 A1 | | 4/2010 | |
| WO | WO-2010036964 A2 | | 4/2010 | |
| WO | WO-2011068233 A1 | | 6/2011 | |
| WO | WO-2012166559 A1 | | 12/2012 | |
| WO | WO-2012166560 A1 | | 12/2012 | |
| WO | WO-2012168430 A2 | | 12/2012 | |
| WO | WO-2013004607 A1 | | 1/2013 | |
| WO | WO-2013068874 A1 | | 5/2013 | |
| WO | WO-2013185115 A1 | | 12/2013 | |
| WO | WO-2014004639 A1 | | 1/2014 | |
| WO | WO-2015006555 A2 | | 1/2015 | |
| WO | 2015/054390 A1 | | 4/2015 | |
| WO | WO-2015103987 A1 | | 7/2015 | |
| WO | 2015/117002 A1 | | 8/2015 | |
| WO | 2016/168612 A1 | | 10/2016 | |
| WO | WO-2017072662 A1 | | 5/2017 | |
| WO | 2017/173321 A1 | | 10/2017 | |
| WO | WO-2018009916 A1 | | 1/2018 | |
| WO | 2018/079740 A1 | | 5/2018 | |
| WO | 2018/086139 A1 | | 5/2018 | |
| WO | WO-2018160552 A1 | | 9/2018 | |
| WO | 2018/185526 A1 | | 10/2018 | |
| WO | 2018/234808 A1 | | 12/2018 | |
| WO | WO-2020168017 A1 | | 8/2020 | |
| WO | 2020/252015 A1 | | 12/2020 | |
| WO | 2020/252043 A1 | | 12/2020 | |

OTHER PUBLICATIONS

Nakamura, T et. al. “Synthesis and evaluation of 8-oxoadenine derivatives as potent Toll-like receptor 7 agonists with high water solubility”, 2013, Bioorganic & Medicinal Chemistry Letters, 23, 669-672. (Year: 2013).*

Meyskens et. al. (Jnci J Natl Cancer Inst, 108(2), 2016).*

Axup, JY et. al. “Synthesis of site-specific antibody-drug conjugates using unnatural amino acids”, 2012, PNAS, 109(40), 16101-16106. (Year: 2012).*

Abhinandan et al., Analysis and Improvements to Kabat and Structurally Correct Numbering of Antibody Variable Domains. Molecular immunology 45(14):3832-3839 (2008).

Abuchowski et al., Cancer therapy with chemically modified enzymes. I. Antitumor properties of polyethylene glycol-asparaginase conjugates. Cancer Biochem. Biophys. 7(2):175-186 (1984).

Altschul et al., Gapped BLAST and PSI-BLAST: A New Generation Of Protein Database Search Programs. Nucleic Acids Research 25(17):3389-3402 (1997).

Anderson et al., Exploring The Limits Of Codon And Anticodon Size. Chemical Biology 9(2):237-244 (2002).

Andresz et al., Chemische synthese verzweigter polysaccharide, 5.Kopplung von oligosacchariden und amylose an verschiedene träger durch hydrazonbindung. Makromol. Chem. 179:301-312 (1978).

Aplin et al., Preparation, Properties, And Applications Of Carbohydrate Conjugates Of Proteins And Lipids. CRC Critical Reviews in Biochemistry 10(4):259-306 (1981).

Arakawa et al., Protein-solvent interactions in pharmaceutical formulations. Pharmaceutical Research 8(3):285-291 (1991).

Ausubel et al., Current Protocols in Molecular Biology. Molecular Biology 1(78):1-12 (1994).

Bain et al., Biosynthetic site-specific incorporation of a non-natural amino acid into a polypeptide. J. Am. Chem. Soc 111:8013-8014 (1989).

Bain et al., Ribosome-mediated incorporation of a non-standard amino acid into a peptide through expansion of the genetic code. Nature 356(6369):537-539 (1992).

Barany et al., Genetic Disease Detection And DNA Amplification Using Cloned Thermostable Ligase. PNAS USA 88(1):189-193 (1991).

Batzer et al., Enhanced Evolutionary PCR Using Oligonucleotides With Inosine At The 3'-terminus. Nucleic Acids Research 19(18):5081 (1991).

Beauchamp et al., A new procedure for the synthesis of polyethylene glycol-protein adducts; effects on function, receptor recognition, and clearance of superoxide dismutase, lactoferrin, and alpha 2-macroglobulin. Anal. Biochem 131(1):25-33 (1983).

Bird et al., Single-Chain Antigen-binding Proteins. Science 242(4877):423-426 (1988).

Blackwell et al., Highly Efficient Synthesis Of Covalently Cross-linked Peptide Helices By Ring-closing Metathesis. Angewandte Chemie International Edition 37(23):3281-3284 (1998).

Braga et al., Crystal Polymorphism and Multiple Crystal Forms. Structure and Bonding 132:25-50 (2009).

Broadhead et al., The Spray Drying of Pharmaceuticals. Drug Dev. Ind. Pharm 18(11-12):1169-1206 (1992).

Buchner et al., A method for increasing the yield of properly folded recombinant fusion proteins: single-chain immunotoxins from renaturation of bacterial inclusion bodies. Anal. Biochem. 205(2):263-270 (1992).

Buckmann et al., Functionalization of poly(ethylene glycol) and monomethoxy-poly(ethylene glycol). Makromol. Chem. 182:1379-1384 (1981).

Budisa et al., Toward the experimental codon reassignment in vivo: protein building with an expanded amino acid repertoire. FASEB J. 13:41-51 (1999).

Carrasco et al., A Versatile Set of Aminooxy Amino Acids for the Synthesis of Neoglycopeptides. The Journal of Organic Chemistry 68:8853-8858 (2003).

Cech, The chemistry of self-splicing RNA and RNA enzymes. Science 236(4808):1532-1539 (1987).

Chan et al., Polytriazoles As Copper(i)Sstabilizing Ligands In Catalysis. Organic Letters 6(17):2853-2855 (2004).

(56) References Cited

OTHER PUBLICATIONS

Chin et al., Addition Of A Photocrosslinking Amino Acid To The Genetic Code Of *Escherichiacoli*. PNAS USA 99(17):11020-11024 (2002).
Chin et al., Addition Of P-Azido-L-phenylalanine To The Genetic Code Of *Escherichia coli*. Journal of the American Chemical Society 124(31):9026-9027 (2002).
Chin et al., An Expanded Eukaryotic Genetic Code. Science 301(5635):964-967 (2003).
Chin et al., In Vivo Photocrosslinking With Unnatural Amino Acid Mutagenesis. ChemBioChem 3(11):1135-1137 (2002).
Coloma et al., Novel vectors for the expression of antibody molecules using variable regions generated by polymerase chain reaction. J. Imm. Methods 152:89-104 (1992).
Cornish et al., Probing Protein Structure and Function with an Expanded Genetic Code. Angew. Chem. Int. Ed. Engl 34:621-633 (1995).
Cornish et al., Site-Specific Protein Modification using a Ketone Handle. Journal of the American Chemical Society 118:8150-8151 (1996).
Creighton. Proteins: Structures and Molecular Properties. W.H. Freeman pp. 79-86 (1983).
Debinski et al., A wide range of human cancers express interleukin 4 (IL4) receptors that can be targeted with chimeric toxin composed of IL4 and Pseudomonas exotoxin. J. Biol. Chem. 268(19):14065-14070 (1993).
Deiters et al., Adding Amino Acids with Novel Reactivity to the Genetic Code of *Saccharomyces cerevisiae*. Journal of the American Chemical Society 125:11782-11783 (2003).
Egel-Mitani et al., A novel aspartyl protease allowing KEX2-independent MF alpha propheromone processing in yeast. Yeast 6(2):127-137 (1990).
Elling et al., Immunoaffinity partitioning: Synthesis and use of polyethylene glycol-oxirane for coupling to bovine serum albumin and monoclonal antibodies. Biotech. Appl. Biochem 13(3):354-362 (1991).
Ellman et al., Biosynthetic method for introducing unnatural amino acids site-specifically into proteins. Meth. Enzym. 202:301-336 (1991).
Ellman et al., Site-specific incorporation of novel backbone structures into proteins. Science 255:197-200 (1992).
Eppstein et al., Biological activity of liposome-encapsulated murine interferon y is mediated by a cell membrane receptor. PNAS USA 82:3688-3692 (1985).
Gaertner et al., Chemo-Enzymic Backbone Engineering of Proteins. Site-specific Incorporation of Synthetic Peptides That Mimic the 64-74 Disulfide Loop of Granulocyte Colony-stimulating Factor. Journal of Biological Chemistry 269:7224-7230 (1994).
Gaertner et al., Construction of Protein Analogues by Site-Specific Condensation of Unprotected Fragments. Bioconjug Chem 3:262-268 (1992).
Gallivan et al., Site-specific incorporation of biotinylated amino acids to identify surface-exposed residues in integral membrane proteins. Chem Biol 4(10):739-749 (1997).
Geoghegan et al., Site-Directed Conjugation Of Nonpeptide Groups To Peptides And Proteins Via Periodate Oxidation Of A 2-amino Alcohol. Application To Modification At N-terminal Serine. Bioconjugate Chemistry 3(2):138-146 (1992).
Gillam et al., Site-Specific Mutagenesis Using Synthetic Oligodeoxyribonucleotide Primers: I. Optimum Conditions And Minimum Ologodeoxyribonucleotide Length. Gene 8(1):81-97 (1979).
Goodson et al., Site-directed pegylation of recombinant interleukin-2 at its glycosylation site. Biotechnology (NY) 8(4):343-346 (1990).
Greene et al., Protective Groups in Organic Synthesis. John Wiley & Sons 3rd Edition: 52 Pages (1999).
Guckian et al., Highly Precise Shape Mimicry by a Difluorotoluene Deoxynucleoside, a Replication-Competent Substitute for Thymidine. Angewandte Chemie International Edition 36(24):2825-2828 (1998).
Hagenbuchle et al., Mouse liver and salivary gland alpha-amylase mRNAs differ only in 5' non-translated sequences. Nature 289(5799):643-646 (1981).
Hallam et al. Antibody conjugates with unnatural amino acids. Mol Pharm 12(6):1848-1862 (2015).
Hang et al., Chemoselective Approaches To Glycoprotein Assembly. Accounts of Chemical Research 34(9):727-736 (2001).
Harris et al., Synthesis and characterization of poly(ethylene glycol) derivatives. J. Polym. Sci. Chem. Ed 22:341 (1984).
Hecht et al., Chemical aminoacylation of tRNA's. Biol. Chem 253(13):4517-4520 (1978).
Hecht. Probing the synthetic capabilities of a center of biochemical catalysis. Acc. Chem. Res 25:545-552 (1992).
Heckler et al., Ribosomal binding and dipeptide formation by misacylated tRNA(Phe). S. Biochemistry 27(19):7254-7262 (1988).
Henikoff et al., Amino Acid Substitution Matrices From Protein Blocks. PNAS USA 89(22):10915-10919 (1992).
Hermanson et al., Chapter 13: Avidin-Biotin Systems. Bioconjugate Techniques. Academic Press, San Diego 13:570-591 (1996).
Hirao et al., An Unnatural Base Pair For Incorporating Amino Acid Analogs Into Proteins. Nature Biotechnology 20(2):177-182 (2002).
Hohsaka et al., Efficient Incorporation Of Non-Natural Amino Acids With Large Aromatic Groups Into Streptavidin in In Vitro Protein Synthesizing Systems. Journal of the American Chemical Society 121(1):34-40 (1999).
Hohsaka et al., Incorporation Of Two Different Non-Natural Amino Acids Independently Into A Single Protein Through Extension Of The Genetic Code. Journal of the American Chemical Society 121:12194-12195 (1999).
Hu et al., Minibody: A Novel Engineered Anti-carcinoembryonic Antigen Antibody Fragment (single-chain Fv-CH3) Which Exhibits Rapid, High-level Targeting Of Xenografts. Cancer Research 56(13):3055-3061 (1996).
Hudson et al., Recombinant Antibody Fragments. Current Opinion in Biotechnology 9(4):395-402 (1998).
Huisgen. 1,3-Dipolar Cycloaddition Chemistry. Ed. Padwa, A., Wiley, New York, p. 1-176 (1984).
Huston et al., Protein Engineering Of Antibody Binding Sites: Recovery Of Specific Activity In An Anti-digoxin Single-chain Fv Analogue Produced In *Escherichia coli*. PNAS USA 85(16):5879-5883 (1988).
Hwang et al., Hepatic uptake and degradation of unilamellar sphingomyelin/cholesterol liposomes: A kinetic study. PNAS USA 77(7):4030-4034 (1980).
Illangakekare et al., Aminoacyl-RNA synthesis catalyzed by an RNA. Science 267(5198):643-647 (1995).
Jackson et al., In Vitro And In Vivo Evaluation Of Cysteine And Site Specific Conjugated Herceptin Antibody-drug Conjugates. PLoS One 9(1):e83865.
Jencks, Studies on the Mechanism of Oxime and Semicarbazone Formation. Journal of the American Chemical Society 81:475-481 (1959).
Jones et al., Replacing The Complementarity-determining Regions In A Human Antibody With Those From A Mouse. Nature 321(6069):522-525 (1986).
Joppich et al., Peptides Flanked by Two Polymer Chains 1, Synthesis of Glycyl-L-tryptophylglycine Substituted by Poly(ethylene oxide) at both the Carboxy and the Amino End Groups. Makromol. Chem. 180:1381-1384 (1979).
Karlin et al., Applications and statistics for multiple high-scoring segments in molecular sequences. PNAS USA 90(12):5873-5877 (1993).
Kayser et al., Alkyne bridged $\alpha$-amino acids by palladium mediated coupling of alkynes with N-t-Boc-4-iodo-phenylalanine methyl ester. Tetrahedron 53(7):2475-2484 (1997).
Kiick et al., Incorporation Of Azides Into Recombinant Proteins For Chemoselective Modification By The Staudinger Ligation. PNAS USA 99(1):19-24 (2002).
Kobayashi et al., Structural basis for orthogonal tRNA specificities of tyrosyl-tRNA synthetases for genetic code expansion. Nature Struct Biol 10(6):425-432 (2003).

(56) References Cited

OTHER PUBLICATIONS

Kogan. The Synthesis of Substituted Methoxy-Poly(Ethyleneglycol) Derivatives Suitable for Selective Protein Modification. Synthetic Comm 22:2417-2424 (1992).
Kolb et al., Click Chemistry: Diverse Chemical Function from a Few Good Reactions. Angewandte Chemie International Edition 40(11):2004-2021 (2001).
Kolb et al., The Growing Impact Of Click Chemistry On Drug Discovery. Drug Discovery Today 8(24):1128-1137 (2003).
Kool et al., Synthetically Modified DNAs As Substrates For Polymerases. Current Opinion in Chemical Biology 4:602-608 (2000).
Kowal et al., Exploiting Unassigned Codons In Micrococcus Luteus For tRNA-based Amino Acid Mutagenesis. Nucleic Acids Research 25(22):4685-4689 (1997).
Kreitman et al., Purification and characterization of IL6-PE4E, a recombinant fusion of interleukin 6 with Pseudomonas exotoxin. Bioconjug Chem. 4(6):581-5 (1993).
Langer et al., Biocompatibility of polymeric delivery systems for macromolecules. J Biomed Mater Res 15(2):267-277 (Mar. 1981).
Langer R., Controlled release of macromolecules. Chem. Tech 12:98-105 (1982).
Lewis et al., Click Chemistry In Situ: Acetylcholinesterase As A Reaction Vessel For The Selective Assembly Of A Femtomolar Inhibitor From An Array Of Building Blocks. Angewandte Chemie International Edition 41(6):1053-1057 (2002).
Liu et al., A method for the generation of glycoprotein mimetics. J. Am. Chem. Soc 125:1702-1703 (2003).
Liu et al., Progress toward the evolution of an organism with an expanded genetic code. PNAS USA 96:4780-4785 (1999).
Lohse et al., Ribozyme-catalysed amino-acid transfer reactions. Nature 381(6581):442-444 (1996).
Ma et al., In Vitro Protein Engineering Using Synthetic tRNA(Ala) With Different Anticodons. Biochemistry 32:7939-7945 (1993).
Ma et al. Potent Antitumor Activity of an Auristatin-Conjugated, Fully Human Monoclonal Antibody to Prostate-Specific Membrane Antigen. Clin Cancer Res 12(8):2591-2596 (2006).
Magliery et al., Expanding the Genetic Code: Selection of Efficient Suppressors of Four-Base Codons and Identification of "Shifty" Four-base Codons with a Library Approach in *Eschericia coli*. Journal of Molecular Biology 307:755-769 (2001).
Mahal et al., Engineering Chemical Reactivity On Cell Surfaces Through Oligosaccharide Biosynthesis. Science 276:1125-1128 (1997).
Mamot et al., Epidermal growth factor receptor (EGFR)-targeted immunoliposomes mediate specific and efficient drug delivery to EGFR- and EGFRvIII-overexpressing tumor cells. Cancer Res. 63(12):3154-3161 (2003).
Manetsch et al., In Situ Click Chemistry: Enzyme Inhibitors Made To Their Own Specifications. Journal of the American Chemical Society 126(40):12809-12818 (2004).
Maynard et al., Antibody Engineering. Annual Review of Biomedical Engineering 2:339-376 (2000).
Mccorkle et al., RNA's as Catalysts. A New Class of Enzymes. Concepts Biochem. 64:221-226 (1987).
McMinn et al., Efforts Toward Expansion Of The Genetic Alphabet: DNA Polymerase Recognition Of A Highly Stable, Self-pairing Hydrophobic Base. Journal of the American Chemical Society 121:11585-11586 (1999).
Meggers et al., A Novel Copper-Mediated DNA Base Pair. Journal of the American Chemical Society 122:10714-10715 (2000).
Mehvar et al., Modulation Of The Pharmacokinetics And Pharmacodynamics Of Proteins By Polyethylene Glycol Conjugation. Journal of Pharmaceutical Sciences 3(1):125-136 (2000).
Mendel et al., Site-directed mutagenesis with an expanded genetic code. Ann. Rev. Biophys. Biomol. Struct. 24:435-462 (1995).
Moore et al., Quadruplet Codons: Implications for Code Expansion and the Specification of Translation Step Size. J. Mol. Biol. 298:195-205 (2000).
Mosbach et al., Formation of proinsulin by immobilized Bacillus subtilis. Nature 302(5908):543-545 (1983).
Murakami et al., Using a solid-phase ribozyme aminoacylation system to reprogram the genetic code. Chemistry and Biology 10:1077-1084 (2003).
Needleman et al., A general method applicable to the search for similarities in the amino acid sequence of two proteins. J. Mol. Biol 48:443-453 (1970).
Nielsen et al., Therapeutic efficacy of anti-ErbB2 immunoliposomes targeted by a phage antibody selected for cellular endocytosis. Biochim. Biophys Acta 1591:109-118 (2002).
Noren et al., A general method for site-specific incorporation of unnatural amino acids into proteins. Science 244:182-188 (1989).
Nowak et al., Nicotinic receptor binding site probed with unnatural amino acid incorporation in intact cells. Science 268(5209):439-442 (1995).
Ogawa et al., Efforts Toward The Expansion Of The Genetic Alphabet: Information Storage And Replication With Unnatural Hydrophobic Base Pairs. Journal of the American Chemical Society 122:3274-3278 (2000).
Ogawa et al., Rational Design of an Unnatural base Pair with Increased Kinetic Selectivity. J. Am. Chem. Soc 122:8803-8804 (2000).
Ohtsuka et al., An Alternative Approach To Deoxyoligonucleotides As Hybridization Probes By Insertion Of Deoxyinosine At Ambiguous Codon Positions. Journal of Biological Chemistry 260(5):2605-2608 (1985).
Olson et al., Preparation and characterization of polyethylene glycosylated human growth hormone antagonist. In J. M. Harris and S. Zalipsky (Eds) Poly(ethylene glycol): Chemistry and Biological Applications. American Chemical Society. Washington, D.C. pp. 170-181 (1997).
Padwa et al., Chapter 4.9: Intermolecular 1,3-Dipolar Cycloadditions. Comprehensive Organic Synthesis. Ed. Trost, B. M. Pergamon, Oxford. Emory University 1069-1109 (1991).
Palva et al., Secretion of interferon by Bacillus subtilis. Gene. 22(2-3):229-235 (1983).
Park et al., Anti-HER2 immunoliposomes: enhanced efficacy attributable to targeted delivery. Clin Cancer Res 8(4):1172-1181 (2002).
Park et al., Development of anti-p185HER2 immunoliposomes for cancer therapy. Proc Natl Acad Sci. 92(5):1327-1331 (1995).
PCT/US2020/018015 International Search Report and Written Opinion dated Aug. 10, 2020.
Pearce et al., Growth hormone binding affinity for its receptor surpasses the requirements for cellular activity. Biochemistry 38:81-89 (1999).
Pearson et al., Improved Tools For Biological Sequence Comparison. PNAS USA 85(8):2444-2448 ( 1988).
Pepinsky et al., Improved pharmacokinetic properties of a polyethylene glycol-modified form of interferon-beta-1a with preserved in vitro bioactivity. J Pharmacol Exp Ther 297(3):1059-1066 (2001).
Pettit, et al. Specific activities of dolastatin 10 and peptide derivatives against Cryptococcus neoformans. Antimicrob Agents Chemother. 42(11):2961-2965 (Nov. 1998).
Piccirilli et al., Enzymatic Incorporation Of A New Base Pair Into DNA And RNA Extends The Genetic Alphabet. Nature 343:33-37 (1990).
Pikal. Freeze-drying of proteins. Part II: Formulation selection. Biopharm. 3(9):26-30 (1990).
Pitha et al., Detergents linked to polysaccharides: preparation and effects on membranes and cells. Eur J Biochem 94(1):11-18 (1979).
Preneta., Protein purification methods, a practical approach. IRL press :293-306 (1989).
Queen et al., A humanized antibody that binds to the interleukin 2 receptor. PNAS USA 86:10029-10033 (1989).
Raibaud et al., Positive control of transcription initiation in bacteria. Annu Rev Genet. 18:173-206 (1984).
Riechmann et al., Reshaping human antibodies for therapy. Nature 332(6162):323-327 (1988).
Roberts et al., Generation Of An Antibody With Enhanced Affinity And Specificity For Its Antigen By Protein Engineering. Nature 328:731-734 (1987).
Robertson et al., A general and efficient route for chemical aminoacylation of transfer RNAs. J. Am. Chem. Soc 113(7):2722-2729 (1991).

(56) References Cited

OTHER PUBLICATIONS

Romani et al., Synthesis of Unsymmetrical Cystine Peptides: Directed Disulfide Pairing with the Sulfenohydrazide Method. Chemistry of Peptides and Proteins 2:29-34 (1984).
Rosenthal, L-Canaline: A Potent Antimetabolite And Anti-cancer Agent From Leguminous Plants. Life Sciences 60(19):1635-1641 (1997).
Rossolini et al., Use Of Deoxyinosine-containing Primers Vs Degenerate Primers For Polymerase Chain Reaction Based On Ambiguous Sequence Information. Molecular and Cellular Probes 8(2):91-98 (1994).
Rostovtsev et al., A Stepwise Huisgen Cycloaddition Process: Copper(i)-catalyzed Regioselective "ligation" Of Azides And Terminal Alkynes. Angewandte Chemie International Edition 41(14):2596-2599 (2002).
Saks et al., An engineered Tetrahymena tRNAGln for in vivo incorporation of unnatural amino acids into proteins by nonsense suppression. J Biol Chem. 271(38):23169-23175 (1996).
Sandler et al., Chapter 5: Polyoxyalkylation of Hydroxy Compounds. Polymer Synthesis, Academic Press. New York. 3:138-161 (1992).
Sapra et al., Abstract 5691: Novel site-specific antibody drug conjugates based on novel amino acid incorporation technology have improved pharmaceutical properties over conventional antibody drug conjugates. Cancer Research, 72(8):5691 (2012).
Sartore et al., Enzyme modification by MPEG with an amino acid or peptide as spacer arms. Appl Biochem Biotechnol 27(1):45-54 (1991).
Sawhney et al., Bioerodible Hydogels Based on Photopolymerized Poly(ethyleneglycol)-co-poly(d-hydroxy acid) Diacrylate Macromers. Macromolecules 26:81-587 (1993).
Saxon et al., Cell Surface Engineering By A Modified Staudinger Reaction. Science 287(5460):2007-2010 (2000).
Sayers et al., 5'-3' exonucleases in phosphorothioate-based oligonucleotide-directed mutagenesis. Nucleic Acids Res 16(3):791-802 (1988).
Schafmeister et al., An All-Hydrocarbon Cross-Linking System for Enhancing the Helicity and Metabolic Stability of Peptides. J. Am. Chem. Soc 122:5891-5892 (2000).
Schafmeister et al., An All-Hydrocarbon Cross-linking System For Enhancing The Helicity And Metabolic Stability Of Peptides. Journal of the American Chemical Society 122:5891-5892 (2000).
Schneider et al., Functional Purification Of A Bacterial Atp-binding Cassette Transporter Protein (MalK) From The Cytoplasmic Fraction Of An Overproducing Strain. Protein Expression and Purification 6(1):10-14 (1995).
Schneider et al., The end of the era of generosity? Global health amid economic crisis. Philos Ethic Humanit Med 4:1, 2009.
Schreier. Chapter 6.3: Pulmonary applications of liposomes. Medical Applications of Liposomes. D.D. Lasic and D. Papahadjopoulos. (pp. 474-475) (1998).
Shao et al., Unprotected Peptides as Building Blocks for the Synthesis of Peptide Dendrimers with Oxime, Hydrazone, and Thiazolidine Linkages. Journal of the American Chemical Society 117:14:3893-3899 (1995).
Sidman et al., Controlled release of macromolecules and pharmaceuticals from synthetic polypeptides based on glutamic acid. Biopolymers 22(1):547-556 (Jan. 1983).
Speers et al., Activity-Based Protein Profiling In Vivo Using A Copper(i)-Catalyzed Azide-Alkyne [3+2] Cycloaddition. Journal of the American Chemical Society 125(16):4686-4687 (2003).
Stemmer., DNA shuffling by random fragmentation and reassembly: In vitro recombination for molecular evolution. PNAS USA 91:10747-10751(1994).
Stemmer., Rapid evolution of a protein in vitro by DNA shuffling. Nature 370(6488):389-391 (1994).
Switzer et al., Enzymatic Incorporation of a New base Pair into DNA and RNA. Journal of the American Chemical Society 111:8322-8323 (1989).
Tae et al., Efforts Toward Expansion Of The Genetic Alphabet: Replication Of DNA With Three Base Pairs. Journal of the American Chemical Society 123:7439-7440 (2001).
Therasse et al., New guidelines to evaluate the response to treatment in solid tumors: European Organization for Research and Treatment of Cancer, National Cancer Institute of the United States, National Cancer Institute of Canada. J Natl Cancer Inst 92:205-216 (2000).
Tian et al., A general approach to site-specific antibody drug conjugates. PNAS USA 111(5):1766-1771 (2014).
Tijssen. Hybridization With Nucleic Acid Probes. Laboratory Techniques in Biochemistry and Molecular Biology 24:19-78 (1993).
Tondelli et al., Poly(ethylene glycol) imidazolyl formates as oligomeric drug-binding matrices. J. Controlled Release 1:251-257 (1985).
Tornoe et al., Peptidotriazoles On Solid Phase: [1,2,3]-triazoles By Regiospecific Copper(i)-Catalyzed 1,3-Dipolar Cycloadditions Of Terminal Alkynes To Azides. The Journal of Organic Chemistry 67(9):3057-3064 (2002).
Turcatti et al., Probing the structure and function of the tachykinin neurokinin-2 receptor through biosynthetic incorporation of fluorescent amino acids at specific sites. J Biol Chem. 16. 271(33):19991-8 (1996).
Valls et al., Protein sorting in yeast: the localization determinant of yeast vacuolar carboxypeptidase Y resides in the propeptide. Cell 48(5):887-897 (1987).
Veronese et al., Surface modification of proteins. Activation of monomethoxy-polyethylene glycols by phenylchloroformates and modification of ribonuclease and superoxide dismutase. Appl Biochem Biotechnol 11(2):141-152 (1985).
Vippagunta et al., Crystalline Solids, Advanced Drug Delivery Reviews 48:3-26 (2001).
Walensky et al., Activation Of Apoptosis In Vivo By A Hydrocarbon-stapled BH3 Helix. Science 305(5689):1466-1470 (2004).
Wang et al., Bioconjugation By Copper(i)-Catalyzed Azide-Alkyne [3+2] Cycloaddition. Journal of the American Chemical Society 125(11):3192-3193 (2003).
Wang et al., Expanding the Genetic Code. Angewandte Chemie Int. Ed, 44:34-66 (2005).
Wang et al., Expanding the Genetic Code of *Escherichia coli*. Science 292:498-500 (2001).
Wang et al. In vitro and in vivo responses of advanced prostate tumors to PSMA ADC, an auristatin-conjugated antibody to prostate-specific membrane antigen. Mol Cancer Ther 10(9):1728-1739 (2011).
Ward et al., Binding Activities of a Repertoire of Single Immunoglobulin Variable Domains Secreted from *Escherichia coli*. Nature 341(6242):544-546 (1989).
Waser et al., Cobalt-Catalyzed Hydroazidation Of Olefins: Convenient Access To Alkyl Azides. Journal of the American Chemical Society 127(23):8294-8295 (2005).
Woghiren et al., Protected thiol-polyethylene glycol: a new activated polymer for reversible protein modification. Bioconjug Chem 4(5):314-318 (1993).
Wu et al., Enzymatic Phosphorylation Of Unnatural Nucleosides. Journal of the American Chemical Society 124:14626-14630 (2002).
Zalipsky et al., Attachment of drugs to polyethylene glycols. Eur. Polym. J. 19(12):1177-1183 (1983).
Zhang et al., A New Strategy For The Site-Specific Modification Of Proteins In Vivo. Biochemistry 42(22):6735-6746 (2003).
Zhang et al., Ruthenium-catalyzed cycloaddition of alkynes and organic azides. J Am Chem Soc 127(46):15998-9 (2005).

* cited by examiner

1

2

3

4

5

Compound 1

Compound 2

DL

DL-pAF

```
                         SEQUENCE LISTING

<160> NUMBER OF SEQ ID NOS: 13

<210> SEQ ID NO 1
<211> LENGTH: 449
<212> TYPE: PRT
<213> ORGANISM: Artificial Sequence
<220> FEATURE:
<223> OTHER INFORMATION: Heavy chain wild type

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
```

-continued 130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Asp
210 215 220

Lys Thr His Thr Cys Pro Pro Cys Pro Ala Pro Glu Leu Leu Gly Gly
225 230 235 240

Pro Ser Val Phe Leu Phe Pro Pro Lys Pro Lys Asp Thr Leu Met Ile
245 250 255

Ser Arg Thr Pro Glu Val Thr Cys Val Val Val Asp Val Ser His Glu
260 265 270

Asp Pro Glu Val Lys Phe Asn Trp Tyr Val Asp Gly Val Glu Val His
275 280 285

Asn Ala Lys Thr Lys Pro Arg Glu Glu Gln Tyr Asn Ser Thr Tyr Arg
290 295 300

Val Val Ser Val Leu Thr Val Leu His Gln Asp Trp Leu Asn Gly Lys
305 310 315 320

Glu Tyr Lys Cys Lys Val Ser Asn Lys Ala Leu Pro Ala Pro Ile Glu
325 330 335

Lys Thr Ile Ser Lys Ala Lys Gly Gln Pro Arg Glu Pro Gln Val Tyr
340 345 350

Thr Leu Pro Pro Ser Arg Asp Glu Leu Thr Lys Asn Gln Val Ser Leu
355 360 365

Thr Cys Leu Val Lys Gly Phe Tyr Pro Ser Asp Ile Ala Val Glu Trp
370 375 380

Glu Ser Asn Gly Gln Pro Glu Asn Asn Tyr Lys Thr Thr Pro Pro Val
385 390 395 400

Leu Asp Ser Asp Gly Ser Phe Phe Leu Tyr Ser Lys Leu Thr Val Asp
405 410 415

Lys Ser Arg Trp Gln Gln Gly Asn Val Phe Ser Cys Ser Val Met His
420 425 430

Glu Ala Leu His Asn His Tyr Thr Gln Lys Ser Leu Ser Leu Ser Pro
435 440 445

Gly

<210> SEQ ID NO 2
<211> LENGTH: 449
<212> TYPE: PRT
<213> ORGANISM: Artificial Sequence
<220> FEATURE:
<223> OTHER INFORMATION: Heavy Chain A114 mutation
<220> FEATURE:
<221> NAME/KEY: misc_feature
<222> LOCATION: (121)..(121)
<223> OTHER INFORMATION: Xaa = non-natural amino acid

<400> SEQUENCE: 2

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr

-continued

```
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Xaa Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445
```

Gly

<210> SEQ ID NO 3
<211> LENGTH: 214
<212> TYPE: PRT
<213> ORGANISM: Artificial Sequence
<220> FEATURE:
<223> OTHER INFORMATION: Light Chain wild type

<400> SEQUENCE: 3

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 4
<211> LENGTH: 214
<212> TYPE: PRT
<213> ORGANISM: Artificial Sequence
<220> FEATURE:
<223> OTHER INFORMATION: Light Chain V110 mutation
<220> FEATURE:
<221> NAME/KEY: misc_feature
<222> LOCATION: (110)..(110)
<223> OTHER INFORMATION: Xaa = non-natural amino acid

<400> SEQUENCE: 4

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
```

```
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Xaa Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 5
<211> LENGTH: 214
<212> TYPE: PRT
<213> ORGANISM: Artificial Sequence
<220> FEATURE:
<223> OTHER INFORMATION: Light Chain A112 mutation
<220> FEATURE:
<221> NAME/KEY: misc_feature
<222> LOCATION: (112)..(112)
<223> OTHER INFORMATION: Xaa = non-natural amino acid

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Xaa
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

```
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 6
<211> LENGTH: 214
<212> TYPE: PRT
<213> ORGANISM: Artificial Sequence
<220> FEATURE:
<223> OTHER INFORMATION: Light Chain S114 mutation
<220> FEATURE:
<221> NAME/KEY: misc_feature
<222> LOCATION: (114)..(114)
<223> OTHER INFORMATION: Xaa = non-natural amino acid

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Xaa Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 7
<211> LENGTH: 214
<212> TYPE: PRT
<213> ORGANISM: Artificial Sequence
<220> FEATURE:
<223> OTHER INFORMATION: Light Chain S121 mutation
<220> FEATURE:
<221> NAME/KEY: misc_feature
<222> LOCATION: (121)..(121)
<223> OTHER INFORMATION: Xaa = non-natural amino acid

<400> SEQUENCE: 7
```

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln His Tyr Thr Thr Pro Pro
85 90 95

Thr Phe Gly Gln Gly Thr Lys Val Glu Ile Lys Arg Thr Val Ala Ala
100 105 110

Pro Ser Val Phe Ile Phe Pro Pro Xaa Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 8
<211> LENGTH: 214
<212> TYPE: PRT
<213> ORGANISM: Artificial Sequence
<220> FEATURE:
<223> OTHER INFORMATION: Light Chain S127 mutation
<220> FEATURE:
<221> NAME/KEY: misc_feature
<222> LOCATION: (127)..(127)
<223> OTHER INFORMATION: Xaa = non-natural amino acid

<400> SEQUENCE: 8

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln His Tyr Thr Thr Pro Pro
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Xaa Gly
115 120 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 9
<211> LENGTH: 214
<212> TYPE: PRT
<213> ORGANISM: Artificial Sequence
<220> FEATURE:
<223> OTHER INFORMATION: Light Chain K149 mutation
<220> FEATURE:
<221> NAME/KEY: misc_feature
<222> LOCATION: (149)..(149)
<223> OTHER INFORMATION: Xaa = non-natural amino acid

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Xaa Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 10
<211> LENGTH: 214
<212> TYPE: PRT

<213> ORGANISM: Artificial Sequence
<220> FEATURE:
<223> OTHER INFORMATION: Light Chain S156 mutation
<220> FEATURE:
<221> NAME/KEY: misc_feature
<222> LOCATION: (156)..(156)
<223> OTHER INFORMATION: Xaa = non-natural amino acid

<400> SEQUENCE: 10

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Xaa Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 11
<211> LENGTH: 214
<212> TYPE: PRT
<213> ORGANISM: Artificial Sequence
<220> FEATURE:
<223> OTHER INFORMATION: Light Chain S168 mutation
<220> FEATURE:
<221> NAME/KEY: misc_feature
<222> LOCATION: (168)..(168)
<223> OTHER INFORMATION: Xaa = non-natural amino acid

<400> SEQUENCE: 11

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
```

```
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Xaa Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 12
<211> LENGTH: 214
<212> TYPE: PRT
<213> ORGANISM: Artificial Sequence
<220> FEATURE:
<223> OTHER INFORMATION: Light Chain S202 mutation
<220> FEATURE:
<221> NAME/KEY: misc_feature
<222> LOCATION: (202)..(202)
<223> OTHER INFORMATION: Xaa = non-natural amino acid

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

-continued

```
Ala Cys Glu Val Thr His Gln Gly Leu Xaa Ser Pro Val Thr Lys Ser
        195                 200                 205

Phe Asn Arg Gly Glu Cys
    210


<210> SEQ ID NO 13
<211> LENGTH: 214
<212> TYPE: PRT
<213> ORGANISM: Artificial Sequence
<220> FEATURE:
<223> OTHER INFORMATION: Light Chain V205 mutation
<220> FEATURE:
<221> NAME/KEY: misc_feature
<222> LOCATION: (205)..(205)
<223> OTHER INFORMATION: Xaa = non-natural amino acid

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Xaa Thr Lys Ser
        195                 200                 205

Phe Asn Arg Gly Glu Cys
    210
```

COMPOSITIONS CONTAINING, METHODS AND USES OF ANTIBODY-TLR AGONIST CONJUGATES

REFERENCE TO RELATED APPLICATIONS

This application is a U.S. National Stage Entry of PCT Application No. PCT/US2020/018015, filed Feb. 12, 2020, which claims the benefit of U.S. Provisional Application No. 62/804,742, filed Feb. 12, 2019, each entitled "Compositions Containing, Methods And Uses Of Antibody-TLR Agonist Conjugates", the contents of each of which are incorporated herein by reference in their entirety.

SEQUENCE LISTING

The instant application contains a Sequence Listing which has been submitted in ASCII format via EFS-Web and is hereby incorporated by reference in its entirety. The ASCII copy created on Feb. 7, 2020 is named AMBX_0230_PCT SL.txt and is 30,527 bytes in size.

FIELD OF THE INVENTION

The present invention disclosure relates to TLR-agonists compounds and TLR-agonist conjugates (TCs) and uses thereof. The invention further pertains to pharmaceutical compositions containing (TCs) as a therapeutic or prophylactic.

BACKGROUND OF THE INVENTION

Targeting molecules or polypeptides such as antibodies and fragments thereof, and TLR agonists compounds can be conjugated together using non-naturally encoded amino acids by site-specific conjugation to produce novel TLR-agonist Conjugates (TC). The novel TCs can be constructed in such a way that during systemic treatment, the circulating TC can target the TLR agonist to the tumor site and stimulate beneficial immune responses locally, thereby minimizing systemic cytokine release syndrome.

SUMMARY OF THE INVENTION

The invention relates to targeting polypeptides with one or more non-naturally encoded amino acids conjugated to agonist compounds of TLRs including but not limited to TLR7 and/or TLR8. Such conjugates are referred to herein as TLR-agonist Conjugates (TCs). TCs of the present invention include targeting biological molecules or polypeptides and TLR agonists compounds conjugated together using non-naturally encoded amino acids by site-specific conjugation to produce novel Biological TLR-agonist Conjugates (BTCs). The targeting biological molecules or polypeptides can be a tumor targeting biological biological molecules or polypeptides.

The invention, in additional embodiments, further relates to TCs further conjugated to a water soluble polymer that forms stable dimers or multimers.

The present invention provides methods of inhibiting or reducing growth of a tumor or cancer comprising contacting the tumor with an effective amount of TC of the invention to stimulate the immune system of the patient in proximity to the tumor. The present invention provides methods of inhibiting or reducing growth of a tumor or cancer comprising contacting the tumor with an effective amount of a PEGylated TC, or stable dimer or multimer of the TC of the invention. In one embodiment, the TC is non-pegylated or monopegylated. In one embodiment, the TC is dipegylated. In one embodiment, the TC has more than one and/or different TLR agonist molecules attached to it. In one embodiment, the TC has more than one and/or same TLR agonist molecules attached to it. Another embodiment of the present invention provides methods of using TCs of the present invention to modulate the immune response to tumor cells. In certain embodiments, the TC is co-administered with at least one chemotherapeutic agent and/or at least one immunotherapeutic agent. The chemotherapeutic agent can be selected from the group consisting of temozolomide, gemietabine, doxorubicin, cyclophosphamide, paclitaxel, cisplatin, fluoropyrimidine, taxane, anthracycline, lapatinib, capecitabine, letrozole, pertuzumab, docetaxel, IFN-α. In another embodiment of the present invention, TC is coadministered with at least one chemotherapeutic agent and/or at least one immunotherapeutic agent.

In some embodiments, the TC comprises a targeting polypeptide including but not limited to an antigen-binding polypeptides (ABP) comprising one or more non-naturally encoded amino acids. In some embodiments, the ABP comprises a complete antibody heavy chain. In some embodiments, the ABP comprises a complete antibody light chain. In some embodiments, the ABP comprises a variable region of an antibody light chain. In some embodiments, the ABP comprises a variable region of an antibody heavy chain. In some embodiments, the ABP comprises at least one CDR of an antibody light chain, in some embodiments, the ABP comprises at least one CDR of an antibody heavy chain. In some embodiments, the ABP comprises at least one CDR of a light chain and at least one CDR of a heavy chain. In some embodiments, the ABP comprises a Fab. In some embodiments, the ABP comprises two or more Fabs. In some embodiments, the ABP comprises a (Fab')2. In some embodiments, the ABP comprises two or more (Fab')2. In some embodiments, the ABP comprises a scFv. In some embodiments, the ABP comprises two or more scFv. In some embodiments, the ABP comprises a minibody. In some embodiments, the ABP comprises two or more minibodies. In some embodiments, the ABP comprises a diabody. In some embodiments, the ABP comprises two or more diabodies. In some embodiments, the ABP comprises a variable region of a light chain and a variable region of a heavy chain. In some embodiments, the ABP comprises a complete light chain and a complete heavy chain. In some embodiments, the ABP comprises one or more Fc domain or portion thereof. In some embodiments, the ABP comprises a combination of any of the above embodiments. In some embodiments, the ABP comprises a homodimer, heterodimer, homomultimer or heteromultimer of any of the above embodiments. In some embodiments, the ABP comprises a polypeptide that binds to a binding partner wherein the binding partner comprises an antigen, a polypeptide, a nucleic acid molecule, a polymer, or other molecule or substance. In some embodiments, the ABP is associated with a non-antibody scaffold molecule or substance. In some embodiments, the antigen is a tumor antigen.

Toll-like receptors (TLRs) detect a wide range of conserved pathogen associated molecular patterns (PAMPs). They play an important role of sensing invading pathogens and subsequent initiation of innate immune responses. There are 10 known members of the TLR family in human, which are type I transmembrane proteins featuring an extracellular leucine-rich domain and a cytoplasmic tail that contains a conserved Toll/interleukin (IL)-1 receptor (TIR) domain. Within this family, TLR3, TLR7, TLR8, and TLR9 are located within endosomes. TLR7 and TLR8 can be activated by binding to a specific small molecule ligand (i.e., TLR7 agonist or TLR8 agonist) or its native ligand (i.e., single-stranded RNA, ssRNA). Following binding of an agonist to TLR7 or TLR8, the receptor in its dimerized form is believed to undergo a structural change leading to the subsequent recruitment of adapter proteins at its cytoplasmic domain, including the myeloid differentiation primary response gene 88 (MyD88). Following the initiation of the receptor signalling cascade via the MyD88 pathway, cytoplasmic transcription factors such as interferon regulatory factor 7 (IRF-7) and nuclear factor kappa B (NF-κB) are activated. These transcription factors then translocate to the nucleus and initiate the transcription of various genes, e.g., IFN-alpha and other antiviral cytokine genes. TLR7 is predominately expressed on plasmacytoid cells, and on B cells. Altered responsiveness of immune cells might contribute to the reduced innate immune responses in cancer patients. Agonist-induced activation of TLR7 and/or TLR8 conjugated to a targeting moiety such as an antibody or fragment thereof may therefore represent a novel approach for the treatment of cancer. Treatment with TC comprising a TLR7 or TLR8 agonist represents a promising solution to provide greater efficacy with better tolerability. Suitable TLR7 and/or TLR8 agonists for use in the present invention to make TCs are found in the following U.S. Patents, each of which is incorporated by reference herein: U.S. Pat. Nos. 6,825,350; 6,656,389; 6,656,398; 6,683,088; 6,756,382; 6,825,350; 6,667,312; 6,677,347; 7,598,382; 8,673,932.

In some embodiments, the TC comprises a targeting polypeptide which further comprises an amino acid substitution, addition, or deletion that increases compatibility of the TC polypeptide with pharmaceutical preservatives (e.g., m-cresol, phenol, benzyl alcohol) when compared to compatibility of the corresponding wild type TC without the substitution, addition, or deletion. This increased compatibility would enable the preparation of a preserved pharmaceutical formulation that maintains the physiochemical properties and biological activity of the protein during storage.

In some embodiments, one or more engineered bonds are created with one or more non-natural amino acids. The intramolecular bond may be created in many ways, including but not limited to, a reaction between two amino acids in the protein under suitable conditions (one or both amino acids may be a non-natural amino acid); a reaction with two amino acids, each of which may be naturally encoded or non naturally encoded, with a linker, polymer, or other molecule under suitable conditions, etc.

In some embodiments, one or more amino acid substitutions in the TC polypeptide may be with one or more naturally occurring or non-naturally occurring amino acids. In some embodiments the amino acid substitutions in the TC may be with naturally occurring or non naturally occurring amino acids, provided that at least one substitution is with a non-naturally encoded amino acid. In some embodiments, one or more amino acid substitutions in the TC polypeptide may be with one or more naturally occurring amino acids, and additionally at least one substitution is with a non-naturally encoded amino acid. In some embodiments the TC polypeptide may be an antibody or antibody fragment. In some embodiments the TC polypeptide may be a tumor targeting polypeptide.

In some embodiments, the non-naturally encoded amino acid comprises a carbonyl group, an acetyl group, an aminooxy group, a hydrazine group, a hydrazide group, a semicarbazide group, an azide group, or an alkyne group.

In some embodiments, the non-naturally encoded amino acid comprises a carbonyl group. In some embodiments, the non-naturally encoded amino acid has the structure:

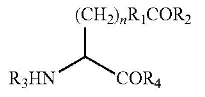

wherein n is 0-10; $R_1$ is an alkyl, aryl, substituted alkyl, or substituted aryl; $R_2$ is H, an alkyl, aryl, substituted alkyl, and substituted aryl; and $R_3$ is H, an amino acid, a polypeptide, or an amino terminus modification group, and $R_4$ is H, an amino acid, a polypeptide, or a carboxy terminus modification group.

In some embodiments, the non-naturally encoded amino acid comprises an aminooxy group. In some embodiments, the non-naturally encoded amino acid comprises a hydrazide group. In some embodiments, the non-naturally encoded amino acid comprises a hydrazine group. In some embodiments, the non-naturally encoded amino acid residue comprises a semicarbazide group.

In some embodiments, the non-naturally encoded amino acid residue comprises an azide group. In some embodiments, the non-naturally encoded amino acid has the structure:

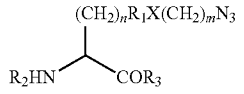

wherein n is 0-10; $R_1$ is an alkyl, aryl, substituted alkyl, substituted aryl or not present; X is O, N, S or not present; m is 0-10; $R_2$ is H, an amino acid, a polypeptide, or an amino terminus modification group, and $R_3$ is H, an amino acid, a polypeptide, or a carboxy terminus modification group.

In some embodiments, the non-naturally encoded amino acid comprises an alkyne group. In some embodiments, the non-naturally encoded amino acid has the structure:

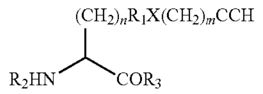

wherein n is 0-10; $R_1$ is an alkyl, aryl, substituted alkyl, or substituted aryl; X is O, N, S or not present; m is 0-10, $R_2$ is H, an amino acid, a polypeptide, or an amino terminus modification group, and $R_3$ is H, an amino acid, a polypeptide, or a carboxy terminus modification group.

In some embodiments, the polypeptide is a TC that comprises a non-naturally encoded amino acid linked to a water soluble polymer. In some embodiments, the water soluble polymer comprises a poly(ethylene glycol) moiety. In seine embodiments, the TC comprises a non-naturally encoded amino acid and one or more post-translational modification, linker, polymer, or biologically active molecule.

The present invention also provides isolated nucleic acids comprising a polynucleotide that encode the targeting polypeptides of TC and the present invention provides isolated nucleic acids comprising a polynucleotide that hybridizes under stringent conditions to the polynucleotides. The present invention also provides isolated nucleic acids comprising a polynucleotide that encode the targeting polypeptides wherein the polynucleotide comprises at least one selector codon. It is readily apparent to those of ordinary skill in the art that a number of different polynucleotides can encode any polypeptide of the present invention.

In some embodiments, the selector codon is selected from the group consisting of an amber codon, ochre codon, opal codon, a unique codon, a rare codon, a five-base codon, and a four-base codon.

The present invention also provides methods of making a TC polypeptide linked to a water soluble polymer or linked to one or more TC polypeptides to form a homodimer or homomultimer. In some embodiments, the method comprises contacting an isolated TC polypeptide comprising a non-naturally encoded amino acid with a water soluble polymer or a linker comprising a moiety that reacts with the non-naturally encoded amino acid. In some embodiments, the non-naturally encoded amino acid incorporated into the TC polypeptide is reactive toward a water soluble polymer or a linker that is otherwise unreactive toward any of the 20 common amino acids. In some embodiments, the non-naturally encoded amino acid incorporated into the TC polypeptide is reactive toward a linker, polymer, or biologically active molecule that is otherwise unreactive toward any of the 20 common amino acids.

In some embodiments, the TC polypeptide linked to the water soluble polymer or a linker is made by reacting a TC polypeptide comprising a carbonyl-containing amino acid with a poly(ethylene glycol) molecule or a linker comprising an aminooxy, hydrazine, hydrazide or semicarbazide group. In some embodiments, the aminooxy, hydrazine, hydrazide or semicarbazide group is linked to the poly(ethylene glycol) molecule or a linker through an amide linkage. In some embodiments, the aminooxy, hydrazine, hydrazide or semicarbazide group is linked to the poly(ethylene glycol) molecule or a linker through a carbamate linkage.

In some embodiments, the TC polypeptide linked to the water soluble polymer is made by reacting a poly(ethylene glycol) molecule or a linker comprising a carbonyl group with a polypeptide comprising a non-naturally encoded amino acid that comprises an aminooxy, hydrazine, hydrazide or semicarbazide group.

In some embodiments, the TC polypeptide linked to the water soluble polymer or a linker is made by reacting a TC comprising an alkyne-containing amino acid with a poly (ethylene glycol) molecule comprising an azide moiety. In some embodiments, the azide or alkyne group is linked to the poly(ethylene glycol) molecule or a linker through an amide linkage.

In some embodiments, the TC polypeptide linked to the water soluble polymer or a linker is made by reacting an TC polypeptide comprising an azide-containing amino acid with a poly(ethylene glycol) molecule comprising an alkyne moiety. In some embodiments, the azide or alkyne group is linked to the poly(ethylene glycol) molecule or a linker through an amide linkage.

In some embodiments, the poly(ethylene glycol) molecule or a linker has a molecular weight of between about 0.1 kDa and about 100 kDa. In some embodiments, the poly(ethylene glycol) molecule or a linker has a molecular weight of between 0.1 kDa and 50 kDa. In some embodiments, the poly(ethylene glycol) molecule or a linker is a branched polymer or linker. In some embodiments, each branch of the poly(ethylene glycol) branched polymer or linker has a molecular weight of between 1 kDa and 100 kDa, or between 1 kDa and 50 kDa.

In some embodiments, the water soluble polymer linked to the TC polypeptide comprises a polyalkylene glycol moiety. In some embodiments, the non-naturally encoded amino acid residue incorporated into the TC comprises a carbonyl group, an aminooxy group, a hydrazide group, a hydrazine, a semicarbazide group, an azide group, or an alkyne group. In some embodiments, the non-naturally encoded amino acid residue incorporated into the TC polypeptide comprises a carbonyl moiety and the water soluble polymer comprises an aminooxy, hydrazide, hydrazine, or semicarbazide moiety. In some embodiments, the non-naturally encoded amino acid residue incorporated into the TC polypeptide comprises an alkyne moiety and the water soluble polymer comprises an azide moiety. In some embodiments, the non-naturally encoded amino acid residue incorporated into the TC polypeptide comprises an azide moiety and the water soluble polymer comprises an alkyne moiety. The present invention also provides compositions comprising a TC polypeptide comprising a non-naturally encoded amino acid and a pharmaceutically acceptable carrier. In some embodiments, the non-naturally encoded amino acid is linked to a water soluble polymer.

The present invention also provides cells comprising a polynucleotide encoding the targeting polypeptide of the TC comprising a selector codon. In some embodiments, the cells comprise an orthogonal RNA synthetase and/or an orthogonal tRNA for substituting a non-naturally encoded amino acid into the targeting polypeptide of the TC.

The present invention also provides methods of making the targeting polypeptide of the TC comprising a non-naturally encoded amino acid. In some embodiments, the methods comprise culturing cells comprising a polynucleotide or polynucleotides encoding the targeting polypeptide of the TC, an orthogonal RNA synthetase and/or an orthogonal tRNA under conditions to permit expression of the targeting polypeptide of the TC or variant thereof; and purifying the TC polypeptide from the cells and/or culture medium.

The present invention also provides methods of increasing therapeutic half-life, serum half-life or circulation time of a TC. The present invention also provides methods of modulating immunogenicity of a TC. In some embodiments, the methods comprise substituting a non-naturally encoded amino acid for any one or more amino acids in naturally occurring targeting polypeptide of the TC and/or linking the targeting polypeptide to a linker, a polymer, a water soluble polymer, or a biologically active molecule.

The present invention also provides methods of treating a patient in need of such treatment with an effective amount of a TC molecule of the present invention. In some embodiments, the methods comprise administering to the patient a therapeutically-effective amount of a pharmaceutical composition comprising a TC comprising a non-naturally-encoded amino acid and a pharmaceutically acceptable carrier. In some embodiments, the non-naturally encoded amino acid is linked to a water soluble polymer. In some embodiments, the TC is glycosylated. In some embodiments, the TC is not glycosylated.

The present invention also provides TCs comprising a water soluble polymer or a linker linked by a covalent bond to the TC at a single amino acid. In some embodiments, the water soluble polymer comprises a poly(ethylene glycol) moiety. In some embodiments, the amino acid covalently linked to the water soluble polymer or a linker is a non-naturally encoded amino acid present in the targeting polypeptide of the TC.

The present invention provides a TC polypeptide comprising at least one linker, polymer, or biologically active molecule, wherein said linker, polymer, or biologically active molecule is attached to the polypeptide through a functional group of a non-naturally encoded amino acid ribosomally incorporated into the targeting polypeptide of the TC. In TC conjugates, the PEG or other water soluble polymer, another TC, polypeptide, or biologically active molecule can be conjugated directly to the TC via a linker. In one embodiment the linker is long enough to permit flexibility and allow for dimer formation. In one embodiment the linker is at least 3 amino acids, or 18 atoms, in length so as to permit dimer formation. In some embodiments, the polypeptide is linked to a linker to permit formation of a multimer. In some embodiments, the linker is a bifunctional linker. In some embodiments, the composition and/or TCs of the present invention can comprise multiple linkers. In other embodiments, each linker may include one or more compounds attached. A linker can also comprise alkylene, alkenylene, alkynylene, polyether, polyester, polyamide group(s) and also, polyamino acids, polypeptides, cleavable peptides, or aminobenzylcarbamates. In some embodiments, the linkers may be the same or different linkers. Suitable linkers include, for example, cleavable and non-cleavable linkers. Suitable cleavable linkers include, for example, a peptide linker cleavable by an intracellular protease, such as lysosomal protease or an endosomal protease. A cleavable linker may comprise a valine-citrulline linker or a valine-alanine peptide. In some embodiments, the linker can be a dipeptide linker, such as a valine-citrulline or a phenylalanine-lysine linker. A valine-citrulline- or valine-alanine-containing linker can contain a maleimide or succinimide group. A valine-citrulline- or valine-alanine-containing linker can contain a para aminobenzyl alcohol (PABA) group or para-aminobenzyl carbamate (PABC). Other suitable linkers include linkers hydrolyzable at a pH of less than 5.5, such as a hydrazone linker. Additional suitable cleavable linkers include disulfide linkers. In some embodiments, the cleavable linker may include a linker cleaved at the tumor microenvironment such as tumor infiltrating T-cells. In some embodiments, a non-cleavable linker includes, but is not limited to, a maleimidocaproyl linker. The maleimidocaproyl linker can comprise N-maleimidomethylcyclohexane-1-carboxylate, a succinimide group, a pentafluorophenyl group, and/or one or more PEG molecules but is not limited to such. In some embodiments, any one of the compositions, compounds or salts thereof of the present invention, can be linked to a polypeptide by way of a linker. In some embodiments, any one of the compounds or salts thereof disclosed herein, in Tables 3, 4, 5, 6, and 7 can be linked to a polypeptide by way of a linker. In some embodiments, the polypeptide is a targeting polypeptide or biological targeting polypeptide or tumor targeting polypeptide. In some embodiments, the targeting polypeptide is an antibody or antibody fragment.

In some embodiments, the TC polypeptide is monoPEGylated. The present invention also provides a TC comprising a linker, polymer, or biologically active molecule that is attached to one or more non-naturally encoded amino acid wherein said non-naturally encoded amino acid is ribosomally incorporated into the polypeptide at pre-selected sites.

In some embodiments, the present invention provides a composition comprising one or more targeting polypeptides having one or more non-naturally encoded amino acids incorporated, wherein at least one of the polypeptides is linked to a TLR agonist molecule via a linker covalently bonded to the non-natural amino acid of the polypeptide.

In another embodiment, the present invention provides a composition wherein the one or more targeting polypeptide is a same or different targeting polypeptide. In another embodiment, the invention provides a composition wherein the one or more targeting polypeptide binds to a cell surface target, or tumor cell target, or cancer cell target. In another embodiment, the one or more targeting polypeptide is a monospecific, bispecific, or multi-specific targeting polypeptide.

In other embodiments, the monospecific, bispecific, or multi-specific targeting polypeptide comprises a drug conjugate or checkpoint inhibitor. Any suitable immune checkpoint inhibitor is contemplated for use with the compositions or TCs of the present invention. In some embodiments, the immune checkpoint inhibitor reduces the expression or activity of one or more immune checkpoint proteins. In another embodiment, the immune checkpoint inhibitor reduces the interaction between one or more immune checkpoint proteins and their ligands. Inhibitory nucleic acids that decrease the expression and/or activity of immune checkpoint molecules can also be used in the present invention. In some embodiments, the immune checkpoint inhibitor is CTLA4, TIGIT, glucocorticoid-induced TNFR-related protein (GITR), inducible T cell costimulatory (ICOS), CD96, poliovirus receptor-related 2 (PVRL2), PD-1, PD-L1, PD-L2, LAG-3, B7-H4, killer immunoglobulin receptor (KIR), OX40, OX40-L indoleamine 2,3-dioxygenase 1 (IDO-1), indoleamine 2, 3-di oxygenase 2 (IDO-2), CEACAM1, CD272, TEVI3, the adenosine A2A receptor, and VISTA protein. In some embodiments, the immune checkpoint inhibitor is an inhibitor of CTLA4, PD-1, or PD-L1.

In another embodiment, the targeting polypeptide comprises an antibody or antibody fragment. In other embodiments, the targeting polypeptide is an antibody or antibody fragment that binds to an antigen of a cell. In another embodiment the targeting polypeptide is an antibody or antibody fragment that binds to a target selected from the group consisting of HER2, HERS, PD-1, PDL-1, EGFR, TROP2, PSMA, VEGFR, CTLA-4, EpCAM, MUC1, MUC16, c-met, GPC3, ENPP3, TIM-1, FOLR1, STEAP1, Mesothelin, 5T4, CEA, CA9, Cadherin 6, ROR1, SLC34A2, SLC39A6, SLC44A4, LY6E, DLL3, ePhA2, GPNMB, SLITRK6, CD3, CD19, CD22, CD24, CD25, CD30, CD33, CD38, CD44, CD47, CD52, CD56, CD70, CD96, CD97, CD99, CD117, CD123, CD179, CD223, and CD276. In some embodiments, the targeting polypeptide comprises an antibody or antibody fragment that binds to HER2. In another embodiment, the targeting polypeptide is trastuzumab.

In another embodiment, the antibody or antibody fragment comprises an IgG, Fab, (Fab')2, Fv, or single chain Fv (scFv). In some embodiments, the antibody or antibody fragment comprises one or more Fab, (Fab')2, Fv, or single chain Fv (scFv) mutations. In some embodiments, the antibody or antibody fragment comprises one or more Fe mutations. In other embodiments, the antibody or antibody fragment comprises one to six Fc mutations. In some embodiments, the antibody or antibody fragment comprises two or more Fc mutations. In other embodiments, the antibody or antibody fragment comprises three or more Fc mutations. In some embodiments, the antibody or antibody fragment comprises four or more Fc mutations. In other embodiments, the antibody or antibody fragment comprises five or more Fe mutations. In other embodiments, the antibody or antibody fragment comprises six Fc mutations.

In another embodiment, the antibody or antibody fragment comprises one or more non-naturally encoded amino acid incorporated in the heavy chain, light chain, or both the heavy and light chains. In another embodiment, the antibody or antibody fragment comprises one or more non-naturally encoded amino acid incorporated in the heavy chain and light chain. In another embodiment, the antibody or antibody fragment comprises one or more non-naturally encoded amino acid incorporated in the heavy chain, light chain, or both the heavy and light chains and further comprises one or more Fc mutations. In another embodiment, the antibody or antibody fragment comprises one or more non-naturally encoded amino acid incorporated in each of the heavy chain and light chain, the antibody or antibody fragment further comprising one or more Fe mutations. In another embodiment, the antibody or antibody fragment comprises one or more non-naturally encoded amino acid incorporated in the heavy chain, light chain, or both the heavy and light chains and further comprises at least two Fc mutations. In another embodiment, the antibody or antibody fragment comprises one or more non-naturally encoded amino acid incorporated in each of the heavy chain and light chain, the antibody or antibody fragment further comprising at least two Fc mutations. In another embodiment, the antibody or antibody fragment comprises one or more non-naturally encoded amino acid incorporated in the heavy chain, light chain, or both the heavy and light chains and further comprises at least three Fc mutations. In another embodiment, the antibody or antibody fragment comprises one or more non-naturally encoded amino acid incorporated in each of the heavy chain and light chain, the antibody or antibody fragment further comprising at least three Fc mutations. In another embodiment, the antibody or antibody fragment comprises one or more non-naturally encoded amino acid incorporated in the heavy chain, light chain, or both the heavy and light chains and further comprises at least four Fe mutations. In another embodiment, the antibody or antibody fragment comprises one or more non-naturally encoded amino acid incorporated in each of the heavy chain and light chain, the antibody or antibody fragment further comprising at least four Fe mutations. In another embodiment, the antibody or antibody fragment comprises one or more non-naturally encoded amino acid incorporated in the heavy chain, light chain, or both the heavy and light chains and further comprises at least five Fe mutations. In another embodiment, the antibody or antibody fragment comprises one or more non-naturally encoded amino acid incorporated in each of the heavy chain and light chain, the antibody or antibody fragment further comprising at least five Fc mutations. In another embodiment, the antibody or antibody fragment comprises one or more non-naturally encoded amino acid incorporated in the heavy chain, light chain, or both the heavy and light chains and further comprises at least six Fe, mutations. In another embodiment, the antibody or antibody fragment comprises one or more non-naturally encoded amino acid incorporated in each of the heavy chain and light chain, the antibody or antibody fragment further comprising at least six Fc mutations.

In another embodiment, the targeting polypeptides comprise one or more non-naturally encoded amino acids selected from the group of para-acetyl phenylalanine, p-nitrophenylalanine, p-sulfotyrosine, p-carboxyphenylalanine, o-nitrophenylalanine, m-nitrophenylalanine, p-boronyl phenylalanine, o-boronylphenylalanine, m-boronylphenylalanine, p-aminophenylalanine, o-aminophenylalanine, m-aminophenylalanine, o-acylphenylalanine, m-acylphenylalanine, p-OMe phenylalanine, o-OMe phenylalanine, m-OMe phenylalanine, p-sulfophenylalanine, o-sulfophenylalanine, m-sulfophenylalanine, 5-nitro His, 3-nitro Tyr, 2-nitro Tyr, nitro substituted Leu, nitro substituted His, nitro substituted De, nitro substituted Trp, 2-nitro Trp, 4-nitro Trp, 5-nitro Trp, 6-nitro Trp, 7-nitro Trp, 3-aminotyrosine, 2-aminotyrosine, O-sulfotyrosine, 2-sulfooxyphenylalanine, 3-sulfooxyphenylalanine, o-carboxyphenylalanine, m-earboxyphenylalanine, p-acetyl-L-phenylalanine, p-propargyl-phenylalanine, O-methyl-L-tyrosine, L-3-(2-naphthyl)alanine, 3-methyl-phenylalanine, O-4-allyl-L-tyrosine, 4-propyl-L-tyrosine, tri-O-acetyl-GlcNAcβ-serine, L-Dopa, fluorinated phenylalanine, isopropyl-L-phenylalanine, p-azido-L-phenylalanine, p-acyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, p-propargyloxy-L-phenylalanine, 4-azido-L-phenylalanine, para-azidoethoxy phenylalanine, and para-azidomethyl-phenylalanine. In another embodiment, the non-natural amino acid is selected from a group consisting of para-acetyl-phenylalanine, 4-azido-L-phenylalanine, para-azidoethoxy phenylalanine or para-azidomethyl-phenylalanine. In other embodiments, the non-naturally encoded amino acid is site specifically incorporated into the one or more targeting polypeptide.

In another embodiment, the TLR agonist is a TLR7 agonist, a TLR8 agonist, or a TLR7/TLR8 dual agonist. In other embodiments, the TLR agonist is a TLR agonist comprising a molecule structure according to any one of structures 1, 2, 3, 4 or 5 of FIG. 1. In another embodiment the TLR agonist is any one of TLR agonists selected from the group of structures according to Tables 3, 4, 5, 6, 7 of the present invention.

In other embodiments, the targeting polypeptide is conjugated to one or more linker, polymer, or biologically active molecule. In some embodiments, the targeting polypeptide is is directly or indirectly conjugated to one or more linker, polymer, or biologically active molecule. In some embodiments, the one or more linker is a cleavable or non-cleavable linker.

In some embodiments, the one or more linker is 0.1 kDa to 50 kDa. In other embodiments, the one or more linker is 0.1 kDa to 10 kDa. In other embodiments, the one or more linker or polymer is linear, branched, multimeric, or dendrimeric. In another embodiment, the one or more linker or polymer is a bifunctional or multifunctional linker or a bifunctional or multifunctional polymer.

In other embodiments, the one or more polymer is a water soluble polymer. In other embodiments, the water soluble polymer is polyethylene glycol (PEG). In some embodiments, the PEG has a molecular weight between 0.1 kDa and 100 kDa. In other embodiments, the PEG has a molecular weight between 0.1 kDa and 50 kDa. In other embodiments, the PEG has a molecular weight between 0.1 kDa and 4010a. In other embodiments, the PEG has a molecular weight between 0.1 kDa and 30 kDa. In other embodiments, the PEG has a molecular weight between 0.1 kDa and 20 kDa. In other embodiments, the PEG has a molecular weight between 0.1 kDa and 10 kDa. In some embodiments, the poly(ethylene glycol) molecule has a molecular weight of between about 0.1 kDa and about 109 kDa. In some embodiments, the poly(ethylene glycol) molecule has a molecular weight of between 0.1 kDa and 50 kDa. In some embodiments, the poly(ethylene glycol) has a molecular weight of between 1 kDa and 25 kDa, or between 2 and 22 kDa, or between 5 kDa and 20 kDa. For example, the molecular weight of the poly(ethylene glycol) polymer may be about 5 kDa, or about 10 kDa, or about 20 kDa, or about 30 kDa. For example, the molecular weight of the poly(ethylene glycol) polymer may be 5 kDa or 10 kDa or 20 kDa, or 30 kDa. In some embodiments the poly(ethylene glycol) molecule is a branched PEG. In some embodiments the poly(ethylene glycol) molecule is a branched 5K PEG. In some embodiments the poly(ethylene glycol) molecule is a branched 10K PEG. In some embodiments the poly(ethylene glycol) molecule is a branched 20K PEG. In some embodiments the poly(ethylene glycol) molecule is a linear PEG. In some embodiments the poly(ethylene glycol) molecule is a linear 5K PEG. In some embodiments the poly(ethylene glycol) molecule is a linear 10K PEG. In some embodiments the poly(ethylene glycol) molecule is a linear 20K PEG. In some embodiments the poly(ethylene glycol) molecule is a linear 30K PEG. In some embodiments, the molecular weight of the poly(ethylene glycol) polymer is an average molecular weight. In certain embodiments, the average molecular weight is the number average molecular weight (Mn). The average molecular weight may be determined or measured using GPC or SEC, SDS/PAGE analysis, RP-HPLC, mass spectrometry, or capillary electrophoresis.

In another embodiment, at least one linker, polymer, or biologically active molecule is linked to at least one non-naturally encoded amino acids. In some embodiments, the linker is a PEG. In other embodiments, the linker is a PEG with a molecular weight between 0.1 kDa and 50 kDa. In other embodiments, the linker is a PEG with a molecular weight between 0.1 kDa and 40 kDa. In other embodiments, the linker is a PEG with a molecular weight between 0.1 kDa and 30 kDa. In other embodiments, the linker is a PEG with a molecular weight between 0.1 kDa and 20 kDa. In other embodiments, the linker is a PEG with a molecular weight between 0.1 kDa and 10 kDa. In other embodiments, the linker is a PEG with a molecular weight between 0.1 kDa and 5 kDa.

In another embodiment, the targeting polypeptide comprises one or more amino acid substitution, addition or deletion that increases the stability or solubility of the composition. In another embodiment, the targeting polypeptide comprises one or more amino acid substitution, addition or deletion that enhances/reduces ADCP or ADCC activity. In another embodiment, the targeting polypeptide comprises one or more amino acid substitution, addition or deletion that increases pharmacokinetics of the composition. In other embodiments, the composition comprises one or more amino acid substitution, addition or deletion that increases the expression of the targeting polypeptide in a recombinant host cell or synthesized in vitro.

In another embodiment, the non-naturally encoded amino acid is reactive toward a linker, polymer, or biologically active molecule that is otherwise unreactive toward any of the 20 common amino acids in the polypeptide. In another embodiment, the non-naturally encoded amino acid comprises a carbonyl group, an aminooxy group, a hydrazine group, a hydrazide group, a semicarbazide group, an azide group, or an alkyne group. In other embodiments, the non-naturally encoded amino acid comprises a carbonyl group.

In another embodiment, the targeting polypeptide is linked to a cytotoxic agent or an immunostimulatory agent. In another embodiment, the TC or BTC of the present invention is linked to a cytotoxic agent or an immunostimulatory agent. In another embodiment, the targeting polypeptide comprises a cytotoxic agent or an immunostimulatory agent. In another embodiment, the TC or BTC of the present invention comprises a cytotoxic agent or an immunostimulatory agent.

In another embodiment, the present invention provides a TLR agonist conjugate (TC) comprising an anti-HER2 antibody or antibody fragment conjugated to a TLR agonist comprising a structure according to any structure of FIG. 1, wherein the TLR agonist is conjugated to the antibody or antibody fragment via a linker covalently bonded to one or more non-naturally encoded amino acids incorporated in the antibody or antibody fragment. In another embodiment, the TLR agonist is a TLR7 agonist, a TLR8 agonist, or a TLR7/TLR8 dual agonist. In another embodiment, the TLR agonist comprises a structure according to structure 1 of FIG. 1. In another embodiment, the TLR agonist comprising a structure according to structure 1 is selected from the group of: AXC-621, AXC-622, AXC-625, AXC-626, AXC-627, AXC-638, AXC-639, AXC-640, AXC-642, AXC-662, AXC-665, AXC-666, AXC-667, AXC-668, AXC-669, AXC-670, AXC-671, AXC-672, AXC-675, AXC-678, AXC-679, AXC-681, AXC-687, AXC-688, AXC-689, AXC-690, AXC-691, AXC-696, AXC-697, AXC-698, AXC-699, AXC-700, AXC-701, AXC-702, AXC-709, AXC-710, AXC-711, AXC-712, AXC-713, AXC-714, AXC-715, AXC-716, AXC-717, AXC-718, AXC-719, AXC-722, AXC-723, AXC-724, AXC-725, AXC-726, AXC-727, AXC-729, AXC-731, AXC-732, AXC-733, AXC-734, AXC-735, AXC-736, AXC-737, AXC-738, AXC-739, AXC-740, AXC-741, AXC-743, AXC-742, AXC-747, AXC-748, AXC-749, AXC-750, AXC-751, AXC-752, AXC-754, AXC-755, AXC-756, AXC-757, AXC-758, AXC-759, AXC-760, AXC-761, AXC-762, AXC-764, AXC-771, AXC-772, AXC-773, AXC-777, AXC-778, AXC-779, AXC-789, AXC-793, AXC-799, AXC-800, AXC-801, AXC-802, AXC-803, AXC-804, AXC-805, AXC-806, AXC-807, AXC-808, AXC-809, AXC-810, AXC-831 and AXC-910 compounds. In another embodiment, present invention provides a the TLR agonist of any one of: AXC-621, AXC-622, AXC-625, AXC-626, AXC-627, AXC-638, AXC-639, AXC-640, AXC-642, AXC-662, AXC-665, AXC-666, AXC-667, AXC-668, AXC-669, AXC-670, AXC-671, AXC-672, AXC-675, AXC-678, AXC-679, AXC-681, AXC-687, AXC-688, AXC-689, AXC-690, AXC-691, AXC-696, AXC-697, AXC-698, AXC-699, AXC-700, AXC-701, AXC-702, AXC-709, AXC-710, AXC-711, AXC-712, AXC-713, AXC-714, AXC-715, AXC-716, AXC-717, AXC-718, AXC-719, AXC-722, AXC-723, AXC-724, AXC-725, AXC-726, AXC-727, AXC-729, AXC-731, AXC-732, AXC-733, AXC-734, AXC-735, AXC-736, AXC-737, AXC-738, AXC-739, AXC-740, AXC-741, AXC-743, AXC-742, AXC-747, AXC-748, AXC-749, AXC-750, AXC-751, AXC-752, AXC-754, AXC-755, AXC-756, AXC-757, AXC-758, AXC-759, AXC-760, AXC-761, AXC-762, AXC-764, AXC-771, AXC-772, AXC-773, AXC-777, AXC-778, AXC-779, AXC-789, AXC-793, AXC-799, AXC-800, AXC-801, AXC-802, AXC-803, AXC-804, AXC-805, AXC-806, AXC-807, AXC-808, AXC-809, AXC-810, AXC-831, or AXC-910 compounds further comprising a linker. In another embodiment, the TLR agonist comprises a structure according to structure 1 further comprising a linker.

In other embodiments, the TLR agonist comprising a structure according to structure 1 is selected from the group of: AXC-625, AXC-626, AXC-638, AXC-639, AXC-640, AXC-642, AXC-662, AXC-667, AXC-668, AXC-669, AXC-670, AXC-671, AXC-672, AXC-675, AXC-681, AXC-687, AXC-688, AXC-689, AXC-690, AXC-691, AXC-697, AXC-699, AXC-700, AXC-701, AXC-702, AXC-709, AXC-710, AXC-711, AXC-713, AXC-714, AXC-717, AXC-719, AXC-722, AXC-723, AXC-724, AXC-725, AXC-726, AXC-727, AXC-731, AXC-732, AXC-733, AXC-734, AXC-735, AXC-736, AXC-737, AXC-738, AXC-739, AXC-740, AXC-741, AXC-743, AXC-742, AXC-747, AXC-748, AXC-750, AXC-751, AXC-752, AXC-754, AXC-755, AXC-756, AXC-757, AXC-758, AXC-759, AXC-760, AXC-761, AXC-762, AXC-764, AXC-771, AXC-772, AXC-773, AXC-777, AXC-778, AXC-779, AXC-789, AXC-793, AXC-800, AXC-801, AXC-802, AXC-803, AXC-804, AXC-805, AXC-806, AXC-807, AXC-808, AXC-809, AXC-810, AXC-831 and AXC-910 compounds. In other embodiments, the TLR agonist comprising a structure according to structure 1 is selected from the group of: AXC-801, AXC-802, AXC-831 and AXC-910 compounds. In other embodiments, the TLR agonist comprising a structure according to structure 1 selected from the group of: AXC-801, AXC-802, AXC-831 and AXC-910 compounds further comprises a linker.

In another embodiment, the anti-HER2 antibody or antibody fragment comprises one or more non-naturally encoded amino acid incorporated in the heavy chain, light chain, or both the heavy and light chains. In another embodiment, the one or more non-naturally encoded amino acids is selected from the group of para-acetyl phenylalanine, p-nitrophenylalanine, p-sulfotyrosine, p-carboxyphenylalanine, o-nitrophenylalanine, m-nitrophenylalanine, p-boronyl phenylalanine, o-boronylphenylalanine, m-boronylphenylalanine, p-aminophenylalanine, o-aminophenylalanine, m-aminophenylalanine, o-acylphenylalanine, m-acylphenylalanine, p-OMe phenylalanine, o-OMe phenylalanine, m-OMe phenylalanine, p-sulfophenylalanine, o-sulfophenylalanine, m-sulfophenylalanine, 5-nitro His, 3-nitro Tyr, 2-nitro Tyr, nitro substituted Leu, nitro substituted His, nitro substituted De, nitro substituted Trp, 2-nitro Trp, 4-nitro Trp, 5-nitro Trp, 6-nitro Trp, 7-nitro Trp, 3-aminotyrosine, 2-aminotyrosine, O-sulfotyrosine, 2-sulfooxyphenylalanine, 3-sulfooxyphenylalanine, o-carboxyphenylalanine, m-carboxyphenylalanine, p-acetyl-L-phenylalanine, p-propargyl-phenylalanine, O-methyl-L-tyrosine, L-3-(2-naphthyl)alanine, 3-methyl-phenylalanine, O-4-allyl-L-tyrosine, 4-propyl-L-tyrosine, tri-O-acetyl-GlcNAcβ-serine, L-Dopa, fluorinated phenylalanine, isopropyl-L-phenylalanine, p-azido-L-phenylalanine, p-acyl-L-phenylalanine, p-benzoyl-L-phenylalanine, L-phosphoserine, phosphonoserine, phosphonotyrosine, p-iodo-phenylalanine, p-bromophenylalanine, p-amino-L-phenylalanine, p-propargyloxy-L-phenylalanine, 4-azido-L-phenylalanine, para-azidoethoxy phenylalanine, and para-azidomethyl-phenylalanine. In other embodiments, the non-natural amino acid is para-acetyl-phenylalanine, 4-azido-L-phenylalanine, para-azidomethyl-phenylalanine, or para-azidoethoxy phenylalanine.

In another embodiment, the anti-HER2 antibody or antibody fragment further comprises one or more mutations in the Fc region. In another embodiment, the anti-HER2 antibody or antibody fragment further comprises two or more mutations in the Fc region. In another embodiment, the anti-HER2 antibody or antibody fragment further comprises three or more mutations in the Fc region. In another embodiment, the anti-HER2 antibody or antibody fragment further comprises four or more mutations in the Fc region. In another embodiment, the anti-HER2 antibody or antibody fragment further comprises five or more mutations in the Fc region. In another embodiment, the anti-HER2 antibody or antibody fragment further comprises six or more mutations in the Fe region. In another embodiment, the anti-HER2 antibody or antibody fragment further comprises six mutations in the Fc region.

In another embodiment, the one or more linker is a cleavable or non-cleavable linker. In other embodiments, the one or more linker is a bifunctional or multifunctional linker.

In another embodiment, the TLR agonist comprises a structure according to structure 2 of FIG. 1. In another embodiment, the TLR agonist comprising a structure according to structure 2 selected from the group of AXC-745, AXC-746, and AXC-753 compounds. In another embodiment, the TLR agonist comprising a structure according to any one of: AXC-745, AXC-746, and AXC-753 compounds further comprises a linker. In another embodiment, the TLR agonist comprises a structure according to structure 2 further comprising a linker.

In another embodiment, the TLR agonist comprises a structure according to structure 3 of FIG. 1. In another embodiment, the TLR agonist comprises a structure according to structure 3 is AXC-837 or AXC-847 compound. In another embodiment, the TLR agonist comprises a structure according to AXC-837 or AXC-847 compound further comprises a linker. In another embodiment, the TLR agonist comprises a structure according to AXC-847 compound further comprises a linker. In another embodiment, the TLR agonist comprises a structure according to structure 3 further comprising a linker.

In another embodiment, the TLR agonist comprises a structure according to structure 4 of FIG. 1. In another embodiment, the TLR agonist comprising a structure according to structure 4 is selected from the group of: AXC-844, AXC-842, AXC-843, AXC-845, AXC-846, AXC-836, or AXC-841 compounds. In another embodiment, the TLR agonist comprising a structure according to structure 4 of any one of: AXC-844, AXC-842, AXC-843, AXC-845, AXC-846, AXC-836, or AXC-841 compounds further comprises a linker. In another embodiment, the TLR agonist comprises a structure according to structure 4 further comprising a linker.

In another embodiment, the TLR agonist comprises a structure according to structure 5 of FIG. 1. In another embodiment, the TLR agonist comprising a structure according to structure 5 is selected from the group of: AXC-862, AXC-863, AXC-867, AXC-868, AXC-869, AXC-872, AXC-873, AXC-876, AXC-877, AXC-878, AXC-879, AXC-880, AXC-881, AXC-882, AXC-883, AXC-884, AXC-885, AXC-886, AXC-887, AXC-888, AXC-889, AXC-890, AXC-891, AXC-892, AXC-893, AXC-895, AXC-896, AXC-897, AXC-898, AXC-901, AXC-903, AXC-904, AXC-905, AXC-906, AXC-907, AXC-908, AXC-909, AXC-911, AXC-912, AXC-913, AXC-914, AXC-915, or AXC-916 compounds. In other embodiments, the TLR agonist comprising a structure according to structure 5 is selected from the group of AXC-862, AXC-863, AXC-867, AXC-868, AXC-869, AXC-873, AXC-876, AXC-879, AXC-880, AXC-882, AXC-889, AXC-893, AXC-896, AXC-897, AXC-901, AXC-907, AXC-909, AXC-913, and AXC-914 compounds. In another embodiment, the TLR agonist comprising a structure according to any one of: AXC-862, AXC-863, AXC-867, AXC-868, AXC-869, AXC-872, AXC-873, AXC-876, AXC-877, AXC-878, AXC-879, AXC-880, AXC-881, AXC-882, AXC-883, AXC-884, AXC-885, AXC-886, AXC-887, AXC-888, AXC-889, AXC-890, AXC-891, AXC-892, AXC-893, AXC-895, AXC-896, AXC-897, AXC-898, AXC-901, AXC-903, AXC-904, AXC-905, AXC-906, AXC-907, AXC-908, AXC-909, AXC-911, AXC-912, AXC-913, AXC-914, AXC-915, or AXC-916 compounds further comprising a linker. In another embodiment, the TLR agonist comprises a structure according to structure 5 further comprising a linker.

In another embodiment, the anti-HER2 antibody or antibody fragment comprises the amino acid sequence of at least one of SEQ ID NOs: 1-13. In another embodiment, the anti-HER2 antibody or antibody fragment comprises the amino acid sequence of at least two of SEQ ID NOs: 1-13. In another embodiment, the anti-HER2 antibody or antibody fragment comprises a) SEQ ID NOs: 1 or 2; and b) any one of SEQ ID NOs: 3, 4, 5, 6, 7, 8, 9, 10, 11, 12, and 13. In another embodiment, the anti-HER2 antibody or antibody fragment comprises a) a heavy chain of SEQ ID NOs: 1 or 2; and b) a light chain of any one of SEQ ID NOs: 3, 4, 5, 6, 7, 8, 9, 10, 11, 12, and 13. In another embodiment, the anti-HER2 antibody or antibody fragment comprises a) SEQ ID NO: 1; and b) any one of SEQ ID NOs: 3, 4, 5, 6, 7, 8, 9, 10, 11, 12, and 13. In another embodiment, the anti-HER2 antibody or antibody fragment comprises a) SEQ ID NO: 2; and b) any one of SEQ ID NOs: 3, 4, 5, 6, 7, 8, 9, 10, 11, 12, and 13. In another embodiment, the anti-HER2 antibody or antibody fragment comprises SEQ ID NO: 2 and SEQ ID NQ: 3. In another embodiment, the anti-HER2 antibody or antibody fragment comprises SEQ ID NO: 2 and SEQ ID NO: 4. In another embodiment, the anti-HER2 antibody or antibody fragment comprises SEQ ID NO: 2 and SEQ ID NO: 5. In another embodiment, the anti-HER2 antibody or antibody fragment comprises SEQ ID NO: 2 and SEQ ID NO: 6. In another embodiment, the anti-HER2 antibody or antibody fragment comprises SEQ ID NO: 2 and SEQ ID NO: 7. In another embodiment, the anti-HER2 antibody or antibody fragment comprises SEQ ID NO: 2 and SEQ ID NO: 8. In another embodiment, the anti-HER2 antibody or antibody fragment comprises SEQ ID NO: 2 and SEQ ID NO: 9. In another embodiment, the anti-HER2 antibody or antibody fragment comprises SEQ ID NO: 2 and SEQ ID NO: 10. In another embodiment, the anti-HER2 antibody or antibody fragment comprises SEQ ID NO: 2 and SEQ ID NO: 11. In another embodiment, the anti-HER2 antibody or antibody fragment comprises SEQ ID NO: 2 and SEQ ID NO: 12. In another embodiment, the anti-HER2 antibody or antibody fragment comprises SEQ ID NO: 2 and SEQ ID NO: 13. In another embodiment, the invention provides an anti-HER2 antibody or antibody fragment wherein the non-naturally encoded amino acid is site specifically incorporated at position 114 according to Kabat numbering.

In another embodiment, the present invention provides a TLR agonist conjugate (TC) comprising an anti-HER2 antibody or antibody fragment conjugated to a TLR agonist comprising a structure according to any structure of FIG. 1, wherein the TLR agonist is conjugated to the antibody or antibody fragment via a linker covalently bonded to one or more non-naturally encoded amino acids incorporated in the antibody or antibody fragment, the TC further comprising a chemotherapeutic or immunotherapeutic agent. In another embodiment, the present invention provides a TLR agonist conjugate (TC) comprising an anti-HER2 antibody or antibody fragment conjugated to a TLR agonist selected from any one of the compounds of Tables 3-7, wherein the TLR agonist is conjugated to the antibody or antibody fragment via a linker covalently bonded to one or more non-naturally encoded amino acids incorporated in the antibody or antibody fragment. In another embodiment, the present invention provides a TLR agonist conjugate (TC) comprising an anti-HER2 antibody or antibody fragment conjugated to a TLR agonist selected from any one of the compounds of Tables 3-7, wherein the TLR agonist is conjugated to the antibody or antibody fragment via a linker covalently bonded to one or more non-naturally encoded amino acids incorporated in the antibody or antibody fragment, the TC further comprising a chemotherapeutic or immunotherapeutic agent.

In another embodiment, the present invention provides a TLR agonist conjugate (TC) comprising an anti-HER2 antibody or antibody fragment conjugated to a TLR agonist comprising a structure according to any structure of FIG. 1, wherein the TLR agonist is conjugated to the antibody or antibody fragment via a linker covalently bonded to one or more non-naturally encoded amino acids incorporated in the antibody or antibody fragment, the TC further comprising an drug conjugate. In other embodiments the drug conjugate is an antibody drug conjugate. In another embodiment, the present invention provides a TLR agonist conjugate (TC) comprising an anti-HER2 antibody or antibody fragment conjugated to a TLR agonist selected from any one of the compounds of Tables 3-7, wherein the TLR agonist is conjugated to the antibody or antibody fragment via a linker covalently bonded to one or more non-naturally encoded amino acids incorporated in the antibody or antibody fragment. In another embodiment, the present invention provides a TLR agonist conjugate (TC) comprising an anti-HER2 antibody or antibody fragment conjugated to a TLR agonist selected from any one of the compounds of Tables 3-7, wherein the TLR agonist is conjugated to the antibody or antibody fragment via a linker covalently bonded to one or more non-naturally encoded amino acids incorporated in the antibody or antibody fragment the TC further comprising an drug conjugate. In other embodiments the drug conjugate is an antibody drug conjugate. In other embodiments the TC further comprises a cytokine or cytotoxin.

In another embodiment, the present invention provides a method of treating a subject or patient having cancer or a disease or condition or indication or disorder comprising administering to the subject or patient a therapeutically-effective amount of a composition or TC of the invention. In certain embodiments, the tumor or cancer is a HER2 positive tumor or cancer. In certain embodiments, the tumor, cancer, indication, disease, disorder or condition is a HER2 positive tumor, cancer, indication, disease, disorder or condition. In certain embodiments, the tumor or cancer is selected from the group consisting of colon cancer, ovarian cancer, breast cancer, melanoma, lung cancer, glioblastoma, prostate cancer, bladder cancer, cervical cancer, pancreatic cancer, renal cancer, esophageal cancer, vaginal cancer, stomach cancer, and leukemia.

In another embodiment, the present invention provides a method of treating a subject or patient having cancer or a disease or condition comprising administering to the subject or patient a therapeutically-effective amount of a composition or TC of the invention, further comprising a chemotherapeutic or immunotherapeutic agent. In certain embodiments, the TC is co-administered with at least one chemotherapeutic agent. The chemotherapeutic agent can be selected from the group consisting of temozolomide, gemictabine, doxorubicin, cyclophosphamide, paclitaxel, cisplatin, fluoropyrimidine, taxane, anthracycline, lapatinib, capecitabine, letrozole, pertuzumab, docetaxel, IFN-α. In another embodiment of the present invention, TC is coadministered with at least one chemotherapeutic agent.

In another embodiment, the present invention provides a method of treating a subject or patient having cancer or a disease or condition comprising administering to the subject or patient a therapeutically-effective amount of a composition or TC of the invention, further comprising an antibody drug conjugate, a cytotoxic agent, or a checkpoint inhibitor.

In another embodiment, the present invention provides a method of killing a cell comprising contacting a cell with a TC of the invention. In other embodiments, the cell is a tumor or cancer cell. In certain embodiments, the tumor or cancer cell is a colon, ovarian, breast, melanoma, lung, glioblastoma, prostate, bladder, cervical, pancreatic, renal, esophageal, vaginal, stomach, or leukemia cancer cell. In certain embodiments, the tumor or cancer is a HER2 positive tumor or cancer. In certain embodiments, the tumor, cancer, indication, disease, disorder or condition to be treated is a HER2 positive tumor, cancer, indication, disease, disorder or condition.

The present invention provides methods of inhibiting or reducing growth of a tumor or cancer comprising contacting the tumor with an effective amount of TC of the present invention to stimulate the immune system of the patient in proximity to the tumor. The present invention provides methods of inhibiting or reducing growth of a tumor or cancer comprising contacting the tumor with an effective amount of a PEGylated TC, or stable dimer or multimer of the TC, of the present invention. In one embodiment, the TC is non-pegylated or monopegylated. In one embodiment, the TC is dipegylated. In one embodiment, the TC has more than one and/or different TLR agonist molecules attached to it. Another embodiment of the present invention provides methods of using TCs of the present invention to modulate the immune response to tumor cells.

In some embodiments, the present invention provides methods of using a TC to treat cancer. In some embodiments, TCs of the present invention can be used in treating or preventing cancer-related diseases, disorders and conditions including conditions that are associated, directly or indirectly, with cancer, for example, angiogenesis and precancerous conditions such as dysplasia. In some embodiments, the tumor is a liquid or solid tumor. In some embodiments the condition to be treated is a cancer. The cancer may be, but is non-limited to, a breast cancer, a brain cancer, a pancreatic cancer, a skin cancer, a lung cancer, a liver cancer, a gall bladder cancer, a colon cancer, an ovarian cancer, a prostate cancer, a uterine cancer, a bone cancer, and a blood cancer (leukemic) cancer or a cancer or disease or conditions related to any of these cancers. Carcinomas are cancers that begin in the epithelial cells, which are cells that cover the surface of the body, produce hormones, and make up glands. By way of non-limiting example, carcinomas include breast cancer, pancreatic cancer, lung cancer, colon cancer, colorectal cancer, rectal cancer, kidney cancer, bladder cancer, stomach cancer, prostate cancer, liver cancer, ovarian cancer, brain cancer, vaginal cancer, vulvar cancer, uterine cancer, oral cancer, penile cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stein glioma, and spinal axis tumors. In some instances, the cancer is a skin cancer, such as a basal cell carcinoma, squamous, melanoma, nonmelanoma, or actinic (solar) keratosis. In some embodiments, the invention also relates to a method for treating an acute leukemia in a mammal, comprising administering a therapeutically effective amount of a TC of the present invention to said mammal. The invention also provides a method for inhibiting proliferation of acute leukemia blast cells comprising administering a therapeutically effective dose of a TC of the present invention to a mammal suffering from an acute leukemia.

In another embodiment, the TCs disclosed herein may be used to modulate an immune response. Modulation of an immune response may comprise stimulating, activating, increasing, enhancing, or up-regulating an immune response. Modulation of an immune response may comprise suppressing, inhibiting, preventing, reducing, or downregulating an immune response.

In another embodiment, the present invention provides a pharmaceutical composition comprising a therapeutically effective amount of a composition or TC of the invention and a pharmaceutically acceptable carrier or excipient.

In another embodiment, the present invention provides a use of the composition of the invention in the manufacture of a medicament.

In another embodiment, the present invention provides an immune stimulating antibody conjugate (ISAC) comprising a TLR-agonist according to any one of the structures of FIG. 1. In another embodiment, the present invention provides an immune stimulating antibody conjugate (ISAC) comprising a TLR-agonist according to any one of the compounds of Tables 3, 4, 5, 6, 7. In another embodiment, the present invention provides ISACs wherein the TLR agonist comprises a compound selected from the group of: AXC-862, AXC-863, AXC-867, AXC-868, AXC-869, AXC-874, AXC-875, AXC-876, AXC-879, AXC-880, AXC-882, AXC-893, AXC-896, AXC-897, AXC-901, AXC-907, and AXC-910 compounds.

In another embodiment, the present invention provides a salt of any one of the compounds having a structure according to FIG. 1. In another embodiment, the present invention provides a salt of any one of the compounds of Tables 3, 4, 5, 6, 7. In another embodiment, the present invention provides a pharmaceutical composition or salt thereof according to compositions, compounds and TC of the invention disclosure. In other embodiments, the pharmaceutical composition or salt further comprises a pharmaceutically acceptable excipient.

DETAILED DESCRIPTION OF THE INVENTION

Figure 1:
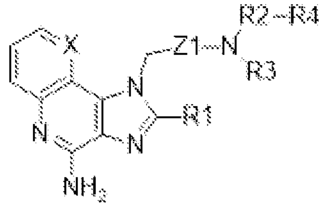
FIG. 1 depicts the general structure of TLR agonists suitable for use in the present invention.
Figure 1:
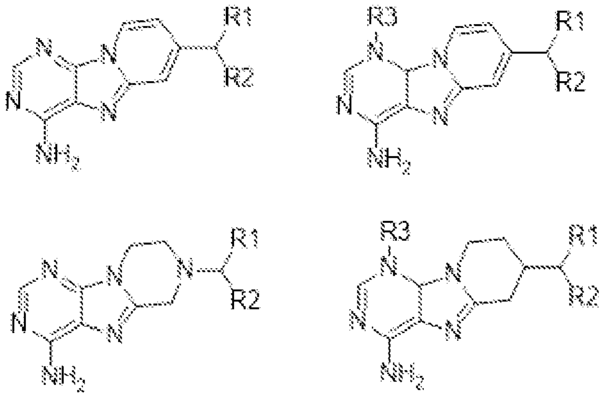
Figure 1:
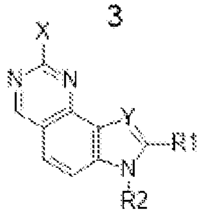
Figure 1:
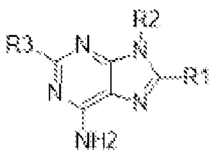
Figure 1:
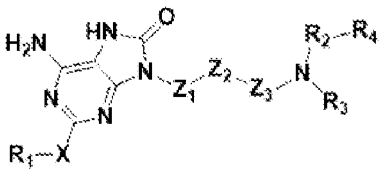

Disclosed herein are TCs comprising a targeting moiety such as an antibody and one or more TLR agonists. The TLR agonist may further comprise one or more linker(s). The TCs of the present invention may comprise TLR agonists linked to non-natural amino acids in the targeting moiety. Also included are methods for making such TCs comprising non-natural amino acids incorporated into the targeting moiety polypeptides.

In certain embodiments, a pharmaceutical composition is provided comprising any of the compounds described and a pharmaceutically acceptable carrier, excipient, or binder.

In further or alternative embodiments are methods for detecting the presence of a polypeptide in a patient, the method comprising administering a polypeptide comprising at least one heterocycle-containing non-natural amino acid and the resulting heterocycle-containing non-natural amino acid polypeptide modulates the immunogenicity of the polypeptide relative to the homologous naturally-occurring amino acid polypeptide.

It is to be understood that the methods and compositions described herein are not limited to the particular methodology, protocols, cell lines, constructs, and reagents described herein and as such may vary. It is also to be understood that the terminology used herein is for the purpose of describing particular embodiments only, and is not intended to limit the scope of the methods and compositions described herein, which will be limited only by the appended claims.

As used herein and in the appended claims, the singular forms "a," "an," and "the" include plural reference unless the context clearly indicates otherwise.

Unless defined otherwise, all technical and scientific terms used herein have the same meaning as commonly understood to one of ordinary skill in the art to which the inventions described herein belong. Although any methods, devices, and materials similar or equivalent to those described herein can be used in the practice or testing of the inventions described herein, the preferred methods, devices and materials are now described.

All publications and patents mentioned herein are incorporated herein by reference in their entirety for the purpose of describing and disclosing, for example, the constructs and methodologies that are described in the publications, which might be used in connection with the presently described inventions. The publications discussed herein are provided solely for their disclosure prior to the filing date of the present application. Nothing herein is to be construed as an admission that the inventors described herein are not entitled to antedate such disclosure by virtue of prior invention or for any other reason.

The terms "aldol-based linkage" or "mixed aldol-based linkage" refers to the acid- or base-catalyzed condensation of one carbonyl compound with the enolate/enol of another carbonyl compound, which may or may not be the same, to generate a β-hydroxy carbonyl compound—an aldol.

The term "affinity label," as used herein, refers to a label which reversibly or irreversibly binds another molecule, either to modify it, destroy it, or form a compound with it. By way of example, affinity labels include enzymes and their substrates, or antibodies and their antigens.

The terms "alkoxy," "alkylamino" and "alkylthio" (or thioalkoxy) are used in their conventional sense and refer to those alkyl groups linked to molecules via an oxygen atom, an amino group, or a sulfur atom, respectively.

The term "alkyl," by itself or as part of another molecule means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, is also meant to include those derivatives of alkyl defined in more detail herein, such as "heteroalkyl", "haloalkyl" and "homoalkyl".

The term "alkylene" by itself or as part of another molecule means a divalent radical derived from an alkane, as exemplified, by $(-CH_2-)_n$, wherein n may be 1 to about 24. By way of example only, such groups include, but are not limited to, groups having 10 or fewer carbon atoms such as the structures $-CH_2CH_2-$ and $-CH_2CH_2CH_2CH_2-$. A "lower alkyl" or "lower alkylene" is a shorter chain alkyl or alkylene group, generally having eight or fewer carbon atoms. The term "alkylene," unless otherwise noted, is also meant to include those groups described herein as "heteroalkylene."

The term "amino acid" refers to naturally occurring and non-natural amino acids, as well as amino acid analogs and amino acid mimetics that function in a manner similar to the naturally occurring amino acids. Naturally encoded amino acids are the 20 common amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine) and pyrolysine and selenocysteine. Amino acid analogs refer to compounds that have the same basic chemical structure as a naturally occurring amino acid, by way of example only, an α-carbon that is bound to a hydrogen, a carboxyl group, an amino group, and an R group. Such analogs may have modified R groups (by way of example, norleucine) or may have modified peptide backbones while still retaining the same basic chemical structure as a naturally occurring amino acid. Non-limiting examples of amino acid analogs include homoserine, norleucine, methionine sulfoxide, methionine methyl sulfonium.

Amino acids may be referred to herein by either their name, their commonly known three letter symbols or by the one-letter symbols recommended by the IUPAC-IUB Biochemical Nomenclature Commission. Additionally, nucleotides, may be referred to by their commonly accepted single-letter codes.

An "amino terminus modification group" refers to any molecule that can be attached to a terminal amine group. By way of example, such terminal amine groups may be at the end of polymeric molecules, wherein such polymeric molecules include, but are not limited to, polypeptides, polynucleotides, and polysaccharides. Terminus modification groups include but are not limited to, various water soluble polymers, peptides or proteins. By way of example only, terminus modification groups include polyethylene glycol or serum albumin. Terminus modification groups may be used to modify therapeutic characteristics of the polymeric molecule, including but not limited to increasing the serum half-life of peptides.

By "antibody" herein is meant a protein consisting of one or more polypeptides substantially encoded by all or part of the antibody genes. The immunoglobulin genes include, but are not limited to, the kappa, lambda, alpha, gamma (IgG1, IgG2, IgG3, and IgG4), delta, epsilon and mu constant region genes, as well as the myriad immunoglobulin variable region genes. Antibody herein is meant to include full-length antibodies and antibody fragments and include antibodies that exist naturally in any organism or are engineered (e.g. are variants).

By "antibody fragment" is meant any form of an antibody other than the full-length form. Antibody fragments herein include antibodies that are smaller components that exist within full-length antibodies, and antibodies that have been engineered. Antibody fragments include but are not limited to Fv, Fe, Fab, and (Fab′)2, single chain Fv (scFv), diabodies, triabodies, tetrabodies, bifunctional hybrid antibodies, CDR1, CDR2, CDR3, combinations of CDR's, variable regions, framework regions, constant regions, heavy chains, light chains, and variable regions, and alternative scaffold non-antibody molecules, bispecific antibodies, and the like (Maynard & Georgiou, 2000, Annu. Rev. Biomed. Eng. 2:339-76; Hudson, 1998, Curr. Opin. Biotechnol. 9:395-402). Another functional substructure is a single chain Fv (scFv), comprised of the variable regions of the immunoglobulin heavy and light chain, covalently connected by a peptide linker (S-z Hu et al., 1996, Cancer Research, 56, 3055-3061). These small (Mr 25,000) proteins generally retain specificity and affinity for antigen in a single polypeptide and can provide a convenient building block for larger, antigen-specific molecules. Unless specifically noted otherwise, statements and claims that use the term "antibody" or "antibodies" specifically includes "antibody fragment" and "antibody fragments".

By "antibody-drug conjugate, or "ADC", as used herein, refers to an antibody molecule, or fragment thereof, that is covalently bonded to one or more biologically active molecule(s). The biologically active molecule may be conjugated to the antibody through a linker, polymer, or other covalent bond.

The term "aromatic" or "aryl", as used herein, refers to a closed ring structure which has at least one ring having a conjugated pi electron system and includes both carbocyclic aryl and heterocyclic aryl (or "heteroaryl" or "heteroaromatic") groups. The carbocyclic or heterocyclic aromatic group may contain from 5 to 20 ring atoms. The term includes monocyclic rings linked covalently or fused-ring polycyclic (i.e., rings which share adjacent pairs of carbon atoms) groups. An aromatic group can be unsubstituted or substituted. Non-limiting examples of "aromatic" or "aryl", groups include phenyl, 1-naphthyl, 2-naphthyl, 4-biphenyl, anthracenyl, and phenanthracenyl. Substituents for each of the above noted aryl and heteroaryl ring systems are selected from the group of acceptable substituents described herein.

For brevity, the term "aromatic" or "aryl" when used in combination with other terms (including but not limited to, aryloxy, arylthioxy, aralkyl) includes both aryl and heteroaryl rings as defined above. Thus, the term "aralkyl" or "alkaryl" is meant to include those radicals in which an aryl group is attached to an alkyl group (including but not limited to, benzyl, phenethyl, pyridylmethyl and the like) including those alkyl groups in which a carbon atom (including but not limited to, a methylene group) has been replaced by a heteroatom, by way of example only; by an oxygen atom. Examples of such aryl groups include, but are not limited to, phenoxymethyl, 2-pyridyloxymethyl, 3-(1-naphthyloxy) propyl, and the like.

The term "arylene", as used herein, refers to a divalent aryl radical. Non-limiting examples of "arylene" include phenylene, pyridinylene, pyrimidinylene and thiophenylene. Substituents for arylene groups are selected from the group of acceptable substituents described herein.

A "bifunctional polymer", also referred to as a "bifunctional linker", refers to a polymer comprising two functional groups that are capable of reacting specifically with other moieties to form covalent or non-covalent linkages. Such moieties may include, but are not limited to, the side groups on natural or non-natural amino acids or peptides which contain such natural or non-natural amino acids. The other moieties that may be linked to the bifunctional linker or bifunctional polymer may be the same or different moieties. By way of example only, a bifunctional linker may have a functional group reactive with a group on a first peptide, and another functional group which is reactive with a group on a second peptide, whereby forming a conjugate that includes the first peptide, the bifunctional linker and the second peptide. Many procedures and linker molecules for attachment of various compounds to peptides are known. See, e.g., European Patent Application No. 188,256; U.S. Pat. Nos. 4,671,958, 4,659,839, 4,414,148, 4,699,784; 4,680,338; and 4,569,789 which are incorporated by reference herein in their entirety. A "multi-functional polymer" also referred to as a "multi-functional linker", refers to a polymer comprising two or more functional groups that are capable of reacting with other moieties. Such moieties may include, but are not limited to, the side groups on natural or non-natural amino acids or peptides which contain such natural or non-natural amino acids. (including but not limited to, amino acid side groups) to form covalent or non-covalent linkages. A bi-functional polymer or multi-functional polymer may be any desired length or molecular weight, and may be selected to provide a particular desired spacing or conformation between one or more molecules linked to a compound and molecules it binds to or the compound.

The term "bioavailability," as used herein, refers to the rate and extent to which a substance or its active moiety is delivered from a pharmaceutical dosage form and becomes available at the site of action or in the general circulation. Increases in bioavailability refers to increasing the rate and extent a substance or its active moiety is delivered from a pharmaceutical dosage form and becomes available at the site of action or in the general circulation. By way of example, an increase in bioavailability may be indicated as an increase in concentration of the substance or its active moiety in the blood when compared to other substances or active moieties. Methods to evaluate increases in bioavailability are known in the art and may be used for evaluating the bioavailability of any polypeptide.

The term "biologically active molecule", "biologically active moiety" or "biologically active agent" when used herein means any substance which can affect any physical or biochemical properties of a biological system, pathway, molecule, or interaction relating to an organism, including but not limited to, viruses, bacteria, bacteriophage, transposon, prion, insects, fungi, plants, animals, and humans. In particular, as used herein, biologically active molecules include but are not limited to any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs, hard drugs, soft drugs, prodrugs, carbohydrates, inorganic atoms or molecules, dyes, lipids, nucleosides, radionuclides, oligonucleotides, toxins, cells, viruses, liposomes, microparticles and micelles. Classes of biologically active agents that are suitable for use with the methods and compositions described herein include, but are not limited to, drugs, prodrugs, radionuclides, imaging agents, polymers, antibiotics, fungicides, anti-viral agents, anti-inflammatory agents, anti-tumor agents, cardiovascular agents, anti-anxiety agents, hormones, growth factors, steroidal agents, microbially derived toxins, and the like.

By "modulating biological activity" is meant increasing or decreasing the reactivity of a polypeptide, altering the selectivity of the polypeptide, enhancing or decreasing the substrate selectivity of the polypeptide. Analysis of modified biological activity can be performed by comparing the biological activity of the non-natural polypeptide to that of the natural polypeptide.

The term "biomaterial," as used herein, refers to a biologically-derived material, including but not limited to material obtained from bioreactors and/or from recombinant methods and techniques.

The term "biophysical probe," as used herein, refers to probes which can detect or monitor structural changes in molecules. Such molecules include, but are not limited to, proteins and the "biophysical probe" may be used to detect or monitor interaction of proteins with other macromolecules. Examples of biophysical probes include, but are not limited to, spin-labels, a fluorophores, and photoactivatable groups.

The term "biosynthetically," as used herein, refers to any method utilizing a translation system (cellular or non-cellular), including use of at least one of the following components: a polynucleotide, a codon, a tRNA, and a ribosome. By way of example, non-natural amino acids may be "biosynthetically incorporated" into non-natural amino acid polypeptides using the methods and techniques described in WO 2002/085923, incorporated herein by reference in its entirety. Additionally, the methods for the selection of useful non-natural amino acids which may be "biosynthetically incorporated" into non-natural amino acid polypeptides are described in WO 2002/085923, incorporated herein by reference in its entirety.

The term "biotin analogue," or also referred to as "biotin mimic", as used herein, is any molecule, other than biotin, which bind with high affinity to avidin and/or streptavidin.

The term "carbonyl" as used herein refers to a group containing at a moiety selecting from the group consisting of —C(O)—, —S(O)—, —S(O)2-, and —C(S)—, including, but not limited to, groups containing a least one ketone group, and/or at least one aldehyde groups, and/or at least one ester group, and/or at least one carboxylic acid group, and/or at least one thioester group. Such carbonyl groups include ketones, aldehydes, carboxylic acids, esters, and thioesters. In addition, such groups may be part of linear, branched, or cyclic molecules.

The term "carboxy terminus modification group" refers to any molecule that can be attached to a terminal carboxy group. By way of example, such terminal carboxy groups may be at the end of polymeric molecules, wherein such polymeric molecules include, but are not limited to, polypeptides, polynucleotides, and polysaccharides. Terminus modification groups include but are not limited to, various water soluble polymers, peptides or proteins. By way of example only, terminus modification groups include polyethylene glycol or serum albumin. Terminus modification groups may be used to modify therapeutic characteristics of the polymeric molecule, including but not limited to increasing the serum half-life of peptides.

The term "chemically cleavable group," also referred to as "chemically labile", as used herein, refers to a group which breaks or cleaves upon exposure to acid, base, oxidizing agents, reducing agents, chemical inititiators, or radical initiators.

"Cofolding," as used herein, refers to refolding processes, reactions, or methods which employ at least two molecules which interact with each other and result in the transformation of unfolded or improperly folded molecules to properly folded molecules. By way of example only, "cofolding," employ at least two polypeptides which interact with each other and result in the transformation of unfolded or improperly folded polypeptides to native, properly folded polypeptides. Such polypeptides may contain natural amino acids and/or at least one non-natural amino acid.

"Conjugate", as used herein, refers to a polypeptide that is linked, e.g., covalently linked, either directly or through a linker to a compound or compound-linker described herein, e.g., a compound or salt of any one of structures according to FIG. 1, or any one of structures of Tables 3-7. The "targeting moiety" refers to a structure that has a selective affinity for a target molecule relative to other non-target molecules. A targeting moiety of the invention binds to a target molecule. A targeting moiety may include, for example, an antibody, a peptide, a ligand, a receptor, or a binding portion thereof. A target biological molecule may be a biological receptor or other structure of a cell such as a tumor antigen. As used herein, the term "conjugate of the invention," "targeting moiety conjugate" "targeting conjugate," "targeting moiety-active molecule conjugate" or "TC" refers to a targeting polypeptide or a portion, analog or derivative thereof that binds to a target present on a cell or subunit thereof conjugated to a biologically active molecule, a portion thereof or an analog thereof, including but not limited to a TLR7 and/or a TLR8 agonist. As used herein, the term "tumor-targeting moiety conjugate" "tumor-targeting moiety-biologically active molecule conjugate" or "BTC" refers to a tumor targeting polypeptide or a portion, analog or derivative thereof that binds to a target present on tumor cells or subunit thereof conjugated to a biologically active molecule, a portion thereof or an analog thereof, including but not limited to a TLR7 and/or a TLR8 agonist. Unless otherwise indicated, the terms "compound of the invention" and "composition of the invention" are used as alternatives for the term "conjugate of the invention."

The term "conservatively modified variants" applies to both natural and non-natural amino acid and natural and non-natural nucleic acid sequences, and combinations thereof. With respect to particular nucleic acid sequences, "conservatively modified variants" refers to those natural and non-natural nucleic acids which encode identical or essentially identical natural and non-natural amino acid sequences, or where the natural and non-natural nucleic acid does not encode a natural and non-natural amino acid sequence, to essentially identical sequences. By way of example, because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Thus, by way of example, every natural or non-natural nucleic acid sequence herein which encodes a natural or non-natural polypeptide also describes every possible silent variation of the natural or non-natural nucleic acid. One of ordinary skill in the art will recognize that each codon in a natural or non-natural nucleic acid (except AUG, which is ordinarily the only codon for methionine, and TGG, which is ordinarily the only codon for tryptophan) can be modified to yield a functionally identical molecule. Accordingly, each silent variation of a natural and non-natural nucleic acid which encodes a natural and non-natural polypeptide is implicit in each described sequence.

As to amino acid sequences, individual substitutions, deletions or additions to a nucleic acid, peptide, polypeptide, or protein sequence which alters, adds or deletes a single natural and non-natural amino acid or a small percentage of natural and non-natural amino acids in the encoded sequence is a "conservatively modified variant" where the alteration results in the deletion of an amino acid, addition of an amino acid, or substitution of a natural and non-natural amino acid with a chemically similar amino acid. Conservative substitution tables providing functionally similar natural amino acids are well known in the art. Such conservatively modified variants are in addition to and do not exclude polymorphic variants, interspecies homologs, and alleles of the methods and compositions described herein.

Conservative substitution tables providing functionally similar amino acids are known to those of ordinary skill in the art. The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M). (See, e.g., Creighton, Proteins: Structures and Molecular Properties (W Freeman & Co.; 2nd edition (December 1993).

The terms "cycloalkyl" and "heterocycloalkyl", by themselves or in combination with other terms, represent, unless otherwise stated, cyclic versions of "alkyl" and "heteroalkyl", respectively. Thus, a cycloalkyl or heterocycloalkyl include saturated, partially unsaturated and fully unsaturated ring linkages. Additionally, for heterocycloalkyl, a heteroatom can occupy the position at which the heterocycle is attached to the remainder of the molecule. The heteroatom may include, but is not limited to, oxygen, nitrogen or sulfur. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. Additionally, the term encompasses multicyclic structures, including but not limited to, bicyclic and tricyclic ring structures. Similarly, the term "heterocycloalkylene" by itself or as part of another molecule means a divalent radical derived from heterocycloalkyl, and the term "cycloalkylene" by itself or as part of another molecule means a divalent radical derived from cycloalkyl.

The term "cyclodextrin," as used herein, refers to cyclic carbohydrates consisting of at least six to eight glucose molecules in a ring formation. The outer part of the ring contains water soluble groups; at the center of the ring is a relatively nonpolar cavity able to accommodate small molecules.

The term "cytotoxic," as used herein, refers to a compound which harms cells.

"Denaturing agent" or "denaturant," as used herein, refers to any compound or material which will cause a reversible unfolding of a polymer. By way of example only, "denaturing agent" or "denaturants," may cause a reversible unfolding of a protein. The strength of a denaturing agent or denaturant will be determined both by the properties and the concentration of the particular denaturing agent or denaturant. By way of example, denaturing agents or denaturants include, but are not limited to, chaotropes, detergents, organic, water miscible solvents, phospholipids, or a combination thereof. Non-limiting examples of chaotropes include, but are not limited to, urea, guanidine, and sodium thiocyanate. Non-limiting examples of detergents may include, but are not limited to, strong detergents such as sodium dodecyl sulfate, or polyoxyethylene ethers (e.g. Tween or Triton detergents), Sarkosyl, mild non-ionic detergents (e.g., digitonin), mild cationic detergents such as N→2,3-(Dioleyoxy)-propyl-N,N,N-trimethylammonium, mild ionic detergents (e.g. sodium cholate or sodium deoxycholate) or zwitterionic detergents including, but not limited to, sulfobetaines (Zwittergent), 3-(3-chlolamidopropyl)dimethylammonio-1-propane sulfate (CHAPS), and 3-(3-chlolamidopropyl)dimethylammonio-2-hydroxy-1-propane sulfonate (CHAPSO). Non-limiting examples of organic, water miscible solvents include, but are not limited to, acetonitrile, lower alkanols (especially C2-C4 alkanols such as ethanol or isopropanol), or lower alkandiols (C2-C4 alkandiols such as ethylene-glycol) may be used as denaturants. Non-limiting examples of phospholipids include, but are not limited to, naturally occurring phospholipids such as phosphatidylethanolamine, phosphatidylcholine, phosphatidylserine, and phosphatidylinositol or synthetic phospholipid derivatives or variants such as dihexanoylphosphatidylcholine or diheptanoylphosphatidylcholine.

The term "diamine," as used herein, refers to groups/molecules comprising at least two amine functional groups, including, but not limited to, a hydrazine group, an amidine group, an imine group, a 1,1-diamine group, a 1,2-diamine group, a 1,3-diamine group, and a 1,4-diamine group. In addition, such groups may be part of linear, branched, or cyclic molecules.

The term "detectable label," as used herein, refers to a label which may be observable using analytical techniques including, but not limited to, fluorescence, chemiluminescence, electron-spin resonance, ultraviolet/visible absorbance spectroscopy, mass spectrometry, nuclear magnetic resonance, magnetic resonance, and electrochemical methods.

The term "dicarbonyl" as used herein refers to a group containing at least two moieties selected from the group consisting of —C(O)—, —S(O)—, $—S(O)_2—$, and —C(S)—, including, but not limited to, 1,2-dicarbonyl groups, a 1,3-dicarbonyl groups, and 1,4-dicarbonyl groups, and groups containing a least one ketone group, and/or at least one aldehyde groups, and/or at least one ester group, and/or at least one carboxylic acid group, and/or at least one thioester group. Such dicarbonyl groups include diketones, ketoaldehydes, ketoacids, ketoesters, and ketothioesters. In addition, such groups may be part of linear, branched, or cyclic molecules. The two moieties in the dicarbonyl group may be the same or different, and may include substituents that would produce, by way of example only, an ester, a ketone, an aldehyde, a thioester, or an amide, at either of the two moieties.

The term "drug," as used herein, refers to any substance used in the prevention, diagnosis, alleviation, treatment, or cure of a disease or condition.

The term "effective amount," as used herein, refers to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. By wry of example, an agent or a compound being administered includes, but is not limited to, a natural amino acid polypeptide, non-natural amino acid polypeptide, modified natural amino acid polypeptide, or modified non-amino acid polypeptide. Compositions containing such natural amino acid polypeptides, non-natural amino acid polypeptides, modified natural amino acid polypeptides, or modified non-natural amino acid polypeptides can be administered for prophylactic, enhancing, and/or therapeutic treatments. An appropriate "effective" amount in any individual case may be determined using techniques, such as a dose escalation study.

The terms "enhance" or "enhancing" means to increase or prolong either in potency or duration a desired effect. By way of example, "enhancing" the effect of therapeutic agents refers to the ability to increase or prolong, either in potency or duration, the effect of therapeutic agents on during treatment of a disease, disorder or condition. An "enhancing-effective amount," as used herein, refers to an amount adequate to enhance the effect of a therapeutic agent in the treatment of a disease, disorder or condition. When used in a patient, amounts effective for this use will depend on the severity and course of the disease, disorder or condition, previous therapy, the patient's health status and response to the drugs, and the judgment of the treating physician.

As used herein, the term "eukaryote" refers to organisms belonging to the phylogenetic domain Eucarya, including but not limited to animals (including but not limited to, mammals, insects, reptiles, birds, etc.), ciliates, plants (including but not limited to, monocots, dicots, and algae), fungi, yeasts, flagellates, microsporidia, and protists.

The term "fatty acid," as used herein, refers to carboxylic acids with about C6 or longer hydrocarbon side chain.

The term "fluorophore," as used herein, refers to a molecule which upon excitation emits photons and is thereby fluorescent.

The terms "functional group", "active moiety", "activating group", "leaving group", "reactive site", "chemically reactive group" and "chemically reactive moiety," as used herein, refer to portions or units of a molecule at which chemical reactions occur. The terms are somewhat synonymous in the chemical arts and are used herein to indicate the portions of molecules that perform some function or activity and are reactive with other molecules.

The term "halogen" includes fluorine, chlorine, iodine, and bromine.

The term "haloacyl," as used herein, refers to acyl groups which contain halogen moieties, including, but not limited to, $—C(O)CH_3$, $—C(O)CF_3$, $—C(O)CH_2OCH_3$, and the like.

The term "haloalkyl," as used herein, refers to alkyl groups which contain halogen moieties, including, but not limited to, $—CF_3$ and $—CH_2CF_3$ and the like.

The term "heteroalkyl," as used herein, refers to straight or branched chain, or cyclic hydrocarbon radicals, or combinations thereof, consisting of an alkyl group and at least one heteroatom selected from the group consisting of O, N, Si and S, and wherein the nitrogen and sulfur atoms may optionally be oxidized, and the nitrogen heteroatom may optionally be quaternized. The heteroatom(s) O, N and S and Si may be placed at any interior position of the heteroalkyl group or at the position at which the alkyl group is attached to the remainder of the molecule. Examples include, but are not limited to, $—CH_2—CH_2—O—CH_3$, $—CH_2—CH_2—NH—CH_3$, $—CH_2—CH_2—N(CH_3)—CH_3$, $—CH_2—S—CH_2—OH_3$, $—CH_2—CH_2$, $—S(O)—CH_3$, $—CH_2—CH_2—S(O)_2—CH_3$, $—CH{=}CH—O—CH_3$, $—Si(CH_3)_3$, $—CH_2—CH{=}N—OCH_3$, and $—CH—CH—N(CH_3)—CH_3$. In addition, up to two heteroatoms may be consecutive, such as, by way of example, $—CH_2—NH—OCH_3$ and $—CH_2—O—Si(CH_3)_3$.

The terms "heterocyclic-based linkage" or "heterocycle linkage" refers to a moiety formed from the reaction of a dicarbonyl group with a diamine group. The resulting reaction product is a heterocycle, including a heteroaryl group or a heterocycloalkyl group. The resulting heterocycle group serves as a chemical link between a non-natural amino acid or non-natural amino acid polypeptide and another functional group. In one embodiment, the heterocycle linkage includes a nitrogen-containing heterocycle linkage, including by way of example only a pyrazole linkage, a pyrrole linkage, an indole linkage, a benzodiazepine linkage, and a pyrazalone linkage.

Similarly, the term "heteroalkylene" refers to a divalent radical derived from heteroalkyl, as exemplified, but not limited by, $—CH_2—CH_2—S—CH_2—CH_2—$ and $—CH_2—S—CH_2—CH_2—NH—CH_2—$. For heteroalkylene groups, the same or different heteroatoms can also occupy either or both of the chain termini (including but not limited to, alkyleneoxy, alkylenedioxy, alkyleneamino, alkylenediamino, aminooxyalkylene, and the like). Still further, for alkylene and heteroalkylene linking groups, no orientation of the linking group is implied by the direction in which the formula of the linking group is written. By way of example, the formula —$C(O)_2R'$-represents both —$C(O)_2R'$— and —$R'C(O)_2$—.

The term "heteroaryl" or "heteroaromatic," as used herein, refers to aryl groups which contain at least one heteroatom selected from N, O, and S; wherein the nitrogen and sulfur atoms may be optionally, oxidized, and the nitrogen atom(s) may be optionally quaternized. Heteroaryl groups may be substituted or unsubstituted. A heteroaryl group may be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl.

The term "homoalkyl," as used herein refers to alkyl groups which are hydrocarbon groups.

The term "identical," as used herein, refers to two or more sequences or subsequences which are the same. In addition, the term "substantially identical," as used herein, refers to two or more sequences which have a percentage of sequential units which are the same when compared and aligned for maximum correspondence over a comparison window, or designated region as measured using comparison algorithms or by manual alignment and visual inspection. By way of example only, two or more sequences may be "substantially identical" if the sequential units are about 60% identical, about 65% identical, about 70% identical, about 75% identical, about 80% identical, about 85% identical, about 90% identical, or about 95% identical over a specified region. Such percentages to describe the "percent identity" of two or more sequences. The identity of a sequence can exists over a region that is at least about 75-100 sequential units in length, over a region that is about 50 sequential units in length, or, where not specified, across the entire sequence. This definition also refers to the complement of a test sequence. By way of example only, two or more polypeptide sequences are identical when the amino acid residues are the same, while two or more polypeptide sequences are "substantially identical" if the amino acid residues are about 60% identical, about 65% identical, about 70% identical, about 75% identical, about 80% identical, about 85% identical, about 90% identical, or about 95% identical over a specified region. The identity can exist over a region that is at least about 75 to about 100 amino acids in length, over a region that is about 50 amino acids in length, or, where not specified, across the entire sequence of a polypeptide sequence. In addition, by way of example only, two or more polynucleotide sequences are identical when the nucleic acid residues are the same, while two or more polynucleotide sequences are "substantially identical" if the nucleic acid residues are about 60% identical, about 65% identical, about 70% identical, about 75% identical, about 80% identical, about 85% identical, about 90% identical, or about 95% identical over a specified region. The identity can exist over a region that is at least about 75 to about 100 nucleic acids in length, over a region that is about 50 nucleic acids in length, or, where not specified, across the entire sequence of a polynucleotide sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

The term "immunogenicity," as used herein, refers to an antibody response to administration of a therapeutic drug. The immunogenicity toward therapeutic non-natural amino acid polypeptides can be obtained using quantitative and qualitative assays for detection of anti-non-natural amino acid polypeptides antibodies in biological fluids. Such assays include, but are not limited to, Radioimmunoassay (RIA), Enzyme-linked immunosorbent assay (ELISA), luminescent immunoassay (LIA), and fluorescent immunoassay (FIA). Analysis of immunogenicity toward therapeutic non-natural amino acid polypeptides involves comparing the antibody response upon administration of therapeutic non-natural amino acid polypeptides to the antibody response upon administration of therapeutic natural amino acid polypeptides.

The term "isolated," as used herein, refers to separating and removing a component of interest from components not of interest. Isolated substances can be in either a dry or semi-dry state, or in solution, including but not limited to an aqueous solution. The isolated component can be in a homogeneous state or the isolated component can be a part of a pharmaceutical composition that comprises additional pharmaceutically acceptable carriers and/or excipients. Purity and homogeneity may be determined using analytical chemistry techniques including, but not limited to, polyacrylamide gel electrophoresis or high performance liquid chromatography. In addition, when a component of interest is isolated and is the predominant species present in a preparation, the component is described herein as substantially purified. The term "purified," as used herein, may refer to a component of interest which is at least 85% pure, at least 90% pure, at least 95% pure, at least 99% or greater pure. By way of example only, nucleic acids or proteins are "isolated" when such nucleic acids or proteins are free of at least some of the cellular components with which it is associated in the natural state, or that the nucleic acid or protein has been concentrated to a level greater than the concentration of its in vivo or in vitro production. Also, by way of example, a gene is isolated when separated from open reading frames which flank the gene and encode a protein other than the gene of interest.

The term "label," as used herein, refers to a substance which is incorporated into a compound and is readily detected, whereby its physical distribution may be detected and/or monitored.

The term "linkage" or "linker" as used herein to refer to bonds or chemical moiety formed from a chemical reaction between the functional group of a linker and another molecule. Such bonds may include, but are not limited to, covalent linkages and non-covalent bonds, while such chemical moieties may include, but are not limited to, esters, carbonates, imines phosphate esters, hydrazones, acetals, orthoesters, peptide linkages, and oligonucleotide linkages. Hydrolytically stable linkages mean that the linkages are substantially stable in water and do not react with water at useful pH values, including but not limited to, under physiological conditions for an extended period of time, perhaps even indefinitely. Hydrolytically unstable or degradable linkages mean that the linkages are degradable in water or in aqueous solutions, including for example, blood. Enzymatically unstable or degradable linkages mean that the linkage can be degraded by one or more enzymes. By way of example only, PEG and related polymers may include degradable linkages in the polymer backbone or in the linker group between the polymer backbone and one or more of the terminal functional groups of the polymer molecule. Such degradable linkages include, but are not limited to, ester linkages formed by the reaction of PEG carboxylic acids or activated PEG carboxylic acids with alcohol groups on a biologically active agent, wherein such ester groups generally hydrolyze under physiological conditions to release the biologically active agent. Other hydrolytically degradable linkages include but are not limited to carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide. Linkers include but are not limited to short linear, branched, multi-armed, or dendrimeric molecules such as polymers. In some embodiments of the invention the linker may be branched. In other embodiments the linker may be a bifunctional linker. In some embodiments, the linker may be a trifunctional linker. A number of different cleavable linkers are known to those of skill in the art. See U.S. Pat. Nos. 4,618,492; 4,542,225, and 4,625,014. The mechanisms for release of an agent from these linker groups include, for example, irradiation of a photolabile bond and acid-catalyzed hydrolysis. U.S. Pat. No. 4,671,958, for example, includes a description of immunoconjugates comprising linkers which are cleaved at the target site in vivo by the proteolytic enzymes of the patient's complement system. The length of the linker may be predetermined or selected depending upon a desired spatial relationship between the polypeptide and the molecule linked to it. In view of the large number of methods that have been reported for attaching a variety of radiodiagnostic compounds, radiotherapeutic compounds, drugs, toxins, and other agents to antibodies one skilled in the art will be able to determine a suitable method for attaching a given agent or molecule to a polypeptide.

The term "modified," as used herein refers to the presence of a change to a natural amino acid, a non-natural amino acid, a natural amino acid polypeptide or a non-natural amino acid polypeptide. Such changes, or modifications, may be obtained by post synthesis modifications of natural amino acids, non-natural amino acids, natural amino acid polypeptides or non-natural amino acid polypeptides, or by co-translational, or by post-translational modification of natural amino acids, non-natural amino acids, natural amino acid polypeptides or non-natural amino acid polypeptides. The form "modified or unmodified" means that the natural amino acid, non-natural amino acid, natural amino acid polypeptide or non-natural amino acid polypeptide being discussed are optionally modified, that is, he natural amino acid, non-natural amino acid, natural amino acid polypeptide or non-natural amino acid polypeptide under discussion can be modified or unmodified.

As used herein, the term "modulated serum half-life" refers to positive or negative changes in the circulating half-life of a modified biologically active molecule relative to its non-modified form. By way of example, the modified biologically active molecules include, but are not limited to, natural amino acid, non-natural amino acid, natural amino acid polypeptide or non-natural amino acid polypeptide. By way of example, serum half-life is measured by taking blood samples at various time points after administration of the biologically active molecule or modified biologically active molecule, and determining the concentration of that molecule in each sample. Correlation of the serum concentration with time allows calculation of the serum half-life. By way of example, modulated serum half-life may be an increased in serum half-life, which may enable improved dosing regimens or avoid toxic effects. Such increases in serum may be at least about two fold, at least about three-fold, at least about five-fold, or at least about ten-fold. Methods to evaluate increases in serum half-life of any polypeptide are well know to the skilled artisan.

The term "modulated therapeutic half-life," as used herein, refers to positive or negative change in the half-life of the therapeutically effective amount of a modified biologically active molecule, relative to its non-modified form. By way of example, the modified biologically active molecules include, but are not limited to, natural amino acid, non-natural amino acid, natural amino acid polypeptide or non-natural amino acid polypeptide. By way of example, therapeutic half-life is measured by measuring pharmacokinetic and/or pharmacodynamic properties of the molecule at various time points after administration. Increased therapeutic half-life may enable a particular beneficial dosing regimen, a particular beneficial total dose, or avoids an undesired effect. By way of example, the increased therapeutic half-life may result from increased potency, increased or decreased binding of the modified molecule to its target, an increase or decrease in another parameter or mechanism of action of the non-modified molecule, or an increased or decreased breakdown of the molecules by enzymes such as, by way of example only, proteases. Methods to evaluate increases in therapeutic half-life of any polypeptide are well known to the skilled artisan.

A "non-natural amino acid" refers to an amino acid that is not one of the 20 common amino acids or pyrolysine or selenocysteine. Other terms that may be used synonymously with the term "non-natural amino acid" is "non-naturally encoded amino acid," "unnatural amino acid," "non-naturally-occurring amino acid," and variously hyphenated and non-hyphenated versions thereof. The term "non-natural amino acid" includes, but is not limited to, amino acids which occur naturally by modification of a naturally encoded amino acid (including but not limited to, the 20 common amino acids or pyrrolysine and selenocysteine) but are not themselves incorporated into a growing polypeptide chain by the translation complex. Examples of such amino acids include, but are not limited to, N-acetylglucosaminyl-L-serine, N-acetylglucosaminyl-L-threonine, and 0-phosphotyrosine. Additionally, the term "non-natural amino acid" includes, but is not limited to, amino acids which do not occur naturally and may be obtained synthetically or may be obtained by modification of non-natural amino acids. In some embodiments, non-natural amino acids comprise a lysine analog, for example, N6-azidoethoxy-L-lysine (AzK), N6-propargylethoxy-L-lysine (PraK), BCN-L-lysine, norbornene lysine, TCO-lysine, methyltetrazine lysine, or allyloxycarbonyl lysine. In some embodiments, non-natural amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature—including but not limited to, an alkene, an oxime, a thioether, an amide and the like. Examples of such amino acids also include saccharides that are not commonly found in naturally-occurring proteins such as 2-deoxy-glucose, 2-deoxygalactose and the like. Specific examples of non-natural amino acids include, but are not limited to, a p-acetyl-L-phenylalanine, a p-propargyloxyphenylalanine, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, a isopropyl-L-phenylalanine, a p-azido-L-phenylalanine, a p-acyl-L-phenylalanine, a p-benzoyl-L-phenylalanine, a L-phosphoserine, a phosphonoserine, a phosphonotyrosine, a p-iodo-phenylalanine, a p-bromophenylalanine, a p-amino-L-phenylalanine, a p-propargyloxy-L-phenylalanine, a 4-azido-L-phenylalanine, a para-azidoethoxy phenylalanine, and a para-azidomethyl-phenylalanine, and the like. In some embodiments, the non-natural amino acid is selected from a group consisting of para-acetyl-phenylalanine, 4-azido-L-phenylalanine, para-azidoethoxy phenylalanine or para-azidomethyl-phenylalanine.

The term "nucleic acid," as used herein, refers to deoxyribonucleotides, deoxyribonucleosides, ribonucleosides or ribonucleotides and polymers thereof in either single- or double-stranded form. By way of example only, such nucleic acids and nucleic acid polymers include, but are not limited to, (i) analogues of natural nucleotides which have similar binding properties as a reference nucleic acid and are metabolized in a manner similar to naturally occurring nucleotides; (ii) oligonucleotide analogs including, but are not limited to, PNA (peptidonucleic acid), analogs of DNA used in antisense technology (phosphorothioates, phosphoroamidates, and the like); (iii) conservatively modified variants thereof (including but not limited to, degenerate codon substitutions) and complementary sequences and sequence explicitly indicated. By way of example, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The term "oxidizing agent," as used herein, refers to a compound or material which is capable of removing an electron from a compound being oxidized. By way of example oxidizing agents include, but are not limited to, oxidized glutathione, cystine, cystamine, oxidized dithiothreitol, oxidized erythreitol, and oxygen. A wide variety of oxidizing agents are suitable for use in the methods and compositions described herein.

The term "pharmaceutically acceptable", as used herein, refers to a material, including but not limited, to a salt, carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "polyalkylene glycol," or "poly(alkene glycol)" as used herein, refers to linear or branched polymeric polyether polyols. Such polyalkylene glycols, including, but are not limited to, polyethylene glycol, polypropylene glycol, polybutylene glycol, and derivatives thereof. Other exemplary embodiments are listed, for example, in commercial supplier catalogs, such as Shearwater Corporation's catalog "Polyethylene Glycol and Derivatives for Biomedical Applications" (2001). By way of example only, such polymeric polyether polyols have average molecular weights between about 0.1 kDa to about 100 kDa. By way of example, such polymeric polyether polyols include, but are not limited to, between about 100 Da and about 100,000 Da or more. The molecular weight of the polymer may be between about 100 Da and about 100,000 Da, including but not limited to, about 100,000 Da, about 95,000 Da, about 90,000 Da, about 85,000 Da, about 80,000 Da, about 75,000 Da, about 70,000 Da, about 65,000 Da, about 60,000 Da, about 55,000 Da, about 50,000 Da, about 45,000 Da, about 40,000 Da, about 35,000 Da, about 30,000 Da, about 25,000 Da, about 20,000 Da, about 15,000 Da, about 10,000 Da, about 9,000 Da, about 8,000 Da, about 7,000 Da, about 6,000 Da, about 5,000 Da, about 4,000 Da, about 3,000 Da, about 2,000 Da, about 1,000 Da, about 900 Da, about 800 Da, about 700 Da, about 600 Da, about 500 Da, 400 Da, about 300 Da, about 200 Da, and about 100 Da. In some embodiments molecular weight of the polymer is between about 100 Da and about 50,000 Da. In some embodiments, the molecular weight of the polymer is between about 100 Da and about 40,000 Da. In some embodiments, the molecular weight of the polymer is between about 1,000 Da and about 40,000 Da. In some embodiments, the molecular weight of the polymer is between about 2,000 to about 50,000 Da. In some embodiments, the molecular weight of the polymer is between about 5,000 Da and about 40,000 Da. In some embodiments, the molecular weight of the polymer is between about 10,000 Da and about 40,000 Da. In some embodiments, the poly(ethylene glycol) molecule is a branched polymer. The molecular weight of the branched chain PEG may be between about 1,000 Da and about 100,000 Da, including but not limited to, about 100,000 Da, about 95,000 Da, about 90,000 Da, about 85,000 Da, about 80,000 Da, about 75,000 Da, about 70,000 Da, about 65,000 Da, about 60,000 Da, about 55,000 Da, about 50,000 Da, about 45,000 Da, about 40,000 Da, about 35,000 Da, about 30,000 Da, about 25,000 Da, about 20,000 Da, about 15,000 Da, about 10,000 Da, about 9,000 Da, about 8,000 Da, about 7,000 Da, about 6,000 Da, about 5,000 Da, about 4,000 Da, about 3,000 Da, about 2,000 Da, and about 1,000 Da. In some embodiments, the molecular weight of the branched chain PEG is between about 1,000 Da and about 50,000 Da. In some embodiments, the molecular weight of the branched chain PEG is between about 1,000 Da and about 40,000 Da. In some embodiments, the molecular weight of the branched chain PEG is between about 5,000 Da and about 40,000 Da. In some embodiments, the molecular weight of the branched chain PEG is between about 5,000 Da and about 20,000 Da. In other embodiments, the molecular weight of the branched chain PEG is between about 2,000 to about 50,000 Da.

The term "polymer," as used herein, refers to a molecule composed of repeated subunits. Such molecules include, but are not limited to, polypeptides, polynucleotides, or polysaccharides or polyalkylene glycols.

The terms "polypeptide," "peptide" and "protein" are used interchangeably herein to refer to a polymer of amino acid residues. That is, a description directed to a polypeptide applies equally to a description of a peptide and a description of a protein, and vice versa. The terms apply to naturally occurring amino acid polymers as well as amino acid polymers in which one or more amino acid residues is a non-natural amino acid. Additionally, such "polypeptides," "peptides" and "proteins" include amino acid chains of any length, including full length proteins, wherein the amino acid residues are linked by covalent peptide bonds.

The term "post-translationally modified" refers to any modification of a natural or non-natural amino acid which occurs after such an amino acid has been translationally incorporated into a polypeptide chain. Such modifications include, but are not limited to, co-translational in vivo modifications, co-translational in vitro modifications (such as in a cell-free translation system), post-translational in viva modifications, and post-translational in vitro modifications.

The terms "prodrug" or "pharmaceutically acceptable prodrug," as used herein, refers to an agent that is converted into the parent drug in vivo or in vitro, wherein which does not abrogate the biological activity or properties of the drug, and is relatively nontoxic, i.e., the material may be administered to an individual without causing undesirable biological effects or interacting in a deleterious manner with any of the components of the composition in which it is contained. Prodrugs are generally drug precursors that, following administration to a subject and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are converted into active drug within the body through enzymatic or non-enzymatic reactions. Prodrugs may provide improved physiochemical properties such as better solubility, enhanced delivery characteristics, such as specifically targeting a particular cell, tissue, organ or ligand, and improved therapeutic value of the drug. The benefits of such prodrugs include, but are not limited to, (i) ease of administration compared with the parent drug; (ii) the prodrug may be bioavailable by oral administration whereas the parent is not; and (iii) the prodrug may also have improved solubility in pharmaceutical compositions compared with the parent drug. A pro-drug includes a pharmacologically inactive, or reduced-activity, derivative of an active drug. Prodrugs may be designed to modulate the amount of a drug or biologically active molecule that reaches a desired site of action through the manipulation of the properties of a drug, such as physiochemical, biopharmaceutical, or pharmacokinetic properties. An example, without limitation, of a prodrug would be a non-natural amino acid polypeptide which is administered as an ester (the "prodrug") to facilitate transmittal across a cell membrane where water solubility is detrimental to mobility, but which then is metabolically hydrolyzed to the carboxylic acid, the active entity, once inside the cell where water solubility is beneficial. Prodrugs may be designed as reversible drug derivatives, for use as modifiers to enhance drug transport to site-specific tissues.

The term "prophylactically effective amount," as used herein, refers that amount of a composition containing at least one non-natural amino acid polypeptide or at least one modified non-natural amino acid polypeptide prophylactically applied to a patient which will relieve to some extent one or more of the symptoms of a disease, condition or disorder being treated. In such prophylactic applications, such amounts may depend on the patient's state of health, weight, and the like. It is considered well within the skill of the art for one to determine such prophylactically effective amounts by routine experimentation, including, but not limited to, a dose escalation clinical trial.

The term "protected," as used herein, refers to the presence of a "protecting group" or moiety that prevents reaction of the chemically reactive functional group under certain reaction conditions. The protecting group will vary depending on the type of chemically reactive group being protected. By way of example only, (i) if the chemically reactive group is an amine or a hydrazide, the protecting group may be selected from tert-butyloxycarbonyl (tBoc) and 9-fluorenylmethoxycarbonyl (Fmoc); (ii) if the chemically reactive group is a thiol, the protecting group may be orthopyridyldisulfide; and (iii) if the chemically reactive group is a carboxylic acid, such as butanoic or propionic acid, or a hydroxyl group, the protecting group may be benzyl or an alkyl group such as methyl, ethyl, or tert-butyl.

By way of example only, blocking/protecting groups may be selected from:

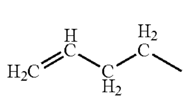

allyl

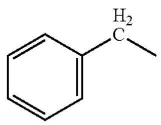

Bn

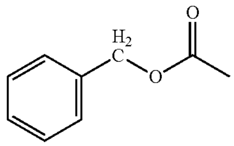

Cbz

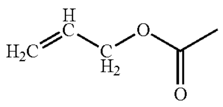

alloc

Me

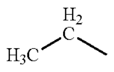

Et

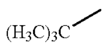

t-butyl

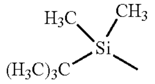

TBDMS

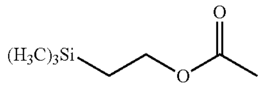

Teoc

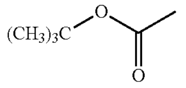

Boc

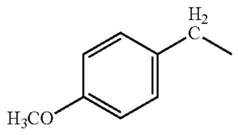

pMBn

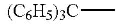

trityl

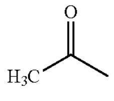

acetyl

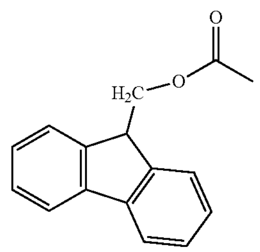

Fmoc

Additionally, protecting groups include, but are not limited to, including photolabile groups such as Nvoc and MeNvoc and other protecting groups known in the art. Other protecting groups are described in Greene and Wuts, Protective Groups in Organic Synthesis, 3rd Ed., John Wiley & Sons, New York, N.Y., 1999, which is incorporated herein by reference in its entirety.

The term "recombinant host cell," also referred to as "host cell," refers to a cell which includes an exogenous polynucleotide, wherein the methods used to insert the exogenous polynucleotide into a cell include, but are not limited to, direct uptake, transduction, f-mating, or other methods known in the art to create recombinant host cells. By way of example only, such exogenous polynucleotide may be a nonintegrated vector, including but not limited to a plasmid, or may be integrated into the host genome.

The term "redox-active agent," as used herein, refers to a molecule which oxidizes or reduces another molecule, whereby the redox active agent becomes reduced or oxidized. Examples of redox active agent include, but are not limited to, ferrocene, quinones, $Ru^{2+/3+}$ complexes, $Co^{2+/3+}$ complexes, and $Os^{2+/3+}$ complexes.

The term "reducing agent," as used herein, refers to a compound or material which is capable of adding an electron to a compound being reduced. By way of example reducing agents include, but are not limited to, dithiothreitol (MT), 2-mercaptoethanol, dithioerythritol, cysteine, cysteamine (2-aminoethanethiol), and reduced glutathione. Such reducing agents may be used, by way of example only, to maintain sulfhydryl groups in the reduced state and to reduce intra- or intermolecular disulfide bonds.

"Refolding," as used herein describes any process, reaction or method which transforms an improperly folded or unfolded state to a native or properly folded conformation. By way of example only; refolding transforms disulfide bond containing polypeptides from an improperly folded or unfolded state to a native or properly folded conformation with respect to disulfide bonds. Such disulfide bond containing polypeptides may be natural amino acid polypeptides or non-natural amino acid polypeptides.

The term "safety" or "safety profile," as used herein, refers to side effects that might be related to administration of a drug relative to the number of times the drug has been administered. By way of example, a drug which has been administered many times and produced only mild or no side effects is said to have an excellent safety profile. Methods used for evaluating the safety profile of any polypeptide are known in the art.

The phrase "selectively hybridizes to" or "specifically hybridizes to," as used herein, refers to the binding, duplexing, or hybridizing of a molecule to a particular nucleotide sequence under stringent hybridization conditions when that sequence is present in a complex mixture including but not limited to, total cellular or library DNA or RNA.

The phrase "stringent hybridization conditions" refers to hybridization of sequences of DNA, RNA, PNA or other nucleic acid mimics, or combinations thereof, under conditions of low ionic strength and high temperature. By way of example, under stringent conditions a probe will hybridize to its target subsequence in a complex mixture of nucleic acid (including but not limited to, total cellular or library DNA or RNA) but does not hybridize to other sequences in the complex mixture. Stringent conditions are sequence-dependent and will be different in different circumstances. By way of example, longer sequences hybridize specifically at higher temperatures. Stringent hybridization conditions include, but are not limited to, (i) about 5-10° C. lower than the thermal melting point (Tm) for the specific sequence at a defined ionic strength and pH; (ii) the salt concentration is about 0.01 M to about 1.0 M at about pH 7.0 to about pH 8.3 and the temperature is at least about 30° C. for short probes (including but not limited to, about 10 to about 50 nucleotides) and at least about 60° C. for long probes (including but not limited to, greater than 50 nucleotides); (iii) the addition of destabilizing agents including, but not limited to, formamide, (iv) 50% formamide, 5×SSC, and 1% SDS, incubating at 42° C., or 5×SSC, about 1% SDS, incubating at 65° C., with wash in 0.2×SSC, and about 0.1% SOS at 65° C. for between about 5 minutes to about 120 minutes. By way of example only, detection of selective or specific hybridization, includes, but is not limited to, a positive signal at least two times background. An extensive guide to the hybridization of nucleic acids is found in Tijssen, Laboratory Techniques in Biochemistry and Molecular Biology—Hybridization with Nucleic Probes, "Overview of principles of hybridization and the strategy of nucleic acid assays" (1993).

The term "subject" as used herein, refers to an animal which is the object of treatment, observation or experiment. By way of example only, a subject may be, but is not limited to, a mammal including, but not limited to, a human.

The term "substantially purified," as used herein, refers to a component of interest that may be substantially or essentially free of other components which normally accompany or interact with the component of interest prior to purification. By way of example only, a component of interest may be "substantially purified" when the preparation of the component of interest contains less than about 30%, less than about 25%, less than about 20%, less than about 15%, less than about 10%, less than about 5%, less than about 4%, less than about 3%, less than about 2%, or less than about 1% (by dry weight) of contaminating components. Thus, a "substantially purified" component of interest may have a purity level of about 70%, about 75%, about 80%, about 85%, about 90%, about 95%, about 96%, about 97%, about 98%, about 99% or greater. By way of example only, a natural amino acid polypeptide or a non-natural amino acid polypeptide may be purified from a native cell, or host cell in the case of recombinantly produced natural amino acid polypeptides or non-natural amino acid polypeptides. By way of example a preparation of a natural amino acid polypeptide or a non-natural amino acid polypeptide may be "substantially purified" when the preparation contains less than about 30%, less than about 25%, less than about 20%, less than about 15%, less than about 10%, less than about 5%, less than about 4%, less than about 3%, less than about 2%, or less than about 1% (by dry weight) of contaminating material. By way of example when a natural amino acid polypeptide or a non-natural amino acid polypeptide is recombinantly produced by host cells, the natural amino acid polypeptide or non-natural amino acid polypeptide may be present at about 30%, about 25%, about 20%, about 15%, about 10%, about 5%, about 4%, about 3%, about 2%, or about 1% or less of the dry weight of the cells. By way of example when a natural amino acid polypeptide or a non-natural amino acid polypeptide is recombinantly produced by host cells, the natural amino acid polypeptide or non-natural amino acid polypeptide may be present in the culture medium at about 5 g/L, about 4 g/L, about 3 g/L, about 2 g/L, about 1 g/L, about 750 mg/L, about 500 mg/L, about 250 mg/L, about 100 mg/L, about 50 mg/L, about 10 mg/L, or about 1 mg/L or less of the dry weight of the cells. By way of example, "substantially purified" natural amino acid polypeptides or non-natural amino acid polypeptides may have a purity level of about 30%, about 35%, about 40%, about 45%, about 50%, about 55%, about 60%, about 65%, about 70%, about 75%, about 80%, about 85%, about 90%, about 95%, about 99% or greater as determined by appropriate methods, including, but not limited to, SDS/PAGE analysis, RP-HPLC, SEC, and capillary electrophoresis.

The term "substituents" also referred to as "non-interfering substituents" "refers to groups which may be used to replace another group on a molecule. Such groups include, but are not limited to, halo, $C_1$-$C_{10}$ alkyl, $C_2$-$C_{10}$ alkenyl, $C_2$-$C_{10}$ alkynyl, $C_1$-$C_{10}$ alkoxy, $C_5$-$C_{12}$ aralkyl, $C_3$-$C_{12}$ cycloalkyl, $C_4$-$C_{12}$ cycloalkenyl, phenyl, substituted phenyl, toluolyl, xylenyl, biphenyl, $C_2$-$C_{12}$ alkoxyalkyl, $C_5$-$C_{12}$ alkoxyaryl, $C_5$-$C_{12}$ aryloxyalkyl, $C_7$-$C_{12}$ oxyaryl, $C_1$-$C_6$ alkylsulfinyl, $C_1$-$C_{10}$ alkylsulfonyl, —$(CH_2)_m$—O—($C_1$-$C_{10}$ alkyl) wherein m is from 1 to 8, aryl, substituted aryl, substituted alkoxy, fluoroalkyl, heterocyclic radical, substituted heterocyclic radical, nitroalkyl, —$NO_2$, —CN, —NRC(O)—($C_1$-$C_{10}$ alkyl), —C(O)—($C_1$-$C_{10}$ alkyl), $C_2$-$C_{10}$ alkthioalkyl, —C(O)O—($C_1$-$C_{10}$ alkyl), —OH, —$SO_2$, =S, —COOH, —$NR_2$, carbonyl, —C(O)—($C_1$-$C_{10}$ alkyl)-$CF_3$, —C(O)—$CF_3$, —C(O)$NR_2$, —($C_1$-$C_{10}$ aryl)-S—($C_6$-$C_{10}$ aryl), —C(O)—($C_6$-$C_{10}$ aryl), —$(CH_2)_m$—O—$(CH_2)_m$—O—($C_1$-$C_{10}$ alkyl) wherein each in is from 1 to 8, —C(O)$NR_2$, —C(S)$NR_2$, —$SO_2NR_2$, —NRC(O)$NR_2$, —NRC(S)$NR_2$, salts thereof, and the like. Each R group in the preceding list includes, but is not limited to, H, alkyl or substituted alkyl, aryl or substituted aryl, or alkaryl. Where substituent groups are specified by their conventional chemical formulas, written from left to right, they equally encompass the chemically identical substituents that would result from writing the structure from right to left; for example, —$CH_2O$— is equivalent to —$OCH_2$—.

By way of example only, substituents for alkyl and heteroalkyl radicals (including those groups referred to as alkylene, alkenyl, heteroalkylene, heteroalkenyl, alkynyl, cycloalkyl, heterocycloalkyl, cycloalkenyl, and heterocycloalkenyl) includes, but is not limited to: —OR, =O, =NR, =N—OR, —$NR_2$, —SR, -halogen, —$SiR_3$, —OC(O)R, —C(O)R, —$CO_2R$, —$CONR_2$, —OC(O)$NR_2$, —NRC(O)R, —NRC(O)$NR_2$, —NR$(O)_2$R, —NR—C($NR_2$)=NR, —S(O)R, —S$(O)_2$R, —S$(O)_2NR_2$, —$NRSO_2R$, —CN and —$NO_2$. Each R group in the preceding list includes, but is not limited to, hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or aralkyl groups. When two R groups are attached to the same nitrogen atom, they can be combined with the nitrogen atom to form a 5-, 6-, or 7-membered ring. For example, —$NR_2$ is meant to include, but not be limited to, 1-pyrrolidinyl and 4-morpholinyl.

By way of example, substituents for aryl and heteroaryl groups include, but are not limited to, —OR, =O, =NR, =N—OR, —$NR_2$, —SR, -halogen, —$SiR_3$, —OC(O)R, —C(O)R, —$CO_2R$, —$CONR_2$, —OC(O)$NR_2$, —NRC(O)R, —NRC(O)$NR_2$, —NR$(O)_2$R, —NR—C($NR_2$)=NR, —S(O)R, —S$(O)_2$R, —S$(O)_2NR_2$, —$NRSO_2R$, —CN, —$NO_2$, —R, —$N_3$, —CH$(Ph)_2$, fluoro($C_1$-$C_4$)alkoxy, and fluoro($C_1$-$C_4$)alkyl, in a number ranging from zero to the total number of open valences on the aromatic ring system; and where each R group in the preceding list includes, but is not limited to, hydrogen, alkyl, heteroalkyl, aryl and heteroaryl.

The term "therapeutically effective amount," as used herein, refers to the amount of a composition containing at least one non-natural amino acid polypeptide and/or at least one modified non-natural amino acid polypeptide administered to a patient already suffering from a disease, condition or disorder, sufficient to cure or at least partially arrest, or relieve to some extent one or more of the symptoms of the disease, disorder or condition being treated. The effectiveness of such compositions depends on conditions including, but not limited to, the severity and course of the disease, disorder or condition, previous therapy, the patient's health status and response to the drugs, and the judgment of the treating physician. By way of example only, therapeutically effective amounts may be determined by routine experimentation, including but not limited to a close escalation, clinical trial.

The term "thioalkoxy," as used herein, refers to sulfur containing alkyl groups linked to molecules via an oxygen atom.

The term "toxic moiety" or "toxic group" as used herein, refers to a compound which can cause harm, disturbances, or death. Toxic moieties include, but are not limited to, auristatin, DNA minor groove binding agent, DNA minor groove alkylating agent, enediyne, lexitropsin, duocarmycin, taxane, puromycin, TLR-agonist, maytansinoid, vinca alkaloid, AFP, MMAF, MMAE, AEB, AEVB, auristatin E, paclitaxel, docetaxel, CC-1065, SN-38, topotecan, morpholino-doxorubicin, rhizoxin, cyanomorpholino-doxorubicin, TLR-agonist-10, echinomycin, combretatstatin, chalicheamicin, maytansine, DM-1, netropsin, podophyllotoxin (e.g. etoposide, teniposide, etc.), baccatin and its derivatives, anti-tubulin agents, cryptophysin, combretastatin, auristatin E, vincristine, vinblastine, vindesine, vinorelbine, VP-16, camptothecin, epothilone A, epothilone B, nocodazole, colchicines, colcimid, estramustine, cemadotin, discodermolide, maytansine, eleutherobin, mechlorethamine, cyclophosphamide, melphalan, carmustine, lomustine, semustine, streptozocin, chlorozotocin, uracil mustard, chlormethine, ifosfamide, chlorambucil, pipobroman, triethylenemelamine, triethylenethiophosphoramine, busulfan, dacarbazine, and temozolomide, ytarabine, cytosine arabinoside, fluorouracil, floxuridine, 6-thioguanine, 6-mercaptopurine, pentostatin, 5-fluorouracil, methotrexate, 10-propargyl-5,8-dideazafolate, 5,8-dideazatetrahydrofolic acid, leucovorin, fludarabine phosphate, pentostatine, gemeitabine, Ara-C, paclitaxel, docetaxel, deoxycoformycin, mitomycin-C, L-asparaginase, azathioprine, brequinar, antibiotics (e.g., anthracycline, gentamicin, cefalotin, vancomycin, telavancin, daptomycin, azithromycin, erythromycin, rocithromycin, furazolidone, amoxicillin, ampicillin, carbenicillin, flucloxacillin, methicillin, penicillin, ciprofloxacin, moxifloxacin, ofloxacin, doxycycline, minocycline, oxytetracycline, tetracycline, streptomycin, rifabutin, ethambutol, rifaximin, etc.), antiviral drugs (e.g., abacavir, acyclovir, ampligen, cidofovir, delavirdine, didanosine, efavirenz, entecavir, fosfonet, ganciclovir, ibacitabine, imunovir, idoxuridine, inosine, lopinavir, methisazone, nexavir, nevirapine, oseltamivir, penciclovir, stavudine, trifluridine, truvada, valaciclovir, zanamivir, etc.), daunorubicin hydrochloride, daunomycin, rubidomycin, cerubidine, idarubicin, doxorubicin, epirubicin and morpholino derivatives, phenoxizone biscyclopeptides (e.g., dactinomycin), basic glycopeptides (e.g., bleomycin), anthraquinone glycosides (e.g., plicamycin, mithramycin), anthracenediones (e.g., mitoxantrone), azirinopyrrolo indolediones (e.g., mitomycin), macrocyclic immunosuppressants (e.g., cyclosporine, FK-506, tacrolimus, prograf, rapamycin etc.), navelbene, CPT-11, anastrazole, letrazole, capecitabine, reloxafine, cyclophosphamide, ifosamide, droloxafine, allocolchicine, Halichondrin B, colchicine, colchicine derivatives, maytansine, rhizoxin, paclitaxel, paclitaxel derivatives, docetaxel, thiocolchicine, trityl cysterin, vinblastine sulfate, vincristine sulfate, cisplatin, carboplatin, hydroxyurea, N-methylhydrazine, epidophyllotoxin, procarbazine, mitoxantrone, leucovorin, and tegafur. "Taxanes" include paclitaxel, as well as any active taxane derivative or pro-drug.

The terms "treat," "treating" or "treatment", as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition. The terms "treat," "treating" or "treatment", include, but are not limited to, prophylactic and/or therapeutic treatments.

As used herein, the term "water soluble polymer" refers to any polymer that is soluble in aqueous solvents. Such water soluble polymers include, but are not limited to, polyethylene glycol, polyethylene glycol propionaldehyde, mono $C_1$-$C_{10}$ alkoxy or aryloxy derivatives thereof (described in U.S. Pat. No. 5,252,714 which is incorporated by reference herein), monomethoxy-polyethylene glycol, polyvinyl pyrrolidone, polyvinyl alcohol, polyamino acids, divinylether maleic anhydride, N-(2-Hydroxypropyl)-methacrylamide, dextran, dextran derivatives including dextran sulfate, polypropylene glycol, polypropylene oxide/ethylene oxide copolymer, polyoxyethylated polyol, heparin, heparin fragments, polysaccharides, oligosaccharides, glycans, cellulose and cellulose derivatives, including but not limited to methylcellulose and carboxymethyl cellulose, serum albumin, starch and starch derivatives, polypeptides, polyalkylene glycol and derivatives thereof, copolymers of polyalkylene glycols and derivatives thereof, polyvinyl ethyl ethers, and alpha-beta-poly[(2-hydroxyethyl)-DL-aspartamide, and the like, or mixtures thereof. By way of example only, coupling of such water soluble polymers to natural amino acid polypeptides or non-natural polypeptides may result in changes including, but not limited to, increased water solubility, increased or modulated serum half-life, increased or modulated therapeutic half-life relative to the unmodified form, increased bioavailability, modulated biological activity, extended circulation time, modulated immunogenicity, modulated physical association characteristics including, but not limited to, aggregation and multimer formation, altered receptor binding, activity modulator, or other targeting polypeptide binding, altered binding to one or more binding partners, and altered targeting polypeptide receptor dimerization or multimerization. In addition, such water soluble polymers may or may not have their own biological activity, and may be utilized as a linker for attaching targeting polypeptide to other substances, including but not limited to one or more targeting polypeptides, or one or more biologically active molecules.

Unless otherwise indicated, conventional methods of mass spectroscopy, NMR, HPLC, protein chemistry, biochemistry, recombinant DNA techniques and pharmacology, within the skill of the art are employed.

Compounds, (including, but not limited to non-natural amino acids, non-natural amino acid polypeptides, modified non-natural amino acid polypeptides, and reagents for producing the aforementioned compounds) presented herein include isotopically-labeled compounds, which are identical to those recited in the various formulas and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as $^{2}H$, $^{3}H$, $^{13}C$, $^{14}C$, $^{15}N$, $^{18}O$, $^{17}O$, $^{35}S$, $^{18}F$, $^{36}Cl$, respectively. Certain isotopically-labeled compounds described herein, for example those into which radioactive isotopes such as $^{3}H$ and $^{14}C$ are incorporated, are useful in drug and/or substrate tissue distribution assays. Further, substitution with isotopes such as deuterium, i.e., $^{2}H$, can afford certain therapeutic advantages resulting from greater metabolic stability, for example increased in vivo half-life or reduced dosage requirements.

Some of the compounds herein (including, but not limited to non-natural amino acids, non-natural amino acid polypeptides and modified non-natural amino acid polypeptides, and reagents for producing the aforementioned compounds) have asymmetric carbon atoms and can therefore exist as enantiomers or diastereomers. Diasteromeric mixtures can be separated into their individual diastereomers on the basis of their physical chemical differences by methods known, for example, by chromatography and/or fractional crystallization. Enantiomers can be separated by converting the enantiomeric mixture into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers, and mixtures thereof are considered as part of the compositions described herein.

In additional or further embodiments, the compounds described herein (including, but not limited to non-natural amino acids, non-natural amino acid polypeptides and modified non-natural amino acid polypeptides, and reagents for producing the aforementioned compounds) are used in the form of pro-drugs. In additional or further embodiments, the compounds described herein (including, but not limited to non-natural amino acids, non-natural amino acid polypeptides and modified non-natural amino acid polypeptides, and reagents for producing the aforementioned compounds) are metabolized upon administration to an organism in need to produce a metabolite that is then used to produce a desired effect, including a desired therapeutic effect. In further or additional embodiments are active metabolites of non-natural amino acids and "modified or unmodified" non-natural amino acid polypeptides.

The methods and formulations described herein include the use of N-oxides, crystalline forms (also known as polymorphs), or pharmaceutically acceptable salts of non-natural amino acids, non-natural amino acid polypeptides and modified non-natural amino acid polypeptides. In certain embodiments, non-natural amino acids, non-natural amino acid polypeptides and modified non-natural amino acid polypeptides may exist as tautomers. All tautomers are included within the scope of the non-natural amino acids, non-natural amino acid polypeptides and modified non-natural amino acid polypeptides presented herein. In addition, the non-natural amino acids, non-natural amino acid polypeptides and modified non-natural amino acid polypeptides described herein can exist in unsolvated as well as solvated forms with pharmaceutically acceptable solvents such as water, ethanol, and the like. The solvated forms of the non-natural amino acids, non-natural amino acid polypeptides and modified non-natural amino acid polypeptides presented herein are also considered to be disclosed herein.

Some of the compounds herein (including, but not limited to non-natural amino acids, non-natural amino acid polypeptides and modified non-natural amino acid polypeptides and reagents for producing the aforementioned compounds) may exist in several tautomeric forms. All such tautomeric forms are considered as part of the compositions described herein. Also, for example all enol-keto forms of any compounds (including, but not limited to non-natural amino acids, non-natural amino acid polypeptides and modified non-natural amino acid polypeptides and reagents for producing the aforementioned compounds) herein are considered as part of the compositions described herein.

Some of the compounds herein (including, but not limited to non-natural amino acids, non-natural amino acid polypeptides and modified non-natural amino acid polypeptides and reagents for producing either of the aforementioned compounds) are acidic and may form a salt with a pharmaceutically acceptable cation. Some of the compounds herein (including, but not limited to non-natural amino acids, non-natural amino acid polypeptides and modified non-natural amino acid polypeptides and reagents for producing the aforementioned compounds) can be basic and accordingly, may form a salt with a pharmaceutically acceptable anion. All such salts, including di-salts are within the scope of the compositions described herein and they can be prepared by conventional methods. For example, salts can be prepared by contacting the acidic and basic entities, in either an aqueous, non-aqueous or partially aqueous medium. The salts are recovered by using at least one of the following techniques: filtration, precipitation with a non-solvent followed by filtration, evaporation of the solvent, or, in the case of aqueous solutions, lyophilization.

Pharmaceutically acceptable salts of the non-natural amino acid polypeptides disclosed herein may be formed when an acidic proton present in the parent non-natural amino acid polypeptides either is replaced by a metal ion, by way of example an alkali metal ion, an alkaline earth ion, or an aluminum ion; or coordinates with an organic base. In addition, the salt forms of the disclosed non-natural amino acid polypeptides can be prepared using salts of the starting materials or intermediates. The non-natural amino acid polypeptides described herein may be prepared as a pharmaceutically acceptable acid addition salt (which is a type of a pharmaceutically acceptable salt) by reacting the free base form of non-natural amino acid polypeptides described herein with a pharmaceutically acceptable inorganic or organic acid. Alternatively, the non-natural amino acid polypeptides described herein may be prepared as pharmaceutically acceptable base addition salts (which are a type of a pharmaceutically acceptable salt) by reacting the free acid form of non-natural amino acid polypeptides described herein with a pharmaceutically acceptable inorganic or organic base.

The type of pharmaceutical acceptable salts, include, but are not limited to: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like.

The corresponding counterions of the non-natural amino acid polypeptide pharmaceutical acceptable salts may be analyzed and identified using various methods including, but not limited to, ion exchange chromatography, ion chromatography, capillary electrophoresis, inductively coupled plasma, atomic absorption spectroscopy, mass spectrometry, or any combination thereof. In addition, the therapeutic activity of such non-natural amino acid polypeptide pharmaceutical acceptable salts may be tested using the techniques and methods described in the examples.

It should be understood that a reference to a salt includes the solvent addition forms or crystal forms thereof, particularly solvates or polymorphs. Solvates contain either stoichiometric or non-stoichiometric amounts of a solvent, and are often formed during the process of crystallization with pharmaceutically acceptable solvents such as water, ethanol, and the like. Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and solubility. Various factors such as the recrystallization solvent, rate of crystallization, and storage temperature may cause a single crystal form to dominate.

The screening and characterization of non-natural amino acid polypeptide pharmaceutical acceptable salts polymorphs and/or solvates may be accomplished using a variety of techniques including, but not limited to, thermal analysis, x-ray diffraction, spectroscopy, vapor sorption, and microscopy. Thermal analysis methods address thermo chemical degradation or thermo physical processes including, but not limited to, polymorphic transitions, and such methods are used to analyze the relationships between polymorphic forms, determine weight loss, to find the glass transition temperature, or for excipient compatibility studies. Such methods include, but are not limited to, Differential scanning calorimetry (DSC), Modulated Differential Scanning calorimetry (MDCS), Thermogravimetric analysis (TGA), and Thermogravi-metric and Infrared analysis (TG/IR). X-ray diffraction methods include, but are not limited to, single crystal and powder diffractometers and synchrotron sources. The various spectroscopic techniques used include, but are not limited to, Raman, FTIR, UVIS, and NMR (liquid and solid state). The various microscopy techniques include, but are not limited to, polarized light microscopy, Scanning Electron Microscopy (SEM) with Energy Dispersive X-Ray Analysis (EDX), Environmental Scanning Electron Microscopy with EDX (in gas or water vapor atmosphere), IR microscopy, and Raman microscopy.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

TLR-Agonist Linker Derivatives

At one level, described herein are the tools (methods, compositions, techniques) for creating and using a targeting polypeptide of the TCs or analogs comprising at least one non-natural amino acid or modified non-natural amino acid with a carbonyl, dicarbonyl, oxime or hydroxylamine group. Such targeting polypeptide of the TCs comprising non-natural amino acids may contain further functionality, including but not limited to, a polymer; a water-soluble polymer; a derivative of polyethylene glycol; a second protein or polypeptide or polypeptide analog; an antibody or antibody fragment; and any combination thereof. Note that the various aforementioned functionalities are not meant to imply that the members of one functionality cannot be classified as members of another functionality. Indeed, there will be overlap depending upon the particular circumstances. By way of example only, a water-soluble polymer overlaps in scope with a derivative of polyethylene glycol, however the overlap is not complete and thus both functionalities are cited above.

In one aspect are methods for selecting and designing a TLR-agonist linker derivative, and the targeting polypeptide, to be modified using the methods, compositions and techniques described herein. The new TLR-agonist linker derivative and the targeting polypeptide may be designed de novo, including by way of example only, as part of high-throughput screening process (in which case numerous polypeptides may be designed, synthesized, characterized and/or tested) or based on the interests of the researcher. The new TLR-agonist linker derivative and the targeting polypeptide may also be designed based on the structure of a known or partially characterized polypeptide. By way of example only, TLR-agonist has been the subject of intense study by the scientific community; a new compound may be designed based on the structure of TLR-agonist. The principles for selecting which amino acid(s) to substitute and/or modify are described separately herein. The choice of which modification to employ is also described herein and can be used to meet the need of the experimenter or end user. Such needs may include, but are not limited to, manipulating the therapeutic effectiveness of the polypeptide, improving the safety profile of the polypeptide, adjusting the pharmacokinetics, pharmacologies and/or pharmacodynamics of the polypeptide, such as, by way of example only, increasing water solubility, bioavailability, increasing serum half-life, increasing therapeutic half-life, modulating immunogenicity, modulating biological activity, or extending the circulation time. In addition, such modifications include, by way of example only, providing additional functionality to the polypeptide, incorporating an antibody, and any combination of the aforementioned modifications.

Also described herein are TLR-agonist linker derivatives and the targeting polypeptide that have or can be modified to contain an oxime, carbonyl, dicarbonyl, or hydroxylamine group. Included with this aspect are methods for producing, purifying, characterizing and using such TLR-agonist linker derivatives and the targeting polypeptides.

The TLR-agonist linker derivative or the targeting polypeptide may contain at least one, at least two, at least three, at least four, at least five, at least six, at least seven, at least eight, at least nine, or ten or more of a carbonyl or dicarbonyl group, oxime group, hydroxylamine group, or protected forms thereof. The TLR-agonist linker derivative or the targeting polypeptide can be the same or different, for example, there can be 1, 2, 3, 4, 5, 6, 7, 8, 9, 10, 11, 12, 13, 14, 15, 16, 17, 18, 19, 20, or more different sites in the derivative that comprise 1, 2, 3, 4, 5, 6, 7, 8, 9, 10, 11, 12, 13, 14, 15, 16, 17, 18, 19, 20, or more different reactive groups.

As described herein, the present disclosures provide targeting polypeptides coupled to another molecule having the formula "targeting polypeptide-L-M", wherein L is a linking group or a chemical bond, and M is any other molecule including but not limited to another targeting polypeptide. In some embodiments, L is stable in vivo. In some embodiments, L is hydrolyzable in vivo. In some embodiments, L is metastable in vivo.

Targeting polypeptide and M can be linked together through L using standard linking agents and procedures known to those skilled in the art. In some aspects, targeting polypeptide and M are fused directly and L is a bond. In other aspects, targeting polypeptide and M are fused through a linking group L. For example, in some embodiments, targeting polypeptide and M are linked together via a peptide bond, optionally through a peptide or amino acid spacer. In some embodiments, targeting polypeptide and M are linked together through chemical conjugation, optionally through a linking group (L). In some embodiments, L is directly conjugated to each of targeting polypeptide and M.

Chemical conjugation can occur by reacting a nucleophilic reactive group of one compound to an electrophilic reactive group of another compound. In some embodiments when L is a bond, targeting polypeptide is conjugated to M either by reacting a nucleophilic reactive moiety on targeting polypeptide with an electrophilic reactive moiety on Y, or by reacting an electrophilic reactive moiety on targeting polypeptide with a nucleophilic reactive moiety on M. In embodiments when L is a group that links targeting polypeptide and M together, targeting polypeptide and/or M can be conjugated to L either by reacting a nucleophilic reactive moiety on targeting polypeptide and/or M with an electrophilic reactive moiety on L, or by reacting an electrophilic reactive moiety on targeting polypeptide and/or M with a nucleophilic reactive moiety on L. Nonlimiting examples of nucleophilic reactive groups include amino, thiol, and hydroxyl. Nonlimiting examples of electrophilic reactive groups include carboxyl, acyl chloride, anhydride, ester, succinimide ester, alkyl halide, sulfonate ester, maleimido, haloacetyl, and isocyanate. In embodiments where targeting polypeptide and M are conjugated together by reacting a carboxylic acid with an amine, an activating agent can be used to form an activated ester of the carboxylic acid.

The activated ester of the carboxylic acid can be, for example, N-hydroxysuccinimide (NHS), tosylate (Tos), mesylate, triflate, a carbodiimide, or a hexafluorophosphate. In some embodiments, the carbodiimide is 1,3-dicyclohexylcarbodiimide (DCC), 1,1'-carbonyldiimidazole (CDI), 1-ethyl-3-(3-dimethylaminopropyl)carbodiimide hydrochloride (EDC), or 1,3-diisopropylcarbodiimide (DICD). In some embodiments, the hexafluorophosphate is selected from a group consisting of hexafluorophosphate benzotriazol-1-yl-oxy-tris(dimethylamino)phosphonium hexafluorophosphate (BOP), benzotriazol-1-yl-oxytripyrrolidinophosphonium hexafluorophosphate (PyBOP), 2-(IH-7-azabenzotriazol-1-yl)-1,1,3,3-tetramethyl uronium hexafluorophosphate (HATU), and o-benzotriazole-N,N,N',N'-tetramethyl-uronium-hexafluoro-phosphate (HBTU).

In some embodiments, targeting polypeptide comprises a nucleophilic reactive group (e.g. the amino group, thiol group, or hydroxyl group of the side chain of lysine, cysteine or serine) that is capable of conjugating to an electrophilic reactive group on M or L. In some embodiments, targeting polypeptide comprises an electrophilic reactive group (e.g. the carboxylate group of the side chain of Asp or Glu) that is capable of conjugating to a nucleophilic reactive group on M or L. In some embodiments, targeting polypeptide is chemically modified to comprise a reactive group that is capable of conjugating directly to M or to L. In some embodiments, targeting polypeptide is modified at the N-terminus or C-terminus to comprise a natural or non-natural amino acid with a nucleophilic side chain. In exemplary embodiments, the N-terminus or C-terminus amino acid of targeting polypeptide is selected from the group consisting of lysine, ornithine, serine, cysteine, and homocysteine. For example, the N-terminus or C-terminus amino acid of targeting polypeptide can be modified to comprise a lysine residue. In some embodiments, targeting polypeptide is modified at the N-terminus or C-terminus amino acid to comprise a natural or non-natural amino acid with an electrophilic side chain such as, for example, Asp and Glu. In some embodiments, an internal amino acid of targeting polypeptide is substituted with a natural or non-natural amino acid having a nucleophilic side chain, as previously described herein. In exemplary embodiments, the internal amino acid of targeting polypeptide that is substituted is selected from the group consisting of lysine, ornithine, serine, cysteine, and homocysteine. For example, an internal amino acid of targeting polypeptide can be substituted with a lysine residue. In some embodiments, an internal amino acid of targeting polypeptide is substituted with a natural or non-natural amino acid with an electrophilic side chain, such as, for example, Asp and Glu.

In some embodiments, M comprises a reactive group that is capable of conjugating directly to targeting polypeptide or to L. In some embodiments, M comprises a nucleophilic reactive group (e.g. amine, thiol, hydroxyl) that is capable of conjugating to an electrophilic reactive group on targeting polypeptide or L. In some embodiments, M comprises electrophilic reactive group (e.g. carboxyl group, activated form of a carboxyl group, compound with a leaving group) that is capable of conjugating to a nucleophilic reactive group on targeting polypeptide or L. In some embodiments, M is chemically modified to comprise either a nucleophilic reactive group that is capable of conjugating to an electrophilic reactive group on targeting polypeptide or L. In some embodiments, M is chemically modified to comprise an electrophilic reactive group that is capable of conjugating to a nucleophilic reactive group on targeting polypeptide or L.

In some embodiments, conjugation can be carried out through organosilanes, for example, aminosilane treated with glutaraldehyde; carbonyldiimidazole (CDI) activation of silanol groups; or utilization of dendrimers. A variety of dendrimers are known in the art and include poly (amidoamine) (PAMAM) dendrimers, which are synthesized by the divergent method starting from ammonia or ethylenediamine initiator core reagents; a sub-class of PAMAM dendrimers based on a tris-aminoethylene-imine core; radially layered poly(amidoamine-organosilicon) dendrimers (PAMAMOS), which are inverted unimolecular micelles that consist of hydrophilic, nucleophilic polyamidoamine (PAMAM) interiors and hydrophobic organosilicon (OS) exteriors; Poly (Propylene Imine) (PPI) dendrimers, which are generally poly-alkyl amines having primary amines as end groups, while the dendrimer interior consists of numerous of tertiary tris-propylene amines; Poly (Propylene Amine) (POPAM) dendrimers; Diaminobutane (DAB) dendrimers; amphiphilic dendrimers; micellar dendrimers which are unimolecular micelles of water soluble hyper branched polyphenylenes; polylysine dendrimers; and dendrimers based on poly-benzyl ether hyper branched skeleton.

In some embodiments, conjugation can be carried out through olefin metathesis. In some embodiments, M and targeting polypeptide, M and L, or targeting polypeptide and L both comprise an alkene or alkyne moiety that is capable of undergoing metathesis. In some embodiments a suitable catalyst (e.g. copper, ruthenium) is used to accelerate the metathesis reaction. Suitable methods of performing olefin metathesis reactions are described in the art. See, for example, Schafmeister et al., *J. Am. Chem. Soc.* 122: 5891-5892 (2000), Walensky et al., *Science* 305: 1466-1470 (2004), and Blackwell et al., *Angew, Chem., Int. Ed.* 37: 3281-3284 (1998).

In some embodiments, conjugation can be carried out using click chemistry. A "click reaction" is wide in scope and easy to perform, uses only readily available reagents, and is insensitive to oxygen and water. In some embodiments, the click reaction is a cycloaddition reaction between an alkynyl group and an azido group to form a triazolyl group. In some embodiments, the click reaction uses a copper or ruthenium catalyst. Suitable methods of performing click reactions are described in the art. See, for example, Kolb et al., *Drug Discovery Today* 8: 1128 (2003); Kolb et al., *Angew. Chem. Int. Ed.* 40:2004 (2001); Rostovtsev et al., *Angew. Chem. Int. Ed.* 41:2596 (2002); Tornoe et al., *J. Org. Chem.* 67:3057 (2002); Manetsch et al., *J. Am. Chem. Soc.* 126: 12809 (2004); Lewis et al., *Angew. Chem. Int. Ed.* 41: 1053 (2002); Speers, *J. Am. Chem. Soc.* 125:4686 (2003); Chan et al. *Org. Lett.* 6:2853 (2004); Zhang et al., *J. Am. Chem. Soc.* 127: 15998 (2005); and Waser et al., *J. Am. Chem. Soc.* 127:8294 (2005).

Indirect conjugation via high affinity specific binding partners, e.g. streptavidin/biotin or avidin/biotin or lectin/carbohydrate is also contemplated.

In some embodiments, targeting polypeptide and/or M are functionalized to comprise a nucleophilic reactive group or an electrophilic reactive group with an organic derivatizing agent. This derivatizing agent is capable of reacting with selected side chains or the N- or C-terminal residues of targeted amino acids on targeting polypeptide and functional groups on M. Reactive groups on targeting polypeptide and/or M include, e.g., aldehyde, amino, ester, thiol, a-haloacetyl, maleimido or hydrazino group. Derivatizing agents include, for example, maleimidobenzoyl sulfosuccinimide ester (conjugation through cysteine residues), N-hydroxysuccinimide (through lysine residues), glutaraldehyde, succinic anhydride or other agents known in the art. Alternatively, targeting polypeptide and/or M can be linked to each other indirectly through intermediate carriers, such as polysaccharide or polypeptide carriers. Examples of polysaccharide carriers include aminodextran. Examples of suitable polypeptide carriers include polylysine, polyglutamic acid, polyaspartic acid, co-polymers thereof, and mixed polymers of these amino acids and others, e.g., serines, to confer desirable solubility properties on the resultant loaded carrier.

Cysteinyl residues most commonly are reacted with a-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, alpha-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0.

Lysinyl and amino-terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate, pyridoxal phosphate, pyridoxal, chloroborohydride, trinitrobenzenesulfonic acid, O-methylisourea, 2,4-pentanedione, and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively.

Carboxyl side groups (aspartyl or glutamyl) are selectively modified by reaction with carbodiimides (R—N═C═N—R'), where R and R' are different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Other modifications include hydroxylation of proline and lysine, phosphorylation of hydroxyl groups of seryl or threonyl residues, methylation of the alpha-amino groups of lysine, arginine, and histidine side chains (T. E. Creighton, Proteins: Structure and Molecular Properties, W.H. Freeman & Co., San Francisco, pp. 79-86 (1983)), deamidation of asparagine or glutamine, acetylation of the N-terminal amine, and/or amidation or esterification of the C-terminal carboxylic acid group.

Another type of covalent modification involves chemically or enzymatically coupling glycosides to the peptide. Sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of tyrosine, or tryptophan, or (f) the amide group of glutamine. These methods are described in WO1987/05330, and in Aplin and Wriston, *CRC Grit. Rev. Biochem., pp.* 259-306 (1981).

In some embodiments, L is a bond. In these embodiments, targeting polypeptide and M are conjugated together by reacting a nucleophilic reactive moiety on targeting polypeptide with and electrophilic reactive moiety on M. In alternative embodiments, targeting polypeptide and M are conjugated together by reacting an electrophilic reactive moiety on targeting polypeptide with a nucleophilic moiety on M. In exemplary embodiments, L is an amide bond that forms upon reaction of an amine on targeting polypeptide (e.g. an ε-amine of a lysine residue) with a carboxyl group on M. In alternative embodiments, targeting polypeptide and or M is derivatized with a derivatizing agent before conjugation.

In some embodiments, L is a linking group. In some embodiments, L is a bifunctional linker and comprises only two reactive groups before conjugation to targeting polypeptide and M. In embodiments where both targeting polypeptide and M have electrophilic reactive groups, L comprises two of the same or two different nucleophilic groups (e.g. amine, hydroxyl, thiol) before conjugation to targeting polypeptide and M. In embodiments where both targeting polypeptide and M have nucleophilic reactive groups, L comprises two of the same or two different electrophilic groups (e.g. carboxyl group, activated form of a carboxyl group, compound with a leaving group) before conjugation to targeting polypeptide and M. In embodiments where one of targeting polypeptide or M has a nucleophilic reactive group and the other of targeting polypeptide or M has an electrophilic reactive group, L comprises one nucleophilic reactive group and one electrophilic group before conjugation to targeting polypeptide and M.

L can be any molecule with at least two reactive groups (before conjugation to targeting polypeptide and M) capable of reacting with each of targeting polypeptide and M. In some embodiments L has only two reactive groups and is bifunctional. L (before conjugation to the peptides) can be represented by Formula VI:

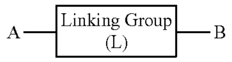

wherein A and B are independently nucleophilic or electrophihc reactive groups. In some embodiments A and B are either both nucleophilic groups or both electrophihc groups. In some embodiments one of A or B is a nucleophilic group and the other of A or B is an electrophihe group. Nonlimiting combinations of A and B are shown below in Table 1.

TABLE 1

Nonlimiting combinations of Nucleophilic and Electrophilic Groups

| Both Nucleophilic | | Both Electrophilic | | Nucleophilic/ Electrophilic | |
|---|---|---|---|---|---|
| A | B | A | B | A | B |
| Amino | Amino | Carboxyl | Carboxyl | Amino | Carboxyl |
| Amino | Thiol | Carboxyl | Acyl chloride | Amino | Acyl chloride |
| Amino | Hydroxyl | Carboxyl | Anhydride | Amino | Anhydride |
| Thiol | Amino | Carboxyl | Ester | Amino | Ester |
| Thiol | Thiol | Carboxyl | NHS | Amino | NHS |
| Thiol | Hydroxyl | Carboxyl | Halogen | Amino | Halogen |
| Hydroxyl | Amino | Carboxyl | Sulfonate ester | Amino | Sulfonate ester |
| Hydroxyl | Thiol | Carboxyl | Maleimido | Amino | Maleimido |
| Hydroxyl | Hydroxyl | Carboxyl | Haloacetyl | Amino | Haloacetyl |
| | | Carboxyl | Isocyanate | Amino | Isocyanate |
| | | Acyl chloride | Carboxyl | Thiol | Carboxyl |
| | | Acyl chloride | Acyl chloride | Thiol | Acyl chloride |
| | | Acyl chloride | Anhydride | Thiol | Anhydride |
| | | Acyl chloride | Ester | Thiol | Ester |
| | | Acyl chloride | NHS | Thiol | NHS |

TABLE 1-continued

| Nonlimiting combinations of Nucleophilic and Electrophilic Groups | | | | | |
|---|---|---|---|---|---|
| Both Nucleophilic | | Both Electrophilic | | Nucleophilic/ Electrophilic | |
| A | B | A | B | A | B |
| | | Acyl chloride | Halogen | Thiol | Halogen |
| | | Acyl chloride | Sulfonate ester | Thiol | Sulfonate ester |
| | | Acyl chloride | Maleimido | Thiol | Maleimido |
| | | Acyl chloride | Haloacetyl | Thiol | Haloacetyl |
| | | Acyl chloride | Isocyanate | Thiol | Isocyanate |
| | | Anhydride | Carboxyl | Hydroxyl | Carboxyl |
| | | Anhydride | Acyl chloride | Hydroxyl | Acyl chloride |
| | | Anhydride | Anhydride | Hydroxyl | Anhydride |
| | | Anhydride | Ester | Hydroxyl | Ester |
| | | Anhydride | NHS | Hydroxyl | NHS |
| | | Anhydride | Halogen | Hydroxyl | Halogen |
| | | Anhydride | Sulfonate | Hydroxyl ester | Sulfonate ester |
| | | Anhydride | Maleimido | Hydroxyl | Maleimido |
| | | Anhydride | Haloacetyl | Hydroxyl | Haloacetyl |
| | | Anhydride | Isocyanate | Hydroxyl | Isocyanate |
| | | Ester | Carboxyl | | |
| | | Ester | Acyl chloride | | |
| | | Ester | Anhydride | | |
| | | Ester | Ester | | |
| | | Ester | NHS | | |
| | | Ester | Halogen | | |
| | | Ester | Sulfonate ester | | |
| | | Ester | Maleimido | | |
| | | Ester | Haloacetyl | | |
| | | Ester | Isocyanate | | |
| | | NHS | Carboxyl | | |
| | | NHS | Acyl chloride | | |
| | | NHS | Anhydride | | |
| | | NHS | Ester | | |
| | | NHS | NHS | | |
| | | NHS | Halogen | | |
| | | NHS | Sulfonate ester | | |
| | | NHS | Maleimido | | |
| | | NHS | Haloacetyl | | |
| | | NHS | Isocyanate | | |
| | | Halogen | Carboxyl | | |
| | | NHS | Haloacetyl | | |
| | | NHS | Isocyanate | | |
| | | Halogen | Carboxyl | | |
| | | Halogen | Acyl chloride | | |
| | | Halogen | Anhydride | | |
| | | Halogen | Ester | | |
| | | Halogen | NHS | | |
| | | Halogen | Halogen | | |
| | | Halogen | Sulfonate ester | | |
| | | Halogen | Maleimido | | |
| | | Halogen | Haloacetyl | | |
| | | Halogen | Isocyanate | | |
| | | Sulfonate ester | Carboxyl | | |
| | | Sulfonate ester | Acyl chloride | | |
| | | Sulfonate ester | Anhydride | | |
| | | Sulfonate ester | Ester | | |
| | | Sulfonate ester | NHS | | |
| | | Sulfonate ester | Halogen | | |
| | | Sulfonate ester | Sulfonate ester | | |
| | | Sulfonate ester | Maleimido | | |
| | | Sulfonate ester | Haloacetyl | | |
| | | Sulfonate ester | Isocyanate | | |
| | | Maleimido | Carboxyl | | |
| | | Maleimido | Acyl chloride | | |
| | | Maleimido | Anhydride | | |
| | | Maleimido | Ester | | |
| | | Maleimido | NHS | | |
| | | Maleimido | Halogen | | |
| | | Maleimido | Sulfonate ester | | |
| | | Maleimido | Maleimido | | |
| | | Maleimido | Haloacetyl | | |
| | | Maleimido | Isocyanate | | |
| | | Haloacetyl | Carboxyl | | |
| | | Haloacetyl | Acyl chloride | | |
| | | Haloacetyl | Anhydride | | |
| | | Haloacetyl | Ester | | |
| | | Haloacetyl | NHS | | |
| | | Haloacetyl | Halogen | | |
| | | Haloacetyl | Sulfonate ester | | |
| | | Haloacetyl | Maleimido | | |
| | | Haloacetyl | Haloacetyl | | |
| | | Haloacetyl | Isocyanate | | |
| | | Isocyanate | Carboxyl | | |
| | | Isocyanate | Acyl chloride | | |
| | | Isocyanate | Anhydride | | |
| | | Isocyanate | Ester | | |
| | | Isocyanate | NHS | | |
| | | Isocyanate | Halogen | | |
| | | Isocyanate | Sulfonate ester | | |
| | | Isocyanate | Maleimido | | |
| | | Isocyanate | Haloacetyl | | |
| | | Isocyanate | Isocyanate | | |

In some embodiments, A and 13 may include alkene and/or alkyne functional groups that are suitable for olefin metathesis reactions. In some embodiments, A and B include moieties that are suitable for click chemistry (e.g. alkene, alkynes, nitriles, azides). Other nonlimiting examples of reactive groups (A and B) include pyridyldithiol, aryl azide, diazirine, carbodiimide, and hydrazide.

In some embodiments, L is hydrophobic. Hydrophobic linkers are known in the art. See, e.g., *Bioconjugate Techniques*, G. T. Hermanson (Academic Press, San Diego, Calif., 1996), which is incorporated by reference in its entirety. Suitable hydrophobic linking groups known in the art include, for example, 8-hydroxy octanoic acid and 8-mercaptooctanoic acid. Before conjugation to the peptides of the composition, the hydrophobic linking group comprises at least two reactive groups (A and B), as described herein and as shown below:

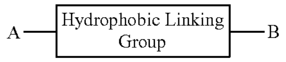

In some embodiments, the hydrophobic linking group comprises either a maleimido or an iodoacetyl group and either a carboxylic acid or an activated carboxylic acid (e.g. NHS ester) as the reactive groups. In these embodiments, the maleimido or iodoacetyl group can be coupled to a thiol moiety on targeting polypeptide or M and the carboxylic acid or activated carboxylic acid can be coupled to an amine on targeting polypeptide or M with or without the use of a coupling reagent. Any coupling agent known to one skilled in the art can be used to couple the carboxylic acid with the free amine such as, for example, DCC, DIC, HATU, HBTU, TBTU, and other activating agents described herein. In specific embodiments, the hydrophilic linking group comprises an aliphatic chain of 2 to 100 methylene groups wherein A and B are carboxyl groups or derivatives thereof (e.g. succinic acid). In other specific embodiments the L is iodoacetic acid.

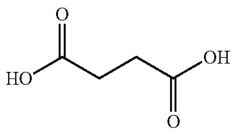

succinic acid

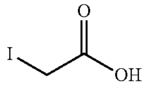

iodoacetic acid

In some embodiments, the linking group is hydrophilic such as, for example, polyalkylene glycol. Before conjugation to the peptides of the composition, the hydrophilic linking group comprises at least two reactive groups (A and 13), as described herein and as shown below:

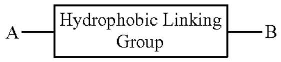

In specific embodiments, the linking group is polyethylene glycol (PEG). The PEG in certain embodiments has a molecular weight of about 100 Daltons to about 10,000 Daltons, e.g. about 500 Daltons to about 5000 Daltons. The PEG in some embodiments has a molecular weight of about 10,000 Daltons to about 40,000 Daltons.

In some embodiments, the hydrophilic linking group comprises either a maleimido or an iodoacetyl group and either a carboxylic acid or an activated carboxylic acid (e.g. NHS ester) as the reactive groups. In these embodiments, the maleimido or iodoacetyl group can be coupled to a thiol moiety on targeting polypeptide or M and the carboxylic acid or activated carboxylic acid can be coupled to an amine on targeting polypeptide or M with or without the use of a coupling reagent. Any appropriate coupling agent known to one skilled in the art can be used to couple the carboxylic acid with the amine such as, for example, DCC, DIC, HATU, HBTU, TBTU, and other activating agents described herein. In some embodiments, the linking group is maleimido-polymer (20-40 kDa)-COOH, iodoacetyl-polymer (20-40 kDa)-COOH, maleimido-polymer (20-40 kDa)-NHS, or iodoacetyl-polymer (20-40 kDa)-NHS.

In some embodiments, the linking group is comprised of an amino acid, a dipeptide, a tripeptide, or a polypeptide, wherein the amino acid, dipeptide, tripeptide, or polypeptide comprises at least two activating groups, as described herein. In some embodiments, the linking group (L) comprises a moiety selected from the group consisting of amino, ether, thioether, maleimido, disulfide, amide, ester, thioester, alkene, cycloalkene, alkyne, trizoyl, carbamate, carbonate, cathepsin B-cleavable, and hydrazone.

In some embodiments, L comprises a chain of atoms from 1 to about 60, or 1 to 30 atoms or longer, 2 to 5 atoms, 2 to 10 atoms, 5 to 10 atoms, or 10 to 20 atoms long. In some embodiments, the chain atoms are all carbon atoms. In some embodiments, the chain atoms in the backbone of the linker are selected from the group consisting of C, O, N, and S. Chain atoms and linkers may be selected according to their expected solubility (hydrophilicity) so as to provide a more soluble conjugate. In some embodiments, L provides a functional group that is subject to cleavage by an enzyme or other catalyst or hydrolytic conditions found in the target tissue or organ or cell. In some embodiments, the length of L is long enough to reduce the potential for steric hindrance.

In some embodiments, L is stable in biological fluids such as blood or blood fractions. In some embodiments, L is stable in blood serum for at least 5 minutes, e.g. less than 25%, 20%, 15%, 10% or 5% of the conjugate is cleaved when incubated in serum for a period of 5 minutes. In other embodiments, L is stable in blood serum for at least 10, or 20, or 25, or 30, or 60, or 90, or 120 minutes, or 3, 4, 5, 6, 7, 8, 9, 10, 12, 15, 18 or 24 hours. In these embodiments, L does not comprise a functional group that is capable of undergoing hydrolysis in vivo. In some exemplary embodiments, L is stable in blood serum for at least about 72 hours. Nonlimiting examples of functional groups that are not capable of undergoing significant hydrolysis in vivo include amides, ethers, and thioethers. For example, the following compound does not undergoing significant hydrolysis in vivo:

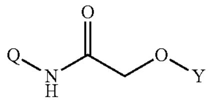

In some embodiments, L is hydrolyzable in vivo. In these embodiments, L comprises a functional group that is capable of undergoing hydrolysis in vivo. Nonlimiting examples of functional groups that are capable of undergoing hydrolysis in vivo include esters, anhydrides, and thioesters. For example the following compound is capable of undergoing hydrolysis in vivo because it comprises an ester group:

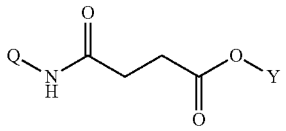

In some exemplary embodiments L is labile and undergoes substantial hydrolysis within 3 hours in blood plasma at 37° C., with complete hydrolysis within 6 hours. In some exemplary embodiments, L is not labile.

In some embodiments, L is metastable in vivo. In these embodiments, L comprises a functional group that is capable of being chemically or enzymatically cleaved in vivo (e.g., an acid-labile, reduction-labile, or enzyme-labile functional group), optionally over a period of time. In these embodiments, L can comprise, for example, a hydrazone moiety, a disulfide moiety, or a cathepsin-cleavable moiety. When L is metastable, and without intending to be bound by any particular theory, the targeting polypeptide-L-M conjugate is stable in an extracellular environment, e.g., stable in blood serum for the time periods described above, but labile in the intracellular environment or conditions that mimic the intracellular environment, so that it cleaves upon entry into a cell. In some embodiments when L is metastable, L is stable in blood serum for at least about 24, 25, 26, 27, 28, 29, 30, 31, 32, 33, 34, 35, 36, 42, or 48 hours, for example, at least about 48, 54, 60, 66, or 72 hours, or about 24-48, 48-72, 24-60, 36-48, 36-72, or 48-72 hours.

In another embodiment, the polymer derivatives of the invention comprise a polymer backbone having the structure:

$$X—CH_2CH_2O—(CH_2CH_2O)_n—CH_2CH_2—O—(CH_2)_m—W—N{=}N{=}N$$ wherein:

W is an aliphatic or aromatic linker moiety comprising between 1-10 carbon atoms;

n is 1 to about 4000; and X is a functional group as described above; m is between 1 and 10.

The azide-containing polymer derivatives of the invention can be prepared by a variety of methods known in the art and/or disclosed herein. In one method, shown below, a water soluble polymer backbone having an average molecular weight from about 800 Da to about 100,000 Da, the polymer backbone having a first terminus bonded to a first functional group and a second terminus bonded to a suitable leaving group, is reacted with an azide anion (which may be paired with any of a number of suitable counter-ions, including sodium, potassium, tert-butylammonium and so forth). The leaving group undergoes a nucleophilic displacement and is replaced by the azide moiety, affording the desired azide-containing polymer polymer;

$$X\text{-polymer-LY}+N_3^- \rightarrow X\text{-polymer-L } N_3$$

As illustrated, a suitable polymer backbone for use in the present invention has the formula X-polymer-LY, wherein polymer is polyethylene glycol) and X is a functional group which does not react with azide groups and Y is a suitable leaving group. Examples of suitable functional groups include, but are not limited to, hydroxyl, protected hydroxyl, acetal, alkenyl, amine, aminooxy, protected amine, protected hydrazide, protected thiol, carboxylic acid, protected carboxylic acid, maleimide, dithiopyridine, and vinylpyridine, and ketone. Examples of suitable leaving groups include, but are not limited to, chloride, bromide, iodide, mesylate, tresylate, and tosylate.

In another method for preparation of the azide-containing polymer derivatives of the present invention, a linking agent bearing an azide functionality is contacted with a water soluble polymer backbone having an average molecular weight from about 800 Da to about 100,000 Da, wherein the linking agent bears a chemical functionality that will react selectively with a chemical functionality on the polymer to form an azide-containing polymer derivative product wherein the azide is separated from the polymer backbone by a linking group.

An exemplary reaction scheme is shown below:

$$X\text{-polymer-Y}+N\text{-linker-}N{=}N{=}N \rightarrow PG\text{-}X\text{-polymer-linker-}N{=}N{=}N$$ wherein:

polymer is poly(ethylene glycol) and X is a capping group such as alkoxy or a functional group as described above; and Y is a functional group that is not reactive with the azide functionality but that will react efficiently and selectively with the N functional group.

Examples of suitable functional groups include, but are not limited to, Y being a carboxylic acid, carbonate or active ester if N is an amine; Y being a ketone if N is a hydrazide or aminooxy moiety; Y being a leaving group if N is a nucleophile. Purification of the crude product may be accomplished by known methods including, but are not limited to, precipitation of the product followed by chromatography, if necessary.

A more specific example is shown below in the case of polymer diamine, in which one of the amines is protected by a protecting group moiety such as tert-butyl-Boc and the resulting mono-protected polymer diamine is reacted with a linking moiety that bears the azide functionality: BocHN-polymer-$NH_2$+$HO_2C—(CH_2)_3—N{=}N{=}N$ In this instance, the amine group can be coupled to the carboxylic acid group using a variety of activating agents such as thionyl chloride or carbodiimide reagents and N-hydroxysuccinimide or N-hydroxybenzotriazole to create an amide bond between the monoamine polymer derivative and the azide-bearing linker moiety. After successful formation of the amide bond, the resulting N-tert-butyl-Boc-protected azide-containing derivative can be used directly to modify bioactive molecules or it can be further elaborated to install other useful functional groups. For instance, the N-t-Boc group can be hydrolyzed by treatment with strong acid to generate an omega-amino-polymer-azide. The resulting amine can be used as a synthetic handle to install other useful functionality such as maleimide groups, activated disulfides, activated esters and so forth for the creation of valuable heterobifunctional reagents.

Heterobifunctional derivatives are particularly useful when it is desired to attach different molecules to each terminus of the polymer. For example, the omega-N-amino-N-azido polymer would allow the attachment of a molecule having an activated electrophilic group, such as an aldehyde, ketone, activated ester, activated carbonate and so forth, to one terminus of the polymer and a molecule having an acetylene group to the other terminus of the polymer.

In another embodiment of the present invention, A is an aliphatic linker of between 1-10 carbon atoms or a substituted aryl ring of between 6-14 carbon atoms. X is a functional group which does not react with azide groups and Y is a suitable leaving group.

Multiple targeting polypeptides may be joined by a linker polypeptide, wherein the linker polypeptide optionally is 6-14, 7-13, 8-12, 7-11, 9-11, or 9 amino acids in length. Other linkers include but are not limited to small polymers such as PEG, which may be multi-armed allowing for multiple targeting polypeptide molecules to be linked together. Multiple targeting polypeptides and modified targeting polypeptides may be linked to each other via their N-termini in a head-to-head configuration through the use of such a linker or by direct chemical bonding between the respective N-terminus of each polypeptide. For example, two targeting polypeptides may be linked to form a dimer by chemical bonding between their N-terminal amino groups or modified N-terminal amino groups, Also, a linking molecule that is designed to comprise multiple chemical functional groups for bonding with the N-terminus of each targeting polypeptide may be used to join multiple targeting polypeptides each at their respective N-terminus. In addition, multiple targeting polypeptides may be linked through bonding between amino acids other than the N-terminal amino acid or C-terminal amino acid. An example of covalent bonds that may be utilized to form the dimmers and multimers of targeting polypeptide that are described herein include, but are not limited to disulphide or sulfhydral or thiol bonds. In addition, certain enzymes, such as sortase, may be used to form covalent bonds between the targeting polypeptides and the linker, including at the N-termini of the targeting polypeptides.

The linker may have a wide range of molecular weight or molecular length. Larger or smaller molecular weight linkers may be used to provide a desired spatial relationship or conformation between targeting polypeptide and the linked entity or between the linked entity and its binding partner, if any. Linkers having longer or shorter molecular length may also be used to provide a desired space or flexibility between targeting polypeptide and the linked entity, or between the linked entity and its binding partner.

In some embodiments, the invention provides water-soluble bifunctional linkers that have a dumbbell structure that includes: a) an azide, an alkyne, a hydrazine, a hydrazide, a hydroxylamine, or a carbonyl-containing moiety on at least a first end of a polymer backbone; and b) at least a second functional group on a second end of the polymer backbone. The second functional group can be the same or different as the first functional group. The second functional group, in some embodiments, is not reactive with the first functional group. The invention provides, in some embodiments, water-soluble compounds that comprise at least one arm of a branched molecular structure. For example, the branched molecular structure can be dendritic.

In exemplary embodiments, the polymer is linked to the targeting polypeptide or modified targeting polypeptide through a linker. For example, the linker can comprise one or two amino acids which at one end bind to the polymer—such as an albumin binding moiety—and at the other end bind to any available position on the polypeptide backbone. Additional exemplary linkers include a hydrophilic linker such as a chemical moiety which comprises at least 5 non-hydrogen atoms where 30-50% of these are either N or O. Additional exemplary linkers which may link a polymer to a targeting polypeptide or modified targeting polypeptide are disclosed in U.S. 2012/0295847 and WO/2012/168430, each of which is hereby incorporated by reference in its entirety.

Optionally, multiple targeting polypeptide or modified targeting polypeptide molecules may be joined by a linker polypeptide, wherein said linker polypeptide optionally is 1, 1-2, 1-3, 1-4, 1-5, 1-6, 1-7, 1-8, 1-9, 1-10, 1-11, 1-12 amino acids in length, and longer in length, wherein optionally the N-terminus of one targeting polypeptide is fused to the C-terminus of the linker polypeptide and the N-terminus of the linker polypeptide is fused to the N-terminus of another targeting polypeptide. Further exemplary linker polypeptides which may be utilized are disclosed in WO/2013/004607, which is hereby incorporated by reference in its entirety.

The terms "electrophilic group", "electrophile" and the like as used herein refers to an atom or group of atoms that can accept an electron pair to form a covalent bond. The "electrophilic group" used herein includes but is not limited to halide, carbonyl and epoxide containing compounds. Common electrophiles may be halides such as thiophosgene, glycerin dichlorohydrin, phthaloyl chloride, succinyl chloride, chloroacetyl chloride, chlorosucciriyl chloride, etc.; ketones such as chloroacetone, bromoacetone, etc.; aldehydes such as glyoxal, etc.; isocyanates such as hexamethylene diisocyanate, tolylene diisocyanate, meta-xylylene diisocyanate, cyclohexylmethane-4,4-diisocyanate, etc and derivatives of these compounds.

The terms "nucleophilic group", "nucleophile" and the like as used herein refers to an atom or group of atoms that have an electron pair capable of forming a covalent bond. Groups of this type may be iohizable groups that react as anionic groups. The "nucleophilic group" used herein includes but is not limited to hydroxyl, primary amines, secondary amines, tertiary amines and thiols.

Table 2 provides various starting electrophiles and nucleophiles which may be combined to create a desired functional group. The information provided is meant to be illustrative and not limiting to the synthetic techniques described herein.

TABLE 2

Examples of Covalent Linkages and Precursors Thereof

| Covalent Linkage Product | Electrophile | Nucleophile |
|---|---|---|
| Carboxamides | Activated esters | amines/anilines |
| Carboxamides | acyl azides | amines/anilines |
| Carboxamides | acyl halides | amines/anilines |
| Esters | acyl halides | alcohols/phenols |
| Esters | acyl nitriles | alcohols/phenols |
| Carboxamides | acyl nitriles | amines/anilines |
| Imines | Aldehydes | amines/anilines |
| Hydrazones | aldehydes or ketones | Hydrazines |
| Oximes | aldehydes or ketones | Hydroxylamines |
| Alkyl amines | alkyl halides | amines/anilines |
| Esters | alkyl halides | carboxylic acids |
| Thioethers | alkyl halides | Thiols |
| Ethers | alkyl halides | alcohols/phenols |
| Thioethers | alkyl sulfonates | Thiols |
| Esters | alkyl sulfonates | carboxylic acids |
| Ethers | alkyl sulfonates | alcohols/phenols |
| Esters | Anhydrides | alcohols/phenols |
| Carboxamides | Anhydrides | amines/anilines |
| Thiophenols | aryl halides | Thiols |
| Aryl amines | aryl halides | Amines |
| Thioethers | Azindines | Thiols |
| Boronate esters | Boronates | Glycols |
| Carboxamides | carboxylic acids | amines/anilines |
| Esters | carboxylic acids | Alcohols |
| hydrazines | Hydrazides | carboxylic acids |
| N-acylureas or Anhydrides | Carbodiimides | carboxylic acids |
| Esters | Diazoalkanes | carboxylic acids |
| Thioethers | Epoxides | Thiols |
| Thioethers | Haloacetanaides | Thiols |
| Ammotriazines | Halotriazines | amines/anilines |
| Triazinyl ethers | Halotriazines | alcohols/phenols |
| Amidines | imido esters | amines/anilines |
| Ureas | Isocyanates | amines/anilines |
| Urethanes | Isocyanates | alcohols/phenols |
| Thioureas | Isothiocyanates | amines/anilines |
| Thioethers | Maleimides | Thiols |
| Phosphite esters | Phosphoramidites | Alcohols |
| Silyl ethers | silyl halides | Alcohols |
| Alkyl amines | sulfonate esters | amines/anilines |
| Thioethers | sulfonate esters | Thiols |
| Esters | sulfonate esters | carboxylic acids |
| Ethers | sulfonate esters | Alcohols |
| Sulfonamides | sulfonyl halides | amines/anilines |
| Sulfonate esters | sulfonyl halides | phenols/alcohols |

In general, carbon electrophiles are susceptible to attack by complementary nucleophiles, including carbon nucleophiles, wherein an attacking nucleophile brings an electron pair to the carbon electrophile in order to form a new bond between the nucleophile and the carbon electrophile.

Non-limiting examples of carbon nucleophiles include, but are not limited to alkyl, alkenyl, aryl and alkynyl Grignard, organolithium, organozinc, alkyl-, alkenyl, aryl- and alkynyl-tin reagents (organostannanes), alkyl-, alkenyl-, aryl- and alkynyl-borane reagents (organoboranes and organoboronates); these carbon nucleophiles have the advantage of being kinetically stable in water or polar organic solvents. Other non-limiting examples of carbon nucleophiles include phosphorus ylids, enol and enolate reagents; these carbon nucleophiles have the advantage of being relatively easy to generate from precursors well known to those skilled in the art of synthetic organic chemistry. Carbon nucleophiles, when used in conjunction with carbon electrophiles, engender new carbon carbon bonds between the carbon nucleophile and carbon electrophile.

Non-limiting examples of non-carbon nucleophiles suitable for coupling to carbon electrophiles include but are not limited to primary and secondary amines, thiols, thiolates, and thioethers, alcohols, alkoxides, azides, semicarbazides, and the like. These non-carbon nucleophiles, when used in conjunction with carbon electrophiles, typically generate heteroatom linkages (C—X—C), wherein X is a hetereoatom, including, but not limited to, oxygen, sulfur, or nitrogen.

In some cases, a polymer used in the invention terminates on one end with hydroxy or methoxy, i.e., X is H or $CH_3$ ("methoxy PEG"). Alternatively, the polymer can terminate with a reactive group, thereby forming a bifunctional polymer. Typical reactive groups can include those reactive groups that are commonly used to react with the functional groups found in the 20 common amino acids (including but not limited to, maleimide groups, activated carbonates (including but not limited to, p-nitrophenyl ester), activated esters (including but not limited to, N-hydroxysuccinimide, p-nitrophenyl ester) and aldehydes) as well as functional groups that are inert to the 20 common amino acids but that react specifically with complementary functional groups (including but not limited to, azide groups, alkyne groups). It is noted that the other end of the polymer, which is shown in the above formula by Y, will attach either directly or indirectly to a targeting polypeptide via a naturally-occurring or non-naturally encoded amino acid. For instance, Y may be an amide, carbamate or urea linkage to an amine group (including but not limited to, the epsilon amine of lysine or the N-terminus) of the polypeptide. Alternatively, Y may be a maleimide linkage to a thiol group (including but not limited to, the thiol group of cysteine). Alternatively, Y may be a linkage to a residue not commonly accessible via the 20 common amino acids. For example, an azide group on the polymer can be reacted with an alkyne group on the targeting polypeptide to form a Huisgen [3+2] cycloaddition product. Alternatively, an alkyne group on the polymer can be reacted with an azide group present in a targeting polypeptide to form a similar product. In some embodiments, a strong nucleophile (including but not limited to, hydrazine, hydrazide, hydroxylamine, semicarbazide) can be reacted with an aldehyde or ketone group present in a targeting polypeptide to form a hydrazone, oxime or semicarbazone, as applicable, which in some cases can be further reduced by treatment with an appropriate reducing agent. Alternatively, the strong nucleophile can be incorporated into the targeting polypeptide via a non-naturally encoded amino acid and used to react preferentially with a ketone or aldehyde group present in the water soluble polymer.

Any molecular mass for a polymer can be used as practically desired, including but not limited to, from about 100 Daltons (Da) to 100,000 Da or more as desired (including but not limited to, sometimes 0.1-50 kDa or 10-40 kDa). The molecular weight of polymer may be of a wide range, including but not limited to, between about 100 Da and about 100,000 Da or more, polymer may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, polymer is between about 100 Da and about 50,000 Da. Branched chain polymers, including but not limited to, polymer molecules with each chain having a molecular weight ranging from 1-100 kDa (including but not limited to, 1-50 kDa or 5-20 kDa) can also be used. The molecular weight of each chain of the branched chain polymer may be, including but not limited to, between about 1,000 Da and about 100,000 Da or more. The molecular weight of each chain of the branched chain polymer may be between about 1,000 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of each chain of the branched chain polymer is between about 1,000 Da and about 50,000 Da. In some embodiments, the molecular weight of each chain of the branched chain polymer is between about 1,000 Da and about 40,000 Da. In some embodiments, the molecular weight of each chain of the branched chain polymer is between about 5,000 Da and about 40,000 Da. In some embodiments, the molecular weight of each chain of the branched chain polymer is between about 5,000 Da and about 20,000 Da. A wide range of polymer molecules are described in, including but not limited to, the Shearwater Polymers, Inc. catalog, Nektar Therapeutics catalog, incorporated herein by reference.

The invention provides in some embodiments azide- and acetylene-containing polymer derivatives comprising a water soluble polymer backbone having an average molecular weight from about 800 Da to about 100,000 Da. The polymer backbone of the water-soluble polymer can be poly(ethylene glycol). However, it should be understood that a wide variety of water soluble polymers including but not limited to poly(ethylene)glycol and other related polymers, including poly(dextran) and poly(propylene glycol), are also suitable for use in the practice of this invention and that the use of the term PEG or poly(ethylene glycol) is intended to encompass and include all such molecules. The term PEG includes, but is not limited to, poly(ethylene glycol) in any of its forms, including bifunctional PEG, multiarmed PEG, derivatized PEG, forked PEG, branched PEG, pendent PEG (i.e. PEG or related polymers having one or more functional groups pendent to the polymer backbone), or PEG with degradable linkages therein.

In addition to these forms of polymer, the polymer can also be prepared with weak or degradable linkages in the backbone. For example, polymer can be prepared with ester linkages in the polymer backbone that are subject to hydrolysis. As shown below, this hydrolysis results in cleavage of the polymer into fragments of lower molecular weight: -polymer-$CO_2$-polymer-+$H_2O$→polymer-$CO_2H$+HO-polymer- Many polymers are also suitable for use in the present invention. In some embodiments, polymer backbones that are water-soluble, with from 2 to about 300 termini, are particularly useful in the invention. Examples of suitable polymers include, but are not limited to, other poly(alkylene glycols), such as poly(propylene glycol) ("PPG"), copolymers thereof (including but not limited to copolymers of ethylene glycol and propylene glycol), terpolymers thereof, mixtures thereof, and the like. Although the molecular weight of each chain of the polymer backbone can vary, it is typically in the range of from about 800 Da to about 100,000 Da, often from about 6,000 Da to about 80,000 Da. The molecular weight of each chain of the polymer backbone may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of each chain of the polymer backbone is between about 100 Da and about 50,000 Da. In some embodiments, the molecular weight of each chain of the polymer backbone is between about 100 Da and about 40,000 Da. In some embodiments, the molecular weight of each chain of the polymer backbone is between about 1,000 Da and about 40,000 Da. In some embodiments, the molecular weight of each chain of the polymer backbone is between about 5,000 Da and about 40,000 Da. In some embodiments, the molecular weight of each chain of the polymer backbone is between about 10,000 Da and about 40,000 Da.

In one feature of this embodiment of the invention, the intact polymer-conjugate, prior to hydrolysis, is minimally degraded upon administration, such that hydrolysis of the cleavable bond is effective to govern the slow rate of release of active targeting polypeptide into the bloodstream, as opposed to enzymatic degradation of targeting polypeptide prior to its release into the systemic circulation.

Appropriate physiologically cleavable linkages include but are not limited to ester, carbonate ester, carbamate, sulfate, phosphate, acyloxyalkyl ether, acetal, and ketal. Such conjugates should possess a physiologically cleavable bond that is stable upon storage and upon administration. For instance, a targeting polypeptide or modified targeting polypeptide linked to a polymer should maintain its integrity upon manufacturing of the final pharmaceutical composition, upon dissolution in an appropriate delivery vehicle, if employed, and upon administration irrespective of route.

The present invention also includes phosphate-based linkers with tunable stability for intracellular delivery of drug conjugates disclosed in US 2017/0182181, incorporated by reference herein. The phosphate-based linkers comprise a monophosphate, diphosphate, triphosphate, or tetraphosphate group (phosphate group) covalently linked to the distal end of a linker arm comprising from the distal to the proximal direction a tuning element, optionally a spacer element, and a reactive functional group. The phosphate group of the phosphate-based linker is capable of being conjugated to a payload and the reactive functional group is capable of being conjugated to a cell-specific targeting ligand such as an antibody. The general structure of the phosphate-based linkers is: Phosphate group-Tuning element-Optional spacer element-Functional reactive group A phosphate-based linker conjugated to a payload has the general structure: Payload-Phosphate group-Tuning element-Optional spacer element-Functional reactive group and when conjugated to a targeting ligand has the general structure Payload-Phosphate group-Tuning element-Optional spacer element-Targeting ligand. These phosphate-based linkers have a differentiated and tunable stability in blood vs. an intracellular environment (e.g. lysosomal compartment). The rate at which the phosphate group is cleaved in the intracellular environment to release the payload in its native or active form may be affected by the structure of the tuning element with further effects mediated by substitutions of the phosphate group as well as whether the phosphate group is a monophosphate, diphosphate, triphosphate, or tetraphosphate. Further, these phosphate-based linkers provide the ability to construct conjugates such as antibody-drug conjugates in which the propensity of the conjugate to form aggregates is reduced compared to conjugates in which the same payload is conjugated to the antibody or targeting ligand using a linker that is not a phosphate-based linker as disclosed herein.

Structure and Synthesis of TLR-Agonist Linker Derivatives: Electrophilic and Nucleophilic Groups TLR-agonist derivatives with linkers containing a hydroxylamine (also called an aminooxy) group allow for reaction with a variety of electrophilic groups to form conjugates (including but not limited to, with PEG or other water soluble polymers). Like hydrazines, hydrazides and semicarbazides, the enhanced nucleophilicity of the aminooxy group permits it to react efficiently and selectively with a variety of molecules that contain carbonyl- or dicarbonyl-groups, including but not limited to, ketones, aldehydes or other functional groups with similar chemical reactivity. See, e.g., Shap, J. and Tam, J., J. Am. Chem. Soc. 117:3893-3899 (1995); H. Hang and C. Bertozzi, Ace. Chem. Res. 34(9): 727-736 (2001). Whereas the result of reaction with a hydrazine group is the corresponding hydrazone, however, an oxime results generally from the reaction of an aminooxy group with a carbonyl- or dicarbonyl-containing group such as, by way of example, a ketones, aldehydes or other functional groups with similar chemical reactivity. In some embodiments, TLR-agonist derivatives with linkers comprising an azide, alkyne or cycloalkyne allow for linking of molecules via cycloaddition reactions (e.g., 1,3-dipolar cycloadditions, azide-alkyne Huisgen cycloaddition, etc.), (Described in U.S. Pat. No. 7,807,619 which is incorporated by reference herein to the extent relative to the reaction).

Thus, in certain embodiments described herein are TLR-agonist derivatives with linkers comprising a hydroxylamine, aldehyde, protected aldehyde, ketone, protected ketone, thioester, ester, dicarbonyl, hydrazine, amidine, imine, diamine, keto-amine, keto-alkyne, and ene-dione hydroxylamine group, a hydroxylamine-like group (which has reactivity similar to a hydroxylamine group and is structurally similar to a hydroxylamine group), a masked hydroxylamine group (which can be readily converted into a hydroxylamine group), or a protected hydroxylamine group (which has reactivity similar to a hydroxylamine group upon deprotection). In some embodiments, the TLR-agonist derivatives with linkers comprise azides, alkynes or cycloalkynes.

Such TLR-agonist linker derivatives or the targeting polypeptide may be in the form of a salt or may be incorporated into a non-natural amino acid polypeptide, polymer, polysaccharide, or a polynucleotide and optionally post translationally modified.

In certain embodiments, compounds of Formula (I)—(VII) are stable in aqueous solution for at least 1 month under mildly acidic conditions. In certain embodiments, compounds of Formula (I)—(VII) are stable for at least 2 weeks under mildly acidic conditions. In certain embodiments, compound of Formula (I)—(VII) are stable for at least 5 days under mildly acidic conditions. In certain embodiments, such acidic conditions are pH 2 to 8.

The methods and compositions provided and described herein include polypeptides comprising non-natural amino acids having at least one carbonyl or dicarbonyl group, oxime group, hydroxylamine group, or protected or masked forms thereof. Introduction of at least one reactive group into a TLR-agonist linker derivative or the targeting polypeptide can allow for the application of conjugation chemistries that involve specific chemical reactions, including, but not limited to, with one or more targeting polypeptide(s) while not reacting with the commonly occurring amino acids. Once incorporated, the targeting polypeptide of the TC side chains can also be modified by utilizing chemistry methodologies described herein or suitable for the particular functional groups or substituents present in the TLR-agonist linker derivative or the targeting polypeptide.

The TLR-agonist linker derivative and the targeting polypeptide methods and compositions described herein provide conjugates of substances having a wide variety of functional groups, substituents or moieties, with other substances including but not limited to a polymer; a water-soluble polymer; a derivative of polyethylene glycol; a second protein or polypeptide or polypeptide analog; an antibody or antibody fragment; and any combination thereof.

In certain embodiments, the TLR-agonist linker derivatives, the targeting polypeptide, TCs, linkers and reagents described herein, including compounds of Formulas (I)—(VII) are stable in aqueous solution under mildly acidic conditions (including but not limited to pH 2 to 8). In other embodiments, such compounds are stable for at least one month under mildly acidic conditions. In other embodiments, such compounds are stable for at least 2 weeks under mildly acidic conditions. In other embodiments, such compounds are stable for at least 5 days under mildly acidic conditions.

In another aspect of the compositions, methods, techniques and strategies described herein are methods for studying or using any of the aforementioned "modified or unmodified" non-natural amino acid targeting polypeptide. Included within this aspect, by way of example only, are therapeutic, diagnostic, assay-based, industrial, cosmetic, plant biology, environmental, energy-production, consumer-products, and/or military uses which would benefit from a targeting polypeptide comprising a "modified or unmodified" non-natural amino acid polypeptide or protein.

TC molecules comprising at least one non-natural amino acid are provided in the invention. In certain embodiments of the invention, the TC with at least one non-natural amino acid includes at least one post-translational modification. In one embodiment, the at least one post-translational modification comprises attachment of a molecule including but not limited to, a label, a dye, a linker, another TC polypeptide, a polymer, a water-soluble polymer, a derivative of polyethylene glycol, a photocrosslinker, a radionuclide, a cytotoxic compound, a drug, an affinity label, a photoaffinity label, a reactive compound, a resin, a second protein or polypeptide or polypeptide analog, an antibody or antibody fragment, a metal chelator, a cofactor, a fatty acid, a carbohydrate, a polynucleotide, a DNA, a RNA, an antisense polynucleotide, a saccharide, a cyclodextrin, an inhibitory ribonucleic acid, a biomaterial, a nanoparticle, a spin label, a fluorophore, a metal-containing moiety, a radioactive moiety, a novel functional group, a group that covalently or noncovalently interacts with other molecules, a photocaged moiety, an actinic radiation excitable moiety, a photoisomerizable moiety, biotin, a derivative of biotin, a biotin analogue, a moiety incorporating a heavy atom, a chemically cleavable group, a photocleavable group, an elongated side chain, a carbon-linked sugar, a redox-active agent, an amino thioacid, a toxic moiety, an isotopically labeled moiety, a biophysical probe, a phosphorescent group, a chemiluminescent group, an electron dense group, a magnetic group, an intercalating group, a chromophore, an energy transfer agent, a biologically active agent, a detectable label, a small molecule, a quantum dot, a nanotransmitter, a radionucleotide, a radiotransmitter, a neutron-capture agent, or any combination of the above or any other desirable compound or substance, comprising a second reactive group to at least one non-natural amino acid comprising a first reactive group utilizing chemistry methodology that is known to one of ordinary skill in the art to be suitable for the particular reactive groups. For example, the first reactive group is an alkynyl moiety (including but not limited to, in the non-natural amino acid p-propargyloxyphenylalanine, where the propargyl group is also sometimes referred to as an acetylene moiety) and the second reactive group is an azido moiety, and [3+2] cycloaddition chemistry methodologies are utilized. In another example, the first reactive group is the azido moiety (including but not limited to, in the non-natural amino acid p-azido-L-phenylalanine or pAZ as it is sometimes referred to within this specification) and the second reactive group is the alkynyl moiety. In certain embodiments of the modified TC of the present invention, at least one non-natural amino acid (including but not limited to, non-natural amino acid containing a keto functional group) comprising at least one post-translational modification, is used where the at least one post-translational modification comprises a saccharide moiety. In certain embodiments, the post-translational modification is made in vivo in a eukaryotic cell or in a non-eukaryotic cell. A linker, polymer, water soluble polymer, or other molecule may attach the molecule to the polypeptide. In an additional embodiment the linker attached to the TC is long enough to permit formation of a dimer. The molecule may also be linked directly to the polypeptide.

In certain embodiments, the TC protein includes at least one post-translational modification that is made in vivo by one host cell, where the post-translational modification is not normally made by another host cell type. In certain embodiments, the protein includes at least one post-translational modification that is made in vivo by a eukaryotic cell, where the post-translational modification is not normally made by a non-eukaryotic cell. Examples of post-translational modifications include, but are not limited to, glycosylation, acetylation, acylation, lipid-modification, palmitoylation, palmitate addition, phosphorylation, glycolipid-linkage modification, and the like.

In some embodiments, the TC comprise one or more non-naturally encoded amino acids for glycosylation, acetylation, acylation, lipid-modification, palmitoylation, palmitate addition, phosphorylation, or glycolipid-linkage modification of the polypeptide. In some embodiments, the TC comprise one or more non-naturally encoded amino acids for glycosylation of the polypeptide. In some embodiments, the TC comprise one or more naturally encoded amino acids for glycosylation, acetylation, acylation, lipid-modification, palmitoylation, palmitate addition, phosphorylation, or glycolipid-linkage modification of the polypeptide. In some embodiments, the TC, comprise one or more naturally encoded amino acids for glycosylation of the polypeptide.

In some embodiments, the TC comprises one or more non-naturally encoded amino acid additions and/or substitutions that enhance glycosylation of the polypeptide. In some embodiments, the TC comprises one or more deletions that enhance glycosylation of the polypeptide. In some embodiments, the TC comprises one or more non-naturally encoded amino acid additions and/or substitutions that enhance glycosylation at a different amino acid in the polypeptide. In some embodiments, the TC comprises one or more deletions that enhance glycosylation at a different amino acid in the polypeptide. In some embodiments, the TC comprises one or more non-naturally encoded amino acid additions and/or substitutions that enhance glycosylation at a non-naturally encoded amino acid in the polypeptide. In some embodiments, the TC comprises one or more non-naturally encoded amino acid additions and/or substitutions that enhance glycosylation at a naturally encoded amino acid in the polypeptide. In some embodiments, the TC comprises one or more naturally encoded amino acid additions and/or substitutions that enhance glycosylation at a different amino acid in the polypeptide. In some embodiments, the TC comprises one or more non-naturally encoded amino acid additions and/or substitutions that enhance glycosylation at a naturally encoded amino acid in the polypeptide. In some embodiments, the TC comprises one or more non-naturally encoded amino acid additions and/or substitutions that enhance glycosylation at a non-naturally encoded amino acid in the polypeptide.

In one embodiment, the post-translational modification comprises attachment of an oligosaccharide to an asparagine by a GlcNAc-asparagine linkage (including but not limited to, where the oligosaccharide comprises $(GlcNAc-Man)_2$-Man-GlcNAc-GlcNAc, and the like). In another embodiment, the post-translational modification comprises attachment of an oligosaccharide (including but not limited to, Gal-GalNAc, Gal-GlcNAc, etc.) to a serine or threonine by a GalNAc-serine, a GalNAc-threonine, a GlcNAc-serine, or a GlcNAc-threonine linkage. In certain embodiments, a protein or polypeptide of the invention can comprise a secretion or localization sequence, an epitope tag, a FLAG tag, a polyhistidine tag, a GST fusion, and/or the like. Examples of secretion signal sequences include, but are not limited to, a prokaryotic secretion signal sequence, a eukaryotic secretion signal sequence, a eukaryotic secretion signal sequence 5'-optimized for bacterial expression, a novel secretion signal sequence, pectate lyase secretion signal sequence, Omp A secretion signal sequence, and a phage secretion signal sequence. Examples of secretion signal sequences include, but are not limited to, STII (prokaryotic), Fd GIII and M13 (phage), Bgl2 (yeast), and the signal sequence bla derived from a transposon. Any such sequence may be modified to provide a desired result with the polypeptide, including but not limited to, substituting one signal sequence with a different signal sequence, substituting a leader sequence with a different leader sequence, etc.

The protein or polypeptide of interest can contain at least one, at least two, at least three, at least four, at least five, at least six, at least seven, at least eight, at least nine, or ten or more non-natural amino acids. The non-natural amino acids can be the same or different, for example, there can be 1, 2, 3, 4, 5, 6, 7, 8, 9, 10 or more different sites in the protein that comprise 1, 2, 3, 4, 5, 6, 7, 8, 9, 10 or more different non-natural amino acids. In certain embodiments, at least one, but fewer than all, of a particular amino acid present in a naturally occurring version of the protein is substituted with an non-natural amino acid.

The present invention provides methods and compositions based on TC comprising at least one non-naturally encoded amino acid. Introduction of at least one non-naturally encoded amino acid into TC can allow for the application of conjugation chemistries that involve specific chemical reactions, including, but not limited to, with one or more non-naturally encoded amino acids while not reacting with the commonly occurring 20 amino acids. In some embodiments, TC comprising the non-naturally encoded amino acid is linked to a water soluble polymer, such as polyethylene glycol (PEG), or a linker, via the side chain of the non-naturally encoded amino acid. This invention provides a highly efficient method for the selective modification of proteins with PEG derivatives or TLR-linker derivatives, which involves the selective incorporation of non-genetically encoded amino acids, including but not limited to, those amino acids containing functional groups or substituents not found in the 20 naturally incorporated amino acids, including but not limited to a ketone, an azide or acetylene moiety, into proteins in response to a selector codon and the subsequent modification of those amino acids with a suitably reactive PEG derivative. Once incorporated, the amino acid side chains can then be modified by utilizing chemistry methodologies known to those of ordinary skill in the art to be suitable for the particular functional groups or substituents present in the non-naturally encoded amino acid. Known chemistry methodologies of a wide variety are suitable for use in the present invention to incorporate a water soluble polymer into the protein. Such methodologies include but are not limited to a Huisgen [3+2] cycloaddition reaction (see, e.g., Padwa, A. in Comprehensive Organic Synthesis, Vol. 4, (1991) Ed. Trost, B. M., Pergamon, Oxford, p. 1069-1109; and, Huisgen, R. in 1,3-Dipolar Cycloaddition Chemistry, (1984) Ed. Padwa, A., Wiley, New York, p. 1-176) with, including but not limited to, acetylene or azide derivatives, respectively.

Because the Huisgen [3+2] cycloaddition method involves a cycloaddition rather than a nueleophilic substitution reaction, proteins can be modified with extremely high selectivity. The reaction can be carried out at room temperature in aqueous conditions with excellent regioselectivity (1,4>1,5) by the addition of catalytic amounts of Cu(I) salts to the reaction mixture. See, e.g., Tornoe, et al., (2002) J. Org. Chem. 67:3057-3064; and, Rostovtsev, et al., (2002) Angew. Chem. Int. Ed. 41:2596-2599; and WO 03/101972. A molecule that can be added to a protein of the invention through a [3+2] cycloaddition includes virtually any molecule with a suitable functional group or substituent including but not limited to an azido or acetylene derivative. These molecules can be added to an non-natural amino acid with an acetylene group, including but not limited to, p-propargyloxyphenylalanine, or azido group, including but not limited to p-azido-phenylalanine, respectively.

The five-membered ring that results from the Huisgen [3+2] cycloaddition is not generally reversible in reducing environments and is stable against hydrolysis for extended periods in aqueous environments. Consequently, the physical and chemical characteristics of a wide variety of substances can be modified under demanding aqueous conditions with the active PEG derivatives or TLR-linker derivatives of the present invention. Even more importantly, because the azide and acetylene moieties are specific for one another (and do not, for example, react with any of the 20 common, genetically-encoded amino acids), proteins can be modified in one or more specific sites with extremely high selectivity.

The invention also provides water soluble and hydrolytically stable derivatives of PEG derivatives or TLR-linker derivatives and related hydrophilic polymers having one or more acetylene or azide moieties. The PEG polymer derivatives that contain acetylene moieties are highly selective for coupling with azide moieties that have been introduced selectively into proteins in response to a selector codon. Similarly, PEG polymer derivatives that contain azide moieties are highly selective for coupling with acetylene moieties that have been introduced selectively into proteins in response to a selector codon. More specifically, the azide moieties comprise, but are not limited to, alkyl azides, aryl azides and derivatives of these azides. The derivatives of the alkyl and aryl azides can include other substituents so long as the acetylene-specific reactivity is maintained. The acetylene moieties comprise alkyl and aryl acetylenes and derivatives of each. The derivatives of the alkyl and aryl acetylenes can include other substituents so long as the azide-specific reactivity is maintained.

The present invention provides conjugates of substances having a wide variety of functional groups, substituents or moieties, with other substances including but not limited to a label; a dye; a polymer; a water-soluble polymer; a derivative of polyethylene glycol; a photocrosslinker; a radionuclide; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide; a water-soluble dendrimer; a cyclodextrin; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; a quantum dot; a nanotransmitter; a radionucleotide; a radiotransmitter; a neutron-capture agent; or any combination of the above, or any other desirable compound or substance. The present invention also includes conjugates of substances having azide or acetylene moieties with PEG polymer derivatives having the corresponding acetylene or azide moieties. For example, a PEG polymer containing an azide moiety can be coupled to a biologically active molecule at a position in the protein that contains a non-genetically encoded amino acid bearing an acetylene functionality. The linkage by which the PEG and the biologically active molecule are coupled includes but is not limited to the Huisgen [3+2] cycloaddition product.

It is well established in the art that PEG can be used to modify the surfaces of biomaterials (see, e.g., U.S. Pat. No. 6,610,281; Mehvar, R., J. Pharm Pharm Sci., 3(1):125-136 (2000) which are incorporated by reference herein). The invention also includes biomaterials comprising a surface having one or more reactive azide or acetylene sites and one or more of the azide- or acetylene-containing polymers of the invention coupled to the surface via the Huisgen [3+2] cycloaddition linkage. Biomaterials and other substances can also be coupled to the azide- or acetylene-activated polymer derivatives through a linkage other than the azide or acetylene linkage, such as through a linkage comprising a carboxylic acid, amine, alcohol or thiol moiety, to leave the azide or acetylene moiety available for subsequent reactions.

The invention includes a method of synthesizing the azide- and acetylene-containing polymers of the invention. In the ease of the azide-containing PEG derivative, the azide can be bonded directly to a carbon atom of the polymer. Alternatively, the azide-containing PEG derivative can be prepared by attaching a linking agent that has the azide moiety at one terminus to a conventional activated polymer so that the resulting polymer has the azide moiety at its terminus. In the case of the acetylene-containing PEG derivative, the acetylene can be bonded directly to a carbon atom of the polymer. Alternatively, the acetylene-containing PEG derivative can be prepared by attaching a linking agent that has the acetylene moiety at one terminus to a conventional activated polymer so that the resulting polymer has the acetylene moiety at its terminus.

More specifically, in the ease of the azide-containing PEG derivative, a water soluble polymer having at least one active hydroxyl moiety undergoes a reaction to produce a substituted polymer having a more reactive moiety, such as a mesylate, tresylate, tosylate or halogen leaving group, thereon. The preparation and use of PEG derivatives or TLR-linker derivatives containing sulfonyl acid halides, halogen atoms and other leaving groups are known to those of ordinary skill in the art. The resulting substituted polymer then undergoes a reaction to substitute for the more reactive moiety an azide moiety at the terminus of the polymer. Alternatively, a water soluble polymer having at least one active nucleophilic or electrophilic moiety undergoes a reaction with a linking agent that has an azide at one terminus so that a covalent bond is formed between the PEG polymer and the linking agent and the azide moiety is positioned at the terminus of the polymer. Nucleophilic and electrophilic moieties, including amines, thiols, hydrazides, hydrazines, alcohols, carboxylates, aldehydes, ketones, thioesters and the like, are known to those of ordinary skill.

More specifically, in the case of the acetylene-containing PEG derivative, a water soluble polymer having at least one active hydroxyl moiety undergoes a reaction to displace a halogen or other activated leaving group from a precursor that contains an acetylene moiety. Alternatively, a water soluble polymer having at least one active nucleophilic or electrophilic moiety undergoes a reaction with a linking agent that has an acetylene at one terminus so that a covalent bond is formed between the PEG polymer and the linking agent and the acetylene moiety is positioned at the terminus of the polymer. The use of halogen moieties, activated leaving group, nucleophilic and electrophilic moieties in the context of organic synthesis and the preparation and use of PEG derivatives or TLR-linker derivatives is well established to practitioners in the art.

The invention also provides a method for the selective modification of proteins to add other substances to the modified protein, including but not limited to water soluble polymers such as PEG and PEG derivatives or TLR-linker derivatives, linkers, or another TC polypeptide, containing an azide or acetylene moiety. The azide- and acetylene-containing PEG derivatives or TLR-linker derivatives can be used to modify the properties of surfaces and molecules where biocompatibility, stability, solubility and lack of immunogenicity are important, while at the same time providing a more selective means of attaching the PEG derivatives or TLR-linker derivatives to proteins than was previously known in the art.

General Recombinant Nucleic Acid Methods for Use with the Invention

In numerous embodiments of the present invention, nucleic acids encoding a targeting polypeptide of the TC of interest will be isolated, cloned and often altered using recombinant methods. Such embodiments are used, including but not limited to, for protein expression or during the generation of variants, derivatives, expression cassettes, or other sequences derived from a targeting polypeptide of the TC. In some embodiments, the sequences encoding the polypeptides of the invention are operably linked to a heterologous promoter.

A nucleotide sequence encoding a targeting polypeptide of the TC comprising a non-naturally encoded amino acid may be synthesized on the basis of the amino acid sequence of the parent polypeptide, and then changing the nucleotide sequence so as to effect introduction (i.e., incorporation or substitution) or removal (i.e., deletion or substitution) of the relevant amino acid residue(s). The nucleotide sequence may be conveniently modified by site-directed mutagenesis in accordance with conventional methods. Alternatively, the nucleotide sequence may be prepared by chemical synthesis, including but not limited to, by using an oligonucleotide synthesizer, wherein oligonucleotides are designed based on the amino acid sequence of the desired polypeptide, and preferably selecting those codons that are favored in the host cell in which the recombinant polypeptide will be produced. For example, several small oligonucleotides coding for portions of the desired polypeptide may be synthesized and assembled by PCR, ligation or ligation chain reaction. See, e.g., Barany, et al., *Proc. Natl. Acad. Sci.* 88: 189-193 (1991); U.S. Pat. No. 6,521,427 which are incorporated by reference herein.

This invention utilizes routine techniques in the field of recombinant genetics. Basic texts disclosing the general methods of use in this invention include Sambrook et al., *Molecular Cloning A Laboratory Manual* (3rd ed. 2001); Kriegler, *Gene Transfer and Expression: A Laboratory Manual* (1990); and *Current Protocols in Molecular Biology* (Ausubel et al., eds., 1994)).

The invention also relates to eukaryotic host cells, non-eukaryotic host cells, and organisms for the in vivo incorporation of a non-natural amino acid via orthogonal tRNA/RS pairs. Host cells are genetically engineered (including but not limited to, transformed, transduced or transfected) with the polynucleotides of the invention or constructs which include a polynucleotide of the invention, including but not limited to, a vector of the invention, which can be, for example, a cloning vector or an expression vector.

Several well-known methods of introducing target nucleic acids into cells are available, any of which can be used in the invention. These include: fusion of the recipient cells with bacterial protoplasts containing the DNA, electroporation, projectile bombardment, and infection with viral vectors (discussed further, below), etc. Bacterial cells can be used to amplify the number of plasmids containing DNA constructs of this invention. The bacteria are grown to log phase and the plasmids within the bacteria can be isolated by a variety of methods known in the art (see, for instance, Sambrook). In addition, kits are commercially available for the purification of plasmids from bacteria, (see, e.g., Easy Prep™, FlexiPrep™, both from Pharmacia Biotech; StrataClean™ from Stratagene; and, QIAprep™ from Qiagen). The isolated and purified plasmids are then further manipulated to produce other plasmids, used to transfect cells or incorporated into related vectors to infect organisms. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (including but not limited to, shuttle vectors) and selection markers for both prokaryotic and eukaryotic systems. Vectors are suitable for replication and integration in prokaryotes, eukaryotes, or both. See, Gillam & Smith, Gene 8:81 (1979); Roberts, et al., Nature, 328:731 (1987); Schneider, E., et al., Protein Expr. Purif. 6(1):10-14 (1995); Ausubel, Sambrook, Berger (all supra). A catalogue of bacteria and bacteriophages useful for cloning is provided, e.g., by the ATCC, e.g., The ATCC Catalogue of Bacteria and Bacteriophage (1992) Gherna et al. (eds) published by the ATCC. Additional basic procedures for sequencing, cloning and other aspects of molecular biology and underlying theoretical considerations are also found in Watson et al. (1992) Recombinant DNA Second Edition Scientific American Books, NY. In addition, essentially any nucleic acid (and virtually any labeled nucleic acid, whether standard or nonstandard) can be custom or standard ordered from any of a variety of commercial sources, such as the Midland Certified Reagent Company (Midland, TX available on the World Wide Web at mere), The Great American Gene Company (Ramona, CA available on the World Wide Web at genco), ExpressGen Inc. (Chicago, IL available on the World Wide Web at expressgen), Operon Technologies Inc. (Alameda, CA) and many others.

Selector Codons

Selector codons of the invention expand the genetic codon framework of protein biosynthetic machinery. For example, a selector codon includes, but is not limited to, a unique three base codon, a nonsense codon, such as a stop codon, including but not limited to, an amber codon (UAG), an ochre codon, or an opal codon (UGA), an unnatural codon, a four or more base codon, a rare codon, or the like. It is readily apparent to those of ordinary skill in the art that there is a wide range in the number of selector codons that can be introduced into a desired gene or polynucleotide, including but not limited to, one or more, two or more, three or more, 4, 5, 6, 7, 8, 9, 10 or more in a single polynucleotide encoding at least a portion of the TC.

In one embodiment, the methods involve the use of a selector codon that is a stop codon for the incorporation of one or more non-natural amino acids in vivo. For example, an O-tRNA is produced that recognizes the stop codon, including but not limited to, UAG, and is aminoacylated by an O—RS with a desired non-natural amino acid. This O-tRNA is not recognized by the naturally occurring host's aminoacyl-tRNA synthetases. Conventional site-directed mutagenesis can be used to introduce the stop codon, including but not limited to, TAG, at the site of interest in a polypeptide of interest. See, e.g., Sayers, J. R., et al. (1988), 5'-3' *Exonucleases in phosphorothioate-based oligonucleotide-directed mutagenesis*. Nucleic Acids Res, 16:791-802. When the O—RS, 0-tRNA and the nucleic acid that encodes the polypeptide of interest are combined in vivo, the non-natural amino acid is incorporated in response to the UAG codon to give a polypeptide containing the non-natural amino acid at the specified position.

The incorporation of non-natural amino acids in vivo can be done without significant perturbation of the eukaryotic host cell. For example, because the suppression efficiency for the UAG codon depends upon the competition between the O-tRNA, including but not limited to, the amber suppressor tRNA, and a eukaryotic release factor (including but not limited to, eRF) (which binds to a stop codon and initiates release of the growing peptide from the ribosome), the suppression efficiency can be modulated by, including but not limited to, increasing the expression level of O-tRNA, and/or the suppressor tRNA.

Non-natural amino acids can also be encoded with rare codons. For example, when the arginine concentration in an in vitro protein synthesis reaction is reduced, the rare arginine codon, AGG, has proven to be efficient for insertion of Ala by a synthetic tRNA acylated with alanine. See, e.g., Ma et al., Biochemistry, 32:7939 (1993). In this case, the synthetic tRNA competes with the naturally occurring tRNAArg, which exists as a minor species in *Escherichia coli*. Some organisms do not use all triplet codons. An unassigned codon AGA in *Micrococcus luteus* has been utilized for insertion of amino acids in an in vitro transcription/translation extract. See, e.g., Kowal and Oliver, Nucl. Acid. Res., 25:4685 (1997). Components of the present invention can be generated to use these rare codons in vivo.

Selector codons also comprise extended codons, including but not limited to, four or more base codons, such as, four, five, six or more base codons. Examples of four base codons include, but are not limited to, AGGA, CUAG, UAGA, CCCU and the like. Examples of five base codons include, but are not limited to, AGGAC, CCCCU, CCCUC, CUAGA, CUACU, UAGGC and the like. A feature of the invention includes using extended codons based on frameshift suppression. Four or more base codons can insert, including but not limited to, one or multiple non-natural amino acids into the same protein. For example, in the presence of mutated O-tRNAs, including but not limited to, a special frameshift suppressor tRNAs, with anticodon loops, for example, with at least 8-10 nt anticodon loops, the four or more base codon is read as single amino acid. In other embodiments, the anticodon loops can decode, including but not limited to, at least a four-base codon, at least a five-base codon, or at least a six-base codon or more. Since there are 256 possible four-base codons, multiple non-natural amino acids can be encoded in the same cell using a four or more base codon. See, Anderson et al., (2002) *Exploring the Limits of Codon and Anticodon Size*, Chemistry and Biology, 9:237-244; Magliery, (2001) *Expanding the Genetic Code: Selection of Efficient Suppressors of Four-base Codons and Identification of "Shifty" Four-base Codons with a Library Approach in Escherichia coli*, J. Mol. Biol. 307: 755-769.

For example, four-base codons have been used to incorporate non-natural amino acids into proteins using in vitro biosynthetic methods. See, e.g., Ma et al., (1993) Biochemistry, 32:7939; and Hohsaka et al., (1999) J. Am, Chem. Soc., 121:34. CGGG and AGGU were used to simultaneously incorporate 2-naphthylalanine and an NBD derivative of lysine into streptavidin in vitro with two chemically acylated frameshift suppressor tRNAs. See, e.g., Hohsaka et al., (1999) J. Am, Chem. Soc., 121:12194. In an in vivo study, Moore et al. examined the ability of tRNALeu derivatives with NCUA anticodons to suppress UAGN codons (N can be U, A, G, or C), and found that the quadruplet UAGA can be decoded by a tRNALeu with a UCUA anticodon with an efficiency of 13 to 26% with little decoding in the 0 or −1 frame. See, Moore et al., (2000) J. Mol. Biol., 298:195. In one embodiment, extended codons based on rare codons or nonsense codons can be used in the present invention, which can reduce missense readthrough and frameshift suppression at other unwanted sites.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al., (2002) *An unnatural base pair for incorporating amino acid analogues into protein*, Nature Biotechnology, 20:177-182. See, also, Wu, Y., et al., (2002) J. Am. Chem. Soc. 124:14626-14630. Other relevant publications are listed below.

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., Switzer et al., (1989) J. Am. Chem. Soc., 111:8322; and Piccirilli et al., (1990) Nature, 343:33; Kool, (2000) Curr. Opin. Chem. Biol., 4:602. These bases in general mispair to some degree with natural bases and cannot be enzymatically replicated. Kool and co-workers demonstrated that hydrophobic packing interactions between bases can replace hydrogen bonding to drive the formation of base pair. See, Kool, (2000) Curr, Opin. Chem. Biol., 4:602; and Guckian and Kool, (1998) Angew. Chem. Int. Ed, Engl., 36, 2825. In an effort to develop an unnatural base pair satisfying all the above requirements, Schultz, Romesberg and co-workers have systematically synthesized and studied a series of unnatural hydrophobic bases. A PICS:PICS self-pair is found to be more stable than natural base pairs and can be efficiently incorporated into DNA by Klenow fragment of *Escherichia coli* DNA polymerase I (KF). See, e.g., McMinn et al., (1999) J. Am. Chem. Soc., 121:11585-6; and Ogawa et al., (2000) J. Am. Chem. Soc., 122:3274. A 3MN:3MN self-pair can be synthesized by KF with efficiency and selectivity sufficient for biological function. See, e.g., Ogawa et al., (2000) J. Am. Chem. Soc., 122:8803. However, both bases act as a chain terminator for further replication. A mutant DNA polymerase has been recently evolved that can be used to replicate the PICS self pair. In addition, a 7AI self pair can be replicated. See, e.g., Tae et al., (2001) J. Am. Chem. Soc., 123:7439. A novel metallobase pair, Dipic:Py, has also been developed, which forms a stable pair upon binding Cu(II). See, Meggers et al., (2000) J. Am. Chem. Soc., 122:10714. Because extended codons and unnatural codons are intrinsically orthogonal to natural codons, the methods of the invention can take advantage of this property to generate orthogonal tRNAs for them.

A translational bypassing system can also be used to incorporate a non-natural amino acid in a desired polypeptide. In a translational bypassing system, a large sequence is incorporated into a gene but is not translated into protein. The sequence contains a structure that serves as a cue to induce the ribosome to hop over the sequence and resume translation downstream of the insertion.

Nucleic acid molecules encoding a protein of interest such as a targeting polypeptide of the TC may be readily mutated to introduce a cysteine at any desired position of the polypeptide. Cysteine is widely used to introduce reactive molecules, water soluble polymers, proteins, or a wide variety of other molecules, onto a protein of interest. Methods suitable for the incorporation of cysteine into a desired position of a polypeptide are known to those of ordinary skill in the art, such as those described in U.S. Pat. No. 6,608,183, which is incorporated by reference herein, and standard mutagenesis techniques.

III. Non-Naturally Encoded Amino Acids

A very wide variety of non-naturally encoded amino acids are suitable for use in the present invention. Any number of non-naturally encoded amino acids can be introduced into a TC. In general, the introduced non-naturally encoded amino acids are substantially chemically inert toward the 20 common, genetically-encoded amino acids (i.e., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine). In some embodiments, the non-naturally encoded amino acids include side chain functional groups that react efficiently and selectively with functional groups not found in the 20 common amino acids (including but not limited to, azido, ketone, aldehyde and aminooxy groups) to form stable conjugates. For example, a targeting polypeptide of the TC that includes a non-naturally encoded amino acid containing an azido functional group can be reacted with a polymer (including but not limited to, poly (ethylene glycol) or, alternatively, a second polypeptide or linker containing an alkyne moiety) to form a stable conjugate resulting from the selective reaction of the azide and the alkyne functional groups to form a Huisgen [3+2] cycloaddition product.

The generic structure of an alpha-amino acid is illustrated as follows (Formula I):

I

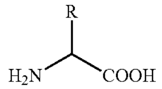

A non-naturally encoded amino acid is typically any structure having the above-listed formula wherein the R group is any substituent other than one used in the twenty natural amino acids, and may be suitable for use in the present invention. Because the non-naturally encoded amino acids of the invention typically differ from the natural amino acids only in the structure of the side chain, the non-naturally encoded amino acids form amide bonds with other amino acids, including but not limited to, natural or non-naturally encoded, in the same manner in which they are formed in naturally occurring polypeptides. However, the non-naturally encoded amino acids have side chain groups that distinguish them from the natural amino acids. For example, R optionally comprises an alkyl-, aryl-, acyl-, keto-, azido-, hydroxyl-, hydrazine, cyano-, halo-, hydrazide, alkenyl, alkynl, ether, thiol, seleno-, sulfonyl-, borate, boronate, phospho, phosphono, phosphine, heterocyclic, enone, imine, aldehyde, ester, thioacid, hydroxylamine, amino group, or the like or any combination thereof. Other non-naturally occurring amino acids of interest that may be suitable for use in the present invention include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto-containing amino acids, amino acids comprising polyethylene glycol or polyether, heavy atom substituted amino acids, chemically cleavable and/or photocleavable amino acids, amino acids with an elongated side chains as compared to natural amino acids, including but not limited to, polyethers or long chain hydrocarbons, including but not limited to, greater than about 5 or greater than about 10 carbons, carbon-linked sugar-containing amino acids, redox-active amino acids, amino thioacid containing amino acids, and amino acids comprising one or more toxic moiety.

Exemplary non-naturally encoded amino acids that may be suitable for use in the present invention and that are useful for reactions with water soluble polymers include, but are not limited to, those with carbonyl, aminooxy, hydrazine, hydrazide, semicarbazide, azide and alkyne reactive groups. In some embodiments, non-naturally encoded amino acids comprise a saccharide moiety. Examples of such amino acids include N-acetyl-L-glucosaminyl-L-serine, N-acetyl-L-galactosaminyl-L-serine, N-acetyl-L-glucosaminyl-L-threonine, N-acetyl-L-glucosaminyl-L-asparagine and O-mannosaminyl-L-serine. Examples of such amino acids also include examples where the naturally-occurring N- or O-linkage between the amino acid and the saccharide is replaced by a covalent linkage not commonly found in nature—including but not limited to, an alkene, an oxime, a thioether, an amide and the like. Examples of such amino acids also include saccharides that are not commonly found in naturally-occurring proteins such as 2-deoxy-glucose, 2-deoxygalactose and the like.

Many of the non-naturally encoded amino acids provided herein are commercially available, e.g., from Sigma-Aldrich (St. Louis, Mo., USA), Novabiochem (a division of EMD Biosciences, Darmstadt, Germany), or Peptech (Burlington, Mass., USA). Those that are not commercially available are optionally synthesized as provided herein or using standard methods known to those of ordinary skill in the art. For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York). See, also, U.S. Pat. Nos. 7,045,337 and 7,083,970, which are incorporated by reference herein. In addition to non-natural amino acids that contain novel side chains, non-natural amino acids that may be suitable for use in the present invention also optionally comprise modified backbone structures, including but not limited to, as illustrated by the structures of Formula II and III:

II

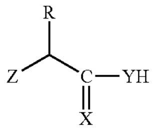

III

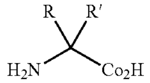

wherein Z typically comprises OH, $NH_2$, SH, NH—R', or S—W; X and Y, which can be the same or different, typically comprise S or O, and R and R', which are optionally the same or different, are typically selected from the same list of constituents for the R group described above for the non-natural amino acids having Formula I as well as hydrogen. For example, nonnatural amino acids of the invention optionally comprise substitutions in the amino or carboxyl group as illustrated by Formulas II and III. nonnatural amino acids of this type include, but are not limited to, α-hydroxy acids, α-thioacids, α-aminothiocarboxylates, including but not limited to, with side chains corresponding to the common twenty natural amino acids or unnatural side chains. In addition, substitutions at the α-carbon optionally include, but are not limited to, L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, β and γ amino acids such as substituted β-alanine and γ-amino butyric acid.

Many nonnatural amino acids are based on natural amino acids, such as tyrosine, glutamine, phenylalanine, and the like, and are suitable for use in the present invention. Tyrosine analogs include, but are not limited to, para-substituted tyrosines, ortho-substituted tyrosines, and meta substituted tyrosines, where the substituted tyrosine comprises, including but not limited to, a keto group (including but not limited to, an acetyl group), a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, an alkynyl group or the like. In addition, multiply substituted aryl rings are also contemplated. Glutamine analogs that may be suitable for use in the present invention include, but are not limited to, α-hydroxy derivatives, γ-substituted derivatives, cyclic derivatives, and amide substituted glutamine derivatives. Example phenylalanine analogs that may be suitable for use in the present invention include, but are not limited to, para-substituted phenylalanines, ortho-substituted phenyalanines, and meta-substituted phenylalanines, where the substituent comprises, including but not limited to, a hydroxy group, a methoxy group, a methyl group, an allyl group, an aldehyde, an azido, an iodo, a bromo, a keto group (including but not limited to, an acetyl group), a benzoyl, an alkynyl group, or the like. Specific examples of non-natural amino acids that may be suitable for use in the present invention include, but are not limited to, a p-acetyl-L-phenylalanine, an O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, and a p-propargyloxy-phenylalanine, and the like. Examples of structures of a variety of nonnatural amino acids that may be suitable for use in the present invention are provided in, for example, WO 2002/085923 entitled "In vivo incorporation of unnatural amino acids." See also Kiick et al., (2002) Incorporation of azides into recombinant proteins for chemoselective modification by the Staudinger ligation, PNAS 99:19-24, which is incorporated by reference herein, for additional methionine analogs. International Application No. PCT/US06/47822 entitled "Compositions Containing, Methods Involving, and Uses of Non-natural Amino Acids and Polypeptides," which is incorporated by reference herein, describes reductive alkylation of an aromatic amine moieties, including but not limited to, p-amino-phenylalanine and reductive amination.

In another embodiment of the present invention, the TC polypeptides with one or more non-naturally encoded amino acids are covalently modified. Selective chemical reactions that are orthogonal to the diverse functionality of biological systems are recognized as important tools in chemical biology. As relative newcomers to the repertoire of synthetic chemistry, these bioorthogonal reactions have inspired new strategies for compound library synthesis, protein engineering, functional proteomics, and chemical remodeling of cell surfaces. The azide has secured a prominent role as a unique chemical handle for bioconjugation. The Staudinger ligation has been used with phosphines to tag azidosugars metabolically introduced into cellular glycoconjugates. The Staudinger ligation can be performed in living animals without physiological harm; nevertheless, the Staudinger reaction is not without liabilities. The requisite phosphines are susceptible to air oxidation and their optimization for improved water solubility and increased reaction rate has proven to be synthetically challenging.

The azide group has an alternative mode of bioorthogonal reactivity: the [3+2] cycloaddition with alkynes described by Huisgen. In its classic form, this reaction has limited applicability in biological systems due to the requirement of elevated temperatures (or pressures) for reasonable reaction rates. Sharpless and coworkers surmounted this obstacle with the development of a copper(I)-catalyzed version, termed "click chemistry," that proceeds readily at physiological temperatures and in richly functionalized biological environs. This discovery has enabled the selective modification of virus particles, nucleic acids, and proteins from complex tissue lysates. Unfortunately, the mandatory copper catalyst is toxic to both bacterial and mammalian cells, thus precluding applications wherein the cells must remain viable. Catalyst-free Huisgen cycloadditions of alkynes activated by electron-withdrawing substituents have been reported to occur at ambient temperatures. However, these compounds undergo Michael reaction with biological nucleophiles.

In one embodiment, compositions of a targeting polypeptide of the TC that include a non natural amino acid (such as p-(propargyloxy)-phenyalanine) are provided. Various compositions comprising p-(propargyloxy)-phenyalanine and, including but not limited to, proteins and/or cells, are also provided. In one aspect, a composition that includes the p-(propargyloxy)-phenyalanine non-natural amino acid, further includes an orthogonal tRNA. The non-natural amino acid can be bonded (including but not limited to, covalently) to the orthogonal tRNA, including but not limited to, covalently bonded to the orthogonal tRNA though an amino-acyl bond, covalently bonded to a 3'OH or a 2'OH of a terminal ribose sugar of the orthogonal tRNA, etc.

The chemical moieties via nonnatural amino acids that can be incorporated into proteins offer a variety of advantages and manipulations of the protein. For example, the unique reactivity of a keto functional group allows selective modification of proteins with any of a number of hydrazine- or hydroxylamine-containing reagents in vitro and in vivo. A heavy atom nonnatural amino acid, for example, can be useful for phasing X-ray structure data. The site-specific introduction of heavy atoms using nonnatural amino acids also provides selectivity and flexibility in choosing positions for heavy atoms. Photoreactive nonnatural amino acids (including but not limited to, amino acids with benzophenone and arylazides (including but not limited to, phenylazide) side chains), for example, allow for efficient in vivo and in vitro photocrosslinking of protein. Examples of photoreactive nonnatural amino acids include, but are not limited to, p-azido-phenylalanine and p-benzoyl-phenylalanine. The protein with the photoreactive nonnatural amino acids can then be crosslinked at will by excitation of the photoreactive group-providing temporal control. In one example, the methyl group of an nonnatural amino can be substituted with an isotopically labeled, including but not limited to, methyl group, as a probe of local structure and dynamics, including but not limited to, with the use of nuclear magnetic resonance and vibrational spectroscopy. Alkynyl or azido functional groups, for example, allow the selective modification of proteins with molecules through a [3+2] cycloaddition reaction.

A nonnatural amino acid incorporated into a polypeptide at the amino terminus can be composed of an R group that is any substituent other than one used in the twenty natural amino acids and a $2^{nd}$ reactive group different from the $NH_2$ group normally present in alpha-amino acids. A similar nonnatural amino acid can be incorporated at the C-terminus with a $2^{nd}$ reactive group different from the COOH group normally present in alpha-amino acids.

The nonnatural amino acids of the invention may be selected or designed to provide additional characteristics unavailable in the twenty natural amino acids. For example, nonnatural amino acid may be optionally designed or selected to modify the biological properties of a protein, e.g., into which they are incorporated. For example, the following properties may be optionally modified by inclusion of an nonnatural amino acid into a protein: toxicity, biodistribution, solubility, stability, e.g., thermal, hydrolytic, oxidative, resistance to enzymatic degradation, and the like, facility of purification and processing, structural properties, spectroscopic properties, chemical and/or photochemical properties, catalytic activity, redox potential, half-life, ability to react with other molecules, e.g., covalently or noncovalently, and the like.

In some embodiments the present invention provides TC linked to a water soluble polymer, e.g., a PEG, by an oxime bond. Many types of non-naturally encoded amino acids are suitable for formation of oxime bonds. These include, but are not limited to, non-naturally encoded amino acids containing a carbonyl, dicarbonyl, or hydroxylamine group. Such amino acids are described in U.S. Patent Publication Nos. 2006/0194256, 2006/0217532, and 2006/0217289 and WO 2006/069246 entitled "Compositions containing, methods involving, and uses of non-natural amino acids and polypeptides," which are incorporated herein by reference in their entirety. Non-naturally encoded amino acids are also described in U.S. Pat. Nos. 7,083,970 and 7,045,337, which are incorporated by reference herein in their entirety.

Some embodiments of the invention utilize TC polypeptides that are substituted at one or more positions with a para-acetylphenylalanine amino acid. The synthesis of p-acetyl-(+/−)-phenylalanine and m-acetyl-(+/−)-phenylalanine are described in Zhang, Z., et al., Biochemistry 42: 6735-6746 (2003), incorporated by reference. Other carbonyl- or dicarbonyl-containing amino acids can be similarly prepared by one of ordinary skill in the art. Further, non-limiting exemplary syntheses of non-natural amino acid that are included herein are presented in U.S. Pat. No. 7,083,970, which is incorporated by reference herein in its entirety.

Amino acids with an electrophilic reactive group allow for a variety of reactions to link molecules via nucleophilic addition reactions among others. Such electrophilic reactive groups include a carbonyl group (including a keto group and a dicarbonyl group), a carbonyl-like group (which has reactivity similar to a carbonyl group (including a keto group and a dicarbonyl group) and is structurally similar to a carbonyl group), a masked carbonyl group (which can be readily converted into a carbonyl group (including a keto group and a dicarbonyl group)), or a protected carbonyl group (which has reactivity similar to a carbonyl group (including a keto group and a dicarbonyl group) upon deprotection). Such amino acids include amino acids having the structure of Formula (IV):

(IV)

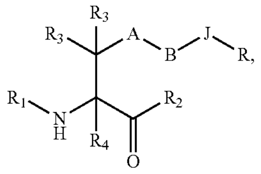

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, $—S(O)_k—$ where k is 1, 2, or 3, $—S(O)_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, $—S(O)_kN(R')—$, —N(R')C(O)N(R')—, —N(R')C(S)N(R')—, $—N(R')S(O)_kN(R')—$, —C(R')=N—, —C(R')=N—N(R')—, —C(R')=N—N=, $—C(R')_2—N=N—$, and $—C(R')_2—N(R')—N(R')—$, where each R' is independently II, alkyl, or substituted alkyl;

J is

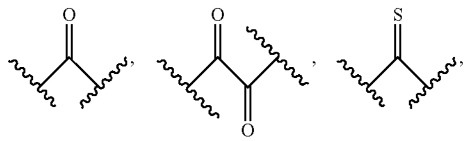

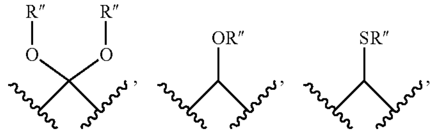

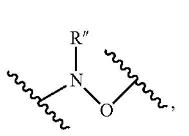

or

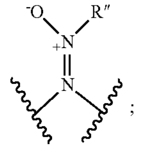

R is H, alkyl, substituted alkyl, cycloalkyl, or substituted cycloalkyl;

each R" is independently H, alkyl, substituted alkyl, or a protecting group, or when more than one R" group is present, two R" optionally form a heterocycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

each of $R_3$ and $R_4$ is independently H, halogen, lower alkyl, or substituted lower alkyl, or $R_3$ and $R_4$ or two $R_3$ groups optionally form a cycloalkyl or a heterocycloalkyl;

or the -A-B-J-R groups together form a bicyclic or tricyclic cycloalkyl or heterocycloalkyl comprising at least one carbonyl group, including a dicarbonyl group, protected carbonyl group, including a protected dicarbonyl group, or masked carbonyl group, including a masked dicarbonyl group;

or the -J-R group together forms a monocyclic or bicyclic cycloalkyl or heterocycloalkyl comprising at least one carbonyl group, including a dicarbonyl group, protected carbonyl group, including a protected dicarbonyl group, or masked carbonyl group, including a masked dicarbonyl group;

with a proviso that when A is phenylene and each $R_3$ is H, B is present; and that when A is —$(CH_2)_4$—and each $R_3$ is H, B is not —$NHC(O)(CH_2CH_2)$—; and that when A and B are absent and each $R_3$ is H, R is not methyl.

In addition, having the structure of Formula (V) are included:

(V)

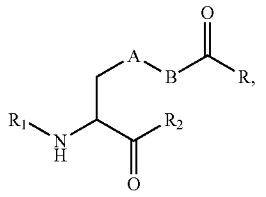

wherein;

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —$S(O)_k$— where k is 1, 2, or 3, —$S(O)_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —$S(O)_k$N(R')—, —N(R')C(O)N(R')—, —N(R')C(S)N(R')—, —N(R')$S(O)_k$N(R')—, —N(R')—N—, —C(R')═N—N(R')—, —C(R')═N—N═, —$C(R')_2$—N═N—, and —$C(R')_2$—N(R')—N(R')—, where each R' is independently H, alkyl, or substituted alkyl;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

with a proviso that when A is phenylene, B is present; and that when A is —$(CH_2)_4$—, B is not —$NHC(O)(CH_2CH_2)$—; and that when A and B are absent, R is not methyl.

In addition, amino acids having the structure of Formula (VI) are included:

(VI)

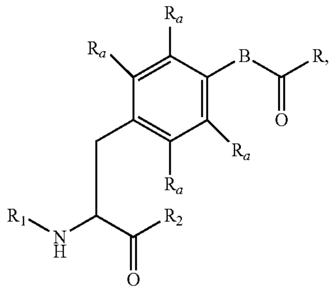

wherein:

B is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —$S(O)_k$— where k is 1, 2, or 3, —$S(O)_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —$S(O)_k$N(R')—, —N(R')C(O)N(R')—, —N(R')C(S)N(R')—, —N(R')$S(O)_k$N(R')—, —N(R')—N═, —C(R')═N—, —C(R')═N—N(R')—, —$C(R')_2$—N═N—, and —$C(R')_2$—N(R')—N(R')—, where each R' is independently H, alkyl, or substituted alkyl;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

each $R_a$ is independently selected from the group consisting of H, halogen, alkyl, substituted alkyl, —$N(R')_2$, —$C(O)_k$R' where k is 1, 2, or 3, —$C(O)N(R')_2$, —OR', and —$S(O)_k$R', where each R' is independently H, alkyl, or substituted alkyl.

In addition, the following amino acids are included:

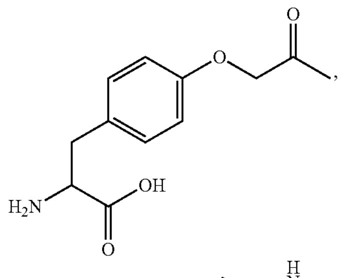
,

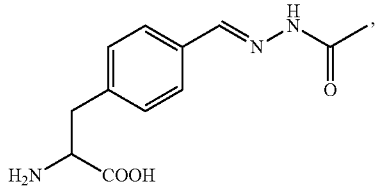
,

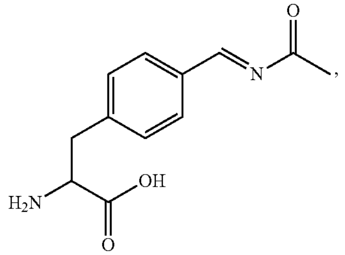
,

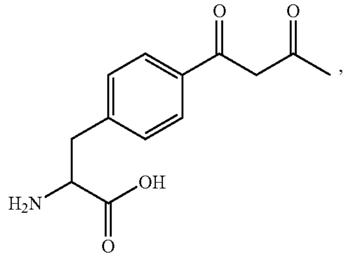
,

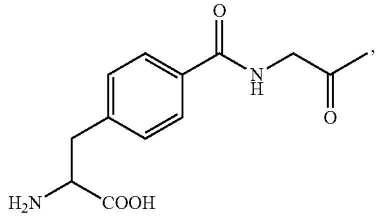
,

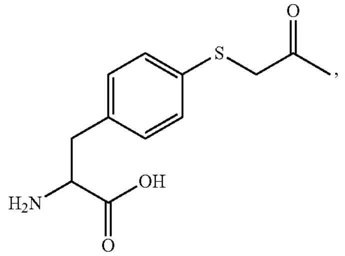
,

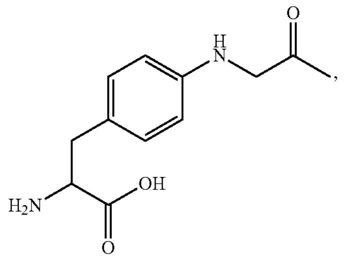
, and

-continued

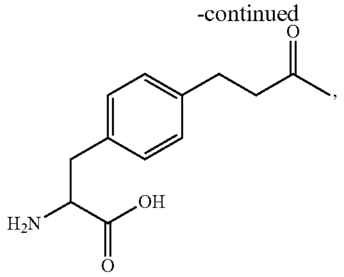
, wherein such compounds are optionally amino protected group, carboxyl protected or a salt thereof. In addition, any of the following non-natural amino acids may be incorporated into a non-natural amino acid polypeptide.

In addition, the following amino acids having the structure of Formula (VII) are included:

(VII)

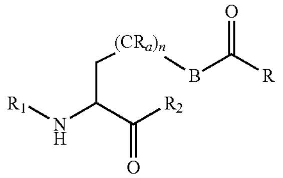

wherein

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —$S(O)_k$— where k is 1, 2, or 3, —$S(O)_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —$S(O)_k$N(R')—, —N(R')C(O)N(R')—, —N(R')C(S)N(R')—, —N(R')$S(O)_k$N(R')—, —C(R')═N—, —C(R')═N—N(R')—, —$C(R')_2$═N—N═, and —$C(R')_2$—N(R')—N(R')—, where each R' is independently H, alkyl, or substituted alkyl;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

each $R_a$ is independently selected from the group consisting of H, halogen, alkyl, substituted alkyl, —$N(R)_2$, —$C(O)_k$R' where k is 1, 2, or 3, —C(O)$N(R')_2$, —OR', and —$S(O)_k$R', where each R' is independently H, alkyl, or substituted alkyl; and n is 0 to 8;

with a proviso that when A is —$(CH_2)_4$—, B is not —NHC(O)($CH_2CH_2$)—.

In addition, the following amino acids are included:

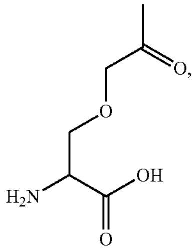
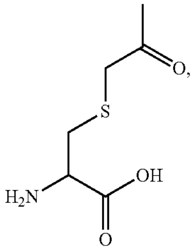
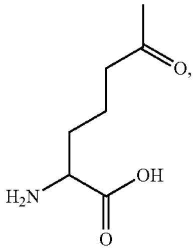
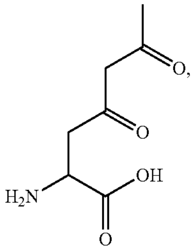
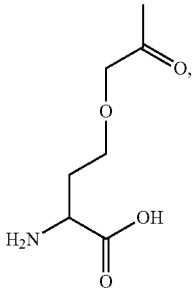
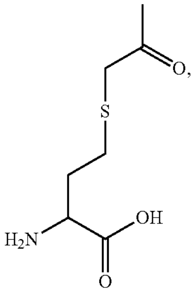
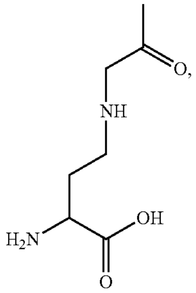
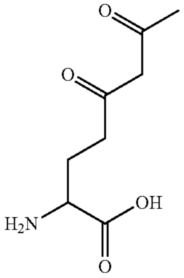
,
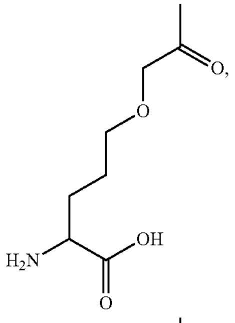
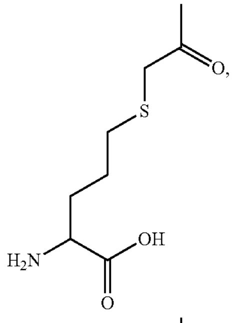
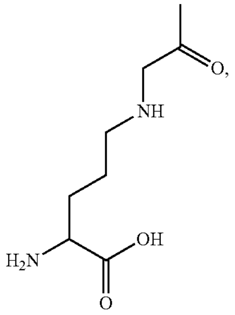
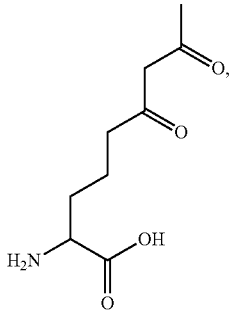

-continued

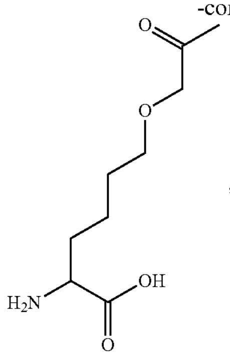
,
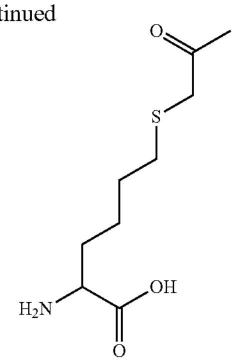
,
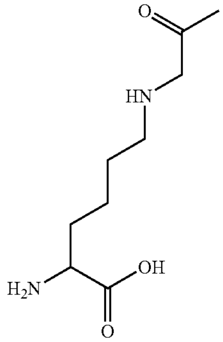
, and
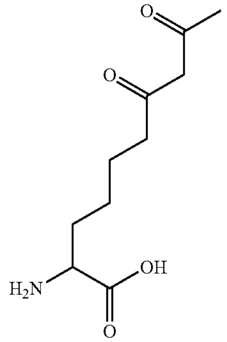
, wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition, the following amino acids having the structure of Formula (VIII) are included:

(VIII)

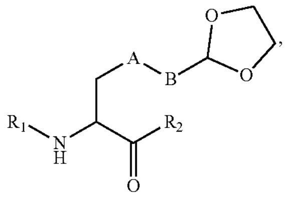

wherein A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-

(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —$S(O)_k$N(R')—, —N(R')C(O)N(R')—, —N(R')C(S)N(R')—, —N(R')$S(O)_k$N(R')—, —N(R')—N=, —C(R')=N—, —C(R')=N—N(R')—, —C(R')=N—N=, —$C(R')_2$—N=N—, and —$C(R')_2$—N(R')—N(R')—, where each R' is independently H, alkyl, substituted alkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide.

In addition, the following amino acids having the structure of Formula (IX) are included:

(IX)

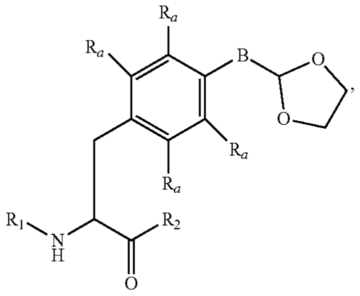

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —$S(O)_k$— where k is 1, 2, or 3, —$S(O)_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —$S(O)_k$N(R')—, —N(R')C(O)N(R')—, —N(R')C(S)N(R')—, —N(R')$S(O)_k$N(R')—, —N(R')—N=, —C(R')=N—, —C(R')=N—N(R')—, —C(R')=N—N=, —$C(R')_2$—N=N—, and —$C(R')_2$—N(R')—N(R')—, where each R' is independently H, alkyl, or substituted alkyl;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

wherein each $R_a$ is independently selected from the group consisting of H, halogen, alkyl, substituted alkyl, —$N(R')_2$, —$C(O)_k$R' where k is 1, 2, or 3, —C(O)$N(R')_2$, —OR', and —$S(O)_k$R', where each R' is independently H, alkyl, or substituted alkyl.

In addition, the following amino acids are included:

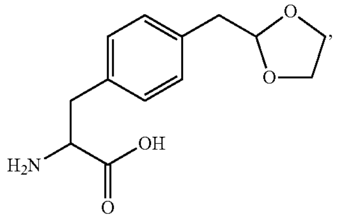

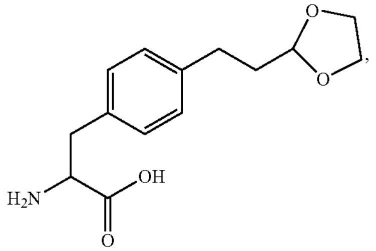

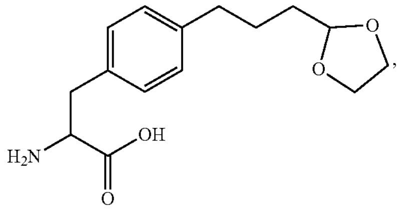

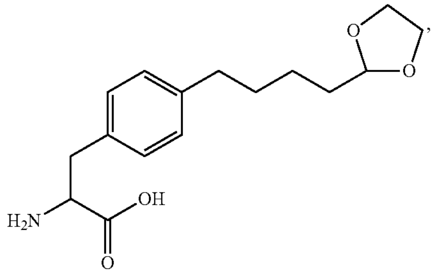

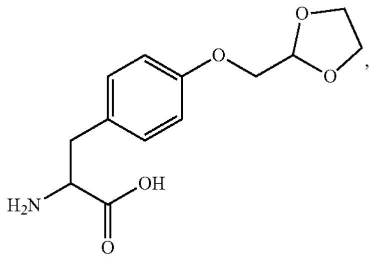

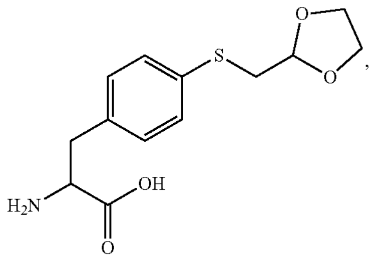

-continued

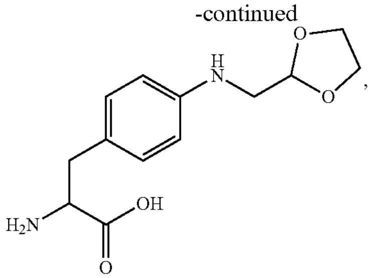

, and

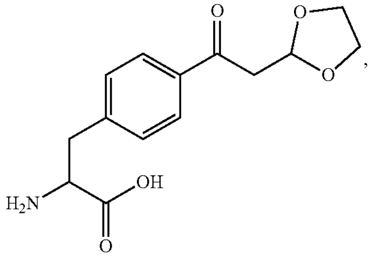

, wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition, the following amino acids having the structure of Formula (X) are included:

(X)

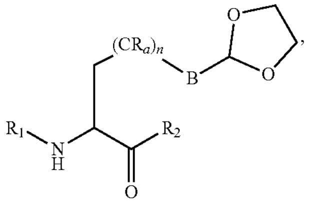

wherein B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —$S(O)_k$— where k is 1, 2, or 3, —$S(O)_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —$S(O)_k$N(R')—, —N(R')C(O)N(R')—, —N(R')C(S)N(R')—, —N(R')S$(O)_k$N(R')—, —C(R')═N—, —C(R')═N—N(R')—, —C(R')═N—N═, —$C(R')_2$—N═N—, and —$C(R')_2$—N(R')—N(R')—, where each R' is independently H, alkyl, or substituted alkyl;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

each $R_a$ is independently selected from the group consisting of H, halogen, alkyl, substituted alkyl, —$N(R')_2$, —$C(O)_k$R' where k is 1, 2, or 3, —$C(O)N(R')_2$, —OR', and —$S(O)_k$R', where each R' is independently H, alkyl, or substituted alkyl; and n is 0 to 8.

In addition, the following amino acids are included:

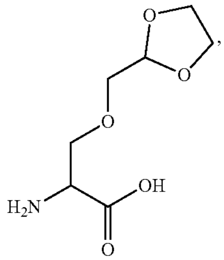

,

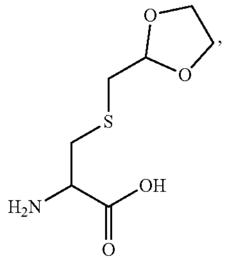

,

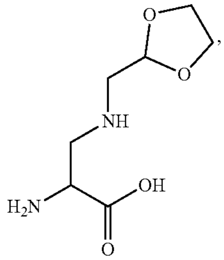

,

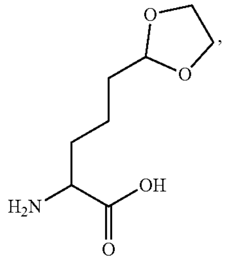

,

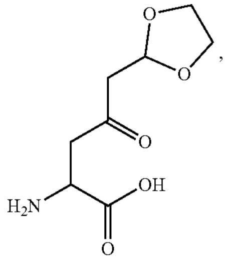

,

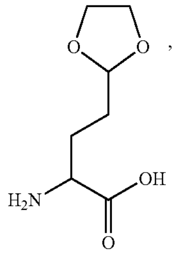

,

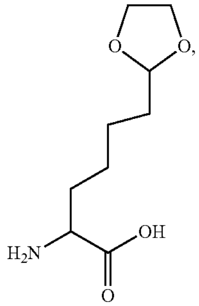

and

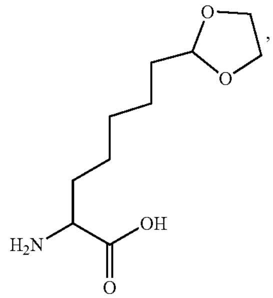

, wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition to monocarbonyl structures, the non-natural amino acids described herein may include groups such as dicarbonyl, dicarbonyl like, masked dicarbonyl and protected dicarbonyl groups.

For example, the following amino acids having the structure of Formula (XI) are included:

(XI)

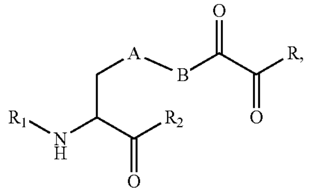

wherein A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene; B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')$_2$—N═N—, and —C(R')$_2$—N(R')—N(R')—, where each R' is independently H, alkyl, or substituted alkyl;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide.

In addition, the following amino acids having the structure of Formula (XII) are included:

(XII)

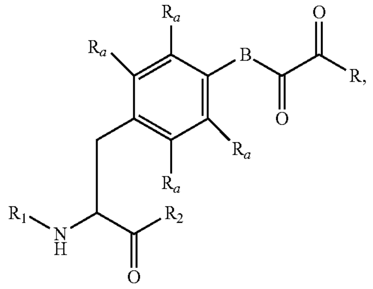

B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —S(O)$_k$— where k is 1, 2, or 3, —S(O)$_k$(alkylene or substituted alkylene)-, —C(O)—, —C(O)-(alkylene or substituted alkylene)-, —C(S)—, —C(S)-(alkylene or substituted alkylene)-, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —S(O)$_k$N(R')—, —N(R')C(O)N(R')—, —N(R')C(S)N(R')—, —N(R')S(O)$_k$N(R')—, —N(R')—N═, —C(R')═N—, —C(R')═N—N(R')—, —C(R')$_2$—N═N—, and —C(R')$_2$—N(R')—N(R')—, where each R' is independently H, alkyl, or substituted alkyl;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

wherein each $R_a$ is independently selected from the group consisting of H, halogen, alkyl, substituted alkyl, —N(R')$_2$, —C(O)$_k$R' where k is 1, 2, or 3, —C(O)N(R')$_2$, —OR', and —S(O)$_k$R', where each R' is independently H, alkyl, or substituted alkyl.

In addition, the following amino acids are included:

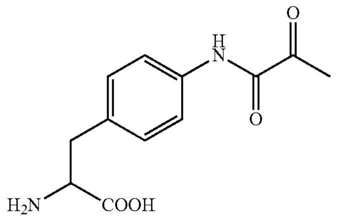

and

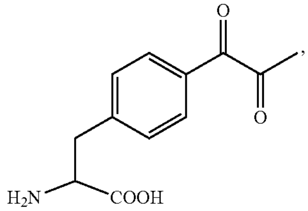

, wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition, the following amino acids having the structure of Formula (XIII) are included:

(XIII)

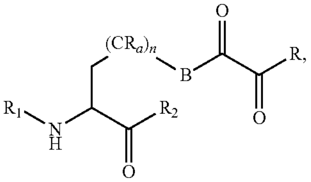

wherein B is optional, and when present is a linker selected from the group consisting of lower alkylene, substituted lower alkylene, lower alkenylene, substituted lower alkenylene, lower heteroalkylene, substituted lower heteroalkylene, —O—, —O-(alkylene or substituted alkylene)-, —S—, —S-(alkylene or substituted alkylene)-, —$S(O)_k$— where k is 1, 2, or 3, —$S(O)_k$(alkylene or substituted alkylene)-, —C(O)—, —C(O)-(alkylene or substituted alkylene)-, —C(S)—, —C(S)-(alkylene or substituted alkylene)-, —N(R')—, —NR'-(alkylene or substituted alkylene)-, —C(O)N(R')—, —CON(R')-(alkylene or substituted alkylene)-, —CSN(R')—, —CSN(R')-(alkylene or substituted alkylene)-, —N(R')CO-(alkylene or substituted alkylene)-, —N(R')C(O)O—, —$S(O)_k$N(R')—, —N(R')C(O)N(R')—, —N(R')C(S)N(R')—, —N(R')$S(O)_k$N(R')—, —N(R')—N=, —C(R')=N—, —C(R')=N—N(R')—, —C(R')=N—N=, —$C(R')_2$—N=N—, and —$C(R')_2$—N(R')—N(R')—, where each R' is independently H, alkyl, or substituted alkyl;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

each $R_a$ is independently selected from the group consisting of H, halogen, alkyl, substituted alkyl, —$N(R')_2$, —$C(O)_k$R' where k is 1, 2, or 3, —$C(O)N(R')_2$, —OR', and —$S(O)_k$R', where each R' is independently H, alkyl, or substituted alkyl; and n is 0 to 8.

In addition, the following amino acids are included:

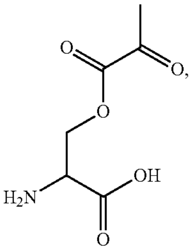

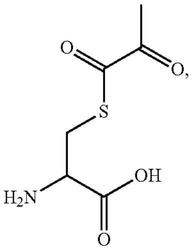

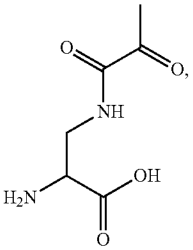

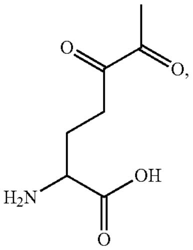

-continued

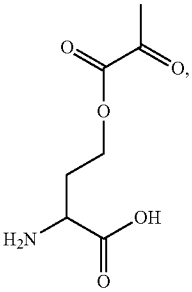

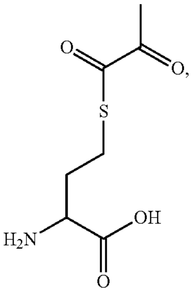

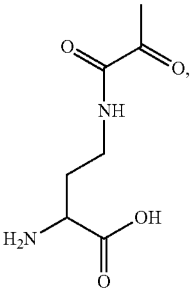

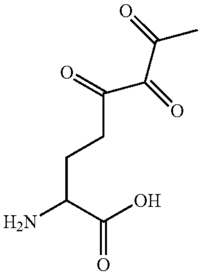

,

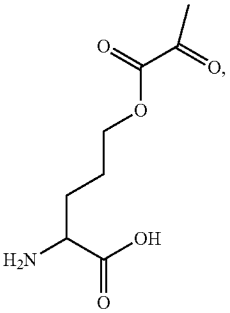

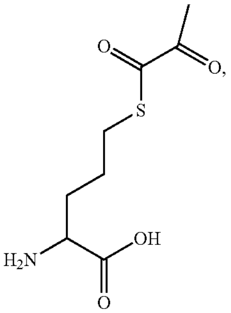

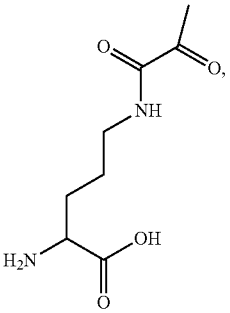

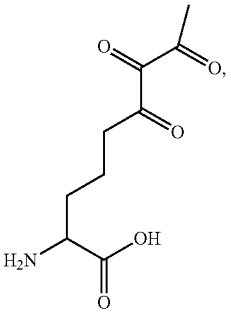

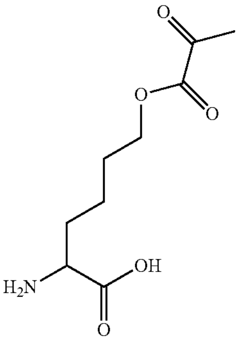

,

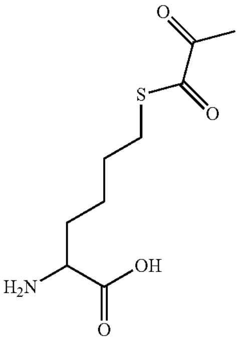

,

-continued

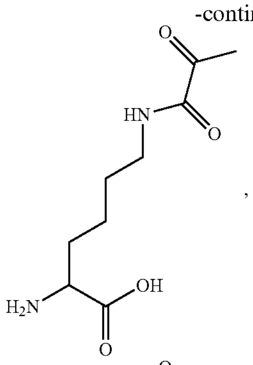

, and

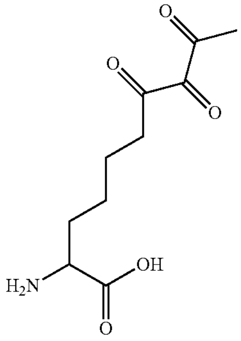

, wherein such compounds are optionally amino protected, optionally carboxyl protected, optionally amino protected and carboxyl protected, or a salt thereof. In addition, these non-natural amino acids and any of the following non-natural amino acids may be incorporated into a non-natural amino acid polypeptide.

In addition, the following amino acids having the structure of Formula (XIV) are included:

(XIV)

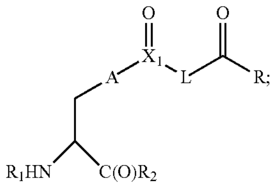

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

$X_1$ is C, S, or S(O); and L is alkylene, substituted alkylene, N(R')(alkylene) or N(R')(substituted alkylene), where R' is H, alkyl, substituted alkyl, cycloalkyl, or substituted cycloalkyl.

In addition, the following amino acids having the structure of Formula (XIV-A) are included:

(XIV-A)

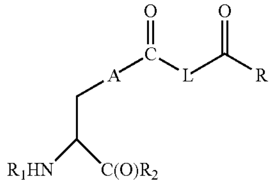

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

L is alkylene, substituted alkylene, N(R')(alkylene) or N(R')(substituted alkylene), where R' is H, alkyl, substituted alkyl, cycloalkyl, or substituted cycloalkyl.

In addition, the following amino acids having the structure of Formula (XIV—B) are included:

(XIV-B)

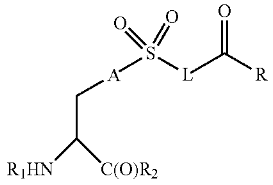

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

L is alkylene, substituted alkylene, N(R')(alkylene) or N(R')(substituted alkylene), where R' is H, alkyl, substituted alkyl, cycloalkyl, or substituted cycloalkyl.

In addition, the following amino acids having the structure of Formula (XV) are included;

(XV)

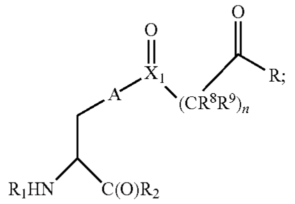

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

$X_1$ is C, S, or S(O); and n is 0, 1, 2, 3, 4, or 5; and each $R^8$ and $R^9$ on each $CR^8R^9$ group is independently selected from the group consisting of H, alkoxy, alkylamine, halogen, alkyl, aryl, or any $R^8$ and $R^9$ can together form =O or a cycloalkyl, or any to adjacent $R^8$ groups can together form a cycloalkyl.

In addition, the following amino acids having the structure of Formula (XV-A) are included:

(XV-A)

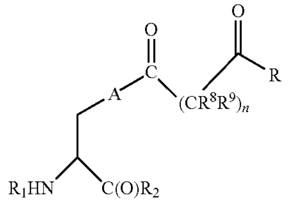

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

n is 0, 1, 2, 3, 4, or 5; and each $R^8$ and $R^9$ on each $CR^8R^9$ group is independently selected from the group consisting of H, alkoxy, alkylamine, halogen, alkyl, aryl, or any $R^8$ and $R^9$ can together form =O or a cycloalkyl, or any to adjacent $R^8$ groups can together form a cycloalkyl.

In addition, the following amino acids having the structure of Formula (XV—B) are included:

(XV-B)

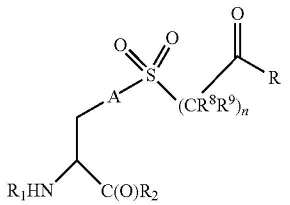

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

n is 0, 1, 2, 3, 4, or 5; and each $R^8$ and $R^9$ on each $CR^8R^9$ group is independently selected from the group consisting of H, alkoxy, alkylamine, halogen, alkyl, aryl, or any $R^8$ and $R^9$ can together form =O or a cycloalkyl, or any to adjacent $R^8$ groups can together form a cycloalkyl.

In addition, the following amino acids having the structure of Formula (XVI) are included:

(XVI)

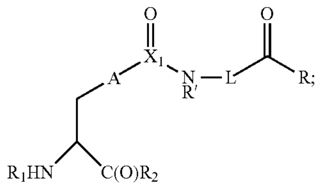

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

$X_1$ is C, S, or S(O); and L is alkylene, substituted alkylene, N(R')(alkylene) or N(R')(substituted alkylene), where R' is H, alkyl, substituted alkyl, cycloalkyl, or substituted cycloalkyl.

In addition, the following amino acids having the structure of Formula (XVI-A) are included:

(XVI-A)

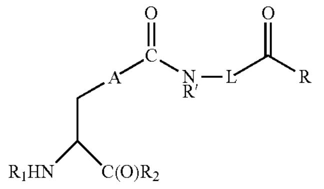

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

L is alkylene, substituted alkylene, N(R')(alkylene) or N(R')(substituted alkylene), where R' is H, alkyl, substituted alkyl, cycloalkyl, or substituted cycloalkyl.

In addition, the following amino acids having the structure of Formula (XVI—B) are included:

(XVI-B)

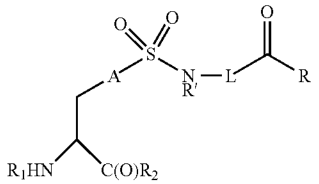

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

R is H, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

L is alkylene, substituted alkylene, N(R')(alkylene) or N(R')(substituted alkylene), where R' is H, alkyl, substituted alkyl, cycloalkyl, or substituted cycloalkyl.

In addition, amino acids having the structure of Formula (XVII) are included:

(XVII)

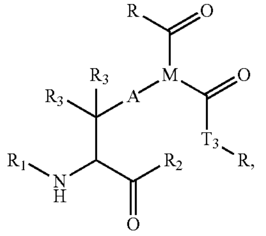

wherein:

A is optional, and when present is lower alkylene, substituted lower alkylene, lower cycloalkylene, substituted lower cycloalkylene, lower alkenylene, substituted lower alkenylene, alkynylene, lower heteroalkylene, substituted heteroalkylene, lower heterocycloalkylene, substituted lower heterocycloalkylene, arylene, substituted arylene, heteroarylene, substituted heteroarylene, alkarylene, substituted alkarylene, aralkylene, or substituted aralkylene;

M is —C($R_3$)—,

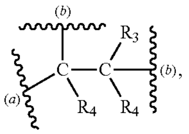

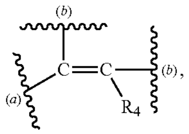

-continued

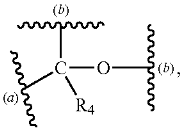, 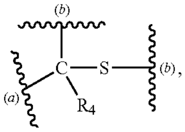,

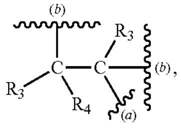, 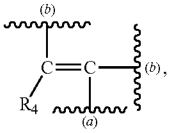,

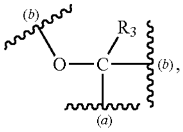, or 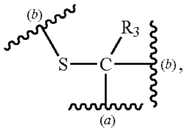, where (a) indicates bonding to the A group and (b) indicates bonding to respective carbonyl groups, $R_3$ and $R_4$ are independently chosen from H, halogen, alkyl, substituted alkyl, cycloalkyl, or substituted cycloalkyl, or $R_3$ and $R_4$ or two $R_3$ groups or two $R_4$ groups optionally form a cycloalkyl or a heterocycloalkyl;

R is H, halogen, alkyl, substituted alkyl, cycloalkyl, or substituted cycloalkyl;

$T_3$ is a bond, C(R)(R), O, or S, and R is H, halogen, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide.

In addition, amino acids having the structure of Formula (XVIII) are included:

wherein:

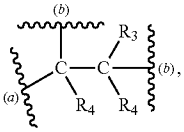, 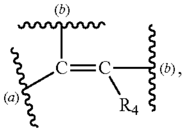,

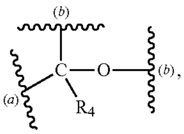, 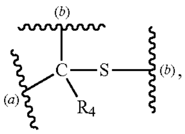,

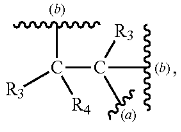, 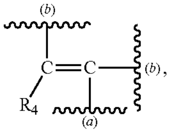,

-continued

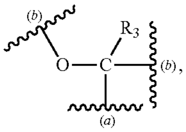, or 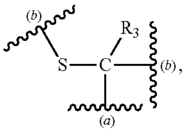,

M is —$C(R_3)$—, (XVIII)

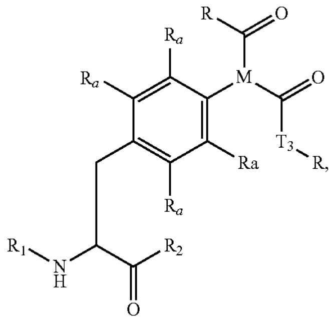

where (a) indicates bonding to the A group and (b) indicates bonding to respective carbonyl groups, $R_3$ and $R_4$ are independently chosen from H, halogen, alkyl, substituted alkyl, cycloalkyl, or substituted cycloalkyl, or $R_3$ and $R_4$ or two $R_3$ groups or two $R_4$ groups optionally form a cycloalkyl or a heterocycloalkyl;

R is H, halogen, alkyl, substituted alkyl, cycloalkyl, or substituted cycloalkyl;

$T_3$ is a bond, C(R)(R), O, or S, and R is H, halogen, alkyl, substituted alkyl, cycloalkyl, or substituted cycloalkyl;

$R_1$ is optional, and when present, is H, an amino protecting group, resin, amino acid, polypeptide, or polynucleotide; and $R_2$ is optional, and when present, is OH, an ester protecting group, resin, amino acid, polypeptide, or polynucleotide;

each $R_a$ is independently selected from the group consisting of H, halogen, alkyl, substituted alkyl, —$N(R')_2$, —$C(O)_kR'$ where k is 1, 2, or 3, —$C(O)N(R')_2$, —OR', and —$S(O)_kR'$, where each R' is independently H, alkyl, or substituted alkyl.

In addition, amino acids having the structure of Formula (XIX) are included:

(XIX)

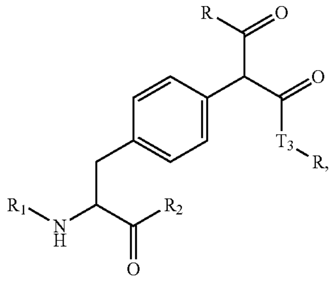

wherein;

R is H, halogen, alkyl, substituted alkyl, cycloalkyl, or substituted cycloalkyl; and $T_3$ is O, or S.

In addition, amino acids having the structure of Formula (XX) are included:

(XX)

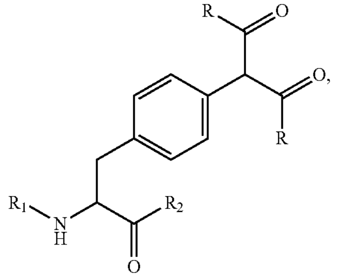

wherein:

R is H, halogen, alkyl, substituted alkyl, cycloalkyl, or substituted cycloalkyl.

In addition, the following amino acids having structures of Formula (XXI) are included:

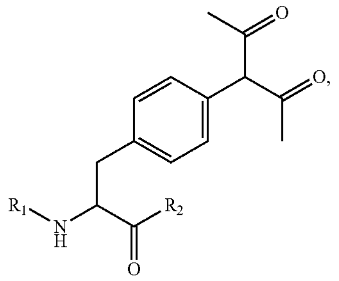

and

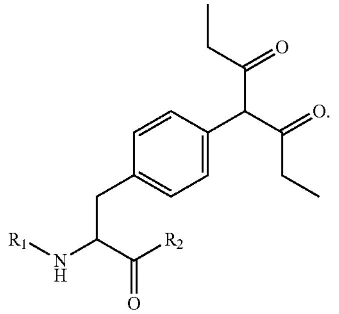

In some embodiments, a polypeptide comprising a non-natural amino acid is chemically modified to generate a reactive carbonyl or dicarbonyl functional group. For instance, an aldehyde functionality useful for conjugation reactions can be generated from a functionality having adjacent amino and hydroxyl groups. Where the biologically active molecule is a polypeptide, for example, an N-terminal serine or threonine (which may be normally present or may be exposed via chemical or enzymatic digestion) can be used to generate an aldehyde functionality under mild oxidative cleavage conditions using periodate. See, e.g., Gaertner, et. al., Bioconjug. Chem. 3: 262-268 (1992); Geoghegan, K. & Stroh, J., Bioconjug. Chem. 3:138-146 (1992); Gaertner et al., J. Biol. Chem. 269:7224-7230 (1994). However, methods known in the art are restricted to the amino acid at the N-terminus of the peptide or protein.

In the present invention, a non-natural amino acid bearing adjacent hydroxyl and amino groups can be incorporated into the polypeptide as a "masked" aldehyde functionality. For example, 5-hydroxylysine bears a hydroxyl group adjacent to the epsilon amine. Reaction conditions for generating the aldehyde typically involve addition of molar excess of sodium metaperiodate under mild conditions to avoid oxidation at other sites within the polypeptide. The pH of the oxidation reaction is typically about 7.0. A typical reaction involves the addition of about 1.5 molar excess of sodium meta periodate to a buffered solution of the polypeptide, followed by incubation for about 10 minutes in the dark. See, e.g. U.S. Pat. No. 6,423,685.

The carbonyl or dicarbonyl functionality can be reacted selectively with a hydroxylamine-containing reagent under mild conditions in aqueous solution to form the corresponding oxime linkage that is stable under physiological conditions. See, e.g., Jencks, W. P., J. Am. Chem. Soc. 81, 475-481 (1959); Shao, J. and Tam, J. P., J. Am, Chem. Soc. 117:3893-3899 (1995). Moreover, the unique reactivity of the carbonyl or dicarbonyl group allows for selective modification in the presence of the other amino acid side chains. See, e.g., Cornish, V. W., et al., J. Am. Chem. Soc. 118: 8150-8151 (1996); Geoghegan, K. F. & Stroh, J. G., Bioconjug. Chem. 3:138-146 (1992); Mahal, L. K., et al., Science 276:1125-1128 (1997).

A. Carbonyl Reactive Groups

Amino acids with a carbonyl reactive group allow for a variety of reactions to link molecules (including but not limited to, PEG or other water soluble molecules) via nucleophilic addition or aldol condensation reactions among others.

Exemplary carbonyl-containing amino acids can be represented as follows:

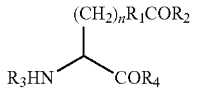

wherein n is 0-10; $R_1$ is an alkyl, aryl, substituted alkyl, or substituted aryl; $R_2$ is H, alkyl, aryl, substituted alkyl, and substituted aryl; and $R_3$ is H, an amino acid, a polypeptide, or an amino terminus modification group, and $R_4$ is H, an amino acid, a polypeptide, or a carboxy terminus modification group. In some embodiments, n is 1, $R_1$ is phenyl and $R_2$ is a simple alkyl (i.e., methyl, ethyl, or propyl) and the ketone moiety is positioned in the para position relative to the alkyl side chain. In some embodiments, n is 1, $R_1$ is phenyl and $R_2$ is a simple alkyl (i.e., methyl, ethyl, or propyl) and the ketone moiety is positioned in the meta position relative to the alkyl side chain.

The synthesis of p-acetyl-(+/−)-phenylalanine and m-acetyl-(+/−)-phenylalanine is described in Zhang, Z., et al., Biochemistry 42: 6735-6746 (2003), which is incorporated by reference herein. Other carbonyl-containing amino acids can be similarly prepared by one of ordinary skill in the art.

In some embodiments, a polypeptide comprising a non-naturally encoded amino acid is chemically modified to generate a reactive carbonyl functional group. For instance, an aldehyde functionality useful for conjugation reactions can be generated from a functionality having adjacent amino and hydroxyl groups. Where the biologically active molecule is a polypeptide, for example, an N-terminal serine or threonine (which may be normally present or may be exposed via chemical or enzymatic digestion) can be used to generate an aldehyde functionality under mild oxidative cleavage conditions using periodate. See, e.g., Gaertner, et al., *Bioconjug. Chem.* 3: 262-268 (1992); Geoghegan, K. & Stroh, J., *Bioconjug. Chem.* 3:138-146 (1992); Gaertner et al., *J. Biol. Chem.* 269:7224-7230 (1994). However, methods known in the art are restricted to the amino acid at the N-terminus of the peptide or protein.

In the present invention, a non-naturally encoded amino acid bearing adjacent hydroxyl and amino groups can be incorporated into the polypeptide as a "masked" aldehyde functionality. For example, 5-hydroxylysine bears a hydroxyl group adjacent to the epsilon amine. Reaction conditions for generating the aldehyde typically involve addition of molar excess of sodium metaperiodate under mild conditions to avoid oxidation at other sites within the polypeptide. The pH of the oxidation reaction is typically about 7.0. A typical reaction involves the addition of about 1.5 molar excess of sodium meta periodate to a buffered solution of the polypeptide, followed by incubation for about 10 minutes in the dark. See, e.g. U.S. Pat. No. 6,423,685, which is incorporated by reference herein.

The carbonyl functionality can be reacted selectively with a hydrazine-, hydrazide-, hydroxylamine-, or semicarbazide-containing reagent under mild conditions in aqueous solution to form the corresponding hydrazone, oxime, or semicarbazone linkages, respectively, that are stable under physiological conditions. See, e.g., Jencks, W. P., *J. Am. Chem. Soc.* 81, 475-481 (1959); Shao, J. and Tam, J. P., *J. Am. Chem. Soc.* 117:3893-3899 (1995). Moreover, the unique reactivity of the carbonyl group allows for selective modification in the presence of the other amino acid side chains. See, e.g., Cornish, V. W., et al., *J. Am. Chem. Soc.* 118:8150-8151 (1996); Geoghegan, K. F. & Stroh, J. G., *Bioconjug. Chem.* 3:138-146 (1992); Mahal, L. K., et al., *Science* 276:1125-1128 (1997).

B. Hydrazine, Hydrazide or Semicarbazide Reactive Groups

Non-naturally encoded amino acids containing a nucleophilic group, such as a hydrazine, hydrazide or semicarbazide, allow for reaction with a variety of electrophilic groups to form conjugates (including but not limited to, with PEG or other water soluble polymers).

Exemplary hydrazine, hydrazide or semicarbazide-containing amino acids can be represented as follows:

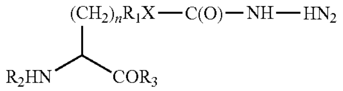

wherein n is 0-10; $R_1$ is an alkyl, aryl, substituted alkyl, or substituted aryl or not present; X, is O, N, or S or not present; $R_2$ is H, an amino acid, a polypeptide, or an amino terminus modification group, and $R_3$ is H, an amino acid, a polypeptide, or a carboxy terminus modification group.

In some embodiments, n is 4, $R_1$ is not present, and X is N. In some embodiments, n is 2, $R_1$ is not present, and X is not present. In some embodiments, n is 1, $R_1$ is phenyl, X is O, and the oxygen atom is positioned para to the alphatic group on the aryl ring.

Hydrazide-, hydrazine-, and semicarbazide-containing amino acids are available from commercial sources. For instance, L-glutamate-□-hydrazide is available from Sigma Chemical (St. Louis, Mo.). Other amino acids not available commercially can be prepared by one of ordinary skill in the art. See, e.g., U.S. Pat. No. 6,281,211, which is incorporated by reference herein.

Polypeptides containing non-naturally encoded amino acids that bear hydrazide, hydrazine or semicarbazide functionalities can be reacted efficiently and selectively with a variety of molecules that contain aldehydes or other functional groups with similar chemical reactivity. See, e.g., Shao, J. and Tam, J., *J. Am. Chem. Soc.* 117:3893-3899 (1995). The unique reactivity of hydrazide, hydrazine and semicarbazide functional groups makes them significantly more reactive toward aldehydes, ketones and other electrophilic groups as compared to the nucleophilic groups present on the 20 common amino acids (including but not limited to, the hydroxyl group of serine or threonine or the amino groups of lysine and the N-terminus).

C. Aminooxy-Containing Amino Acids

Non-naturally encoded amino acids containing an aminooxy (also called a hydroxylamine) group allow for reaction with a variety of electrophilic groups to form conjugates (including but not limited to, with PEG or other water soluble polymers). Like hydrazines, hydrazides and semicarbazides, the enhanced nucleophilicity of the aminooxy group permits it to react efficiently and selectively with a variety of molecules that contain aldehydes or other functional groups with similar chemical reactivity. See, e.g., Shao, J. and Tam, *J., Am. Chem. Soc.* 117:3893-3899 (1995); H. Hang and C. Bertozzi, *Acc. Chem. Res.* 34: 727-736 (2001). Whereas the result of reaction with a hydrazine group is the corresponding hydrazone, however, an oxime results generally from the reaction of an aminooxy group with a carbonyl-containing group such as a ketone.

Exemplary amino acids containing aminooxy groups can be represented as follows:

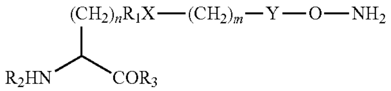

wherein n is 0-10; $R_1$ is an alkyl, aryl, substituted alkyl, or substituted aryl or not present; X is O, N, S or not present; m is 0-10; Y=C(O) or not present; $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is O, m is 1, and Y is present. In some embodiments, n is 2, $R_1$ and X are not present, m is 0, and Y is not present.

Aminooxy-containing amino acids can be prepared from readily available amino acid precursors (homoserine, serine and threonine). See, e.g., M. Carrasco and R. Brown, *J. Org. Chem.* 68: 8853-8858 (2003). Certain aminooxy-containing amino acids, such as L-2-amino-4-(aminooxy)butyric acid), have been isolated from natural sources (Rosenthal, G., Life Sci. 60: 1635-1641 (1997). Other aminooxy-containing amino acids can be prepared by one of ordinary skill in the art.

D. Azide and Alkyne Reactive Groups

The unique reactivity of azide and alkyne functional groups makes them extremely useful for the selective modification of polypeptides and other biological molecules. Organic azides, particularly alphatic azides, and alkynes are generally stable toward common reactive chemical conditions. In particular, both the azide and the alkyne functional groups are inert toward the side chains (i.e., R groups) of the 20 common amino acids found in naturally-occurring polypeptides. When brought into close proximity however, the "spring-loaded" nature of the azide and alkyne groups is revealed, and they react selectively and efficiently via Huisgen [3+2] cycloaddition reaction to generate the corresponding triazole. See, e.g., Chin J., et al., *Science* 301:964-7

(2003); Wang, Q., et al., *J. Am. Chem. Soc.* 125, 3192-3193 (2003); Chin, J. W., et al., *J. Am. Chem. Soc.* 124:9026-9027 (2002).

Because the Huisgen cycloaddition reaction involves a selective cycloaddition reaction (see, e.g., Padwa, A., in Comprehensive Organic Synthesis, Vol. 4, (ed. Trost, B. M., 1991), p. 1069-1109; Huisgen, R. in 1,3-Dipolar Cycloaddition Chemistry, (ed. Padwa, A., 1984), p. 1-176) rather than a nucleophilic substitution, the incorporation of non-naturally encoded amino acids bearing azide and alkyne-containing side chains permits the resultant polypeptides to be modified selectively at the position of the non-naturally encoded amino acid. Cycloaddition reaction involving azide or alkyne-containing TC can be carried out at room temperature under aqueous conditions by the addition of Cu(II) (including but not limited to, in the form of a catalytic amount of $CuSO_4$) in the presence of a reducing agent for reducing Cu(II) to Cu(I), in situ, in catalytic amount. See, e.g., Wang, Q., et al., *J. Am. Chem. Soc.* 125, 3192-3193 (2003); Tornoe, C. W., et al., *J. Org. Chem.* 67:3057-3064 (2002); Rostovtsev, et al., *Angew. Chem. Int. Ed.* 41:2596-2599 (2002). Exemplary reducing agents include, including but not limited to, ascorbate, metallic copper, quinine, hydroquinone, vitamin K, glutathione, cysteine, $Fe^{2+}$, $Co^{2+}$, and an applied electric potential.

In some cases, where a Huisgen [3+2] cycloaddition reaction between an azide and an alkyne is desired, the TC comprises a non-naturally encoded amino acid comprising an alkyne moiety and the water soluble polymer to be attached to the amino acid comprises an azide moiety. Alternatively, the converse reaction (i.e., with the azide moiety on the amino acid and the alkyne moiety present on the water soluble polymer) can also be performed.

The azide functional group can also be reacted selectively with a water soluble polymer containing an aryl ester and appropriately functionalized with an aryl phosphine moiety to generate an amide linkage. The aryl phosphine group reduces the azide in situ and the resulting amine then reacts efficiently with a proximal ester linkage to generate the corresponding amide. See, e.g., E. Saxon and C. Bertozzi, *Science* 287, 2007-2010 (2000). The azide-containing amino acid can be either an alkyl azide (including but not limited to, 2-amino-6-azido-1-hexanoic acid) or an aryl azide (p-azido-phenylalanine).

Exemplary water soluble polymers containing an aryl ester and a phosphine moiety can be represented as follows:

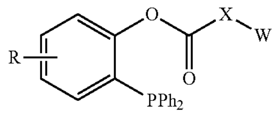

wherein X can be O, N, S or not present, Ph is phenyl, W is a water soluble polymer and R can be H, alkyl, aryl, substituted alkyl and substituted aryl groups. Exemplary R groups include but are not limited to —$CH_2$, —$C(CH_3)_3$, —OR', —NR'R", —SR', -halogen, —C(O)R', —CONR'R", —$S(O)_2R'$, —$S(O)_2NR'R"$, —CN and —$NO_2$, R', R", R"' and R"" each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R"' and groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, —$CF_3$ and —$CH_2CF_3$) and acyl (including but not limited to, —$C(O)CH_3$, —$C(O)CF_3$, —$C(O)CH_2OCH_3$, and the like).

The azide functional group can also be reacted selectively with a water soluble polymer containing a thioester and appropriately functionalized with an aryl phosphine moiety to generate an amide linkage. The aryl phosphine group reduces the azide in situ and the resulting amine then reacts efficiently with the thioester linkage to generate the corresponding amide. Exemplary water soluble polymers containing a thioester and a phosphine moiety can be represented as follows:

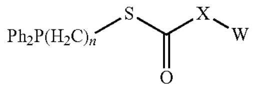

wherein n is 1-10; X can be O, N, S or not present, Ph is phenyl, and W is a water soluble polymer.

Exemplary alkyne-containing amino acids can be represented as follows:

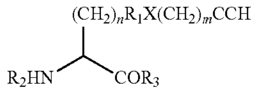

wherein n is 0-10; $R_3$ is an alkyl, aryl, substituted alkyl, or substituted aryl or not present; X is O, N, S or not present; m is 0-10, $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is not present, m is 0 and the acetylene moiety is positioned in the para position relative to the alkyl side chain. In some embodiments, n is 1, $R_1$ is phenyl, X is O, m is 1 and the propargyloxy group is positioned in the para position relative to the alkyl side chain (i.e., O-propargyl-tyrosine). In some embodiments, n is 1, $R_1$ and X are not present, and m is 0 (i.e., proparylglycine).

Alkyne-containing amino acids are commercially available. For example, propargylglycine is commercially available from Peptech (Burlington, Mass.). Alternatively, alkyne-containing amino acids can be prepared according to standard methods. For instance, p-propargyloxyphenylalanine can be synthesized, for example, as described in Deiters, A., et al., *J. Am. Chem. Soc.* 125: 11782-11783 (2003), and 4-alkynyl-L-phenylalanine can be synthesized as described in Kayser, B., et al., *Tetrahedron* 53(7): 2475-2484 (1997). Other alkyne-containing amino acids can be prepared by one of ordinary skill in the art.

Exemplary azide-containing amino acids can be represented as follows:

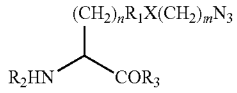

wherein n is 0-10; $R_1$ is an alkyl, aryl, substituted alkyl, substituted aryl or not present; X is O, N, S or not present; m is 0-10; $R_2$ is H, an amino acid, a polypeptide, or an amino terminus modification group, and $R_3$ is H, an amino acid, a polypeptide, or a carboxy terminus modification group. In some embodiments, n is 1, $R_1$ is phenyl, X is not present, in is 0 and the azide moiety is positioned para to the alkyl side chain. In some embodiments, n is 0-4 and $R_1$ and X are not present, and m=0. In some embodiments, n is 1, $R_1$ is phenyl, X is O, m is 2 and the -azidoethoxy moiety is positioned in the para position relative to the alkyl side chain.

Azide-containing amino acids are available from commercial sources. For instance, 4-azidophenylalanine can be obtained from Chem-Impex International, Inc. (Wood Dale, Ill.). For those azide-containing amino acids that are not commercially available, the azide group can be prepared relatively readily using standard methods known to those of ordinary skill in the art, including but not limited to, via displacement of a suitable leaving group (including but not limited to, halide, mesylate, tosylate) or via opening of a suitably protected lactone. See, e.g., Advanced Organic Chemistry by March (Third Edition, 1985, Wiley and Sons, New York).

E. Aminothiol Reactive Groups

The unique reactivity of beta-substituted aminothiol functional groups makes them extremely useful for the selective modification of polypeptides and other biological molecules that contain aldehyde groups via formation of the thiazolidine. See, e.g., J. Shao and J. Tam, *J. Am. Chem. Soc.* 1995, 117 (14) 3893-3899. In some embodiments, beta-substituted aminothiol amino acids can be incorporated into TC polypeptides and then reacted with water soluble polymers comprising an aldehyde functionality. In some embodiments, a water soluble polymer, drug conjugate or other payload can be coupled to a targeting polypeptide of the TC comprising a beta-substituted aminothiol amino acid via formation of the thiazolidine.

F. Additional Reactive Groups

Additional reactive groups and non-naturally encoded amino acids, including but not limited to para-amino-phenylalanine, that can be incorporated into TC polypeptides of the invention are described in the following patent applications which are all incorporated by reference in their entirety herein: U.S. Patent Publication No. 2006/0194256, U.S. Patent Publication No. 2006/0217532, U.S. Patent Publication No. 2006/0217289, U.S. Provisional Patent No. 60/755,338; U.S. Provisional Patent No. 60/755,711; U.S. Provisional Patent No. 60/755,018; International Patent Application No. PCT/US06/49397; WO 2006/069246; U.S. Provisional Patent No. 60/743,041; U.S. Provisional Patent No. 60/743,040; International Patent Application No. PCT/US06/47822; U.S. Provisional Patent No. 60/882,819; U.S. Provisional Patent No. 60/882,500; and U.S. Provisional Patent No. 60/870,594. These applications also discuss reactive groups that may be present on PEG or other polymers, including but not limited to, hydroxylamine (aminooxy) groups for conjugation.

Location of Non-Natural Amino Acids in TC Polypeptides

The methods and compositions described herein include incorporation of one or more non-natural amino acids into a targeting polypeptide to make a TC of the present invention. One or more non-natural amino acids may be incorporated at one or more particular positions which do not disrupt activity of the targeting polypeptide. This can be achieved by making "conservative" substitutions, including but not limited to, substituting hydrophobic amino acids with non-natural or natural hydrophobic amino acids, bulky amino acids with non-natural or natural bulky amino acids, hydrophilic amino acids with non-natural or natural hydrophilic amino acids) and/or inserting the non-natural amino acid in a location that is not required for activity.

A variety of biochemical and structural approaches can be employed to select the desired sites for substitution with a non-natural amino acid within the targeting polypeptide of the TC. In some embodiments, the non-natural amino acid is linked at the C-terminus of the TLR-agonist derivative. In other embodiments, the non-natural amino acid is linked at the N-terminus of the TLR-agonist derivative. Any position of the targeting polypeptide of the TC is suitable for selection to incorporate a non-natural amino acid, and selection may be based on rational design or by random selection for any or no particular desired purpose. Selection of desired sites may be based on producing a non-natural amino acid polypeptide (which may be further modified or remain unmodified) having any desired property or activity, including but not limited to a receptor binding modulators, receptor activity modulators, modulators of binding to binder partners, binding partner activity modulators, binding partner conformation modulators, dimer or multimer formation, no change to activity or property compared to the native molecule, or manipulating any physical or chemical property of the polypeptide such as solubility, aggregation, or stability. Alternatively, the sites identified as critical to biological activity may also be good candidates for substitution with a non-natural amino acid, again depending on the desired activity sought for the polypeptide. Another alternative would be to simply make serial substitutions in each position on the polypeptide chain with a non-natural amino acid and observe the effect on the activities of the polypeptide. Any means, technique, or method for selecting a position for substitution with a non-natural amino acid into any polypeptide is suitable for use in the methods, techniques and compositions described herein.

The structure and activity of naturally-occurring mutants of a polypeptide that contain deletions can also be examined to determine regions of the protein that are likely to be tolerant of substitution with a non-natural amino acid. Once residues that are likely to be intolerant to substitution with non-natural amino acids have been eliminated, the impact of proposed substitutions at each of the remaining positions can be examined using methods including, but not limited to, the three-dimensional structure of the relevant polypeptide, and any associated ligands or binding proteins. X-ray crystallographic and NMR structures of many polypeptides are available in the Protein Data Bank (PDB, on the World Wide Web at resb.org), a centralized database containing three-dimensional structural data of large molecules of proteins and nucleic acids, one can be used to identify amino acid positions that can be substituted with non-natural amino acids. In addition, models may be made investigating the secondary and tertiary structure of polypeptides, if three-dimensional structural data is not available. Thus, the identity of amino acid positions that can be substituted with non-natural amino acids can be readily obtained.

Exemplary sites of incorporation of a non-natural amino acid include, but are not limited to, those that are excluded from potential receptor binding regions, or regions for binding to binding proteins or ligands may be fully or partially solvent exposed, have minimal or no hydrogen-bonding interactions with nearby residues, may be minimally exposed to nearby reactive residues, and/or may be in regions that are highly flexible as predicted by the three-dimensional crystal structure of a particular polypeptide with its associated receptor, ligand or binding proteins.

A wide variety of non-natural amino acids can be substituted for, or incorporated into, a given position in a polypeptide. By way of example, a particular non-natural amino acid may be selected for incorporation based on an examination of the three-dimensional crystal structure of a polypeptide with its associated ligand, receptor and/or binding proteins, a preference for conservative substitutions In one embodiment, the methods described herein include incorporating a non-natural amino acid into the targeting polypeptide of the TC, where the targeting polypeptide of the TC comprises a first reactive group; and contacting the targeting polypeptide of the TC with a molecule (including but not limited to a second protein or polypeptide or polypeptide analog; an antibody or antibody fragment; and any combination thereof) that comprises a second reactive group. In certain embodiments, the first reactive group is a hydroxylamine moiety and the second reactive group is a carbonyl or dicarbonyl moiety, whereby an oxime linkage is formed. In certain embodiments, the first reactive group is a carbonyl or dicarbonyl moiety and the second reactive group is a hydroxylamine moiety, whereby an oxime linkage is formed. In certain embodiments, the first reactive group is a carbonyl or dicarbonyl moiety and the second reactive group is an oxime moiety, whereby an oxime exchange reaction occurs. In certain embodiments, the first reactive group is an oxime moiety and the second reactive group is carbonyl or dicarbonyl moiety, whereby an oxime exchange reaction occurs.

In some cases, the targeting polypeptide of the TC incorporation(s) of a non-natural amino acid will be combined with other additions, substitutions, or deletions within the polypeptide to affect other chemical, physical, pharmacologic and/or biological traits. In some cases, the other additions, substitutions or deletions may increase the stability (including but not limited to, resistance to proteolytic degradation) of the polypeptide or increase affinity of the polypeptide for its appropriate receptor, ligand and/or binding proteins. In some cases, the other additions, substitutions or deletions may increase the solubility (including but not limited to, when expressed in *E. coli* or other host cells) of the polypeptide. In some embodiments, sites are selected for substitution with a naturally encoded or non-natural amino acid in addition to another site for incorporation of a non-natural amino acid for the purpose of increasing the polypeptide solubility following expression in *E. coli*, or other recombinant host cells. In some embodiments, the polypeptides comprise another addition, substitution, or deletion that modulates affinity for the associated ligand, binding proteins, and/or receptor, modulates (including but not limited to, increases or decreases) receptor dimerization, stabilizes receptor dimers, modulates circulating half-life, modulates release or bio-availability, facilitates purification, or improves or alters a particular route of administration. Similarly, the non-natural amino acid polypeptide can comprise chemical or enzyme cleavage sequences, protease cleavage sequences, reactive groups, antibody-binding domains (including but not limited to, FLAG or poly-His) or other affinity based sequences (including but not limited to, FLAG, poly-His, GST, etc.) or linked molecules (including but not limited to, biotin) that improve detection (including but not limited to, GFP), purification, transport thru tissues or cell membranes, prodrug release or activation, size reduction, or other traits of the polypeptide.

Anti-HER2 Antibody as Exemplar for Targeting Moiety

The methods, compositions, strategies and techniques described herein are not limited to a particular type, class or family of targeting moiety polypeptides or proteins. Indeed, virtually any targeting moiety polypeptides may be designed or modified to include at least one "modified or unmodified" non-natural amino acids containing targeting polypeptide of the TC described herein. By way of example only, the targeting moiety polypeptide can be homologous to a therapeutic protein selected from the group consisting of: alpha-1 antitrypsin, angiostatin, antihemolytic factor, antibody, antibody fragment, monoclonal antibody (e.g., bevacizumab, cetuximab, panitumumab, infliximab, adalimumab, basiliximab, daclizumab, omalizumab, ustekinumab, etanercept, gemituzumab, alemtuzumab, rituximab, trastuzumab, nimotuzumab, palivizumab, and abciximab), apolipoprotein, apoprotein, atrial natriuretic factor, atrial natriuretic polypeptide, atrial peptide, C—X—C chemokine, T39765, NAP-2, ENA-78, gro-a, gro-b, gro-c, IP-10, GCP-2, NAP-4, SDF-1, PF4, MIG, calcitonin, c-kit ligand, CC chemokine, monocyte chemoattractant protein-1, monocyte chemoattractant protein-2, monocyte chemoattractant protein-3, monocyte inflammatory protein-1 alpha, monocyte inflammatory protein-i beta, RANTES, 1309, R83915, R91733, HCC1, T58847, D31065, T64262, CD40, CD40 ligand, c-kit ligand, collagen, colony stimulating factor (CSF), complement factor 5a, complement inhibitor, complement receptor 1, cytokine, epithelial neutrophil activating peptide-78, MIP-16, MCP-1, epidermal growth factor (EGF), epithelial neutrophil activating peptide, erythropoietin (EPO), exfoliating toxin, Factor IX, Factor VII, Factor VIII, Factor X, fibroblast growth factor (FGF), fibrinogen, fibronectin, four-helical bundle protein, G-CSF, glp-1, GM-CSF, glucocerebrosidase, gonadotropin, growth factor, growth factor receptor, growth hormone releasing factor, hedgehog protein, hemoglobin, hepatocyte growth factor (hGF), hirudin, human growth hormone (hGH), human serum albumin, ICAM-1, ICAM-1 receptor, LFA-1, LFA-1 receptor, insulin, insulin-like growth factor (IGF), IGF-I, IGF-II, interferon (IFN), IFN-alpha, IFN-beta, IFN-gamma, interleukin (IL), IL-1, IL-2, IL-3, IL-4, IL-5, IL-6, IL-7, IL-8, IL-9, IL-10, IL-11, IL-12, keratinocyte growth factor (KGF), lactoferrin, leukemia inhibitory factor, luciferase, neurturin, neutrophil inhibitory factor (NIF), oncostatin M, osteogenic protein, oncogene product, paracitonin, parathyroid hormone (PTH), PD-ECGF, PDGF, peptide hormone, pleiotropin, protein A, protein G, pyrogenic exotoxin A, pyrogenic exotoxin B, pyrogenic exotoxin C, Peptide YY (PYY), relaxin, renin, SCF, small biosynthetic protein, soluble complement receptor I, soluble 1-CAM 1, soluble interleukin receptor, soluble TNF receptor, somatomedin, somatostatin, somatotropin, streptokinase, superantigens, staphylococcal enterotoxin, SEA, SEB, SEC1, SEC2, SEC3, SED, SEE, steroid hormone receptor, superoxide dismutase, toxic shock syndrome toxin, thymosin alpha 1, tissue plasminogen activator, tumor growth factor (TGF), tumor necrosis factor, tumor necrosis factor alpha, tumor necrosis factor beta, tumor necrosis factor receptor (TNFR), VLA-4 protein, VCAM-1 protein, vascular endothelial growth factor (VEGF), urokinase, mos, ras, raf, met, p53, tat, fos, myc, jun, myb, rel, estrogen receptor, progesterone receptor, testosterone receptor, aldosterone receptor, LDL receptor, and corticosterone.

In one embodiment is a method for treating solid tumor which overexpresses HER-2 selected from the group consisting of breast cancer, small cell lung carcinoma, ovarian cancer, endometrial cancer, bladder cancer, head and neck cancer, prostate cancer, gastric carcinoma, cervical cancer, uterine cancer, esophageal carcinoma, and colon cancer. In another embodiment, the solid tumor is breast cancer. In a further embodiment the solid tumor is ovarian cancer.

Thus, the following description of trastuzumab is provided for illustrative purposes and by way of example only, and not as a limit on the scope of the methods, compositions, strategies and techniques described herein. Further, reference to trastuzumab in this application is intended to use the generic term as an example of any antibody. Thus, it is understood that the modifications and chemistries described herein with reference to trastuzumab can be equally applied to any antibody or monoclonal antibody, including those specifically listed herein.

Trastuzumab is a humanized monoclonal antibody that binds to the domain IV of the extracellular segment of the HER2/neu receptor. The HER2 gene (also known as HER2/neu and ErbB2 gene) is amplified in 20-30% of early-stage breast cancers, which makes it overexpressed. Also, in cancer, HER2 may send signals without mitogens arriving and binding to any receptor, making it overactive.

HER2 extends through the cell membrane and carries signals from outside the cell to the inside. In healthy people, signaling compounds called mitogens arrive at the cell membrane, and bind to the outside part of other members of the HER family of receptors. Those bound receptors then link (dimerize) with HER2, activating it. HER2 then sends a signal to the inside of the cell. The signal passes through different biochemical pathways. This includes the PI3K/Akt pathway and the MAPK pathway. These signals promote invasion, survival and growth of blood vessels (angiogenesis) of cells.

Cells treated with trastuzumab undergo arrest during the G1 phase of the cell cycle so there is reduced proliferation. It has been suggested that trastuzumab induces some of its effect by downregulation of HER2/neu leading to disruption of receptor dimerization and signaling through the downstream PI3K cascade. P27Kip1 is then not phosphorylated and is able to enter the nucleus and inhibit cdk2 activity, causing cell cycle arrest. Also, trastuzumab suppresses angiogenesis by both induction of antiangiogenic factors and repression of proangiogenic factors. It is thought that a contribution to the unregulated growth observed in cancer could be due to proteolytic cleavage of HER2/neu that results in the release of the extracellular domain. Trastuzumab has been shown to inhibit HER2/neu ectodomain cleavage in breast cancer cells.

Expression in Non-Eukaryotes and Eukaryotes

To obtain high level expression of a cloned TC polynucleotide, one typically subclones polynucleotides encoding a targeting polypeptide of the TC polypeptide of the invention into an expression vector that contains a strong promoter to direct transcription, a transcription/translation terminator, and if for a nucleic acid encoding a protein, a ribosome binding site for translational initiation. Suitable bacterial promoters are known to those of ordinary skill in the art and described, e.g., in Sambrook et al. and Ausubel et al.

Bacterial expression systems for expressing TC polypeptides of the invention are available in, including but not limited to, *E. coli, Bacillus* sp., *Pseudomonas fluorescens, Pseudomonas aeruginosa, Pseudomonas putida*, and *Salmonella* (Palva et al., *Gene* 22:229-235 (1983); Mosbach et al., *Nature* 302:543-545 (1983)). Kits for such expression systems are commercially available. Eukaryotic expression systems for mammalian cells, yeast, and insect cells are known to those of ordinary skill in the art and are also commercially available. In cases where orthogonal tRNAs and aminoacyl tRNA synthetases (described above) are used to express the TC polypeptides of the invention, host cells for expression are selected based on their ability to use the orthogonal components. Exemplary host cells include Gram-positive bacteria (including but not limited to *B. brevis, B. subtilis*, or *Streptomyces*) and Gram-negative bacteria (*E. coli, Pseudomonas fluorescens, Pseudomonas aeruginosa, Pseudomonas putida*), as well as yeast and other eukaryotic cells. Cells comprising O-tRNA/O—RS pairs can be used as described herein.

A eukaryotic host cell or non-eukaryotic host cell of the present invention provides the ability to synthesize proteins that comprise non-natural amino acids in large useful quantities. In one aspect, the composition optionally includes, including but not limited to, at least 10 micrograms, at least 50 micrograms, at least 75 micrograms, at least 100 micrograms, at least 200 micrograms, at least 250 micrograms, at least 500 micrograms, at least 1 milligram, at least 10 milligrams, at least 100 milligrams, at least one gram, or more of the protein that comprises an non-natural amino acid, or an amount that can be achieved with in vivo protein production methods (details on recombinant protein production and purification are provided herein). In another aspect, the protein is optionally present in the composition at a concentration of, including but not limited to, at least 10 micrograms of protein per liter, at least 50 micrograms of protein per liter, at least 75 micrograms of protein per liter, at least 100 micrograms of protein per liter, at least 200 micrograms of protein per liter, at least 250 micrograms of protein per liter, at least 500 micrograms of protein per liter, at least 1 milligram of protein per liter, or at least 10 milligrams of protein per liter or more, in, including but not limited to, a cell lysate, a buffer, a pharmaceutical buffer, or other liquid suspension (including but not limited to, in a volume of, including but not limited to, anywhere from about 1 nl to about 100 L or more). The production of large quantities (including but not limited to, greater that that typically possible with other methods, including but not limited to, in vitro translation) of a protein in a eukaryotic cell including at least one non-natural amino acid is a feature of the invention.

The nucleotide sequence encoding a targeting polypeptide of the TC polypeptide may or may not also include sequence that encodes a signal peptide. The signal peptide is present when the polypeptide is to be secreted from the cells in which it is expressed. Such signal peptide may be any sequence. The signal peptide may be prokaryotic or eukaryotic. Coloma, M (1992) J. Imm. Methods 152:89 104) describe a signal peptide for use in mammalian cells (murine Ig kappa light chain signal peptide). Other signal peptides include but are not limited to, the alpha-factor signal peptide from *S. cerevisiae* (U.S. Pat. No. 4,870,008 which is incorporated by reference herein), the signal peptide of mouse salivary amylase (O. Hagenbuchle et al., Nature 289, 1981, pp. 643-646), a modified carboxypeptidase signal peptide (L. A. Valls et al., Cell 48, 1987, pp. 887-897), the yeast BAR1 signal peptide (WO 87/02670, which is incorporated by reference herein), and the yeast aspartic protease 3 (YAPS) signal peptide (cf. M. Egel-Mitani et al., Yeast 6, 1990, pp. 127-137).

Examples of suitable mammalian host cells are known to those of ordinary skill in the art. Such host cells may be Chinese hamster ovary (CHO) cells, (e.g. CHO-K1; ATCC CCL-61), Green Monkey cells (COS) (e.g. COS 1 (ATCC CRL-1650), COS 7 (ATCC CRL-1651)); mouse cells (e.g. NS/O), Baby Hamster Kidney (BHK) cell lines (e.g. ATCC CRL-1632 or ATCC CCL-10), and human cells (e.g. HEK 293 (ATCC CRL-1573)), as well as plant cells in tissue culture. These cell lines and others are available from public depositories such as the American Type Culture Collection, Rockville, Md. In order to provide improved glycosylation of the TC polypeptide, a mammalian host cell may be modified to express sialyltransferase, e.g. 1,6-sialyltransferase, e.g. as described in U.S. Pat. No. 5,047,335, which is incorporated by reference herein.

Methods for the introduction of exogenous DNA into mammalian host cells include but are not limited to, calcium phosphare-mediated transfection, electroporation, DEAE-dextran mediated transfection, liposome-mediated transfection, viral vectors and the transfection methods described by Life Technologies Ltd, Paisley, UK using Lipofectamin 2000 and Roche Diagnostics Corporation, Indianapolis, USA using FuGENE 6. These methods are well known in the art and are described by Ausbel et al. (eds.), 1996, Current Protocols in Molecular Biology, John Wiley & Sons, New York, USA. The cultivation of mammalian cells may be performed according to established methods, e.g. as disclosed in (Animal Cell Biotechnology, Methods and Protocols, Edited by Nigel Jenkins, 1999, Human Press Inc. Totowa, N.J., USA and Harrison Mass. and Rae IF, General Techniques of Cell Culture, Cambridge University Press 1997).

I. *E. coli, Pseudomonas* species, and other Prokaryotes

Bacterial expression techniques are known to those of ordinary skill in the art. A wide variety of vectors are available for use in bacterial hosts. The vectors may be single copy or low or high multicopy vectors. Vectors may serve for cloning and/or expression. In view of the ample literature concerning vectors, commercial availability of many vectors, and even manuals describing vectors and their restriction maps and characteristics, no extensive discussion is required here. As is well-known, the vectors normally involve markers allowing for selection, which markers may provide for cytotoxic agent resistance, prototrophy or immunity. Frequently, a plurality of markers is present, which provide for different characteristics.

A bacterial promoter is any DNA sequence capable of binding bacterial RNA polymerase and initiating the downstream (3') transcription of a coding sequence (e.g. structural gene) into mRNA. A promoter will have a transcription initiation region which is usually placed proximal to the 5' end of the coding sequence. This transcription initiation region typically includes an RNA polymerase binding site and a transcription initiation site. A bacterial promoter may also have a second domain called an operator that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*) (see, Raibaud et al., Annu. Rev. Genet. (1984) 18:173). Regulated expression may therefore be either positive or negative, thereby either enhancing or reducing transcription.

The term "bacterial host" or "bacterial host cell" refers to bacteria that can be, or has been, used as a recipient for recombinant vectors or other transfer DNA. The term includes the progeny of the original bacterial host cell that has been transfected. It is understood that the progeny of a single parental cell may not necessarily be completely identical in morphology or in genomic or total DNA complement to the original parent, due to accidental or deliberate mutation. Progeny of the parental cell that are sufficiently similar to the parent to be characterized by the relevant property, such as the presence of a nucleotide sequence encoding a TC polypeptide, are included in the progeny intended by this definition.

The selection of suitable host bacteria for expression of TC polypeptides is known to those of ordinary skill in the art. In selecting bacterial hosts for expression, suitable hosts may include those shown to have, inter alia, good inclusion body formation capacity, low proteolytic activity, and overall robustness. Bacterial hosts are generally available from a variety of sources including, but not limited to, the Bacterial Genetic Stock Center, Department of Biophysics and Medical Physics, University of California (Berkeley, Calif.); and the American Type Culture Collection ("ATCC") (Manassas, Va.). Industrial/pharmaceutical fermentation generally use bacterial derived from K strains (e.g. W3110) or from bacteria derived from B strains (e.g. BL21). These strains are particularly useful because their growth parameters are extremely well known and robust. In addition, these strains are non-pathogenic, which is commercially important for safety and environmental reasons. Other examples of suitable *E. coli* hosts include, but are not limited to, strains of BL21, DH10B, or derivatives thereof. In another embodiment of the methods of the present invention, the *E. coli* host is a protease minus strain including, but not limited to, OMP- and LON-. The host cell strain may be a species of *Pseudomonas*, including but not limited to, *Pseudomonas fluorescens, Pseudomonas aeruginosa*, and *Pseudomonas putida. Pseudomonas fluorescens* biovar 1, designated strain MB101, is known to be useful for recombinant production and is available for therapeutic protein production processes. Examples of a *Pseudomonas* expression system include the system available from The Dow Chemical Company as a host strain (Midland, Mich. available on the worldwide web at dow.com).

Once a recombinant host cell strain has been established (i.e., the expression construct has been introduced into the host cell and host cells with the proper expression construct are isolated), the recombinant host cell strain is cultured under conditions appropriate for production of TC polypeptides. As will be apparent to one of skill in the art, the method of culture of the recombinant host cell strain will be dependent on the nature of the expression construct utilized and the identity of the host cell. Recombinant host strains are normally cultured using methods that are known to those of ordinary skill in the art. Recombinant host cells are typically cultured in liquid medium containing assimilatable sources of carbon, nitrogen, and inorganic salts and, optionally, containing vitamins, amino acids, growth factors, and other proteinaceous culture supplements known to those of ordinary skill in the art. Liquid media for culture of host cells may optionally contain antibiotics or anti-fungals to prevent the growth of undesirable microorganisms and/or compounds including, but not limited to, antibiotics to select for host cells containing the expression vector.

Recombinant host cells may be cultured in batch or continuous formats, with either cell harvesting (in the case where the TC polypeptide accumulates intracellularly) or harvesting of culture supernatant in either batch or continuous formats. For production in prokaryotic host cells, batch culture and cell harvest are preferred.

The TC polypeptides of the present invention are normally purified after expression in recombinant systems. The TC polypeptide may be purified from host cells or culture medium by a variety of methods known to the art. TC polypeptides produced in bacterial host cells may be poorly soluble or insoluble (in the form of inclusion bodies). In one embodiment of the present invention, amino acid substitutions may readily be made in the TC polypeptide that are selected for the purpose of increasing the solubility of the recombinantly produced protein utilizing the methods disclosed herein as well as those known in the art. In the case of insoluble protein, the protein may be collected from host cell lysates by centrifugation and may further be followed by homogenization of the cells. In the case of poorly soluble protein, compounds including, but not limited to, polyethylene imine (PEI) may be added to induce the precipitation of partially soluble protein. The precipitated protein may then be conveniently collected by centrifugation. Recombinant host cells may be disrupted or homogenized to release the inclusion bodies from within the cells using a variety of methods known to those of ordinary skill in the art. Host cell disruption or homogenization may be performed using well known techniques including, but not limited to, enzymatic cell disruption, sonication, dounce homogenization, or high pressure release disruption. In one embodiment of the method of the present invention, the high pressure release technique is used to disrupt the *E. coli* host cells to release the inclusion bodies of the TC polypeptides. When handling inclusion bodies of TC polypeptide, it may be advantageous to minimize the homogenization time on repetitions in order to maximize the yield of inclusion bodies without loss due to factors such as solubilization, mechanical shearing or proteolysis.

Insoluble or precipitated TC polypeptide may then be solubilized using any of a number of suitable solubilization agents known to the art. The TC polypeptide may be solubilized with urea or guanidine hydrochloride. The volume of the solubilized TC polypeptide should be minimized so that large batches may be produced using conveniently manageable batch sizes. This factor may be significant in a large-scale commercial setting where the recombinant host may be grown in batches that are thousands of liters in volume. In addition, when manufacturing TC polypeptide in a large-scale commercial setting, in particular for human pharmaceutical uses, the avoidance of harsh chemicals that can damage the machinery and container, or the protein product itself, should be avoided, if possible. It has been shown in the method of the present invention that the milder denaturing agent urea can be used to solubilize the TC polypeptide inclusion bodies in place of the harsher denaturing agent guanidine hydrochloride. The use of urea significantly reduces the risk of damage to stainless steel equipment utilized in the manufacturing and purification process of TC polypeptide while efficiently solubilizing the TC polypeptide inclusion bodies.

In the case of soluble targeting polypeptide of the TC protein, the targeting polypeptide of the TC may be secreted into the periplasmic space or into the culture medium. In addition, soluble TC may be present in the cytoplasm of the host cells. It may be desired to concentrate soluble TC prior to performing purification steps. Standard techniques known to those of ordinary skill in the art may be used to concentrate soluble targeting polypeptide from, for example, cell lysates or culture medium. In addition, standard techniques known to those of ordinary skill in the art may be used to disrupt host cells and release soluble TC from the cytoplasm or periplasmic space of the host cells.

In general, it is occasionally desirable to denature and reduce expressed polypeptides and then to cause the polypeptides to re-fold into the preferred conformation. For example, guanidine, urea, DTT, DTE, and/or a chaperonin can be added to a translation product of interest. Methods of reducing, denaturing and renaturing proteins are known to those of ordinary skill in the art (see, the references above, and Debinski, et al. (1993) J. Biol. Chem., 268: 14065-14070; Kreitman and Pastan (1993) Bioconjug. Chem., 4: 581-585; and Buchner, et al., (1992) Anal. Biochem., 205: 263-270). Debinski, et al., for example, describe the denaturation and reduction of inclusion body proteins in guanidine-DTE. The proteins can be refolded in a redox buffer containing, including but not limited to, oxidized glutathione and L-arginine. Refolding reagents can be flowed or otherwise moved into contact with the one or more polypeptide or other expression product, or vice-versa.

In the case of prokaryotic production of TC polypeptide, the TC polypeptide thus produced may be misfolded and thus lacks or has reduced biological activity. The bioactivity of the protein may be restored by “refolding”. In general, misfolded TC polypeptide is refolded by solubilizing (where the TC polypeptide is also insoluble), unfolding and reducing the polypeptide chain using, for example, one or more chaotropic agents (e.g. urea and/or guanidine) and a reducing agent capable of reducing disulfide bonds (e.g. dithiothreitol, DTT or 2-mercaptoethanol, 2-ME). At a moderate concentration of chaotrope, an oxidizing agent is then added (e.g., oxygen, cystine or cystamine), which allows the reformation of disulfide bonds. TC polypeptide may be refolded using standard methods known in the art, such as those described in U.S. Pat. Nos. 4,511,502, 4,511,503, and 4,512,922, which are incorporated by reference herein. The TC polypeptide may also be cofolded with other proteins to form heterodimers or heteromultimers.

After refolding, the targeting polypeptide of the TC may be further purified. Purification of TC may be accomplished using a variety of techniques known to those of ordinary skill in the art, including hydrophobic interaction chromatography, size exclusion chromatography, ion exchange chromatography, reverse-phase high performance liquid chromatography, affinity chromatography, and the like or any combination thereof. Additional purification may also include a step of drying or precipitation of the purified protein.

After purification, the targeting polypeptide of the TC may be exchanged into different buffers and/or concentrated by any of a variety of methods known to the art, including, but not limited to, diafiltration and dialysis. TC that is provided as a single purified protein may be subject to aggregation and precipitation.

The purified targeting polypeptide of the TC may be at least 90% pure (as measured by reverse phase high performance liquid chromatography, RP-HPLC, or sodium dodecyl sulfate-polyacrylamide gel electrophoresis, SDS-PAGE) or at least 95% pure, or at least 96% pure, or at least 97% pure, or at least 98% pure, or at least 99% or greater pure. Regardless of the exact numerical value of the purity of the targeting polypeptide of the TC, the targeting polypeptide of the TC is sufficiently pure for use as a pharmaceutical product or for further processing, such as conjugation with a water soluble polymer such as PEG.

Certain TC molecules may be used as therapeutic agents in the absence of other active ingredients or proteins (other than excipients, carriers, and stabilizers, serum albumin and the like), or they may be complexed with another protein or a polymer.

Previously, it has been shown that non-natural amino acids can be site-specifically incorporated into proteins in vitro by the addition of chemically aminoacylated suppressor tRNAs to protein synthesis reactions programmed with a gene containing a desired amber nonsense mutation. Using these approaches, one can substitute a number of the common twenty amino acids with close structural homologues, e.g., fluorophenylalanine for phenylalanine, using strains auxotropic for a particular amino acid. See, e.g., Noren, C. J., Anthony-Cahill, Griffith, M. C., Schultz, P. G. *A general method for site-specific incorporation of unnatural amino acids into proteins*, Science, 244: 182-188 (1989); M. W. Nowak, et al., Science 268:439-42 (1995); Bain, J. D., Glabe, C. G., Dix, T. A., Chamberlin, A. R., Diala, E. S. *Biosynthetic site-specific Incorporation of a non-natural amino acid into a polypeptide*, J. Am Chem Soc, 111:8013-8014 (1989); N. Budisa et al., FASEB J. 13:41-51 (1999); Ellman, J. A., Mendel, D., Anthony-Cahill, S., Noren, C. J., Schultz, P. G. *Biosynthetic method for introducing unnatural amino acids site-specifically into proteins*, Methods in Enz., vol. 202, 301-336 (1992); and, Mendel, D., Cornish, V. W. & Schultz, P. G. *Site-Directed Mutagenesis with an Expanded Genetic Code*, Annu Rev Biophys. Biomol Struct, 24, 435-62 (1995).

For example, a suppressor tRNA was prepared that recognized the stop codon UAG and was chemically aminoacylated with a non-natural amino acid. Conventional site-directed mutagenesis was used to introduce the stop codon TAG, at the site of interest in the protein gene. See, e.g., Sayers, J. R., Schmidt, W. Eckstein, F. *5'-3' Exonucleases in phosphorothioate-based oligonucleotide-directed mutagenesis*, Nucleic Acids Res, 16(3):791-802 (1988). When the acylated suppressor tRNA and the mutant gene were combined in an in vitro transcription/translation system, the non-natural amino acid was incorporated in response to the UAG codon which gave a protein containing that amino acid at the specified position. Experiments using [$^3$H]-Phe and experiments with $\alpha$-hydroxy acids demonstrated that only the desired amino acid is incorporated at the position specified by the UAG codon and that this amino acid is not incorporated at any other site in the protein. See, e.g., Noren, et al, supra; Kobayashi et al., (2003) Nature Structural Biology 10(6):425-432; and, Ellman, J. A., Mendel, D., Schultz, P. G. *Site-specific incorporation of novel backbone structures into proteins*, Science, 255(5041):197-200 (1992).

A tRNA may be aminoacylated with a desired amino acid by any method or technique, including but not limited to, chemical or enzymatic aminoacylation.

Aminoacylation may be accomplished by aminoacyl tRNA synthetases or by other enzymatic molecules, including but not limited to, ribozymes. The term “ribozyme” is interchangeable with “catalytic RNA.” Cech and coworkers (Cech, 1987, Science, 236:1532-1539; McCorkle et al., 1987, Concepts Biochem. 64:221-226) demonstrated the presence of naturally occurring RNAs that can act as catalysts (ribozymes). However, although these natural RNA catalysts have only been shown to act on ribonucleic acid substrates for cleavage and splicing, the recent development of artificial evolution of ribozymes has expanded the repertoire of catalysis to various chemical reactions. Studies have identified RNA molecules that can catalyze aminoacyl-RNA bonds on their own (2')3'-termini (Illangakekare et al., 1995 Science 267:643-647), and an RNA molecule which can transfer an amino acid from one RNA molecule to another (Lohse et al., 1996, Nature 381:442-444).

U.S. Patent Application Publication 2003/0228593, which is incorporated by reference herein, describes methods to construct ribozymes and their use in aminoacylation of tRNAs with naturally encoded and non-naturally encoded amino acids. Substrate-immobilized forms of enzymatic molecules that can aminoacylate tRNAs, including but not limited to, ribozymes, may enable efficient affinity purification of the aminoacylated products. Examples of suitable substrates include agarose, sepharose, and magnetic beads. The production and use of a substrate-immobilized form of ribozyme for aminoacylation is described in Chemistry and Biology 2003, 10:1077-1084 and U.S. Patent Application Publication 2003/0228593, which are incorporated by reference herein.

Chemical aminoacylation methods include, but are not limited to, those introduced by Hecht and coworkers (Hecht, S. M. Acc. Chem. Res. 1992, 25, 545; Heckler, T. G.; Roesser, J. R.; Xu, C.; Chang, P.; Hecht, S. M. Biochemistry 1988, 27, 7254; Hecht, S. M.; Alford, B. L.; Kuroda, Y.; Kitano, S. J. Biol. Chem. 1978, 253, 4517) and by Schultz, Chamberlin, Dougherty and others (Cornish, V. W.; Mendel, D.; Schultz, P. G. Angew. Chem, Int. Ed. Engl. 1995, 34, 621; Robertson, S. A.; Ellman, J. A.; Schultz, P. G. J. Am. Chem. Soc. 1991, 113, 2722; Noren, C. J.; Anthony-Cahill, S. J.; Griffith, M, C.; Schultz, P. G. Science 1989, 244, 182; Bain, J. D.; Glabe, C. G.; Dix, T. A.; Chamberlin, A. R. J. Am. Chem. Soc. 1989, 111, 8013; Bain, J. D. et al. Nature 1992, 356, 537; Gallivan, J. P.; Lester, H. A.; Dougherty, D. A. Chem. Biol. 1997, 4, 740; Turcatti, et al. J. Biol. Chem. 1996, 271, 19991; Nowak, M. W. et al. Science, 1995, 268, 439; Saks, M. E. et al. J. Biol. Chem. 1996, 271, 23169; Hohsaka, T, et al. J. Am. Chem. Soc. 1999, 121, 34), which are incorporated by reference herein, to avoid the use of synthetases in aminoacylation. Such methods or other chemical aminoacylation methods may be used to aminoacylate tRNA molecules.

Methods for generating catalytic RNA may involve generating separate pools of randomized ribozyme sequences, performing directed evolution on the pools, screening the pools for desirable aminoacylation activity, and selecting sequences of those ribozymes exhibiting desired aminoacylation activity.

Reconstituted translation systems may also be used. Mixtures of purified translation factors have also been used successfully to translate mRNA into protein as well as combinations of lysates or lysates supplemented with purified translation factors such as initiation factor-1 (IF-1), IF-2, IF-3 ($\alpha$ or $\beta$), elongation factor T (EF-Tu), or termination factors. Cell-free systems may also be coupled transcription/translation systems wherein DNA is introduced to the system, transcribed into mRNA and the mRNA translated as described in *Current Protocols in Molecular Biology* (F. M. Ausubel et al. editors, Wiley Interscience, 1993), which is hereby specifically incorporated by reference. RNA transcribed in eukaryotic transcription system may be in the form of heteronuclear RNA (hnRNA) or 5'-end caps (7-methyl guanosine) and 3'-end poly A tailed mature mRNA, which can be an advantage in certain translation systems. For example, capped mRNAs are translated with high efficiency in the reticulocyte lysate system.

Macromolecular Polymers Coupled TC Polypeptides

Various modifications to the non-natural amino acid polypeptides described herein can be effected using the compositions, methods, techniques and strategies described herein. These modifications include the incorporation of further functionality onto the non-natural amino acid component of the polypeptide, including but not limited to, a label; a dye; a polymer; a water-soluble polymer; a derivative of polyethylene glycol; a photocrosslinker; a radionuclide; a cytotoxic compound; a drug; an affinity label; a photoaffinity label; a reactive compound; a resin; a second protein or polypeptide or polypeptide analog; an antibody or antibody fragment; a metal chelator; a cofactor; a fatty acid; a carbohydrate; a polynucleotide; a DNA; a RNA; an antisense polynucleotide; a saccharide; a water-soluble dendrimer; a cyclodextrin; an inhibitory ribonucleic acid; a biomaterial; a nanoparticle; a spin label; a fluorophore, a metal-containing moiety; a radioactive moiety; a novel functional group; a group that covalently or noncovalently interacts with other molecules; a photocaged moiety; an actinic radiation excitable moiety; a photoisomerizable moiety; biotin; a derivative of biotin; a biotin analogue; a moiety incorporating a heavy atom; a chemically cleavable group; a photocleavable group; an elongated side chain; a carbon-linked sugar; a redox-active agent; an amino thioacid; a toxic moiety; an isotopically labeled moiety; a biophysical probe; a phosphorescent group; a chemiluminescent group; an electron dense group; a magnetic group; an intercalating group; a chromophore; an energy transfer agent; a biologically active agent; a detectable label; a small molecule; a quantum dot; a nanotransmitter; a radionucleotide; a radiotransmitter; a neutron-capture agent; or any combination of the above, or any other desirable compound or substance. As an illustrative, non-limiting example of the compositions, methods, techniques and strategies described herein, the following description will focus on adding macromolecular polymers to the non-natural amino acid polypeptide with the understanding that the compositions, methods, techniques and strategies described thereto are also applicable (with appropriate modifications, if necessary and for which one of skill in the art could make with the disclosures herein) to adding other functionalities, including but not limited to those listed above.

A wide variety of macromolecular polymers and other molecules can be linked to TC polypeptides of the present invention to modulate biological properties of the TC polypeptide, and/or provide new biological properties to the TC molecule. These macromolecular polymers can be linked to the TC polypeptide via a naturally encoded amino acid, via a non-naturally encoded amino acid, or any functional substituent of a natural or non-natural amino acid, or any substituent or functional group added to a natural or non-natural amino acid. The molecular weight of the polymer may be of a wide range, including but not limited to, between about 100 Da and about 100,000 Da or more. The molecular weight of the polymer may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of the polymer is between about 100 Da and about 50,000 Da. In some embodiments, the molecular weight of the polymer is between about 100 Da and about 40,000 Da. In some embodiments, the molecular weight of the polymer is between about 1,000 Da and about 40,000 Da. In some embodiments, the molecular weight of the polymer is between about 5,000 Da and about 40,000 Da. In some embodiments, the molecular weight of the polymer is between about 10,000 Da and about 40,000 Da.

The present invention provides substantially homogenous preparations of polymer:protein conjugates. "Substantially homogenous" as used herein means that polymer:protein conjugate molecules are observed to be greater than half of the total protein. The polymer:protein conjugate has biological activity and the present "substantially homogenous" PEGylated TC polypeptide preparations provided herein are those which are homogenous enough to display the advantages of a homogenous preparation, e.g., ease in clinical application in predictability of lot to lot pharmacokinetics.

One may also choose to prepare a mixture of polymer:protein conjugate molecules, and the advantage provided herein is that one may select the proportion of mono-polymer:protein conjugate to include in the mixture. Thus, if desired, one may prepare a mixture of various proteins with various numbers of polymer moieties attached (i.e., di-, tri-, tetra-, etc.) and combine said conjugates with the mono-polymer:protein conjugate prepared using the methods of the present invention, and have a mixture with a predetermined proportion of mono-polymer:protein conjugates.

The polymer selected may be water soluble so that the protein to which it is attached does not precipitate in an aqueous environment, such as a physiological environment. The polymer may be branched or unbranched. For therapeutic use of the end-product preparation, the polymer will be pharmaceutically acceptable.

Examples of polymers include but are not limited to polyalkyl ethers and alkoxy-capped analogs thereof (e.g., polyoxyethylene glycol, polyoxyethylene/propylene glycol, and methoxy or ethoxy-capped analogs thereof, especially polyoxyethylene glycol, the latter is also known as polyethyleneglycol or PEG); polyvinylpyrrolidones; polyvinylalkyl ethers; polyoxazolines, polyalkyl oxazolines and polyhydroxyalkyl oxazolines; polyacrylamides, polyalkyl acrylamides, and polyhydroxyalkyl acrylamides (e.g., polyhydroxypropylmethacrylamide and derivatives thereof); polyhydroxyalkyl acrylates; polysialic acids and analogs thereof; hydrophilic peptide sequences; polysaccharides and their derivatives, including dextran and dextran derivatives, e.g., carboxymethyldextran, dextran sulfates, aminodextran; cellulose and its derivatives, e.g., carboxymethyl cellulose, hydroxyalkyl celluloses; chitin and its derivatives, e.g., chitosan, succinyl chitosan, carboxymethylchitin, carboxymethylchitosan; hyaluronic acid and its derivatives; starches; alginates; chondroitin sulfate; albumin; pullulan and carboxymethyl pullulan; polyaminoacids and derivatives thereof, e.g., polyglutamic acids, polylysines, polyaspartic acids, polyaspartamides; maleic anhydride copolymers such as: styrene maleic anhydride copolymer, divinylethyl ether maleic anhydride copolymer; polyvinyl alcohols; copolymers thereof; terpolymers thereof; mixtures thereof; and derivatives of the foregoing.

The proportion of polyethylene glycol molecules to protein molecules will vary, as will their concentrations in the reaction mixture. In general, the optimum ratio (in terms of efficiency of reaction in that there is minimal excess unreacted protein or polymer) may be determined by the molecular weight of the polyethylene glycol selected and on the number of available reactive groups available. As relates to molecular weight, typically the higher the molecular weight of the polymer, the fewer number of polymer molecules which may be attached to the protein. Similarly, branching of the polymer should be taken into account when optimizing these parameters. Generally, the higher the molecular weight (or the more branches) the higher the polymer: protein ratio.

As used herein, and when contemplating PEG:TC polypeptide conjugates, the term "therapeutically effective amount" refers to an amount which gives the desired benefit to a patient. The amount will vary from one individual to another and will depend upon a number of factors, including the overall physical condition of the patient and the underlying cause of the condition to be treated. The amount of TC polypeptide used for therapy gives an acceptable rate of change and maintains desired response at a beneficial level. A therapeutically effective amount of the present compositions may be readily ascertained by one of ordinary skill in the art using publicly available materials and procedures.

The water soluble polymer may be any structural form including but not limited to linear, forked or branched. Typically, the water soluble polymer is a poly(alkylene glycol), such as poly(ethylene glycol) (PEG), but other water soluble polymers can also be employed. By way of example, PEG is used to describe certain embodiments of this invention.

PEG is a well-known, water soluble polymer that is commercially available or can be prepared by ring-opening polymerization of ethylene glycol according to methods known to those of ordinary skill in the art (Sandler and Karo, Polymer Synthesis, Academic Press, New York, Vol. 3, pages 138-161). The term "PEG" is used broadly to encompass any polyethylene glycol molecule, without regard to size or to modification at an end of the PEG, and can be represented as linked to the TC polypeptide by the formula:

$$XO—(CH_2CH_2O)_n—CH_2CH_2—Y$$

where n is 2 to 10,000 and X is H or a terminal modification, including but not limited to, a $C_{1-4}$ alkyl, a protecting group, or a terminal functional group.

In some cases, a PEG used in the invention terminates on one end with hydroxy or methoxy, i.e., X is H or $CH_3$ ("methoxy PEG"). Alternatively, the PEG can terminate with a reactive group, thereby forming a bifunctional polymer. Typical reactive groups can include those reactive groups that are commonly used to react with the functional groups found in the 20 common amino acids (including but not limited to, maleimide groups, activated carbonates (including but not limited to, p-nitrophenyl ester), activated esters (including but not limited to, N-hydroxysuccinimide, p-nitrophenyl ester) and aldehydes) as well as functional groups that are inert to the 20 common amino acids but that react specifically with complementary functional groups present in non-naturally encoded amino acids (including but not limited to, azide groups, alkyne groups). It is noted that the other end of the PEG, which is shown in the above formula by Y, will attach either directly or indirectly to a TC polypeptide via a naturally-occurring or non-naturally encoded amino acid. For instance, Y may be an amide, carbamate or urea linkage to an amine group (including but not limited to, the epsilon amine of lysine or the N-terminus) of the polypeptide. Alternatively, Y may be a maleimide linkage to a thiol group (including but not limited to, the thiol group of cysteine). Alternatively, Y may be a linkage to a residue not commonly accessible via the 20 common amino acids. For example, an azide group on the PEG can be reacted with an alkyne group on the TC polypeptide to form a Huisgen [3+2] cycloaddition product. Alternatively, an alkyne group on the PEG can be reacted with an azide group present in a non-naturally encoded amino acid to form a similar product. In some embodiments, a strong nucleophile (including but not limited to, hydrazine, hydrazide, hydroxylamine, semicarbazide) can be reacted with an aldehyde or ketone group present in a non-naturally encoded amino acid to form a hydrazone, oxime or semicarbazone, as applicable, which in some cases can be further reduced by treatment with an appropriate reducing agent. Alternatively, the strong nucleophile can be incorporated into the TC polypeptide via a non-naturally encoded amino acid and used to react preferentially with a ketone or aldehyde group present in the water soluble polymer.

Any molecular mass for a PEG can be used as practically desired, including but not limited to, from about 100 Daltons (Da) to 100,000 Da or more as desired (including but not limited to, sometimes 0.1-50 kDa or 10-40 kDa). The molecular weight of PEG may be of a wide range, including but not limited to, between about 100 Da and about 100,000 Da or more. PEG may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, PEG is between about 100 Da and about 50,000 Da. In some embodiments, PEG is between about 100 Da and about 40,000 Da. In some embodiments, PEG is between about 1,000 Da and about 40,000 Da. In some embodiments, PEG is between about 5,000 Da and about 40,000 Da. In some embodiments, PEG is between about 10,000 Da and about 40,000 Da. Branched chain PEGs, including but not limited to, PEG molecules with each chain having a molecular weight ranging from 1-100 kDa (including but not limited to, 1-50 kDa or 5-20 kDa) can also be used. The molecular weight of each chain of the branched chain PEG may be, including but not limited to, between about 1,000 Da and about 100,000 Da or more. The molecular weight of each chain of the branched chain PEG may be between about 1,000 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, and 1,000 Da. In some embodiments, the molecular weight of each chain of the branched chain PEG is between about 1,000 Da and about 50,000 Da. In some embodiments, the molecular weight of each chain of the branched chain PEG is between about 1,000 Da and about 40,000 Da. In some embodiments, the molecular weight of each chain of the branched chain PEG is between about 5,000 Da and about 40,000 Da. In some embodiments, the molecular weight of each chain of the branched chain PEG is between about 5,000 Da and about 20,000 Da. A wide range of PEG molecules are described in, including but not limited to, the Shearwater Polymers, Inc. catalog, Nektar Therapeutics catalog, incorporated herein by reference.

Generally, at least one terminus of the PEG molecule is available for reaction with the non-naturally-encoded amino acid. For example, PEG derivatives or TLR-linker derivatives bearing alkyne and azide moieties for reaction with amino acid side chains can be used to attach PEG to non-naturally encoded amino acids as described herein. If the non-naturally encoded amino acid comprises an azide, then the PEG will typically contain either an alkyne moiety to effect formation of the [3+2] cycloaddition product or an activated PEG species (i.e., ester, carbonate) containing a phosphine group to effect formation of the amide linkage. Alternatively, if the non-naturally encoded amino acid comprises an alkyne, then the PEG will typically contain an azide moiety to effect formation of the [3+2] Huisgen cycloaddition product. If the non-naturally encoded amino acid comprises a carbonyl group, the PEG will typically comprise a potent nucleophile (including but not limited to, a hydrazide, hydrazine, hydroxylamine, or semicarbazide functionality) in order to effect formation of corresponding hydrazone, oxime, and semicarbazone linkages, respectively. In other alternatives, a reverse of the orientation of the reactive groups described above can be used, i.e., an azide moiety in the non-naturally encoded amino acid can be reacted with a PEG derivative containing an alkyne.

In some embodiments, the TC polypeptide with a PEG derivative contains a chemical functionality that is reactive with the chemical functionality present on the side chain of the non-naturally encoded amino acid.

The invention provides in some embodiments azide- and acetylene-containing polymer derivatives comprising a water soluble polymer backbone having an average molecular weight from about 800 Da to about 100,000 Da. The polymer backbone of the water-soluble polymer can be poly(ethylene glycol). However, it should be understood that a wide variety of water soluble polymers including but not limited to poly(ethylene)glycol and other related polymers, including poly(dextran) and poly(propylene glycol), are also suitable for use in the practice of this invention and that the use of the term PEG or poly(ethylene glycol) is intended to encompass and include all such molecules. The term PEG includes, but is not limited to, poly(ethylene glycol) in any of its forms, including bifunctional PEG, multiarmed PEG, derivatized PEG, forked PEG, branched PEG, pendent PEG (i.e. PEG or related polymers having one or more functional groups pendent to the polymer backbone), or PEG with degradable linkages therein.

PEG is typically clear, colorless, odorless, soluble in water, stable to heat, inert to many chemical agents, does not hydrolyze or deteriorate, and is generally non-toxic. Poly (ethylene glycol) is considered to be biocompatible, which is to say that PEG is capable of coexistence with living tissues or organisms without causing harm. More specifically, PEG is substantially non-immunogenic, which is to say that PEG does not tend to produce an immune response in the body. When attached to a molecule having some desirable function in the body, such as a biologically active agent, the PEG tends to mask the agent and can reduce or eliminate any immune response so that an organism can tolerate the presence of the agent. PEG conjugates tend not to produce a substantial immune response or cause clotting or other undesirable effects. PEG having the formula $—CH_2CH_2O—(CH_2CH_2O)_n—CH_2CH_2—$, where n is from about 3 to about 4000, typically from about 20 to about 2000, is suitable for use in the present invention. PEG having a molecular weight of from about 800 Da to about 100,000 Da are in some embodiments of the present invention particularly useful as the polymer backbone. The molecular weight of PEG may be of a wide range, including but not limited to, between about 100 Da and about 100,000 Da or more. The molecular weight of PEG may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of PEG is between about 100 Da and about 50,000 Da. In some embodiments, the molecular weight of PEG is between about 100 Da and about 40,000 Da. In some embodiments, the molecular weight of PEG is between about 1,000 Da and about 40,000 Da. In some embodiments, the molecular weight of PEG is between about 5,000 Da and about 40,000 Da. In some embodiments, the molecular weight of PEG is between about 10,000 Da and about 40,000 Da.

The polymer backbone can be linear or branched. Branched polymer backbones are generally known in the art. Typically, a branched polymer has a central branch core moiety and a plurality of linear polymer chains linked to the central branch core. PEG is commonly used in branched forms that can be prepared by addition of ethylene oxide to various polyols, such as glycerol, glycerol oligomers, pentaerythritol and sorbitol. The central branch moiety can also be derived from several amino acids, such as lysine. The branched poly(ethylene glycol) can be represented in general form as $R(\text{-PEG-OH})_m$ in which R is derived from a core moiety, such as glycerol, glycerol oligomers, or pentaerythritol, and m represents the number of arms. Multi-armed PEG molecules, such as those described in U.S. Pat. Nos. 5,932,462; 5,643,575; 5,229,490; 4,289,872; U.S. Pat. Appl. 2003/0143596; WO 96/21469; and WO 93/21259, each of which is incorporated by reference herein in its entirety, can also be used as the polymer backbone.

Branched PEG can also be in the form of a forked PEG represented by $PEG(—YCHZ_2)_n$, where Y is a linking group and Z is an activated terminal group linked to CH by a chain of atoms of defined length. Yet another branched form, the pendant PEG, has reactive groups, such as carboxyl, along the PEG backbone rather than at the end of PEG chains.

In addition to these forms of PEG, the polymer can also be prepared with weak or degradable linkages in the backbone. For example, PEG can be prepared with ester linkages in the polymer backbone that are subject to hydrolysis. As shown below, this hydrolysis results in cleavage of the polymer into fragments of lower molecular weight:

$$\text{-PEG-}CO_2\text{-PEG-}+H_2O \rightarrow \text{PEG-}CO_2H+\text{HO-PEG-}$$

It is understood by those of ordinary skill in the art that the term poly(ethylene glycol) or PEG represents or includes all the forms known in the art including but not limited to those disclosed herein.

Many other polymers are also suitable for use in the present invention. In some embodiments, polymer backbones that are water-soluble, with from 2 to about 300 termini, are particularly useful in the invention. Examples of suitable polymers include, but are not limited to, other poly(alkylene glycols), such as poly(propylene glycol) ("PPG"), copolymers thereof (including but not limited to copolymers of ethylene glycol and propylene glycol), terpolymers thereof, mixtures thereof, and the like. Although the molecular weight of each chain of the polymer backbone can vary, it is typically in the range of from about 800 Da to about 100,000 Da, often from about 6,000 Da to about 80,000 Da. The molecular weight of each chain of the polymer backbone may be between about 100 Da and about 100,000 Da, including but not limited to, 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, 1,000 Da, 900 Da, 800 Da, 700 Da, 600 Da, 500 Da, 400 Da, 300 Da, 200 Da, and 100 Da. In some embodiments, the molecular weight of each chain of the polymer backbone is between about 100 Da and about 50,000 Da. In some embodiments, the molecular weight of each chain of the polymer backbone is between about 100 Da and about 40,000 Da. In some embodiments, the molecular weight of each chain of the polymer backbone is between about 1,000 Da and about 40,000 Da. In some embodiments, the molecular weight of each chain of the polymer backbone is between about 5,000 Da and about 40,000 Da. In some embodiments, the molecular weight of each chain of the polymer backbone is between about 10,000 Da and about 40,000 Da.

Those of ordinary skill in the art will recognize that the foregoing list for substantially water soluble backbones is by no means exhaustive and is merely illustrative, and that all polymeric materials having the qualities described above are contemplated as being suitable for use in the present invention.

In some embodiments of the present invention the polymer derivatives are "multi-functional", meaning that the polymer backbone has at least two termini, and possibly as many as about 300 termini, functionalized or activated with a functional group. Multifunctional polymer derivatives include, but are not limited to, linear polymers having two termini, each terminus being bonded to a functional group which may be the same or different.

The term "protected" refers to the presence of a protecting group or moiety that prevents reaction of the chemically reactive functional group under certain reaction conditions. The protecting group will vary depending on the type of chemically reactive group being protected. For example, if the chemically reactive group is an amine or a hydrazide, the protecting group can be selected from the group of tert-butyloxycarbonyl (t-Boc) and 9-fluorenylmethoxycarbonyl (Fmoc). If the chemically reactive group is a thiol, the protecting group can be orthopyridyldisulfide. If the chemically reactive group is a carboxylic acid, such as butanoic or propionic acid, or a hydroxyl group, the protecting group can be benzyl or an alkyl group such as methyl, ethyl, or Cert-butyl. Other protecting groups known in the art may also be used in the present invention.

Specific examples of terminal functional groups in the literature include, but are not limited to, N-succinimidyl carbonate (see e.g., U.S. Pat. Nos. 5,281,698, 5,468,478), amine (see, e.g., Buckmann et al. Makromol. Chem. 182: 1379 (1981), Zalipsky et al. Eur. Polym. J. 19:1177 (1983)), hydrazide (See, e.g., Andresz et al. Makromol. Chem. 179: 301 (1978)), succinimidyl propionate and succinimidyl butanoate (see, e.g., Olson et al. in Polyethylene glycol) Chemistry & Biological Applications, pp 170-181, Harris & Zalipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al. Makromol. Chem. 180:1381 (1979), succinimidyl ester (see, e.g., U.S. Pat. No. 4,670,417), benzotriazole carbonate (see, e.g., U.S. Pat. No. 5,650,234), glycidyl ether (see, e.g., Pitha et al. Eur. J Biochem. 94:11 (1979), Elling et al., Biotech, Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11: 141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. Nos. 5,824,784, 5,252,714), maleimide (see, e.g., Goodson et al. Biotechnology (NY) 8:343 (1990), Romani et al. in Chemistry of Peptides and Proteins 2:29 (1984)), and Kogan, Synthetic Comm. 22:2417 (1992)), orthopyridyl-disulfide (see, e.g., Woghiren, et al. Bioconj. Chem. 4:314(1993)), acrylol (see, e.g., Sawhney et al., Macromolecules, 26:581 (1993)), vinylsulfone (see, e.g., U.S. Pat. No. 5,900,461). All of the above references and patents are incorporated herein by reference.

PEGylation (i.e., addition of any water soluble polymer) of TC polypeptides containing a non-naturally encoded amino acid, such as p-azido-L-phenylalanine, is carried out by any convenient method. For example, TC polypeptide is PEGylated with an alkyne-terminated mPEG derivative. Briefly, an excess of solid mPEG(5000)-O—$CH_2$—C≡CH is added, with stirring, to an aqueous solution of p-azido-L-Phe-containing TC polypeptide at room temperature. Typically, the aqueous solution is buffered with a buffer having a $pK_a$ near the pH at which the reaction is to be carried out (generally about pH 4-10). Examples of suitable buffers for PEGylation at pH 7.5, for instance, include, but are not limited to, HEPES, phosphate, borate, TRIS-HCl, EPPS, and TES. The pH is continuously monitored and adjusted if necessary. The reaction is typically allowed to continue for between about 1-48 hours.

The reaction products are subsequently subjected to hydrophobic interaction chromatography to separate the PEGylated TC polypeptides from free mPEG(5000)—O—$CH_2$—C≡CH and any high-molecular weight complexes of the pegylated TC polypeptide which may form when unblocked PEG is activated at both ends of the molecule, thereby crosslinking TC polypeptide molecules. The conditions during hydrophobic interaction chromatography are such that free mPEG(5000)—O—$CH_2$—C≡CH flows through the column, while any crosslinked PEGylated TC polypeptide complexes elute after the desired forms, which contain one TC polypeptide molecule conjugated to one or more PEG groups. Suitable conditions vary depending on the relative sizes of the cross-linked complexes versus the desired conjugates and are readily determined by those of ordinary skill in the art. The eluent containing the desired conjugates is concentrated by ultrafiltration and desalted by diafiltration.

Substantially purified PEG-TC can be produced using the elution methods outlined above where the PEG-TC produced has a purity level of at least about 30%, at least about 35%, at least about 40%, at least about 45%, at least about 50%, at least about 55%, at least about 60%, at least about 65%, at least about 70%, specifically, a purity level of at least about 75%, 80%, 85%, and more specifically, a purity level of at least about 90%, a purity level of at least about 95%, a purity level of at least about 99% or greater as determined by appropriate methods such as SDS/PAGE analysis, RP-HPLC, SEC, and capillary electrophoresis. If necessary, the PEGylated TC polypeptide obtained from the hydrophobic chromatography can be purified further by one or more procedures known to those of ordinary skill in the art including, but are not limited to, affinity chromatography; anion- or cation-exchange chromatography (using, including but not limited to, DEAE SEPHAROSE); chromatography on silica; reverse phase HPLC; gel filtration (using, including but not limited to, SEPHADEX G-75); hydrophobic interaction chromatography; size-exclusion chromatography, metal-chelate chromatography; ultrafiltration/diafiltration; ethanol precipitation; ammonium sulfate precipitation; chromatofocusing; displacement chromatography; electrophoretic procedures (including but not limited to preparative isoelectric focusing), differential solubility (including but not limited to ammonium sulfate precipitation), or extraction. Apparent molecular weight may be estimated by GPC by comparison to globular protein standards (Preneta, A Z in PROTEIN PURIFICATION METHODS, A PRACTICAL APPROACH (Harris & Angal, Eds.) IRL Press 1989, 293-306). The purity of the TC-PEG conjugate can be assessed by proteolytic degradation (including but not limited to, trypsin cleavage) followed by mass spectrometry analysis. Pepinsky R B., et al., *J. Pharmcol. & Exp. Ther.* 297(3): 1059-66 (2001).

A water soluble polymer linked to an amino acid of a targeting polypeptide of the TC polypeptide of the invention can be further derivatized or substituted without limitation.

Azide-Containing PEG Derivatives or TLR-Linker Derivatives

In another embodiment of the invention, a targeting polypeptide of the TC is modified with a PEG derivative that contains an azide moiety that will react with an alkyne moiety present on the side chain of the non-naturally encoded amino acid. In general, the PEG derivatives or TLR-linker derivatives will have an average molecular weight ranging from 1-100 kDa and, in some embodiments, from 10-40 kDa.

In some embodiments, the azide-terminal PEG derivative will have the structure:

$RO—(CH_2CH_2O)_n—O—(CH_2)_m—N_3$ where R is a simple alkyl (methyl, ethyl, propyl, etc.), m is 2-10 and n is 100-1,000 (i.e., average molecular weight is between 5-40 kDa).

In another embodiment, the azide-terminal PEG derivative will have the structure:

$RO—(CH_2CH_2O)_n—O—(CH_2)_m—NH—C(O)—(CH_2)_p—N_3$ where R is a simple alkyl (methyl, ethyl, propyl, etc.), in is 2-10, p is 2-10 and n is 100-1,000 (i.e., average molecular weight is between 5-40 kDa).

In another embodiment of the invention, a targeting polypeptide of the TC comprising a alkyne-containing amino acid is modified with a branched PEG derivative that contains a terminal azide moiety, with each chain of the branched PEG having a molecular weight ranging from 10-40 kDa and may be from 5-20 kDa. For instance, in some embodiments, the azide-terminal PEG derivative will have the following structure:

$[RO—(CH_2CH_2O)_n—O—(CH_2)_2—NH—C(O)]_2CH(CH_2)_m—X—(CH_2)_pN_3$ where R is a simple alkyl (methyl, ethyl, propyl, etc.), in is 2-10, p is 2-10, and n is 100-1,000, and X is optionally an O, N, S or carbonyl group (C═O), in each case that can be present or absent.

Alkene-Containing PEG Derivatives or TLR-Linker Derivatives

In another embodiment of the invention, a targeting polypeptide of the TC is modified with a PEG derivative that contains an alkyne moiety that will react with an azide moiety present on the side chain of the non-naturally encoded amino acid.

In some embodiments, the alkyne-terminal PEG derivative will have the following structure:

$RO—(CH_2CH_2O)_n—O—(CH_2)_m—C≡CH$ where R is a simple alkyl (methyl, ethyl, propyl, etc.), m is 2-10 and n is 100-1,000 (i.e., average molecular weight is between 5-40 kDa).

In another embodiment of the invention, a targeting polypeptide of the TC comprising an alkyne-containing non-naturally encoded amino acid is modified with a PEG derivative that contains a terminal azide or terminal alkyne moiety that is linked to the PEG backbone by means of an amide linkage.

In some embodiments, the alkyne-terminal PEG derivative will have the following structure:

$RO—(CH_2CH_2O)_n—O—(CH_2)_m—NH—C(O)—(CH_2)_p—C≡CH$ where R is a simple alkyl (methyl, ethyl, propyl, etc.), m is 2-10, p is 2-10 and n is 100-1,000.

In another embodiment of the invention, a targeting polypeptide of the TC comprising an azide-containing amino acid is modified with a branched PEG derivative that contains a terminal alkyne moiety, with each chain of the branched PEG having a molecular weight ranging from 10-40 kDa and may be from 5-20 kDa. For instance, in some embodiments, the alkyne-terminal PEG derivative will have the following structure:

$[RO—(CH_2CH_2O)_n—O—(CH_2)_2—NH—C(O)]_2CH(CH_2)_m—X—(CH_2)_pC≡CH$ where R is a simple alkyl (methyl, ethyl, propyl, etc.), m is 2-10, p is 2-10, and n is 100-1,000, and X is optionally an O, N, S or carbonyl group (C═O), or not present.

Phosphine-Containing PEG Derivatives or TLR-Linker Derivatives

In another embodiment of the invention, a targeting polypeptide of the TC is modified with a PEG derivative that contains an activated functional group (including but not limited to, ester, carbonate) further comprising an aryl phosphine group that will react with an azide moiety present on the side chain of the non-naturally encoded amino acid. In general, the PEG derivatives or TLR-linker derivatives will have an average molecular weight ranging from 1-100 kDa and, in some embodiments, from 10-40 kDa.

In some embodiments, the PEG derivative will have the structure:

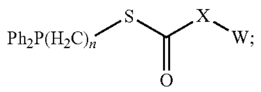

wherein n is 1-10; X can be O, N, S or not present, Ph is phenyl, and W is a water soluble polymer.

In some embodiments, the PEG derivative will have the structure:

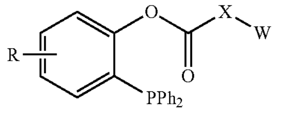

wherein X can be O, N, S or not present, Ph is phenyl, W is a water soluble polymer and R can be H, alkyl, aryl, substituted alkyl and substituted aryl groups. Exemplary R groups include but are not limited to $—CH_2$, $—C(CH_3)_3$, —OR', —NR'R", —SR', -halogen, —C(O)R', —CONR'R", $—S(O)_2R'$, $—S(O)_2NR'R"$, —CN and $—NO_2$, R', R", R'" and R" each independently refer to hydrogen, substituted or unsubstituted heteroalkyl, substituted or unsubstituted aryl, including but not limited to, aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (including but not limited to, $—CF_3$ and $—CH_2CF_3$) and acyl (including but not limited to, $—C(O)CH_3$, $—C(O)CF_3$, $—C(O)CH_2OCH_3$, and the like).

Other PEG Derivatives or TLR-Linker Derivatives and General Conjugation Techniques Other exemplary PEG molecules that may be linked to TC polypeptides, as well as PEGylation methods include, but are not limited to, those described in, e.g., U.S. Patent Publication No, 2004/0001838; 2002/0052009; 2003/0162949; 2004/0013637; 2003/0228274; 2003/0220447; 2003/0158333; 2003/0143596; 2003/0114647; 2003/0105275; 2003/0105224; 2003/0023023; 2002/0156047; 2002/0099133; 2002/0086939; 2002/0082345; 2002/0072573; 2002/0052430; 2002/0040076; 2002/0037949; 2002/0002250; 2001/0056171; 2001/0044526; 2001/0021763; U.S. Pat. Nos. 6,646,110; 5,824,778; 5,476,653; 5,219,564; 5,629,384; 5,736,625; 4,902,502; 5,281,698; 5,122,614; 5,473,034; 5,516,673; 5,382,657; 6,552,167; 6,610,281; 6,515,100; 6,461,603; 6,436,386; 6,214,966; 5,990,237; 5,900,461; 5,739,208; 5,672,662; 5,446,090; 5,808,090; 5,612,460; 5,324,844; 5,252,714; 6,420,339; 6,201,072; 6,451,346; 6,306,821; 5,559,213; 5,747,646; 5,834,594; 5,849,860; 5,980,948; 6,004,573; 6,129,912; WO 97/32607, EP 229,108, EP 402,378, WO 92/16555, WO 94/04193, WO 94/14758, WO 94/17039, WO 94/18247, WO 94/28024, WO 95/00162, WO 95/11924, WO95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, WO 98/05363, EP 809 996, WO 96/41813, WO 96/07670, EP 605 963, EP 510 356, EP 400 472, EP 183 503 and EP 154 316, which are incorporated by reference herein. Any of the PEG molecules described herein may be used in any form, including but not limited to, single chain, branched chain, multiarm chain, single functional, bi-functional, multi-functional, or any combination thereof.

Additional polymer and PEG derivatives or TLR-linker derivatives including but not limited to, hydroxylamine (aminooxy) PEG derivatives or TLR-linker derivatives, are described in the following patent applications which are all incorporated by reference in their entirety herein: U.S. Patent Publication No. 2006/0194256, U.S. Patent Publication No. 2006/0217532, U.S. Patent Publication No. 2006/0217289, U.S. Provisional Patent No. 60/755,338; U.S. Provisional Patent No. 60/755,711; U.S. Provisional Patent No. 60/755,018; International Patent Application No. PCT/US06/49397; WO 2006/069246; U.S. Provisional Patent No. 60/743,041; U.S. Provisional Patent No. 60/743,040; International Patent Application No. PCT/US06/47822; U.S. Provisional Patent No. 60/882,819; U.S. Provisional Patent No. 60/882,500; and U.S. Provisional Patent No. 60/870,594.

Glycosylation of TC Polypeptides

Glycosylation can dramatically affect the physical properties (e.g., solubility) of polypeptides such as TC polypeptides and can also be important in protein stability, secretion, and subcellular localization. Glycosylated polypeptides can also exhibit enhanced stability or can improve one or more pharmacokinetic properties, such as half-life. In addition, solubility improvements can, for example, enable the generation of formulations more suitable for pharmaceutical administration than formulations comprising the non-glycosylated polypeptide.

The invention includes TC polypeptides incorporating one or more non-naturally encoded amino acids bearing saccharide residues. The saccharide residues may be either natural (including but not limited to, N-acetylglucosamine) or non-natural (including but not limited to, 3-fluorogalactose). The saccharides may be linked to the non-naturally encoded amino acids either by an N- or O-linked glycosidic linkage (including but not limited to, N-acetylgalactose-L-serine) or a non-natural linkage (including but not limited to, an oxime or the corresponding C- or S-linked glycoside).

The saccharide (including but not limited to, glycosyl) moieties can be added to TC polypeptides either in vivo or in vitro. In some embodiments of the invention, a targeting polypeptide of the TC comprising a carbonyl-containing non-naturally encoded amino acid is modified with a saccharide derivatized with an aminooxy group to generate the corresponding glycosylated polypeptide linked via an oxime linkage. Once attached to the non-naturally encoded amino acid, the saccharide may be further elaborated by treatment with glycosyltransferases and other enzymes to generate an oligosaccharide bound to the TC polypeptide. See, e.g., H. Liu, et al. *J. Am. Chem. Soc.* 125: 1702-1703 (2003).

In some embodiments of the invention, a TC polypeptide comprising a carbonyl-containing non-naturally encoded amino acid is modified directly with a glycan with defined structure prepared as an aminooxy derivative. One of ordinary skill in the art will recognize that other functionalities, including azide, alkyne, hydrazide, hydrazine, and semicarbazide, can be used to link the saccharide to the non-naturally encoded amino acid.

In some embodiments of the invention, a targeting polypeptide of the TC comprising an azide or alkynyl-containing non-naturally encoded amino acid can then be modified by, including but not limited to, a Huisgen [3+2] cycloaddition reaction with, including but not limited to, alkynyl or azide derivatives, respectively. This method allows for proteins to be modified with extremely high selectivity.

TC Dimers and Multimers

The present invention also provides for TC and TC analog combinations such as homodimers, heterodimers, homomultimers, or heteromultimers (i.e., trimers, tetramers, etc.) where TC containing one or more non-naturally encoded amino acids is bound to another TC or any other polypeptide that is not TC, either directly to the polypeptide backbone or via a linker. Due to its increased molecular weight compared to monomers, the TC dimer or multimer conjugates may exhibit new or desirable properties, including but not limited to different pharmacological, pharmacokinetic, pharmacodynamic, modulated therapeutic half-life, or modulated plasma half-life relative to the monomeric TC. In some embodiments, TC dimers of the invention will modulate signal transduction of the TC receptor. In other embodiments, the TC dimers or multimers of the present invention will act as a TC receptor antagonist, agonist, or modulator.

In some embodiments, one or more of the TC molecules present in a TC containing dimer or multimer comprises a non-naturally encoded amino acid linked to a water soluble polymer.

In some embodiments, the TC polypeptides are linked directly, including but not limited to, via an Asn-Lys amide linkage or Cys-Cys disulfide linkage. In some embodiments, the TC polypeptides, and/or the linked non-TC molecule, will comprise different non-naturally encoded amino acids to facilitate dimerization, including but not limited to, an alkyne in one non-naturally encoded amino acid of a first TC polypeptide and an azide in a second non-naturally encoded amino acid of a second molecule will be conjugated via a Huisgen [3+2] cycloaddition. Alternatively, TC, and/or the linked non-TC molecule comprising a ketone-containing non-naturally encoded amino acid can be conjugated to a second polypeptide comprising a hydroxylamine-containing non-naturally encoded amino acid and the polypeptides are reacted via formation of the corresponding oxime.

Alternatively, the two TC polypeptides, and/or the linked non-peptide TC molecule, are linked via a linker. Any hetero- or homo-bifunctional linker can be used to link the two molecules, and/or the linked non-peptide TC molecules, which can have the same or different primary sequence. In some cases, the linker used to tether the TC, and/or the linked non-peptide TC molecules together can be a bifunctional PEG reagent. The linker may have a wide range of molecular weight or molecular length. Larger or smaller molecular weight linkers may be used to provide a desired spatial relationship or conformation between TC and the linked entity or between TC and its receptor, or between the linked entity and its binding partner, if any. Linkers having longer or shorter molecular length may also be used to provide a desired space or flexibility between TC and the linked entity, or between the linked entity and its binding partner, if any.

In some embodiments, the invention provides water-soluble bifunctional linkers that have a dumbbell structure that includes: a) an azide, an alkyne, a hydrazine, a hydrazide, a hydroxylamine, or a carbonyl-containing moiety on at least a first end of a polymer backbone; and b) at least a second functional group on a second end of the polymer backbone. The second functional group can be the same or different as the first functional group. The second functional group, in some embodiments, is not reactive with the first functional group. The invention provides, in some embodiments, water-soluble compounds that comprise at least one arm of a branched molecular structure. For example, the branched molecular structure can be dendritic.

In some embodiments, the invention provides multimers comprising one or more TC polypeptide, formed by reactions with water soluble activated polymers that have the structure: $R—(CH_2CH_2O)_n—O—(CH_2)_m—X$ wherein n is from about 5 to 3,000, m is 2-10, X can be an azide, an alkyne, a hydrazine, a hydrazide, an aminooxy group, a hydroxylamine, an acetyl, or carbonyl-containing moiety, and R is a capping group, a functional group, or a leaving group that can be the same or different as X. R can be, for example, a functional group selected from the group consisting of hydroxyl, protected hydroxyl, alkoxyl, N-hydroxysuccinimidyl ester, 1-benzotriazolyl ester, N-hydroxysuccinimidyl carbonate, 1-benzotriazolyl carbonate, acetal, aldehyde, aldehyde hydrates, alkenyl, acrylate, methacrylate, acrylamide, active sulfone, amine, aminooxy, protected amine, hydrazide, protected hydrazide, protected thiol, carboxylic acid, protected carboxylic acid, isocyanate, isothiocyanate, maleimide, vinylsulfone, dithiopyridine, vinylpyridine, iodoacetamide, epoxide, glyoxals, diones, mesylates, tosylates, and tresylate, alkene, and ketone.

Measurement of TC Polypeptide Activity and Affinity of TC Polypeptide for HER2 Target TC polypeptide activity can be determined using standard or known in vitro or in vivo assays. TC may be analyzed for biological activity by suitable methods known in the art. Such assays include, but are not limited to, activation of TC-responsive genes, receptor binding assays, anti-viral activity assays, cytopathic effect inhibition assays, anti-proliferative assays, immunomodulatory assays and assays that monitor the induction of MHC molecules.

TC polypeptides may be analyzed for their ability to activate TC-sensitive signal transduction pathways. One example is the interferon-stimulated response element (ISRE) assay. Cells which constitutively express the TC receptor are transiently transfected with an ISRE-luciferase vector (pISRE-luc, Clontech). After transfection, the cells are treated with a targeting polypeptide of the TC. A number of protein concentrations, for example from 0.0001-10 ng/mL, are tested to generate a dose-response curve. If the TC polypeptide binds and activates the TC receptor, the resulting signal transduction cascade induces luciferase expression. Luminescence can be measured in a number of ways, for example by using a TopCount™ or Fusion™ microplate reader and Steady-Glo® Luciferase Assay System (Promega).

TC polypeptides may be analyzed for their ability to bind to the TC receptor. For a non-PEGylated or PEGylated TC polypeptide comprising a non-natural amino acid, the affinity of TC for its receptor can be measured by using a BIAcore™ biosensor (Pharmacia). Suitable binding assays include, but are not limited to, BIAcore assays (Pearce et al., Biochemistry 38:81-89 (1999)) and AlphaScreen™ assays (PerkinElmer).

Regardless of which methods are used to create the TC polypeptides, the TC polypeptides are subject to assays for biological activity. In general, the test for biological activity should provide analysis for the desired result, such as increase or decrease in biological activity (as compared to modified TC), different biological activity (as compared to modified TC), receptor or binding partner affinity analysis, conformational or structural changes of the TC itself or its receptor (as compared to the modified TC), or serum half-life analysis.

Measurement of Potency, Functional In Vivo Half-Life, and Pharmacokinetic Parameters An important aspect of the invention is the prolonged biological half-life that is obtained by construction of the TC with or without conjugation of the polypeptide to a water soluble polymer moiety. The rate of post administration decrease of TC serum concentrations may make it important to evaluate biological responses to treatment with conjugated and non-conjugated TC polypeptide and variants thereof. The conjugated and non-conjugated TC polypeptide and variants thereof of the present invention may have prolonged serum half-lives also after administration via, e.g. subcutaneous or i.v. administration, making it possible to measure by, e.g. ELISA method or by a primary screening assay. ELISA or RIA kits from commercial sources may be used such as Invitrogen (Carlsbad, Calif.). Measurement of in vivo biological half-life is carried out as described herein.

The potency and functional in vivo half-life of a targeting polypeptide of the TC comprising a non-naturally encoded amino acid can be determined according to protocols known to those of ordinary skill in the art.

Pharmacokinetic parameters for a TC polypeptide comprising a non-naturally encoded amino acid can be evaluated in normal Sprague-Dawley male rats (N=5 animals per treatment group). Animals will receive either a single dose of 25 ug/rat iv or 50 ug/rat sc, and approximately 5-7 blood samples will be taken according to a pre-defined time course, generally covering about 6 hours for a TC polypeptide comprising a non-naturally encoded amino acid not conjugated to a water soluble polymer and about 4 days for a TC polypeptide comprising a non-naturally encoded amino acid and conjugated to a water soluble polymer. Pharmacokinetic data for TC without a non-naturally encoded amino acid can be compared directly to the data obtained for TC polypeptides comprising a non-naturally encoded amino acid.

Administration and Pharmaceutical Compositions

The polypeptides or proteins of the invention (including but not limited to, TC, synthetases, proteins comprising one or more non-natural amino acid, etc.) are optionally employed for therapeutic uses, including but not limited to, in combination with a suitable pharmaceutical carrier. Such compositions, for example, comprise a therapeutically effective amount of the compound, and a pharmaceutically acceptable carrier or excipient. Such a carrier or excipient includes, but is not limited to, saline, buffered saline, dextrose, water, glycerol, ethanol, and/or combinations thereof. The formulation is made to suit the mode of administration. In general, methods of administering proteins are known to those of ordinary skill in the art and can be applied to administration of the polypeptides of the invention. Compositions may be in a water-soluble form, such as being present as pharmaceutically acceptable salts, which is meant to include both acid and base addition salts.

Therapeutic compositions comprising one or more polypeptide of the invention are optionally tested in one or more appropriate in vitro and/or in vivo animal models of disease, to confirm efficacy, tissue metabolism, and to estimate dosages, according to methods known to those of ordinary skill in the art. In particular, dosages can be initially determined by activity, stability or other suitable measures of unnatural herein to natural amino acid homologues (including but not limited to, comparison of a targeting polypeptide of the TC modified to include one or more non-natural amino acids to a natural amino acid TC polypeptide and comparison of a targeting polypeptide of the TC modified to include one or more non-natural amino acids to a currently available TC treatment), i.e., in a relevant assay.

Administration is by any of the routes normally used for introducing a molecule into ultimate contact with blood or tissue cells. The non-natural amino acid polypeptides of the invention are administered in any suitable manner, optionally with one or more pharmaceutically acceptable carriers. Suitable methods of administering such polypeptides in the context of the present invention to a patient are available, and, although more than one route can be used to administer a particular composition, a particular route can often provide a more immediate and more effective action or reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention.

TC polypeptides of the invention may be administered by any conventional route suitable for proteins or peptides, including, but not limited to parenterally, e.g. injections including, but not limited to, subcutaneously or intravenously or any other form of injections or infusions. Polypeptide compositions can be administered by a number of routes including, but not limited to oral, intravenous, intraperitoneal, intramuscular, transdermal, subcutaneous, topical, sublingual, or rectal means. Compositions comprising non-natural amino acid polypeptides, modified or unmodified, can also be administered via liposomes. Such administration routes and appropriate formulations are generally known to those of skill in the art. The TC polypeptide, may be used alone or in combination with other suitable components such as a pharmaceutical carrier. The TC polypeptide may be used in combination with other agents or therapeutics.

The TC polypeptide comprising a non-natural amino acid, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of TC can be presented in unit-dose or multi-dose sealed containers, such as ampules and vials.

Parenteral administration and intravenous administration are preferred methods of administration. In particular, the routes of administration already in use for natural amino acid homologue therapeutics (including but not limited to, those typically used for EPO, GH, G-CSF, GM-CSF, IFNs e.g. TC, interleukins, antibodies, FGFs, and/or any other pharmaceutically delivered protein), along with formulations in current use, provide preferred routes of administration and formulation for the polypeptides of the invention.

The dose administered to a patient, in the context of the present invention, is sufficient to have a beneficial therapeutic response in the patient over time, or other appropriate activity, depending on the application. The dose is determined by the efficacy of the particular vector, or formulation, and the activity, stability or serum half-life of the non-natural amino acid polypeptide employed and the condition of the patient, as well as the body weight or surface area of the patient to be treated. The size of the dose is also determined by the existence, nature, and extent of any adverse side-effects that accompany the administration of a particular vector, formulation, or the like in a particular patient.

In determining the effective amount of the vector or formulation to be administered in the treatment or prophylaxis of disease (including but not limited to, neutropenia, aplastic anemia, cyclic neutropenia, idiopathic neutropenia, Chdiak-Higashi syndrome, systemic lupus erythematosus (SLE), leukemia, myelodysplastic syndrome and myelofibrosis, or the like), the physician evaluates circulating plasma levels, formulation toxicities, and disease progression.

The dose administered, for example, to a 70 kilogram patient, is typically in the range equivalent to dosages of currently-used therapeutic proteins, adjusted for the altered activity or serum half-life of the relevant composition. The vectors or pharmaceutical formulations of this invention can supplement treatment conditions by any known conventional therapy, including antibody administration, vaccine administration, administration of cytotoxic agents, natural amino acid polypeptides, nucleic acids, nucleotide analogues, biologic response modifiers, and the like.

For administration, formulations of the present invention are administered at a rate determined by the LD-50 or ED-50 of the relevant formulation, and/or observation of any side-effects of the non-natural amino acid polypeptides at various concentrations, including but not limited to, as applied to the mass and overall health of the patient. Administration can be accomplished via single or divided doses.

If a patient undergoing infusion of a formulation develops fevers, chills, or muscle aches, he/she receives the appropriate dose of aspirin, ibuprofen, acetaminophen or other pain/fever controlling drug. Patients who experience reactions to the infusion such as fever, muscle aches, and chills are premedicated 30 minutes prior to the future infusions with either aspirin, acetaminophen, or, including but not limited to, diphenhydramine. Meperidine is used for more severe chills and muscle aches that do not quickly respond to antipyretics and antihistamines. Cell infusion is slowed or discontinued depending upon the severity of the reaction.

Human forms of a targeting polypeptide of the TCs of the invention can be administered directly to a mammalian subject. Administration is by any of the routes normally used for introducing TC polypeptide to a subject. The TC polypeptide compositions according to embodiments of the present invention include those suitable for oral, rectal, topical, inhalation (including but not limited to, via an aerosol), buccal (including but not limited to, sub-lingual), vaginal, parenteral (including but not limited to, subcutaneous, intramuscular, intradermal, intraarticular, intrapleural, intraperitoneal, intracerebral, intraarterial, or intravenous), topical (i.e., both skin and mucosal surfaces, including airway surfaces), pulmonary, intraocular, intranasal, and transdermal administration, although the most suitable route in any given case will depend on the nature and severity of the condition being treated. Administration can be either local or systemic. The formulations of compounds can be presented in unit-dose or multi-dose sealed containers, such as ampoules and vials. TC polypeptides of the invention can be prepared in a mixture in a unit dosage injectable form (including but not limited to, solution, suspension, or emulsion) with a pharmaceutically acceptable carrier, TC polypeptides of the invention can also be administered by continuous infusion (using, including but not limited to, minipumps such as osmotic pumps), single bolus or slow-release depot formulations.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. Solutions and suspensions can be prepared from sterile powders, granules, and tablets of the kind previously described.

Freeze-drying is a commonly employed technique for presenting proteins which serves to remove water from the protein preparation of interest. Freeze-drying, or lyophilization, is a process by which the material to be dried is first frozen and then the ice or frozen solvent is removed by sublimation in a vacuum environment. An excipient may be included in pre-lyophilized formulations to enhance stability during the freeze-drying process and/or to improve stability of the lyophilized product upon storage. Pikal M. Biopharm. 3(9)26-30 (1990) and Arakawa et al. Pharm. Res. 8(3):285-291 (1991).

The spray drying of pharmaceuticals is also known to those of ordinary skill in the art. For example, see Broadhead, J. et al., "The Spray Drying of Pharmaceuticals," in Drug Dev. Ind. Pharm, 18 (11 & 12), 1169-1206 (1992). In addition to small molecule pharmaceuticals, a variety of biological materials have been spray dried and these include: enzymes, sera, plasma, micro-organisms and yeasts. Spray drying is a useful technique because it can convert a liquid pharmaceutical preparation into a fine, dustless or agglomerated powder in a one-step process. The basic technique comprises the following four steps: a) atomization of the feed solution into a spray; b) spray-air contact; c) drying of the spray; and d) separation of the dried product from the drying air. U.S. Pat. Nos. 6,235,710 and 6,001,800, which are incorporated by reference herein, describe the preparation of recombinant erythropoietin by spray drying.

The pharmaceutical compositions and formulations of the invention may comprise a pharmaceutically acceptable carrier, excipient, or stabilizer. Pharmaceutically acceptable carriers are determined in part by the particular composition being administered, as well as by the particular method used to administer the composition. Accordingly, there is a wide variety of suitable formulations of pharmaceutical compositions (including optional pharmaceutically acceptable carriers, excipients, or stabilizers) of the present invention (see, e.g., *Remington's Pharmaceutical Sciences,* $17^{th}$ ed. 1985)).

Suitable carriers include but are not limited to, buffers containing succinate, phosphate, borate, HEPES, citrate, histidine, imidazole, acetate, bicarbonate, and other organic acids; antioxidants including but not limited to, ascorbic acid; low molecular weight polypeptides including but not limited to those less than about 10 residues; proteins, including but not limited to, serum albumin, gelatin, or immunoglobulins; hydrophilic polymers including but not limited to, polyvinylpyrrolidone; amino acids including but not limited to, glycine, glutamine, asparagine, arginine, histidine or histidine derivatives, methionine, glutamate, or lysine; monosaccharides, disaccharides, and other carbohydrates, including but not limited to, trehalose, sucrose, glucose, mannose, or dextrins; chelating agents including but not limited to, EDTA and edentate disodium; divalent metal ions including but not limited to, zinc, cobalt, or copper; sugar alcohols including but not limited to, mannitol or sorbitol; salt-forming counter ions including but not limited to, sodium and sodium chloride; fillers such as microcrystalline cellulose, lactose, corn and other starches; binding agents; sweeteners and other flavoring agents; coloring agents; and/or nonionic surfactants including but not limited to Tween™ (including but not limited to, Tween 80 (polysorbate 80) and Tween 20 (polysorbate 20), Pluronics™ and other pluronic acids, including but not limited to, pluronic acid F68 (poloxamer 188), or PEG. Suitable surfactants include for example but are not limited to polyethers based upon polyethylene oxide)-poly(propylene oxide)-polyethylene oxide), i.e., (PEO-PPO-PEO), or polypropylene oxide)-poly(ethylene oxide)-poly(propylene oxide), i.e., (PPO-PEO-PPO), or a combination thereof. PEO-PPO-PEO and PPO-PEO-PPO are commercially available under the trade names Pluronics™, R-Pluronics™, Tetronics™ and R-Tetronics™ (BASF Wyandotte Corp., Wyandotte, Mich.) and are further described in U.S. Pat. No. 4,820,352 incorporated herein in its entirety by reference. Other ethylene/polypropylene block polymers may be suitable surfactants. A surfactant or a combination of surfactants may be used to stabilize PEGylated TC against one or more stresses including but not limited to stress that results from agitation. Some of the above may be referred to as "bulking agents." Some may also be referred to as "tonicity modifiers." Antimicrobial preservatives may also be applied for product stability and antimicrobial effectiveness; suitable preservatives include but are not limited to, benzyl alcohol, benzalkonium chloride, metacresol, methyl/propyl parabene, cresol, and phenol, or a combination thereof. U.S. Pat. No. 7,144,574, which is incorporated by reference herein, describe additional materials that may be suitable in pharmaceutical compositions and formulations of the invention and other delivery preparations.

TC polypeptides of the invention, including those linked to water soluble polymers such as PEG can also be administered by or as part of sustained-release systems. Sustained-release compositions include, including but not limited to, semi-permeable polymer matrices in the form of shaped articles, including but not limited to, films, or microcapsules. Sustained-release matrices include from biocompatible materials such as poly(2-hydroxyethyl methacrylate) (Langer et al., *J. Biomed. Mater. Res.*, 15: 267-277 (1981); Langer, Chem. Tech., 12: 98-105 (1982), ethylene vinyl acetate (Langer et al., supra) or poly-D-(−)-3-hydroxybutyric acid (EP 133,988), polylactides (polylactic acid) (U.S. Pat. No. 3,773,919; EP 58,481), polyglycolide (polymer of glycolic acid), polylactide co-glycolide (copolymers of lactic acid and glycolic acid) polyanhydrides, copolymers of L-glutamic acid and gamma-ethyl-L-glutamate (Sidman et al., *Biopolymers,* 22, 547-556 (1983), poly(ortho)esters, polypeptides, hyaluronic acid, collagen, chondroitin sulfate, carboxylic acids, fatty acids, phospholipids, polysaccharides, nucleic acids, polyamino acids, amino acids such as phenylalanine, tyrosine, isoleucine, polynucleotides, polyvinyl propylene, polyvinylpyrrolidone and silicone. Sustained-release compositions also include a liposomally entrapped compound. Liposomes containing the compound are prepared by methods known per se: DE 3,218,121; Eppstein et al., *Proc. Natl. Acad. Sci. U.S.A.,* 82: 3688-3692 (1985); Hwang et al., *Proc. Natl. Acad. Sci. U.S.A.,* 77: 4030-4034 (1980); EP 52,322; EP 36,676; U.S. Pat. No. 4,619,794; EP 143,949; U.S. Pat. No. 5,021,234; Japanese Pat. Appln. 83-118008; U.S. Pat. Nos. 4,485,045 and 4,544,545; and EP 102,324. All references and patents cited are incorporated by reference herein.

Liposomally entrapped TC polypeptides can be prepared by methods described in, e.g., DE 3,218,121; Eppstein et al., *Proc. Natl. Acad Sci. U.S.A.,* 82: 3688-3692 (1985); Hwang et al., *Proc. Natl. Acad. Sci. U.S.A.,* 77: 4030-4034 (1980); EP 52,322; EP 36,676; U.S. Pat. No. 4,619,794; EP 143,949; U.S. Pat. No. 5,021,234; Japanese Pat. Appln. 83-118008; U.S. Pat. Nos. 4,485,045 and 4,544,545; and EP 102,324. Composition and size of liposomes are well known or able to be readily determined empirically by one of ordinary skill in the art. Some examples of liposomes as described in, e.g., Park J W, et al., *Proc. Natl. Acad Sci. USA* 92:1327-1331 (1995); Lasic D and Papahadjopoulos D (eds): Medical Applications of Liposomes (1998); Drummond D C, et al., Liposomal drug delivery systems for cancer therapy, in Teicher B (ed): Cancer Drug Discovery and Development (2002); Park J W, et al., *Clin. Cancer Res.* 8:1172-1181 (2002); Nielsen U B, et al., *Biochim. Biophys. Acta* 1591 (1-3):109-118 (2002); Mamot C, et al., *Cancer Res.* 63: 3154-3161 (2003). All references and patents cited are incorporated by reference herein.

The dose administered to a patient in the context of the present invention should be sufficient to cause a beneficial response in the subject over time. Generally, the total pharmaceutically effective amount of the TC polypeptide of the present invention administered parenterally per dose is in the range of about 0.01 μg/kg/day to about 100 μg/kg, or about 0.05 mg/kg to about 1 mg/kg, of patient body weight, although this is subject to therapeutic discretion. In specific aspects of this embodiment, the conjugate can be administered at a dose in a range of greater than 4 μ/kg per day to about 20 μg/kg per day. In yet other aspects, the conjugate can be administered at a dose in a range of greater than 4 μg/kg per day to about 9 μg/kg per day. In yet other aspects, the conjugate can be administered at a dose in a range of about 4 μg/kg per day to about 12.5 μg/kg per day. In a specific aspect, the conjugate can be administered at or below a dose that is the maximum dose tolerated without undue toxicity. Further, the conjugate can be administered at least two times a week or the conjugate can be administered at least three times a week, at least four times a week, at least five times a week, at least six times a week, or seven times a week. In a specific aspect, where the conjugate is administered more than once, the conjugate can be administered at a dose of greater than 4 μg/kg per day each time. In particular, the conjugate can be administered over a period of two weeks or greater. In certain aspects, the growth of interleukin-10 receptor expressing cells can be inhibited by at least 50%, at least 65%, at least 75%, at least 80%, at least 85%, at least 90%, at least 95% or by at least 99% as compared to a reference sample, i.e., a sample of cells not contacted with a conjugate of the invention. In a specific aspect of this embodiment, the conjugate can be administered at a dose of about 5.3 μg/kg per day, or at a dose of about 7.1 μg/kg per day, or at a dose of about 9.4 μg/kg per day, or at a dose of about 12.5 μg/kg per day. The frequency of dosing is also subject to therapeutic discretion and may be more frequent or less frequent than the commercially available TC polypeptide products approved for use in humans. Generally, a targeting polypeptide of the TC, PEGylated TC polypeptide, conjugated TC polypeptide, or PEGylated conjugated TC polypeptide of the invention can be administered by any of the routes of administration described above.

Therapeutic Uses of TC of the Invention

The TC of the invention are useful for treating a wide range of disorders. The invention also includes a method of treating a mammal that is at risk for, is having, and/or has had a cancer responsive to TC, CD8+ T-cell stimulation, and/or TC formulations. Administration of TCs may result in a short term effect, i e. an immediate beneficial effect on several clinical parameters observed and this may 12 or 24 hours from administration, and, on the other hand, may also result in a long term effect, a beneficial slowing of progression of tumor growth, reduction in tumor size, and/or increased circulating CD8+ T cell levels and the TC of the present invention may be administered by any means known to those skilled in the art, and may beneficially be administered via infusion, e.g. by arterial, intraperitoneal or intravenous injection and/or infusion in a dosage which is sufficient to obtain the desired pharmacological effect.

The TC dosage may range from 10-200 mg, or 40-80 mg TC polypeptide per kg body weight per treatment. For example, the dosage of TC which is administered may be about 20-100 mg TC polypeptide per kg body weight given as a bolus injection and/or as an infusion for a clinically necessary period of time, e.g. for a period ranging from a few minutes to several hours, e.g. up to 24 hours. If necessary, the TC administration may be repeated one or several times. The administration of TC may be combined with the administration of other pharmaceutical agents such as chemotherapeutic agents. Furthermore, the present invention relates to a method for prophylaxis and/or treatment of cancer comprising administering a subject in need thereof an effective amount of TC.

Average quantities of the TC may vary and in particular should be based upon the recommendations and prescription of a qualified physician. The exact amount of TC is a matter of preference subject to such factors as the exact type of condition being treated, the condition of the patient being treated, as well as the other ingredients in the composition. The invention also provides for administration of a therapeutically effective amount of another active agent. The amount to be given may be readily determined by one of ordinary skill in the art based upon therapy with TC.

EXAMPLES

The following examples are offered to illustrate, but not to limit the claimed invention.

Example 1: General Methodology for Synthesis of TLR Agonists

This Example provides the general methodology used in synthesizing TLR-agonists of the present invention.

All commercially available anhydrous solvents were used without further purification and were stored under a nitrogen atmosphere. TLC was performed on Merck Silica gel 60 F254 plates using UV light and/or staining with aqueous KMnO4 solution for visualization. Chromatographic purification was performed on Combi Flash Rf from Teledyne ISCO using conditions detailed in the experimental procedure. Analytical HPLC was performed on Shimadzu system using Phenomenex Gemini—NX C18 5 μm 50×4.6 mm column, which was eluted at 1 ml/min with a linear gradient of acetonitrile in water containing 0.05% TFA. (Mobile phase A: 0.05% trifluoroacetic acid in water; Mobile phase B: 0.05% trifluoroacetic acid in 90% acetonitrile (ACN) aqueous solution) or Waters BEH 1.7 μm v2.1×50 mm column. Analytic Method 1: 0% B in 1 min, 0-50% B in 11 min, 50-100% B in 0.5 min, 100% B for 1.5 min, 100-0% 13 in 1 min, 0% B for 2 min; Method 2: 10-20% 13 in 1 min, 20-70% B in 11 min, 70-100% B in 0.5 min, 100% B for 1.5 min, 100-10% B in 1 min, 10% B for 2 min; Method 3: Method 2: 0-40% B in 1 min, 40-90% B in 11 min, 90-100% Bin 0.5 min, 100% B for 1.5 min, 100-10% B in 1 min, 10% B for 2 min; Method 4: 5% B in 0.3 min, 5% to 100% B from 0.3 to 1.5 min. 100% B from 1.5 min to 1.8 min flow rate from 0.8 ml/min to 1.1 min/min from 0 min to 1.8 min.

Preparative HPLC was performed on Shimadzu system using Gemini—NX C18 5 μm 100×30 mm, 150×30 mm or 250×50 mm column, depending on the scale. Mass spectra (MS) were recorded on a Shimadzu LCMS-2020 system and data were processed using Shimadzu LabSolutions software. Agilent 1260 Infinity Binary LC coupled with 6230 Accurate-Mass TOFMS system was used for HR-ESI-TOF analysis. NMR spectral data were collected on a 500 MHz Bruker NMR spectrometer. Chemical shifts (δ) were reported in ppm and referenced off the deuterium solvent signal. Coupling constants (J) are reported in hertz (Hz). Spin multiplicities are described as: s (singlet), br (broad), d (doublet), dd (doublet of doublets), t (triplet), q (quartet), or m (multiplet). monomeric antibody was pooled, 0.22 μM filtered, and stored at ≤65° C. until further use.

Example 2: Synthesis of TLR Agonists Comprising the Following Structure—Core 1, (FIG. 1)

Core 1

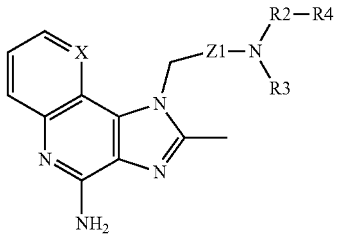

In some embodiments, X is CH or NH;

$R_2$ and $R_3$ are each connected to form $C_4$ to $C_8$ cyclo alkyl or independently —H, $C_1$ to $C_{12}$ alkyl, nitro containing alkyl, aromatic cylele or —C(NH)$NH_2$;

$R_4$ is $C_1$ to $C_{12}$ alkyl, $C_1$ to $C_{12}$ substituted alkyl, $C_4$ to $C_8$ cycloalkyl, $C_4$ to $C_8$ substituted cycloalkyl, aromatic cycle, substituted aromatic cycle, aromatic hetero cycle, substituted, aromatic hetero cycle, —$ONH_2$ terminal $C_1$ to $C_{12}$ alkyl, or absent. In some embodiments, $Z_1$═$C_1$ to $C_6$ alkyl, $C_3$ to $C_8$ cycloalkyl, or $C_3$ to $C_8$ nitro containing heterocycle.

TLR-agonist having Core 1 structure were synthesized as disclosed in the schemes below.

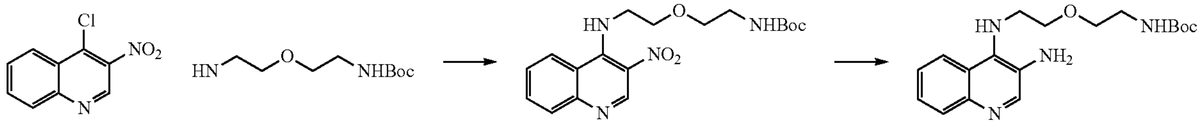

1

2

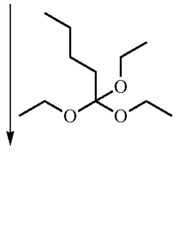

-continued

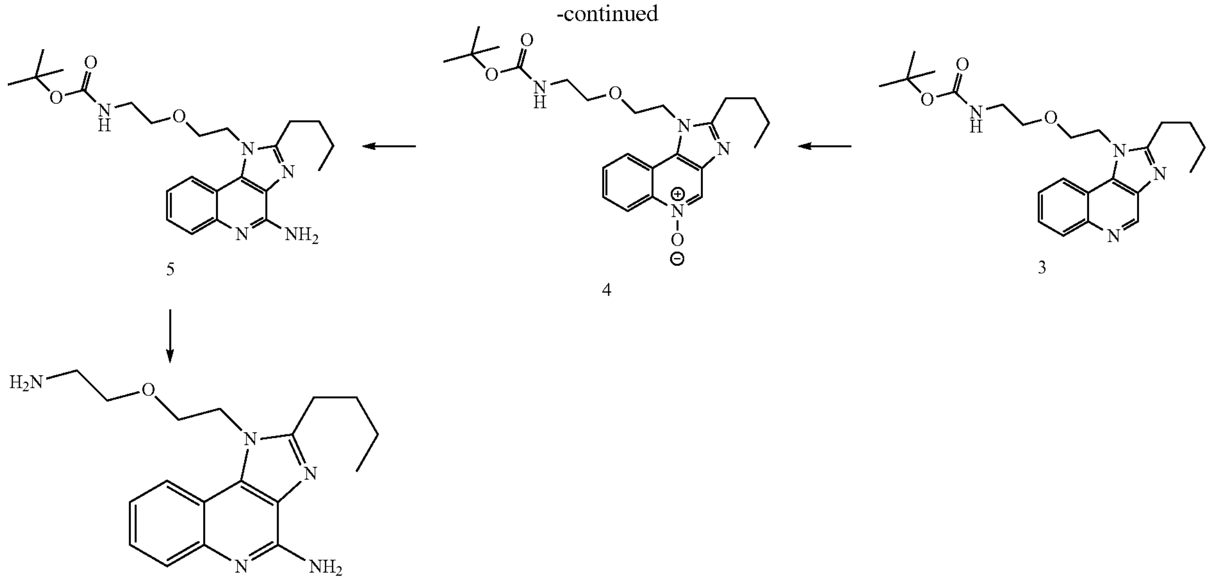

5 4 3

A tert-Butyl 2-(2-(3-nitroquinolin-4-ylamino)ethoxy)ethylcarbamate (1): 4-Chloro-3-nitroquinoline (1750 mg, 8.39 mmol) was dissolved in DCM (30 mL) and treated with free amine (1800 mg, 8.55 mmol) followed by TEA (2.29 mL, 17.3 mmol). The reaction was kept at room temperature for 18 h, then washed with $H_2O$ (20 mL), brine (10 mL), dried over $MgSO_4$ and concentrated in vacuo. Target compound (1) was obtained as a yellow solid (3130 mg, 99%), MS m/z 399 $(M+Na)^+$.

tert-Butyl 2-(2-(3-aminoquinolin-4-ylamino)ethoxy)ethylcarbamate (2): The nitro compound (1) (3.12 g, 8.29 mmol) was dissolved in THF (100 mL) and water (80 mL). Zinc (13.55 g, 207.2 mmol) was added in one portion followed by $NH_4Cl$ (13.3 g, 248.6 mmol). The suspension was stirred vigorously at room temperature for 1 h (HPLC). After filtration, the cake was washed with THF (20 mL×2). To the filtrate was added NaCl until the aqueous phase was saturated. The liquid phase was collected and the THF layer separated. The aqueous layer was extracted with THF/EA (50 ml/50 ml). The organic layers were combined, dried over $MgSO_4$, and concentrated to obtain residue (2) for the next step (3.1 g, >100%). MS m/z 347 $(M+H)^+$.

tert-Butyl 2-(2-(2-butyl-1H-imidazo[4,5-c]quinolin-1-yl)ethoxy)ethylcarbamate (3): Amine compound (2) (3.1 g, crude, <8.95 mmol) and triethylorthovalerate (3.1 mL, 13.5 mmol) were suspended in toluene (200 mL) and heated to 110° C. Then pyridine HCl (55 mg, 0.48 mmol) was added. The reaction was heated for 4 h. The mixture was kept at room temperature for 48 h. The liquid was decanted, and the remaining solid/residue was agitated with toluene (20 mL×2) merged with the liquid and concentrated. The residue was dissolved in DCM and purified by column chromatography (methanol in DCM, 0-10-20%, 80 g column) to obtain target compound (3) (1.05 g, 30% 2-step from nitro compound 1). MS m/z 413 $(M+H)^+$.

1-(2-(2-(tert-Butoxycarbonylamino)ethoxy)ethyl)-2-butyl-1H-imidazo[4,5-c]quinoline 5-oxide (4): Compound 3 (1.05 g, 2.54 mmol) was dissolved in DCM (20 mL) and treated with mCPBA (750 mg, 2.83 mmol). The reaction was kept at room temperature for 4 h. The mixture was washed with $NaHCO_3$ saturated solution (15 mL×3), dried and concentrated to obtain crude syrup for the next step (4) (900 mg, 83%), MS m/z 429 $(M+H)^+$.

tert-Butyl 2-(2-(4-amino-2-butyl-1H-imidazo[4,5-c]quinolin-1-yl)ethoxy)ethylcarbamate (5): In a pressure tube, compound 4 (900 mg, 2.18 mmol) was dissolved in dichloroethane (25 mL) and treated with concentrated ammonium hydroxide (28%, 1 mL) and the temperature brought to 80° C. To this mixture, tosyl chloride (470 mg, 2.46 mmol) was slowly added over 5 min after cooling. Concentrated ammonium hydroxide (0.5 mL) was added and the tube sealed. The tube was heated at 80° C. for 4 h. After cooling down, the mixture was diluted with DCM (60 mL), washed with water (40 mL), dried and purified by silica gel column chromatography to obtain target compound (5) (750 mg, 80%). MS m/z 428 $(M+H)^+$.

1-(2-(2-Aminoethoxy)ethyl)-2-butyl-1H-imidazo[4,5-c]quinolin-4-amine (A): Compound 5 (750 mg, 1.75 mmol) was treated with 1.25 M HCl in EtOH (20 mL) at room temperature for 17 h. Next the reaction was dried in vacuo, and the residue re-suspended in $EtOH/Et_2O$ (1/10; 20 mL) and filtered. The solid was collected to obtain target compound (A) (600 mg, 85%). HPLC (Method 1): 5.8 min, MS m/z 328 $(M+H)^+$.

A

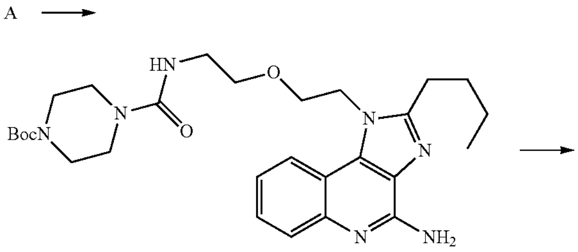

6

-continued

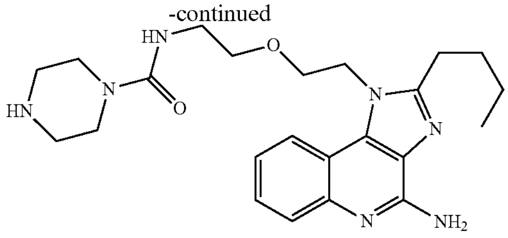

7 tert-Butyl 4-(2-(2-(4-amino-2-butyl-1H-imidazo[4,5-c]quinolin-1-yl)ethoxy)ethylcarbamoyl)piperazine-1-carboxylate (6): Compound A, HCl salt (100 mg, 0.25 mmol) was dissolved in DCM (10 mL) and treated with TEA (68 uL, 0.511 mmol). To the suspension was added Cert-butyl 4-(chlorocarbonyl)piperazine-1-carboxylate (75 mg, 0.286 mmol). The reaction was kept at room temperature for 17 h and diluted with DCM/MeOH (4 mL/1 mL), the solution was then washed with brine. The organic phase was purified by silica gel column chromatography to obtain pure product 6 (130 mg, 0.24 mmol, 96%). MS m/z 540 $(M+H)^+$.

N-(2-(2-(4-Amino-2-butyl-1H-imidazo[4,5-c]quinolin-1-yl)ethoxy)ethyl)piperazine-1-carboxamide (7): Compound (6) (10 mg, 0.018 mmol) was treated with HCl in EtOH (~1.5M, 1 mL) at room temperature for 1 h, then 60° C. for 1 h and dried in vacu. The residue was washed with diethyl ether and dried to obtain target compound (7) (9 mg, 0.018 mmol, quant). MS m/z 440 $(M+H)^+$.

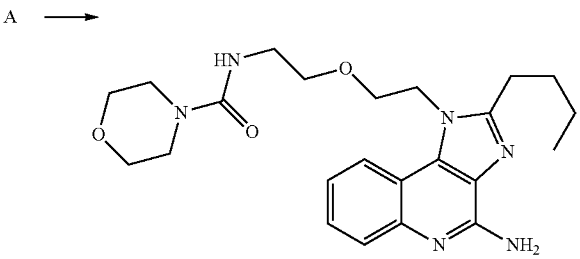

8

N-(2-(2-(4-Amino-2-butyl-1H-imidazo[4,5-c]quinolin-1-yl)ethoxy)ethyl)morpholine-4-carboxamide (8): Compound 7 was prepared by reacting compound A with morpholine-4-carbonyl chloride using a similar procedure as described for 6 to obtain target compound 7 (7 mg, 42%). MS m/z 441 (M+H).

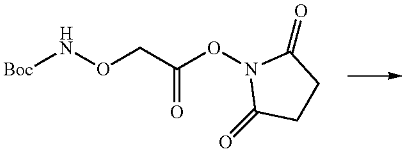

7

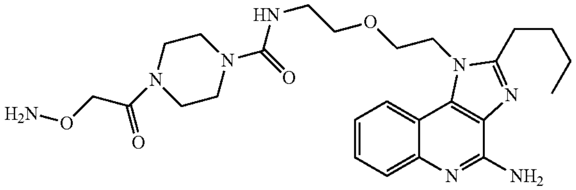

9

4-((R)-2-((R)-2-(2-(Aminooxy)acetamido)-3-methylbutanamido)-5-ureidopentanamido)benzyl 4-(2-(2-(4-amino-2-butyl-1H-imidazo[4,5-c]quinolin-1-yl)ethoxy)ethylcarbamoyl)piperazine-1-carboxylate (9): Compound 7 (22 mg, 0.02 mmol) was dissolved in DCM (1 mL) and treated with DIPEA (3.5 uL, 0.02 mmol), followed by 2,5-dioxopyrrolidin-1-yl 2-(tert-butoxycarbonylaminooxy)acetate (3.3 mg, 0.011 mmol). The reaction was kept at room temperature for 17 h. To the mixture was added TFA (0.3 mL), and stirred for 15 min. After drying in vacuo, the residue was purified by Prep-HPLC to obtain compound 9 (15 mg, 22% from 7). MS m/z 918 $(M+H)^+$.

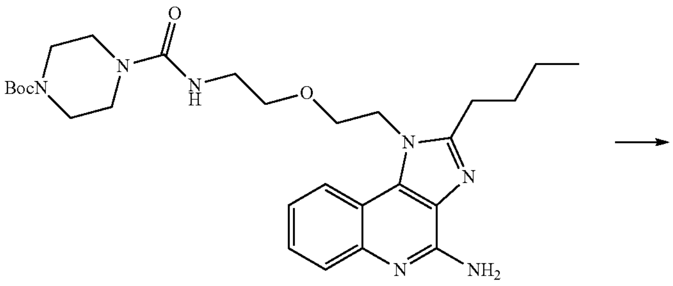

6

-continued

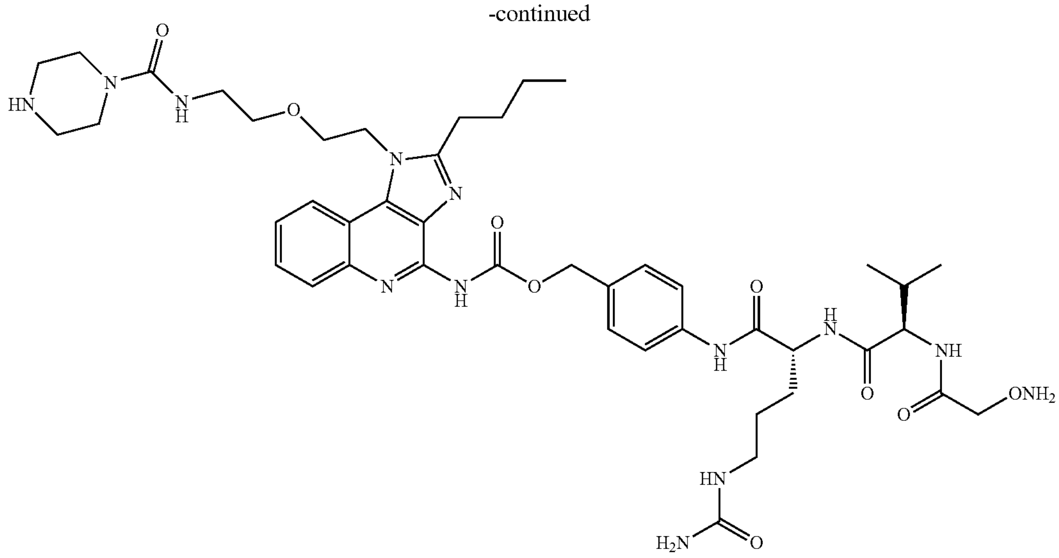

10

4-((R)-2-((R)-2-(2-(Aminooxy)acetamido)-3-methylbutanamido)-5-ureidopentanamido)benzyl 2-butyl-1-(2-(2-(piperazine-1-carboxamido)ethoxy)ethyl)-1H-imidazo[4,5-c]quinolin-4-ylcarbamate (10)): Compound 6 (65 mg, 0.097 mmol) was dissolved in DMF (2 mL) and treated with DIPEA (34 uL, 0.194 mmol), followed by Fmoc-VC-PAB-PNP (94 mg, 0.116 mmol). The reaction was kept at room temperature for 1 h, and water (10 mL) was added. The solid was collected, washed with water (2 mL), and dried. The yellow solid was dissolved in DMF (2 mL) and treated with diethylamine (100 uL, 0.97 mmol) at room temperature for 30 min. The reaction mixture was purified by Prep-LC to give intermediate Val-Cit-PAB-OCO-(Compound 6). This intermediate (11 mg, 0.01 mmol) was dissolved in DCM (1 mL) and treated with DIPEA (3.5 uL, 0.02 mmol), followed by 2,5-dioxopyrrolidin-1-yl 2-(tert-butoxycarbonylaminooxy)acetate (3.3 mg, 0.011 momol). The reaction was kept at room temperature for 17 h. TFA (0.3 mL) was added and the mixture was stirred for 15 min. After drying in vacuo, the residue was purified by Prep-HPLC to obtain compound 10 (15 mg, 16% from compound 6). MS m/z 918 $(M+H)^+$.

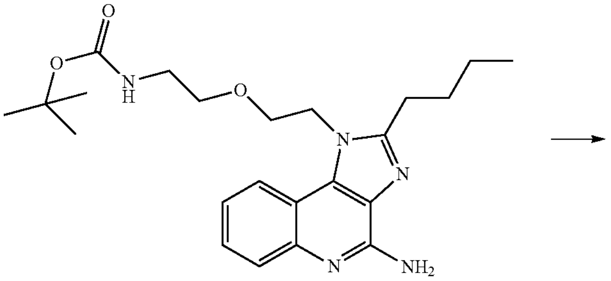

5

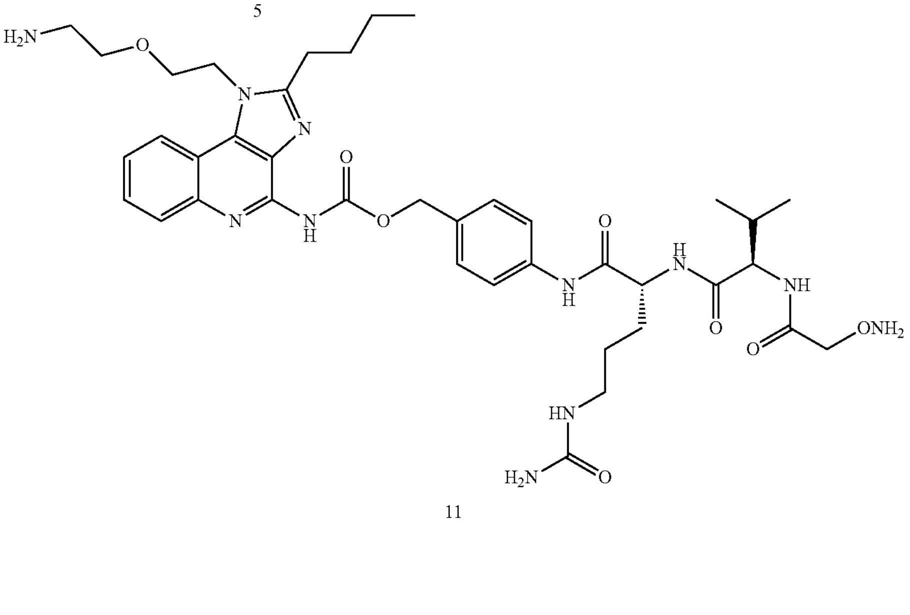

11

4-((R)-2-((R)-2-(2-(aminooxy)acetamido)-3-methylbutanamido)-5-ureidopentanamido)benzyl 1-(2-(2-aminoethoxy)ethyl)-2-butyl-1H-imidazo[4,5-c]quinolin-4-ylcarbamate (11): Compound 11 was prepared using 5 as starting material, with similar procedure as described for 10 to obtain target compound 11 (22 mg, 21% from 5). MS m/z 806 $(M+H)^+$.

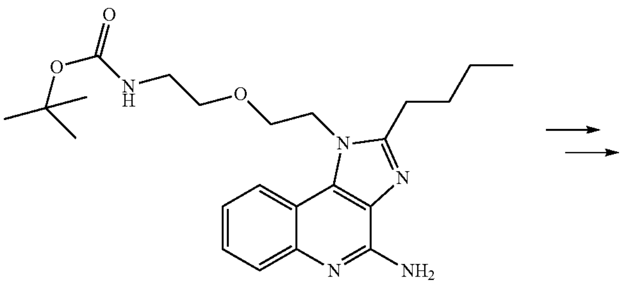

5

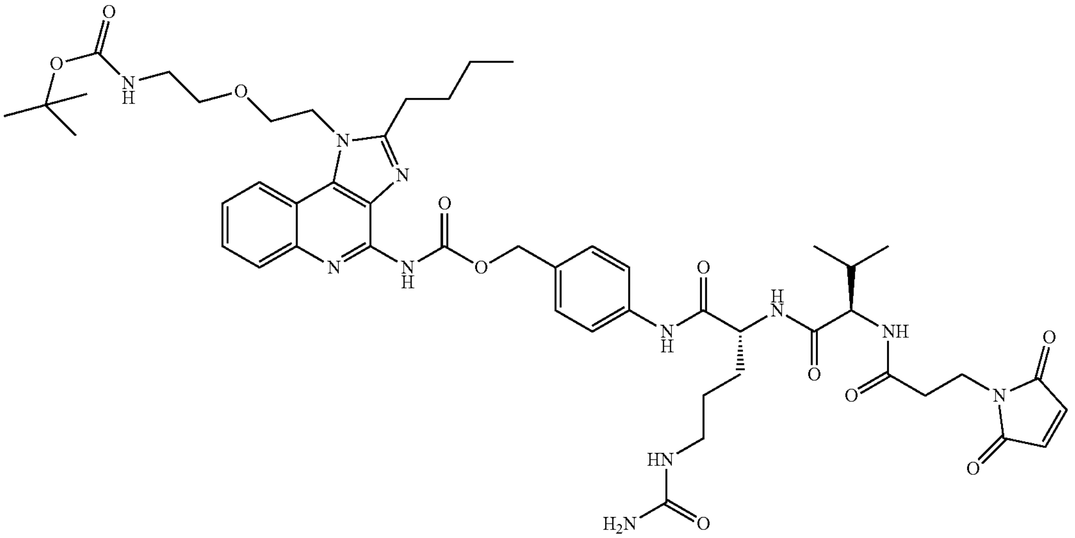

12

4-((R)-2-((R)-2-((2,5-Dioxo-2,5-dihydro-1H-pyrrol-1-yl)propanamido)-3-methylbutanamido)-5-ureidopentanamido)benzyl 2-butyl-1-(2-(2-(piperazine-1-carboxamido)ethoxy)ethyl)-1H-imidazo[4,5-c]quinolin-4-ylcarbamate (12): Compound 12 was prepared using 5, 2,5-dioxopyrrolidin-1-yl 3-(2,5-dioxo-2,5-dihydro-1H-pyrrol-1-yl)propanoate as starting material, with similar procedure as described for 10 to obtain target compound 12 (No TFA treatment) (15 mg, 17% from 5). MS ink 984 $(M+H)^+$.

7 +

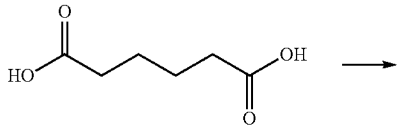

-continued

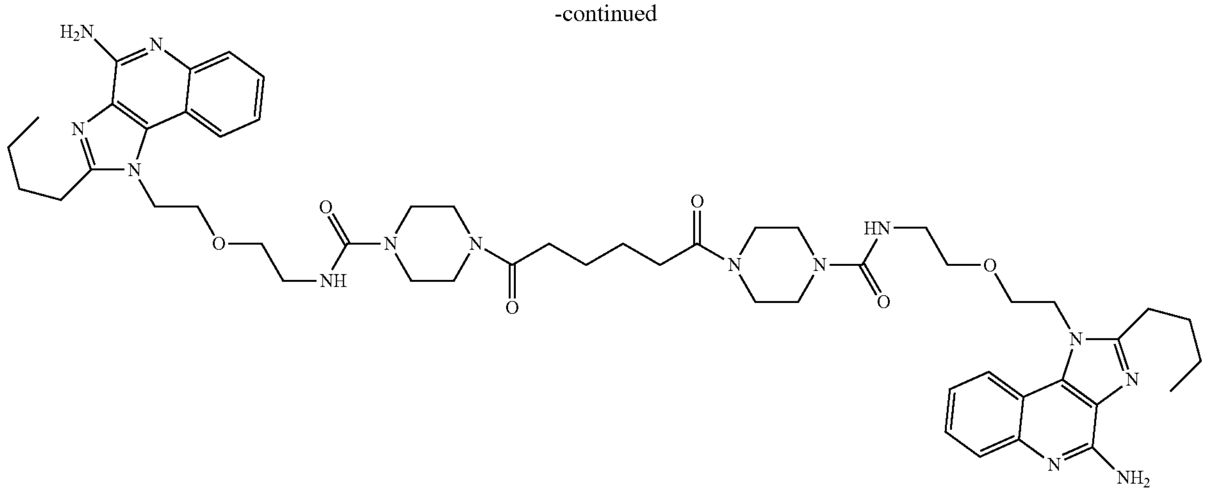

13

Adipic-Bis-(N-(2-(2-(4-amino-2-butyl-1H-imidazo[4,5-c]quinolin-1-yl)ethoxy)ethyl)piperazine-1-carboxamide (13): To a solution of compound 7 (8 mg, 0.018 mmol) and adipic acid (2 mg, 0.07 mmol) in DMF (1 mL) was added EDC (3 mg, 0.016 mmol), HOBt (1 mg, 0.018 mmol) and DIEA (4 ul, 0.23 mmol) at 23° C. After 24 h, the mixture was purified by Prep-LC, and dried to obtain compound 13 (5 mg, 0.004 mmol, 23%). MS m/z 1217 $(M+H)^+$.

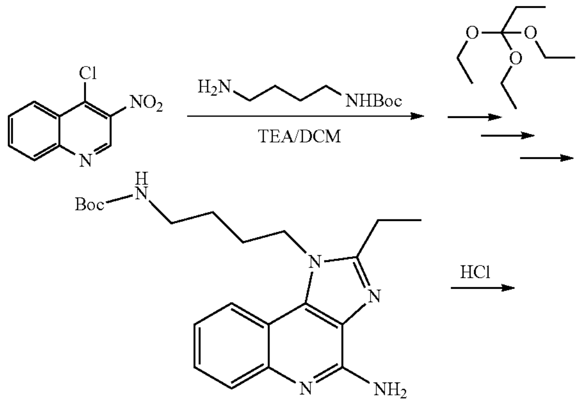

14

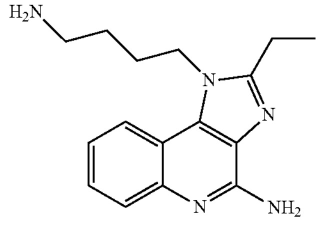

B tert-butyl 4-(4-amino-2-ethyl-1H-imidazo[4,5-c]quinolin-1-yl)butylcarbamate (14): Compound 14 was prepared using Boc-1,4-butanediamine and triethylorthopropionate as starting materials, and a similar procedure as described for 5 to obtain target compound 14 (420 mg, 1.095 mmol, 14.5% from starting material). MS m/z 384 $(M+H)^+$.

1-(4-aminobutyl)-2-ethyl-1H-imidazo[4,5-c]quinolin-4-amine, 2HCl (B): Compound 14 (400 mg, 1.043 mmol) was added to DCM (0.5 mL) and 4 M HCl in dioxane (10 mL, 40 mmol) at 23° C. After 1 h, LCMS showed the reaction complete. The solvent was removed in vacuo and dried for 6 h at high vacuum pump to obtain compound B (400 mg, 1.129 mmol, 99%) as a light yellow solid. MS m/z 284 $(M+H)^+$.

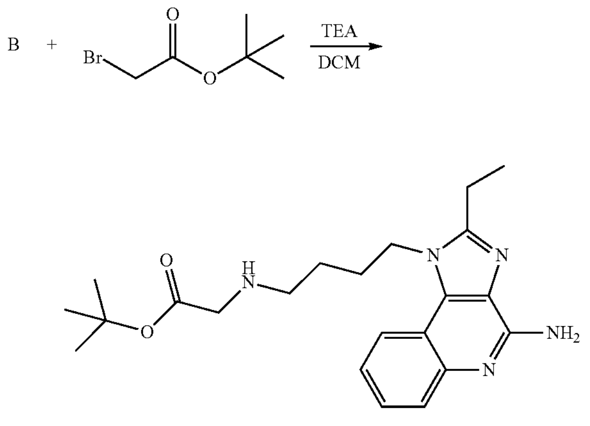

15 tert-butyl 2-(4-(4-amino-2-ethyl-1H-imidazo[4,5-c]quinolin-1-yl)butylamino)acetate (15): To a solution of compound B (31 mg 0.109 mmol) in DCM (5 mL) was added tert-butyl bromoacetate (15 uL, 0.102 mmol), followed by addition of TEA (88 uL, 0.681 mmol) at 23° C. After 24 h, the mixture was purified by Prep-LC to obtain compound 15 (4 mg, 0.006 mmol, 6%) as a yellow solid. MS m/z 398 $(M+H)^+$.

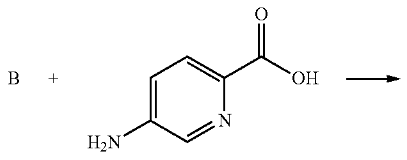

-continued

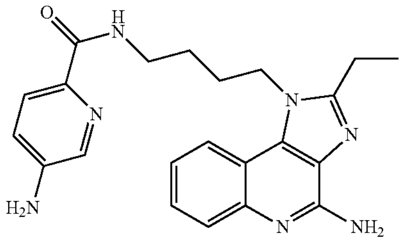

16

5-amino-N-(4-(4-amino-2-ethyl-1H-imidazo[4,5-c]quinolin-1-yl)butyl)picolinamide (16): To a solution of compound B (25 mg, 0.071 mmol) and 5-aminopyridine-2-carboxylic acid (10 mg, 0.072 mmol) in DMF (1 mL) was added 1-HATU (20 mg, 0.083 mmol) and DIEA (50 uL, 0.287 mmol) at 23° C. After 1 h, the mixture was purified by Prep-LC and dried to obtain compound 16 (21 mg, 0.033 mmol, 46%) as a white solid. MS m/z 404 $(M+H)^+$.

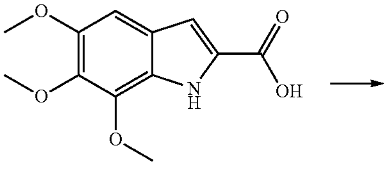

B

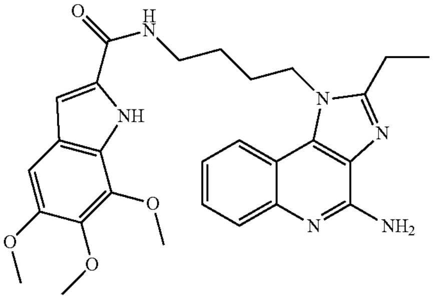

17

N-(4-(4-amino-2-ethyl-1H-imidazo[4,5-c]quinolin-1-yl)butyl)-5,6,7-trimethoxy-1H-indole-2-carboxamide (17)a: Compound 17 was prepared using compound B and 5,6,7-trimethoxy-1h-indole-2-carboxylic acid as starting materials, with similar procedure as described for 16 to obtain target compound 17 (13 mg, 0.017 mmol, 44%). MS m/z 517 $(M+H)^+$.

A +

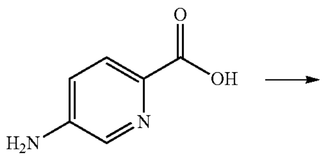

-continued

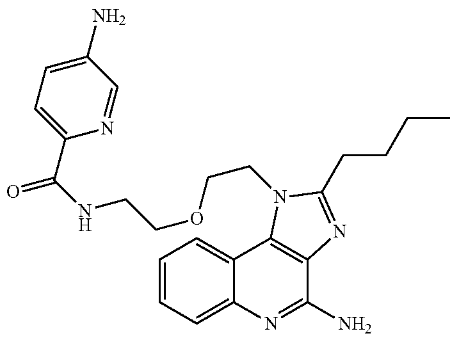

18

5-amino-N-(2-(2-(4-amino-2-butyl-1H-imidazo[4,5-c]quinolin-1-yl)ethoxy)ethyl)picolinamide (18): Compound 18 was prepared using compound A and 5-aminopyridine-2-carboxylic acid as starting materials, and a similar procedure as described for 16 to obtain target compound 18 (24 mg, 0.036 mmol, 82%) MS m/z 448 $(M+H)^+$.

B +

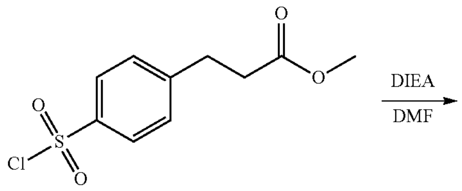

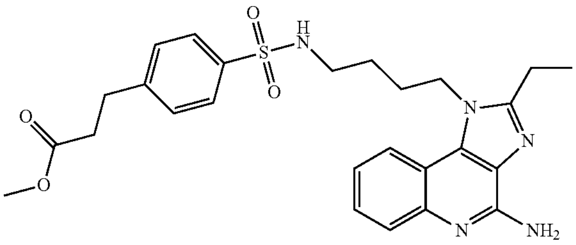

19 methyl 3-(4-(N-(4-(4-amino-2-ethyl-1H-imidazo[4,5-c]quinolin-1-yl)butyl)sulfamoyl)phenyl)propanoate (19): To a solution of compound B (14 mg, 0.035 mmol) and 5-aminopyridine-2-carboxylic acid (6 mg, 0.043 mmol) in DMF (1 mL) was added DIEA (40 uL, 0.230 mmol) at 23° C. After 30 min, the mixture was purified by Prep-LC, and dried to obtain compound 19 (15 mg, 0.020 mmol, 58%) as a light yellow solid. MS m/z 510 $(M+H)^+$.

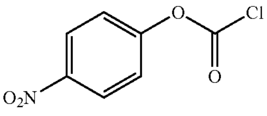

+

B

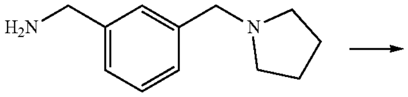

-continued

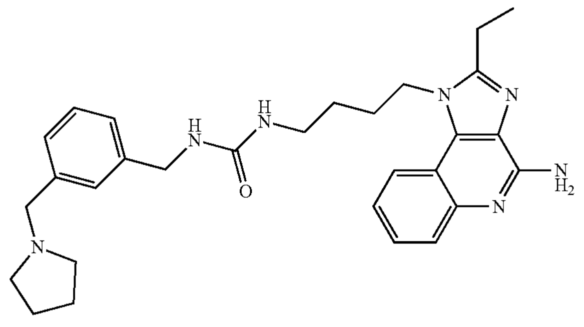

20

1-(4-(4-amino-2-ethyl-1H-imidazo[4,5-c]quinolin-1-yl)butyl)-3-(3-(pyrrolidin-1-ylmethyl)benzyl)urea (20): To a solution of (3-(pyrrolidin-1-ylmethyl)phenyl)methanamine (19 mg, 0.100 mmol) and Nitrophenylchloroformate (21 mg, 0.104 mmol) in DMF (1 mL) was added DIEA (34 uL, 0.195 mmol) at 23° C. After 10 min, LCMS showed the nitrophenol activation complete. To this mixture was added compound B. After 2 h, the mixture was purified by Prep-LC and dried to obtain compound 20 (3 mg, 0.006 mmol, 6%) as a white solid.

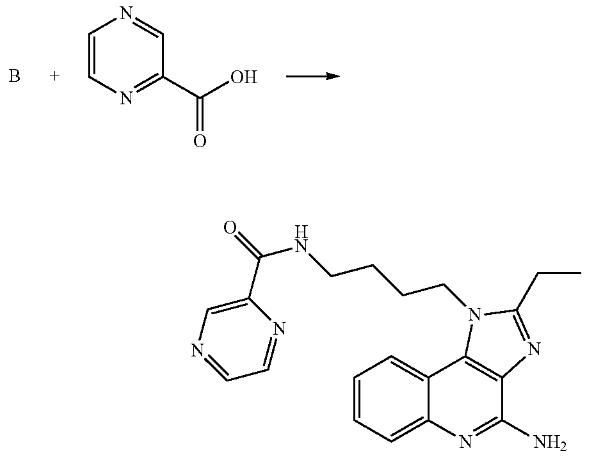

21

N-(4-(4-amino-2-ethyl-1H-imidazo[4,5-c]quinolin-t-yl)butyl)pyrazine-2-carboxamide (21): Compound 28 was prepared using compound B and Pyrazine carboxylic acid as starting materials, with similar procedure as described for 16 to obtain target compound 21 (11 mg, 0.013 mmol, 23%). MS m/z 390 $(M+H)^+$.

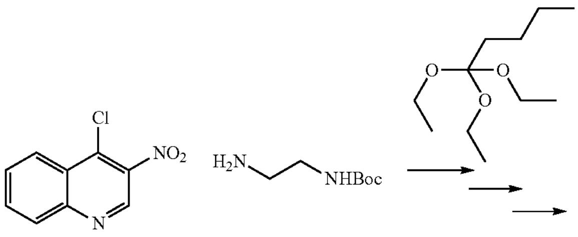

-continued

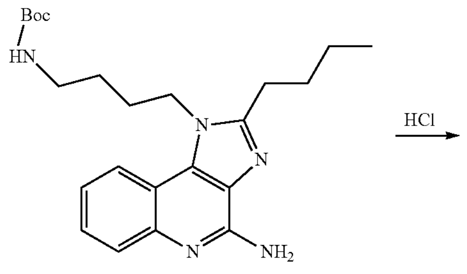

22

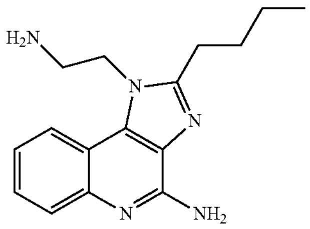

C tert-butyl 2-(4-amino-2-butyl-1H-imidazo[4,5-c]quinolin-1-yl)ethylcarbamate (22): Compound 22 was prepared using 4-chloro-3-nitroquinoline, tert-butyl 2-aminoethylcarbamate and triethylorthovalerate as starting materials, with similar procedure as described for compound 5 to obtain target compound 22 (140 mg, 0.365 mmol, 33%). MS m/z 384 $(M+H)^+$.

1-(4-aminobutyl)-2-ethyl-1H-imidazo[4,5-c]quinolin-4-amine, 3 HCl (C): Compound C was prepared using compound 22 as starting materials, with similar procedure as described for A to obtain target compound C (60 mg, 0.169 mmol, quant). MS m/z 284 $(M+H)^+$.

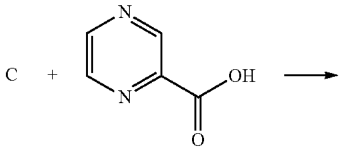

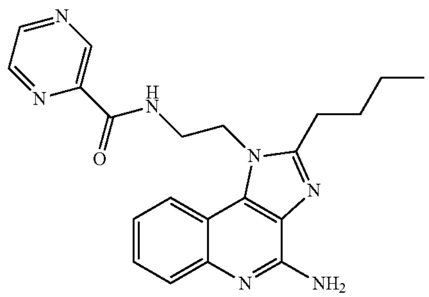

23

N-(2-(4-amino-2-butyl-1H-imidazo[4,5-c]quinolin-1-yl)ethyl)pyrazine-2-carboxamide (23): Compound 23 was prepared using compound C and Pyrazine carboxylic acid as starting materials, with similar procedure as described for 16 to obtain target compound 23 (8 mg, 0.09 mmol, 29%). MS m/z 390 $(M+H)^+$.

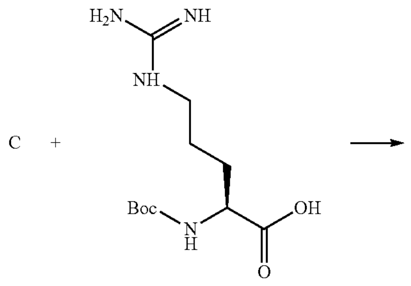

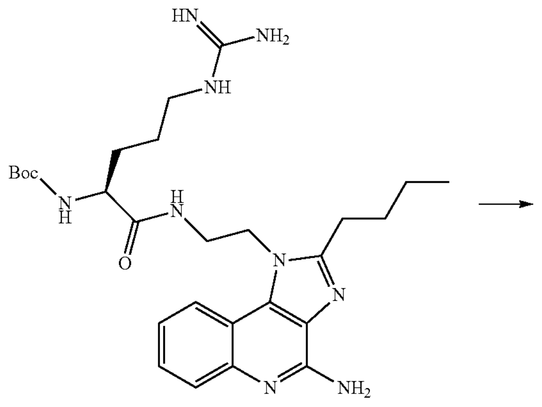

24

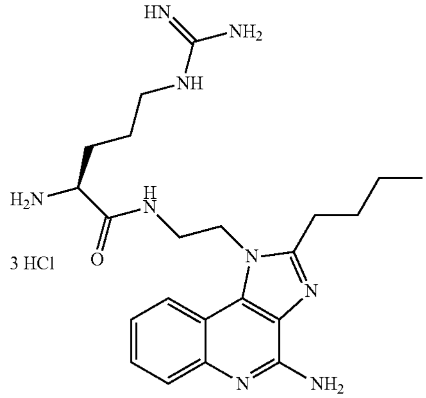

25

(S)-tert-butyl 1-(2-(4-amino-2-butyl-1H-imidazo[4,5-c]quinolin-1-yl)ethylamino)-5-guanidino-1-oxopentan-2-ylcarbamate (24): Compound 24 was prepared using compound C and Boc-Arg-OH as starting materials, with similar procedure as described for 16 to obtain target compound 24 (75 mg, 0.098 mmol, 79%). MS m/z 540 $(M+H)^+$.

(S)-2-amino-N-(2-(4-amino-2-butyl-1H-imidazo[4,5-c]quinolin-1-yl)ethyl)-5-guanidinopentanamide, 3HCl (25): To compound 24 (60 mg, 0.111 mmol) was added 4 M HCl in dioxane (1 mL, 4 mmol) at 23° C. After 2 h, the reaction was dried in vacuo. The residue was dried under high vacuum pump to obtain compound 25 (64 mg, 0.110 mmol, quant) as a white solid.

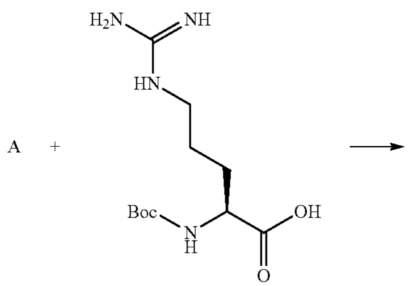

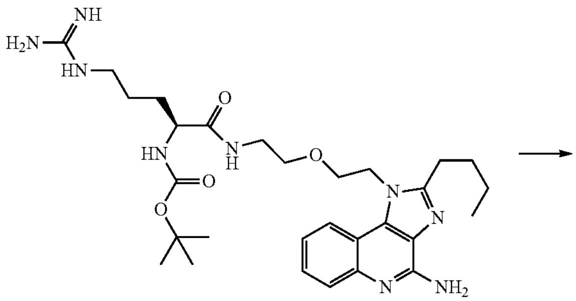

26

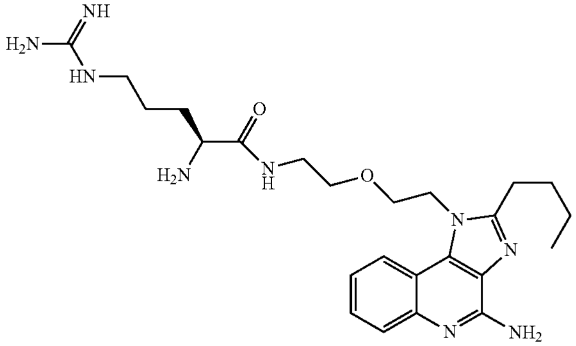

27

(S)-tert-butyl 1-(2-(2-(4-amino-2-butyl-1H-imidazo[4,5-c]quinolin-1-yl)ethoxy)ethylamino)-5-guanidino-1-oxopentan-2-ylcarbamate (26): Compound 26 was prepared using compound A and Boc-Arg-OH as starting materials, with similar procedure as described for 16 to obtain target compound 26 (20 mg, 0.019 mmol, 59%,). MS m/z 584 $(M+H)^+$.

(S)-2-amino-N-(2-(4-amino-2-butyl-1H-imidazo[4,5-c]quinolin-1-yl)ethyl)-5-guanidinopentanamide (27): Compound 27 was prepared using compound 26 as starting materials, with similar procedure as described for 25 to obtain target compound 27 (14 mg, 0.016 mmol, quant). MS m/z 484 $(M+H)^+$.

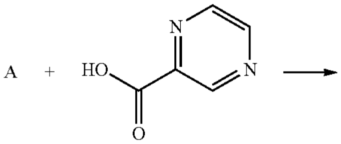

-continued

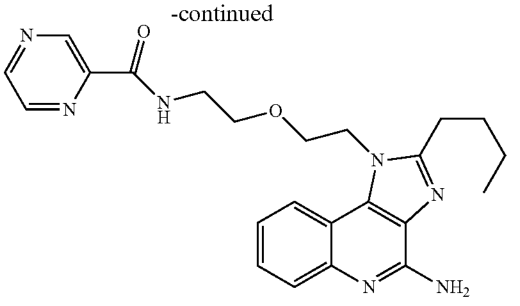

28

N-(2-(2-(4-amino-2-butyl-1H-imidazo[4,5-c]quinolin-1-yl)ethoxy)ethyl)pyrazine-2-carboxamide (28): Compound 28 was prepared using compound A and Pyrazine carboxylic acid as starting materials, with similar procedure as described for 16 to obtain target compound 28 (1.3 mg, 0.001 mmol, 4%). MS m/z 434 (M+H)+.

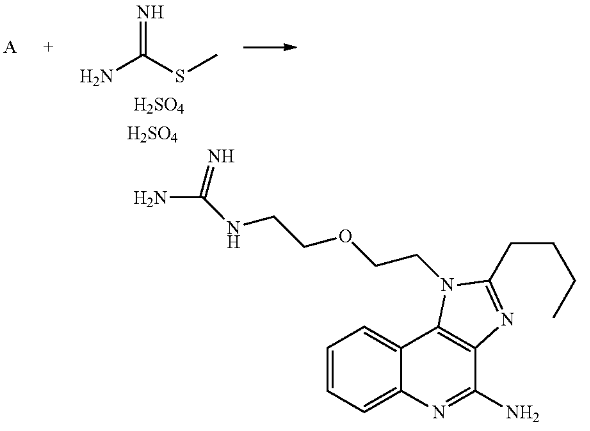

29

1-(2-(2-(4-amino-2-butyl-1H-imidazo[4,5-c]quinolin-1-yl)ethoxy)ethyl)guanidine (29): To a solution of compound A (15 mg, 0.038 mmol) and methyl carbamimidothioate bis(sulfate) (25 mg, 0.090 mmol) in DMF (1 mL) and water (1 mL) was added TEA (50 uL, 0.358 mmol) at 80° C. After 18 h, the mixture was purified by Prep-LC to obtain compound 29 (12 mg, 0.017 mmol, 45%). MS m/z 370 (M+H)+.

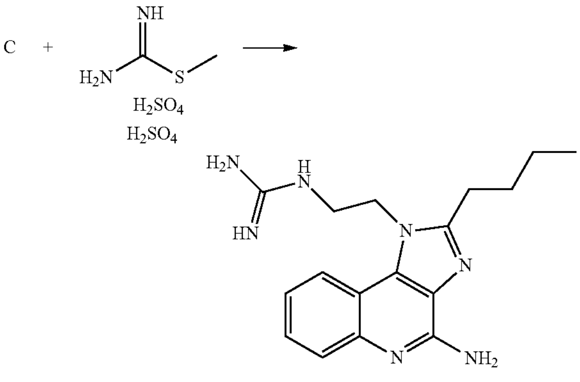

30

1-(2-(4-amino-2-butyl-1H-imidazo[4,5-c]quinolin-1-yl)ethyl)guanidine (30): Compound 30 was prepared using compound C as starting material, with similar procedure as described for 29 to obtain target compound 30 (10 mg, 0.013 mmol, 29%). MS m/z 434 (M+H)+.

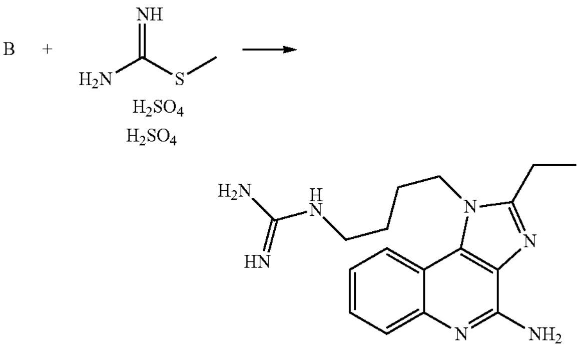

31

1-(4-(4-amino-2-ethyl-1H-imidazo[4,5-c]quinolin-1-yl)butyl)guanidine (31): Compound 31 was prepared using compound B as starting material, with similar procedure as described for 29 to obtain target compound 31 (8 mg, 0.010 mmol, 29%). MS m/z 326 (M+H)+.

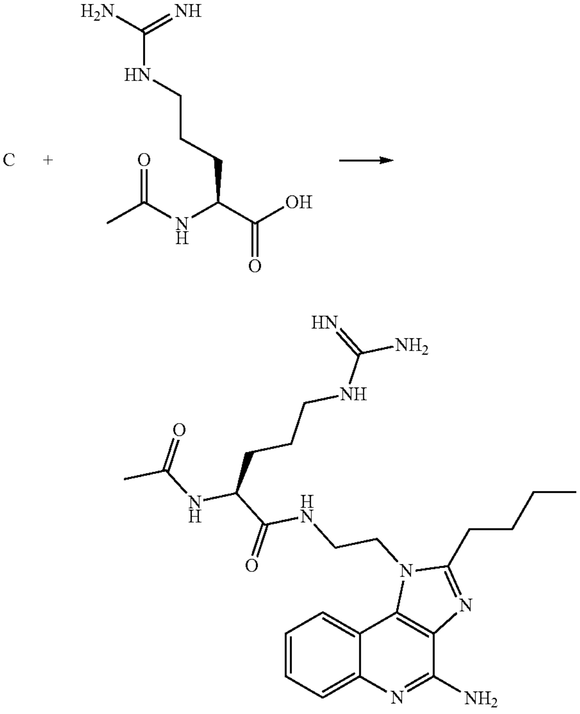

32

(S)-2-acetamido-N-(2-(4-amino-2-butyl-1H-imidazo[4,5-c]quinolin-1-yl)ethyl)-5-guanidinopentanamide (32): Compound 32 was prepared using compound C and Acetyl-argine as starting materials, with similar procedure as described for 16 to obtain target compound 32 (18 mg, 0.025 mmol, 69%). MS m/z 482 (M+H)+.

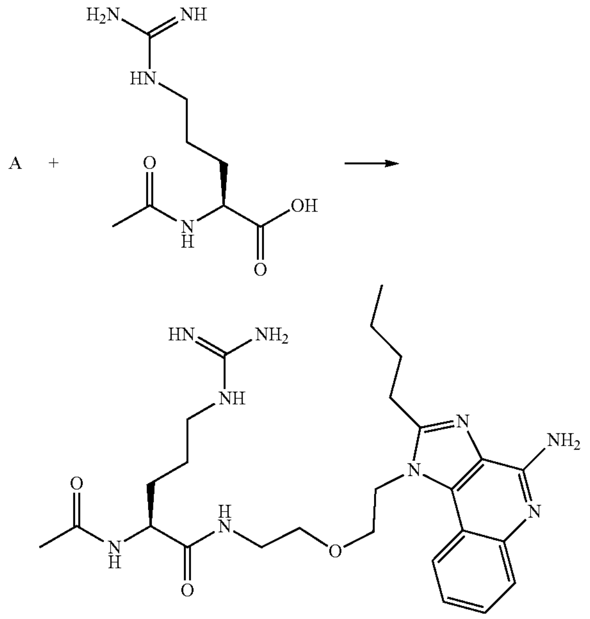

33

(S)-2-acetamido-N-(2-(2-(4-amino-2-butyl-1H-imidazo [4,5-c]quinolin-1-yl)ethoxy)ethyl)-5-guanidinopentanamide (33): Compound 33 was prepared using compound A and Acetyl-argine as starting materials, with similar procedure as described for 16 to obtain target compound 33 (4 mg, 0.019 mmol, 67%). MS m/z 526 (M+H)$^+$.

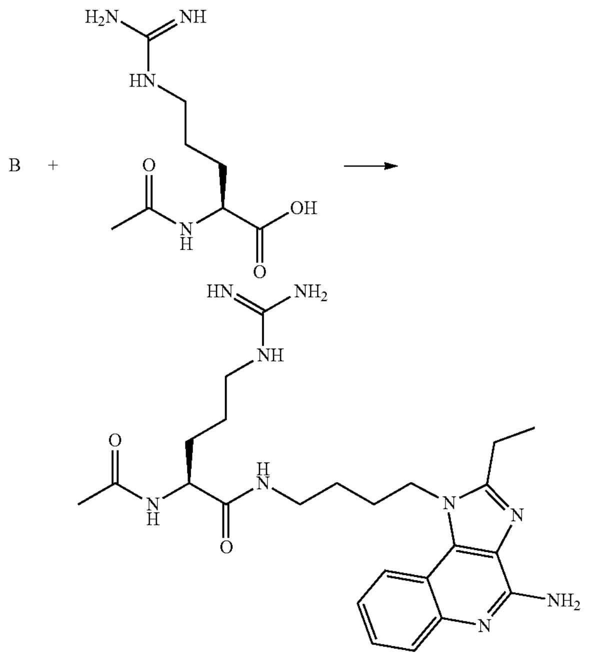

34

(S)-2-acetamido-N-(4-(4-amino-2-ethyl-1H-imidazo[4,5-c]quinolin-1-yl)butyl)-5-guanidinopentanamide (34): Compound 34 was prepared using compound B and Acetyl-argine as starting materials, with similar procedure as described for 16 to obtain target compound 34 (5 mg, 0.007 mmol, 30%). MS m/z 482 (M+H)$^+$.

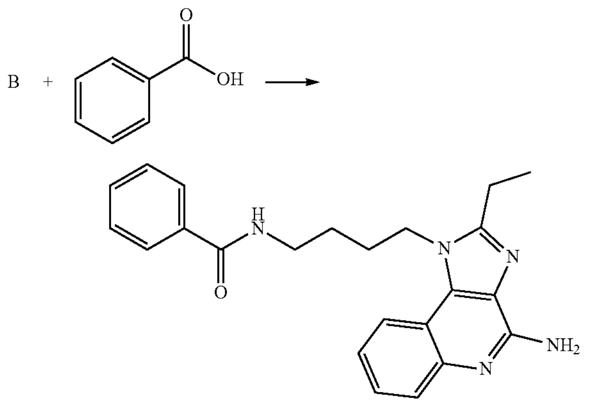

35

N-(4-(4-amino-2-ethyl-1H-imidazo[4,5-c]quinolin-1-yl) butyl)benzamide (35): Compound 35 was prepared using compound B and Benzoic acid as starting materials, with similar procedure as described for 16 to obtain target compound 35 (8 mg, 0.013 mmol, 53%). MS m/z 388 (M+H)$^+$.

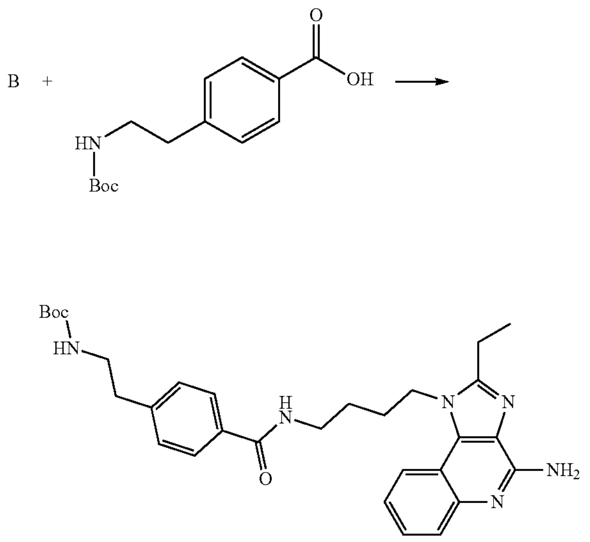

36 tert-butyl 4-(4-(4-amino-2-ethyl-1H-imidazo[4,5-c]quinolin-1-yl)butylcarbamoyl)phenethylcarbamate (36): Compound 36 was prepared using compound B and 4-((2-boc-amino)ethyl)Benzoic acid as starting materials, with similar procedure as described for 16 to obtain target compound 36 (25 mg, 0.033 mmol, 38%). MS m/z 531 (M+H)$^+$.

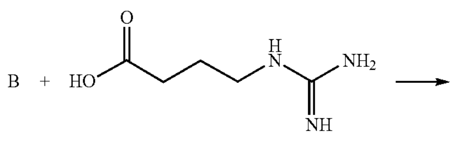

-continued

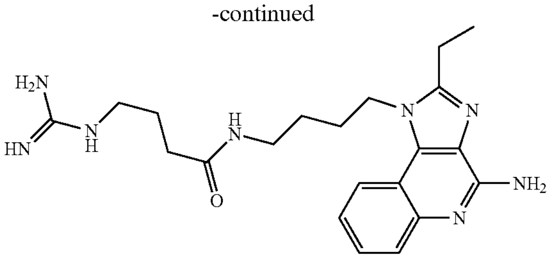

37

N-(4-(4-amino-2-ethyl-1H-imidazo[4,5-c]quinolin-1-yl)butyl)-4-guanidinobutanamide (37): Compound 37 was prepared using compound B and 4-guanido butyric acid as starting materials, with similar procedure as described for 16 to obtain target compound 37 (10 mg, 0.016 mmol, 45%). MS m/z 411 $(M+H)^+$.

B +

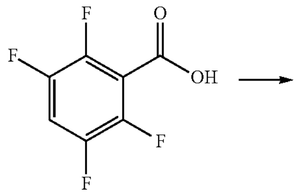

-continued

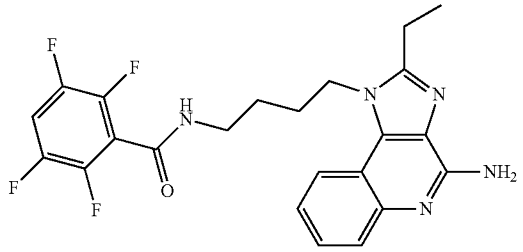

38

N-(4-(4-amino-2-ethyl-1H-imidazo[4,5-c]quinolin-1-yl)butyl)-2,3,5,6-tetrafluorobenzamide (38): Compound 38 was prepared using compound B and 2,3,5,6-tetra fluoro Benzoic acid as starting materials, with similar procedure as described for 16 to obtain target compound 38 (7 mg, 0.010 mmol, 36%). MS m/z 460 $(M+H)^+$.

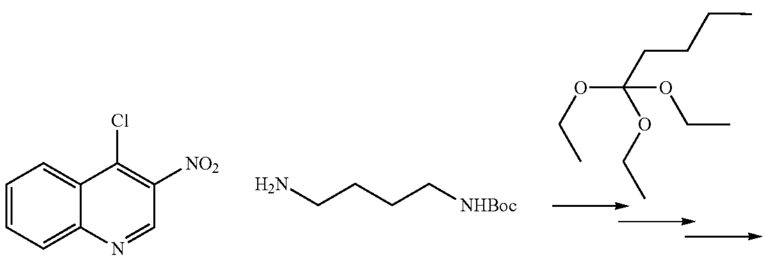

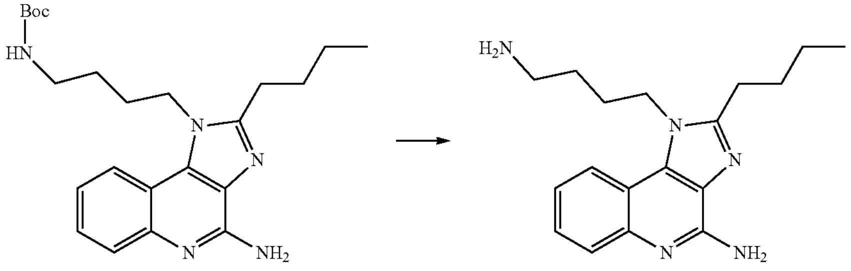

39 D tert-butyl 4-(4-amino-2-butyl-1H-imidazo[4,5-c]quinolin-1-yl)butylcarbamate (39): Compound 39 was prepared using 4-chloro-3-nitroquinoline, tert-butyl 4-aminobutylcarbamate and triethylorthovalerate as starting materials, with similar procedure as described for compound 5 to obtain target compound 39 (177 mg, 0.430 mmol, 20% from starting material). MS m/z 412 $(M+H)^+$.

1-(4-aminobutyl)-2-butyl-1H-imidazo[4,5-c]quinolin-4-amine, 3 HCl (D): Compound D was prepared using compound 39 as starting materials, with similar procedure as described for A to obtain target compound D (180 mg, 0.431 mmol, quant). MS m/z 312 $(M+H)^+$.

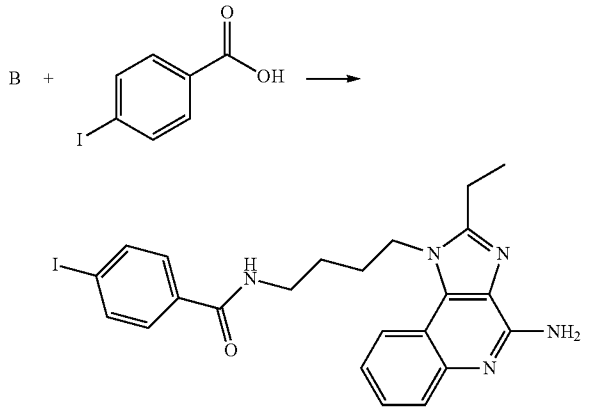

40

N-(4-(4-amino-2-ethyl-1H-imidazo[4,5-c]quinolin-1-yl)butyl)-4-iodobenzamide (40): Compound 40 was prepared using compound B and 4-iodo Benzoic acid as starting materials, with similar procedure as described for 16 to obtain target compound 40 (15 mg, 0.020 mmol, 72%). MS m/z 514 $(M+H)^+$.

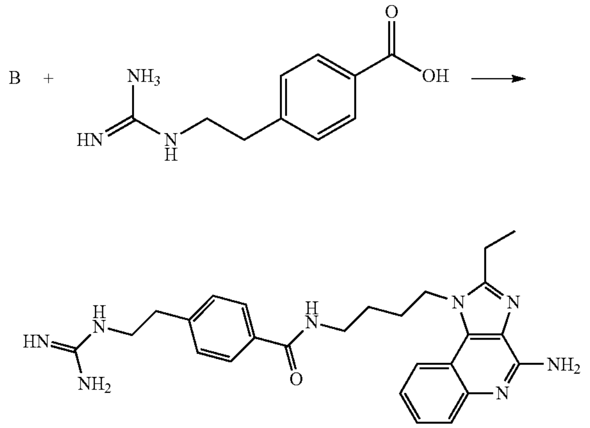

41

N-(4-(4-amino-2-ethyl-1H-imidazo[4,5-c]quinolin-1-yl)butyl)-4-(2-guanidinoethyl)benzamide (41): Compound 41 was prepared using compound B and 4-(2-guanidinoethyl)benzoic acid as starting materials, with similar procedure as described for 16 to obtain target compound 41 (7 mg, 0.009 mmol, 29%) MS m/z 473 $(M+H)^+$.

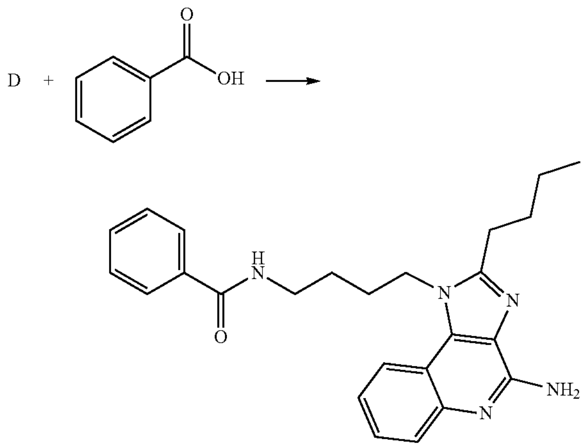

42

N-(4-(4-amino-2-butyl-1H-imidazo[4,5-c]quinolin-1-yl)butyl)benzamide (42): Compound 42 was prepared using compound D and benzoic acid as starting materials, with similar procedure as described for 16 to obtain target compound 42 (6 mg, 0.012 mmol, 38%). MS m/z 416 $(M+H)^+$.

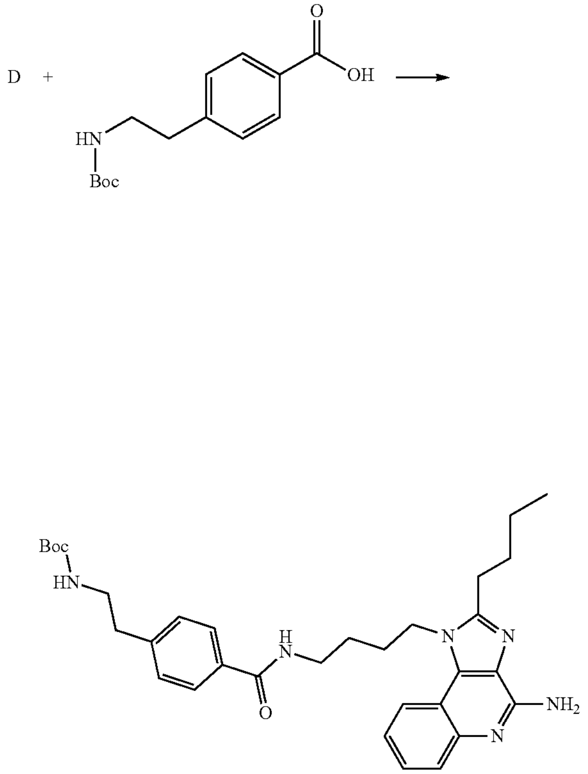

43 tert-butyl 4-(4-(4-amino-2-butyl-1H-imidazo[4,5-c]quinolin-1-yl)butylcarbamoyl)phenethylcarbamate (43): Compound 43 was prepared using compound D and 4-((2-boc-amino)ethyl)Benzoic acid as starting materials, with similar procedure as described for 16 to obtain target compound 43 (9 mg, 0.010 mmol, 38%). MS m/z 559 $(M+H)^+$.

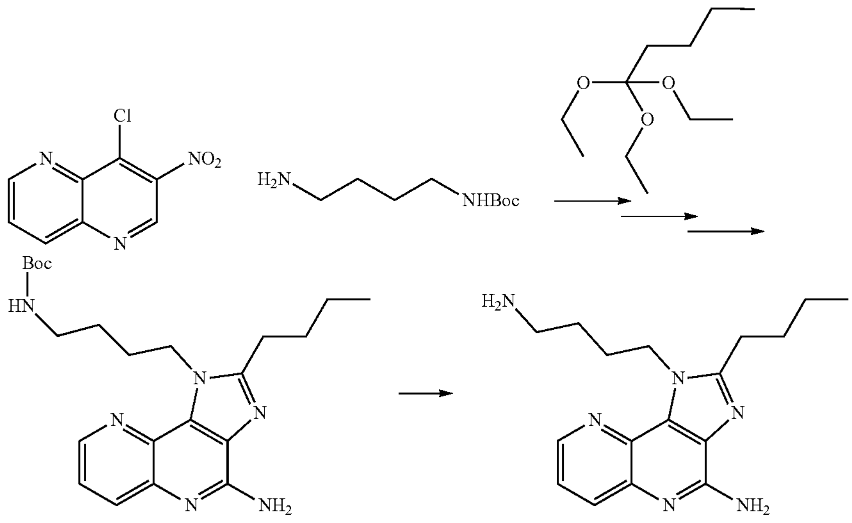

44 E tert-butyl 4-(4-amino-2-butyl-1H-imidazo[4,5-c]quinolin-1-yl)butylcarbamate (44): Compound 44 was prepared using 4-chloro-3-nitro-1,5-naphthyridine, tert-butyl 4-aminobutylcarbamate and triethylorthovalerate as starting materials, with similar procedure as described for 5 to obtain target compound 44 (120 mg, 0.159 mmol, 5.3% from starting material), MS m/z 413 $(M+H)^+$.

1-(4-aminobutyl)-2-butyl-1H-imidazo[4,5-c][1,5]naphthyridin-4-amine, 4 HCl (E): Compound E was prepared using compound 44 as starting materials, with similar procedure as described for A to obtain target compound E (145 mg, 0.296 mmol, quant). MS m/z 313 $(M+H)^+$

D +

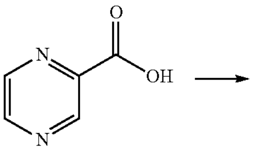

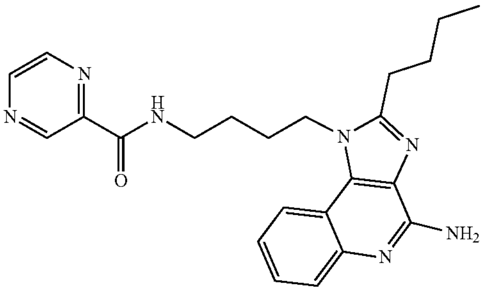

45

N-(4-(4-amino-2-butyl-1H-imidazo[4,5-c]quinolin-1-yl)butyl)pyrazine-2-carboxamide (45): Compound 45 was prepared using compound D and Pyrazine carboxylic acid as starting materials, with similar procedure as described for 16 to obtain target compound 45 (4 mg, 0.04 mmol, 14%) MS m/z 418 $(M+H)^+$.

B +

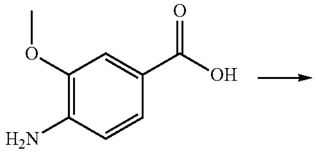

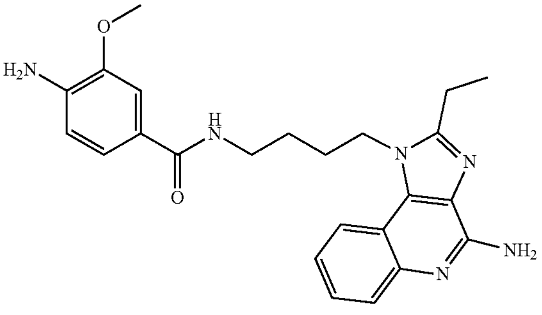

46

4-amino-N-(4-(4-amino-2-ethyl-1H-imidazo[4,5-c]quinolin-1-yl)butyl)-3-methoxybenzamide (46): Compound 46 was prepared using compound B and 4-Amino-3-methoxybenzoic acid as starting materials, with similar procedure as described for 16 to obtain target compound 46 (12.1 mg, 0.014 mmol, 58%). MS m/z 433 $(M+H)^+$.

B +

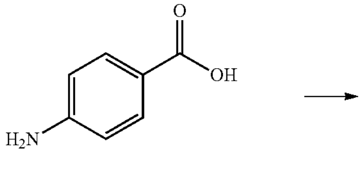

-continued

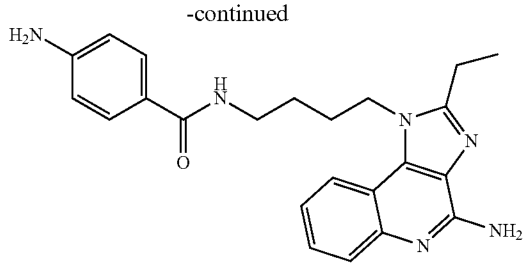

47

4-amino-N-(4-(4-amino-2-ethyl-1H-imidazo[4,5-c]quinolin-1-yl)butyl)benzamide (47): Compound 47 was prepared using compound B and 4-Aminobenzoic acid as starting materials, with similar procedure as described for 16 to obtain target compound 47 (6 mg, 0.007 mmol, 30%) MS n/z 403 $(M+H)^+$.

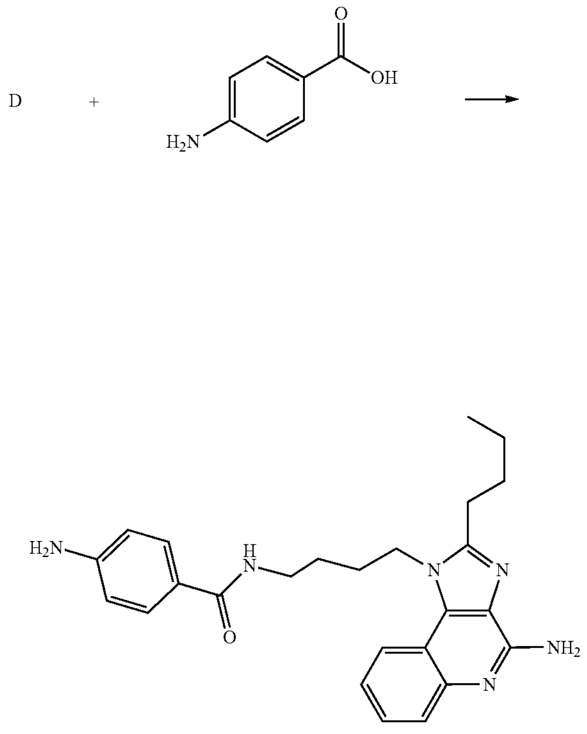

48

4-amino-N-(4-(4-amino-2-butyl-1H-imidazo[4,5-c]quinolin-1-yl)butyl)benzamide (48): Compound 48 was prepared using compound D and 4-Aminobenzoic acid as starting materials, with similar procedure as described for 16 to obtain target compound 48 (0.4 mg, 0.0005 mmol, 2%). MS m/z 431 $(M+H)^+$.

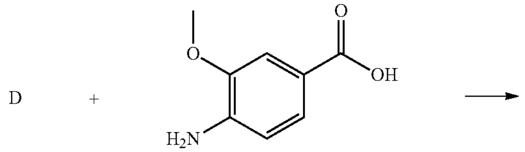

-continued

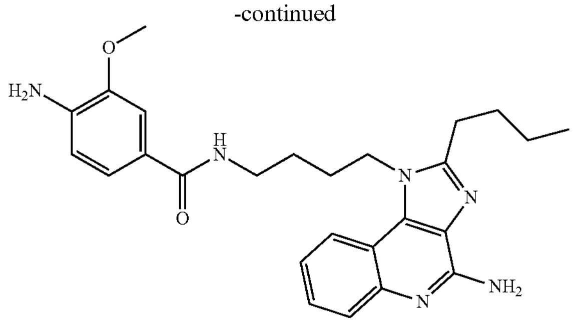

49

4-amino-N-(4-(4-amino-2-butyl-1H-imidazo[4,5-c]quinolin-1-yl)butyl)-3-methoxybenzamide (49): Compound 49 was prepared using compound D and 4-Amino-3-methoxybenzoic acid as starting materials, with similar procedure as described for 16 to obtain target compound 49 (4.2 mg, 0.005 mmol, 21%). MS m/z 461 $(M+H)^+$.

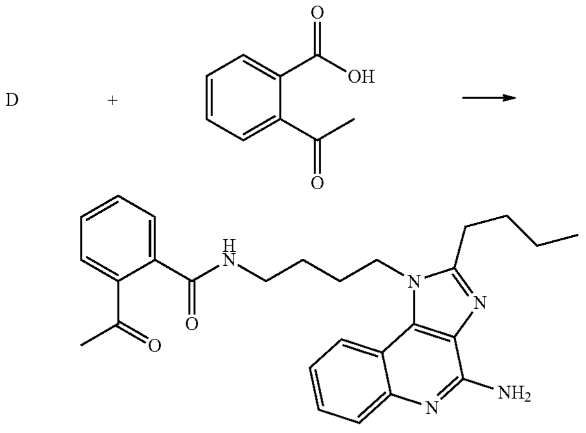

50

2-acetyl-N-(4-(4-amino-2-butyl-1H-imidazo[4,5-c]quinolin-1-yl)butyl)benzamide (50): Compound 50 was prepared using compound D and 2-Acetylbenzoic acid as starting materials, with similar procedure as described for 16 to obtain target compound 50 (7.6 mg, 0.01 mmol, 43%). MS m/z 458 $(M+H)^+$.

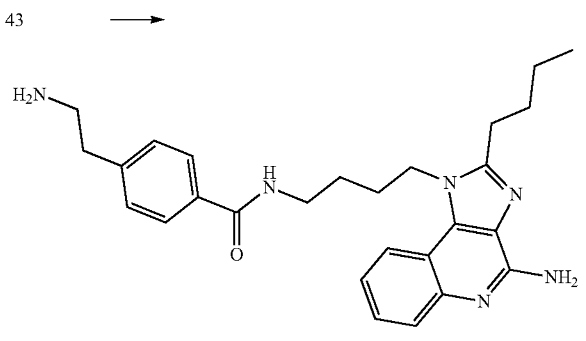

51

N-(4-(4-amino-2-butyl-1H-imidazo[4,5-c]quinolin-1-yl)butyl)-4-(2-aminoethyl)benzamide, 4 HCl (51): Compound 51 was prepared using compound 43 as starting material, with similar procedure as described for A to obtain target compound 51 (10 mg, 0.017 mmol, quant). MS m/z 459 $(M+H)^+$.

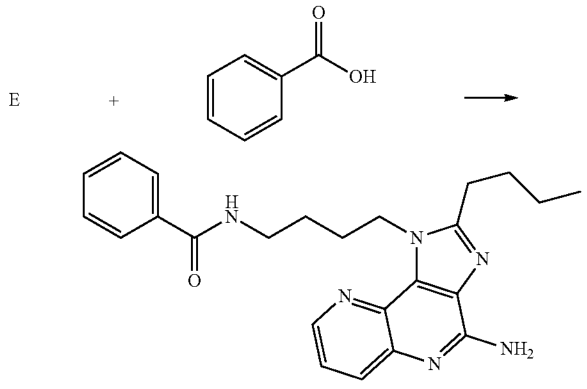

52

N-(4-(4-amino-2-butyl-1H-imidazo[4,5-c][1,5]naphthyridin-1-yl)butyl)benzamidebenzamide (52): Compound 52 was prepared using compound E and benzoic acid as starting materials, with similar procedure as described for 16 to obtain target compound 52 (1.5 mg, 0.002 mmol, 8%). MS m/z 417 $(M+H)^+$.

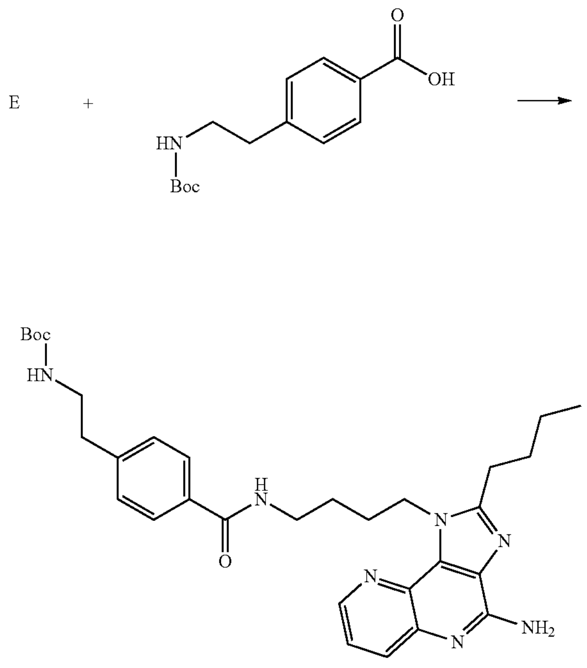

53 tert-butyl 4-(4-(4-amino-2-butyl-1H-imidazo[4,5-c][1,5]naphthyridin-1-yl)butylcarbamoyl)phenethylcarbamate (53): Compound 53 was prepared using compound E and 4-((2-boc-amino)ethyl)Benzoic acid as starting materials, with similar procedure as described for 16 to obtain target compound 53 (3.8 mg, 0.004 mmol, 16%). MS m/z 560 $(M+H)^+$.

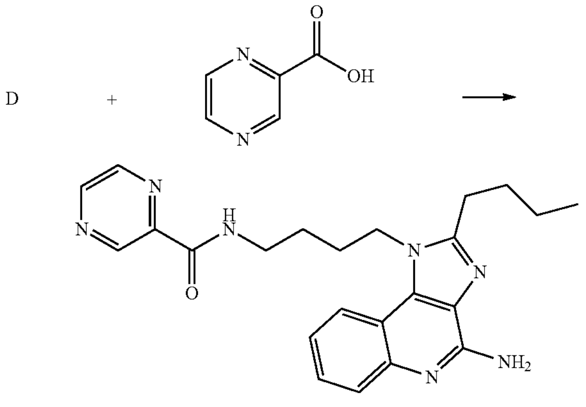

54

N-(4-(4-amino-2-butyl-1H-imidazo[4,5-c][1,5]naphthyridin-1-yl)butyl)pyrazine-2-carboxamide (54): Compound 54 was prepared using compound D and Pyrazinecarboxylic acid as starting materials, with similar procedure as described for 16 to obtain target compound 54 (3 mg, 0.004 mmol, 20%). MS m/z 419 $(M+H)^+$.

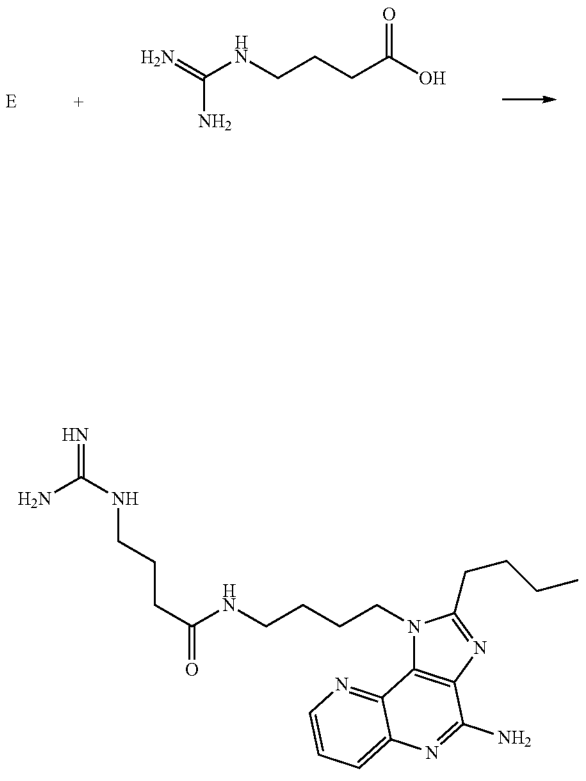

55

N-(4-(4-amino-2-butyl-1H-imidazo[4,5-c][1,5]naphthyridin-1-yl)butyl)-4-guanidinobutanamide (55): Compound 55 was prepared using compound E and 4-guanidocarboxylic acid as starting materials, with similar procedure as described for 16 to obtain target compound 55 (2 mg, 0.003 mmol, 12%). MS m/z 440 $(M+H)^+$.

53

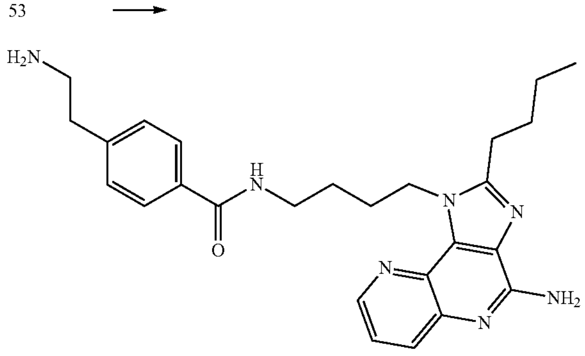

56

N-(4-(4-amino-2-butyl-1H-imidazo[4,5-c][1,5]naphthyridin-1-yl)butyl)-4-(2-aminoethyl)benzamide, 4TFA (56): To compound 53 (3.6 mg, 0.006 mmol) was added DCM (0.5 mL) and TFA (1 ml) at 23° C. After 20 min, the reaction was dried in vacuo then dried overnight at high vacuum pump to obtain target compound 56 (7 mg, 0.008 mmol, quant). MS m/z 460 $(M+H)^+$.

E +

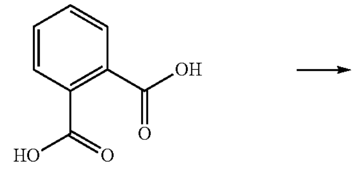

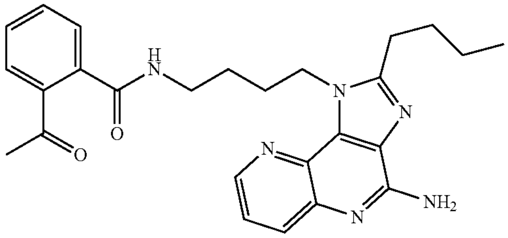

57

2-acetyl-N-(4-(4-amino-2-butyl-1H-imidazo[4,5-c][1,5]naphthyridin-1-yl)butyl)benzamide (57): Compound 57 was prepared using compound E and 2-Acetylbenzoic acid as starting materials, with similar procedure as described for 16 to obtain target compound 57 (5.2 mg, 0.006 mmol, 27%). MS m/z 459 $(M+H)^+$.

E +

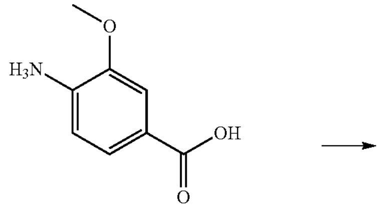

-continued

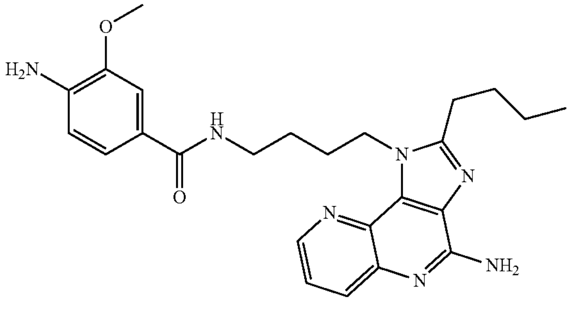

58

4-amino-N-(4-(4-amino-2-butyl-1H-imidazo[4,5-c][1,5]naphthyridin-1-yl)butyl)-3-metboxybenzamide (58): Compound 58 was prepared using compound E and 4-Amino-3-methoxybenzoic acid as starting materials, with similar procedure as described for 16 to obtain target compound 58 ((4.3 mg, 0.04 mmol, 20%) MS m/z 462 $(M+H)^+$.

E +

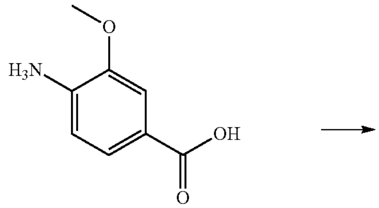

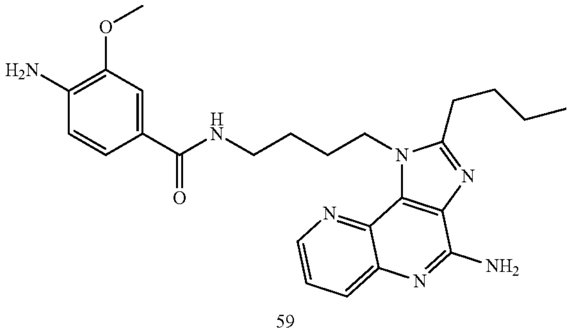

59

4-amino-N-(4-(4-amino-2-butyl-1H-imidazo[4,5-c]quinolin-1-yl)butyl)benzamide (59): Compound 59 was prepared using compound E and 4-Aminobenzoic acid as starting materials, with similar procedure as described for 16 to obtain target compound 59 (1.6 mg, 0.002 mmol, 8%) MS m/z 432 $(M+H)^+$.

B +

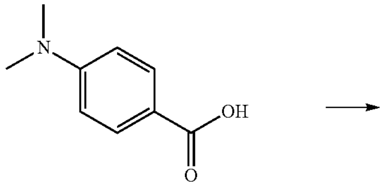

-continued

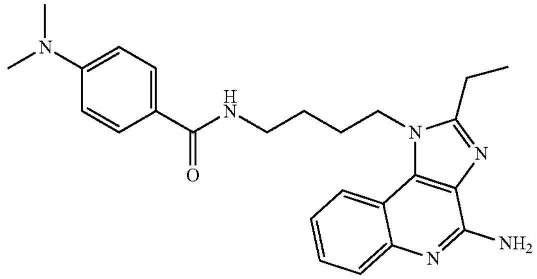

60

N-(4-(4-amino-2-ethyl-1H-imidazo[4,5-c]quinolin-1-yl) butyl)-4-(dimethylamino)benzamide (60): Compound 60 was prepared using compound B and 4-Dimethyl amino benzoic acid as starting materials, with similar procedure as described for 16 to obtain target compound 60 (1 mg, 0.001 mmol, 6%). MS m/z 431 $(M+H)^+$.

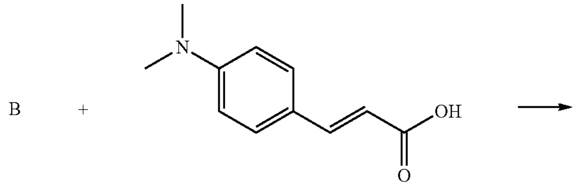

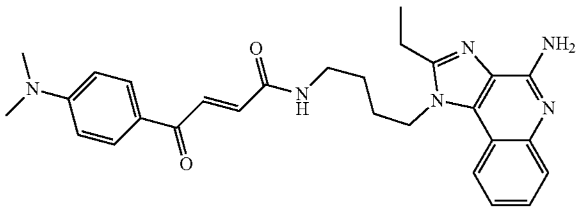

61

(E)-N-(4-(4-amino-2-ethyl-1H-imidazo[4,5-c]quinolin-1-yl)butyl)-3-(4-(dimethylamino)phenyl)acrylamide (61): Compound 61 was prepared using compound B and 4-Dimethyl amino cinnamic acid as starting materials, with similar procedure as described for 16 to obtain target compound 61 (2 mg, 0.003 mmol, 11%). MS m/z 457 $(M+H)^+$.

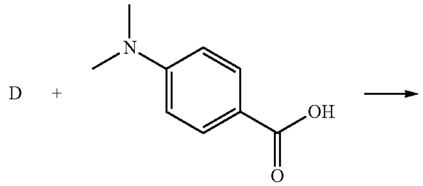

-continued

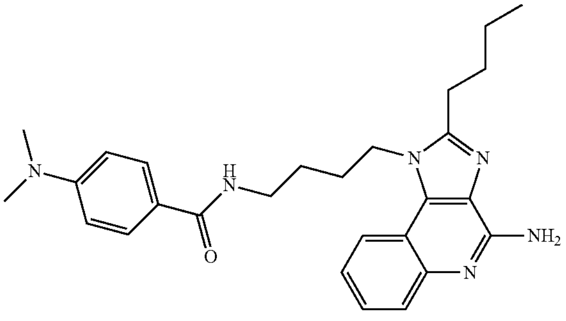

62

N-(4-(4-amino-2-butyl-1H-imidazo[4,5-c]quinolin-1-yl) butyl)-4-(dimethylamino)benzamide (62): Compound 62 was prepared using compound D and 4-Dimethyl amino benzoic acid as starting materials, with similar procedure as described for 16 to obtain target compound 62 (3.5 mg, 0.004 mmol, 20%). MS m/z 459 $(M+H)^+$.

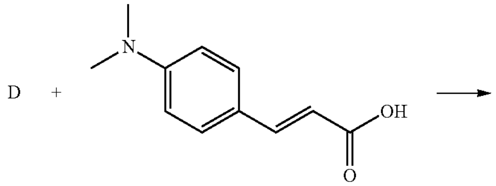

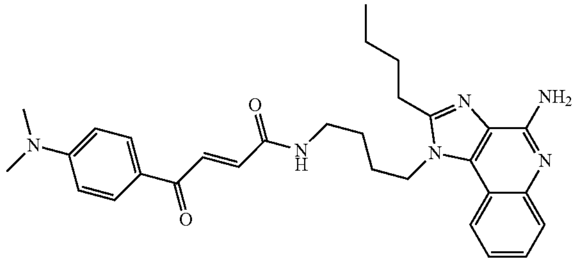

63

(E)-N-(4-(4-amino-2-butyl-1H-imidazo[4,5-c]quinolin-1-yl)butyl)-3-(4-(dimethylamino)phenyl)acrylamide (63): Compound 63 was prepared using compound D and 4-Dimethyl amino cinnamic acid as starting materials, with similar procedure as described for 16 to obtain target compound 63 (4.5 mg, 0.005 mmol, 25%). MS m/z 485 $(M+H)^+$

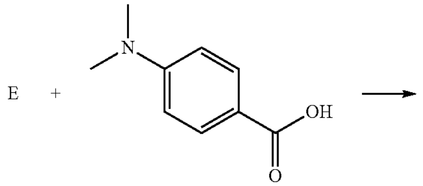

-continued

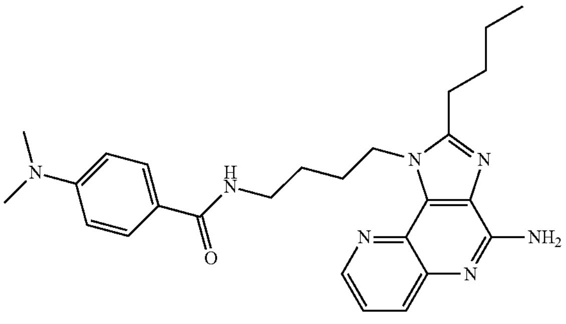

64

N-(4-(4-amino-2-butyl-1H-imidazo[4,5-c][1,5]naphthyridin-1-yl)butyl)-4-(dimethylamino)benzamide (64): Compound 64 was prepared using compound E and 4-Dimethyl amino benzoic acid as starting materials, with similar procedure as described for 16 to obtain target compound 64 (0.5 mg, 0.001 mmol, 7%). MS m/z 460 $(M+H)^+$.

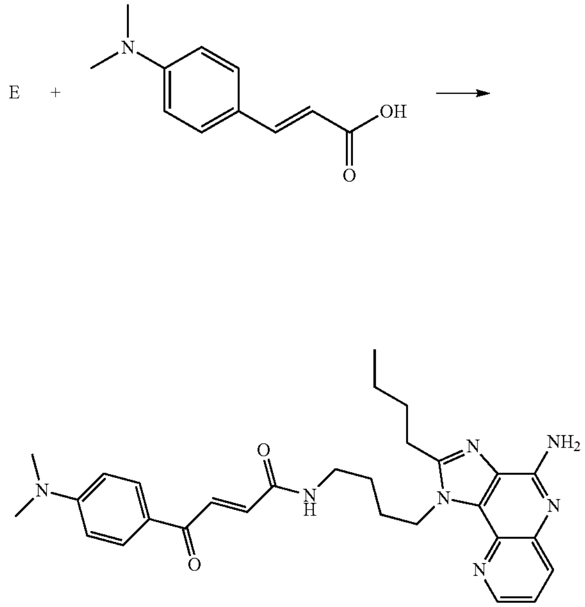

65

(E)-N-(4-(4-amino-2-butyl-1H-imidazo[4,5-c][1,5]naphthyridin-1-yl)butyl)-3-(4-(dimethylamino)phenyl)acrylamide (65): Compound 65 was prepared using compound E and 4-Dimethyl amino cinnamic acid as starting materials, with similar procedure as described for 16 to obtain target compound 65 (0.5 mg, 0.001 mmol, 7%). MS m/z 486 $(M+H)^+$.

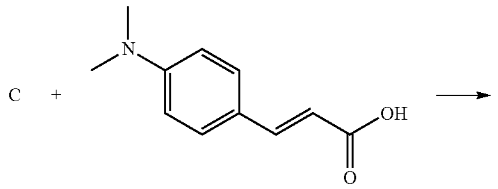

-continued

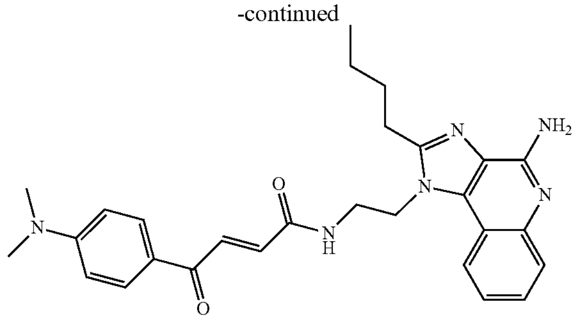

66

(E)-N-(2-(4-amino-2-butyl-1H-imidazo[4,5-c]quinolin-1-yl)ethyl)-3-(4-(dimethylamino)phenyl)acrylamide (66): Compound 66 was prepared using compound C and 4-Dimethyl amino cinnamic acid as starting materials, with similar procedure as described for 16 to obtain target compound 66 (3 mg, 0,004 mmol, 16%). MS m/z 457 $(M+H)^+$.

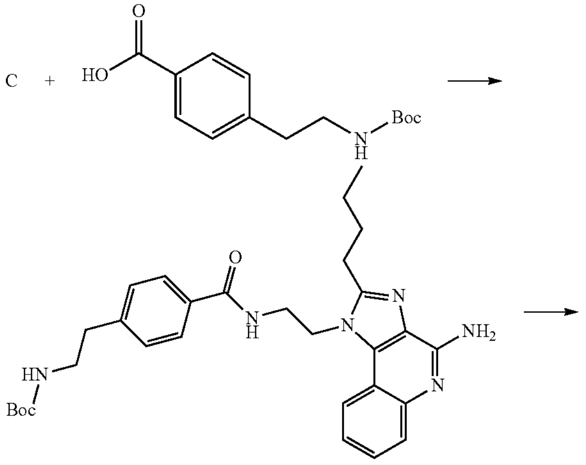

67

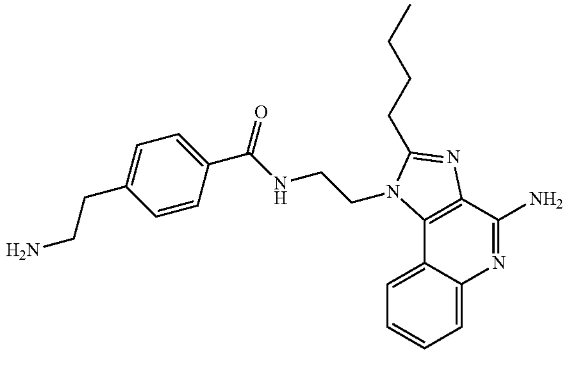

68 tert-butyl 4-(2-(4-amino-2-butyl-1H-imidazo[4,5-c]quinolin-1-yl)ethylcarbamoyl)phenethylcarbamate (67): Compound 67 was prepared using compound C and 4-(2-(tert-butoxycarbonylamino)ethyl)benzoic acid as starting materials, with similar procedure as described for 16 to obtain target compound 67 (1.5 mg, 0.002 mmol, 11%). MS m/z 457 $(M+H)^+$.

N-(2-(4-amino-2-butyl-1H-imidazo[4,5-c]quinolin-1-yl)ethyl)-4-(2-aminoethyl)benzamide (68): Compound 68 was prepared using compound 67 as starting materials, with similar procedure as described for 56 to obtain target compound 68 (2.9 mg, 0.003 mmol, quant.). MS m/z 431 $(M+H)^+$.

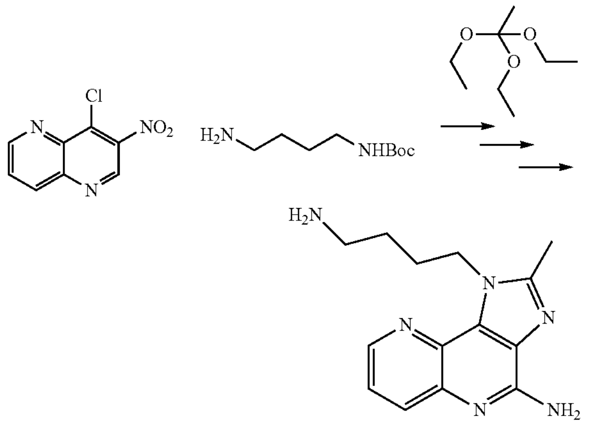

F 1-(4-aminobutyl)-2-ethyl-1H-imidazo[4,5-c]quinolin-4-amine (F): Compound F was prepared using 4-chloro-3-nitro-1,5-naphthyridine, tert-butyl 4-aminobutylcarbamate and triethylorthoacetate as starting materials, with similar procedure as described for A to obtain target compound F (130 mg, 0.316 mmol, 9% from starting material). MS m/z 270 $(M+H)^+$.

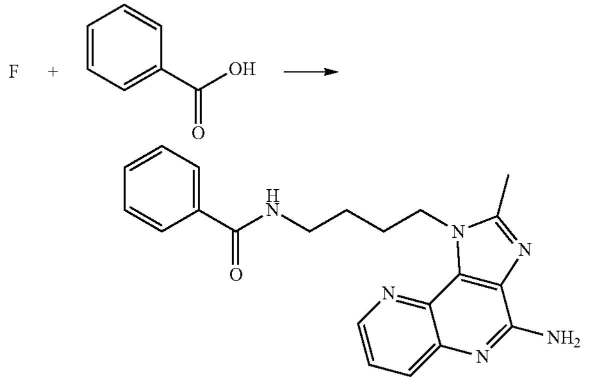

69

N-(4-(4-amino-2-methyl-1H-imidazo[4,5-c]quinolin-1-yl)butyl)benzamide (69): Compound 69 was prepared using compound F and benzoic acid as starting materials, with similar procedure as described for 16 to obtain target compound 69 (6.5 mg, 0.008 mmol, 42%). MS m/z 374 $(M+H)^+$.

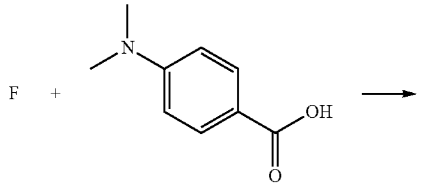

-continued

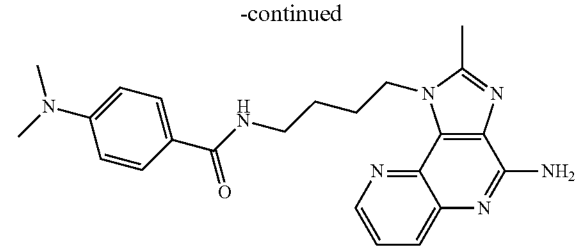

70

N-(4-(4-amino-2-methyl-1H-imidazo[4,5-c]quinolin-1-yl)butyl)-4-(dimethylamino)benzamide (70): Compound 70 was prepared using compound F and 4-Dimethyl amino benzoic acid as starting materials, with similar procedure as described for 16 to obtain target compound 70 (6.5 mg, 0.009 mmol, 39%). MS m/z 417 $(M+H)^+$.

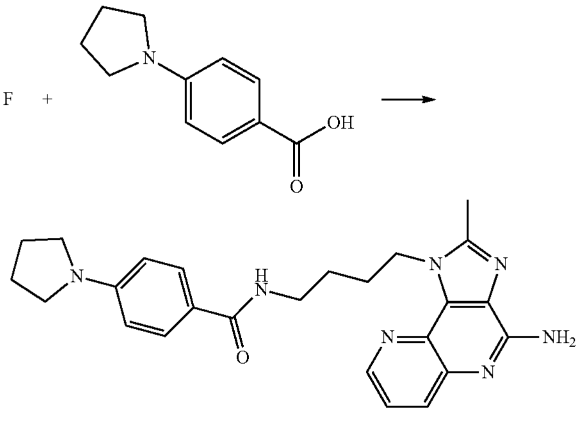

71

N-(4-(4-amino-2-methyl-1H-imidazo[4,5-c]quinolin-1-yl)butyl)-4-(pyrrolidin-1-yl)benzamide (71): Compound 71 was prepared using compound F and 4-(1-Pyrrolidinylbenzoic acid as starting materials, with similar procedure as described for 16 to obtain target compound 71 (3.1 mg, 0.004 mmol, 18%). MS m/z 443 $(M+H)^+$.

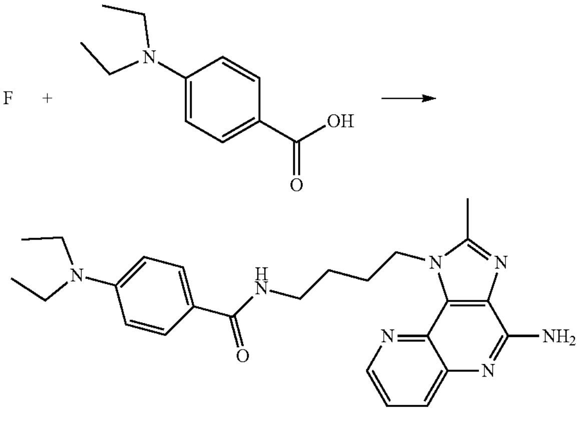

72

N-(4-(4-amino-2-methyl-1H-imidazo[4,5-c]quinolin-1-yl)butyl)-4-(diethylamino)benzamide (72): Compound 72 was prepared using compound F and 4-(Diethylamino) benzoic acid as starting materials, with similar procedure as described for 16 to obtain target compound 72 (6.4 mg, 0.008 mmol, 41%). MS m/z 445 $(M+H)^+$.

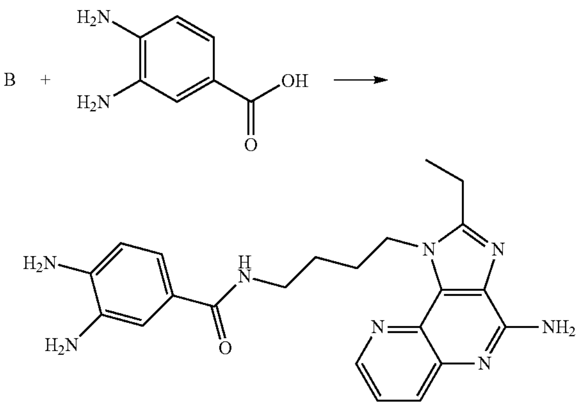

73

3,4-diamino-N-(4-(4-amino-2-ethyl-1H-imidazo[4,5-c] quinolin-1-yl)butyl)benzamide (73): Compound 73 was prepared using compound B and 3,4-diamino benzoic acid as starting materials, with similar procedure as described for 16 to obtain target compound 73 (1.1 mg, 0.001 mmol, 4%). MS m/z 418 $(M+H)^+$.

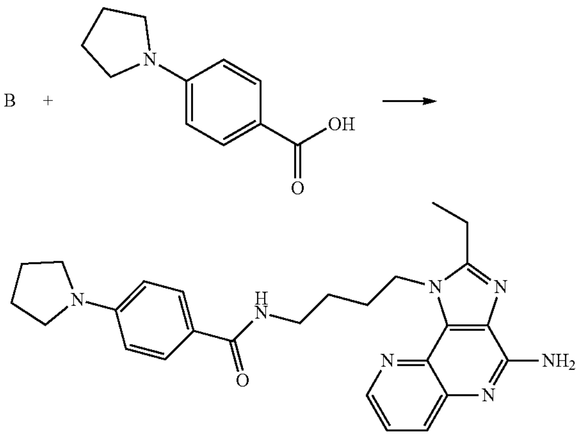

74

N-(4-(4-amino-2-ethyl-1H-imidazo[4,5-c]quinolin-1-yl) butyl)-4-(pyrrolidin-1-yl)benzamide (74): Compound 74 was prepared using compound B and 4-(pyrrolidin-1-yl) benzoic acid as starting materials, with similar procedure as described for 16 to obtain target compound 74 (4.5 mg, 0.005 mmol, 19%). MS m/z 457 $(M+H)^+$.

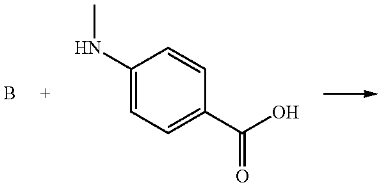

-continued

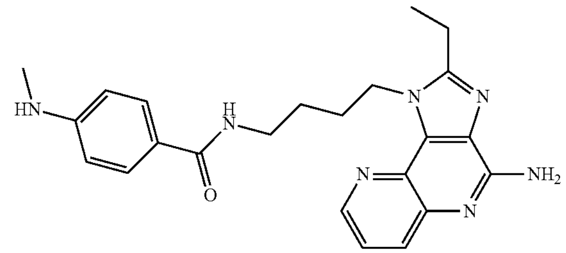

75

N-(4-(4-amino-2-ethyl-1H-imidazo[4,5-c]quinolin-1-yl) butyl)-4-(methylamino)benzamide (75): Compound 75 was prepared using compound B and 4-methylamino benzoic acid as starting materials, with similar procedure as described for 16 to obtain target compound 75 (7.6 mg, 0.009 mmol, 33%). MS m/z 417 $(M+H)^+$.

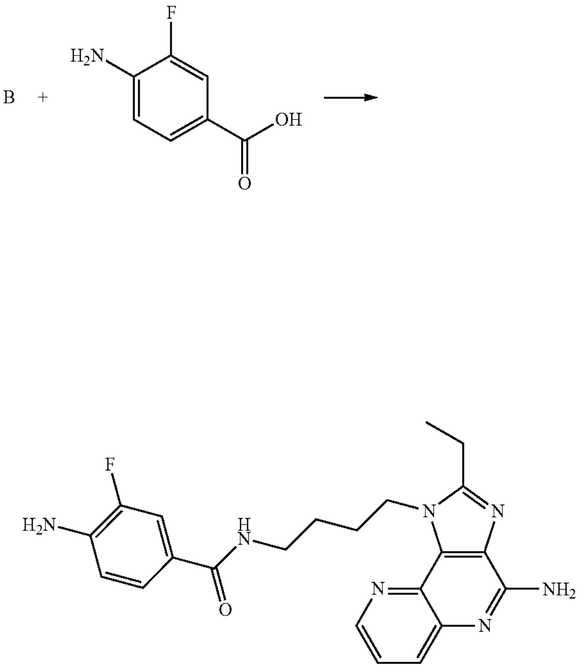

76

4-amino-N-(4-(4-amino-2-ethyl-1H-imidazo[4,5-c]quinolin-1-yl)butyl)-3-fluorobenzamide (76): Compound 76 was prepared using compound B and 3-fluoro-4-amino benzoic acid as starting materials, with similar procedure as described for 16 to obtain target compound 76 (7 mg, 0.008 mmol, 31%). MS m/z 421 $(M+H)^+$.

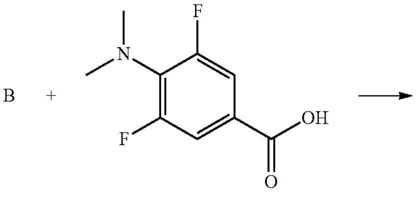

-continued

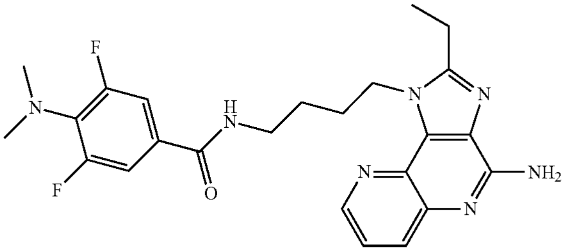

77

N-(4-(4-amino-2-ethyl-1H-imidazo[4,5-c]quinolin-1-yl) butyl)-4-(dimethylamino)-3,5-difluorobenzamide (77): Compound 77 was prepared using compound B and 4-(dimethylamino)-3,5-difluoro benzoic acid as starting materials, with similar procedure as described for 16 to obtain target compound 77 (9.5 mg, 0.010 mmol, 41%). MS m/z 467 (M+H)$^+$.

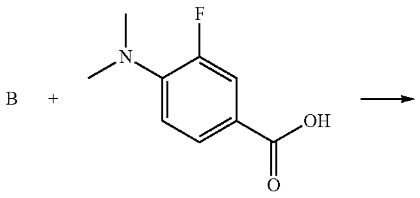

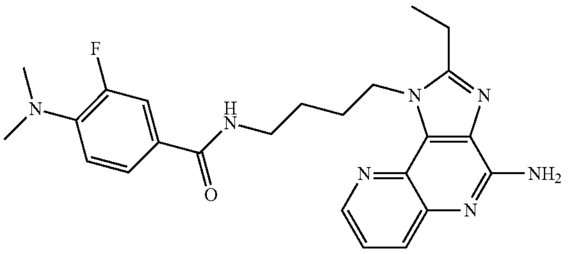

78

N-(4-(4-amino-2-ethyl-1H-imidazo[4,5-c]quinolin-1-yl) butyl)-4-(dimethylamino)-3-fluorobenzamide (78): Compound 78 was prepared using compound B and 4-(dimethylamino)-3-fluoro benzoic acid as starting materials, with similar procedure as described for 16 to obtain target compound 78 (12 mg, 0.013 mmol, 49%). MS m/z 449 (M+H)$^+$.

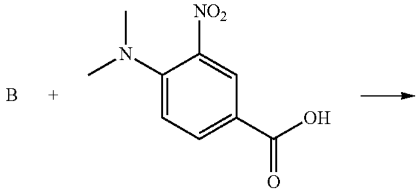

-continued

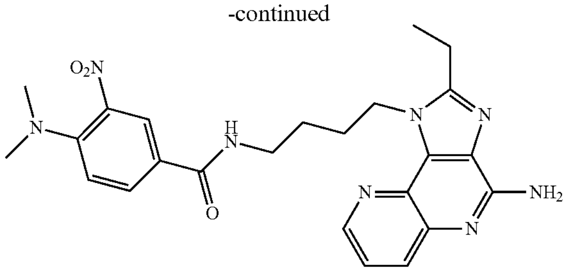

79

N-(4-(4-amino-2-ethyl-1H-imidazo[4,5-c]quinolin-1-yl) butyl)-4-(dimethylamino)-3-nitrobenzamide (79): Compound 79 was prepared using compound B and 4-(dimethylamino)-3-nitro benzoic acid as starting materials, with similar procedure as described for 16 to obtain target compound 79 (11 mg, 0.012 mmol, 50%). MS m/z 476 (M+H)$^+$.

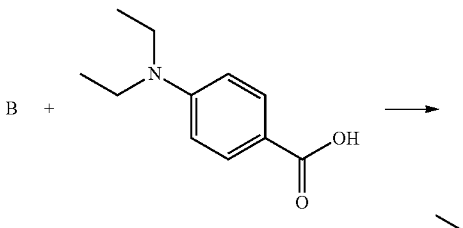

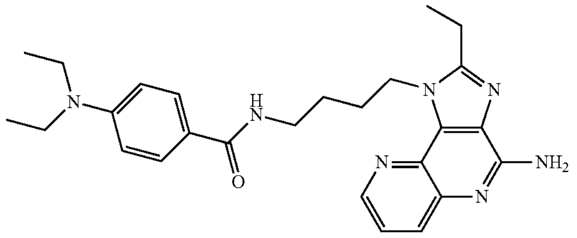

80

N-(4-(4-amino-2-ethyl-1H-imidazo[4,5-c]quinolin-1-yl) butyl)-4-(diethylamino)benzamide (80): Compound 80 was prepared using compound B and 4-(diethylamino) benzoic acid as starting materials, with similar procedure as described for 16 to obtain target compound 80 (10 mg, 0.011 mmol, 42%). MS m/z 459 (M+H)$^+$.

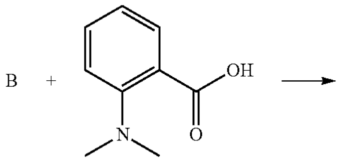

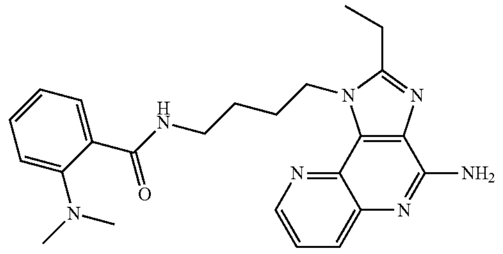

81

N-(4-(4-amino-2-ethyl-1H-imidazo[4,5-c]quinolin-1-yl)butyl)-2-(dimethylamino)benzamide (81): Compound 81 was prepared using compound B and 2-(diethylamino) benzoic acid as starting materials, with similar procedure as described for 16 to obtain target compound 81 (12.2 mg, 0.014 mmol, 57%). MS m/z 431 $(M+H)^+$.

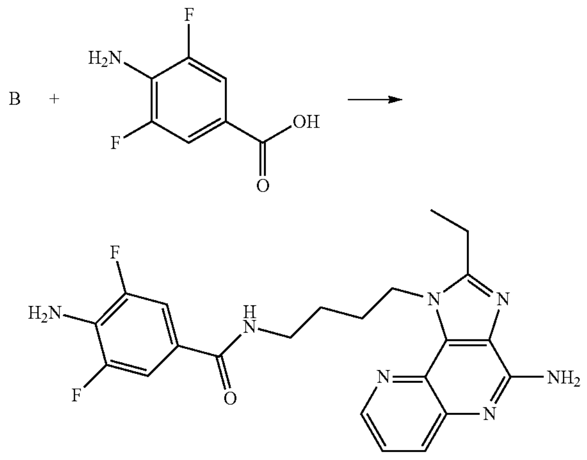

82

4-amino-N-(4-(4-amino-2-ethyl-1H-imidazo[4,5-c]quinolin-1-yl)butyl)-3,5-difluorobenzamide (82): Compound 82 was prepared using compound B and 4-amino-3,5-difluorobenzoic acid as starting materials, with similar procedure as described for 16 to obtain target compound 82 (10.2 mg, 0.011 mmol, 49%,). MS m/z 439 $(M+H)^+$.

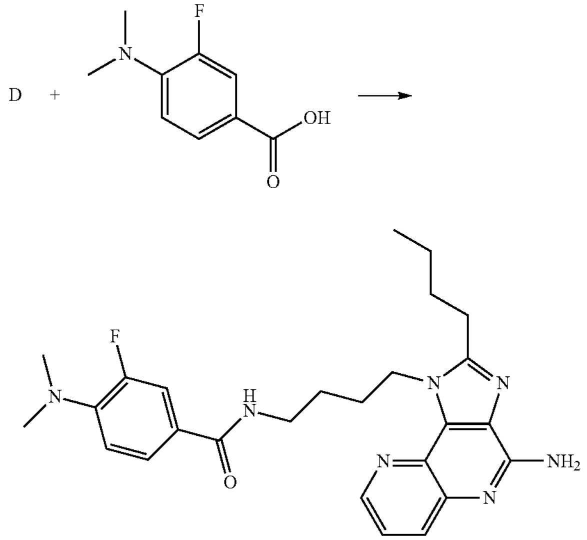

83

N-(4-(4-amino-2-butyl-1H-imidazo[4,5-c]quinolin-1-yl)butyl)-4-(dimethylamino)-3-fluorobenzamide (83): Compound 83 was prepared using compound D and 4-(Dimethylamino)-3-fluoro benzoic acid as starting materials, with similar procedure as described for 16 to obtain target compound 83 (9 mg, 0.011 mmol, 50%). MS m/z 477 $(M+H)^+$.

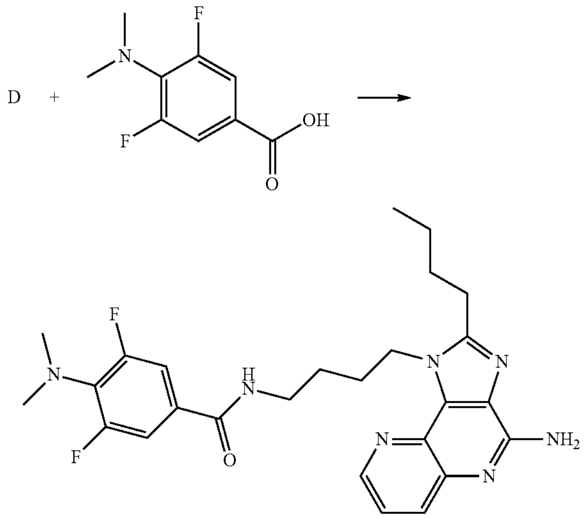

84

N-(4-(4-amino-2-butyl-1H-imidazo[4,5-c]quinolin-1-yl)butyl)-4-(dimethylamino)-3,5-difluorobenzamide (84): Compound 84 was prepared using compound D and 4-(Dimethylamino)-3,5-Difluoro benzoic acid as starting materials, with similar procedure as described for 16 to obtain target compound 84 (7 mg, 0.008 mmol, 38%). MS m/z 495 $(M+H)^+$.

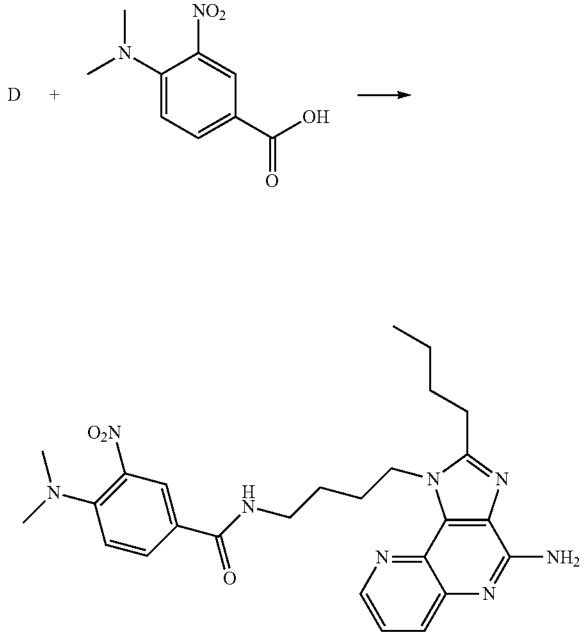

85

N-(4-(4-amino-2-butyl-1H-imidazo[4,5-c]quinolin-1-yl)butyl)-4-(dimethylamino)-3-nitrobenzamide (85): Compound 85 was prepared using compound D and 4-(Dimethylamino)-3-nitro benzoic acid as starting materials, with similar procedure as described for 16 to obtain target compound 85 (10 mg, 0.012 mmol, 54%). MS m/z 504 $(M+H)^+$.

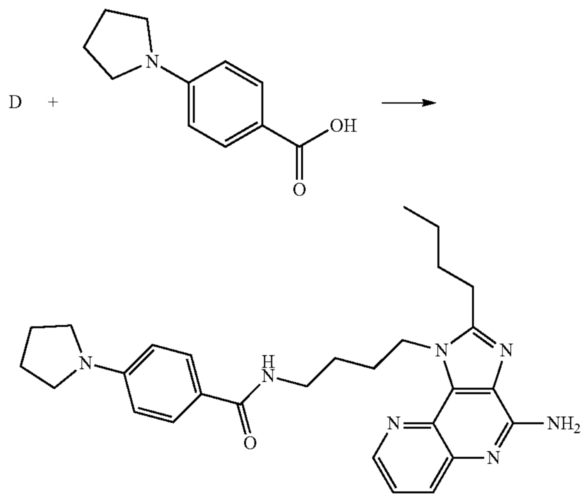

86

N-(4-(4-amino-2-butyl-1H-imidazo[4,5-c]quinolin-1-yl) butyl)-4-(pyrrolidin-1-yl)benzamide (86): Compound 86 was prepared using compound D and 4-(1-pyrrolidinylamino) benzoic acid as starting materials, with similar procedure as described for 16 to obtain target compound 86 (2 mg, 0.002 mmol, 11%). MS m/z 485 $(M+H)^+$.

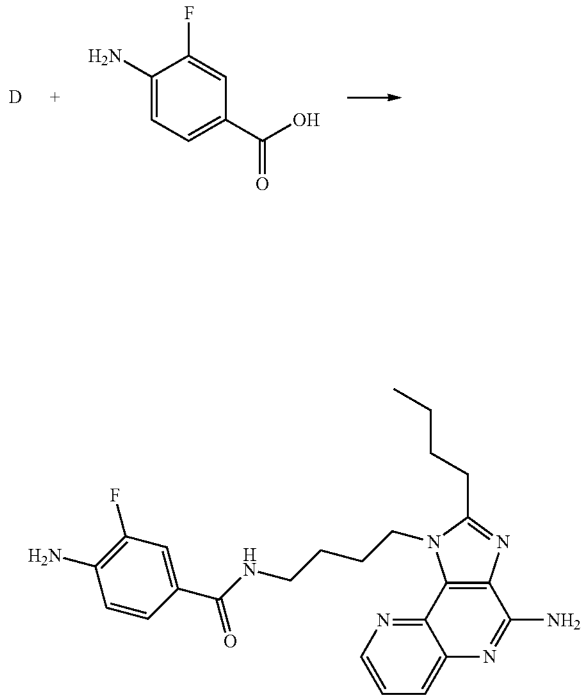

87

4-amino-N-(4-(4-amino-2-butyl-1H-imidazo[4,5-c]quinolin-1-yl)butyl)-3-fluorobenzamide (87): Compound 87 was prepared using compound D and 4-amino-3-fluoro-benzoic acid as starting materials, with similar procedure as described for 16 to obtain target compound 87 (6 mg, 0.008 mmol, 20%). MS m/z 449 $(M+H)^+$.

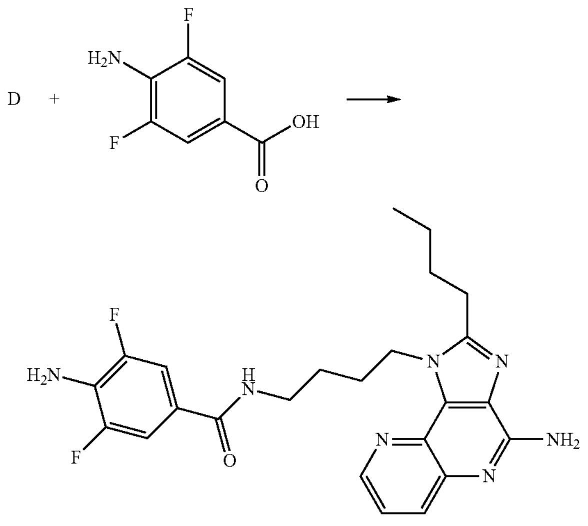

88

4-amino-N-(4-(4-amino-2-butyl-1H-imidazo[4,5-c]quinolin-1-yl)butyl)-3,5-difluorobenzamide (88); Compound 88 was prepared using compound D and 4-amino-3,5-difluoro-benzoic acid as starting materials, with similar procedure as described for 16 to obtain target compound 88 (6 mg, 0.007 mmol, 34%). MS m/z 467 $(M+H)^+$.

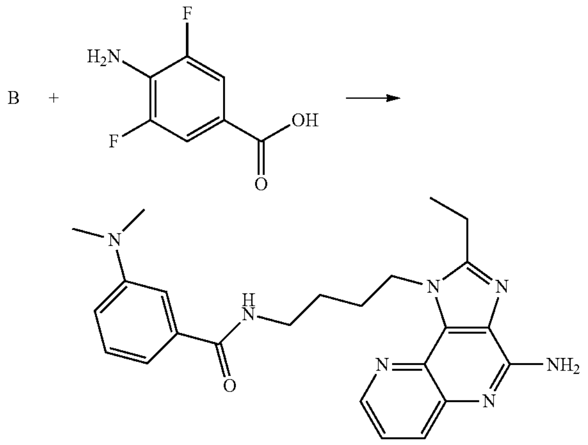

89

N-(4-(4-amino-2-ethyl-1H-imidazo[4,5-c]quinolin-1-yl) butyl)-4-(dimethylamino)benzamide (89): Compound 89 was prepared using compound B and 4-amino-3,5-difluorobenzoic acid acid as starting materials, with similar procedure as described for 16 to obtain target compound 89 (10 mg, 0.011 mmol, 27%). MS m/z 431 $(M+H)^+$.

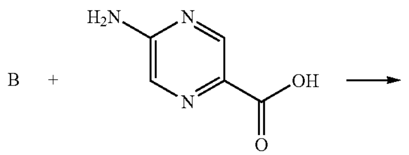

-continued

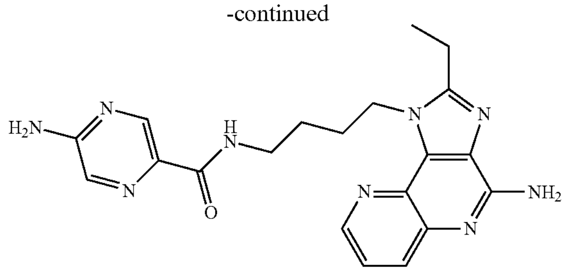

90

5-amino-N-(4-(4-amino-2-ethyl-1H-imidazo[4,5-c]quinolin-1-yl)butyl)pyrazine-2-carboxamide (90): Compound 90 was prepared using compound B and 5-aminopyrizine-2-carboxylic acid as starting materials, with similar procedure as described for 16 to obtain target compound 90 (8 mg, 0.009 mmol, 37%). MS m/z 405 (M+H)$^+$.

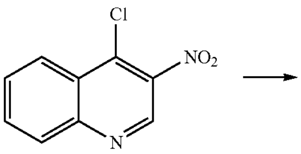

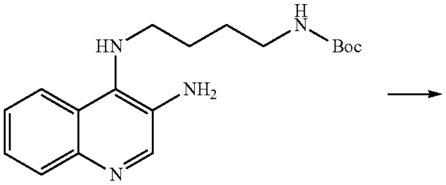

91

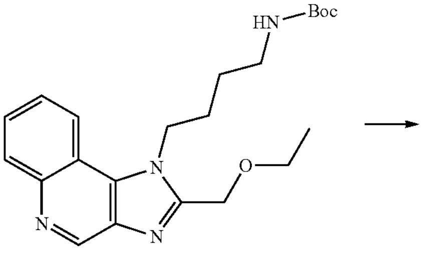

92

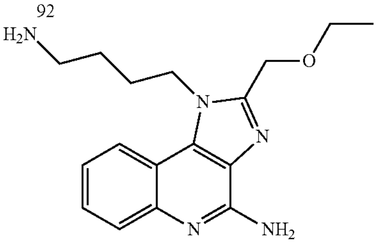

G tert-butyl 4-(3-aminoquinolin-4-ylamino)butylcarbamate (91): Compound 91 was prepared using 4-chloro-3-nitroquinoline and tert-butyl 4-aminobutylcarbamate with similar procedure as described for 2 to obtain target compound 91 (5050 mg, 15.284 mmol, 97% from starting material). MS m/z 331 (M+H)$^+$.

tert-butyl 4-(2-(ethoxymethyl)-1H-imidazo[4,5-c]quinolin-1-yl)butylcarbamatebutylcarbamate (92): To a solution of tert-butyl 4-(3-aminoquinolin-4-ylamino)butylcarbamate (1070 mg, 3.238 mmol) in anhydrous THF (12 mL) were added triethylamine (885 uL, 8.746 mmol) and 2-ethoxyacetyl chloride (500 mg, 4.078 mmol) at 23° C. After 20 h, the solvent was removed in vacuo. The residue was dissolved in DCM (50 mL), washed with saturated sodium bicarbonate (50 mL) and brine (50 mL), and dried over $MgSO_4$ to obtain the intermediate (tert-butyl 4-(3-(2-ethoxyacetamido)quinolin-4-ylamino)butylcarbamate) as crude. This crude was dissolved in MeOH (5 mL), followed by the addition of calcium oxide (0.5 g) in sealed tube. The reaction mixture was heated at 120° C. for 2.5 h. The solvent was removed under vacuum after CaO removed by filtration, and the residue purified by Prep-LC to obtain compound 92 (346 mg, 0.868 mmol, 27%). MS m/z 399 (M+H)$^+$.

1-(4-aminobutyl)-2-(ethoxymethyl)-1H-imidazo[4,5-c]quinolin-4-amine, 3HCl (G): Compound G was prepared using compound 92 with similar procedure as described for A to obtain target compound G (5270 mg, 0.595 mmol, 4% from starting material). MS m/z 312 (M+H)$^+$.

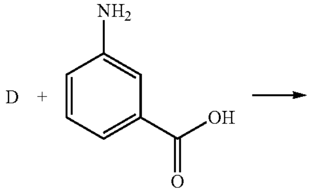

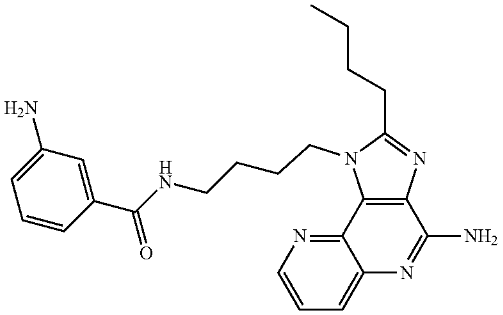

93

3-amino-N-(4-(4-amino-2-butyl-1H-imidazo[4,5-c]quinolin-1-yl)butyl)benzamide (93): Compound 93 was prepared using compound D and 3-amino benzoic acid as starting materials, with similar procedure as described for 16 to obtain target compound 93 (5 mg, 0.006 mmol, 19%) MS m/z 431 (M+H)$^+$.

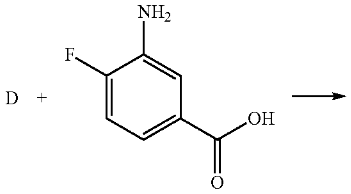

-continued

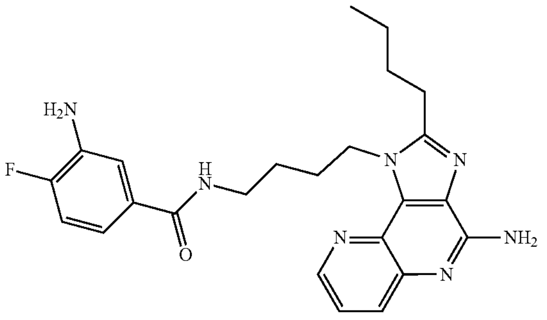

94

3-amino-N-(4-(4-amino-2-butyl-H-imidazo[4,5-c]quinolin-1-yl)butyl)-4-fluorobenzamide (94): To a solution of D (10 mg, 0.024 mmol) and 3-amino-4-Flouro-benzoic acid (4 mg, 0.026 mmol) in DMF (1 ml) was added DMTMMT (7 mg, 0.029 mmol) and DIEA (30 ul, 0.172 mmol) at 23° C. After 10 min, the mixture was purified by Prep-LC to obtain target compound 94 (5 mg, 0.006 mmol, 21%) MS m/z 449 $(M+H)^+$.

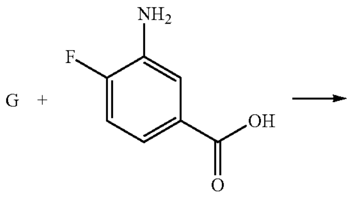

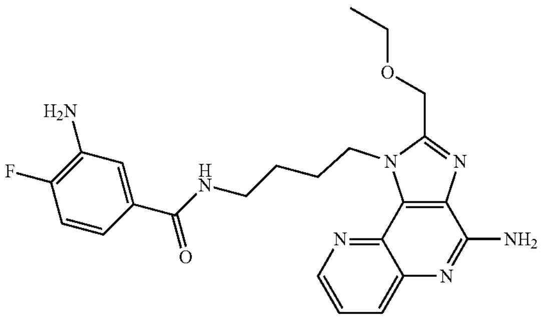

95

3-amino-N-(4-(4-amino-2-(ethoxymethyl)-1H-imidazo[4,5-c]quinolin-1-yl)butyl)-4-fluorobenzamide (95)): Compound 95 was prepared using compound G and 3-amino-4-Flouro-benzoic acid as starting materials, with similar procedure as described for 94 to obtain target compound 95 (6 mg, 0.007 mmol, 26%). MS m/z 451 $(M+H)^+$.

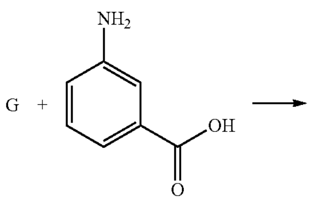

-continued

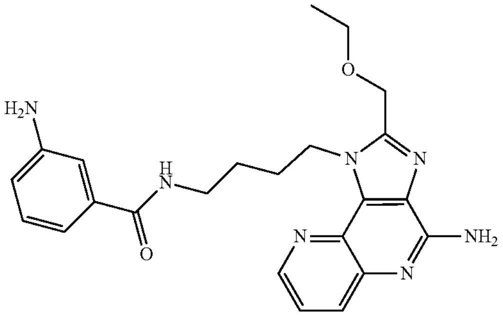

96

3-amino-N-(4-(4-amino-2-(ethoxymethyl)-1H-imidazo[4,5-c]quinolin-1-yl)butyl)-4-fluorobenzamide (96)): Compound 96 was prepared using compound G and 3-amino benzoic acid as starting materials, with similar procedure as described for 94 to obtain target compound 96 (5 mg, 0.006 mmol, 19%). MS m/z 433 $(M+H)^+$.

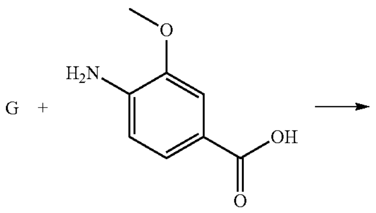

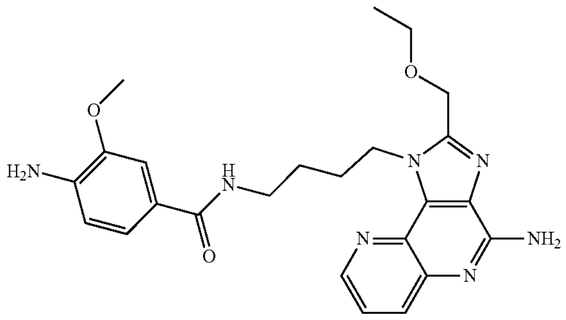

97

3-amino-N-(4-(4-amino-2-(ethoxymethyl)-1H-imidazo[4,5-c]quinolin-1-yl)butyl)benzamide (97)): Compound 97 was prepared using compound G and 4-amino-3-methoxy benzoic acid as starting materials, with similar procedure as described for 94 to obtain target compound 97 (5 mg, 0.005 mmol, 23%). MS m/z 463 $(M+H)^+$.

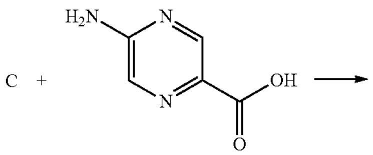

-continued

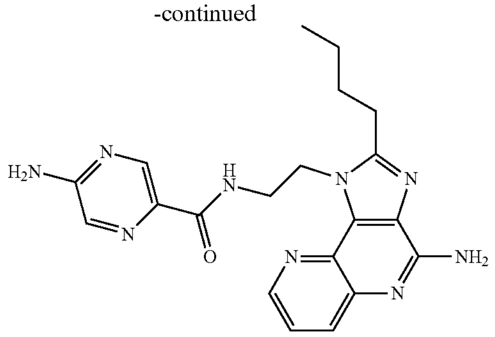

98

5-amino-N-(2-(4-amino-2-butyl-1H-imidazo[4,5-c]quinolin-1-yl)ethy)pyrazine-2-carboxamide (98)): Compound 98 was prepared using compound C and 5-amino-pyrazine-2-carboxylic acid as starting materials, with similar procedure as described for 16 to obtain target compound 98 (2.13 mg, 0.002 mmol, 11%). MS m/z 405 $(M+H)^+$.

G +

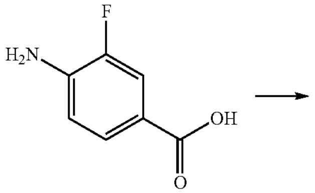

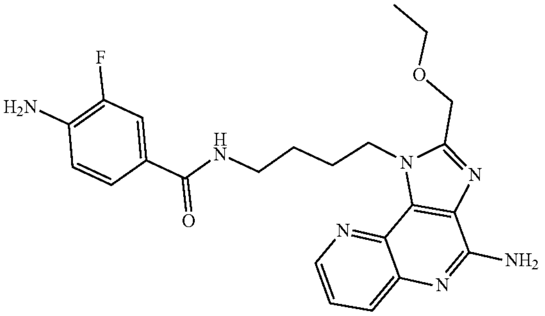

99

4-amino-N-(4-(4-amino-2-(ethoxymethyl)-1H-imidazo[4,5-c]quinolin-1-yl)butyl)-3-fluorobenzamide (99): Compound 99 was prepared using compound G and 3-Fluoro-4-aminobenzoic acid as starting materials, with similar procedure as described for 94 to obtain target compound 99 (7.37 mg, 0.008 mmol, 37%). MS m/z 451 $(M+H)^+$.

G +

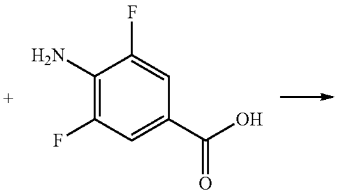

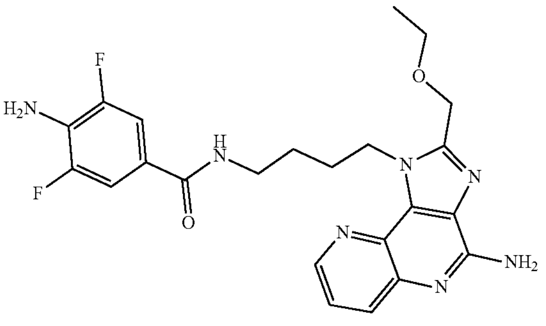

100

4-amino-N-(4-(4-amino-2-(ethoxymethyl)-1H-imidazo[4,5-c]quinolin-1-yl)butyl)-3,5-difluorobenzamide (100): Compound 100 was prepared using compound G and 4-amino-3,5-difluorobenzoic acid as starting materials, with similar procedure as described for 94 to obtain target compound 100 (9.7 mg, 0.011 mmol, 51%). MS m/z 469 $(M+H)^+$.

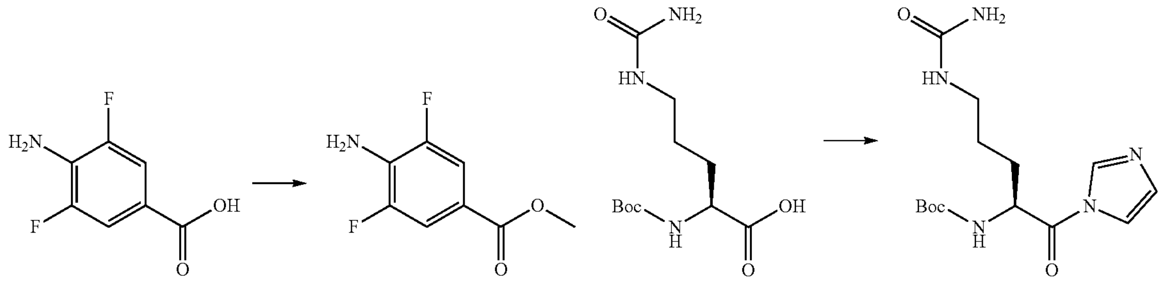

101

102

-continued

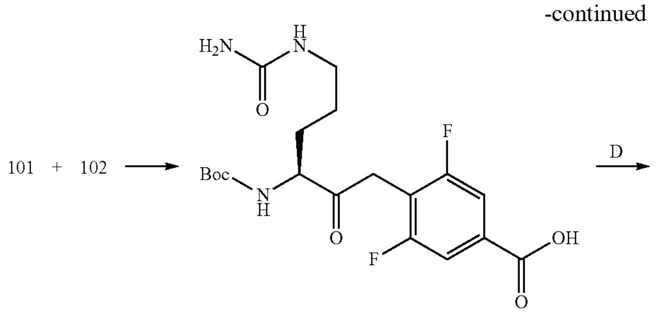

103

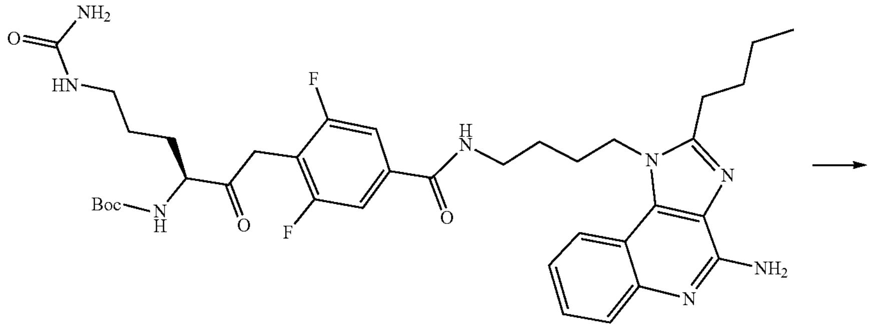

104

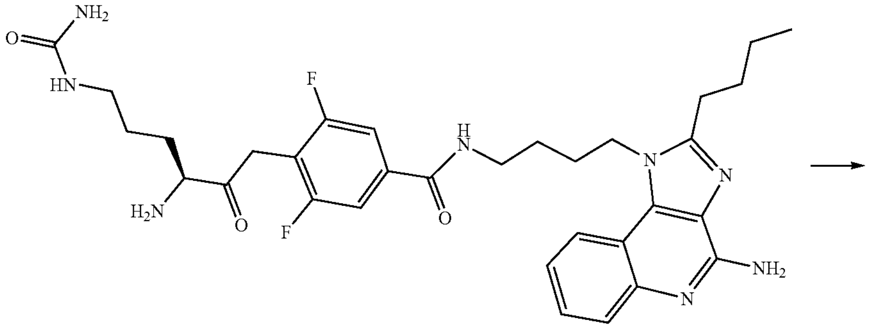

105

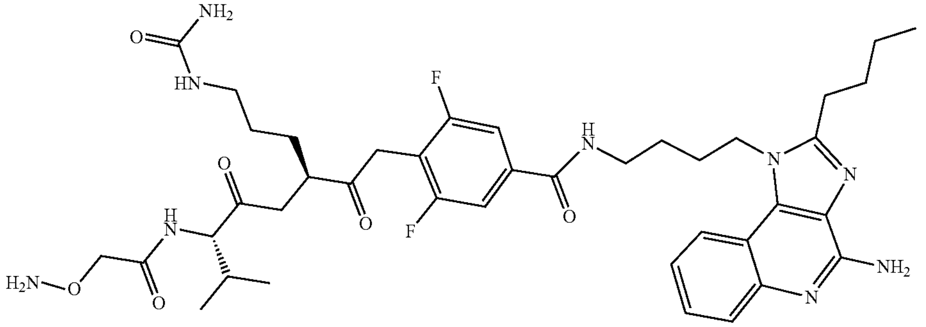

106

Methyl-4-amino-3,5-difluorobenlzoate (101): To a solution of 4-amino-3,5-difluorobenzoic acid (2087 mg, 12.055 mmol) in acetonitrile (15 ML) was added thionyichloride (12 mL), and then heated to 80° C. After 1 h, the solvent was removed in vacuo. Toluene (10 mL), was added to the mixture followed by evaporation in vacuo. The residue was dissolved in MeOH anhydrous (5 mL). After 0.5 h, solvent was removed in vacuo. The residue was dissolved in DCM (20 mL), washed with saturated sodium bicarbonate (50 mL) and brine (50 mL), followed by drying in $MgSO_4$ and filtration. The solvent was removed in vacuo to obtain compound 101 (1730 mg, 9.244 mmol, 77%). MS m/z 188 $(M+H)^+$.

(S)-tert-butyl 1-(1H-imidazol-1-yl)-1-oxo-5-ureidopentan-2-ylcarbamate (102): To a solution of Boc-Cit-OH (1150 mg, 4.177 mmol) in DMF (5 mL) was added CDI (880 mg, 5.427 mmol) at room temperature, and then heated to 60° C. After 2 h, to this mixture was added CDI (220 mg, 1.357 mmol). The reaction was stirred for 1 h at 60° C. After 3 h, the reaction was dried in vacuo. The residue was diluted with EtOAc (50 mL), and washed with water (50 mL), saturated sodium bicarbonate (20 mL) and brine (20 mL). The organic layer was dried with $MgSO_4$, followed by filtration, and the solvent removed in vacuo to obtain compound 102 (1465 mg, 4.503 mmol, crude). MS m/z 326 $(M+H)^+$.

(S)-4-(2-(tert-butoxycarbonylamino)-5-ureidopentanamido)-3,5-difluorobenzoic acid (103): To a solution of compound 103 (188 mg, 0.578 mmol) and compound 102 (108 mg, 0.577 mmol) in THF (2 mL) was added NaH, 60% (70 mg, 1.826 mmol) at 23° C. After 20 h, 1 mL of water as added, and the mixture stirred for 10 min. The solvent was removed in vacuo, and the residue purified by Prep-LC to obtain compound 103 (17 mg, 0.049 mmol, 9%). MS m/z 345 $(M+H)^+$.

residue was dried on high vacuum pump to obtain compound 105 (24 mg, 0.022 mmol, quant.). MS m/z 624 $(M+H)^+$.

N-(4-(4-amino-2-butyl-1H-imidazo[4,5-c]quinolin-1-yl)butyl)-4-((S)-2-((S)-2-(2-(aminooxy)acetamido)-3-methylbutanamido)-5-ureidopentanamido)-3,5-difluorobenzamide (106): To a solution of Fmoc-Aoa-Val-OH (11 mg, 0.027 mmol) and compound 105 (24 mg, 0.022 mmol) in DMF (1 mL) was added HATU (9 mg, 0.037 mmol) and DIEA (40 ul, 0.023 mmol) at 23° C. After 10 min, to this mixture was added piperidine (50 uL, 5%). After 5 min, the mixture was purified by Prep-LC to obtain compound 106 (9 mg, 0.007 mmol, 27%). MS m/z 796 $(M+H)^+$.

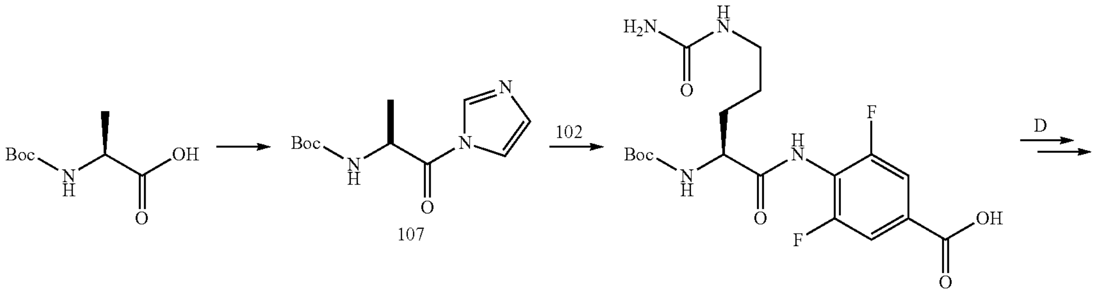

107

108

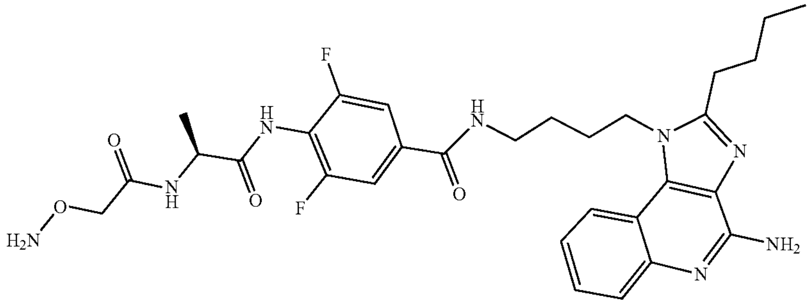

109

(S)-tert-butyl 1-(4-(4-(4-amino-2-butyl-1H-imidazo[4,5-c]quinolin-1-yl)butylcarbamoyl)-2,6-difluorophenylamino)-1-oxo-5-ureidopentan-2-ylcarbamate (104): To a solution of compound D (20 mg, 0.044 mmol) and compound 103 (17 mg, 0.040 mmol) in DMF (1 mL) was added HATU (16 mg, 0.042 mmol) and DIEA (60 uL, 0.344 mmol) at 23° C. After 20 min, the mixture was purified by Prep-LC to obtain compound 104 (23 mg, 0.022 mmol, 55%). MS m/z 724 $(M+H)^+$.

(S)—N-(4-(4-amino-2-butyl-1H-imidazo[4,5-c]quinolin-1-yl)butyl)-4-(2-amino-5-ureidopentanamido)-3,5-difluorobenzamide (105): To a solution of compound 104 (23 mg, 0.022 mmol) in DCM (1 mL) was added TFA (1 mL) at 23° C. After 15 min, the solvent was removed in vacuo. To the residue was added 10 mL of toluene and re-evaporated. The (S)-tert-butyl 1-(1H-imidazol-1-yl)-1-oxopropan-2-ylcarbamate (107): Compound 107 was prepared using Boc-alanine with similar procedure as described for 102 to obtain target compound 107 (730 mg, 3.051 mmol, 75% crude), MS m/z 326 $(M+H)^+$.

(S)-4-(2-(tert-butoxycarbonylamino)-5-ureidopentanamido)-3,5-difluorobenzoic acid (108): Compound 108 was prepared using 107 with similar procedure as described for 103 to obtain target compound 108 (17 mg, 0.049 mmol, 9%). MS m/z 431 $(M+H)^+$.

(S)—N-(4-(4-amino-2-butyl-1H-imidazo[4,5-c]quinolin-1-yl)butyl)-4-(2-(2-(aminooxy)acetamido)propanamido)-3,5-difluorobenzamide (109): Compound 109 was prepared using 108 and compound D with similar procedure as described for 106 to obtain target compound 109 (9 mg, 0.007 mmol, 31% from 108). MS m/z 796 $(M+H)^+$.

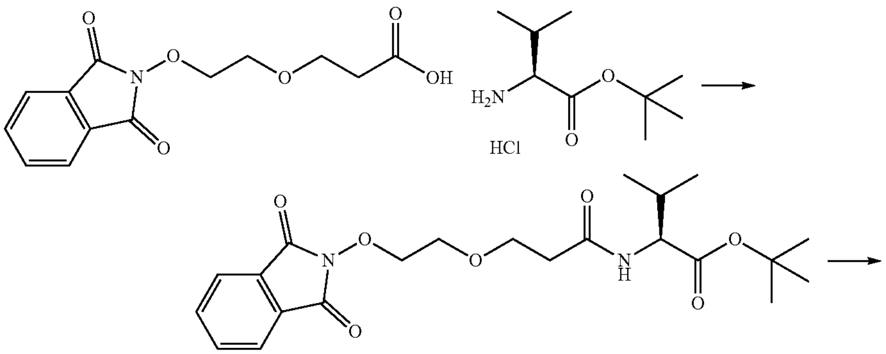

110

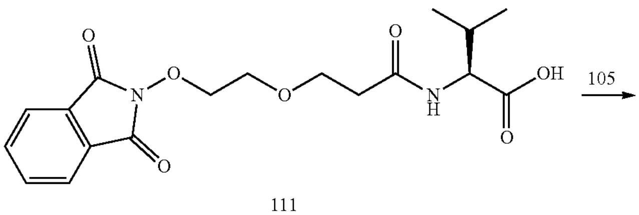

111

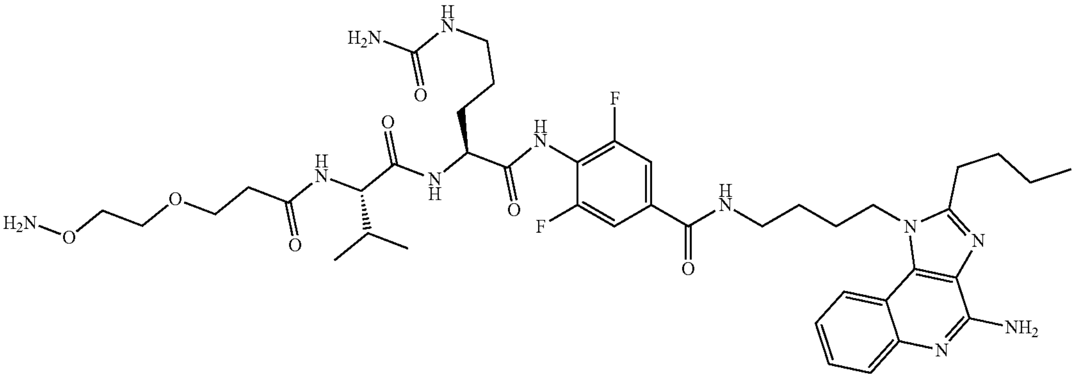

112

(S)-tert-butyl 2-(3-(2-(1,3-dioxoisoindolin-2-yloxy)ethoxy)propanamido)-3-methylbutanoate (110): To a solution of 3-(2-(1,3-dioxoisoindolin-2-yloxy)ethoxy)propanoic acid (295 mg, 1.056 mmol) and Val-OtBu, HCl (225 mg, 1.078 mmol) in DCM (5 mL) was added DMTMMT (304 mg, 1.260 mmol) and DIEA (460 uL, 2.641 mmol) at 23° C. After 1.5 h, the solution was diluted with EtOAC (100 mL) and washed with 1 N HCl (100 mL), saturated sodium bicarbonate (100 mL) and brine (50 mL). The organic layer was dried with $MgSO_4$, filtered, and solvent removed in vacuo. The residue was purified by flash chromatography to obtain compound 110 (379 mg, 0.872 mmol, 83%). MS m/z 435 $(M+H)^+$.

(S)-2-(3-(2-(1,3-dioxoisoindolin-2-yloxy)ethoxy)propanamido)-3-methylbutanoic acid (111): To a solution of compound 110 (379 mg, 0.872 mmol) was added 4M HCl in dioxane (5 mL, 20 mmol) at 23° C. After 20 h, the solvent was removed in vacuo, and dried using a high vacuum pump to obtain compound 111 (320 mg, 0.846 mmol, 97%). MS m/z 379 $(M+H)^+$.

N-(4-(4-amino-2-butyl-1H-imidazo[4,5-c]quinolin-1-yl)butyl)-4-((S)-2-((S)-2-(3-(2-(aminooxy)ethoxy)propanamido)-3-methylbutanamido)-5-ureidopentanamido)-3,5-difluorobenzamide (112): To a solution of compound 111 (3 mg, 0.007 mmol) and compound 105 (5 mg, 0.005 mmol) in DMF (1 mL) was added DMTMMT (3 mg, 0.012 mmol) and DIEA (20 uL, 0.115 mmol) at 23° C. After 1.5 h, to this mixture was added hydrazine, $H_2O$ (2 uL, 0.506 mmol). After 5 min, the mixture was purified by Prep-LC to obtain compound 112 (2 mg, 0.002 mmol, 21%). MS m/z 855 $(M+H)^+$.

30

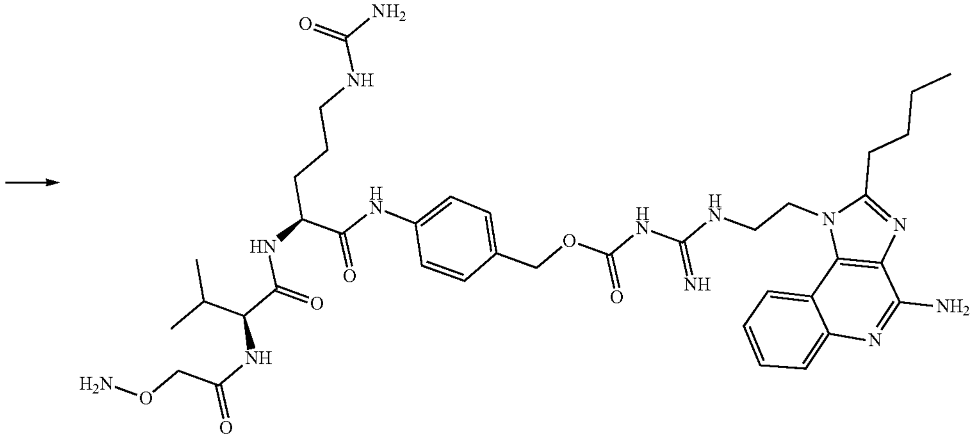

113

(S)—N-(4-((N-(2-(4-amino-2-butyl-1H-imidazo[4,5-c]quinolin-1-yl)ethyl)carbamimidoylcarbamoyloxy)methyl)phenyl)-2-((S)-2-(2-(aminooxy)acetamido)-3-methylbutanamido)-5-ureidopentanamide (113): Compound 113 was prepared using compound 30 as starting materials, with similar procedure as described for 106 to obtain target compound 113 (2 mg, 0.001 mmol, 2% from compound 30). MS m/z 805 $(M+H)^+$.

TABLE 3

| TLR Agonists - Core 1 Compounds | | |
|---|---|---|
| Compound No. | Compound Name | Structure - Core 1 Compounds |
| 5 | AXC-621 | 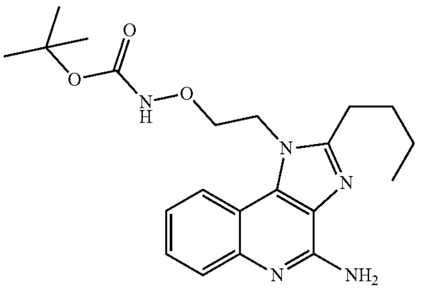 [SMILES: CCCCc1nc2c(N)nc3ccccc3c2n1CCONC(=O)OC(C)(C)C] |
| A | AXC-622 | 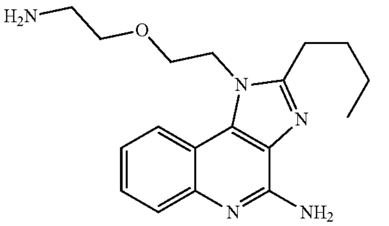 [SMILES: CCCCc1nc2c(N)nc3ccccc3c2n1CCOCCN] |
| 6 | AXC-625 | 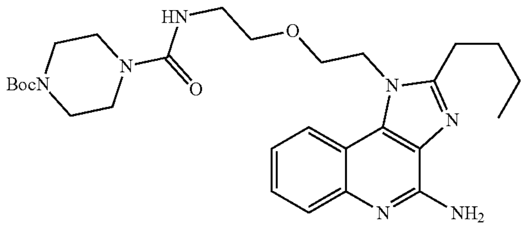 [SMILES: CCCCc1nc2c(N)nc3ccccc3c2n1CCOCCNC(=O)N1CCN(C(=O)OC(C)(C)C)CC1] |

TABLE 3-continued
| TLR Agonists - Core 1 Compounds | | |
|---|---|---|
| Compound No. | Compound Name | Structure - Core 1 Compounds |
| 7 | AXC-626 | 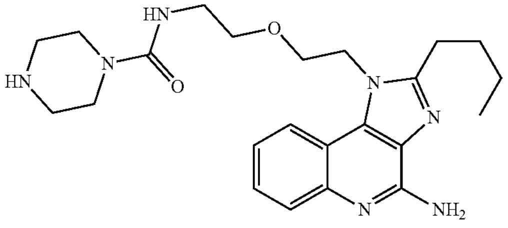 [SMILES: CCCCc1nc2c(N)nc3ccccc3c2n1CCOCCNC(=O)N1CCNCC1] |
| 8 | AXC-627 | 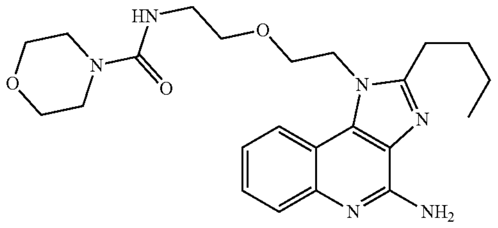 [SMILES: CCCCc1nc2c(N)nc3ccccc3c2n1CCOCCNC(=O)N1CCOCC1] |
| 9 | AXC-638 | 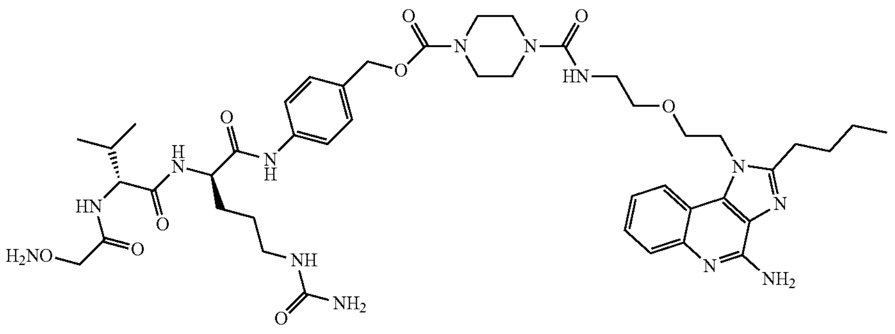 |
| 10 | AXC-639 | 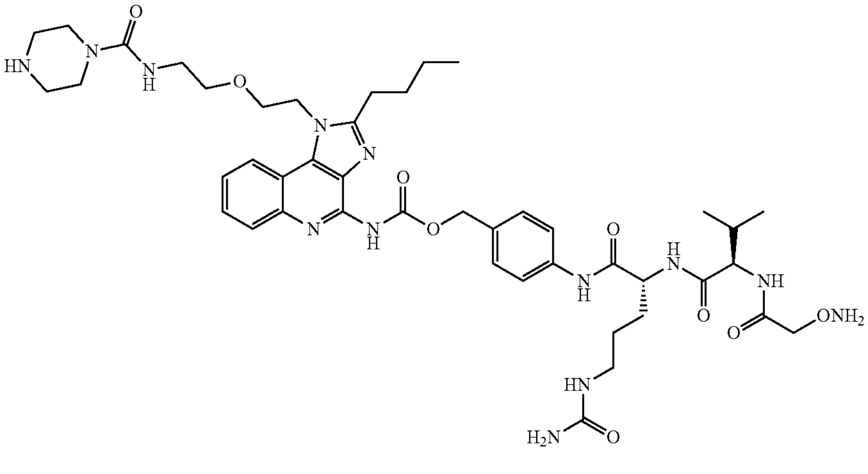 |

TABLE 3-continued
| TLR Agonists - Core 1 Compounds | | |
|---|---|---|
| Compound No. | Compound Name | Structure - Core 1 Compounds |
| 11 | AXC-640 | 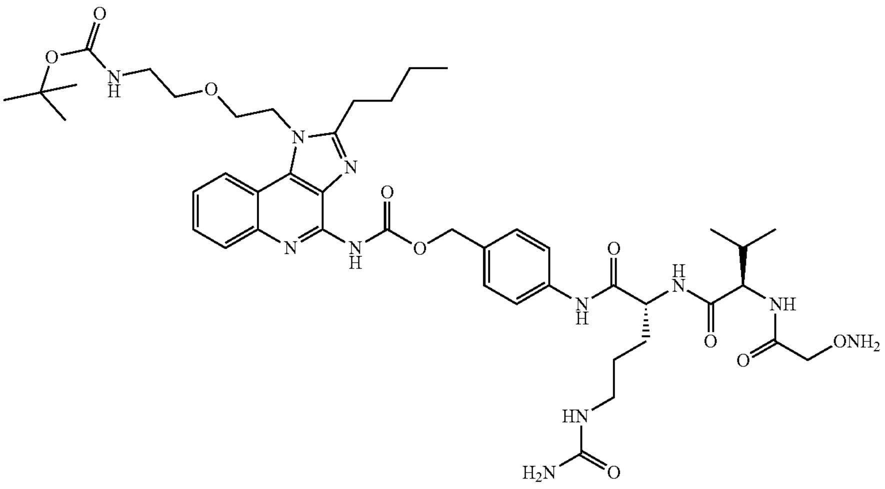 |
| 12 | AXC-642 | 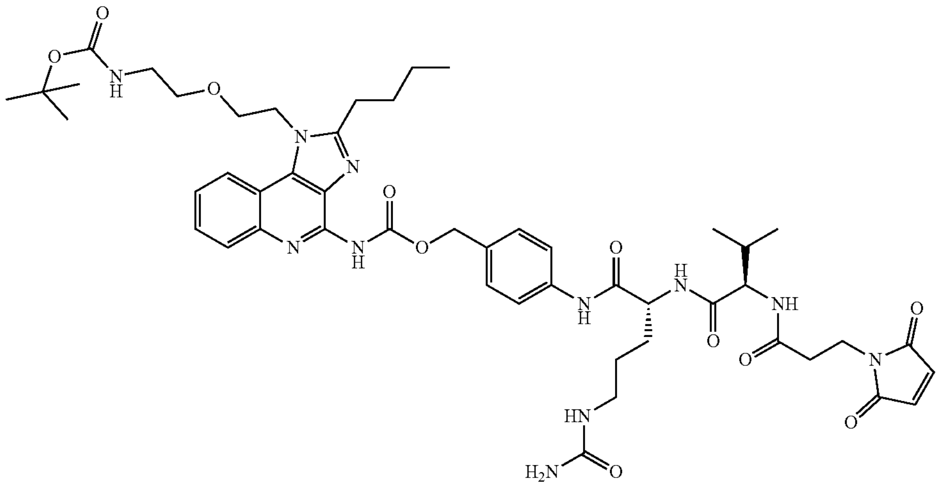 [SMILES: CCCCc1nc2c(NC(=O)OCc3ccc(NC(=O)[C@@H](CCCNC(N)=O)NC(=O)[C@H](NC(=O)CCN4C(=O)C=CC4=O)C(C)C)cc3)nc3ccccc3c2n1CCOCCNC(=O)OC(C)(C)C] |
| 13 | AXC-662 | 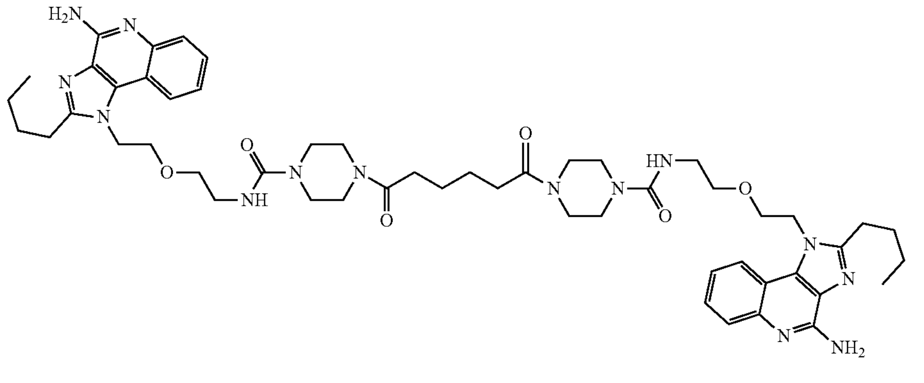 [SMILES: CCCCc1nc2c(N)nc3ccccc3c2n1CCOCCNC(=O)N1CCN(C(=O)CCCCC(=O)N2CCN(C(=O)NCCOCCn3c(CCCC)nc4c(N)nc5ccccc5c43)CC2)CC1] |

TABLE 3-continued
| TLR Agonists - Core 1 Compounds | | |
|---|---|---|
| Compound No. | Compound Name | Structure - Core 1 Compounds |
| 14 | AXC-665 | 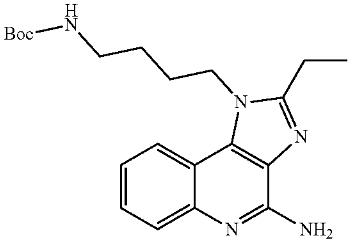 [SMILES: CCc1nc2c(N)nc3ccccc3c2n1CCCCNC(=O)OC(C)(C)C] Molecular Weight: 383.49 |
| B | AXC-666 | 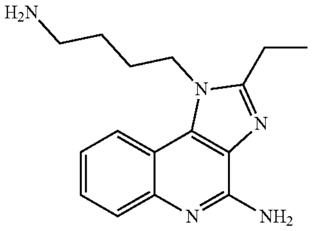 [SMILES: CCc1nc2c(N)nc3ccccc3c2n1CCCCN] Molecular Weight: 283.37 |
| 15 | AXC-667 | 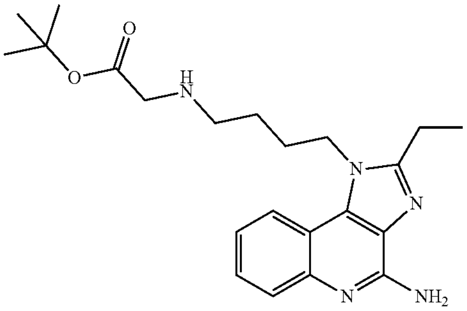 [SMILES: CCc1nc2c(N)nc3ccccc3c2n1CCCCNCC(=O)OC(C)(C)C] Molecular Weight: 397.51 |
| 16 | AXC-668 | 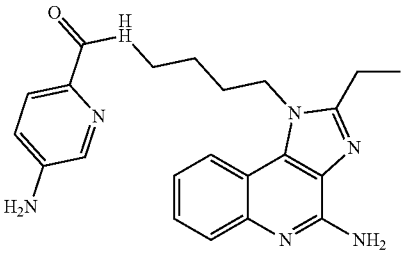 Molecular Weight: 403.48 |

TABLE 3-continued
| TLR Agonists - Core 1 Compounds | | |
|---|---|---|
| Compound No. | Compound Name | Structure - Core 1 Compounds |
| 17 | AXC-669 | 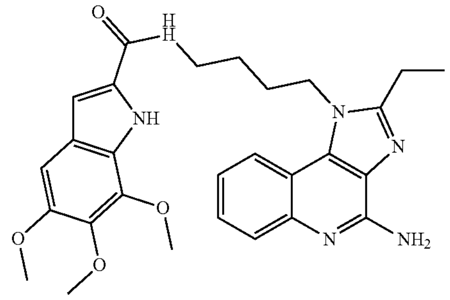 Molecular Weight: 516.59 |
| 18 | AXC-670 | 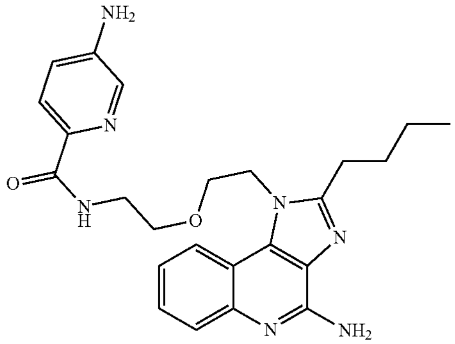 [SMILES: CCCCc1nc2c(N)nc3ccccc3c2n1CCOCCNC(=O)c1ccc(N)cn1] Molecular Weight: 447.53 |
| 19 | AXC-671 | 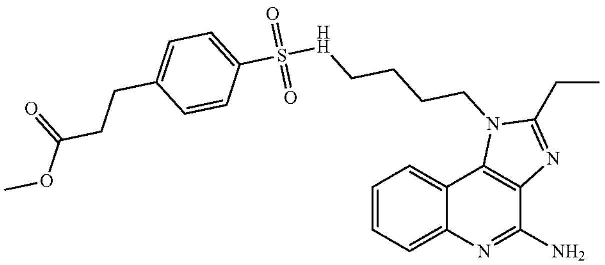 Molecular Weight: 509.62 |
| 20 | AXC-672 | 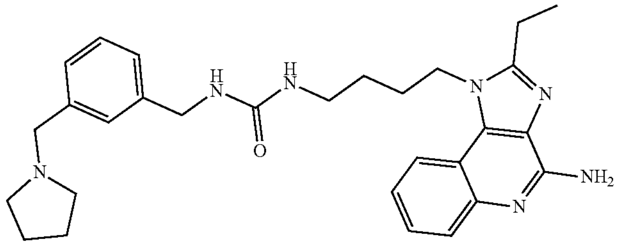 [SMILES: CCc1nc2c(N)nc3ccccc3c2n1CCCCNC(=O)NCc1cccc(CN2CCCC2)c1] Molecular Weight: 499.65 |

TABLE 3-continued
TLR Agonists - Core 1 Compounds
| Compound No. | Compound Name | Structure - Core 1 Compounds |
|---|---|---|
| 21 | AXC-675 | 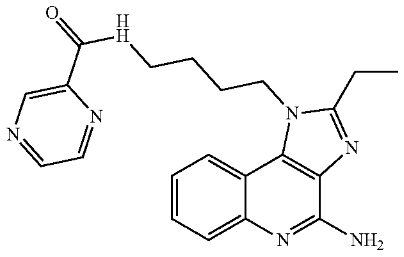 Molecular Weight: 389.45 |
| 22 | AXC-678 | 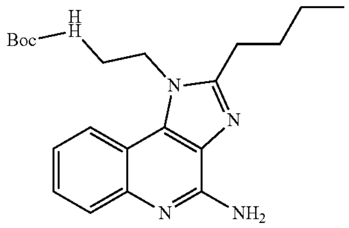 Molecular Weight: 383.49 |
| C | AXC-679 | 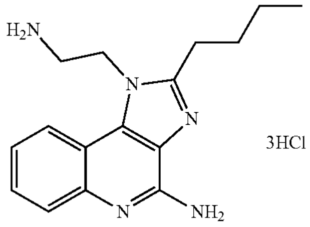 [SMILES: CCCCc1nc2c(N)nc3ccccc3c2n1CCN] Molecular Weight: 283.37 |
| 23 | AXC-681 | 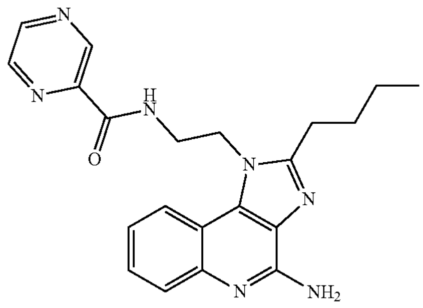 [SMILES: CCCCc1nc2c(N)nc3ccccc3c2n1CCNC(=O)c1cnccn1] Molecular Weight: 389.45 |

TABLE 3-continued
| TLR Agonists - Core 1 Compounds | | |
|---|---|---|
| Compound No. | Compound Name | Structure - Core 1 Compounds |
| 24 | AXC-687 | 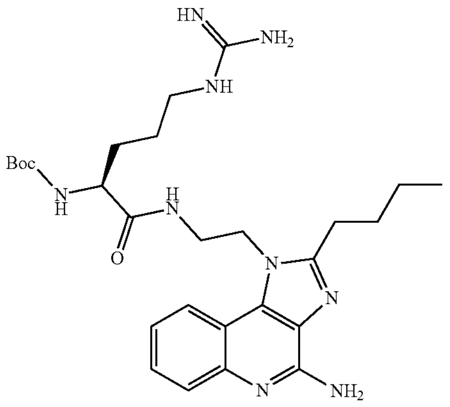 [SMILES: CCCCc1nc2c(N)nc3ccccc3c2n1CCNC(=O)[C@H](CCCNC(=N)N)NC(=O)OC(C)(C)C] Molecular Weight: 539.67 |
| 26 | AXC-688 | 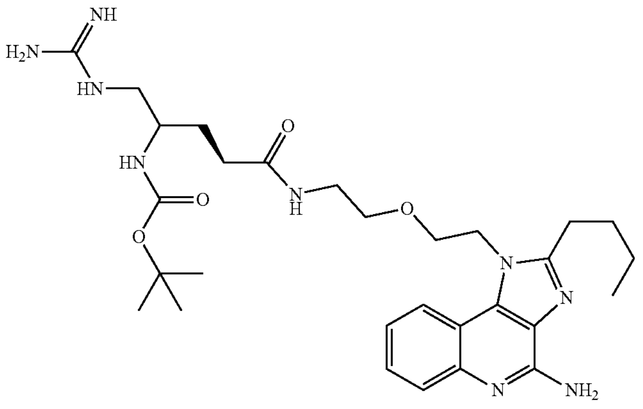 Molecular Weight: 583.73 |
| 28 | AXC-689 | 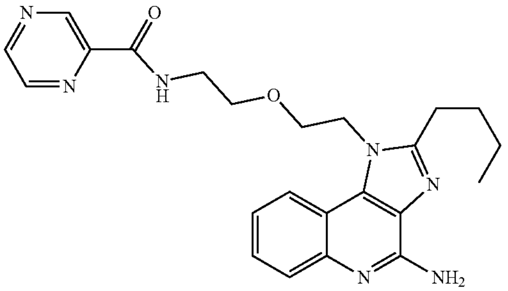 [SMILES: CCCCc1nc2c(N)nc3ccccc3c2n1CCOCCNC(=O)c1cnccn1] Molecular Weight: 433.51 |

TABLE 3-continued
| TLR Agonists - Core 1 Compounds | | |
|---|---|---|
| Compound No. | Compound Name | Structure - Core 1 Compounds |
| 25 | AXC-690 | 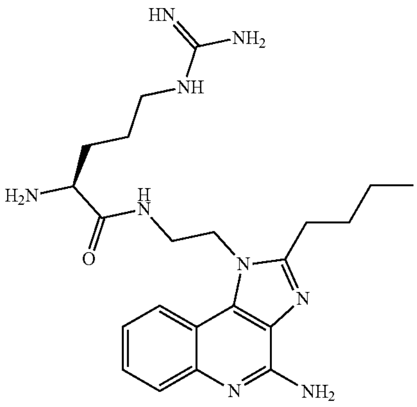 [SMILES: CCCCc1nc2c(N)nc3ccccc3c2n1CCNC(=O)[C@@H](N)CCCNC(=N)N] Molecular Weight: 439.56 |
| 27 | AXC-691 | 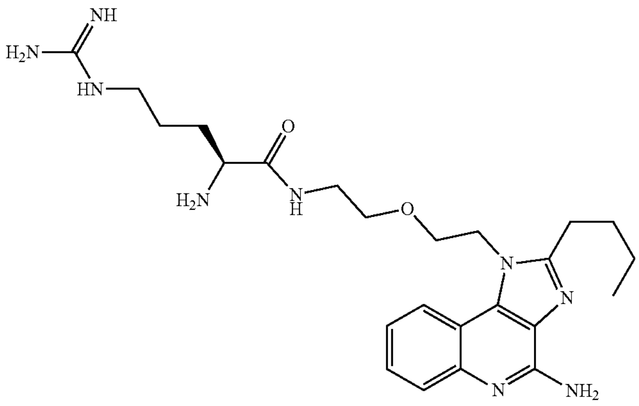 [SMILES: CCCCc1nc2c(N)nc3ccccc3c2n1CCOCCNC(=O)[C@@H](N)CCCNC(=N)N] |
| 29 | AXC-696 | 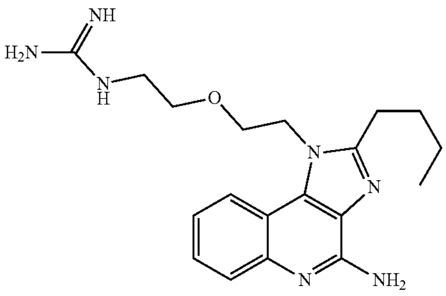 [SMILES: CCCCc1nc2c(N)nc3ccccc3c2n1CCOCCNC(=N)N] Molecular Weight: 369.46 |
| 30 | AXC-697 | 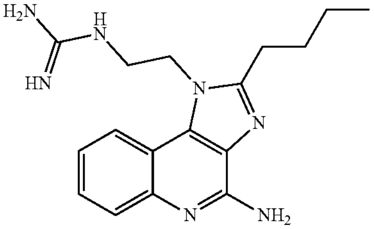 [SMILES: CCCCc1nc2c(N)nc3ccccc3c2n1CCNC(=N)N] Molecular Weight: 325.41 |

TABLE 3-continued
| TLR Agonists - Core 1 Compounds | | |
|---|---|---|
| Compound No. | Compound Name | Structure - Core 1 Compounds |
| 31 | AXC-698 | 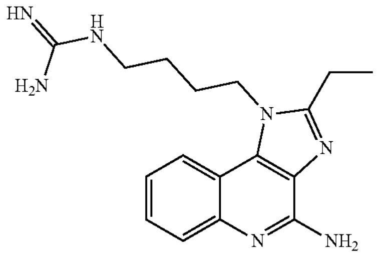 [SMILES: CCc1nc2c(N)nc3ccccc3c2n1CCCCNC(=N)N] Molecular Weight: 325.41 |
| 32 | AXC-699 | 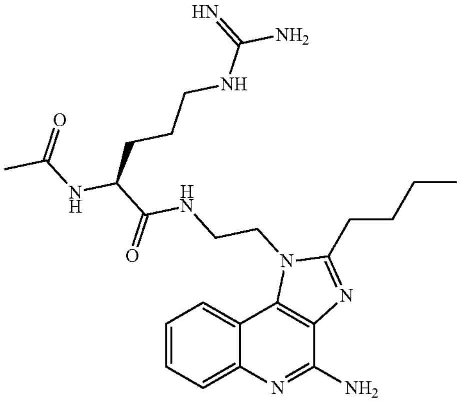 [SMILES: CCCCc1nc2c(N)nc3ccccc3c2n1CCNC(=O)[C@H](CCCNC(=N)N)NC(C)=O] Molecular Weight: 481.59 |
| 33 | AXC-700 | 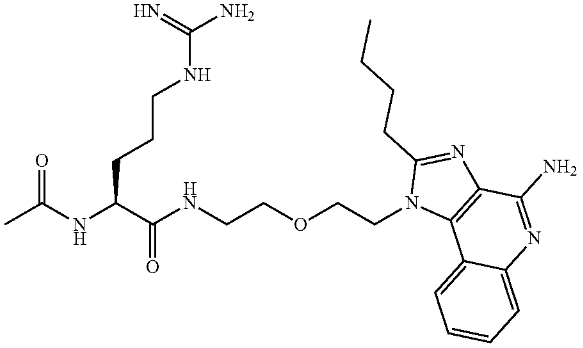 [SMILES: CCCCc1nc2c(N)nc3ccccc3c2n1CCOCCNC(=O)[C@H](CCCNC(=N)N)NC(C)=O] Molecular Weight: 525.65 |

TABLE 3-continued
| TLR Agonists - Core 1 Compounds | | |
|---|---|---|
| Compound No. | Compound Name | Structure - Core 1 Compounds |
| 34 | AXC-701 | 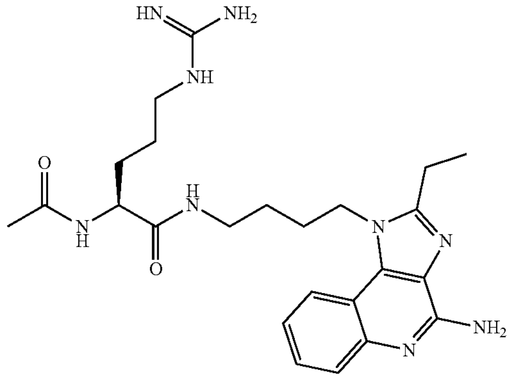 [SMILES: CCc1nc2c(N)nc3ccccc3c2n1CCCCNC(=O)[C@H](CCCNC(=N)N)NC(C)=O] Molecular Weight: 481.59 |
| 35 | AXC-702 | 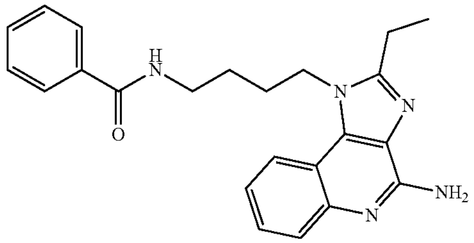 [SMILES: CCc1nc2c(N)nc3ccccc3c2n1CCCCNC(=O)c1ccccc1] Molecular Weight: 387.48 |
| 36 | AXC-709 | 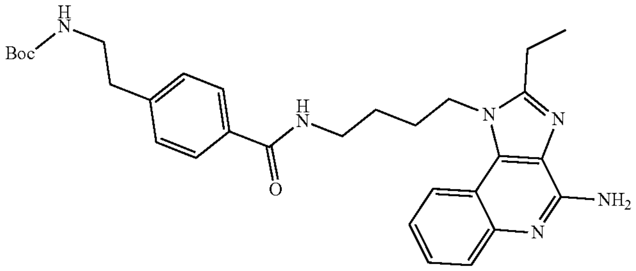 [SMILES: CCc1nc2c(N)nc3ccccc3c2n1CCCCNC(=O)c1ccc(CCNC(=O)OC(C)(C)C)cc1] Molecular Weight: 530.66 |
| 37 | AXC-710 | 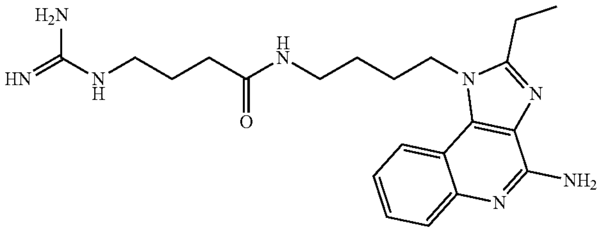 [SMILES: CCc1nc2c(N)nc3ccccc3c2n1CCCCNC(=O)CCCNC(=N)N] Molecular Weight: 410.52 |

TABLE 3-continued
| TLR Agonists - Core 1 Compounds | | |
|---|---|---|
| Compound No. | Compound Name | Structure - Core 1 Compounds |
| 38 | AXC-711 | 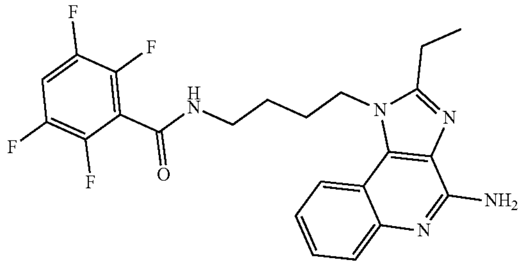 [SMILES: CCc1nc2c(N)nc3ccccc3c2n1CCCCNC(=O)c1c(F)c(F)cc(F)c1F] Molecular Weight: 459.44 |
| 39 | AXC-712 | 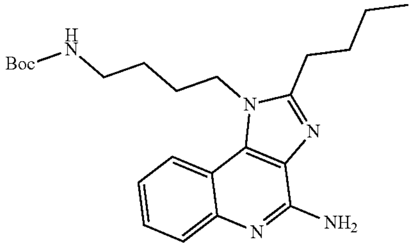 [SMILES: CCCCc1nc2c(N)nc3ccccc3c2n1CCCCNC(=O)OC(C)(C)C] Molecular Weight: 411.54 |
| 40 | AXC-713 | 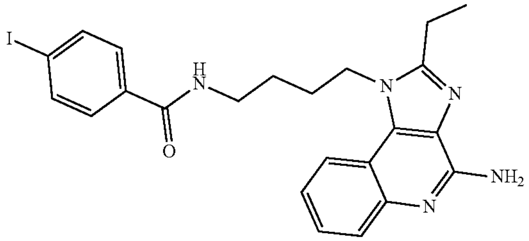 [SMILES: CCc1nc2c(N)nc3ccccc3c2n1CCCCNC(=O)c1ccc(I)cc1] Molecular Weight: 513.37 |
| 41 | AXC-714 | 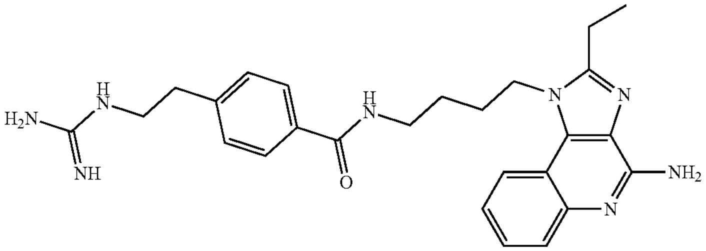 [SMILES: CCc1nc2c(N)nc3ccccc3c2n1CCCCNC(=O)c1ccc(CCNC(=N)N)cc1] Molecular Weight: 472.6 |
| D | AXC-715 | 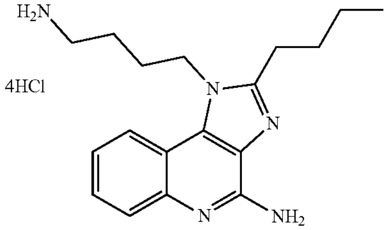 [SMILES: CCCCc1nc2c(N)nc3ccccc3c2n1CCCCN] Molecular Weight: 311.42 |

TABLE 3-continued
| TLR Agonists - Core 1 Compounds | | |
|---|---|---|
| Compound No. | Compound Name | Structure - Core 1 Compounds |
| 42 | AXC-716 | 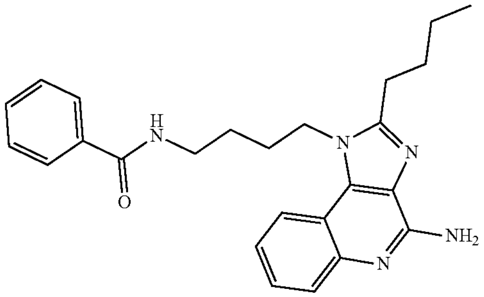 [SMILES: CCCCc1nc2c(N)nc3ccccc3c2n1CCCCNC(=O)c1ccccc1]<br>Molecular Weight: 415.53 |
| 43 | AXC-717 | 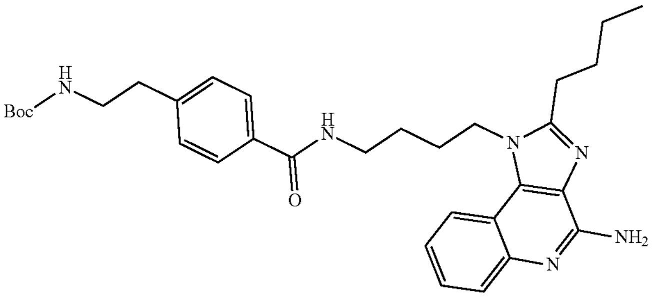 [SMILES: CCCCc1nc2c(N)nc3ccccc3c2n1CCCCNC(=O)c1ccc(CCNC(=O)OC(C)(C)C)cc1]<br>Molecular Weight: 558.71 |
| 44 | AXC-718 | 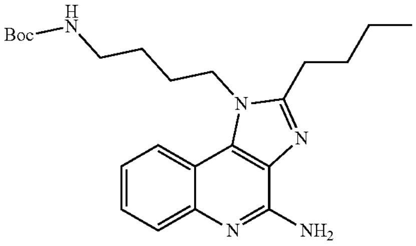 [SMILES: CCCCc1nc2c(N)nc3ccccc3c2n1CCCCNC(=O)OC(C)(C)C]<br>Molecular Weight: 412.53 |
| 45 | AXC-719 | 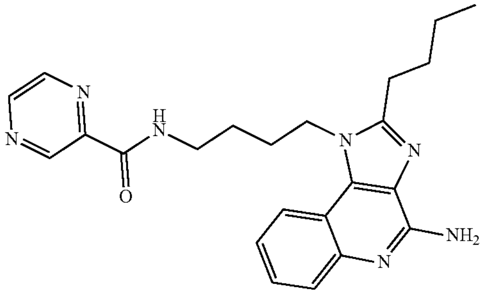 [SMILES: CCCCc1nc2c(N)nc3ccccc3c2n1CCCCNC(=O)c1cnccn1]<br>Molecular Weight: 417.51 |

TABLE 3-continued
| TLR Agonists - Core 1 Compounds | | |
|---|---|---|
| Compound No. | Compound Name | Structure - Core 1 Compounds |
| 46 | AXC-722 | 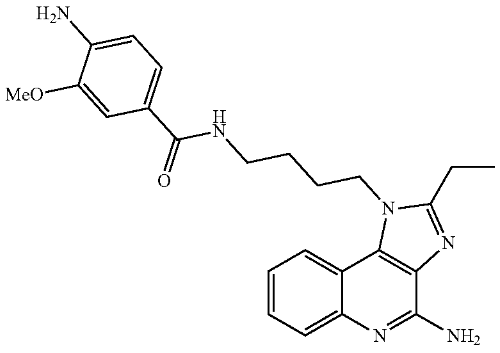 [SMILES: CCc1nc2c(N)nc3ccccc3c2n1CCCCNC(=O)c1ccc(N)c(OC)c1] Molecular Weight: 432.53 |
| 47 | AXC-723 | 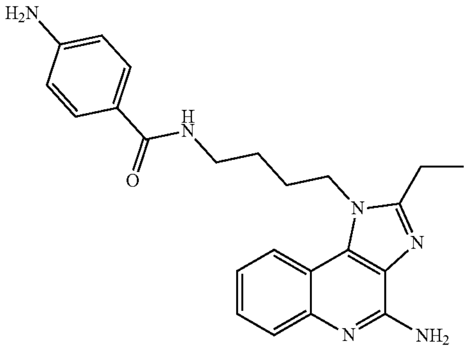 [SMILES: CCc1nc2c(N)nc3ccccc3c2n1CCCCNC(=O)c1ccc(N)cc1] Molecular Weight: 402.50 |
| 48 | AXC-724 | 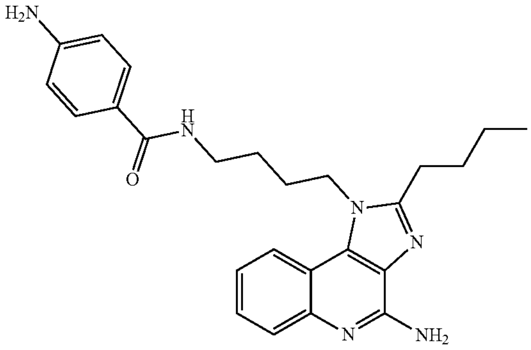 [SMILES: CCCCc1nc2c(N)nc3ccccc3c2n1CCCCNC(=O)c1ccc(N)cc1] Molecular Weight: 430.56 |

TABLE 3-continued
| TLR Agonists - Core 1 Compounds | | |
|---|---|---|
| Compound No. | Compound Name | Structure - Core 1 Compounds |
| 49 | AXC-725 | 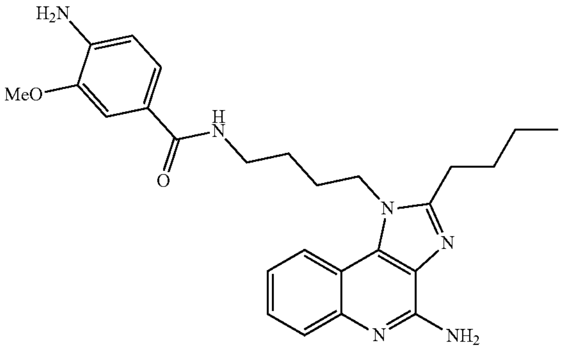 [SMILES: CCCCc1nc2c(N)nc3ccccc3c2n1CCCCNC(=O)c1ccc(N)c(OC)c1] Molecular Weight: 460.58 |
| 50 | AXC-726 | 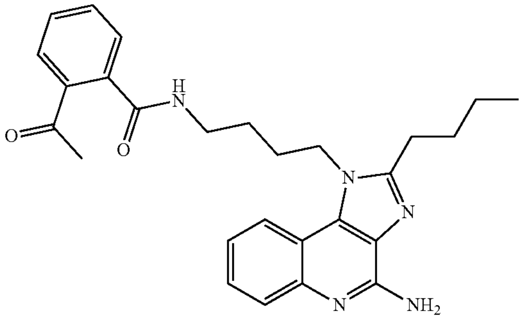 [SMILES: CCCCc1nc2c(N)nc3ccccc3c2n1CCCCNC(=O)c1ccccc1C(C)=O] Molecular Weight: 457.58 |
| 51 | AXC-727 | 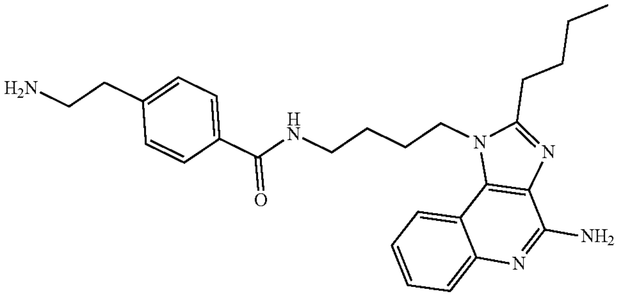 [SMILES: CCCCc1nc2c(N)nc3ccccc3c2n1CCCCNC(=O)c1ccc(CCN)cc1] Molecular Weight: 458.60 |
| 52 | AXC-729 | 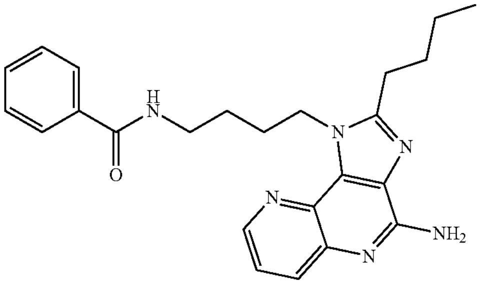 [SMILES: CCCCc1nc2c(N)nc3cccnc3c2n1CCCCNC(=O)c1ccccc1] Molecular Weight: 416.52 |

TABLE 3-continued
| TLR Agonists - Core 1 Compounds | | |
|---|---|---|
| Compound No. | Compound Name | Structure - Core 1 Compounds |
| 53 | AXC-731 | 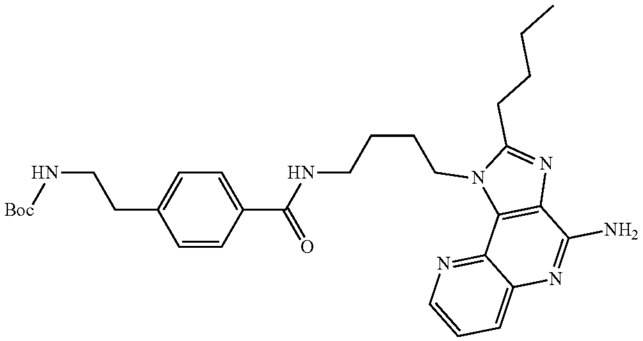 [SMILES: CCCCc1nc2c(N)nc3cccnc3c2n1CCCCNC(=O)c1ccc(CCNC(=O)OC(C)(C)C)cc1] Molecular Weight: 559.70 |
| 54 | AXC-732 | 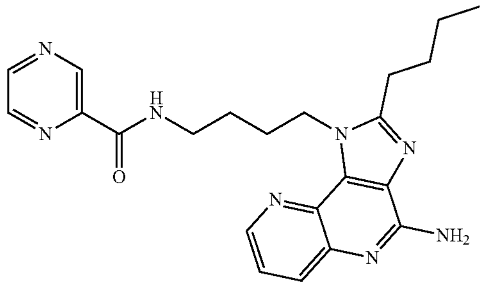 [SMILES: CCCCc1nc2c(N)nc3cccnc3c2n1CCCCNC(=O)c1cnccn1] Molecular Weight: 418.49 |
| 55 | AXC-733 | 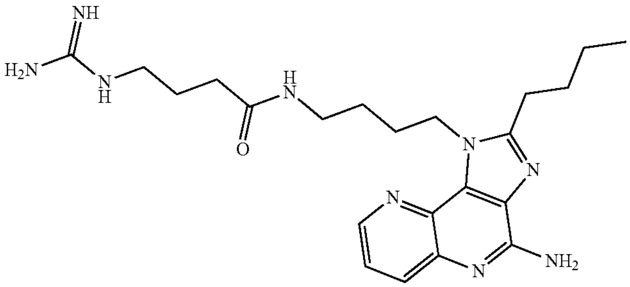 [SMILES: CCCCc1nc2c(N)nc3cccnc3c2n1CCCCNC(=O)CCCNC(=N)N] Molecular Weight: 439.56 |
| 56 | AXC-734 | 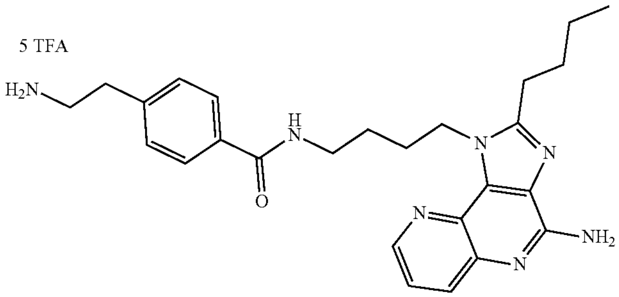 [SMILES: CCCCc1nc2c(N)nc3cccnc3c2n1CCCCNC(=O)c1ccc(CCN)cc1] Molecular Weight: 459.59 |

TABLE 3-continued
| TLR Agonists - Core 1 Compounds | | |
|---|---|---|
| Compound No. | Compound Name | Structure - Core 1 Compounds |
| 57 | AXC-735 | 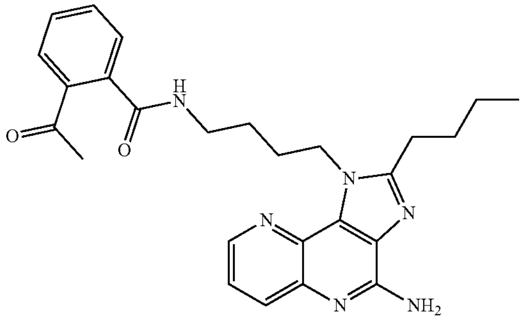 [SMILES: CCCCc1nc2c(N)nc3cccnc3c2n1CCCCNC(=O)c1ccccc1C(C)=O] Molecular Weight: 458.57 |
| 58 | AXC-736 | 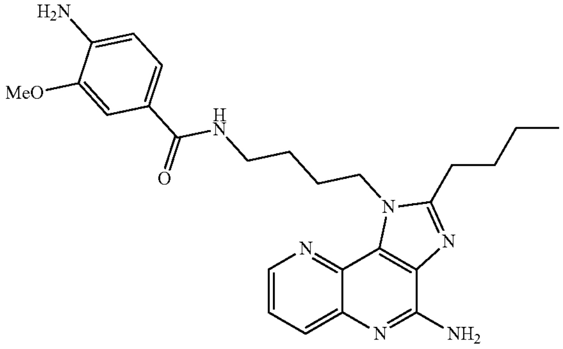 [SMILES: CCCCc1nc2c(N)nc3cccnc3c2n1CCCCNC(=O)c1ccc(N)c(OC)c1] Molecular Weight: 461.57 |
| 59 | AXC-737 | 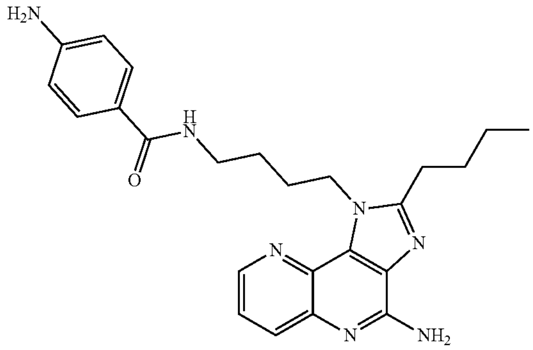 [SMILES: CCCCc1nc2c(N)nc3cccnc3c2n1CCCCNC(=O)c1ccc(N)cc1] Molecular Weight: 431.54 |
| 60 | AXC-738 | 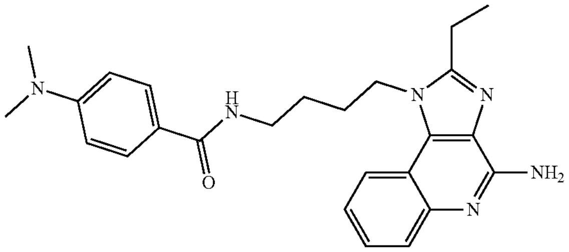 [SMILES: CCc1nc2c(N)nc3ccccc3c2n1CCCCNC(=O)c1ccc(N(C)C)cc1] Molecular Weight: 430.55 |

TABLE 3-continued
| TLR Agonists - Core 1 Compounds | | |
|---|---|---|
| Compound No. | Compound Name | Structure - Core 1 Compounds |
| 61 | AXC-739 | 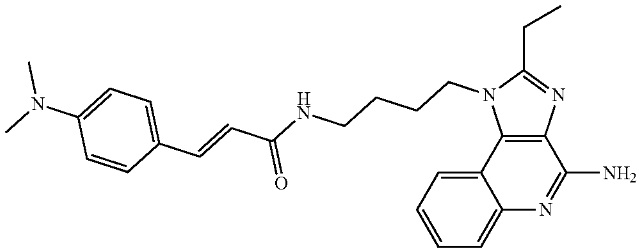 [SMILES: CCc1nc2c(N)nc3ccccc3c2n1CCCCNC(=O)/C=C/c1ccc(N(C)C)cc1] Molecular Weight: 456.58 |
| 62 | AXC-740 | 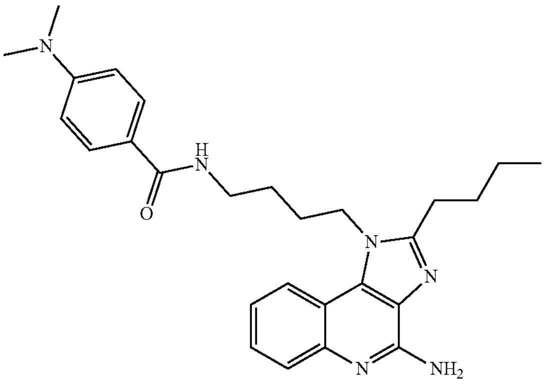 [SMILES: CCCCc1nc2c(N)nc3ccccc3c2n1CCCCNC(=O)c1ccc(N(C)C)cc1] Molecular Weight: 458.61 |
| 63 | AXC-741 | 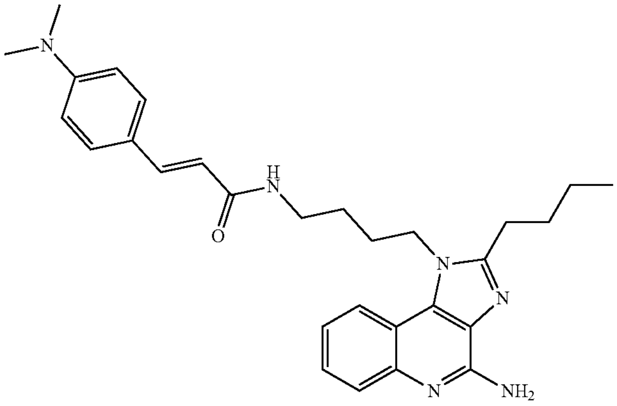 [SMILES: CCCCc1nc2c(N)nc3ccccc3c2n1CCCCNC(=O)/C=C/c1ccc(N(C)C)cc1] Molecular Weight: 484.65 |

TABLE 3-continued
| TLR Agonists - Core 1 Compounds | | |
|---|---|---|
| Compound No. | Compound Name | Structure - Core 1 Compounds |
| 64 | AXC-743 | 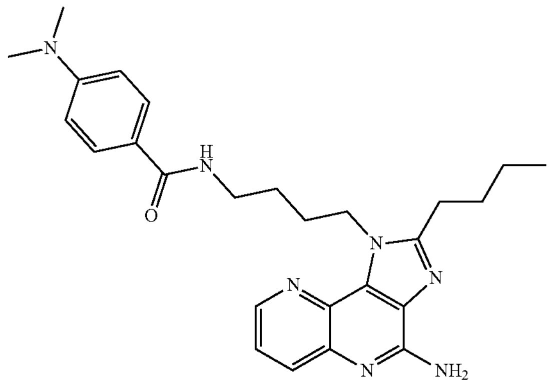 [SMILES: CCCCc1nc2c(N)nc3cccnc3c2n1CCCCNC(=O)c1ccc(N(C)C)cc1] Molecular Weight: 459.60 |
| 65 | AXC-742 | 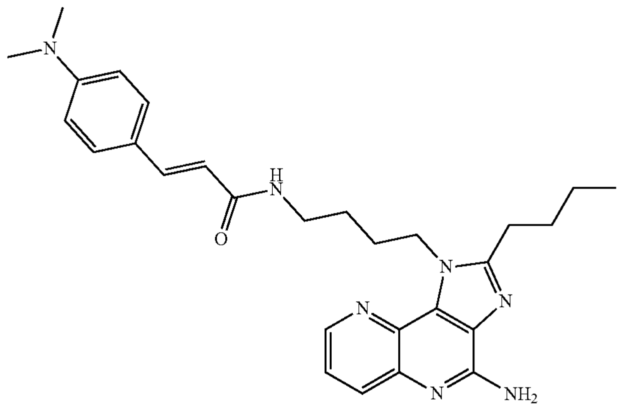 [SMILES: CCCCc1nc2c(N)nc3cccnc3c2n1CCCCNC(=O)/C=C/c1ccc(N(C)C)cc1] Molecular Weight: 485.64 |
| 66 | AXC-747 | 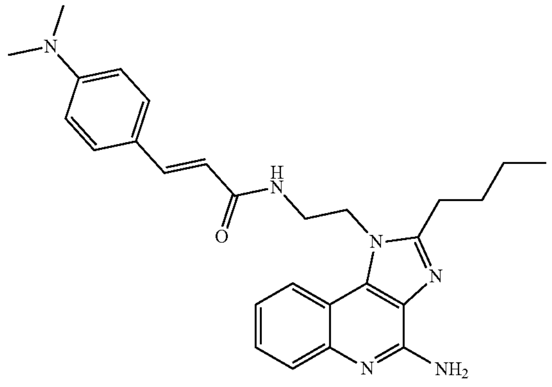 [SMILES: CCCCc1nc2c(N)nc3ccccc3c2n1CCNC(=O)/C=C/c1ccc(N(C)C)cc1] Molecular Weight: 456.58 |

TABLE 3-continued
| TLR Agonists - Core 1 Compounds | | |
|---|---|---|
| Compound No. | Compound Name | Structure - Core 1 Compounds |
| 68 | AXC-748 | 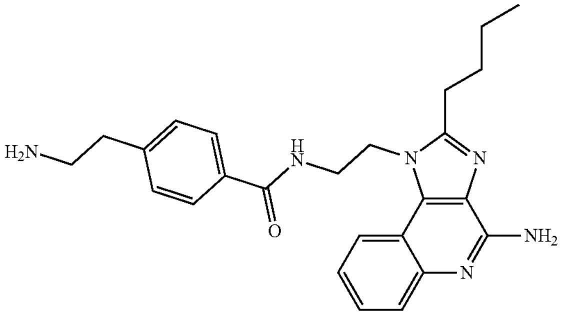 [SMILES: CCCCc1nc2c(N)nc3ccccc3c2n1CCNC(=O)c1ccc(CCN)cc1] Molecular Weight: 430.55 |
| 69 | AXC-749 | 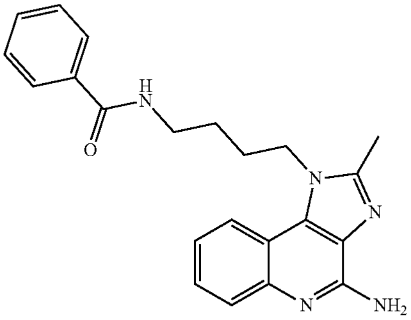 [SMILES: Cc1nc2c(N)nc3ccccc3c2n1CCCCNC(=O)c1ccccc1] Molecular Weight: 373.46 |
| 70 | AXC-750 | 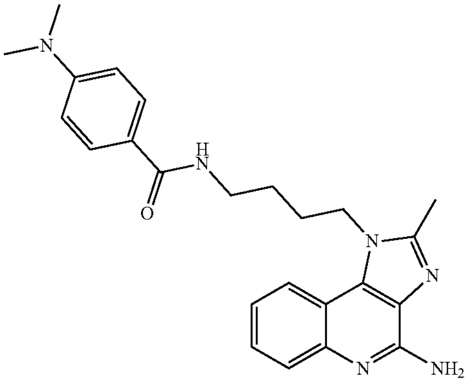 [SMILES: Cc1nc2c(N)nc3ccccc3c2n1CCCCNC(=O)c1ccc(N(C)C)cc1] Molecular Weight: 416.53 |

TABLE 3-continued
| TLR Agonists - Core 1 Compounds | | |
|---|---|---|
| Compound No. | Compound Name | Structure - Core 1 Compounds |
| 71 | AXC-751 | 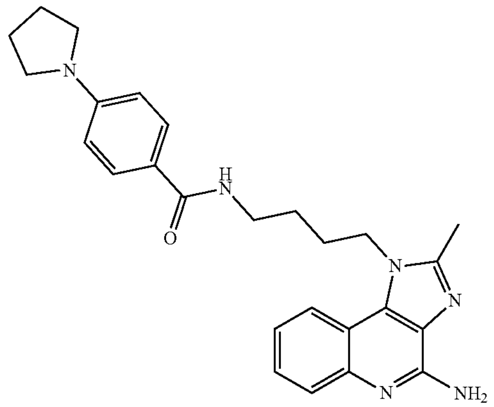 [SMILES: Cc1nc2c(N)nc3ccccc3c2n1CCCCNC(=O)c1ccc(N2CCCC2)cc1] Molecular Weight: 442.57 |
| 72 | AXC-752 | 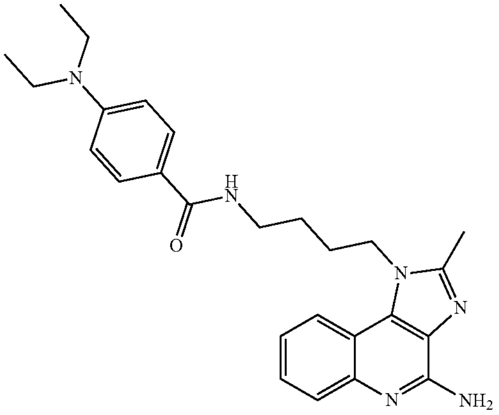 [SMILES: CCN(CC)c1ccc(C(=O)NCCCCn2c(C)nc3c(N)nc4ccccc4c32)cc1] Molecular Weight: 444.58 |
| 73 | AXC-754 | 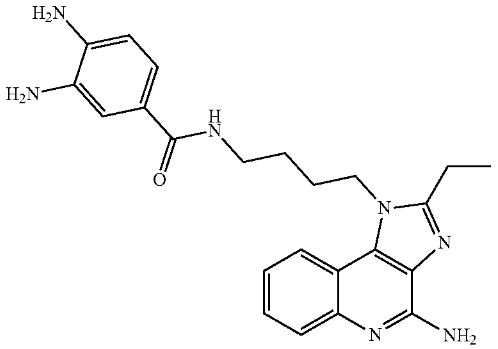 [SMILES: CCc1nc2c(N)nc3ccccc3c2n1CCCCNC(=O)c1ccc(N)c(N)c1] Molecular Weight: 417.51 |

TABLE 3-continued
| TLR Agonists - Core 1 Compounds | | |
|---|---|---|
| Compound No. | Compound Name | Structure - Core 1 Compounds |
| 74 | AXC-755 | 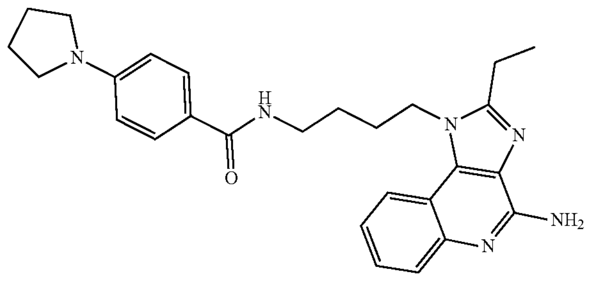 [SMILES: CCc1nc2c(N)nc3ccccc3c2n1CCCCNC(=O)c1ccc(N2CCCC2)cc1] Molecular Weight: 456.58 |
| 75 | AXC-756 | 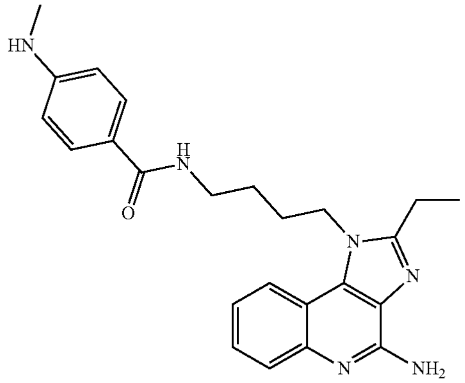 [SMILES: CCc1nc2c(N)nc3ccccc3c2n1CCCCNC(=O)c1ccc(NC)cc1] Molecular Weight: 416.52 |
| 76 | AXC-757 | 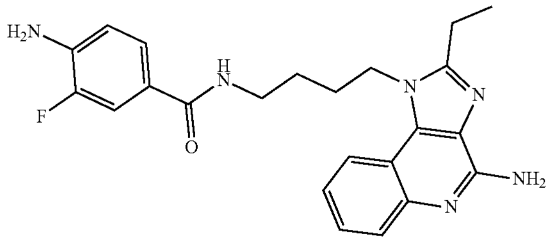 [SMILES: CCc1nc2c(N)nc3ccccc3c2n1CCCCNC(=O)c1ccc(N)c(F)c1] Molecular Weight: 420.48 |
| 77 | AXC-758 | 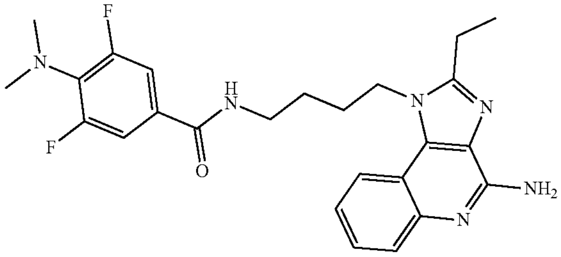 [SMILES: CCc1nc2c(N)nc3ccccc3c2n1CCCCNC(=O)c1cc(F)c(N(C)C)c(F)c1] Molecular Weight: 466.53 |

TABLE 3-continued
TLR Agonists - Core 1 Compounds
| Compound No. | Compound Name | Structure - Core 1 Compounds |
|---|---|---|
| 78 | AXC-759 | 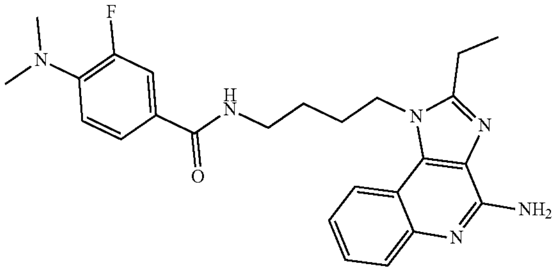 [SMILES: CCc1nc2c(N)nc3ccccc3c2n1CCCCNC(=O)c1ccc(N(C)C)c(F)c1] Molecular Weight: 448.54 |
| 79 | AXC-760 | 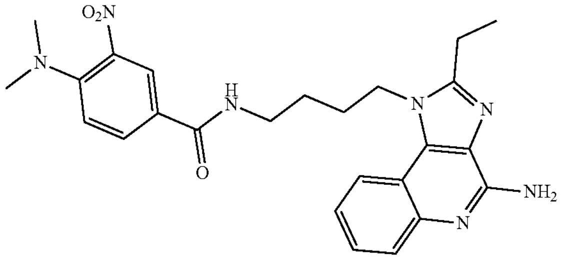 [SMILES: CCc1nc2c(N)nc3ccccc3c2n1CCCCNC(=O)c1ccc(N(C)C)c([N+](=O)[O-])c1] Molecular Weight: 475.54 |
| 80 | AXC-761 | 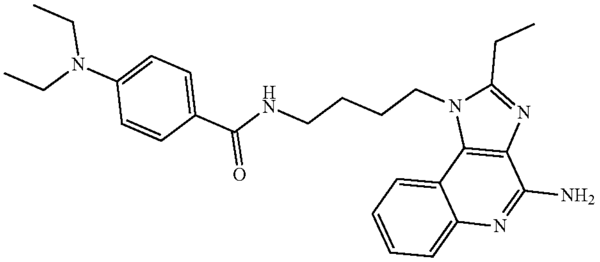 [SMILES: CCc1nc2c(N)nc3ccccc3c2n1CCCCNC(=O)c1ccc(N(CC)CC)cc1] Molecular Weight: 458.60 |
| 81 | AXC-762 | 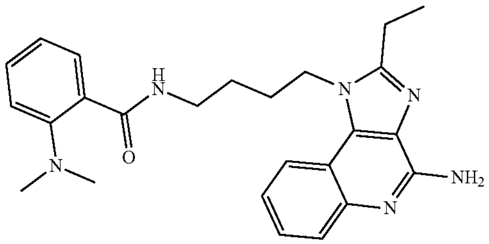 [SMILES: CCc1nc2c(N)nc3ccccc3c2n1CCCCNC(=O)c1ccccc1N(C)C] Molecular Weight: 430.55 |
| 82 | AXC-764 | 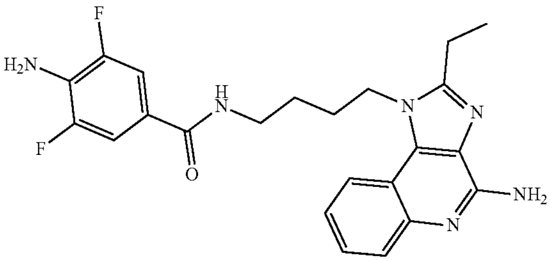 [SMILES: CCc1nc2c(N)nc3ccccc3c2n1CCCCNC(=O)c1cc(F)c(N)c(F)c1] Molecular Weight: 438.47 |

TABLE 3-continued
TLR Agonists - Core 1 Compounds
| Compound No. | Compound Name | Structure - Core 1 Compounds |
|---|---|---|
| 83 | AXC-771 | 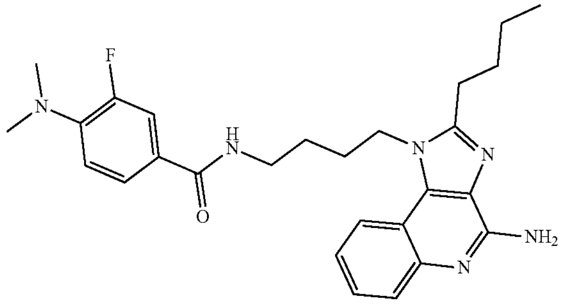 [SMILES: CCCCc1nc2c(N)nc3ccccc3c2n1CCCCNC(=O)c1ccc(N(C)C)c(F)c1] Molecular Weight: 476.59 |
| 84 | AXC-772 | 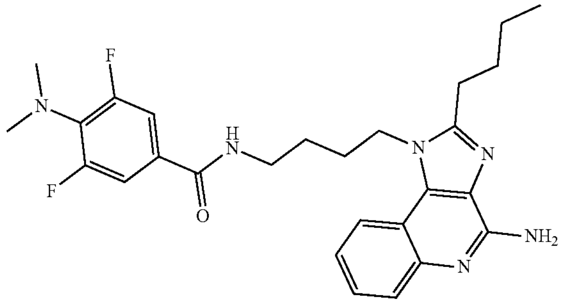 [SMILES: CCCCc1nc2c(N)nc3ccccc3c2n1CCCCNC(=O)c1cc(F)c(N(C)C)c(F)c1] Molecular Weight: 494.58 |
| 85 | AXC-773 | 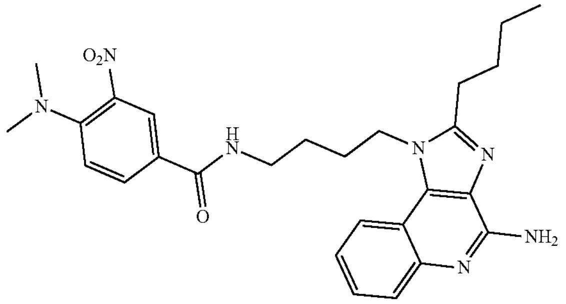 [SMILES: CCCCc1nc2c(N)nc3ccccc3c2n1CCCCNC(=O)c1ccc(N(C)C)c([N+](=O)[O-])c1] Molecular Weight: 503.60 |
| 86 | AXC-777 | 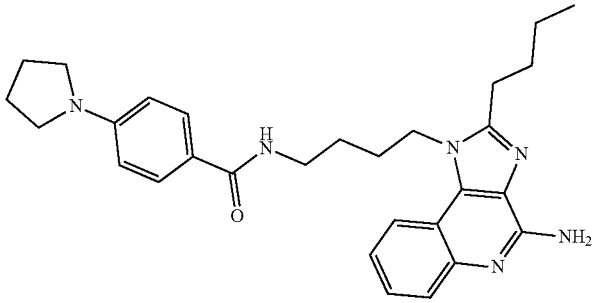 [SMILES: CCCCc1nc2c(N)nc3ccccc3c2n1CCCCNC(=O)c1ccc(N2CCCC2)cc1] Molecular Weight: 484.64 |

TABLE 3-continued
| TLR Agonists - Core 1 Compounds | | |
|---|---|---|
| Compound No. | Compound Name | Structure - Core 1 Compounds |
| 87 | AXC -778 | 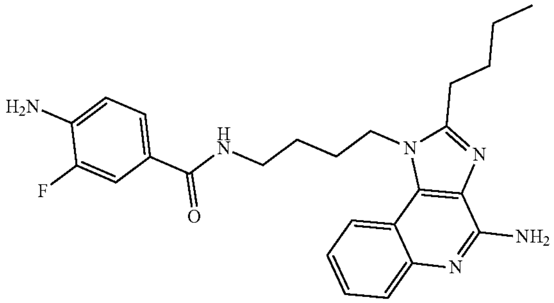 [SMILES: CCCCc1nc2c(N)nc3ccccc3c2n1CCCCNC(=O)c1ccc(N)c(F)c1] Molecular Weight: 448.54 |
| 88 | AXC-779 | 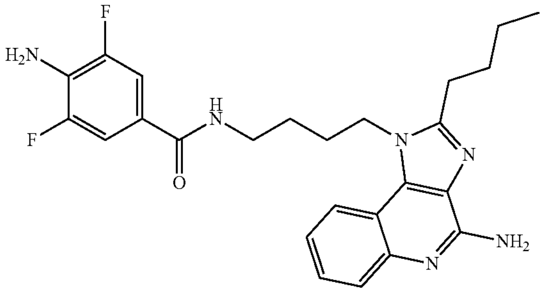 [SMILES: CCCCc1nc2c(N)nc3ccccc3c2n1CCCCNC(=O)c1cc(F)c(N)c(F)c1] Molecular Weight: 466.63 |
| 89 | AXC-789 | 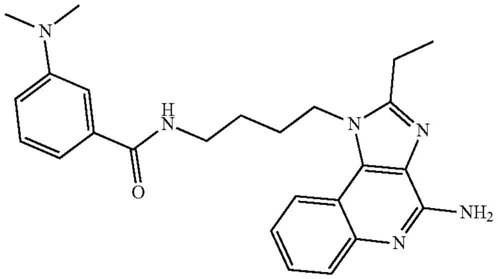 [SMILES: CCc1nc2c(N)nc3ccccc3c2n1CCCCNC(=O)c1cccc(N(C)C)c1] Molecular Weight: 430.55 |
| 90 | AXC-793 | 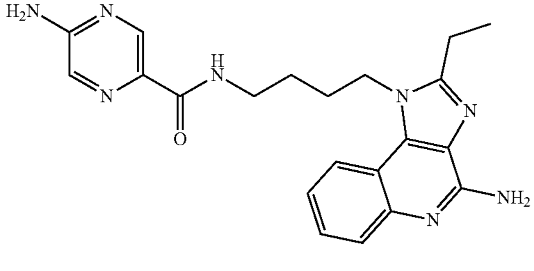 [SMILES: CCc1nc2c(N)nc3ccccc3c2n1CCCCNC(=O)c1cnc(N)cn1] Molecular Weight: 404.47 |

TABLE 3-continued
| TLR Agonists - Core 1 Compounds | | |
|---|---|---|
| Compound No. | Compound Name | Structure - Core 1 Compounds |
| G | AXC-799 | 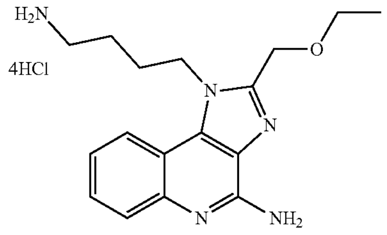 [SMILES: CCOCc1nc2c(N)nc3ccccc3c2n1CCCCN] Molecular Weight: 313.40 |
| 109 | AXC-800 | 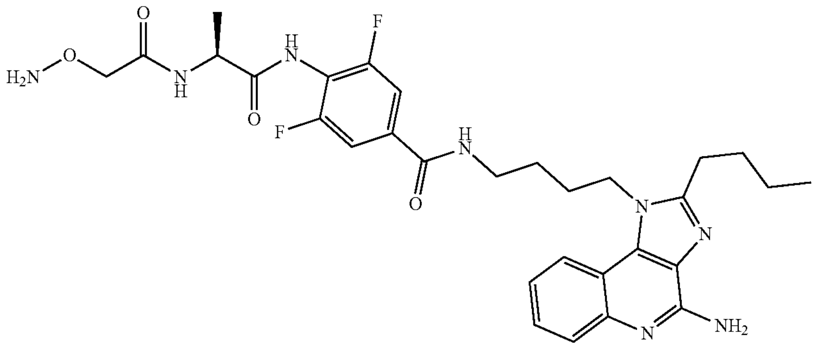 [SMILES: CCCCc1nc2c(N)nc3ccccc3c2n1CCCCNC(=O)c1cc(F)c(NC(=O)[C@H](C)NC(=O)CON)c(F)c1] Molecular Weight: 610.65 |
| 106 | AXC-801 | 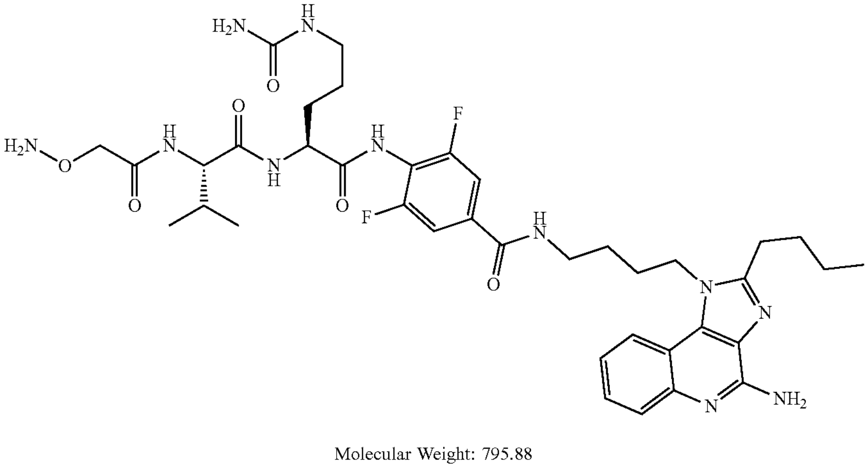 Molecular Weight: 795.88 |

TABLE 3-continued
| TLR Agonists - Core 1 Compounds | | |
|---|---|---|
| Compound No. | Compound Name | Structure - Core 1 Compounds |
| 112 | AXC-802 | 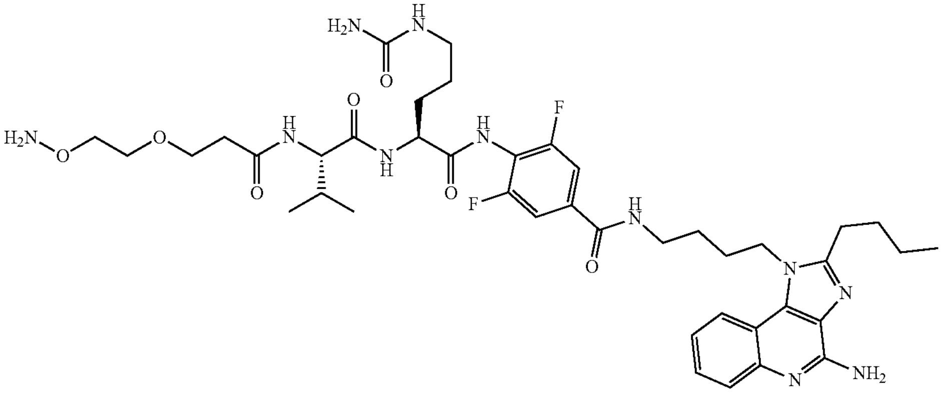 [SMILES: CCCCc1nc2c(N)nc3ccccc3c2n1CCCCNC(=O)c1cc(F)c(NC(=O)[C@H](CCCNC(N)=O)NC(=O)[C@@H](NC(=O)CCOCCON)C(C)C)c(F)c1] Molecular Weight: 853.96 |
| 93 | AXC-803 | 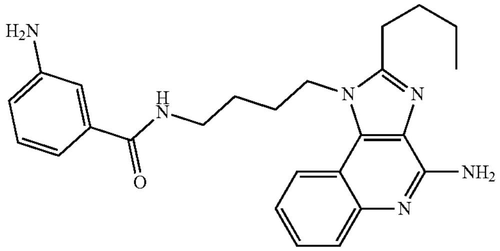 [SMILES: CCCCc1nc2c(N)nc3ccccc3c2n1CCCCNC(=O)c1cccc(N)c1] Molecular Weight: 430.55 |
| 94 | AXC-804 | 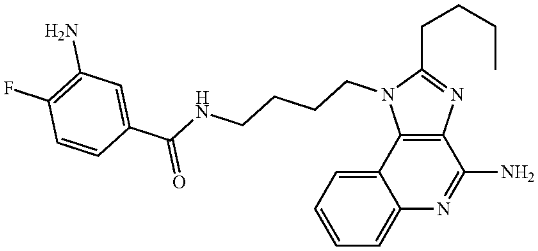 [SMILES: CCCCc1nc2c(N)nc3ccccc3c2n1CCCCNC(=O)c1ccc(F)c(N)c1] Molecular Weight: 448.54 |
| 95 | AXC-805 | 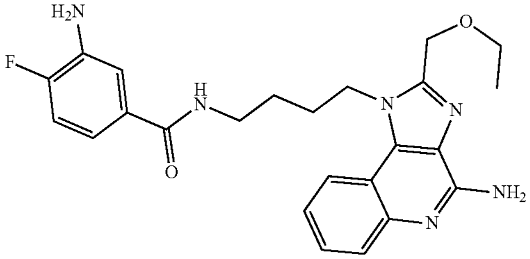 [SMILES: CCOCc1nc2c(N)nc3ccccc3c2n1CCCCNC(=O)c1ccc(F)c(N)c1] Molecular Weight: 450.51 |

TABLE 3-continued
| TLR Agonists - Core 1 Compounds | | |
|---|---|---|
| Compound No. | Compound Name | Structure - Core 1 Compounds |
| 96 | AXC-806 | 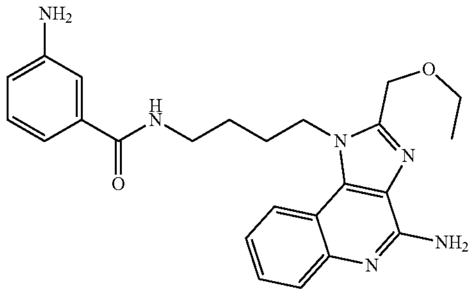 [SMILES: CCOCc1nc2c(N)nc3ccccc3c2n1CCCCNC(=O)c1cccc(N)c1] Molecular Weight: 432.52 |
| 97 | AXC-807 | 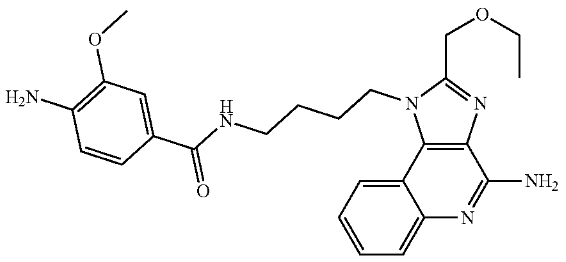 [SMILES: CCOCc1nc2c(N)nc3ccccc3c2n1CCCCNC(=O)c1ccc(N)c(OC)c1] Molecular Weight: 462.54 |
| 98 | AXC-808 | 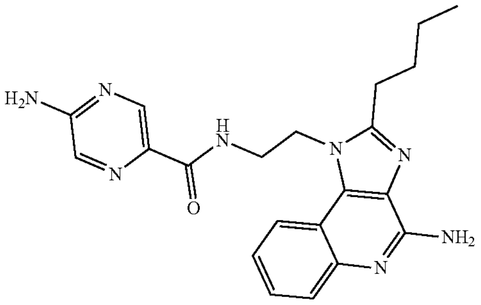 [SMILES: CCCCc1nc2c(N)nc3ccccc3c2n1CCNC(=O)c1cnc(N)cn1] Molecular Weight: 404.47 |
| 99 | AXC-809 | 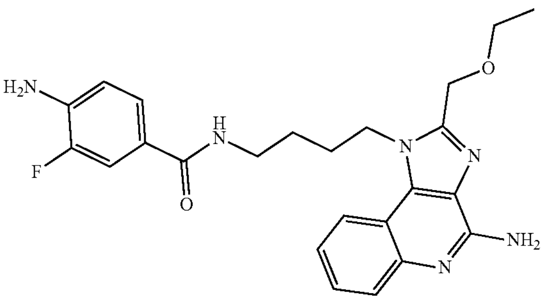 [SMILES: CCOCc1nc2c(N)nc3ccccc3c2n1CCCCNC(=O)c1ccc(N)c(F)c1] Molecular Weight: 450.51 |

TABLE 3-continued
| TLR Agonists - Core 1 Compounds | | |
|---|---|---|
| Compound No. | Compound Name | Structure - Core 1 Compounds |
| 100 | AXC-810 | 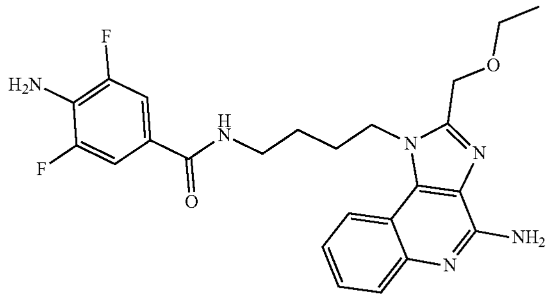 [SMILES: CCOCc1nc2c(N)nc3ccccc3c2n1CCCCNC(=O)c1cc(F)c(N)c(F)c1] Molecular Weight: 468.50 |
| 113 | AXC-831 | 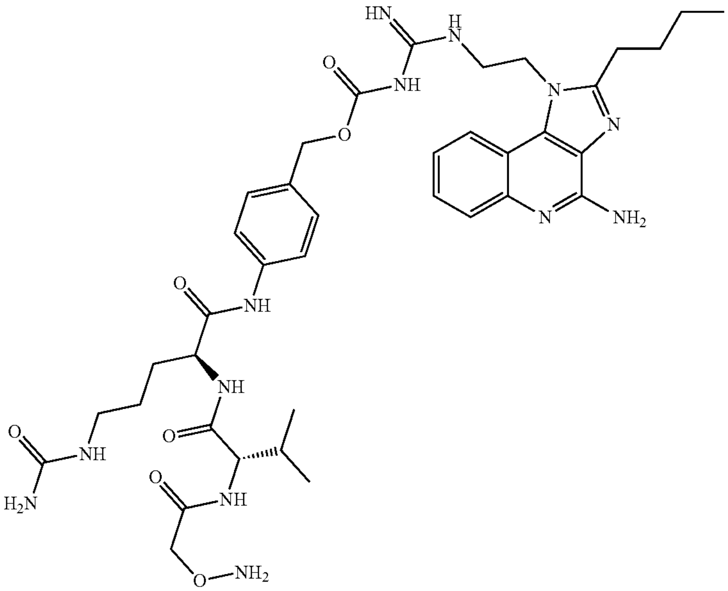 [SMILES: CCCCc1nc2c(N)nc3ccccc3c2n1CCNC(=N)NC(=O)OCc1ccc(NC(=O)[C@H](CCCNC(N)=O)NC(=O)[C@@H](NC(=O)CON)C(C)C)cc1] Molecular Weight: 803.93 |
| 192 | AXC-910 | 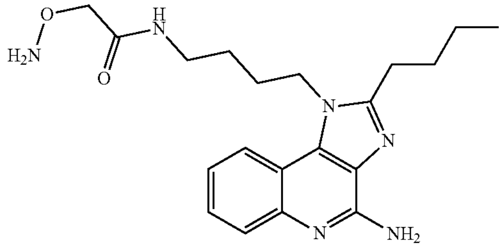 [SMILES: CCCCc1nc2c(N)nc3ccccc3c2n1CCCCNC(=O)CON] Molecular Weight: 384.5 |

Example 3: Synthesis of TLR Agonists Comprising the Following Representative Structures—Core 5 (FIG. 1)

Core 5

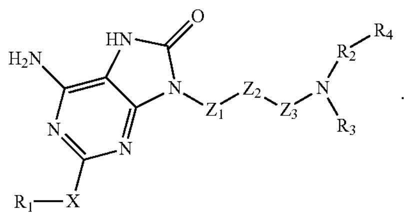

In some embodiments, X is O, S, NH or H;

$R_1$ is $C_1$ to $C_{12}$ alkyl, substituted $C_1$ to $C_{12}$ alkyl, oxygen containing $C_1$ to $C_{12}$ alkyl, heterocycle, substituted heterocycle, cycloalkyl, substituted cycloalkyl, —$N_3$, terminal $C_1$ to $C_{12}$ alkyl, terminal substituted $C_1$ to $C_{12}$ alkyl, or absent;

$R_2$ or $R_3$ is each connected to form $C_4$ to $C_8$ cycloalkyl or independently —H, $C_1$ to $C_{12}$ alkyl, nitro containing alkyl, oxygen containing alkyl or aryl;

$R_4$ is —$ONH_2$, terminal $C_1$ to $C_{12}$ alkyl, $C_1$ to $C_{12}$ alkyl, $C_1$ to $C_{12}$ substituted alkyl, $C_4$ to $C_8$ cycloalkyl, aromatic cycle, substituted aromatic cycle, aromatic heterocycle, substituted aromatic heterocycle or absent;

$Z_1$ is $C_1$ to $C_6$ alkyl, $C_3$ to $C_{10}$ cycloalkyl or $C_3$ to $C_{10}$ nitrogen containing heterocycle;

$Z_2$ is aromatic cycle, aromatic heterocycle, $C_2$ to $C_8$ cycloalkyl or absent;

$Z_3$ is $C_1$ to $C_{12}$ alkyl, substituted $C_1$ to $C_{12}$ alkyl, $C_3$ to $C_8$ cycloalkyl, substituted $C_3$ to $C_8$ cycloalkyl, substituted $C_3$ to $C_8$ nitro containing heterocycle, $C_3$ to $C_8$ nitro containing heterocycle or absent.

TLR-agonists having Core 5 structures were synthesized as disclosed in the schemes below.

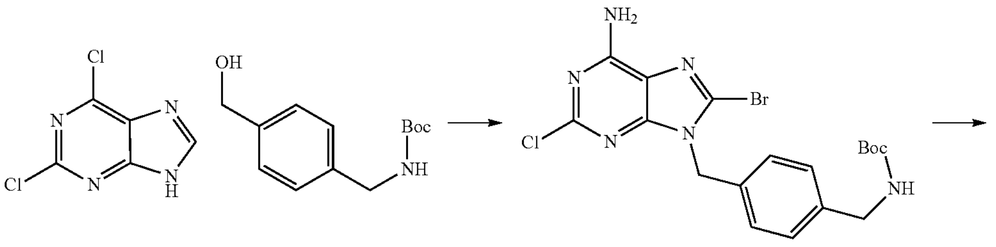

114

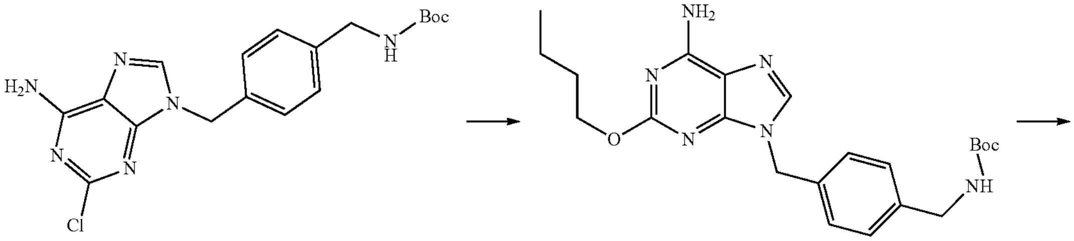

115 116

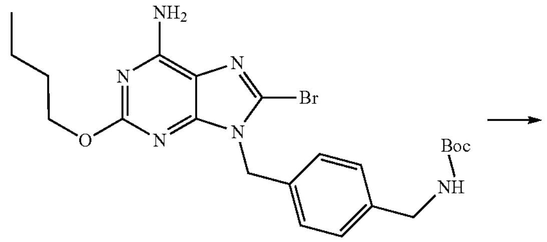

117

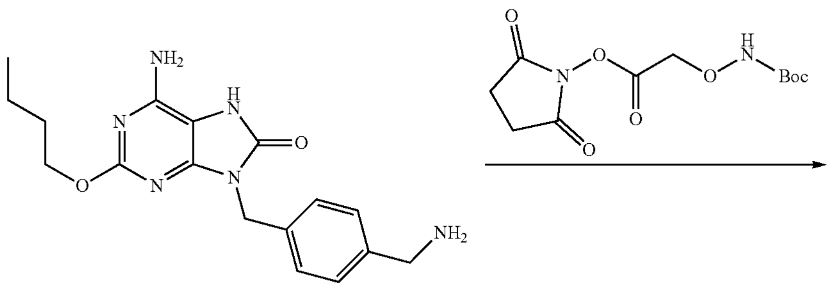

118

-continued

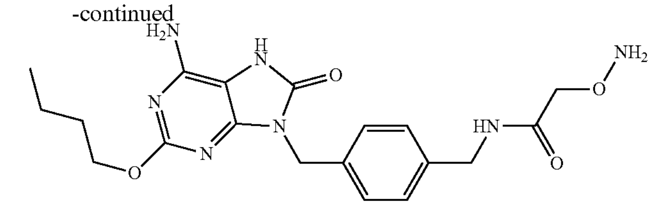

119 tert-butyl 4-((2,6-dichloro-9H1-purin-9-yl)methyl)benzylcarbamate, tert-butyl 4-((2,6-dichloro-7H-purin-7-yl) methyl)benzylcarbamate(114): To a solution of tert-butyl 4-(hydroxymethyl)benzylcarbamate (1280 mg, 5.394 mmol) and 2,6-dichloropurine (1050 mg, 5.556 mmol) in THE (10 mL) was added $PPh_3$ (1560 mg, 5.948 mmol) at 23° C. After 30 min, DIAD (1600 uL, 8.126 mmol) was added at 0° C. over 5 min. The mixture was stirred at 50° C. After 2 h, the solvent was removed in vacuo. The residue mixture was diluted by EtOAc (100 mL) and washed using half saturated sodium bicarbonate (100 mL) and brine (20 mL). The organic layer was dried with $MgSO_4$ and filtered. The solvent was removed in vacuo. The residue was purified by flash chromatography to obtain compound 114 (2268 mg, <5.555 mmol, crude mixture with $PPh_3$). MS m/z 409 $(M+H)^+$.

tert-butyl 4-((6-amino-2-chloro-9H-purin-9-yl)methyl) benzylcarbamate(115): Compound 114 (crude mixture of PPh3, 2268 mg, <5.555 mmol) was placed in a pressure resistant glass vessel equipped with a stirring bar. To this vessel was added 7N $NH_3$ in MeOH (12 mL, 84 mmol). The tube was sealed and heated at 120° C. After 1 h, the solvent was removed in vacuo, and the residue dissolved in DCM (100 mL). The precipitate was removed by filtration. The liquid was purified by flash chromatography to obtain compound 115 (1043 mg, 2.682 mmol, 50% from 2,6-dichloropurine). MS m/z 400 $(M+H)^+$.

tert-butyl 4-((6-amino-2-butoxy-9H-purin-9-yl)methyl) benzylcarbamate (116): Compound 115 (1043 mg, 2.682 mmol) was dissolved in 20% sodium n-butoxide (5 mL, 10.4 mmol) at 23° C. under dry nitrogen gas, and the temperature raised to 110° C. After 1.5 h, 1 ml of water was added to the mixture followed by Boc anhydride (170 mg, 0.779 mmol). After 5 min, the solvent was removed in vacuo. The residue was dissolved in DCM (30 ml), washed with half saturated sodium bicarbonate (50 ml) and brine (50 ml), dried with $MgSO_4$, and filtered. The organic solvent was removed in vacuo. The residue was purified by flash chromatography to obtain compound 116 (560 mg, 1.313 mmol, 49%). MS m/z 427 $(M+H)^+$.

tert-butyl 4-((6-amino-8-bromo-2-butoxy-9H-purin-9-yl) methyl)benzylcarbamate (117): To a solution of compound 116 (560 mg, 1.313 mmol) in DCM (10 mL) was added bromine (135 uL, 0.507 mmol) at 23° C. After 10 min, the reaction was dried in vacuo. The residue was dissolved in DCM (50 mL), washed with half saturated sodium bicarbonate (50 mL) and brine (50 mL), dried with $MgSO_4$ and filtered. The solvent was removed in vacuo. The residue was purified by flash chromatography to obtain compound 117 (440 mg, 0.871 mmol, 66%) as HBr salt MS m/z 506 $(M+H)^+$.

6-amino-9-(4-(aminomethyl)benzyl)-2-butoxy-7H-purin-8(9H)-one (118): Compound 117 (240 mg, 0.410 mmol) was dissolved in concentrated HCl solution, 37% (10 mL) and refluxed. After 4.5 h, the solvent was removed in vacuo. Water (10 mL) and MeOH (4 mL) were added to the residue, this was neutralized by adding $NH_3$, 28% solution (9 mL). The solvent was removed in vacuo. The residue was purified by Prep-LC to obtain compound 118 (11 mg, 0.019 mmol, 5%). MS m/z 343 $(M+H)^+$.

N-(4-((6-amino-2-butoxy-8-oxo-7H-purin-9(8H)-yl) methyl)benzyl)-2-(aminooxy)acetamide (119): To a solution of compound 118 (5 mg, 0.007 mmol) and 2,5-dioxopyrrolidin-1-yl 2-(tert-butoxycarbonylaminooxy)acetate (3 mg, 0.010 mmol) in DMF (1 mL) was added DIEA (5 uL, 0.057 mmol) at 23° C. After 10 min, the solvent was removed in vacuo. To the residue was added DCM (1 mL) and TFA (1 mL) at 23° C. After 10 min, the mixture was purified by Prep-LC to obtain compound 119 (3.6 mg, 0,005 mmol, 65%). MS m/z 416 $(M+H)^+$.

118 +

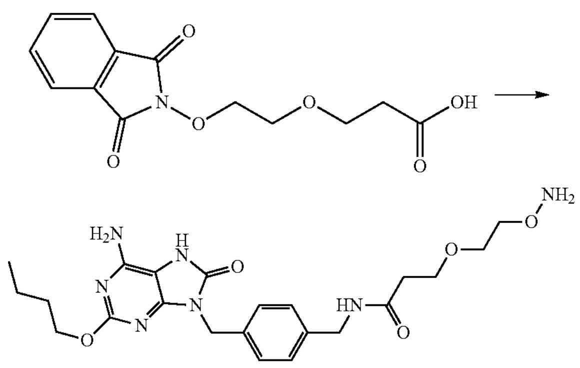

120

N-(4-((6-amino-2-butoxy-8-oxo-7H-purin-9(8H)-yl) methyl)benzyl)-3-(2-(aminooxy)ethoxy)propanamide (120): To a solution of 118 (5 mg, 0.007 mmol) and 3-(2-(1,3-dioxoisoindolin-2-yloxy)ethoxy)propanoic acid (3 mg, 0.011 mmol) in DMF (1 mL) was added DMTMMT (3 mg, 0.012 mmol) and DIEA (8 uL, 0.046 mmol) at 23° C. After 15 min, to the mixture was added hydrazine, $H_2O$ (3 uL, 0.06 mmol). After 20 min, the mixture was purified by Prep-LC to obtain compound 120 (3.5 mg, 0.004 mmol, 59%). MS m/z 474 $(M+H)^+$.

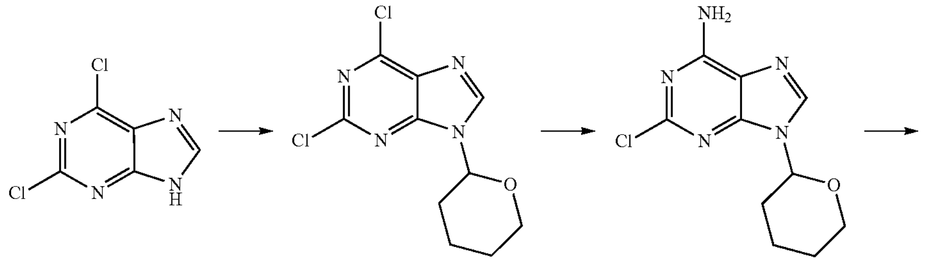

121 122

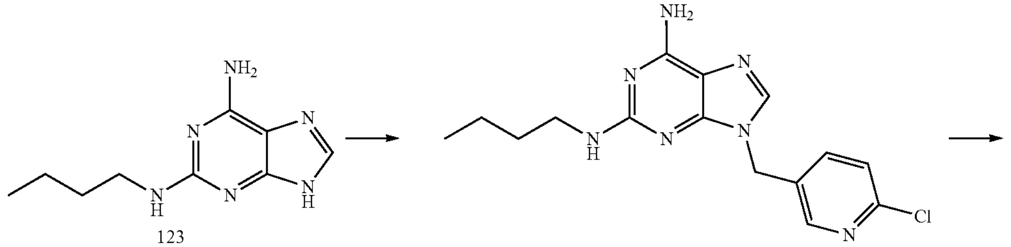

123 124

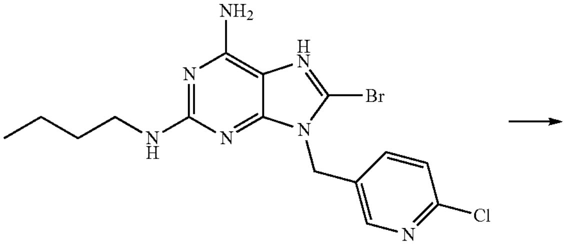

125

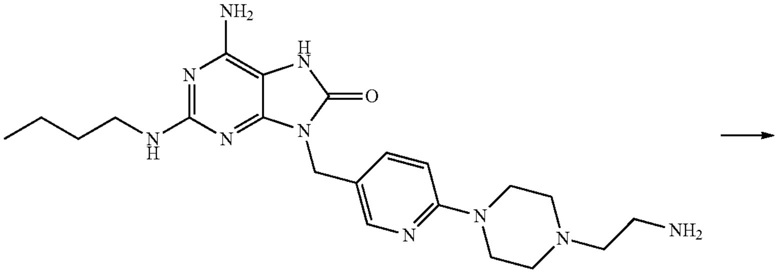

126

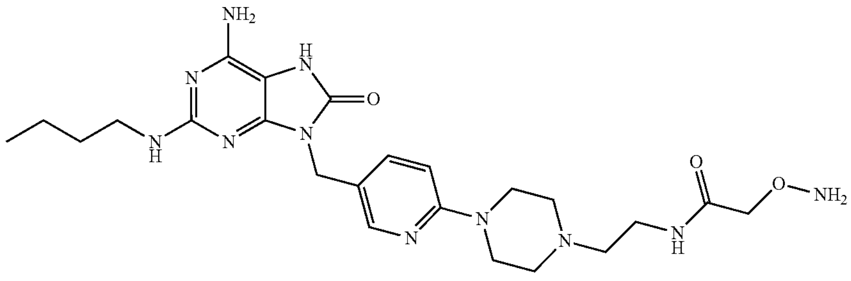

127

2,6-dichloro-9-(tetrahydro-2H-pyran-2-yl)-9H-purine (121): To a magnetically stirred solution of 2,6-dichloropurine (2950 mg, 15.608 mmol) in ethyl acetate (100 mL) was added benzenesulfonic acid (30 mg, 0.19 mmol), and the mixture was heated to 50° C. under dry nitrogen. To the stirred mixture was added 3,4-dihydro-2H-pyran (2200 uL, 26.153 mmol) over a period of 1 h at 50° C. The temperature was lowered to 23° C. After 1 h, the mixture was washed with half saturated $NaHCO_3$ (50 ml) and brine (50 ml), dried with $MgSO_4$ and filtered. The organic solvent was removed in vacuo, the residue was dried in high vacuum pump to obtain compound 121 (4170 mg, 15.269 mmol, 98%). MS m/z 274 $(M+H)^+$.

2-chloro-9-(tetrahydro-2H-pyran-2-yl)-9H-purin-6-amine (122): Compound 121 (4170 mg, 15.269 mmol) was placed in a pressure resistant glass vessel equipped with a stirring bar. To this vessel was added 7N $NH_3$ in MeOH (12.84 mmol). The tube was sealed and heated at 110° C.

After 3.5 h, the mixture was cooled to room temperature and allowed to stand overnight. The precipitate was filtered and washed with MeOH (5 mL). The solid was dried on high vacuum pump to obtain compound 122 (3450 mg, 13.6 mmol, 89%). MS m/z 254 $(M+H)^+$.

2-chloro-9-(tetrahydro-2H-pyran-2-yl)-9H-purin-6-amine (123): Compound 122 (1746 mg, 6,882 mmol) was placed in a pressure resistant glass vessel equipped with a stirring bar. To this vessel was added n-butylamine (7 mL, 70.86 mmol)) and DIEA (23 mL, 13.25 mmol). The tube was sealed and heated at 150° C. After 5 h, the mixture was cooled to room temperature and the solvent removed in vacuo. The residue was dissolved in DCM (100 mL), washed with water (30 mL) and brine (50 mL), dried with $MgSO_4$ and filtered. The organic solvent was removed in vacuo. The residue (intermediate) was dissolved in MeOH (10 mL) and TFA (2 mL), and stirred overnight at 23° C. After 18 h, the solvent was removed in vacuo. To the residue was added EtOAc (10 mL) and Hexane (50 mL) to precipitate. The precipitate was collected by filtration and drying in a vacuum pump to obtain compound 123 (1640 mg, 3.777 mmol, 55%) as 2 TFA salt. MS m/z 207 $(M+H)^+$.

N2-butyl-9-((6-chloropyridin-3-yl)methyl)-9H-purine-2,6-diamine (124): To a solution of compound 123 (1640 mg, 3.777 mmol) and 2-chloro-5-(chloromethyl)pyridine (900 mg, 5.556 mmol) in DMF (5 mL) was added $K_2CO_3$ (2600 mg, 18.813 mmol), and the mixture was stirred at 50° C. under nitrogen gas. After 24 h, iced water (100 mL) was added to the mixture, and the precipitate was separated. The precipitate was dissolved in DCM (100 mL), washed with brine (50 mL), dried with $MgSO_4$ and filtered. The organic solvent was removed in vacuo. The residue was purified by flash chromatograph (silica gel) with 1% to 10% MeOH/DCM gradient to obtain compound 124 (1020 mg, 3.074 mmol, 81%). MS m/z 332 $(M+H)^+$.

6-amino-2-(butylamino)-9-((6-chloropyridin-3-yl)methyl)-7H-purin-8(9H)-one (125): To a solution of compound 124 (1020 mg, 3.074 mmol) in DCM (10 mL) was added bromine (250 uL, 0.939 mmol) at 23° C. After 1.5 h, the solvent was removed in vacuo. The residue was dried on high vacuum pump. The crude intermediate of 8-bromo-N2-butyl-9-((6-chloropyridin-3-yl)methyl)-9H-purine-2,6-diamine, HBr (1500 mg, <3.074 mmol) was dissolved in concentrated HCl solution, 37% (15 mL), and the solution refluxed. After 8 h, the solvent was removed in vacuo. To the residue was added water (10 mL) and MeOH (4 mL), and then neutralized by adding NHL, 28% solution (5 mL). The precipitated solid was separated by centrifuge (5 min, 4000 rpm), and washed with MeOH (2 mL) and water (10 mL). The precipitate was dried to obtain compound 125 (1100 mg, 2,421 mmol, 79%). MS m/z 348 $(M+H)^+$.

6-amino-9-((6-(4-(2-aminoethyl)piperazin-1-yl)pyridin-3-yl)methyl)-2-(butylamino)-7H-purin-8(9H)-one (126): The mixture of compound 125 (30 mg, 0.086 mmol) and tert-butyl 2-(piperazin-1-yl)ethylcarbamate (26 mg, 0.113 mmol) was heated at 140° C. After 20 h, the mixture was cooled to 23° C. To the residue was added DCM (0.5 mL) and TFA (0.5 mL). After 30 min. the solvent was removed in vacuo and the residue was purified by Prep-LC to obtain compound 126 (9 mg, 0.010 mmol, 12%) as TFA salt. MS m/z 441 $(M+H)^+$.

N-(2-(4-(5-((6-amino-2-(butylamino)-8-oxo-7H-purin-9(8H)-yl)methyl)pyridin-2-yl)piperazin-1-yl)ethyl)-2-(aminooxy)acetamide (127): To a solution of compound 126 (9 mg, 0.010 mmol) and 2,5-dioxopyrrolidin-1-yl 2-(tert-butoxycarbonylaminooxy)acetate (2.5 mg, 0.011 mmol) in DMF (1 mL) was added DIEA (10 uL, 0.060 mmol) at 23° C. After 15 min, the solvent was removed in vacuo. To the residue was added DCM (1 mL) and TFA (1 mL). After 5 min, the solvent was removed in vacuo. The residue was purified by Prep-LC to obtain compound 127 (8 mg, 0.008 mmol, 82%) as TFA salt. MS m/z 514 $(M+H)^+$.

126

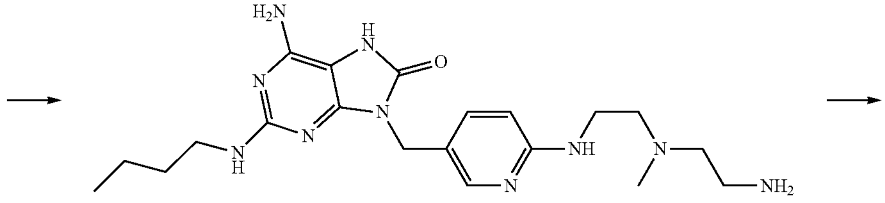

128

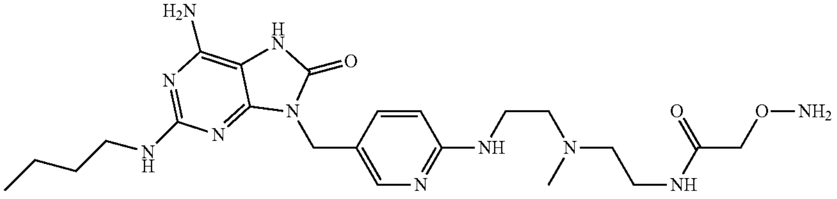

129

6-amino-9-((6-(2-((2-aminoethyl)(methyl)amino)ethylamino)pyridin-3-yl)methyl)-2-(butylamino)-7H-purin-8(9H)-one (128): The mixture of compound 125 (30 mg, 0.086 mmol) and 2,2'diamino-N-methyldiethylamine (100 uL, 0.853 mmol) was heated at 130° C. After 20 h, the mixture was cooled to 23° C., and purified by Prep-LC to obtain compound 128 (40 mg, 0.045 mmol, 52%). MS m/z 423 $(M+H)^+$.

N-(2-((2-(5-((6-amino-2-(butylamino)-8-oxo-7H-purin-9(8H)-yl)methyl)pyridin-2-ylamino)ethyl)(methyl)amino)ethyl)-2-(aminooxy)acetamide (129): Compound 129 was prepared using compound 128 as starting material, with similar procedure as described for 127 to obtain target compound 129 (13 mg, 0.012 mmol, 54%). MS m/z 502 $(M+H)^+$.

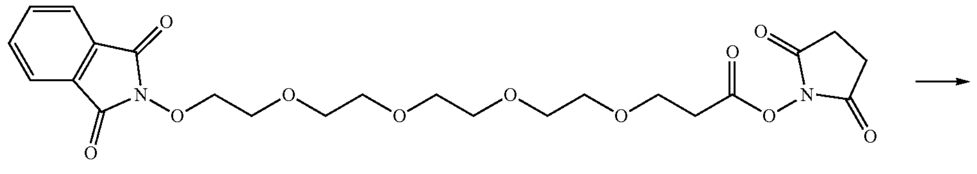

128

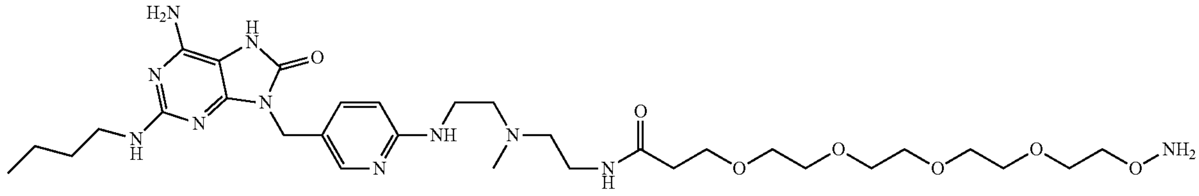

130

NH2O-PEG3-Pr-(6-amino-9-((6-(2-((2-aminoethyl)(methyl)amino)ethylamino)pyridin-3-yl)methyl)-2-(butylamino)-7H-purin-8(9H)-one)acetamide (130): To a solution of compound 128 (20 mg, 0.023 mmol) and Phth-PEG4-OSu (10 mg, 0.022 mmol) in DMF (1 mL) was added DIEA (50 uL, 0.287 mmol) at 23° C. After 5 min, hydrazine, $H_2O$ (10 uL) at 23° C. was added to the mixture. After 5 min, the mixture was purified by Prep-LC to obtain compound 130 (20 mg, 0.016 mmol, 70%). MS m/z 692 $(M+H)^+$.

125

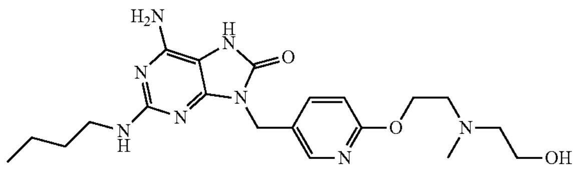

131

6-amino-2-(butylamino)-9-((6-(2-((2-hydroxyethyl)(methyl)amino)ethoxy)pyridin-3-yl)methyl)-7H-purin-8(9H)-one (131): To a solution of compound 125 (124 mg, 0.215 mmol) in DMF (4 mL) was added N-Methyldiethanolamine (200 uL, 1.007 mmol) and NaI, 60% (350 mg, 8.750 mmol) at 23° C. The mixture was stirred at 60° C. under dry nitrogen. After 3 h, 1N HCl (4 mL) was added to the mixture and purified by Prep LC with to obtain compound 131 (75 mg, 0.085 mmol, 39%). MS m/z 431 $(M+H)^+$.

122

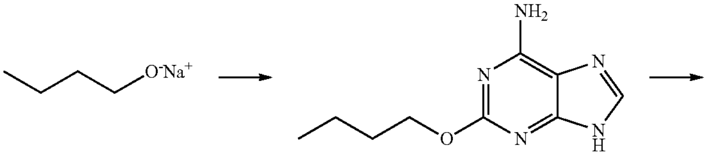

132

-continued

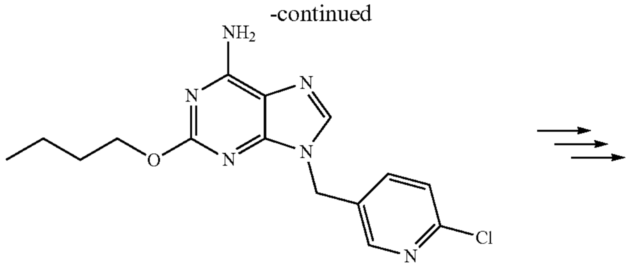

133

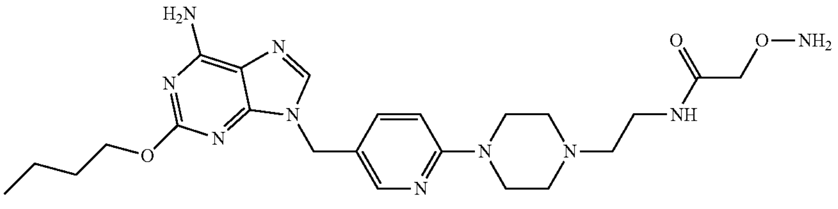

134

2-butoxy-9H-purin-6-amine (132): Compound 122 (690 mg, 2.720 mmol) was dissolved in 20% sodium n-butoxide (8 mL, 16.71 mmol) at 23° C. under dry nitrogen gas. After addition, the temperature was raised to 100° C. After 20 h, the solvent was removed in vacuo. The residue was dissolved in DCM (30 mL), washed with half saturated sodium bicarbonate (50 mL) and brine (50 mL), dried with $MgSO_4$ and filtered. The organic solvent was removed in vacuo. MeOH (5 mL) and TFA (1 mL) were added to the residue and stirred at 23° C. After 18 h, the solvent was removed in vacuo. The residue was dissolved in DCM (30 ml), washed with sodium bicarbonate (50 mL) and brine (50 mL), dried with $MgSO_4$ and filtered. The organic solvent was removed in vacuo to obtain 2-butoxy-9H-purin-6-amine (1300 mg, 2.987, quant) as crude. MS m/z 208 $(M+H)^+$.

N2-butyl-9-((6-chloropyridin-3-yl)methyl)-9H-purine-2,6-diamine (133): Compound 133 was prepared using compound 132 as starting material, with similar procedure as described for 124 to obtain target compound 133 (468 mg, 1.406 mmol, 47%). MS m/z 333 $(M+H)^+$.

N-(2-(4-(5-((6-amino-2-butoxy-9H-purin-9-yl)methyl)pyridin-2-yl)piperazin-1-yl)ethyl)-2-(aminooxy)acetamide (134): Compound 134 was prepared using compound 133 as starting material, with similar procedure as described for 127 to obtain target compound 134 (12 mg, 0.012 mmol, 10% from compound 133). MS m/z 514 $(M+H)^+$.

133

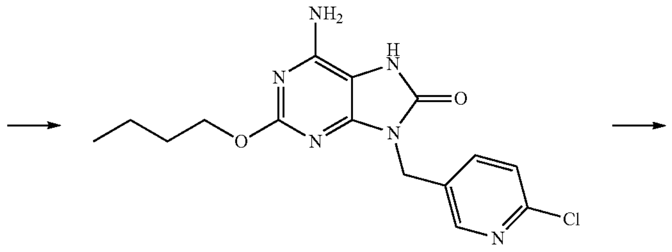

135

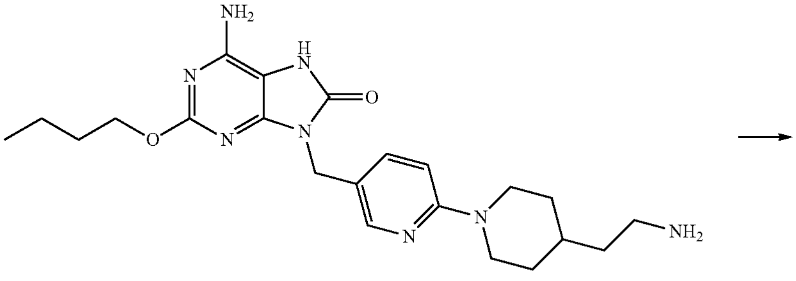

136

-continued

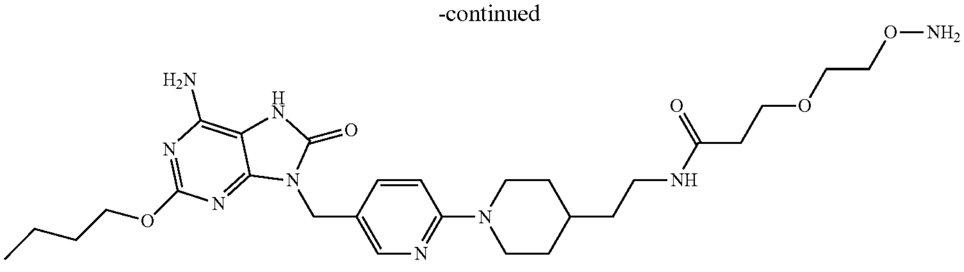

137

6-amino-2-butoxy-9-((6-chloropyridin-3-yl)methyl)-7H-purin-8(9H)-one (135): To a solution of compound 133 (124 mg, 0.373 mmol) in DCM (10 mL) was added bromine (30 uL, 0.113 mmol) at 23° C. After 2 h, the reaction was dried in vacuo. The crude residue of 8-bromo-2-butoxy-9-((6-chloropyridin-3-yl)methyl)-9H-purin-6-amine, HBr (150 mg, <0.373 mmol, crude) was dissolved in 3N HCl solution (15 mL) and refluxed. After 20 h, the solvent was removed in vacuo. The mixture was purified by Prep-LC to obtain compound 135 (47 mg, 0.110 mmol, 29%). MS m/z 349 $(M+H)^+$.

6-amino-9-((6-(4-(2-aminoethyl)piperidin-1-yl)pyridin-3-yl)methyl)-2-butoxy-7H-purin-8(9H)-one (136): Compound 135 (46 mg, 0.132 mmol) and 4-(2-boc-aminoethyl)-piperidine (120 mg, 0.526 mmol) was mixed, and the mixture stirred at 140° C. After 25 h, to the mixture was added DCM (1 mL) and TFA (1 mL) after cooling to 23° C. After 10 min, the organic solvent was removed in vacuo. The mixture was purified by Prep-LC to obtain compound 136 (11 mg, 0.014 mmol, 11%). MS m/z 441 $(M+H)^+$.

N-(2-(1-(5-((6-amino-2-butoxy-8-oxo-7H-purin-9(8H)-yl)methyl)pyridin-2-yl)piperidin-4-yl)ethyl)-3-(2-(aminooxy)ethoxy)propanamide (137): Compound 137 was prepared using compound 136 and 3-(2-(1,3-dioxoisoindolin-2-yloxy)ethoxy)propanoic acid as starting materials, with similar procedure as described for 130 to obtain target compound 137 (9 mg, 0.010 mmol, 70%). MS m/z 572 $(M+H)^+$.

122

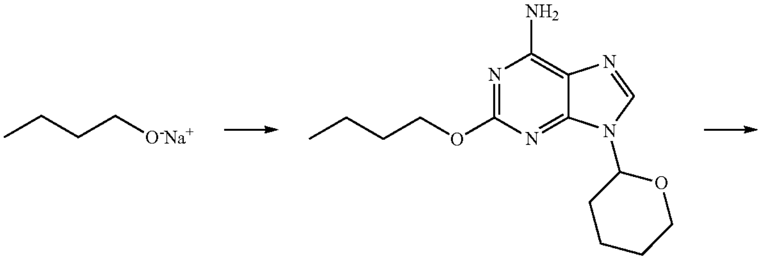

138

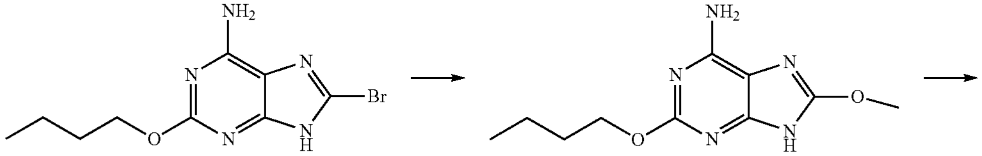

139 140

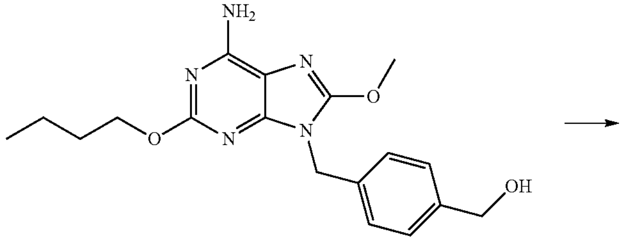

141

-continued

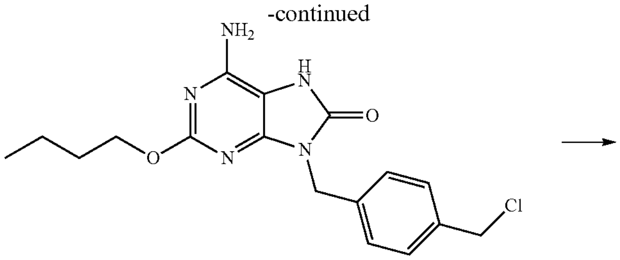

142

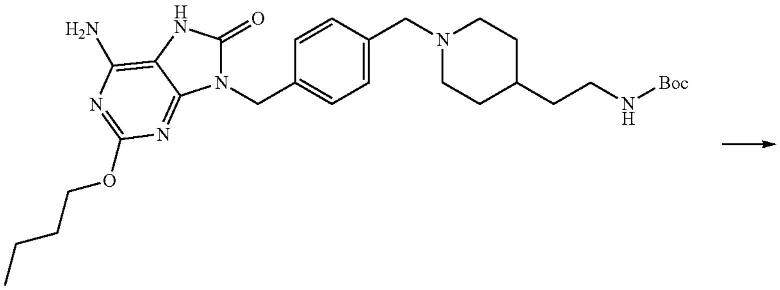

143

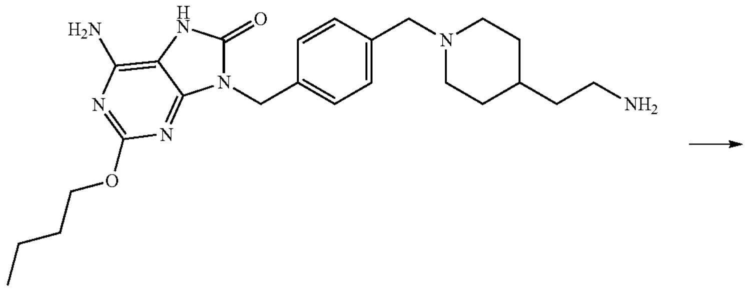

144

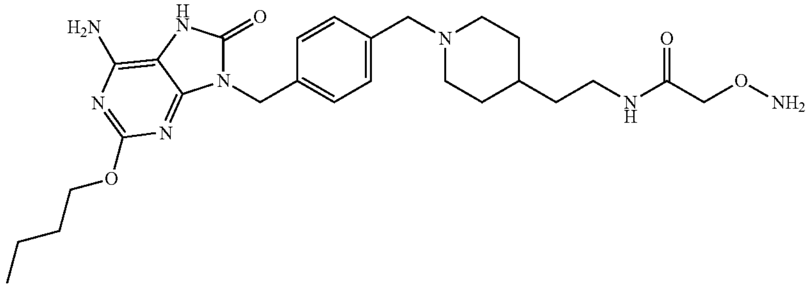

145

9-(4-(2-aminoethyl)benzyl)-2-butoxy-9H-purin-6-amine (138): Compound 122 (3330 mg, 13.126 mmol) was dissolved in 20% sodium n-butoxide (25 mL) at 23° C. under dry nitrogen gas and the temperature was raised to 100° C. After 1.5 h, the solvent was removed in vacuo. The residue was dissolved in DCM (30 mL), washed with half saturated sodium bicarbonate (50 mL) and brine (50 mL), dried with $MgSO_4$ and filtered. The organic solvent was removed in vacuo. The residue was purified by flash chromatography with 1% to 4% of MeOH/DCM gradient to obtain compound 138 (2687 mg, 9.224 mmol, 70%). MS m/z 292 $(M+H)^+$.

8-bromo-2-butoxy-9-(tetrahydro-2H-pyran-2-yl)-9H-purin-6-amine (139): To a solution of compound 138 (2687 mg, 9224 mmol) in DCM (50 ml) was added N-bromosuccinimide (2000 mg, 11069 mmol) at 23° C. After 1 h, saturated sodium thiosulfate (20 mL), was added to the mixture. The material was extracted with DCM (20 ml). The organic layer was washed with saturated sodium bicarbonate (50 mL) and brine (50 mL), dried with $MgSO_4$ and filtered. The organic solvent was removed in vacuo. The residue was purified by flash chromatography with 20% to 70% of EtOAc/Hexane gradient to obtain compound 139 (2517 mg, 6.799 mmol, 74%). MS m/z 371 $(M+H)^+$.

2-butoxy-8-methoxy-9H-purin-6-amine (140): Compound 139 (2517 mg, 6.799 mmol) was dissolved in 25% sodium methoxide (20 mL, 42 mmol) at 23° C. under dry nitrogen gas. After addition, the temperature was raised to 70° C. After 2.5 h, the mixture was concentrated in vacuo, dissolved in EtOAc (100 mL), washed with water (100 mL) and brine (100 mL), dried with $MgSO_4$ and filtered. The organic layer was collected and evaporated in vacuo. To the residue was added MeOH (10 mL) and TFA (3 mL). After 48 h of TFA addition, the solvent was removed in vacuo. The mixture was purified by Prep-LC to obtain compound 140 (708 mg, 2.984, 44%). MS m/z 238 $(M+H)^+$.

(4-((6-amino-2-(butylamino)-8-methoxy-9H-purin-9-yl) methyl)phenyl)methanol (141): To a solution of compound 140, TFA salt (25 mg, 0.054 mmol) in DMF (2 mL), potassium carbonate (20 mg, 0.524 mmol) and (4-hydroxymethyl)benzyl chloride (11 mg, 0.070 mmol) were added and stirred at 50° C. After 2 h, the solvent was concentrated. To the residue was added water, and then the mixture was extracted with DCM (50 mL). The organic layer was washed with water (10 mL) and brine (20 mL), followed by drying over $MgSO_4$ and filtration. The solvent was removed in vacuo. The mixture was purified by Prep-LC to obtain compound 141 (29 mg, 0.042 mmol, 77%) as TFA salt. MS m/z 357 $(M+H)^+$.

6-amino-2-butoxy-9-(4-(chloromethyl)benzyl)-7H-purin-8(9H)-one (142): To compound 141 (607 mg, 1.037 mmol), dichloromethane (10 mL) was added. To the resulting suspension thionyl chloride (1000 uL) was added and the mixture stirred at 5° C. for 3 hours. Toluene (30 mL) was added to the mixture and the solvent was evaporated. Toluene (100 mL) was again added to the residue, the solvent was evaporated and dried under reduced pressure to obtain compound 142 (402 mg, 1.111 mmol, quant). MS m/z 362 $(M+H)^+$.

tert-butyl 2-(1-(4-((6-amino-2-butoxy-8-oxo-7H-purin-9(8H)-yl)methyl)benzyl)piperidin-4-yl)ethylcarbamate (143): To a solution of compound 142 (166 mg, 0.384 mmol) and 4-(2-boc-aminoethyl)-piperidine (180 mg, 0.788 mmol) in DMF (2 mL) was added DIEA (1000 uL, 5.741 mmol), and the temperature raised to 80° C. After 3.5 h, the solvent was removed in vacuo. The mixture was purified by Prep-LC to obtain compound 143 (205 mg, 0.229 mmol, 29%). MS m/z 554 $(M+H)^+$.

6-amino-9-(4-((4-(2-aminoethyl)piperidin-1-yl)methyl) benzyl)-2-butoxy-7H-purin-8(9H)-one (144): Compound 143 (41 mg, 0.052 mmol) was dissolved in DCM (2 mL) and TFA (1 mL). After 5 min, the solvent was removed in vacuo. Toluene (5 ml) was added to the residue and evaporated in vacuo. The residue was dried on high vacuum pump to obtain compound 144 (41 mg, 0.052 mmol, quant) as TFA salt. MS m/z 454 $(M+H)^+$.

N-(2-(1-(4-((6-amino-2-butoxy-8-oxo-7H-purin-9(8H)-yl)methyl)benzyl)piperidin-4-yl)ethyl)-2-(aminooxy)acetamide (145): Compound 145 was prepared using compound 144 as starting material, with similar procedure as described for 127 to obtain target compound 145 (15 mg, 0.015 mmol, 87%). MS m/z 527 $(M+H)^+$.

144

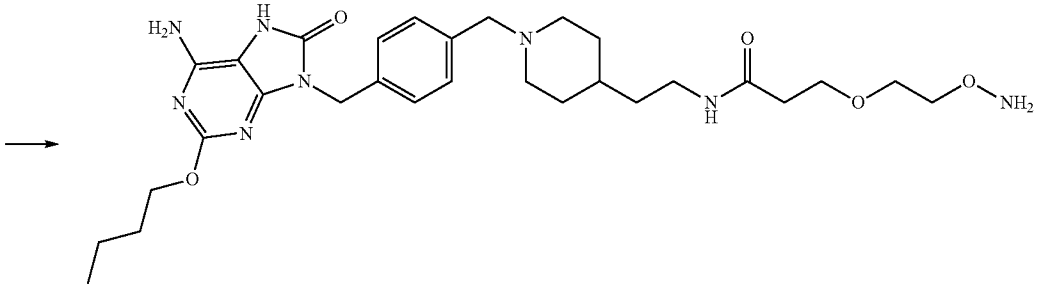

146

N-(2-(1-(4-((6-amino-2-butoxy-8-oxo-7H-purin-9(8H)-yl)methyl)benzyl)piperidin-4-yl)ethyl)-3-(2-(aminooxy) ethoxy)propenamide (146): Compound 146 was prepared using compound 144 as starting material, with similar procedure as described for 137 to obtain target compound 146 (16 mg, 0.015 mmol, 87%). MS m/z 585 $(M+H)^+$.

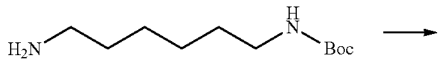

142

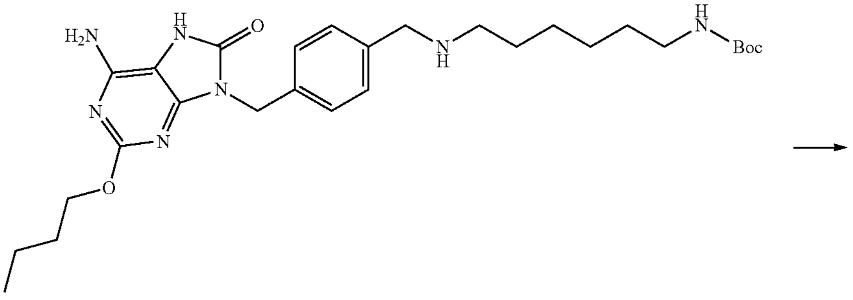

147

-continued

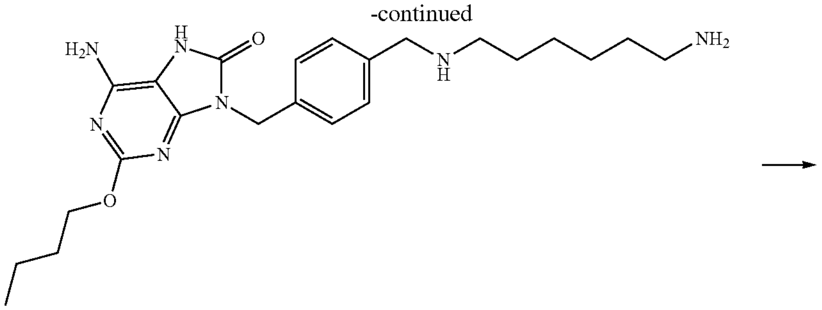

148

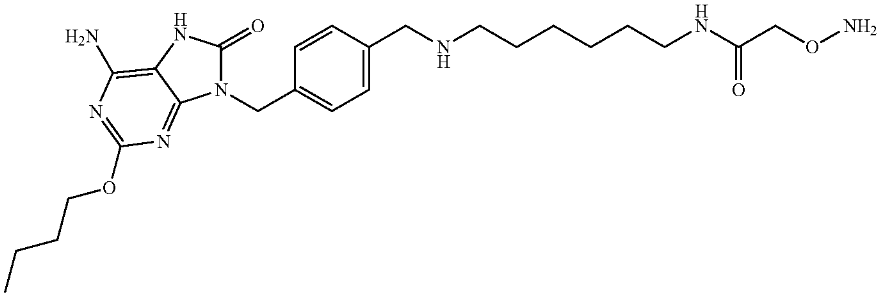

149 tert-butyl 2-(1-(4-((6-amino-2-butoxy-8-oxo-7H-purin-9 (8H)-yl)methyl)benzyl)piperidin-4-yl)ethylcarbamate (147): Compound 147 was prepared using compound 142 and tert-butyl 6-aminohexylcarbamate as starting materials, with similar procedure as described for 143 to obtain target compound 147 (23 mg, 0.026 mmol, 14%). MS m/z 542 $(M+H)^+$.

6-amino-9-(4-((6-aminohexylamino)methyl)benzyl)-2-butoxy-7H-purin-8(9H)-one (148): Compound 148 was prepared using compound 147 as starting material, with similar procedure as described for 144 to obtain target compound 148 (24 mg, 0.027 mmol, quant). MS m/z 442 $(M+H)^+$.

N-(6-(4-((6-amino-2-butoxy-8-oxo-7H-purin-9(8H)-yl) methyl)benzylamino)hexyl)-2-(aminooxy)acetamide (149): Compound 149 was prepared using compound 148 as starting material, with similar procedure as described for 127 to obtain target compound 149 (7 mg, 0.008 mmol, 31%). MS m/z 515 $(M+H)^+$.

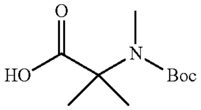

144

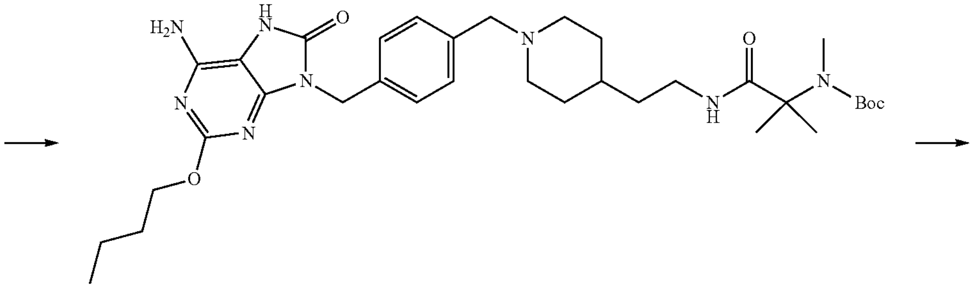

150

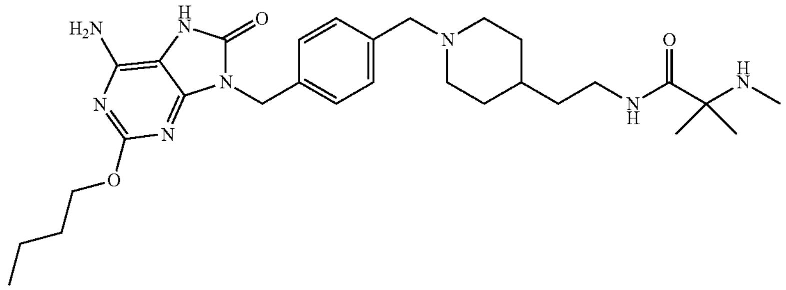

151

N-(2-(1-(4-((6-amino-2-butoxy-8-oxo-7H-purin-9(8H)-yl)methyl)benzyl)piperidin-4-yl)ethyl)-3-(2-(aminooxy)ethoxy)propanamide (150): To a solution of compound 144 (14 mg, 0.018 mmol) and N-Boc-N,2-dimethyl-alanine (5.5 mg, 0.020 mmol) in DMF (1 mL) was added DMTMMT (5 mg, 0.021 mmol) and DIEA (20 uL, 0.115 mmol) at 23° C. After 30 min, the mixture was purified by Prep-LC to obtain compound 150 (7 mg, 0.007 mmol, 37%). MS m/z 653 $(M+H)^+$.

N-(2-(1-(4-((6-amino-2-butoxy-8-oxo-7H-purin-9(8H)-yl)methyl)benzyl)piperidin-4-yl)ethyl)-2-methyl-2-(methylamino)propanamide (151): Compound 151 was prepared using compound 150 as starting material, with similar procedure as described for 144 to obtain target compound 151 (5.5 mg, 0.005 mmol, quant). MS m/z 553 $(M+H)^+$.

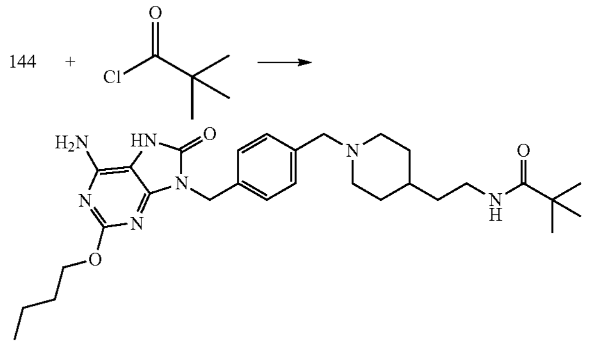

152

N-(2-(1-(4-((6-amino-2-butoxy-8-oxo-71-purin-9(8H)-yl)methyl)benzyl)piperidin-4-yl)ethyl)pivalamide (152): To a solution of compound 144 (14 mg, 0.018 mmol) and Trimethyl acetyl chloride (2.8 ul, 0.022 mmol) in DMF (1 mL) was added DIEA (20 uL, 0.115 mmol) at 23° C. After 1 h, the mixture was purified by Prep-LC to obtain compound 152 (7 mg, 0.008 mmol, 36%). MS m/z 538 $(M+H)^+$.

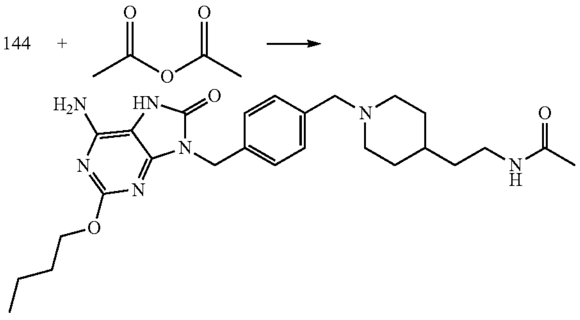

153

N-(2-(1-(4-((6-amino-2-butoxy-8-oxo-7H-purin-9(8H)-yl)methyl)benzyl)piperidin-4-yl)ethyl)acetamide (153): To a solution of compound 144 (20 mg, 0.022 mmol) and Acetic anhydride (2.1 uL, 0,021 mmol) in DMF (1 mL) was added DIEA (20 uL, 0.115 mmol) at 23° C. After 1 h, the mixture was purified by Prep-LC to obtain compound 153 (8 mg, 0.010 mmol, 43%). MS m/z 496 $(M+H)^+$.

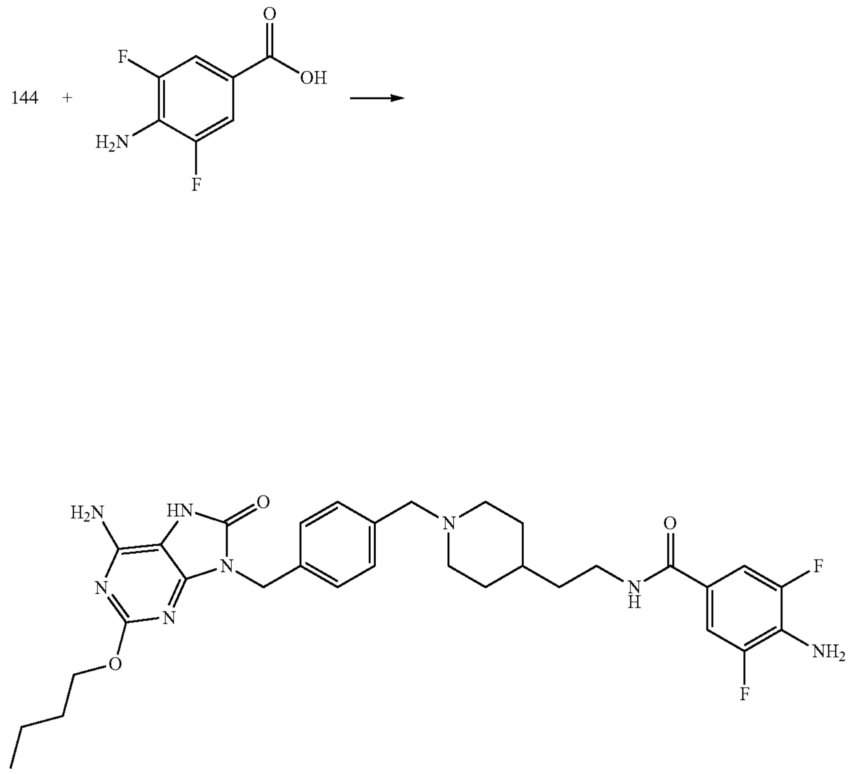

154

4-amino-N-(2-(1-(4-((6-amino-2-butoxy-8-oxo-7H-purin-9(8H)-yl)methyl)benzyl)piperidin-4-yl)ethyl)-3,5-difluorobenzamide (154): Compound 154 was prepared using compound 144 and 4-amino-3,5-difluoro benzoic acid as starting materials, with similar procedure as described for 150 to obtain target compound 154 (8 mg, 0.008 mmol, 38%). MS m/z 609 (M+H)+.

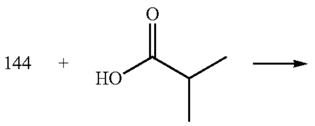

-continued

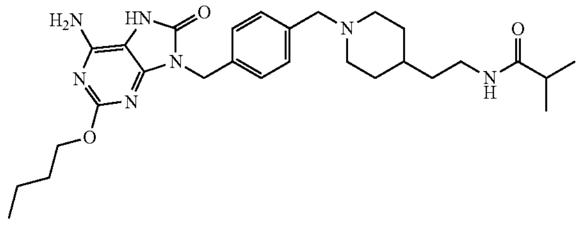

155

N-(2-(1-(4-((6-amino-2-butoxy-8-oxo-7H-purin-9(8H)-yl)methyl)benzyl)piperidin-4-yl)ethyl)isobutyramide (155): Compound 155 was prepared using compound 144 and isobutyric acid as starting materials, with similar procedure as described for 150 to obtain compound 155 (6 mg, 0,007 mmol, 32%). MS m/z 524 (M+H)+.

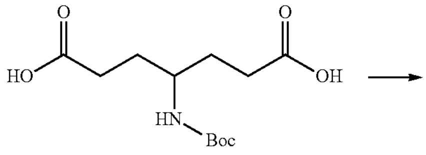

144

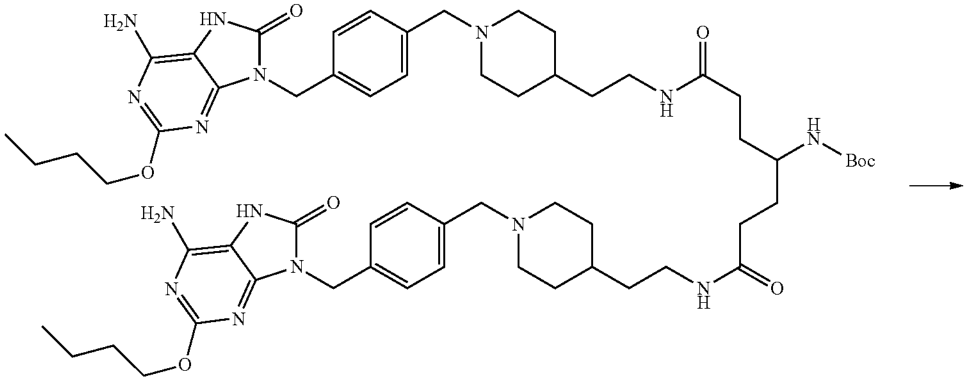

166

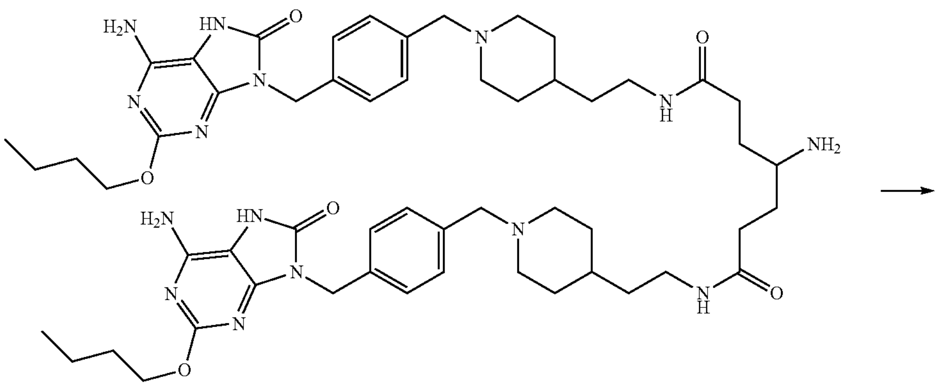

167

-continued

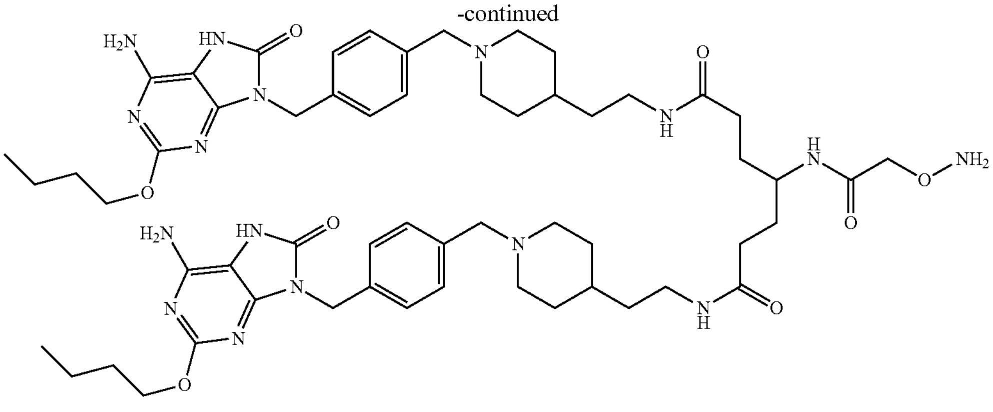

158 tert-butyl 1,7-bis(2-(1-(4-((6-amino-2-butoxy-8-oxo-7H-purin-9(8H)-yl)methyl)benzyl)piperidin-4-yl)ethylamino)-1,7-dioxoheptan-4-ylcarbamate (156): Compound 156 was prepared using compound 144 and 4-(N-Boc-amino)-1,6-heptanedioic acid as starting materials, with similar procedure as described for 150 to obtain target compound 156 (15 mg, 0.009 mmol, 34%). MS m/z 1147 $(M+H)^+$.

4-amino-N1,N7-bis(2-(1-(4-((6-amino-2-butoxy-8-oxo-7H-purin-9(8H)-yl)methyl)benzyl)piperidin-4-yl)ethyl)heptanediamide (157): Compound 157 was prepared using compound 156 as starting material, with similar procedure as described for 144 to obtain target compound 157 (15 mg, 0.01 mmol, quant). MS m/z 1047 $(M+H)^+$.

N1,N7-bis(2-(1-(4-((6-amino-2-butoxy-8-oxo-7H-purin-9(8H)-yl)methyl)benzyl)piperidin-4-yl)ethyl)-4-(2-(aminooxy)acetamido)heptanediamide (158): Compound 158 was prepared using compound 157 and 2,5-dioxopyrrolidin-1-yl 2-(tert-butoxycarbonylaminooxy)acetate as starting materials, with similar procedure as described for 145 to obtain target compound 158 (5 mg, 0.003 mmol, 34%). MS m/z 1120 $(M+H)^+$.

144

+

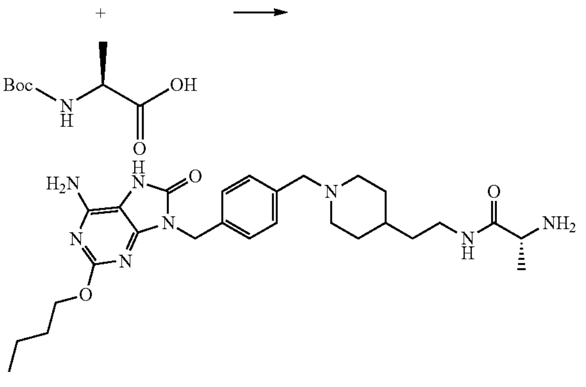

173

(S)-2-amino-N-(2-(1-(4-((6-amino-2-butoxy-8-oxo-7H-purin-9(8H)-yl)methyl)benzyl)piperidin-4-yl)ethyl)propanamide (173): To a solution of compound 144 (20 mg, 0.022 mmol) and N-Boc-alanine (5 mg, 0.026 mmol) in DMF (1 mL) was added DMTMMT (6 mg, 0,025 mmol) and DIEA (20 uL, 0.115 mmol) at 23° C. After 10 min, the solvent was removed in vacuo. To the residue was added DCM (1 ml) and TFA (1 ml). After 10 min, the solvent was removed in vacuo, and the residue purified by Prep-LC to obtain compound 173 (8 mg, 0.009 mmol, 42%). MS m/z 525 $(M+H)^+$.

144 +

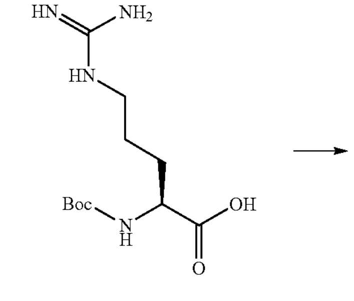

-continued
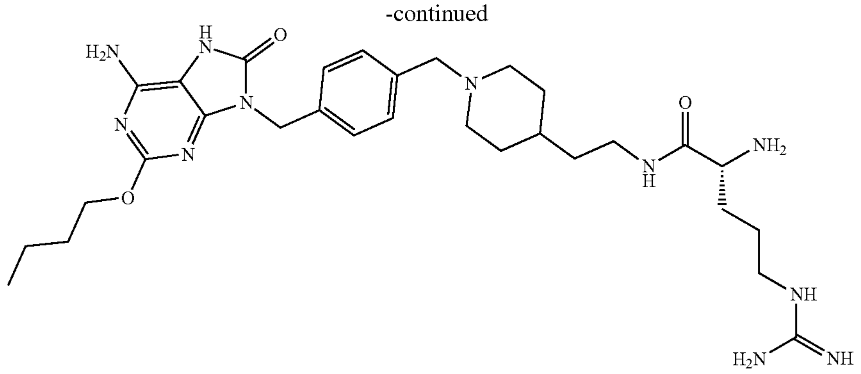
174
(S)-2-amino-N-(2-(1-(4-((6-amino-2-butoxy-8-oxo-7H-purin-9(8H)-yl)methyl)benzyl)piperidin-4-yl)ethyl)-5-guanidinopentanamide (174): Compound 174 was prepared using compound 144 and N-Boc-Arginine as starting materials, with similar procedure as described for 173 to obtain target compound 174 (10 mg, 0.011 mmol, 48%). MS m/z 610 $(M+H)^+$.
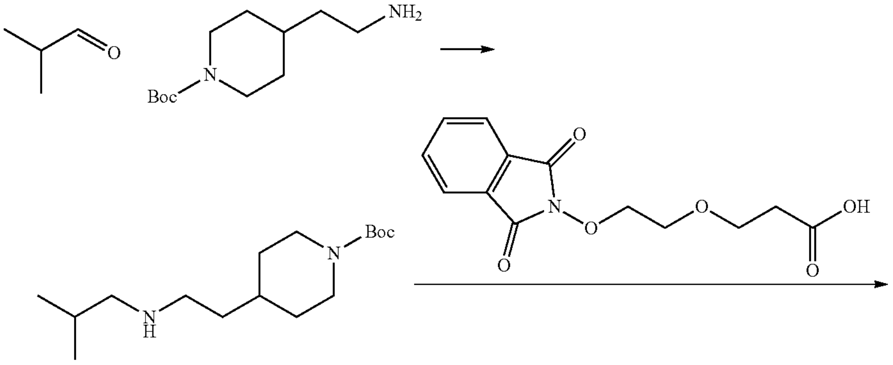
175
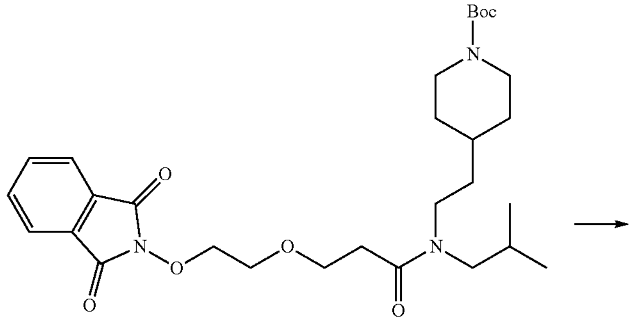
176
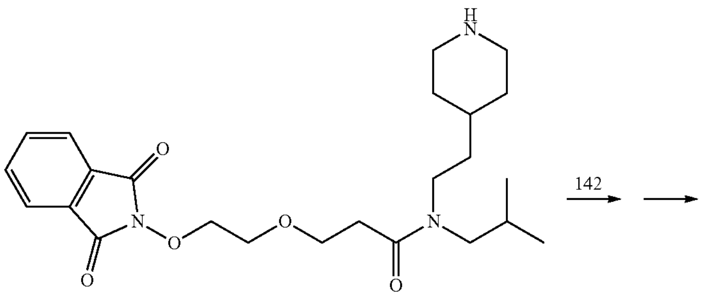
177

-continued

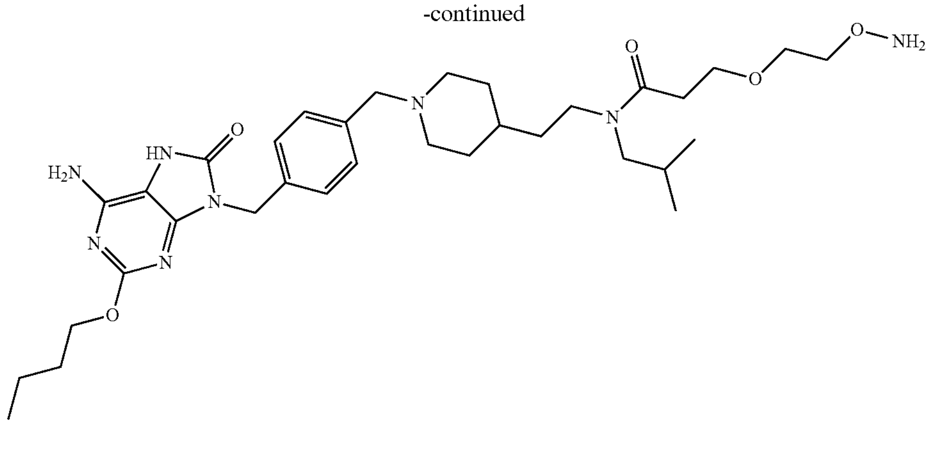

178 tert-butyl 4-(2-(isobutylamino)ethyl)piperidine-1-carboxylate (175): 4-(2-aminoethyl)-1-Boc-piperidine (520 mg, 2.278 mmol) and isobutyraldehyde (230 ul, 3.190 mmol) were dissolved in methanol (10 ml) at 23° C. After 2 h, sodium borohydride (142 mg, 3.754 mmol) was added to this mixture. After 10 min, the solvent was removed in vacuo. The residue was dissolved in DCM (100 mL), washed with saturated $NaHCO_3$ (50 mL) and brine (50 ml), dried over $MgSO_4$, and filtered. The solvent was removed in vacuo. The residue was purified by Prep-LC to obtain compound 175 (499 mg, 1.755 mmol, 55%) as a glassy colorless solid. MS m/z 285 $(M+H)^+$.

tert-butyl 4-(2-(3-(2-(1,3-dioxoisoindolin-2-yloxy)ethoxy)-N-isobutylpropanamido)ethyl)piperidine-1-carboxylate (176): To a solution of compound 175 (80 mg, 0.201 mmol) and Phth-PEG1-COOH (56 mg, 0.201 mmol) in EtOAc (10 ml) was added CMPI (62 mg, 0.243 mmol) and DIEA (70 ul, 0.402 mmol) at 23° C. After 3 h, the precipitate was removed by filtration, and the filtrate purified with flash chromatography to obtain compound 176 (65 mg, 0.119 mmol, 59%) as a white solid. MS m/z 546 $(M+H)^+$.

3-(2-(1,3-dioxoisoindolin-2-yloxy)ethoxy)-N-isobutyl-N-(2-(piperidin-4-yl)ethyl)propanamide (177): Compound 177 was prepared using compound 176 as starting material, with similar procedure as described for 144 to obtain target compound 177 (66 mg, 0.118 mmol, quant). MS m/z 446 $(M+H)^+$.

N-(2-(1-(4-((6-amino-2-butoxy-8-oxo-7H-purin-9(8H)-yl)methyl)benzyl)piperidin-4-yl)ethyl)-3-(2-(aminooxy)ethoxy)-N-isobutylpropanamide (178): Compound 178 was prepared using compound 177 and compound 142 as starting materials, with similar procedure as described for 143, followed by treatment with hydrazine, $H_2O$ (10 uL) as described for 130 to obtain compound 178 (19 mg, 0.019 mmol, 7%). MS m/z 641 $(M+H)^+$.

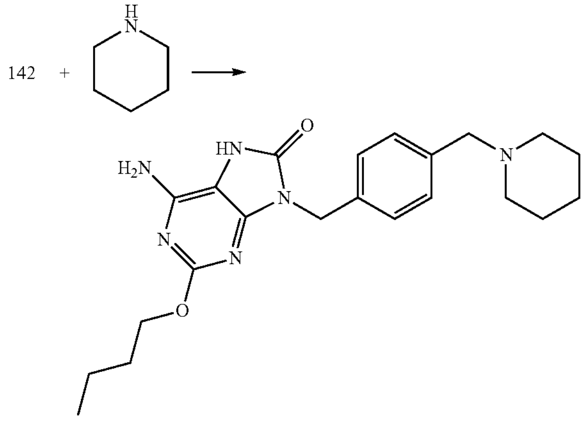

179

6-amino-2-butoxy-9-(4-(piperidin-1-ylmethyl)benzyl)-7H-purin-8(9H)-one (179): Compound 179 was prepared using compound 142 and piperidine as starting materials, with similar procedure as described for 143 to obtain compound 179 (31 mg, 0,041 mmol, 54%). MS m/z 411 $(M+H)^+$.

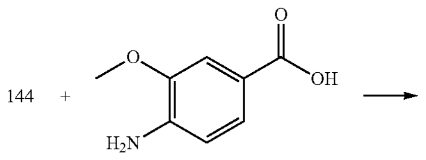

-continued

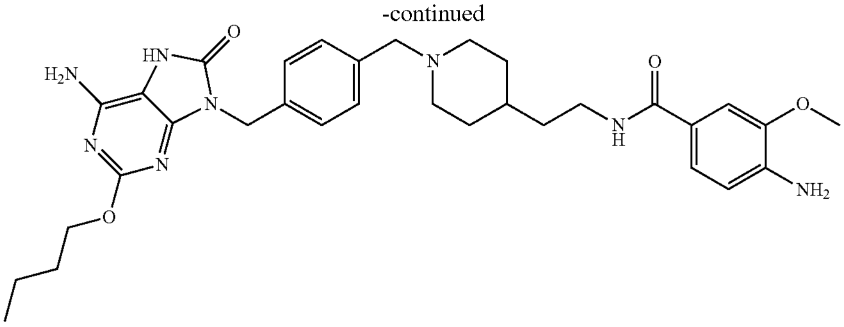

180

4-amino-N-(2-(1-(4-((6-amino-2-butoxy-8-oxo-7H-purin-9(8H)-yl)methyl)benzyl)piperidin-4-yl)ethyl)-3-methoxybenzamide (180): Compound 180 was prepared using compound 144 and 4-amino-3-methoxybenzoic acid as starting materials, with similar procedure as described for 150 to obtain target compound 180 (8 mg, 0.008 mmol, 39%). MS m/z 603 $(M+H)^+$.

173 +

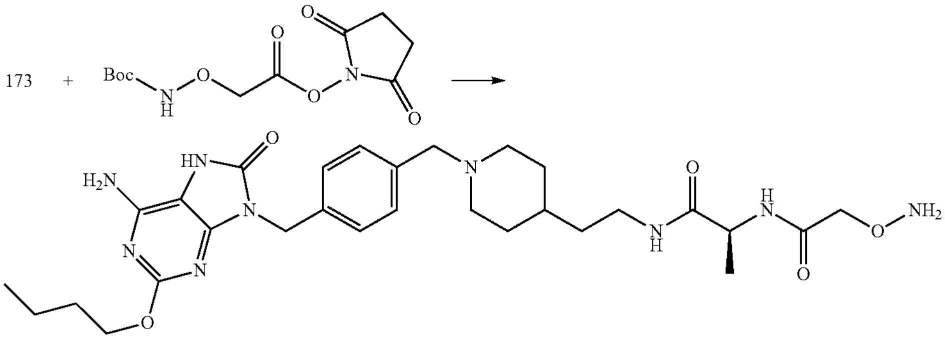

181

(S)—N-(2-(1-(4-((6-amino-2-butoxy-8-oxo-7H-purin-9(8H)-yl)methyl)benzyl)piperidin-4-yl)ethyl)-2-(2-(aminooxy)acetamido)propanamide (181): Compound 181 was prepared using compound 173 and 2,5-dioxopyrrolidin-1-yl 2-(tert-butoxycarbonylaminooxy)acetate as starting materials, with similar procedure as described for 127 to obtain target compound 181 (5 mg, 0.005 mmol, 58%). MS m/z 598 $(M+H)^+$.

174 +

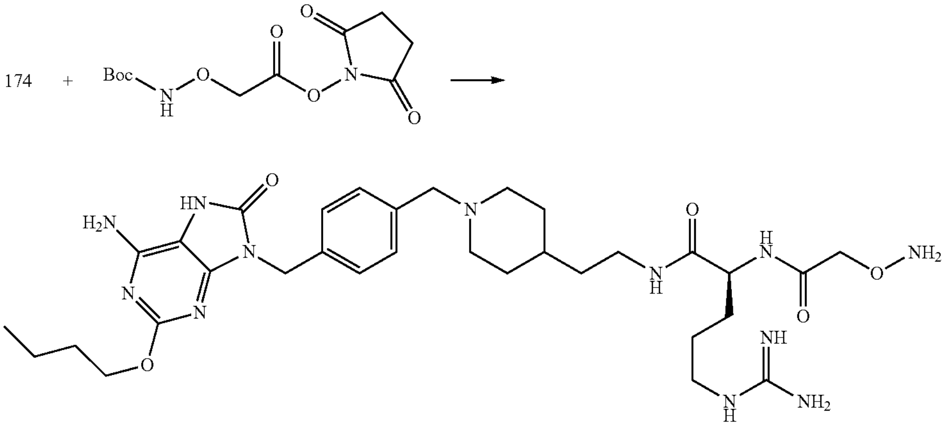

182

(S)—N-(2-(1-(4-((6-amino-2-butoxy-8-oxo-7H-purin-9(8H)-yl)methyl)benzyl)piperidin-4-yl)ethyl)-2-(2-(aminooxy)acetamido)-5-guanidinopentanamide (182): Compound 182 was prepared using compound 174 and 2,5-dioxopyrrolidin-1-yl 2-(tert-butoxycarbonylaminooxy) acetate as starting materials, with similar procedure as described for 127 to obtain target compound 182 (5 mg, 0.004 mmol, 42%). MS m/z 683 (M+H)+.

142 +

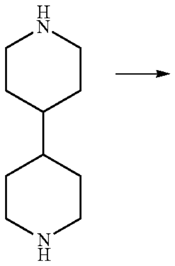

-continued

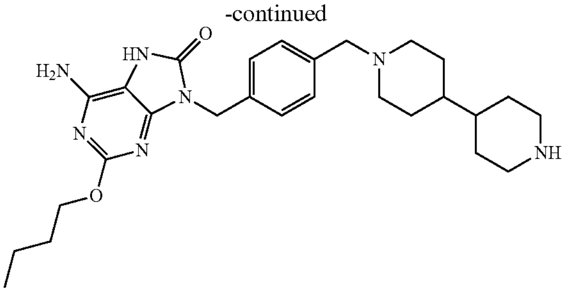

183

9-(4-(4,4'-bipiperidin-1-ylmethyl)benzyl)-6-amino-2-butoxy-7H-purin-8(9H)-oneone (183): Compound 183 was prepared using compound 142 and 4,4'-bipiperidine as starting materials, with similar procedure as described for 143 to obtain compound 183 (13 mg, 0.016 mmol, 7%). MS m/z 494 (M+H)+.

183 +

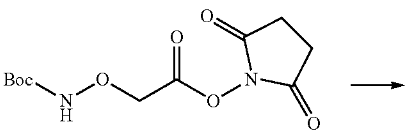

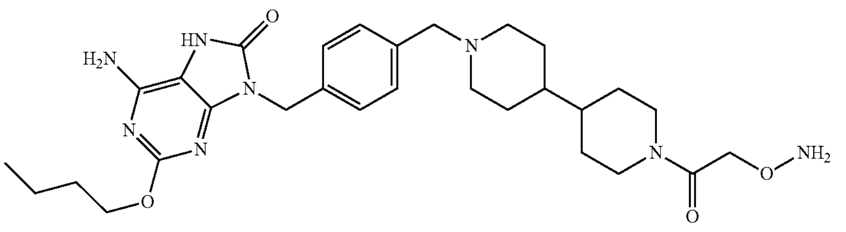

184

6-amino-9-(4-((1'-(2-(aminooxy)acetyl)-4,4'-bipiperidin-1-yl)methyl)benzyl)-2-butoxy-7H-purin-8(9H)-one (184): Compound 184 was prepared using compound 183 and 2,5-dioxopyrrolidin-1-yl 2-(tert-butoxycarbonylaminooxy) acetate as starting materials, with similar procedure as described for 127 to obtain target compound 184 (5 mg, 0,005 mmol, 18%). MS m/z 567 (M+H)+.

144 +

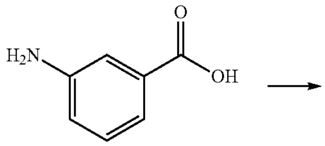

-continued

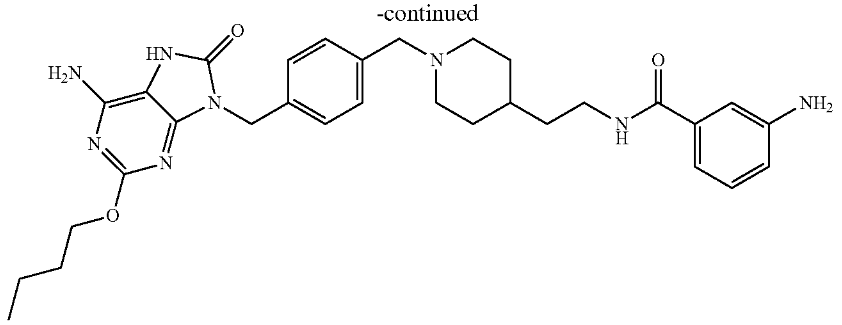

185

3-amino-N-(2-(1-(4-((6-amino-2-butoxy-8-oxo-7,8-dihydro-9H-purin-9-yl)methyl)benzyl)piperidin-4-yl)ethyl) benzamide (185): Compound 185 was prepared using compound 144 and 3-aminobenzoic acid as starting materials, with similar procedure as described for 150 to obtain target compound 185 (8 mg, 0.009 mmol, 53%). MS m/z 572 $(M+H)^+$.

144 +

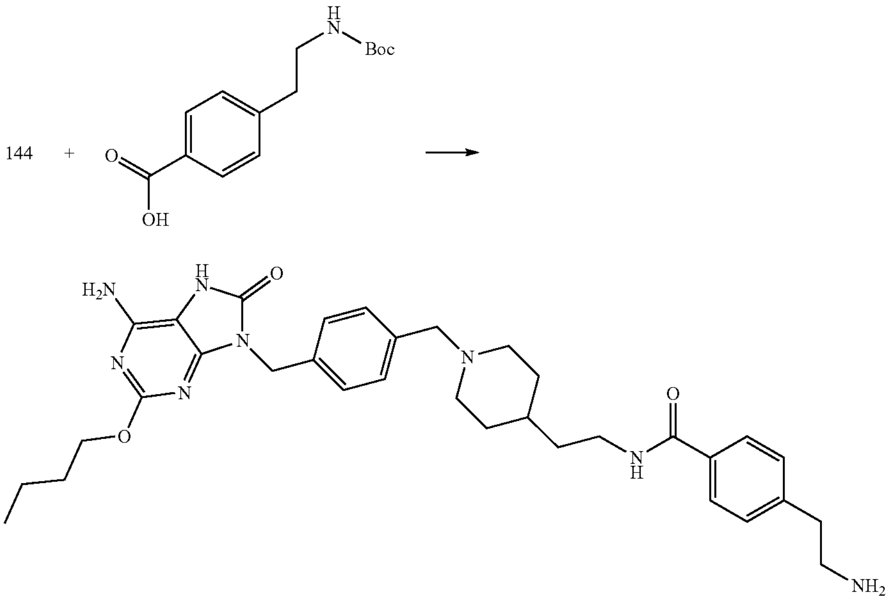

186

N-(2-(1-(4-((6-amino-2-butoxy-8-oxo-7,8-dihydro-9H-purin-9-yl)methyl)benzyl)piperidin-4-yl)ethyl)-4-(2-aminoethyl)benzamide (186): Compound 186 was prepared using compound 144 and 4-(2-Boc-amino)ethylbenzoic acid as starting materials, with similar procedure as described for 173 to obtain target compound 186 (9 mg, 0.010 mmol, 58%). MS m/z 600 $(M+H)^+$.

144 +

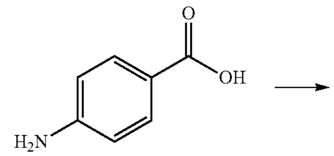

-continued

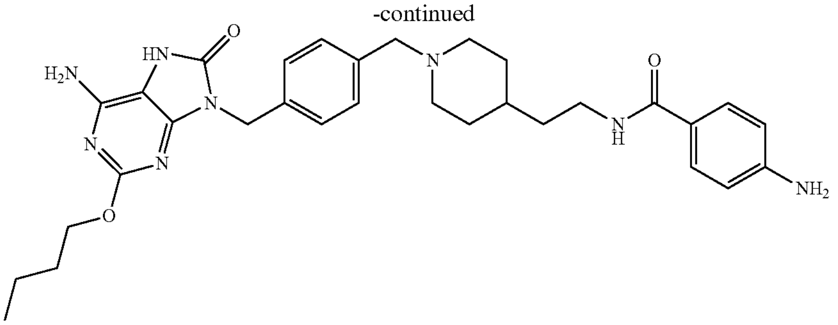

187

4-amino-N-(2-(1-(4-((6-amino-2-butoxy-8-oxo-7,8-dihydro-9H-purin-9-yl)methyl)benzyl)piperidin-4-yl)ethyl) benzamide (187): Compound 187 was prepared using compound 144 and 4-aminobenzoic acid as starting materials, with similar procedure as described for 150 to obtain target compound 187 (8 mg, 0.009 mmol, 53%). MS m/z 572 $(M+H)^+$.

144 +

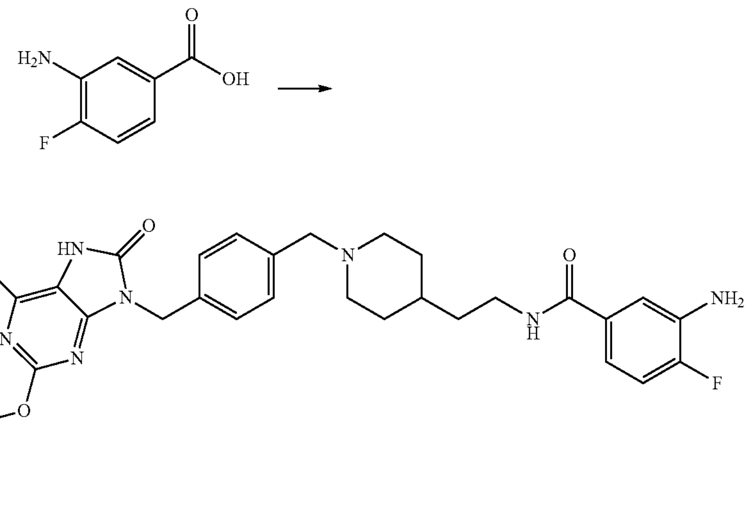

188

3-amino-N-(2-(1-(4-((6-amino-2-butoxy-8-oxo-7,8-dihydro-9H-purin-9-yl)methyl)benzyl)piperidin-4-yl)ethyl)-4-fluorobenzamide (188): Compound 188 was prepared using compound 144 and 3-amino-4-fluoro benzoic acid as starting materials, with similar procedure as described for 150 to obtain target compound 188 (11 mg, 0.011 mmol, 64%). MS m/z 590 $(M+H)^+$.

186 +

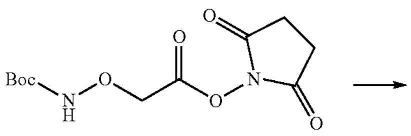

-continued

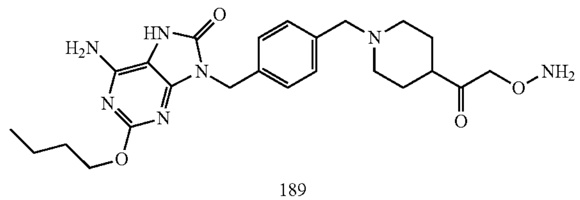

189

N-(2-(1-(4-((6-amino-2-butoxy-8-oxo-7,8-dihydro-9H-purin-9-yl)methyl)benzyl)piperidin-4-yl)ethyl)-4-(2-(2-(aminooxy)acetamido)ethyl)benzamide (189): Compound 189 was prepared using compound 186 and 2,5-dioxopyrrolidin-1-yl 2-(tert-butoxycarbonylaminooxy)acetate as starting materials, with similar procedure as described for 127 to obtain target compound 189 (11 mg, 0.010 mmol, 94%). MS m/z 673 $(M+H)^+$.

142 +
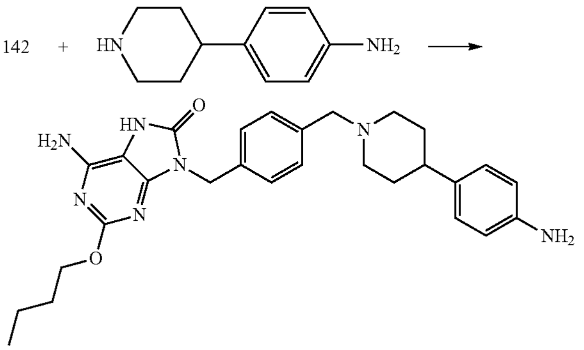

190

6-amino-9-(4-((4-(4-aminophenyl)piperidin-1-yl)methyl)benzyl)-2-butoxy-7H-purin-8(9H)-one (190): Compound 190 was prepared using compound 142 and 4-(4-aminophenyl)-piperidine as starting materials, with similar procedure as described for 143 to obtain compound 190 (3 mg, 0.004 mmol, 5%). MS m/z 502 $(M+H)^+$.

183
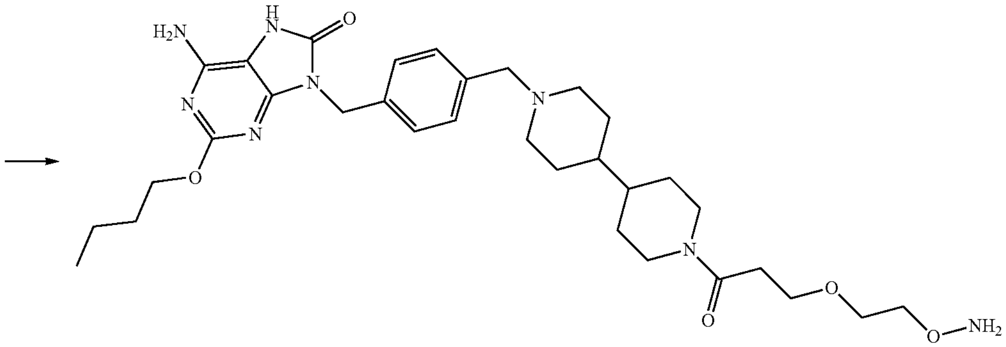

191

6-amino-9-(4-((1'-(3-(2-(aminooxy)ethoxy)propanoyl)-4,4'-bipiperidin-1-yl)methyl)benzyl)-2-butoxy-7H-purin-8(9H)-one (191): Compound 191 was prepared using compound 183 as starting material, with similar procedure as described for 137 to obtain target compound 191 (13 mg, 0.012 mmol, 48%). MS m/z 625 $(M+H)^+$.

144 +
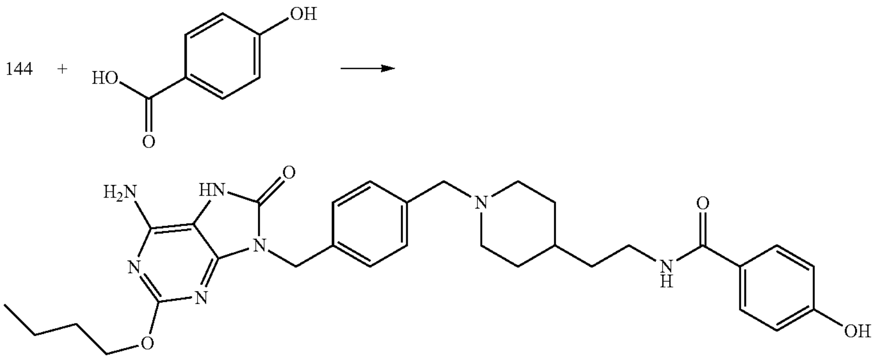

213

N-(2-(1-(4-((6-amino-2-butoxy-8-oxo-7,8-dihydro-9H-purin-9-yl)benzyl)piperidin-4-yl)ethyl)-4-hydroxybenzamide (213): Compound 213 was prepared using compound 144 and 4-hydroxy benzoic acid as starting materials, with similar procedure as described for 150 to obtain target compound 213 (10 mg, 0.011 mmol, 66%). MS m/z 573 $(M+H)^+$.

(399 mg, 1.384 mmol) and Boc-Lys-OH (335 mg, 1.360 mmol) in DMF (5 mL), was added DIEA (750 ul, 4.306 mmol) at 23° C. After 2 h, the solvent was removed in vacuo. The residue was dissolved in EtOAc (50 ml) and washed with 1N HCl (50 ml) and brine (20 mL). The organic layer was dried over $MgSO_4$, filtered, and the solvent removed in vacuo. The residue was purified by flash chromatography to

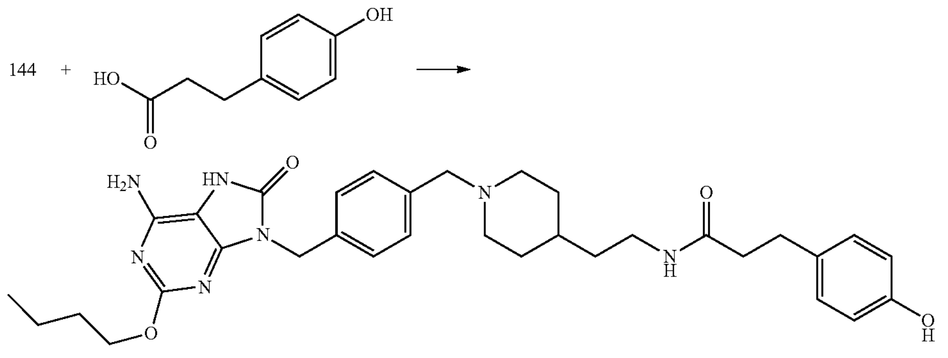

214

N-(2-(1-(4-((6-amino-2-butoxy-8-oxo-7,8-dihydro-9H-purin-9-yl)benzyl)piperidin-4-yl)ethyl)-3-(4-hydroxyphenyl)propanamide (214): Compound 214 was prepared using compound 144 and 3-(4-hydroxyphenyl)propanoic acid as starting materials, with similar procedure as described for 150 to obtain target compound 214 (9 mg, 0.010 mmol, 58%). MS m/z 601 $(M+H)^+$.

obtain compound 215 (480 mg, 1.144 mmol, 83%) as a white solid. MS m/z 420 $(M+H)^+$.

(S)-2-amino-N-(2-(1-(4-((6-amino-2-butoxy-8-oxo-7,8-dihydro-9H-purin-9-yl)benzyl)piperidin-4-yl)ethyl)-6-(2-(aminooxy)acetamido)hexanamide (216): Compound 216 was prepared using compound 144 and compound 215 as starting materials, with similar procedure as described for

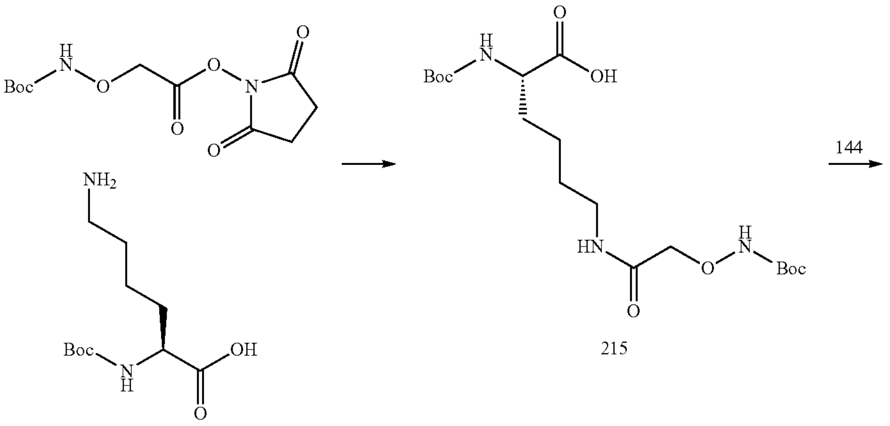

215

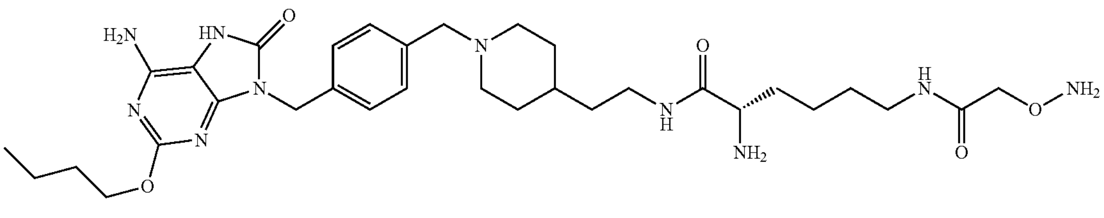

216

Boc-Lys(Boc-Aminooxy acetyl)-OH (215): To 2,5-dioxopyrrolidin-1-yl 2-(tert-butoxycarbonylaminooxy)acetate 173 to obtain target compound 216 (6 mg, 0.006 mmol, 37%). MS m/z 654 $(M+H)^+$.

183 + 215

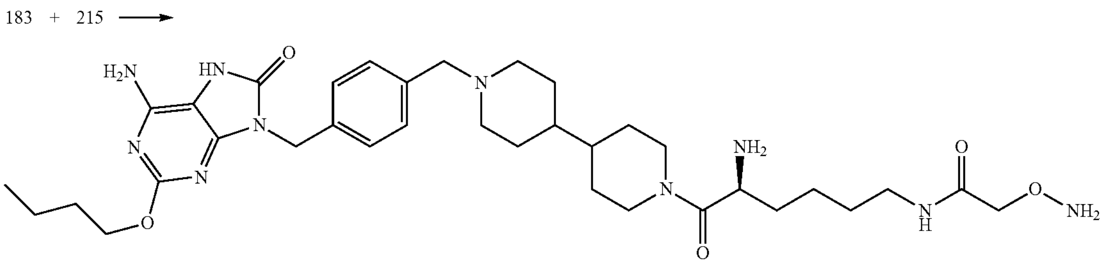

217

(S)—N-(5-amino-6-(1'-(4-((6-amino-2-butoxy-8-oxo-7,8-dihydro-9H-purin-9-yl)methyl)benzyl)-4,4'-bipiperidin-1-yl)-6-oxohexyl)-2-(aminooxy)acetamide (217): Compound 217 was prepared using compound 183 and compound 215 as starting materials, with similar procedure as described for 173 to obtain target compound 217 (6 mg, 0.006 mmol, 37%). MS m/z 654 $(M+H)^+$.

144 +

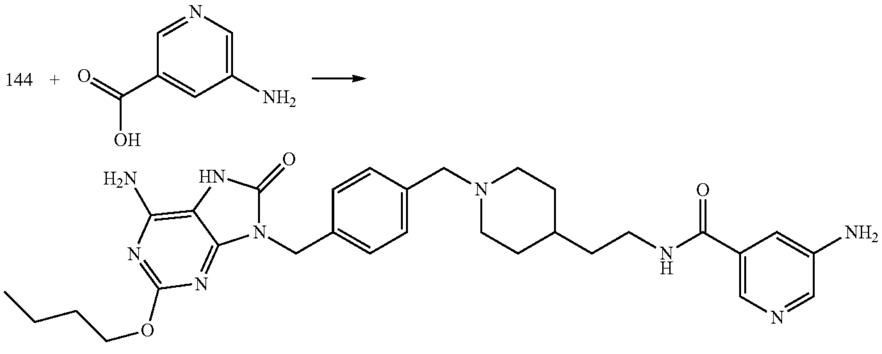

218

5-amino-N-(2-(1-(4-((6-amino-2-butoxy-8-oxo-7,8-dihydro-9H-purin-9-yl)methyl)benzyl)piperidin-4-yl)ethyl) nicotinamide (218): Compound 218 was prepared using compound 144 and 5-aminonicotinic acid as starting materials, with similar procedure as described for 150 to obtain target compound 218 (1 mg, 0.001 mmol, 7%). MS m/z 573 $(M+H)^+$.

144 +

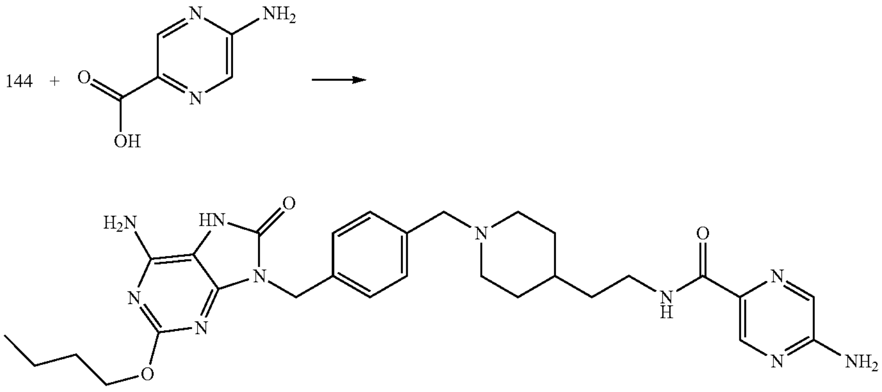

219

5-amino-N-(2-(1-(4-((6-amino-2-butoxy-8-oxo-7,8-dihydro-9H-purin-9-yl)benzyl)piperidin-4-yl)ethyl)pyrazine-2-carboxamide (219): Compound 219 was prepared using compound 144 and 5-amino-pyrazine-carboxylic acid as starting materials, with similar procedure as described for 150 to obtain target compound 219 (10 mg, 0.11 mmol, 66%). MS m/z 574 $(M+H)^+$.

TABLE 4

TLR Agonists - Core 5 Compounds

| Compound No. | Compound Name | Structure - Core 5 Compounds |
|---|---|---|
| 119 | AXC-862 | 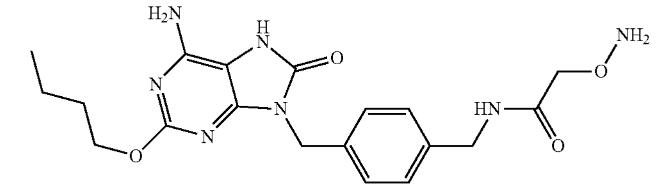 [SMILES: CCCCOc1nc(N)c2[nH]c(=O)n(Cc3ccc(CNC(=O)CON)cc3)c2n1]<br>Molecular Weight: 415.4 |
| 120 | AXC-863 | 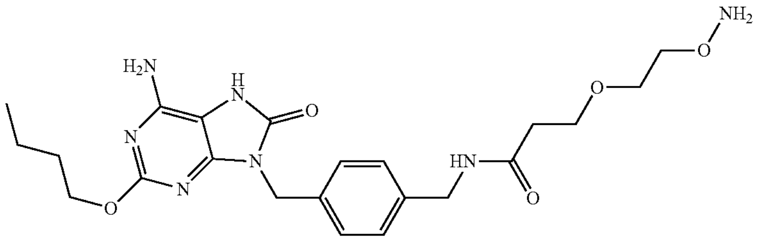 [SMILES: CCCCOc1nc(N)c2[nH]c(=O)n(Cc3ccc(CNC(=O)CCOCCON)cc3)c2n1]<br>Molecular Weight: 473.5 |
| 127 | AXC-867 | 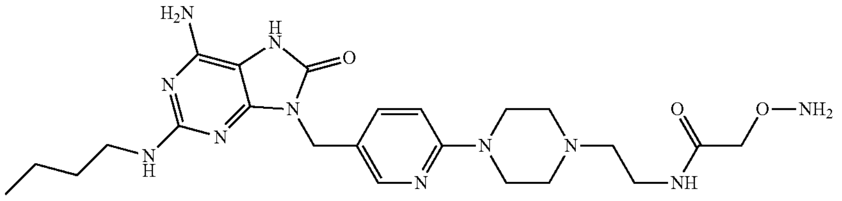 [SMILES: CCCCNc1nc(N)c2[nH]c(=O)n(Cc3ccc(N4CCN(CCNC(=O)CON)CC4)nc3)c2n1]<br>Molecular Weight: 513.6 |
| 129 | AXC-868 | 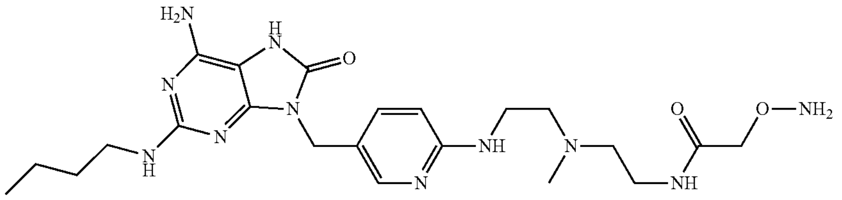 [SMILES: CCCCNc1nc(N)c2[nH]c(=O)n(Cc3ccc(NCCN(C)CCNC(=O)CON)nc3)c2n1]<br>Molecular Weight: 501.6 |
| 130 | AXC-869 | 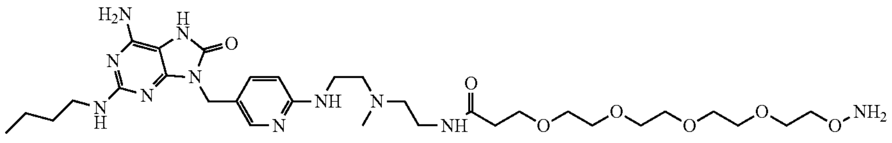 [SMILES: CCCCNc1nc(N)c2[nH]c(=O)n(Cc3ccc(NCCN(C)CCNC(=O)CCOCCOCCOCCOCCON)nc3)c2n1]<br>Molecular Weight: 691.8 |

TABLE 4-continued
| TLR Agonists - Core 5 Compounds | | |
|---|---|---|
| Compound No. | Compound Name | Structure - Core 5 Compounds |
| 131 | AXC-872 | 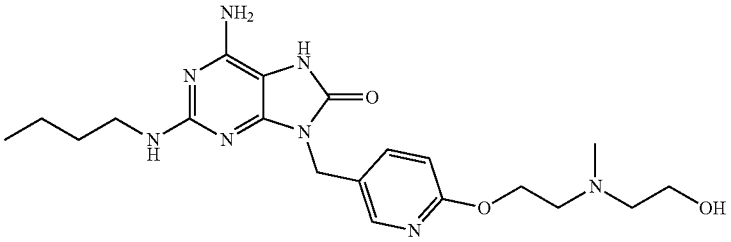 [SMILES: CCCCNc1nc(N)c2[nH]c(=O)n(Cc3ccc(OCCN(C)CCO)nc3)c2n1] Molecular Weight: 430.5 |
| 134 | AXC-873 | 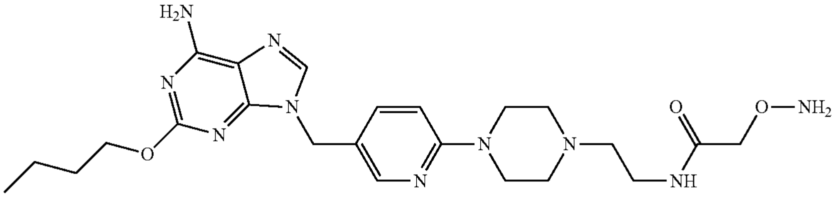 [SMILES: CCCCOc1nc(N)c2ncn(Cc3ccc(N4CCN(CCNC(=O)CON)CC4)nc3)c2n1] Molecular Weight: 498.6 |
| 137 | AXC-876 | 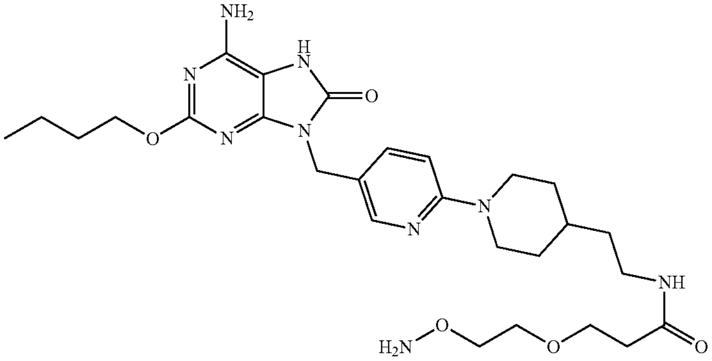 [SMILES: CCCCOc1nc(N)c2[nH]c(=O)n(Cc3ccc(N4CCC(CCNC(=O)CCOCCON)CC4)nc3)c2n1] Molecular Weight: 571.7 |
| 143 | AXC-877 | 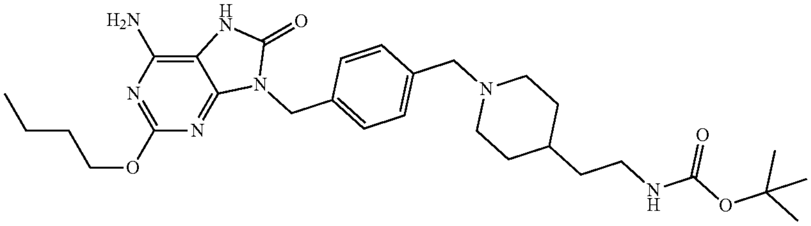 [SMILES: CCCCOc1nc(N)c2[nH]c(=O)n(Cc3ccc(CN4CCC(CCNC(=O)OC(C)(C)C)CC4)cc3)c2n1] Molecular Weight: 553.7 |
| 144 | AXC-878 | 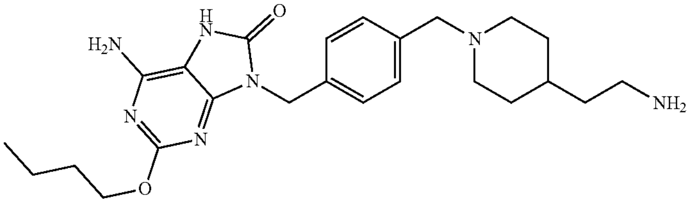 [SMILES: CCCCOc1nc(N)c2[nH]c(=O)n(Cc3ccc(CN4CCC(CCN)CC4)cc3)c2n1] Exact Mass: 453.3 |

TABLE 4-continued
| TLR Agonists - Core 5 Compounds | | |
|---|---|---|
| Compound No. | Compound Name | Structure - Core 5 Compounds |
| 145 | AXC-879 | 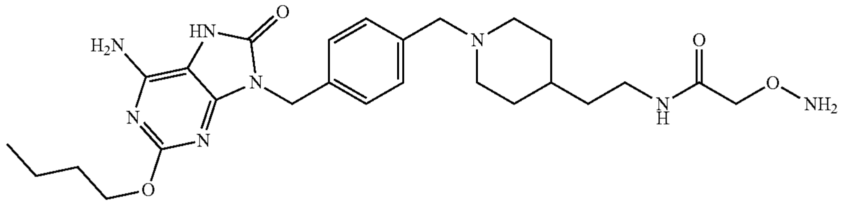 [SMILES: CCCCOc1nc(N)c2[nH]c(=O)n(Cc3ccc(CN4CCC(CCNC(=O)CON)CC4)cc3)c2n1] Exact Mass: 526.3 |
| 146 | AXC-880 | 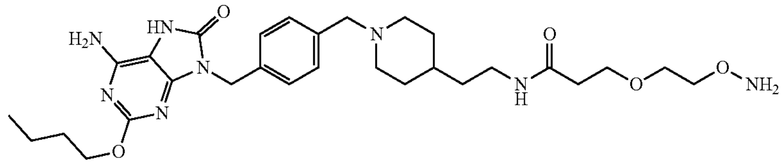 [SMILES: CCCCOc1nc(N)c2[nH]c(=O)n(Cc3ccc(CN4CCC(CCNC(=O)CCOCCON)CC4)cc3)c2n1] Exact Mass: 584.3 |
| 148 | AXC-881 | 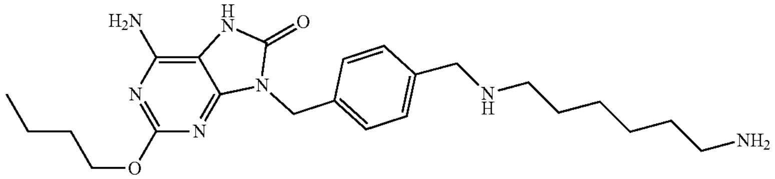 [SMILES: CCCCOc1nc(N)c2[nH]c(=O)n(Cc3ccc(CNCCCCCCN)cc3)c2n1] Exact Mass: 441.3 |
| 149 | AXC-882 | 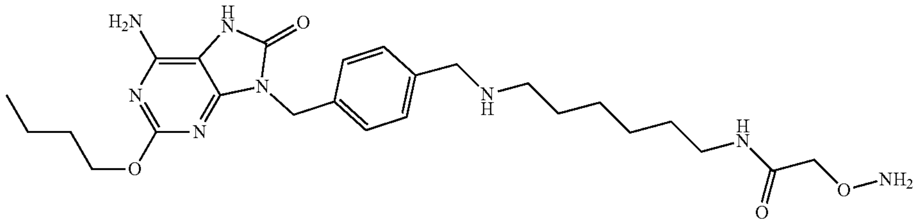 [SMILES: CCCCOc1nc(N)c2[nH]c(=O)n(Cc3ccc(CNCCCCCCNC(=O)CON)cc3)c2n1] Exact Mass: 514.3 |
| 150 | AXC-883 | 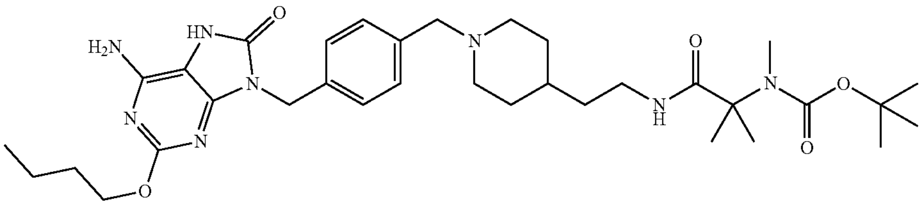 [SMILES: CCCCOc1nc(N)c2[nH]c(=O)n(Cc3ccc(CN4CCC(CCNC(=O)C(C)(C)N(C)C(=O)OC(C)(C)C)CC4)cc3)c2n1] Molecular Weight: 652.8 |
| 151 | AXC-884 | 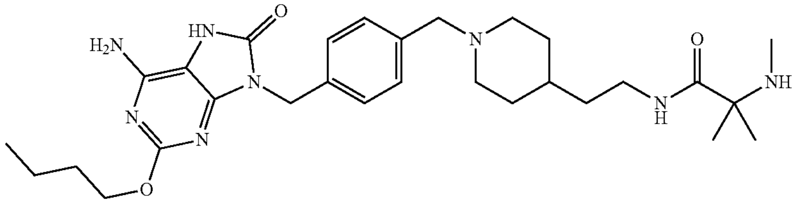 [SMILES: CCCCOc1nc(N)c2[nH]c(=O)n(Cc3ccc(CN4CCC(CCNC(=O)C(C)(C)NC)CC4)cc3)c2n1] Molecular Weight: 552.7 |

TABLE 4-continued
| TLR Agonists - Core 5 Compounds | | |
|---|---|---|
| Compound No. | Compound Name | Structure - Core 5 Compounds |
| 152 | AXC-885 | 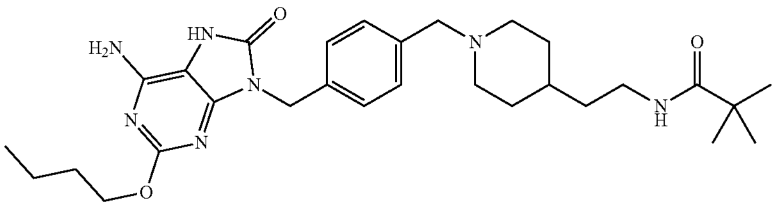 [SMILES: CCCCOc1nc(N)c2[nH]c(=O)n(Cc3ccc(CN4CCC(CCNC(=O)C(C)(C)C)CC4)cc3)c2n1] Molecular Weight: 537.7 |
| 153 | AXC-886 | 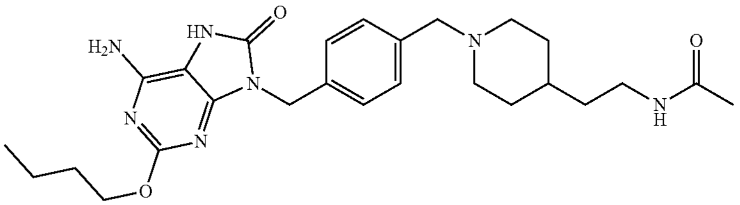 [SMILES: CCCCOc1nc(N)c2[nH]c(=O)n(Cc3ccc(CN4CCC(CCNC(C)=O)CC4)cc3)c2n1] Molecular Weight: 495.6 |
| 154 | AXC-887 | 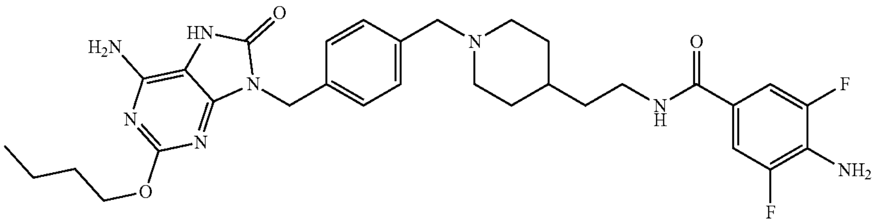 [SMILES: CCCCOc1nc(N)c2[nH]c(=O)n(Cc3ccc(CN4CCC(CCNC(=O)c5cc(F)c(N)c(F)c5)CC4)cc3)c2n1] Molecular Weight: 608.7 |
| 157 | AXC-888 | 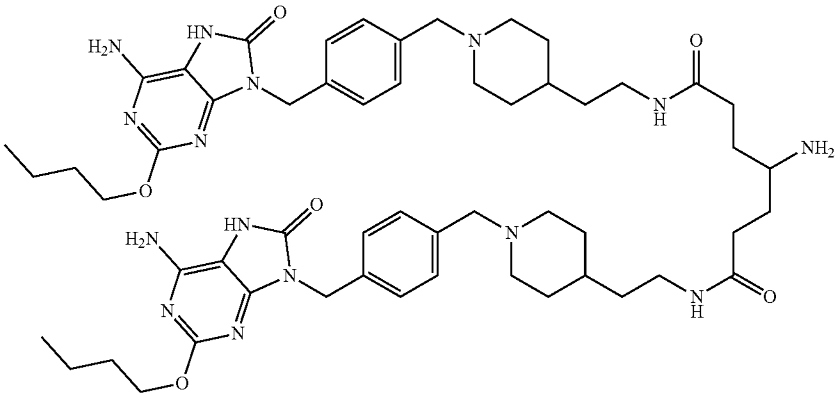 [SMILES: CCCCOc1nc(N)c2[nH]c(=O)n(Cc3ccc(CN4CCC(CCNC(=O)CCC(N)CCC(=O)NCCC5CCN(Cc6ccc(Cn7c(=O)[nH]c8c(N)nc(OCCCC)nc87)cc6)CC5)CC4)cc3)c2n1] Molecular Weight: 1046.3 |

TABLE 4-continued
| TLR Agonists - Core 5 Compounds | | |
|---|---|---|
| Compound No. | Compound Name | Structure - Core 5 Compounds |
| 158 | AXC-889 | 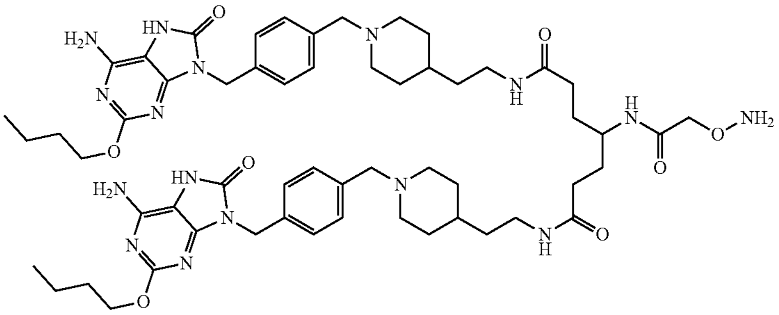 [SMILES: CCCCOc1nc(N)c2[nH]c(=O)n(Cc3ccc(CN4CCC(CCNC(=O)CCC(CCC(=O)NCCC5CCN(Cc6ccc(Cn7c(=O)[nH]c8c(N)nc(OCCCC)nc87)cc6)CC5)NC(=O)CON)CC4)cc3)c2n1] Molecular Weight: 1119.4 |
| 155 | AXC-890 | 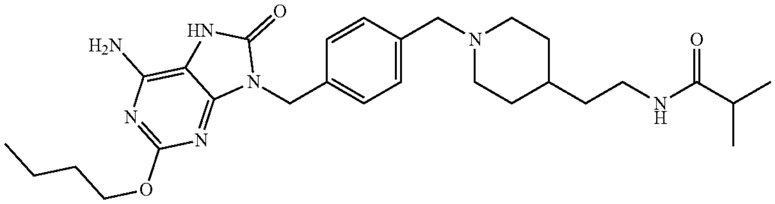 [SMILES: CCCCOc1nc(N)c2[nH]c(=O)n(Cc3ccc(CN4CCC(CCNC(=O)C(C)C)CC4)cc3)c2n1] Molecular Weight: 523.7 |
| 173 | AXC-891 | 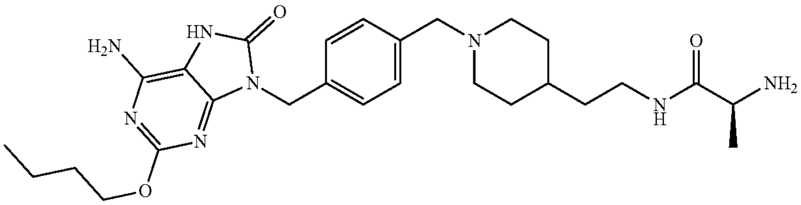 [SMILES: CCCCOc1nc(N)c2[nH]c(=O)n(Cc3ccc(CN4CCC(CCNC(=O)[C@H](C)N)CC4)cc3)c2n1] Molecular Weight: 524.7 |
| 174 | AXC-892 | 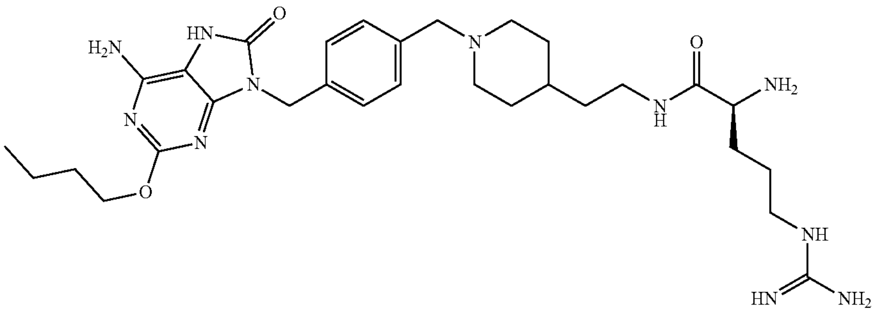 [SMILES: CCCCOc1nc(N)c2[nH]c(=O)n(Cc3ccc(CN4CCC(CCNC(=O)[C@@H](N)CCCNC(=N)N)CC4)cc3)c2n1] Molecular Weight: 609.8 |

TABLE 4-continued
| TLR Agonists - Core 5 Compounds | | |
|---|---|---|
| Compound No. | Compound Name | Structure - Core 5 Compounds |
| 178 | AXC-893 | 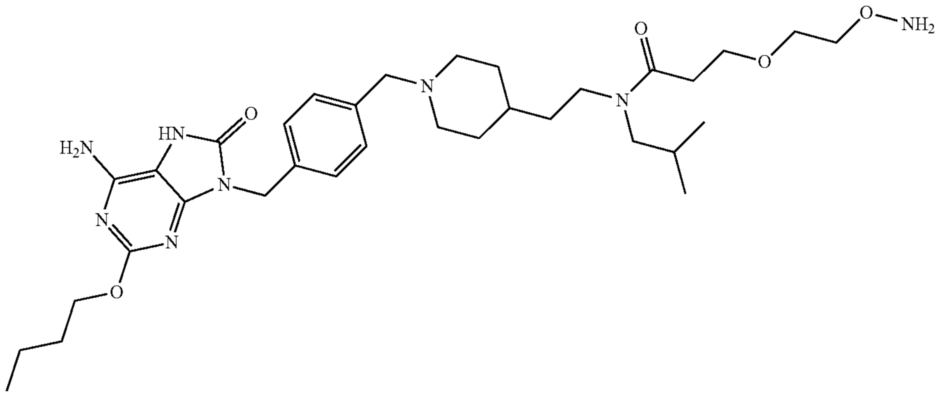 [SMILES: CCCCOc1nc(N)c2[nH]c(=O)n(Cc3ccc(CN4CCC(CCN(CC(C)C)C(=O)CCOCCON)CC4)cc3)c2n1] Molecular Weight: 640.8 |
| 179 | AXC-894 | 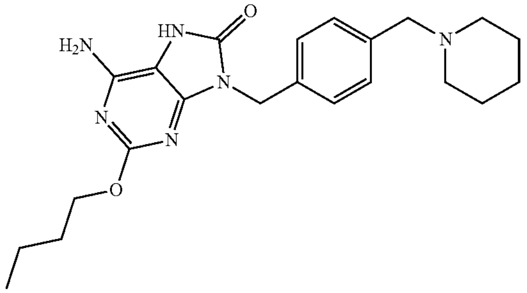 [SMILES: CCCCOc1nc(N)c2[nH]c(=O)n(Cc3ccc(CN4CCCCC4)cc3)c2n1] Molecular Weight: 410.5 |
| 180 | AXC-895 | 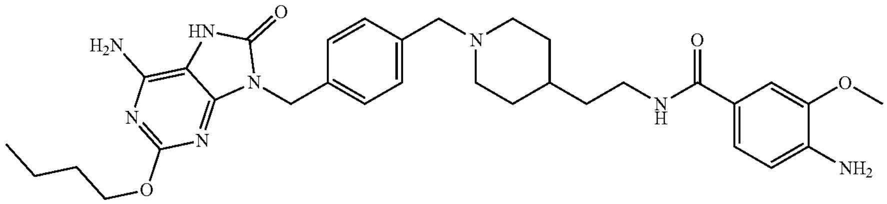 [SMILES: CCCCOc1nc(N)c2[nH]c(=O)n(Cc3ccc(CN4CCC(CCNC(=O)c5ccc(N)c(OC)c5)CC4)cc3)c2n1] Molecular Weight: 602.7 |
| 181 | AXC-896 | 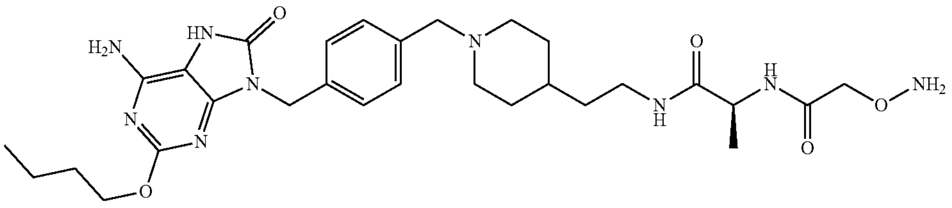 [SMILES: CCCCOc1nc(N)c2[nH]c(=O)n(Cc3ccc(CN4CCC(CCNC(=O)[C@H](C)NC(=O)CON)CC4)cc3)c2n1] Molecular Weight: 597.7 |

TABLE 4-continued
| TLR Agonists - Core 5 Compounds | | |
|---|---|---|
| Compound No. | Compound Name | Structure - Core 5 Compounds |
| 182 | AXC-897 | 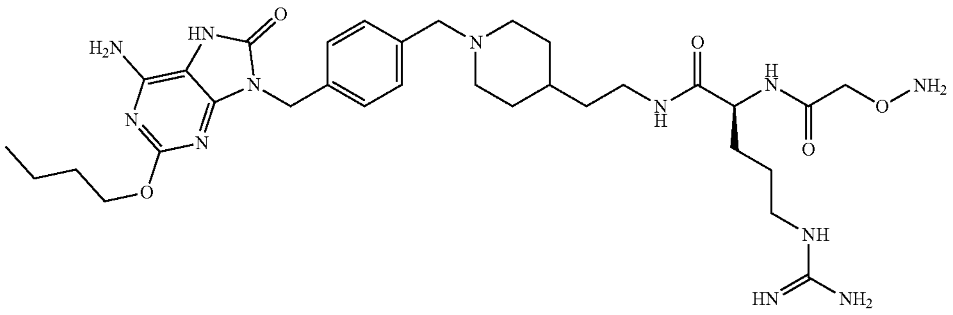 [SMILES: CCCCOc1nc(N)c2[nH]c(=O)n(Cc3ccc(CN4CCC(CCNC(=O)[C@H](CCCNC(=N)N)NC(=O)CON)CC4)cc3)c2n1] Molecular Weight: 682.8 |
| 183 | AXC-898 | 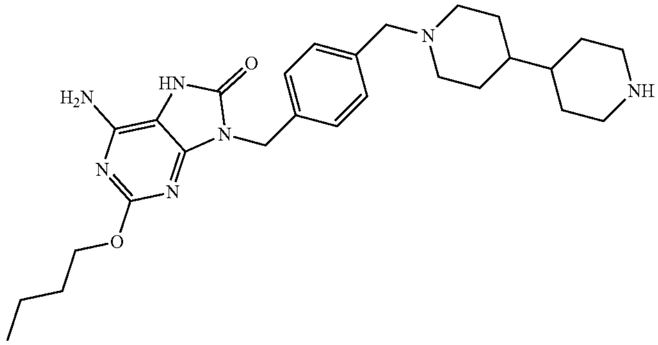 [SMILES: CCCCOc1nc(N)c2[nH]c(=O)n(Cc3ccc(CN4CCC(C5CCNCC5)CC4)cc3)c2n1] Molecular Weight: 493.6 |
| 184 | AXC-901 | 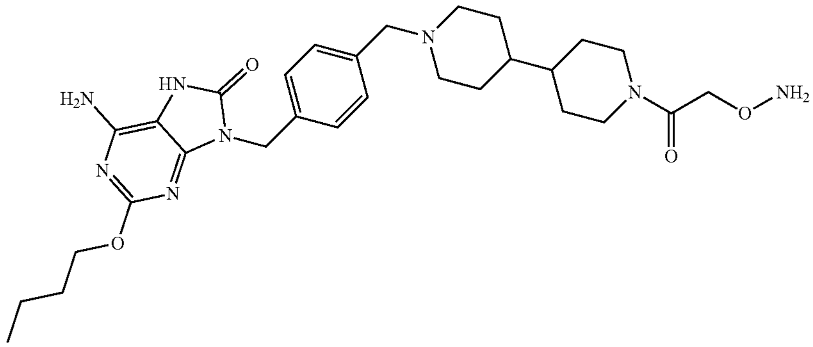 [SMILES: CCCCOc1nc(N)c2[nH]c(=O)n(Cc3ccc(CN4CCC(C5CCN(C(=O)CON)CC5)CC4)cc3)c2n1] Molecular Weight: 566.7 |
| 185 | AXC-903 | |
| 186 | AXC-904 | |
| 187 | AXC-905 | |
| 188 | AXC-906 | 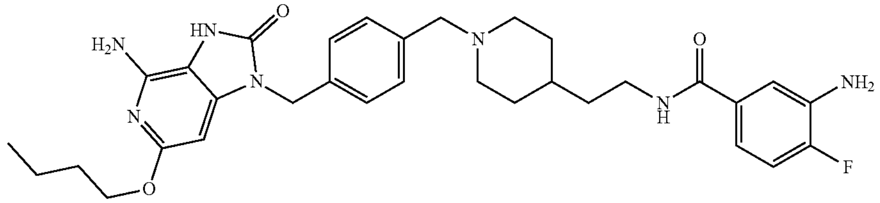 [SMILES: CCCCOc1cc2c([nH]c(=O)n2Cc2ccc(CN3CCC(CCNC(=O)c4ccc(F)c(N)c4)CC3)cc2)c(N)n1] Molecular Weight: 590.7 |

TABLE 4-continued
| TLR Agonists - Core 5 Compounds | | |
|---|---|---|
| Compound No. | Compound Name | Structure - Core 5 Compounds |
| 189 | AXC-907 | 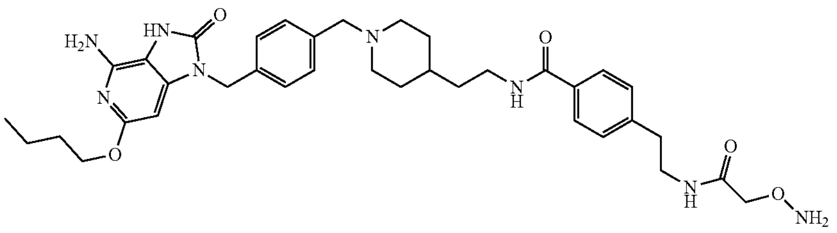 [SMILES: CCCCOc1cc2c([nH]c(=O)n2Cc2ccc(CN3CCC(CCNC(=O)c4ccc(CCNC(=O)CON)cc4)CC3)cc2)c(N)n1] Molecular Weight: 673.8 |
| 190 | AXC-908 | 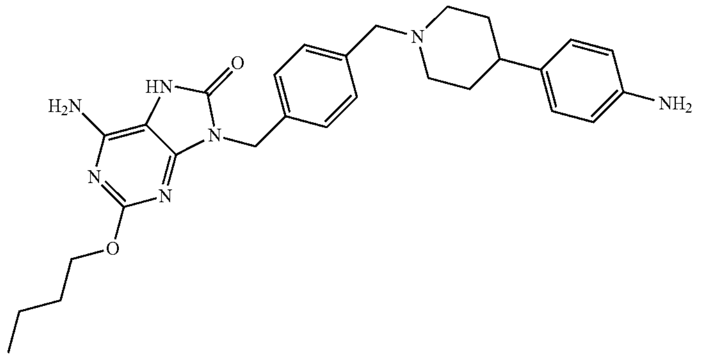 [SMILES: CCCCOc1nc(N)c2[nH]c(=O)n(Cc3ccc(CN4CCC(c5ccc(N)cc5)CC4)cc3)c2n1] Molecular Weight: 501.6 |
| 191 | AXC-909 | 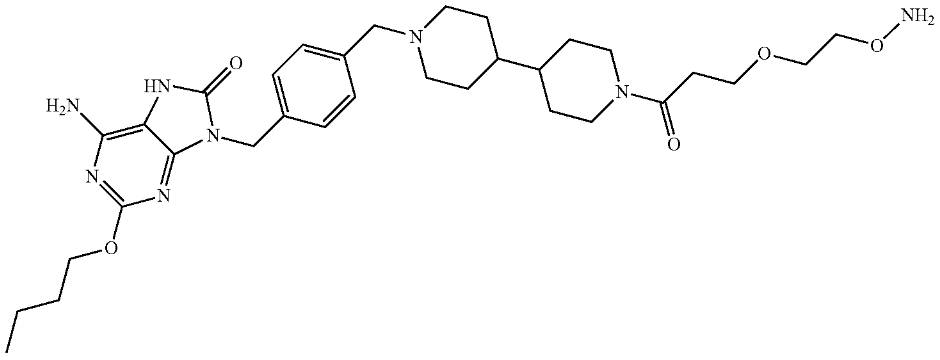 [SMILES: CCCCOc1nc(N)c2[nH]c(=O)n(Cc3ccc(CN4CCC(C5CCN(C(=O)CCOCCON)CC5)CC4)cc3)c2n1] Molecular Weight: 624.8 |
| 213 | AXC-911 | 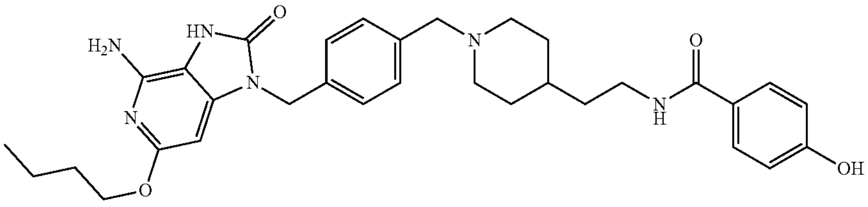 [SMILES: CCCCOc1cc2c([nH]c(=O)n2Cc2ccc(CN3CCC(CCNC(=O)c4ccc(O)cc4)CC3)cc2)c(N)n1] Molecular Weight: 573.7 |

TABLE 4-continued
| TLR Agonists - Core 5 Compounds | | |
|---|---|---|
| Compound No. | Compound Name | Structure - Core 5 Compounds |
| 214 | AXC-912 | 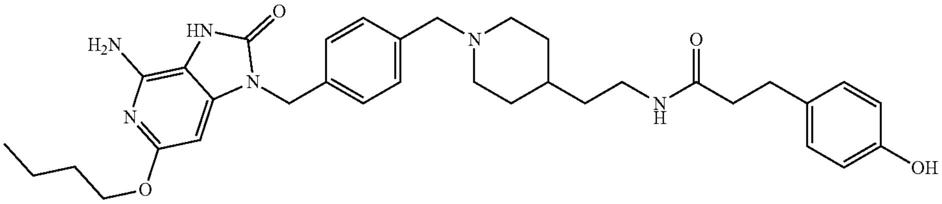 [SMILES: CCCCOc1cc2c([nH]c(=O)n2Cc2ccc(CN3CCC(CCNC(=O)CCc4ccc(O)cc4)CC3)cc2)c(N)n1]<br>Molecular Weight: 601.8 |
| 216 | AXC-913 | 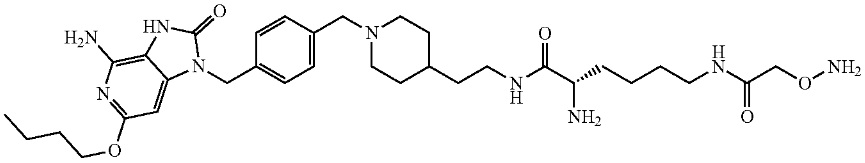 [SMILES: CCCCOc1cc2c([nH]c(=O)n2Cc2ccc(CN3CCC(CCNC(=O)[C@@H](N)CCCCNC(=O)CON)CC3)cc2)c(N)n1]<br>Molecular Weight: 654.8 |
| 217 | AXC-914 | 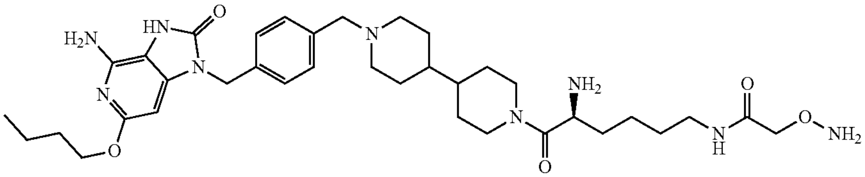 [SMILES: CCCCOc1cc2c([nH]c(=O)n2Cc2ccc(CN3CCC(C4CCN(C(=O)[C@@H](N)CCCCNC(=O)CON)CC4)CC3)cc2)c(N)n1]<br>Molecular Weight: 694.9 |
| 218 | AXC-915 | 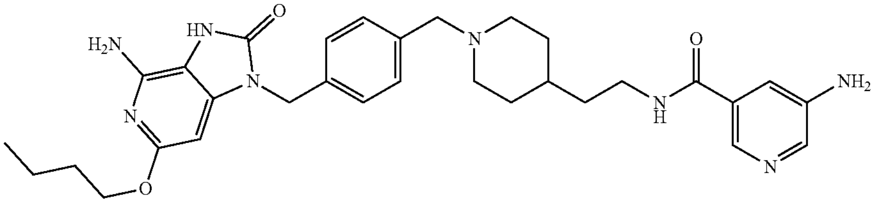 [SMILES: CCCCOc1cc2c([nH]c(=O)n2Cc2ccc(CN3CCC(CCNC(=O)c4cncc(N)c4)CC3)cc2)c(N)n1]<br>Molecular Weight: 573.7 |
| 219 | AXC-916 | 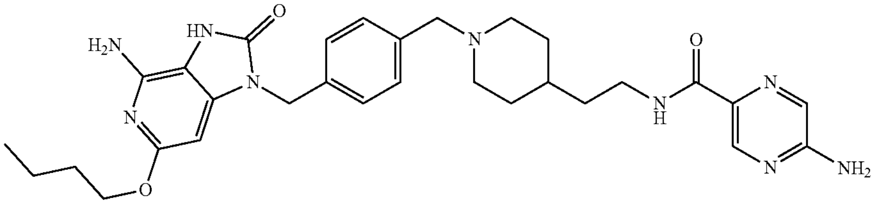 [SMILES: CCCCOc1cc2c([nH]c(=O)n2Cc2ccc(CN3CCC(CCNC(=O)c4cnc(N)cn4)CC3)cc2)c(N)n1]<br>Molecular Weight: 574.7 |

Example 4: Synthesis of TLR Agonists Comprising the Following Structures—Core 3, (FIG. 1)

Core 3

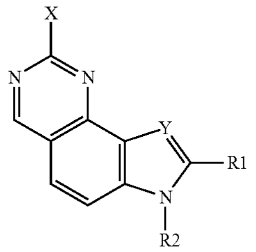

In some embodiments, X is N or H; Y is C, or N;

$R_1$ is $C_1$ to $C_{12}$ alkyl, substituted $C_1$ to $C_{12}$ alkyl, oxygen containing $C_1$ to $C_{12}$ alkyl, heterocycle, substituted heterocycle, or H $R_2$ is $C_1$ to $C_{12}$ alkyl, $C_1$ to $C_{12}$ substituted alkyl, $C_4$ to $C_8$ cycloalkyl, aromatic cycle, substituted aromatic cycle, aromatic hetero cycle, substituted aromatic hetero cycle, —$ONH_2$, terminal $C_1$ to $C_{12}$ alkyl, or H TLR-agonists having Core 3 structures were synthesized as disclosed in the schemes below.

Core 3

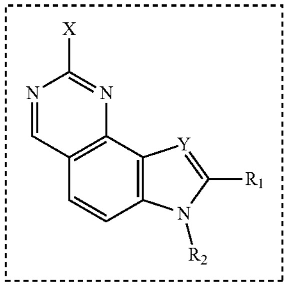

Representative Structures

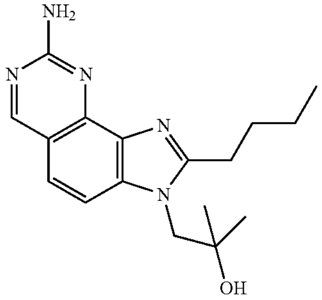

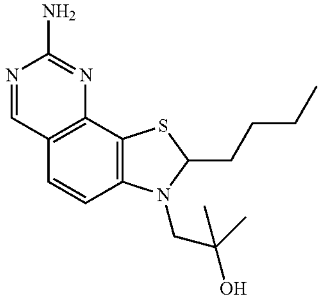

-continued

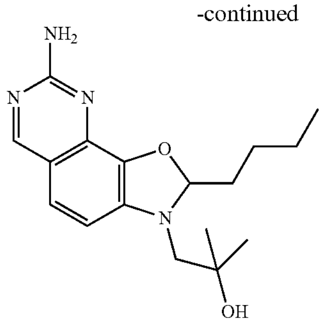

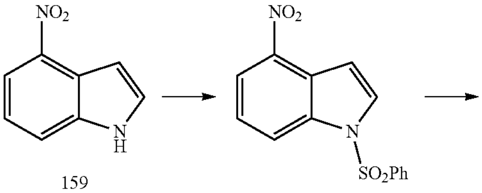

159

160

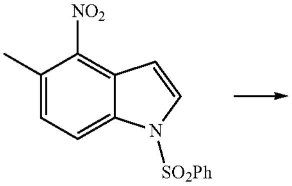

161

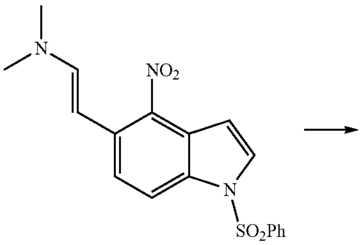

162

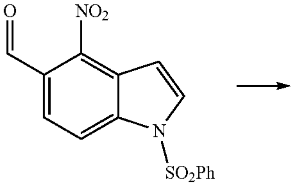

163

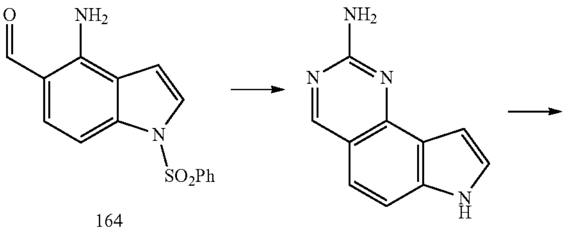

164

165

-continued

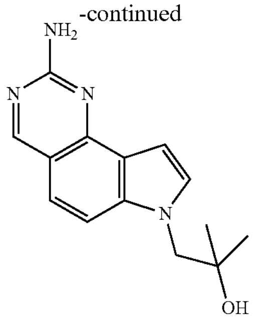

166

4-Nitro-1-tosyl-1H-indole (160): Compound 159 (4-Nitro-1H-Indole), (2.43 g, 15.0 mmol), was dissolved in THF (15 mL). Sodium hydride (900 mg, 22.5 mmol) in THF (30 mL) was added dropwise to the suspension at 0° C. The solution was warmed to room temperature and stirred for an additional 1 h. Next, tosyl chloride (3.0 g, 15.75 mmol) in THF (15 mL) was added slowly and the reaction stirred overnight, the solution was partitioned between $NaHCO_3$ and $Et_2O$. The aqueous layer was extracted (3×75 mL), the combined organic layers were washed with brine, dried over $MgSO_4$, and concentrated in vacuo. The resulting solid was taken up in AcCN, sonicated and filtered. The solid (starting material) was not used. The liquid was rotovapped and the residue (160) used in the next step (3.12 g). MS m/z NO2 not observed.

5-methyl-4-nitro-1-(phenylsulfonyl)-1H-indole (161): Compound 160 (3.11 g, 9.83 mmol) was dissolved in THF (98.3 ml) at −15° C. Methylmagnesium Chloride (4.9 mL, 14.75 mmol) was added and the solution allowed to stir for 1 h 45 min. DDQ (3.79 g, 16.71 mmol) was added next while maintaining the temperature below −10° C. The reaction was warmed to room temperature and stirred overnight. Next, the reaction was diluted with DCM to quench the reaction followed by rotovapping. The crude was passed through a plug of $SiO_2$ eluting with DCM. The eluent was dried and purified by column chromatography (Hexanes in DCM, 0-40%, 40 g column) to obtain target compound 161 (2.06 g, 63% over two steps). MS m/z NO2 not observed.

(E)N,N-dimethyl-2-(4-nitro-1-(phenylsulfonyl)-1H-indol-5-yl)ethen-1-amine (162): 5-methyl-4-nitro-1-(phenylsulfonyl)-1H-indole (161) (0.83 g, 2.63 mmol) was dissolved in DMF (26.3 ml), N, N-Dimethylformamide dimethyl acetal (3.54 mL, 26.3 mmol) was added and the reaction heated at 115° C. The reaction was evaporated by rotary evaporator. The residue (compound 162) was used in the next reaction (0.98 g). MS m/z N02 not observed.

4-nitro-1-(phenylsulfonyl)-1H-indole-5-carbaldehyde (163): To a solution of compound 162 (0.98 g, 2.6 mmol) in THF (13.2 ml) and water (13.2 mL), sodium metaperiodate (1.7 g mg, 7.9 mmol) was added and stirred. The reaction was filtered and washed with EtOAc (50 mL). The organic layer was washed with $NaHCO_3$, dried over $MgSO_4$, filtered, and evaporated by rotary evaporator. The residue (compound 163, 0.56 g) was dried on a vacuum pump and used in the next reaction. MS m/z $NO_2$ not observed.

4-amino-1-(phenylsulfonyl)-1H-indole-5-carbaldehyde (164): To a solution of compound 163 (0.56 g, 1.7 mmol) in MeOH (47 mL) was added Pd/C (0.03 g). The reaction was stirred under an atmosphere of hydrogen (double ballooned/1 atm). The reaction was filtered with celite and washed With MeOH. The solvent was dried in vacuo and the residue purified by column chromatography (Hexanes in EtOAc, 0-50%, 12 g column) to obtain target compound 164 (93 mg, 12% over three steps), MS m/z 301 $(M+H)^+$.

7H-pyrrolo[2,3-h]quinazolin-2-amine (165): To a solution of compound 164 (0.092 g, 0.31 mmol) in DMA (3.1 mL) was added Guanidine carbonate (279 mg, 3.09 mmol) and stirred at 150° C. LCMS showed the reaction completed and the mixture was purified by Prep-LC to obtain target compound 165 (6 mg, 11%), MS m/z 257 $(M+H)^+$.

1-(2-amino-7H-pyrrolo[2,3-h]quinazolin-7-yl)-2-methylpropan-2-ol (166): To a solution of sodium hydride (60% dispersion in mineral oil, 2.2 mg, 0.054 mmol), 5 mL of hexanes at 0° C. was added and the solution agitated. The hexanes were removed to wash away the mineral oil. Next, compound 165 (2 mg, 0.011 mmol) in DMF (1.1 mL) was added dropwise to the solution and stirred for 1 h. Next, isobutylene oxide (1 uL, 0.011 mmol) was added dropwise and the reaction stirred. The reaction was filtered, and the mixture purified by Prep-LC to obtain target compound 166 (1.5 mg, 23%), MS m/z 185 $(M+H)^+$.

TABLE 5

| TLR Agonists - Core 3 Compounds | | |
|---|---|---|
| Compound No. | Compound Name | Structure - Core 3 Compounds |
| 165 | AXC-837 | 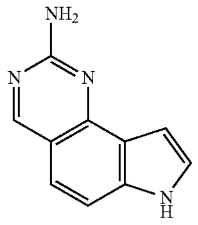 [SMILES: Nc1ncc2ccc3[nH]ccc3c2n1] Molecular Weight: 184.20 |
| 166 | AXC-847 | 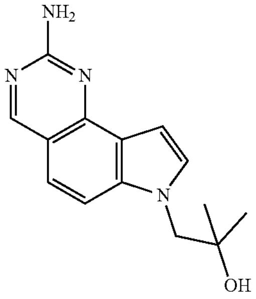 [SMILES: CC(C)(O)Cn1ccc2c3nc(N)ncc3ccc21] Molecular Weight: 256.31 |

Example 5: Synthesis of TLR Agonists Comprising the Following Representative Structures—Core 2, (FIG. 1)

Core 2

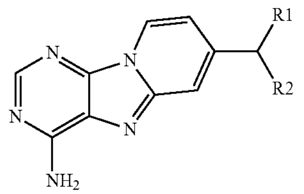

-continued

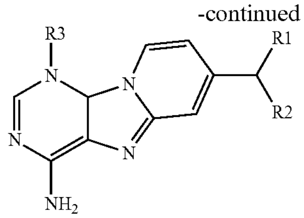

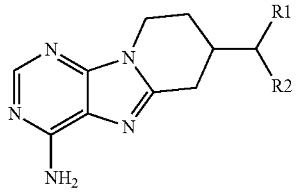

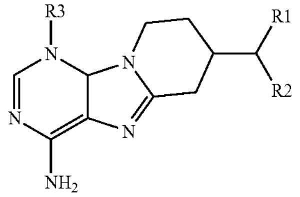

In some embodiments, $R_1$ or $R_2$ is each connected to form $C_4$ to $C_8$ cylclo alkyl or independently —H, $C_1$ to $C_{12}$ alkyl, nitro containing alkyl, aromatic cylcle or —C(NH)$NH_2$; $R_3$ is $C_1$ to $C_{12}$ alkyl, substituted $C_1$ to $C_{12}$ alkyl, oxygen containing $C_1$ to $C_{12}$ alkyl, heterocycle substituted heterocycle, or H.

TLR-agonists having Core 2 structures were synthesized as disclosed in the schemes below.

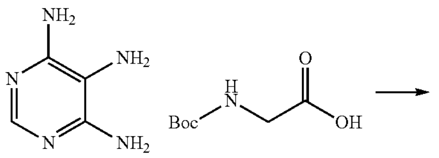

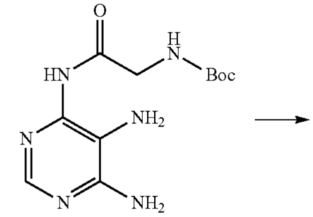

167

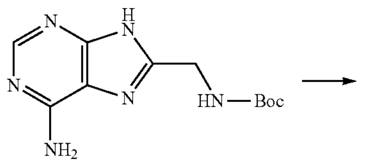

168

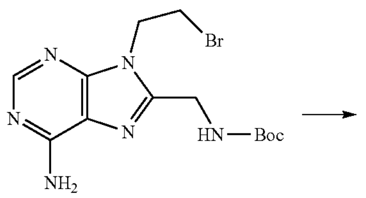

169

-continued

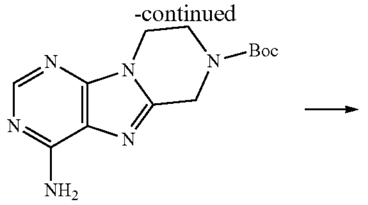

170

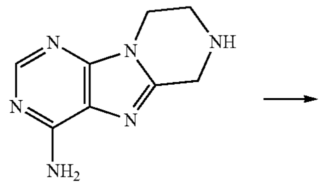

171

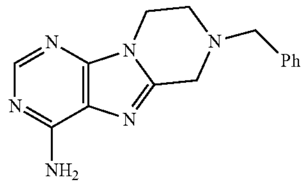

172 tert-butyl 2-(5,6-diaminopyrimidin-4-ylamino)-2-oxoethylcarbamate (167): To a solution of pyrimidine-4,5,6-triamine (2050 mg, 16.383 mmol) and Boc-Gly-OH (2880, 16.440 mmol) in DCM (50 ml) was added DCC (3800 mg, 18.417 mmol) and DMAP (80 mg, 0.655 mmol) at 23° C. After 3 h, the precipitate was removed by filtration. The mixture was purified by Prep-LC to obtain target compound 167 (2458 mg, 8.707 mmol, 53%), MS m/z 283 $(M+H)^+$.

tert-butyl (6-amino-9H-purin-8-yl)methylcarbamate (168): To a solution of compound 167 (620 mg, 2.196 mmol) in n-BuOH (20 ml) was added NaOMe 25% in MeOH (2500 ul, 11.570 mmol) at 23° C. The temperature was raised to 70° C. After 1 h, 6N HCl (1.83 ml, 11 mmol) was added to the mixture in an ice bath, and the mixture was diluted with EtOAc (50 ml). The mixture was washed by saturated sodium bicarbonate (50 ml) and brine (50 ml), dried with $MgSO_4$, and filtered. The mixture was purified by flash chromatography to obtain target compound 168 (250 mg, 0.946 mmol, 43%), MS m/z 265 $(M+H)^+$.

tert-butyl (6-amino-9-(2-bromoethyl)-9H-purin-8-yl)methylcarbamate (169): To a solution of compound 168 (250 mg, 0.946 mmol) in DMF (5 ml) was added dibromoethane (2100 mg, 2.795 mmol) and $CsCO_3$ (2400 mg, 1.842 mmol) at 23° C. After 2.5 h, the mixture was diluted with 20 ml DCM, and washed with saturated sodium bicarbonate (50 ml) and brine (50 m). The organic layer was dried with $MgSO_4$ and filtered. The mixture was purified by Prep-LC to obtain compound 169 (144 mg, 0.545 mmol, 58%), MS m/z 372 $(M+H)^+$.

tert-butyl 4-amino-8,9-dihydropyraziuo[1,2-e]purine-7(6H)-carboxylate (170): To a solution of sodium hydride (60% dispersion in mineral oil, 51.4 mg, 1.286 mmol) was added 5 mL of hexanes. The solution was agitated followed by removal of the hexanes to wash away the mineral oil. Compound 169 (159.2 mg, 0.429 mmol) in DMF (2.9 mL) was added dropwise to the solution with stirring at 23° C. After 1 h, LCMS showed the reaction complete. The mixture was purified by Prep-LC with 5% to 60% of water/90% ACN 0.05% TFA gradient for 20 min by using Gemini NX, 150x30 C18 column. The fractions containing product were combined and evaporated by rotary evaporator. The residue was dried on high vacuum pump to obtain target compound 170 (36.7 mg, 0.05 mmol, 11%), MS m/z 291 $(M+H)^+$.

6,7,8,9-tetrahydropyrazino[1,2-e]purin-4-amine (171): To a solution of 170 (35.7 mg, 0.123 mmol) was added 1.2 mL of DCM. Trifluoroacetic acid (45.7 uL, 0.615 mmol) was added dropwise with stirring at 23° C. After 1 h, LCMS showed the reaction complete. The mixture was evaporated by rotary evaporator with additional azeotroping using PhMe to give obtain compound 171. (38.5 mg, 0.05 mmol, 41%), MS m/z 191 $(M+H)^+$.

7-benzyl-6,7,8,9-tetrahydropyrazino[1,2-e]purin-4-amine (172): To a solution of 171 (10 mg, 0.053 mmol) in DMF (1.1 mL) was added benzaldehyde (6.7 uL, 0.066 mmol), DIEA (18.3 uL, 0.105 mmol) was added and the reaction stirred for 15 minutes. Next, Borone-Pyridine complex (6.7 uL, 0.067 mmol) was added and the reaction stirred overnight at 23° C. The mixture was purified by Prep-LC with 5% to 60% of water/90% ACN 0.05% TFA gradient for 20 min by using Gemini NX, 150x30 C18 column. The fractions containing product were combined and evaporated by rotary evaporator. The residue was dried on high vacuum pump to obtain compound 172 (1.3 mg, 0.002 mmol, 3%), MS m/z 281 $(M+H)^+$.

TABLE 6

TLR Agonists - Core 2 Compounds

| Compound No. | Compound Name | Structure - Core 2 Compounds |
|---|---|---|
| 170 | AXC-745 | 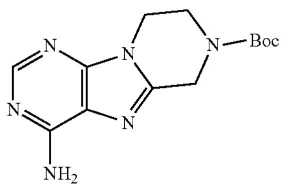 [SMILES: CC(C)(C)OC(=O)N1CCn2c(nc3c(N)ncnc32)C1] Molecular Weight: 290.33 |
| 171 | AXC-746 | 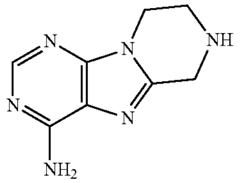 [SMILES: Nc1ncnc2c1nc1n2CCNC1] Molecular Weight: 190.21 |
| 172 | AXC-753 | 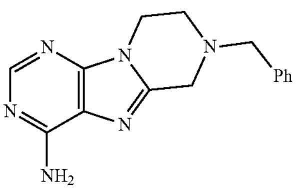 [SMILES: Nc1ncnc2c1nc1n2CCN(Cc2ccccc2)C1] Molecular Weight: 280.34 |

Example 6: Synthesis of TLR Agonists Comprising the Following Representative Structures—Core 4, (FIG. 1)

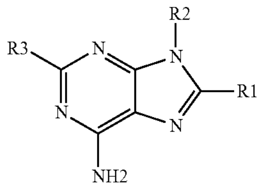

In some embodiments, $R_1$ is $C_1$ to $C_{12}$ alkyl, substituted $C_1$ to $C_{12}$ alkyl, oxygen containing $C_1$ to $C_{12}$ alkyl, $C_3$ to $C_8$ cocloalkyl, heterocycle, substituted heterocycle, halogen or H;

$R_2$ is $C_1$ to $C_{12}$ alkyl, $C_1$ to $C_{12}$ substituted alkyl, C4 to $C_8$ cycloalkyl, aromatic cycle, substituted aromatic cycle, aromatic heterocycle, substituted aromatic heterocycle, —$ONH_2$ terminal $C_1$ to $C_{12}$ alkyl, or H;

$R_3$ is $C_1$ to $C_{12}$ alkyl, substituted $C_1$ to $C_{12}$ alkyl, oxygen/nitrogen/sulfur containing $C_1$ to $C_{12}$ alkyl, heterocycle, substituted heterocycle, cyclo alkyl, substituted cyclo alkyl, —$N_3$, terminal $C_1$ to $C_{12}$ alkyl, terminal substituted $C_1$ to $C_{12}$ alkyl, or absent.

TLR-agonists having Core 4 structures were synthesized as disclosed in the schemes below,

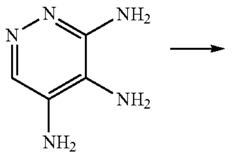

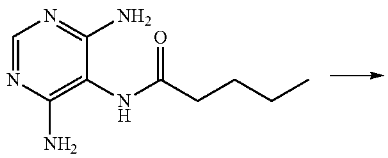

193

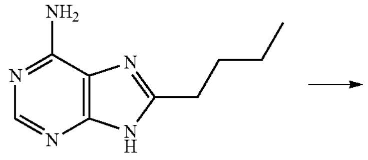

194

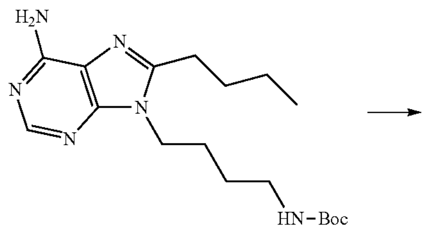

195

-continued

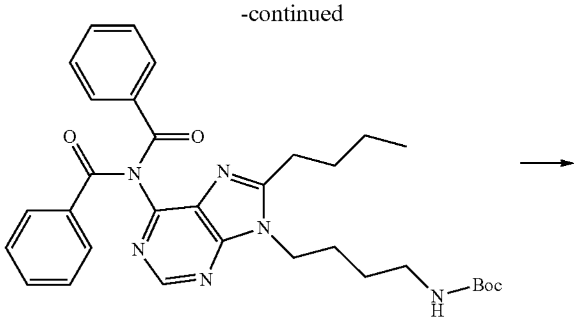

196

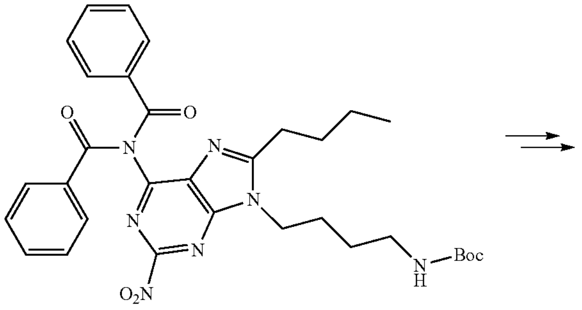

197

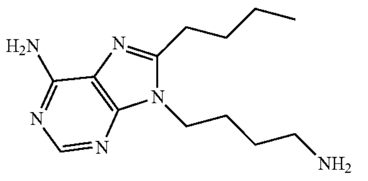

+

198

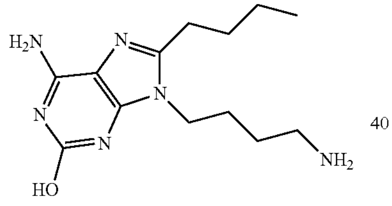

199

N-(4,6-diaminopyrimidin-5-yl)pentanamide (193): Pyrimidine-4,5,6-triamine (1015 mg, 8.112 mmol) was dissolved in N-methyl-2-pyrrolidone (10 mL) at 70° C. After the solution turned clear, it was cooled to 23° C. To the mixture was added valeryl chloride (980 ul, 8.127 mmol) and the temperature raised to 50° C. After 20 h, the temperature was lowered to 23° C., EtOAc (50 ml, precipitate) was added to the mixture, and the precipitate was separated by filtered. The solid was washed with EtOAc (10 ml) and acetone (10 ml), and dried to obtain compound 193 (1780 mg, 7.237 mmol, 90%) as a light brown solid. The product was used for the next step without further purification. MS m/z 210 $(M+H)^+$.

8-butyl-9H-purin-6-amine (194): To a solution of crude compound 193 (1780 mg, 7.273 mmol) in n-BuOH (30 mL) was added sodium methoxide (1570 mg, 29.063 mmol) at 23° C., and heated to reflux. After 1 h, the solution was cooled to room temperature, neutralized with 6 M HCl (3.2 ml), and brine (20 ml) added to obtain a biphasic mixture. The organic layer was separated, dried by $MgSO_4$ followed by concentration in vacuo to obtain target compound 194 (1148 mg 6.003 mmol, 83%) as a light brown solid. MS m/z 192 $(M+H)^+$.

tert-butyl 4-(6-amino-8-butyl-9H-purin-9-yl)butylcarbamate (195): To a solution of N-Boc-amino-butanol (1520 mg, 8.032 mmol) and compound 194 (1420 mg, 7.426 mmol) in THF (20 ml) was added $PPh_3$ (2080 mg, 7.930 mmol) at 0° C. After 30 min, to this mixture was added DIAD (2200 ul, 11.174 mmol) at 0° C. over 5 min. After 3 h, the solvent was removed in vacuo. The residue was diluted by DCM (100 ml) and washed with half saturated sodium bicarbonate (100 ml) and brine (20 ml). The organic layer was dried over $MgSO_4$ and filtered. The solvent was removed in vacuo. The residue was purified by flash chromatography to obtain compound 195 (1064 mg, 2.935 mmol, 37%) as a light brown solid. MS m/z 363 $(M+H)^+$.

tert-butyl 4-(6-(N-benzoylbenzamido)-8-butyl-9H-purin-9-yl)butylcarbamate (196): To a solution of compound 195 (1064 mg, 2.935 mmol) in DCM (10 ml) was added benzoylchloride (700 ul, 4.980 mmol) and TEA (900 ul, 17.788 mmol) at 0° C., and the temperature raised to 20° C. After 2.5 h, the mixture was washed with saturated sodium bicarbonate (50 ml) and brine (50 ml), dried over $MgSO_4$ and filtered. The solvent was removed in vacuo and the residue purified by flash chromatography to obtain compound 196 (1650 mg, 2.891 mmol, 98%) as a light brown oil. MS m/z 571 $(M+H)^+$.

tert-butyl 4-(6-(N-benzoylbenzamido)-8-butyl-2-nitro-9H-purin-9-yl)butylcarbamate (197): To a solution of tetramethyl ammonium nitrate (780 mg, 5.729 mmol) in DCM (10 ml) was added trifluoroacetic anhydride (1200 ul, 17.118 mmol) at 23° C. After 1 h, the mixture was cooled to 0° C., and a solution of compound 196 (1650 mg, 2.891 mmol) in DCM (20 ml) was added. The temperature was raised to 23° C. After 2 h, the mixture was diluted with DCM (20 ml), washed with half saturated sodium bicarbonate (20 ml) and brine (20 ml), dried over $MgSO_4$, and filtered. The solvent was removed in vacuo and the residue purified by flash chromatography to obtain compound 197 (1067 mg, 1.733 mmol, 60%) as a glassy light yellow solid. MS m/z 616 $(M+H)^+$.

9-(4-aminobutyl)-8-butyl-9H-purin-6-amine (198) and 6-amino-9-(4-aminobutyl)-8-butyl-9H-purin-2-ol (199): To a solution of compound 197 (220 mg, 0.357 mmol) in EtOH (20 ml) was added Pd/C (10%, 0.1 g) at 23° C., and hydrogen gas bubbled. After 18 h, LCMS showed that denitrated compound was made. NaOMe (30 mg, 0.6 mmol) was added, and the mixture stirred for 4 h. Next, TFA (3 ml) was added. After 20 min, the solvent was removed in vacuo and the mixture was purified by Prep-LC to obtain compound 198 (94 mg, 0.156 mmol, 44%) as a light brown solid, MS m/z 263 $(M+H)^+$, and compound 199 (0.024 mmol, 7%) as a light brown solid, MS m/z 279 $(M+H)^+$.

199 +

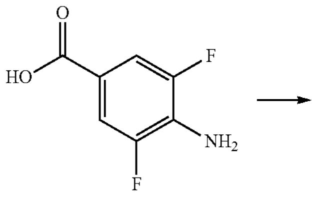

-continued

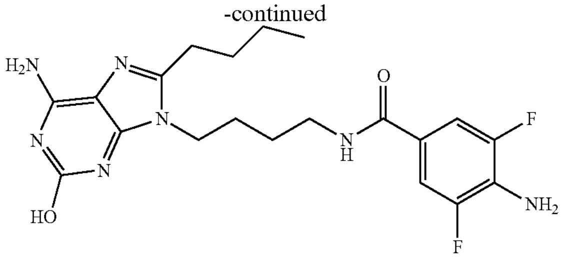

200

4-amino-N-(4-(6-amino-8-butyl-2-hydroxy-9H-purin-9-yl)butyl)-3,5-difluorobenzamide (200): Compound 200 was prepared using compound 199 and 4-amino-3,5-difluoro-benzoic acid as starting materials, with similar procedure as described for 150 to obtain target compound 200 (14 mg, 0,018 mmol, 61%) as a light brown solid, MS m/z 434 $(M+H)^+$.

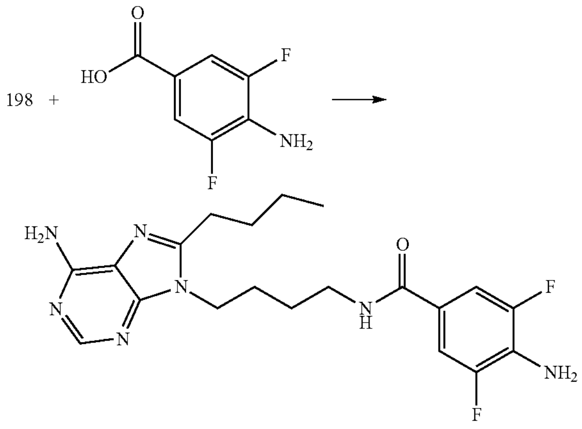

201

4-amino-N-(4-(6-amino-8-butyl-9H-purin-9-yl)butyl)-3,5-difluorobenzamide (201): Compound 201 was prepared using compound 198 and 4-amino-3,5-difluoro-benzoic acid as starting materials, with similar procedure as described for 150 to obtain target compound 201 (13 mg, 0.017 mmol, 93%) as a light brown solid, MS m/z 418 $(M+H)^+$.

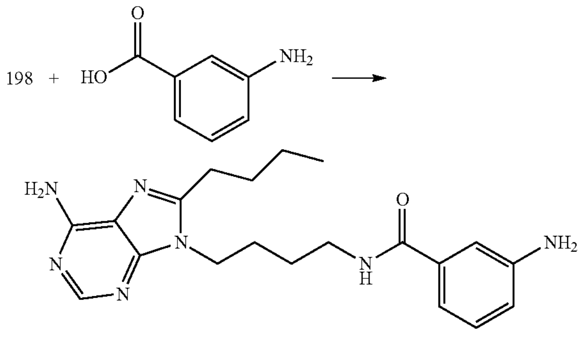

202

3-amino-N-(4-(6-amino-8-butyl-9H-purin-9-yl)butyl) benzamide (202): Compound 202 was prepared using compound 198 and 3-aminobenzoic acid as starting materials, with similar procedure as described for 150 to obtain target compound 202 (10 mg, 0.014 mmol, 88%) as a light brown solid, MS m/z 382 $(M+H)^+$.

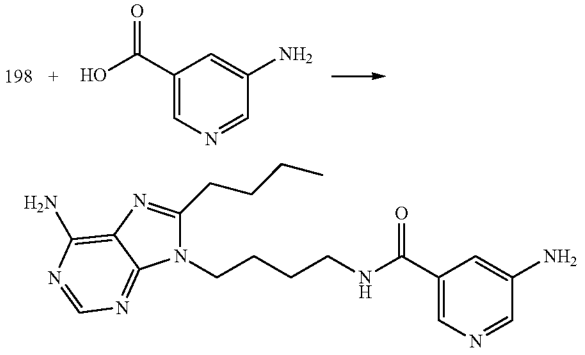

203

5-amino-N-(4-(6-amino-8-butyl-9H-purin-9-yl)butyl) nicotinamide (203): Compound 203 was prepared using compound 198 and 5-amino-nicotinic acid as starting materials, with similar procedure as described for 150 to obtain target compound 203 (14 mg, 0.019 mmol, quant) as a light brown solid, MS m/z 383 $(M+H)^+$.

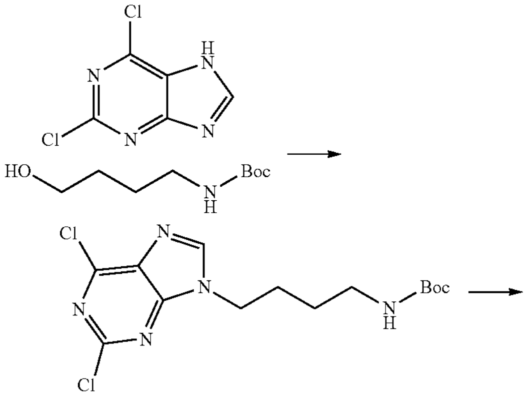

204

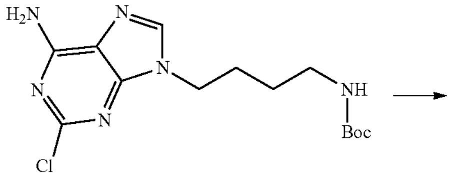

205

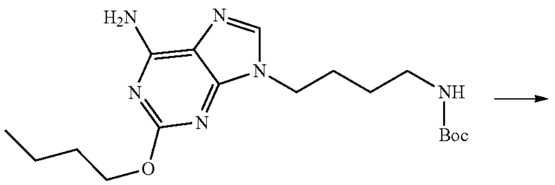

206

-continued

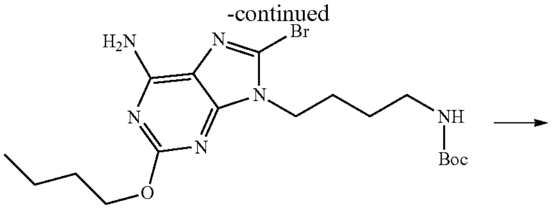

207

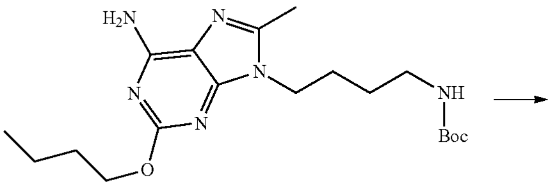

208

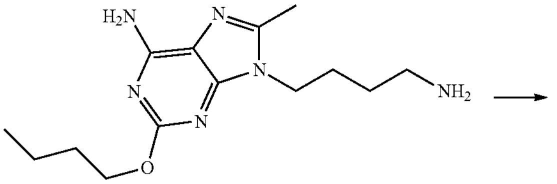

208

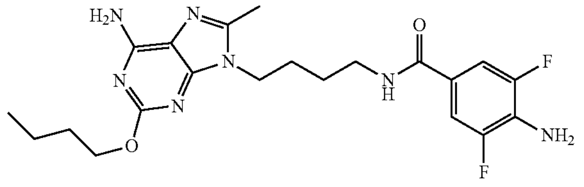

210 tert-butyl 4-(2,6-dichloro-9H-purin-9-yl)butylcarbamate (204): To a solution of N-Boc-amino-butanol (1620 mg, 8.560 mmol) and 2,6-dichloropurine (1495 mg, 7.910 mmol) in THF (10 ml) was added $PPh_3$ (2280 mg, 8.693 mmol) at 0° C. After 30 min, DIAD (2300 ul, 11.681 mmol) was added at 0° C. over 5 min. The mixture was stirred at 50° C. After 6 h, the solvent was removed in vacuo. The residue was diluted with EtOAc (100 ml), and washed with half saturated sodium bicarbonate (100 ml) and brine (20 ml). The organic layer was dried by $MgSO_4$ and filtered. The solvent was removed in vacuo. The residue was purified by flash chromatography to obtain compound 204 (4500 mg, <12.492 mmol, <100%) as a yellow oil. (~20% of impurity is PPh3). MS m/z 361 $(M+H)^+$.

tert-butyl 4-(6-amino-2-chloro-9H-purin-9-yl)butylcarbamate (205): Compound 204 (crude mixture of $PPh_3$, 4500 mg, <12.492 mmol) was placed in a pressure resistant glass vessel equipped with a stirring bar. To this vessel was added 7N $NH_3$ in MeOH (12 mL, 84 mmol). The tube was sealed and then heated at 120° C. After 30 min, the solvent was removed in vacuo and the residue dissolved in DCM (100 ml). The solution was washed with saturated sodium bicarbonate (100 ml) and brine (30 ml). The organic layer was dried over $MgSO_4$ and filtered. The solvent was removed in vacuo. The residue was purified by flash chromatography to obtain compound 205 (1310 mg, 3.844 mmol, 37%) as light yellow solid. MS m/z 341 $(M+H)^+$.

tert-butyl 4-(6-amino-2-butoxy-9H-purin-9-yl)butylcarbamate (206): To a solution of compound 205 (257 mg, 0.754 mmol) in n-butanol (5 ml) was added sodium metal (90 mg, 2.455 mmol) at 23° C. under dry nitrogen gas. The temperature was raised to 100° C. After 18 h, the solvent was removed in vacuo. The residue was dissolved in DCM (50 ml) and washed with half saturated sodium bicarbonate (50 ml) and brine (50 ml). The organic layer was dried over $MgSO_4$ and filtered. The solvent was removed in vacuo. Compound 206 (310 mg, <0.819 mmol, quant.) was obtained as a light brown crude solid. MS m/z 379 $(M+H)^+$.

tert-butyl 4-(6-amino-8-bromo-2-butoxy-9H-purin-9-yl)butylcarbamate (207): To a solution of compound 206 (310 mg, 0.819 mmol, crude) in DCM (10 ml) was added bromine (150 ul, 0.563 mmol) at 23° C. After 1 h, the solvent was removed in vacuo. The mixture was purified by flash chromatography to obtain compound 207 (250 mg, 0.547 mmol, 67%) as glassy light yellow solid. MS m/z 458 $(M+H)^+$.

tert-butyl 4-(6-amino-2-butoxy-8-methyl-9H-purin-9-yl)butylcarbamate (208): To a solution of compound 207 (82 mg, 0.179 mmol) in dry THF (5 ml) was added trimethylaluminum, 1 M (360 ul, 0.36 mmol) in THF and $PdCl_2(PPh_3)_2$ (44 mg, 0.063 mmol) at 23° C. The mixture was refluxed. After 20 h, the mixture was diluted by 20 ml of DCM and washed with half saturated sodium bicarbonate (20 ml) and brine (20 ml). The organic layer was dried over $MgSO_4$ and filtered. The solvent was removed in vacuo. The residue was purified by flash chromatography to obtain compound 208 (12 mg, 0.031 mmol, 17%) as a light brown solid. MS m/z 393 $(M+H)^+$.

9-(4-aminobutyl)-2-butoxy-8-methyl-9H-purin-6-amine (209): To a solution of compound 208 (12 mg, 0.031 mmol) in DCM (0.5 ml) was added trifluoroacetic acid (0.5 ml) at 23° C. After 1 h, the solvent was removed in vacuo. The residue was dried on high vacuum pump over night to obtain compound 209 (15 mg, 0.02 mmol, quant) as a light brown solid. MS m/z 293 $(M+H)^+$.

4-amino-N-(4-(6-amino-2-butoxy-8-methyl-9H-purin-9-yl)butyl)-3,5-difluorobenzamide (210): Compound 210 was prepared using compound 209 and 4-amino-3,5-difluorobenzoic acid as starting materials, with similar procedure as described for 150 to obtain target compound 210 (3.5 mg, 0.004 mmol, 22%) as a light brown solid, MS m/z 469 $(M+H)^+$.

207

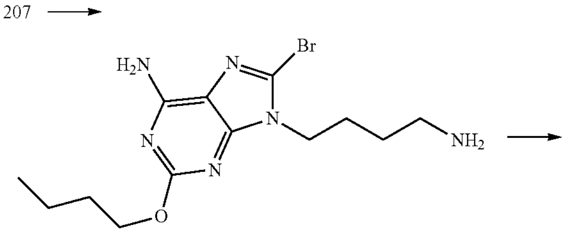

211

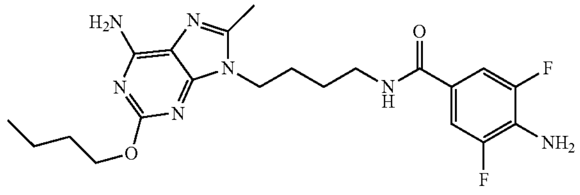

212

9-(4-aminobutyl)-8-bromo-2-butoxy-9H-purin-6-amine (211): Compound 211 was prepared using compound 207 with similar procedure as described for 209 to obtain target compound 211 ((8 mg, 0.011 mmol, quant) as a light brown solid, MS m/z 358 $(M+H)^+$.

4-amino-N-(4-(6-amino-8-bromo-2-butoxy-9H-purin-9-yl)butyl)-3,5-difluorobenzamide (212): Compound 212 was prepared using compound 211 and 4-amino-3,5-difluorobenzoic acid as starting materials, with similar procedure as described for 150 to obtain target compound 212 (8 mg, 0.009 mmol, 82%) as a light brown solid, MS m/z 513 $(M+H)^+$.

TABLE 7

| TLR Agonists - Core 4 Compounds | | |
|---|---|---|
| Compound No. | Compound Name | Structure - Core 4 Compounds |
| 198 | AXC-844 | 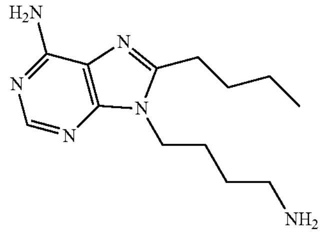 [SMILES: CCCCc1nc2c(N)ncnc2n1CCCCN] Molecular Weight: 262.4 |
| 200 | AXC-842 | 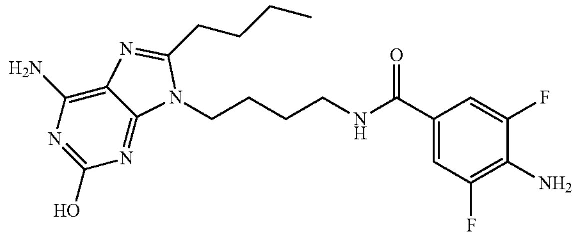 [SMILES: CCCCc1nc2c(N)nc(O)nc2n1CCCCNC(=O)c1cc(F)c(N)c(F)c1] Molecular Weight: 433.5 |
| 201 | AXC-843 | 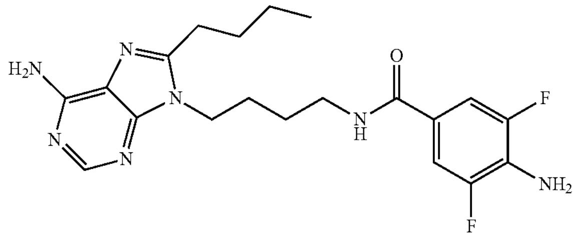 [SMILES: CCCCc1nc2c(N)ncnc2n1CCCCNC(=O)c1cc(F)c(N)c(F)c1] Molecular Weight: 417.5 |
| 202 | AXC-845 | 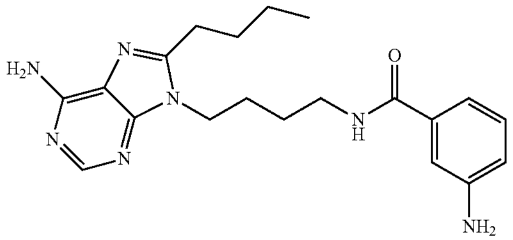 [SMILES: CCCCc1nc2c(N)ncnc2n1CCCCNC(=O)c1cccc(N)c1] Molecular Weight: 381.5 |
| 203 | AXC-846 | 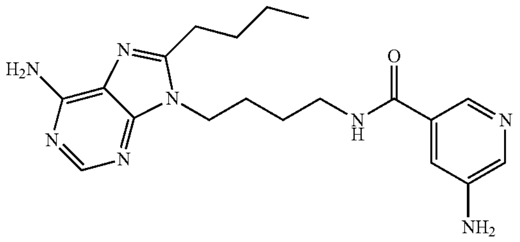 [SMILES: CCCCc1nc2c(N)ncnc2n1CCCCNC(=O)c1cncc(N)c1] Molecular Weight: 382.5 |

TABLE 7-continued

| TLR Agonists - Core 4 Compounds | | |
|---|---|---|
| Compound No. | Compound Name | Structure - Core 4 Compounds |
| 210 | AXC-836 | 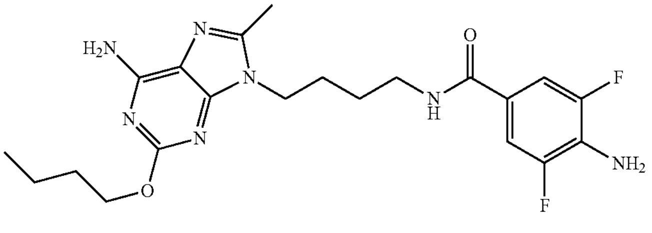 [SMILES: CCCCOc1nc(N)c2nc(C)n(CCCCNC(=O)c3cc(F)c(N)c(F)c3)c2n1] Molecular Weight: 447.5 |
| 212 | AXC-841 | 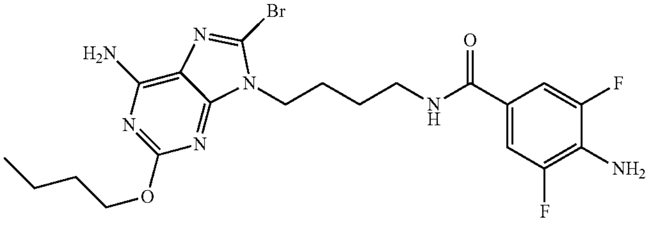 [SMILES: CCCCOc1nc(N)c2nc(Br)n(CCCCNC(=O)c3cc(F)c(N)c(F)c3)c2n1] Molecular Weight: 512.4 |

Example 7: This Example Discloses Various Methodologies and Techniques Used in the Present Invention Molecular Cloning—CHO cell codon-optimized antibody heavy chain and light chain cDNA sequences were obtained from commercial DNA synthesis service (IDT, San Diego, Calif.). The synthesized DNA fragments were digested with Hind III and EcoR I (both from New England Biolabs (NEB), Ipswich, Mass.) and purified by PCR purification kit (Qiagen, Valencia, Calif.). The digested antibody gene fragments were ligated into the expression vector via quick ligation kit (NEB) to yield the constructs for expression of wild type antibody heavy chain and light chain. The resulting plasmids were propagated in *E. coli* and verified by DNA sequencing service (Eton).

Generation of amber codon-containing mutants—Based on the crystal structure of anti-HER2 Fab, 10 different surface-accessible sites located at light chain constant region were chosen to genetically incorporate non-natural amino acid (for example, para-acetyl-phenylalanine (pAF), or para-azido-phenylalanine). Those sites are not critical for antigen-antibody binding. Each genetic codon of the chosen site was then mutated to amber codon (TAG) via site-directed mutagenesis to generate expression plasmid for that antibody mutant. Primers were purchased from IDT. All site directed mutagenesis experiments were carried out using Q5 site-directed mutagenesis kit following instruction manuals (NEB). The expression plasmids for the mutants were propagated in *E. coli* and verified by DNA sequencing service (Eton). Table 8 provides a list of amber mutations sites in the heavy chain or light chain constant region of anti-HER2 Fab with their Kabat numbering and the corresponding amino acid sequences, SEQ ID NOs.: 2, and 4 to 11. SEQ ID NOs.: 1 and 3 shows the wild type heavy and light chains of anti-HER2 Fab, respectively. Anti-HER2 Fabs include the heavy chain and light chain sequences of: SEQ ID NO: 2 and SEQ ID NO: 4; SEQ ID NO: 2 and SEQ ID NO: 5; SEQ ID NO: 2 and SEQ ID NO: 6; SEQ ID NO: 2 and SEQ ID NO: 7; SEQ ID NO: 2 and SEQ ID NO: 8; SEQ ID NO: 2 and SEQ ID NO: 9; SEQ ID NO: 2 and SEQ ID NO: 10; SEQ ID NO: 2 and SEQ ID NO: 11; SEQ ID NO: 2 and SEQ ID NO: 12; SEQ ID NO: 2 and SEQ ID NO: 13.

TABLE 8

Anti-HER2 Fab heavy chain (HC) and light chain (LC) amino acid sequences with Amber sites for non-natural amino acid incorporation. Also disclosed are all of the sequences in the table below where pAF is replaced by any other non-natural amino acid.

| SEQ ID NO. | Description | Sequence |
|---|---|---|
| 1 | Heavy chain wild type | EVQLVESGGGLVQPGGSLRLSCAASGFNIKDTYIH<br>WVRQAPGKGLEWVARIYPTNGYTRYADSVKGRFT<br>ISADTSKNTAYLQMNSLRAEDTAVYYCSRWGGDG<br>FYAMDYWGQGTLVTVSSASTKGPSVFPLAPSSKST<br>SGGTAALGCLVKDYFPEPVTVSWNSGALTSGVHT<br>FPAVLQSSGLYSLSSVVTVPSSSLGTQTYICNVNH<br>KPSNTKVDKKVEPKSCDKTHTCPPCPAPELLGGPS<br>VFLFPPKPKDTLMISRTPEVTCVVVDVSHEDPEVK<br>FNWYVIDGVEVHNAKTKPREEQYNSTYRVVSVLT |

TABLE 8-continued

Anti-HER2 Fab heavy chain (HC) and light chain (LC) amino acid sequences with Amber sites for non-natural amino acid incorporation. Also disclosed are all of the sequences in the table below where pAF is replaced by any other non-natural amino acid.

| SEQ ID NO. | Description | Sequence |
|---|---|---|
| | | VLHQDWLNGKEYKCKVSNKALPAPIEKTISKAKG<br>QPREPQVYTLPPSRDELTKNQVSLTCLVKGFYPSD<br>IAVEWESNGQPENNYKTTPPVLDSDGSFFLYSKLT<br>VDKSRWQQGNVFSCSVMHEALHNHYTQKSLSLS<br>PG |
| 2 | Heavy Chain A114 mutation | EVQLVESGGGLVQPGGSLRLSCAASGFNIKDTYIH<br>WVRQAPGKGLEWVARIYPTNGYTRYADSVKGRFT<br>ISADTSKNTAYLQMNSLRAEDTAVYYCSRWGGDG<br>FYAMDYWGQGTLVTVSS**X**STKGPSVFPLAPSSKST<br>SGGTAALGCLVKDYFPEPVTVSWNSGALTSGVHT<br>FPAVLQSSGLYSLSSVVTVPSSSLGTQTYICNVNH<br>KPSNTKVDKKVEPKSCDKTHTCPPCPAPELLGGPS<br>VFLFPPKPKDTLMISRTPEVTCVVVDVSHEDPEVK<br>FNWYVDGVEVHNAKTKPREEQYNSTYRVVSVLT<br>VLHQDWLNGKEYKCKVSNKALPAPIEKTISKAKG<br>QPREPQVYTLPPSRDELTKNQVSLTCLVKGFYPSD<br>IAVEWESNGQPENNYKTTPPVLDSDGSFFLYSKLT<br>VDKSRWQQGNVFSCSVMHEALHNHYTQKSLSLS<br>PG |
| 3 | Light Chain wild type | DIQMTQSPSSLSASVGDRVTITCRASQDVNTAVAW<br>YQQKPGKAPKLLIYSASFLYSGVPSRFSGSRSGTD<br>FTLTISSLQPEDFATYYCQQHYTTPPTFGQGTKVEI<br>KRTVAAPSVFIFPPSDEQLKSGTASVVCLLNNFYPR<br>EAKVQWKVDNALQSGNSQESVTEQDSKDSTYSLS<br>STLTLSKADYEKHKVYACEVTHQGLSSPVTKSFN<br>RGEC |
| 4 | Light Chain V110 mutation | DIQMTQSPSSLSASVGDRVTITCRASQDVNTAVAW<br>YQQKPGKAPKLLIYSASFLYSGVPSRFSGSRSGTD<br>FTLTISSLQPEDFATYYCQQHYTTPPTFGQGTKVEI<br>KRT**X**AAPSVFIFPPSDEQLKSGTASVVCLLNNFYPR<br>EAKVQWKVDNALQSGNSQESVTEQDSKDSTYSLS<br>STLTLSKADYEKHKVYACEVTHQGLSSPVTKSFN<br>RGEC |
| 5 | Light Chain A112 mutation | DIQMTQSPSSLSASVGDRVTITCRASQDVNTAVAW<br>YQQKPGKAPKLLIYSASFLYSGVPSRFSGSRSGTD<br>FTLTISSLQPEDFATYYCQQHYTTPPTEGQGTKVEI<br>KRTVA**X**PSVFIFPPSDEQLKSGTASVVCLLNNFYP<br>REAKVQWKVDNALQSGNSQESVTEQDSKDSTYS<br>LSSTLTLSKADYEKHKVYACEVTHQGLSSPVTKSF<br>NRGEC |
| 6 | Light Chain S114 mutation | DIQMTQSPSSLSASVGDRVTITCRASQDVNTAVAW<br>YQQKPGKAPKLLIYSASFLYSGVPSRFSGSRSGTD<br>FTLTISSLQPEDFATYYCQQHYTTPPTEGQGTKVEI<br>KRTVAAP**X**VFIFPPSDEQLKSGTASVVCLLNNFYP<br>REAKVQWKVDNALQSGNSQESVTEQDSKDSTYS<br>LSSTLTLSKADYEKHKVYACEVTHQGLSSPVTKSF<br>NRGEC |
| 7 | Light Chain S121 mutation | DIQMTQSPSSLSASVGDRVTITCRASQDVNTAVAW<br>YQQKPGKAPKLLIYSASFLYSGVPSRFSGSRSGTD<br>FTLTISSLQPEDFATYYCQQHYTTPPTFGQGTKVEI<br>KRTVAAPSVFIFPP**X**DEQLKSGTASVVCLLNNFYP<br>REAKVQWKVDNALQSGNSQESVTEQDSKDSTYS<br>LSSTLTLSKADYEKHKVYACEVTHQGLSSPVTKSF<br>NRGEC |
| 8 | Light Chain S127 mutation | DIQMTQSPSSLSASVGDRVTITCRASQDVNTAVAW<br>YQQKPGKAPKLLIYSASFLYSGVPSRFSGSRSGTD<br>FTLTISSLQPEDFATYYCQQHYTTPPTEGQGTKVEI<br>KRTVAAPSVFIFPPSDEQLK**X**GTASVVCLLNNFYP<br>REAKVQWKVDNALQSGNSQESVTEQDSKDSTYS<br>LSSTLTLSKADYEKHKVYACEVTHQGLSSPVTKSF<br>NRGEC |

TABLE 8-continued

Anti-HER2 Fab heavy chain (HC) and light chain (LC) amino acid sequences with Amber sites for non-natural amino acid incorporation. Also disclosed are all of the sequences in the table below where pAF is replaced by any other non-natural amino acid.

| SEQ ID NO. | Description | Sequence |
|---|---|---|
| 9 | Light Chain K149 mutation | DIQMTQSPSSLSASVGDRVTITCRASQDVNTAVAW YQQKPGKAPKLLIYSASFLYSGVPSRFSGSRSGTD FTLTISSLQPEDFATYYCQQHYTTPPTFGQGTKVEI KRTVAAPSVFIFPPSDEQLKSGTASVVCLLNNFYPR EAKVQW**X**VDNALQSGNSQESVTEQDSKDSTYSLS STLTLSKADYEKHKVYACEVTHQGLSSPVTKSFN RGEC |
| 10 | Light Chain S156 mutation | DIQMTQSPSSLSASVGDRVTITCRASQDVNTAVAW YQQKPGKAPKLLIYSASFLYSGVPSRFSGSRSGTD FTLTISSLQPEDFATYYCQQHYTTPPTFGQGTKVEI KRTVAAPSVFIFPPSDEQLKSGTASVVCLLNNFYPR EAKVQWKVDNALQ**X**GNSQESVTEQDSKDSTYSL SSTLTLSKADYEKHKVYACEVTHQGLSSPVTKSFN RGEC |
| 11 | Light Chain S168 mutation | DIQMTQSPSSLSASVGDRVTITCRASQDVNTAVAW YQQKPGKAPKLLIYSASFLYSGVPSRFSGSRSGTD FTLTISSLQPEDFATYYCQQHYTTPPTFGQGTKVEI KRTVAAPSVFIFPPSDEQLKSGTASVVCLLNNFYPR EAKVQWKVDNALQSGNSQESVTEQD**X**KDSTYSL SSTLTLSKADYEKHKVYACEVTHQGLSSPVTKSFN RGEC |
| 12 | Light Chain S202 mutation | DIQMTQSPSSLSASVGDRVTITCRASQDVNTAVAW YQQKPGKAPKWYSASFLYSGVPSRFSGSRSGTD FTLTISSLQPEDFATYYCQQHYTTPPTEGQGTKVEI KRTVAAPSVFIFPPSDEQLKSGTASVVCLLNNFYPR EAKVQWKVDNALQSGNSQESVTEQDSKDSTYSLS STLTLSKADYEKHKVYACEVTHQGL**X**SPVTKSFN RGEC |
| 13 | Light Chain V205 mutation | DIQMTQSPSSLSASVGDRVTITCRASQDVNTAVAW YQQKPGKAPKWYSASFLYSGVPSRFSGSRSGTD FTLTISSLQPEDFATYYCQQHYTTPPTFGQGTKVEI KRTVAAPSVFIFPPSDEQLKSGTASVVCLLNNFYPR EAKVQWKVDNALQSGNSQESVTEQDSKDSTYSLS STLTLSKADYEKHKVYACEVTHQGLSSP**X**TKSFN RGEC |

X Denotes non-natural amino acid (nnAA);
underlined denotes Fc mutation in Table 7

In addition to an amber mutation in the heavy chain at position 114, Fc mutations were also generated at various positions of the anti-HER2 antibody or antibody fragment to improve the pharmacokinetics and/or enhance antibody dependent cellular phagocytosis (ADCP) and/or antibody dependent cellular cytoxicity ADCC activity, (Table 9).

TABLE 9 anti-HER2 Fc mutations

| Fc Mutations | Targeting Fc Receptor | Purpose |
|---|---|---|
| WT | N/A | Control |
| E233P/L234V/L235A | FcγRIII | ADCC Null |
| N434A | FcRn | Improved PK |
| M252Y/S254T/T256E | FcRn | Improved PK |
| M252Y/S254T/T256E G236A/S239D/I332E | FcRn/FcγRII/FcγRIII | PK and ADCP enhance |
| G236A/S239D/I332E | FcγRII/RIII | ADCP/ADCC enhance |
| G236A | FcγRII | ADCP enhance |

TABLE 9-continued anti-HER2 Fc mutations

| Fc Mutations | Targeting Fc Receptor | Purpose |
|---|---|---|
| D270E | FcγRII | ADCP enhance |
| Y300L | FcγRII | ADCP enhance |

Transient expression—Platform cell line 301-14 was maintained in EX-Cell 302 (Sigma) supplemented with 3 mM L-glutamine (Gibco) and 3 mM GlutaMAX (Gibco). Cells were passaged every 3-4 days seeded at density of 0.4 million cells per ml. One day prior to transfection, cells were seeded at 0.6 million cells per ml. On day 0, cells were transfected with antibody expression plasmids encoding the light chain and heavy chain using MaxCyte electroporation platform following instruction manual. After transfection, cells were rested in an empty 125 ml shaking flask and incubated in 37° C. static incubator for 30 mins. The transfected cells were then inoculated into basal expression media (50% Dynamis—50% ExCell 302 supplemented with 50 μM MSX) at density of $3\times10^6$/ml in shake flask. The transfected cells were incubated at 37° C., 5% $CO_2$ on orbital shaker set to 140 rpm. The 1 mM pAF was added to culture on day 1, together with 7 g/L of Cell Boost 5 (GE healthcare), 120 μg/L of Long R3 IGF-1 (sigma) and 2 mM GlutaMAX. Temperature was shifted from 37° C. to 32° C. inside the incubator. Another 7 g/L, of Cell Boost 5 and 2 mM GlutaMAX was added on day 3 and supernatant was collected on day 5. Glucose level was monitored using glucose meters and additional glucose was added to culture when glucose level was below 2 g/L in culture media. Viable cell count and viability were measured by Vi-Cell instrument. Productivity was measured by Octet using Protein G sensors.

Stable bulk pool generation—The expression plasmid was linearized using Pvu I (NEB) digestion for 6 hours. After linearization, the DNA was purified using phenol extraction and dissolved in endotoxin-free water at the concentration of 2.5 μg/μl. Platform cell line BB-117 was maintained in EX-Cell 302 supplemented with 3 mM L-glutamine and 3 mM GlutaMAX. Cells were passaged every 3-4 days seeded at density of $0.4\times10^6$/ml. One day prior to transfection, cells were seeded at $0.6\times10^6$/ml. On day 0, cells were transfected with linearized antibody expression plasmids using MaxCyte electroporation platform following instruction manual. After transfection, cells were rested in an empty 125 ml shaking flask and incubated in 37° C. static incubator for 30 mins. Then 30 ml recovery media (50% Ex-302-50% CD-CHO supplemented with 3 mM glutamine and 3 mM GlutaMAX) was added into the flask and shake overnight. One day one, transfected cells were counted, spin down, washed and re-suspended in selection media (50% Ex-302-50% CD-CHO with 50-100 μM MSX) for stable bulk pool generation. The viable cell numbers and viability were monitored, and media was changed every 3-4 days until the viability of the stable bulk pool goes back to 90%. When selection ends, frozen cell stocks were made, and the resulting stable bulk pool was used to generate material for fed-batch expression.

Fed-batch expression—Previously generated antibody stable bulk pools were inoculated into basal expression media (50% Dynamis—50% ExCell 302 supplemented with 50 μM MSX) at density of $0.5\times10^6$/ml in shake flask on day 0. The transfected cells were incubated at 37° C., 5% $CO_2$ on orbital shaker set to 140 rpm. The 0.5 mM pAF was added to culture on day 3, together with 10 g/L Cell Boost 4 (GE health care) and 0.52 g/L Cell Boost 7b (GE healthcare). 120 μg/L of Long R3 IGF-1 was added to culture on day 5. Glucose level was monitored using glucose meters and additional glucose was added to culture when glucose level was below 2 g/L in culture media. Viable cell count and viability were measured by Vi-Cell instrument. The supernatant was collected for purification on day 7. Productivity was measured by Octet using Protein G sensors.

Purification of Antibodies Containing nnAAs from EuCODE Expression System—Clarified Cell culture media containing the target antibody containing a nnAA was loaded over a protein A ProSep Ultra column (EMD Millipore) equilibrated in 20 mM sodium phosphate, 100 mM sodium chloride, pH 7.5. After loading, the column was washed with buffer A (20 mM sodium phosphate, 100 mM sodium chloride, pH 7.5) followed by wash buffer B (5 mM succinic acid, pH 5.8) to remove host cell contaminants. The target antibody was eluted from the column with elution buffer C (50 mM glycine, 10 mM succinic acid, pH 3.2). The target antibody was pooled, and pH adjusted to pH 5.0 with 2.0 M tris base. The target antibody was further purified by loading the conditioned protein A pool over a Capto SP Impres column (GE Healthcare) equilibrated in 30 mM sodium acetate, pH 5.0. The target antibody was eluted from the column with a linear gradient to 100% buffer B (30 mM sodium acetate, 0.5M sodium chloride, pH 5.0) and fractions containing monomeric antibody were pooled, 0.22 μM filtered, and stored at ≤65° C. until further use.

Figure 2:
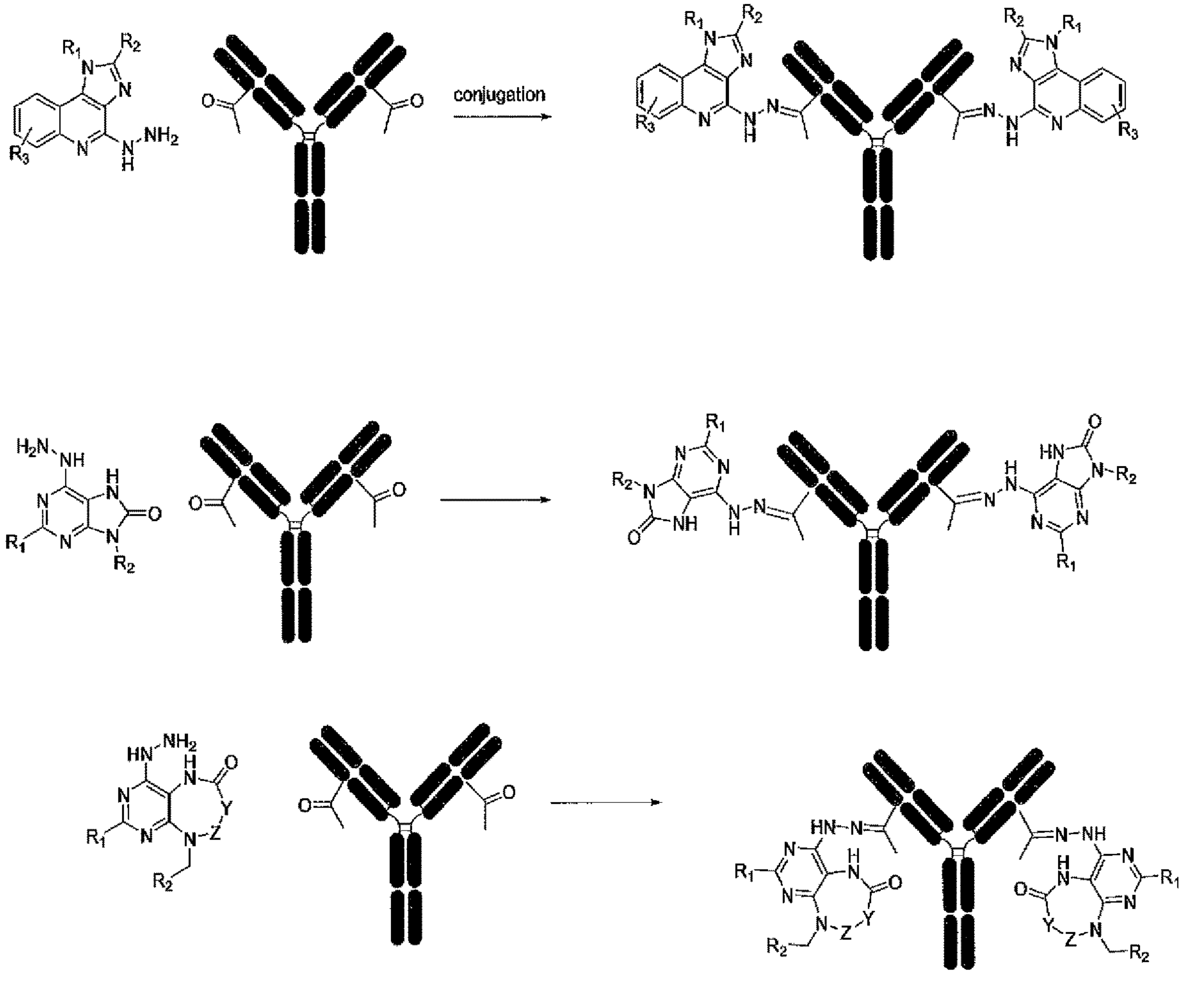
FIG. 2 depicts the structure of various TC conjugates.
Figure 3:
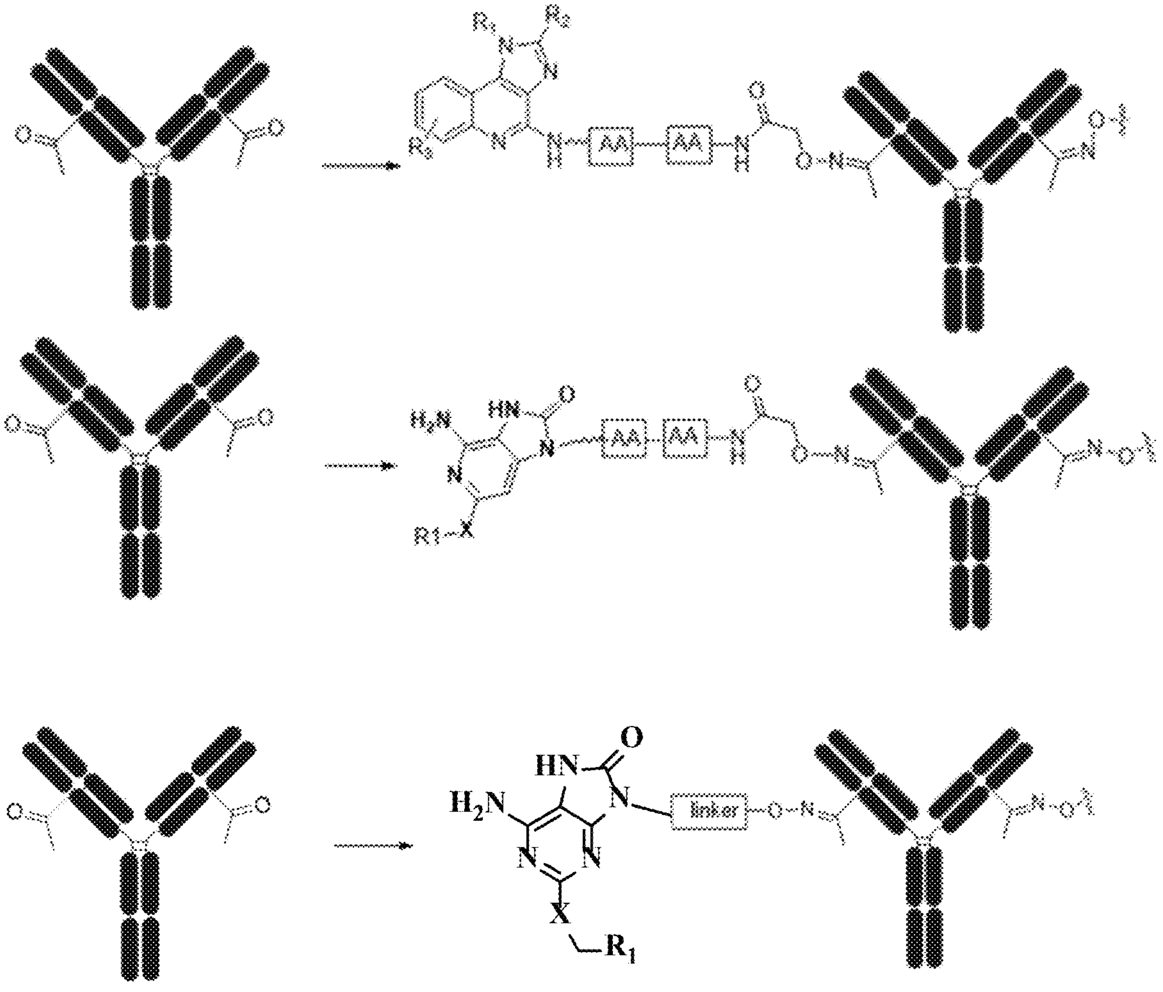
FIG. 3 depicts the structure of additional TC conjugates.

Site Specific. Conjugation of TLR agonist Linkers Payloads—Antibodies containing nnAA, for example para-acetyl phenylalanine, were buffer exchanged into conjugation buffer (30 mM sodium acetate, pH 4.0) and concentrated to 10-20 mg/mL. A final of 100 mM acetic hydrazide was added to the antibodies followed by 10 molar equivalents of hydroxyl-amine functionalized TLR agonist drug-linker. The conjugation reactions were incubated for 18-20 hours at 25-30° C. followed by purification over a Capto SP Impres column (GE Healthcare) to remove excess reagents. The purified ADCs were buffer exchanged into formulation buffer (50 mM histidine, 100 mM NaCl, 5% trehalose, pH 6.0) and stored at ≤65° C. until further use. FIGS. 2 and 3 illustrate site specific conjugation of the TCs of the present invention. TLR agonist drug-linker antibody conjugation is illustrated with various TLR-agonists. As shown in FIG. 3, AA indicates a cleavable amino acid linker; and L indicates a non-cleavable linker.

Example 8: In Vitro Function Assay for Small Molecule TLR Agonists

HEK-Blue™ hTLR7 cells were incubated in HEK-Blue™ Detection medium and stimulated with increasing concentrations of TLR7 or TLR8 or TLR7/8 agonists. After 24 h incubation, the levels of NF-kB-induced SEAP were determined by Quanti-Blue detection reagents (Invivogen, San Diego, Calif.), readings were obtained at OD of 655 nm. The $EC_{50}$ was determined from dose-response curve using Prism Software. The following Tables and Figures show the activity of exemplary TLR-agonists of the present invention described in Examples 1-6 herein. $EC_{50}$ values of less than 500 nM suggest compounds with higher potency than those with $EC_{50}$ values from 50 nM to 1 uM, or greater than 1 uM to 3 uM.

Figure 4:
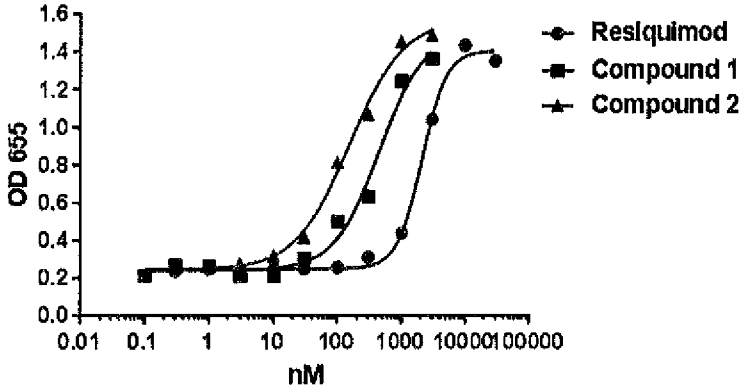
FIG. 4 depicts the biological activity of selected TC conjugates in a cell proliferation assay.
Figure 4:
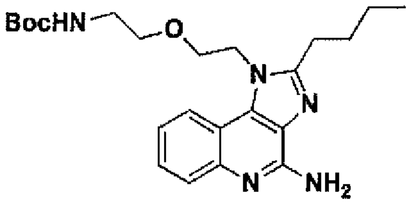
Figure 4:
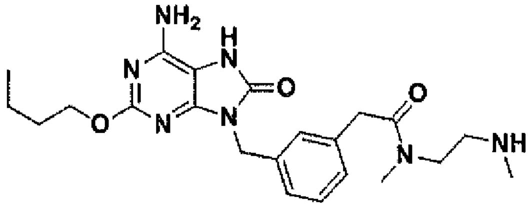

FIG. 4 shows TLR7 agonists stimulation in HEK-Blue hTLR7 reporter cell line using commercial TLR7 agonist Resiquimod (R848) with an $EC_{50}$ of 2.08 uM, Compound 1 with an $EC_{50}$ of 0.435 uM, and Compound 2 with an $EC_{50}$ of 0.153 uM.

Figure 5A:
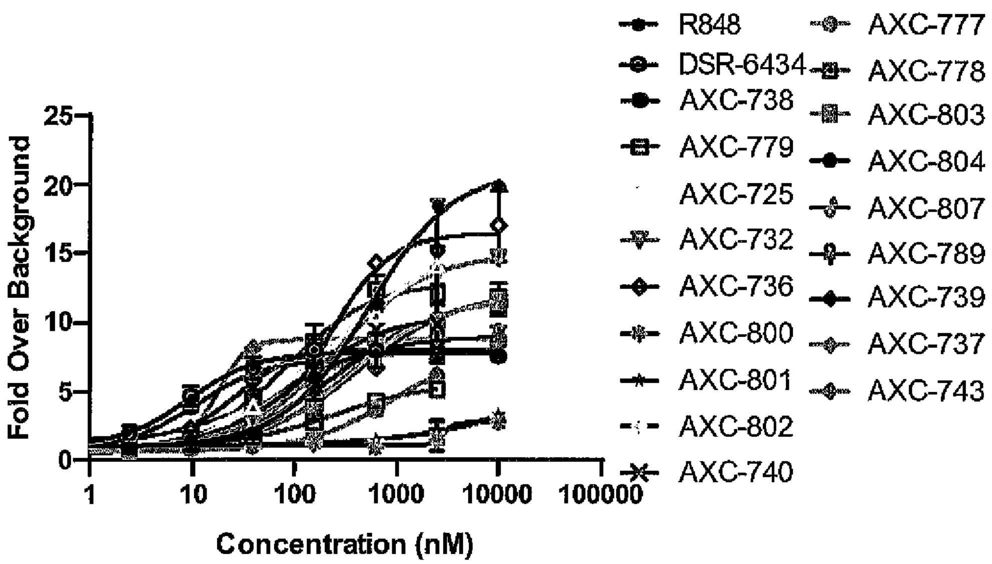
FIGS. 5A and 5B depict TLR7 activities of various TLR7 agonists.

Activity of exemplary TLR-agonists, disclosed in Examples 1-6 above, were assayed. FIG. 5A, Table 10 shows the $EC_{50}$ values compared to commercial controls DSR-6434, Resiquimod and Motolimod.

TABLE 10

Activity of Exemplary TLR Agonists

| Compound Number | Compound | TLR7 $EC_{50}$ (nM) |
|---|---|---|
| N/A | control - DSR-6434 | 9.203 |
| N/A | R848 - Resiquimod | 519.7 |
| 88 | AXC-779 | 242.1 |
| 60 | AXC-738 | 11.08 |
| 49 | AXC-725 | 249.4 |
| 54 | AXC-732 | 255.5 |
| 58 | AXC-736 | 213.4 |
| 62 | AXC-740 | 115.6 |
| 86 | AXC-777 | 910.4 |
| 87 | AXC-778 | 83.34 |
| 89 | AXC-789 | 71.34 |

TABLE 10-continued

| Activity of Exemplary TLR Agonists | | |
|---|---|---|
| Compound Number | Compound | TLR7 $EC_{50}$ (nM) |
| 109 | AXC-800 | >5000 |
| 106 | AXC-801 | >5000 |
| 112 | AXC-802 | >5000 |
| 93 | AXC-803 | 331.5 |
| 94 | AXC-804 | 260.3 |
| 97 | AXC-807 | 412.6 |
| 61 | AXC-739 | 28.17 |
| 59 | AXC-737 | 18.7 |
| 64 | AXC-743 | 56.11 |

Figure 5B:
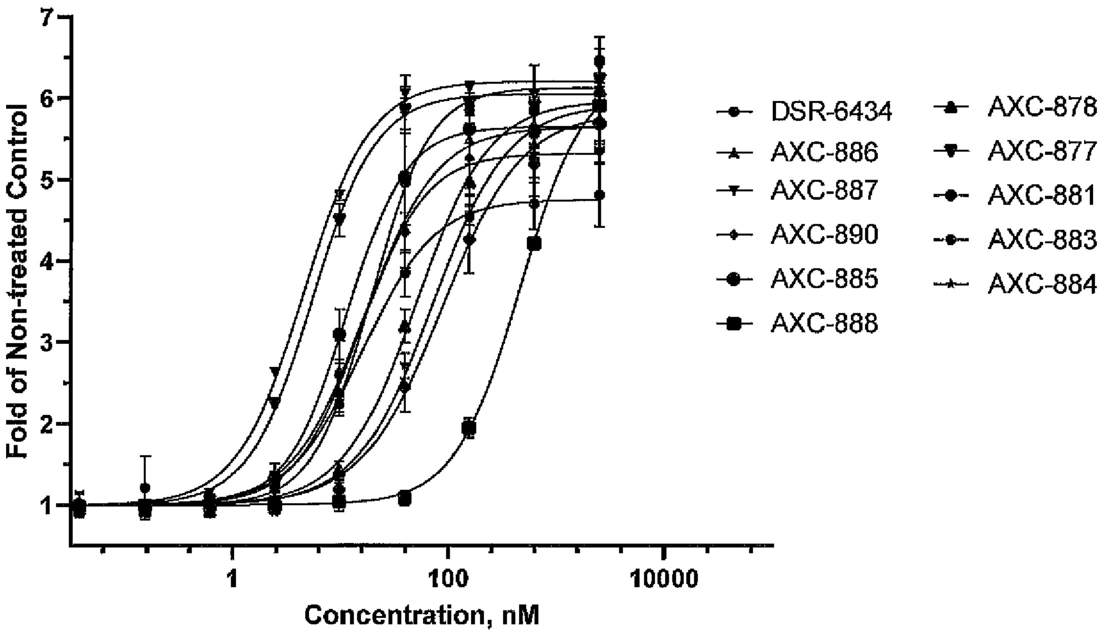

FIG. 5B and Table 11 show TLR7 activities of selected TLR7 agonists. AXC-887 and AXC-877 show $EC_{50}$ values below 10 nM suggesting these compounds are very potent TLR7 agonist. In a TLR8 reporter assay AXC-887 showed measurable activity with an $EC_{50}$ of 3733 nM compared to the commercial compound Motolimod with an $EC_{50}$ of 1427 nM. This suggested that ACX-887 is TLR7/8 dual agonist.

TABLE 11

| Activity of Exemplary TLR Agonists | |
|---|---|
| Compound | $EC_{50}$ (nM) |
| DSR-6434 | 15.8 |
| AXC-886 | 16.7 |
| AXC-887 | 4.6 |
| AXC-890 | 15.3 |
| AXC-885 | 11.3 |
| AXC-888 | 467.9 |
| AXC-878 | 50.4 |
| AXC-877 | 5.5 |
| AXC-881 | 87.3 |
| AXC-883 | 19.3 |
| AXC-884 | 71.3 |

Figure 6:
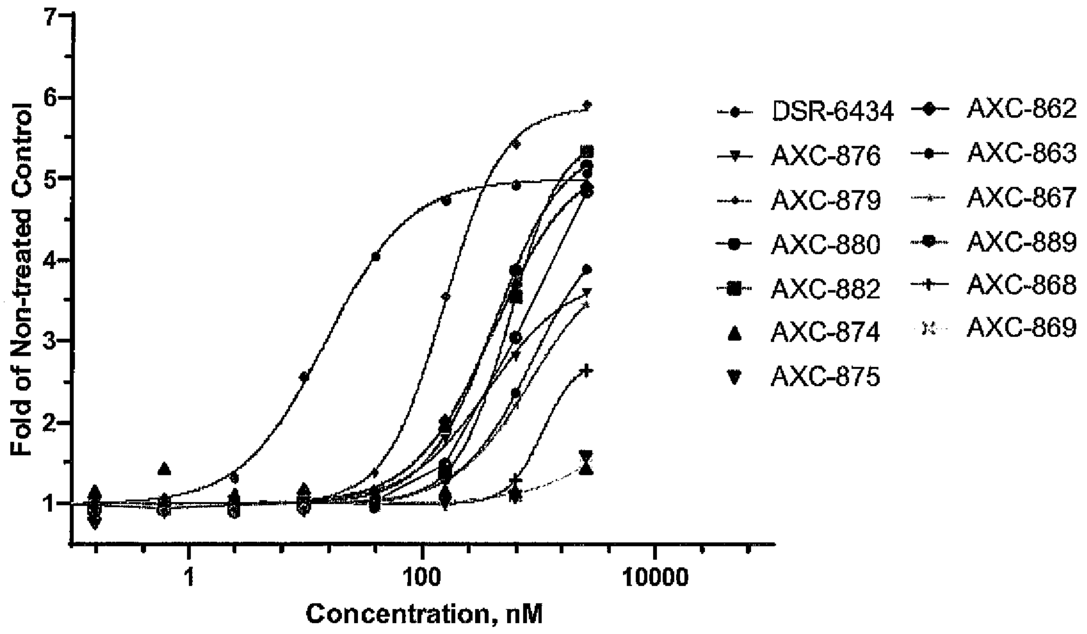
FIG. 6 depicts TLR7 activities of various TLR7 agonists attached to a linker.

FIG. 6 and Table 12 shows TLR7 activities of selected TLR7 agonists attached to a linker. AXC-879 demonstrated the highest potency among different TLR-agonist (payload) linkers.

TABLE 12

| Activity of Exemplary TLR Agonists and linkers | |
|---|---|
| Compound | TLR Agonist Payload + Linkers $EC_{50}$ (nM) |
| DSR-6434 | 14.8 |
| AXC-876 | 362.4 |
| AXC-879 | 151.2 |
| AXC-880 | 409.5 |
| AXC-882 | 550.8 |
| AXC-874 | >10,000 |
| AXC-875 | >10,000 |
| AXC-862 | 400.1 |
| AXC-863 | 864.2 |
| AXC-867 | 829.0 |
| AXC-868 | >5,000 |
| AXC-869 | >10,000 |
| AXC-889 | 696.5 |

Figure 7:
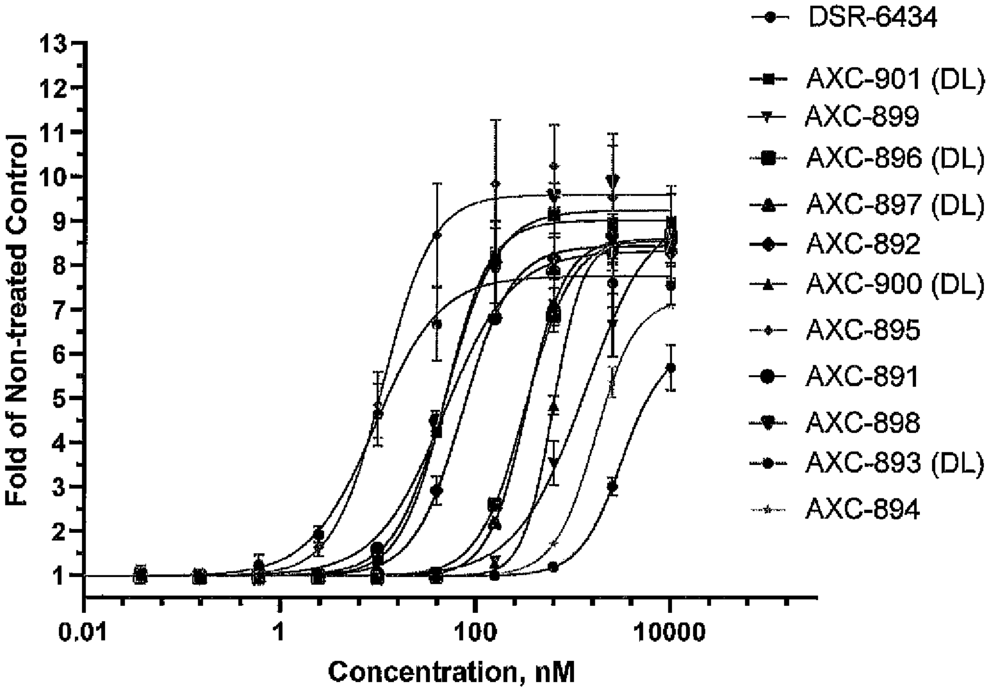
FIG. 7 depicts TLR7 activities of additional TLR7 agonists and TLR7 agonists attached to a linker.

FIG. 7 and Table 13 showed TLR7 activities of additional TLR7 agonists and TLR7 agonists attached to a linker. AXC-895 demonstrated the highest potency among different payloads tested and AXC-901 demonstrated the highest potency among different payload linkers. (DL) denotes drug linker or TLR-agonist attached to a linker or TLR agonist (payload) attached to a linker.

TABLE 13

| Activity of Exemplary TLR Agonists and linkers | |
|---|---|
| Compound | $EC_{50}$ (nM) |
| DSR-6434 | 9 |
| AXC-901 (DL) | 48 |
| AXC-900 (DL) | 615 |
| AXC-899 | 1302 |
| AXC-895 | 11 |
| AXC-891 | 47 |
| AXC-896 (DL) | 325 |
| AXC-897 (DL) | 330 |
| AXC-898 | 50 |
| AXC-892 | 73 |
| AXC-893 (DL) | 3120 |
| AXC-894 | 1672 |

Figure 8:
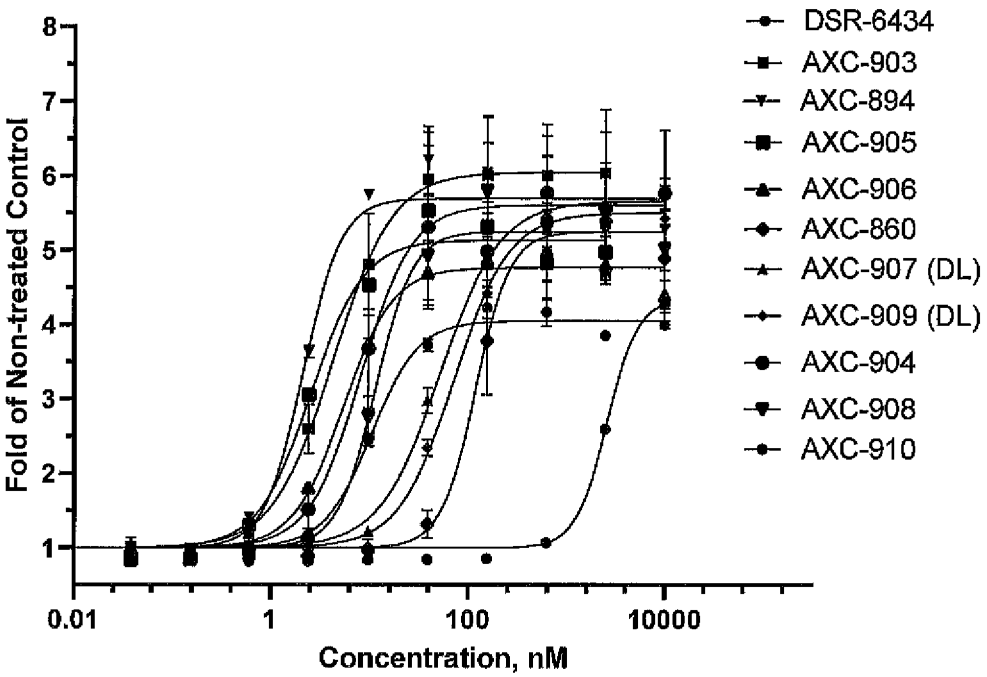
FIG. 8 depicts TLR7 activities of additional TLR7 agonists and TLR7 agonists attached to a linker.

FIG. 8 and Table 14 shows TLR7 activities of additional TLR7 agonists and TLR7 agonists attached to a linker. All tested compounds have TLR7 agonist activities. AXC-894, AXC-903, AXC-904, AXC905, and AXC-906 demonstrated the highest potency of the different payloads tested with $EC_{50}$ values below 10 nM.

TABLE 14

| Activity of Exemplary TLR Agonists and linkers | |
|---|---|
| Compound | TLR7 $EC_{50}$ (nM) |
| DSR-6434 | 10.5 |
| AXC-903 | 4.3 |
| AXC-907 (DL) | 51.8 |
| AXC-894 | 2.1 |
| AXC-909 (DL) | 71.9 |
| AXC-904 | 8.1 |
| AXC-905 | 2.6 |
| AXC-906 | 5.4 |
| AXC-908 | 11.5 |
| AXC-860 | 119.5 |
| AXC-910 | 2591.1 |

Figure 9:
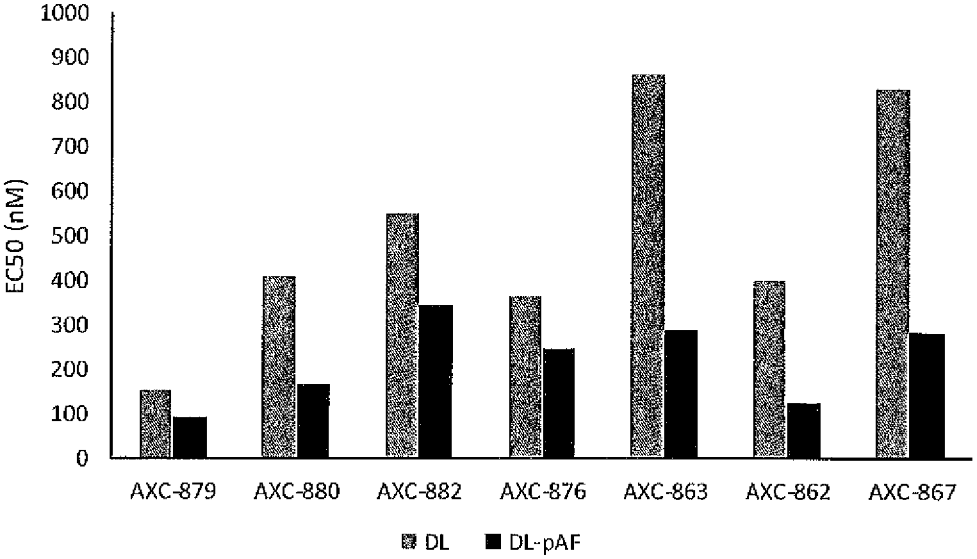
FIG. 9 depicts TLR7 activities of different TLR7 agonist attached to a linker, (drug linker or DL), compared to a non-natural amino acid, pAF, (DL-pAF).
Figure 9:
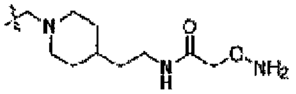
Figure 9:
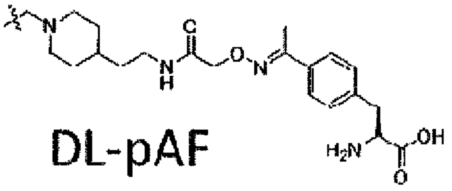

FIG. 9 and Table 15 compared the TLR7 activities of different TLR7 agonist attached to a linker, (drug linker or DL), and a non-natural amino acid, for example pAF, containing final metabolites (DL-pAF). In all cases, the pAF containing final metabolites demonstrated higher potency than their respective payloads with drug linkers. AXC-879 demonstrated the highest potency among different TLR payload linkers.

TABLE 15

| Activity of Exemplary TLR Agonists + linkers in the presence or absence of a non-natural amino acid (nnAA) | | |
|---|---|---|
| Compound | TLR Agonist + Linker (DL) - $EC_{50}$ (nM) | TLR Agonist +Linker + nnAA (DL-pAF) - $EC_{50}$ (nM) |
| AXC-879 | 151.2 | 90 |
| AXC-880 | 409.5 | 167 |
| AXC-882 | 550.8 | 343 |
| AXC-876 | 362.4 | 245 |
| AXC-863 | 864.2 | 287 |
| AXC-862 | 400.1 | 121 |
| AXC-867 | 829 | 283 |
| DSR6434 | 15 | 11 |

DL = Drug linker;
DL-pAF = pAF containing final metabolite

Example 9: Site Specific Conjugation of TCs

Figure 10A:
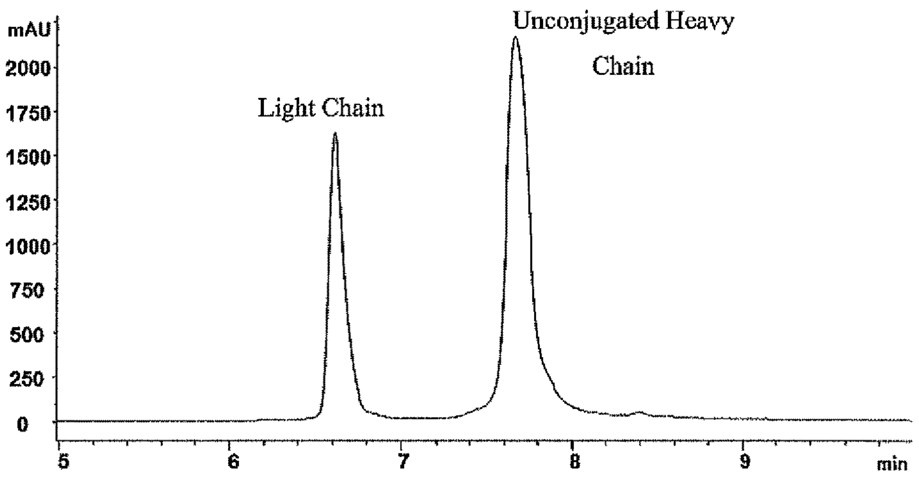
FIGS. 10A-10C depict HPLC chromatograms of unconjugated anti-HER2 antibody with a non-natural amino acid at amino acid position HA114 (FIG. 10A), and anti-HER2 antibody conjugated at amino acid position HA114 with TLR agonist AXC-875 (FIG. 10B) and AXC-880 (FIG. 10C).
Figure 10B:
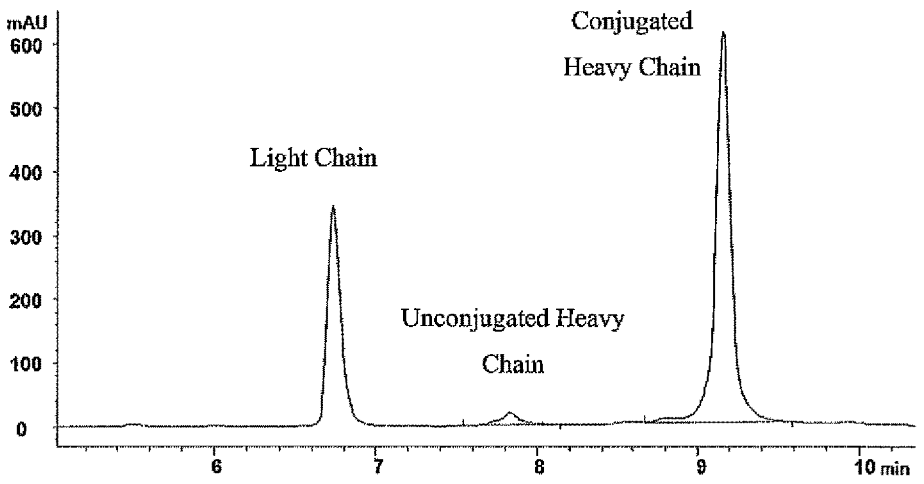
Figure 10C:
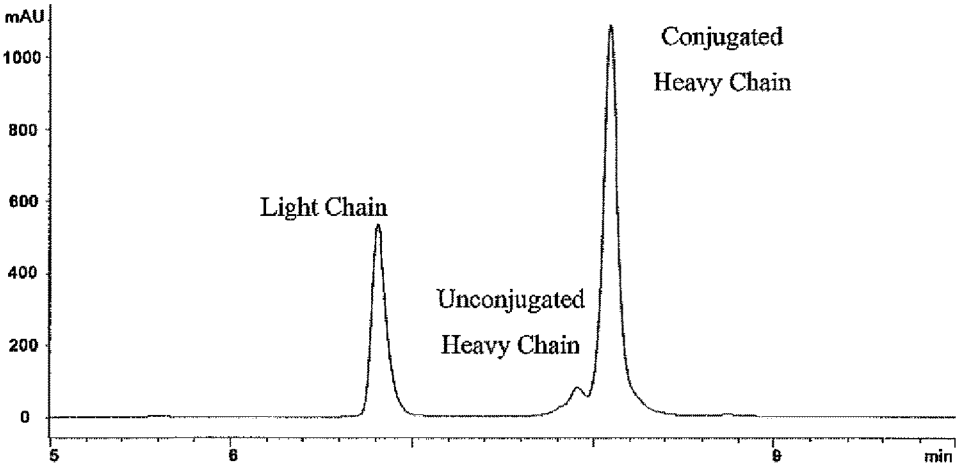

Site specific conjugation of TCs was conducted as described in Example 7 using analytical reverse phase HPLC. FIG. 10A shows, under reducing conditions, the analytical reverse phase HPLC chromatograms of unconjugated anti-HER2 antibody with a non-natural amino acid, for example pAF, at amino acid position HA114. FIGS. 10B and 10C show anti-HER2 antibody conjugated at amino acid position HA114 with TLR agonist AXC-875 and AXC-880, respectively. Table 16 shows drug-antibody ratio (DAR) for TLR conjugates from standard conjugation conditions described above. Varying DAR levels (0.3-2.0) can be seen between TLR conjugates primarily due the different properties of the associated TLR linker-payload.

TABLE 16

Drug-antibody ratios (DAR) of TLR conjugates determined by RP-HPLC.

| Conjugate | Drug Antibody Ratio |
|---|---|
| HER2-HA114-AXC638 | 1.7 |
| HER2-HA114-AXC800 | 1.7 |
| HER2-HA114-AXC801 | 1.9 |
| HER2-HA114-AXC802 | 1.5 |
| HER2-HA114-AXC874 | 2.0 |
| HER2-HA114-AXC875 | 1.9 |
| HER2-HA114-AXC862 | 0.8 |
| HER2-HA114-AXC863 | 1.8 |
| HER2-HA114-AXC867 | 1.5 |
| HER2-HA114-AXC868 | 1.2 |
| HER2-HA114-AXC869 | 0.3 |

Example 10: In Vitro Co-Culture Assay with Various Tumor Cells

RAW-Blue™ cells (Invivogen, San Diego, Calif.) were co-cultured with human tumor cells with different levels of HER2 expression level at 1:1 E:T ratio with total number of 1 million cells per well in the 96 wells plate. Different concentration of small molecule TLR7 agonist and conjugated ISACs, (Immune Stimulating Antibody Conjugates), were added to the co-culture cell medium. After 24 h incubation, the levels of NF-kB-induced SEAP from the RAW-Blue™ cells were determined by Quanti-Blue detection reagents (Invivogen, San Diego, Calif.) with readings at OD 655 nm. The dose-response curves were generated using Prism Software.

Figure 11A:
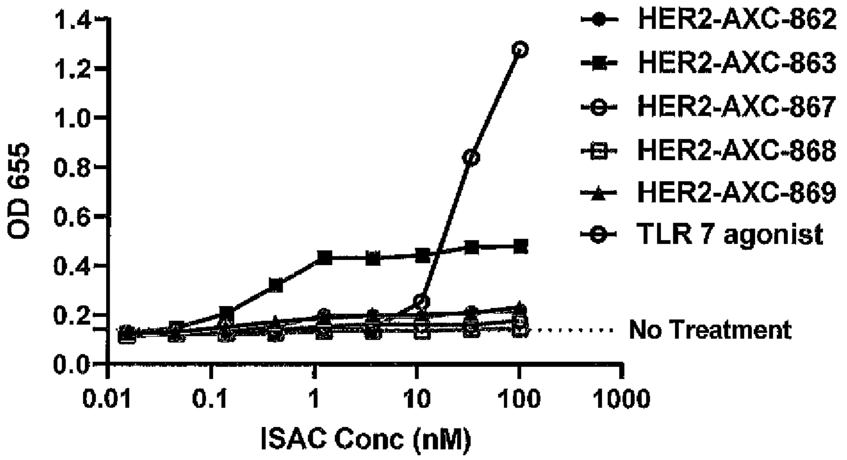
FIGS. 11A-11C compare tumor dependent ISAC activities of various payload linkers conjugated to anti-HER2 antibody in SKOV3 HER2 high expressing tumor cell line (FIG. 11A); JIMT-1 HER2 medium/low expressing tumor cell line (FIG. 11B); and A431 HER2 low expressing tumor cell line (FIG. 11C).
Figure 11B:
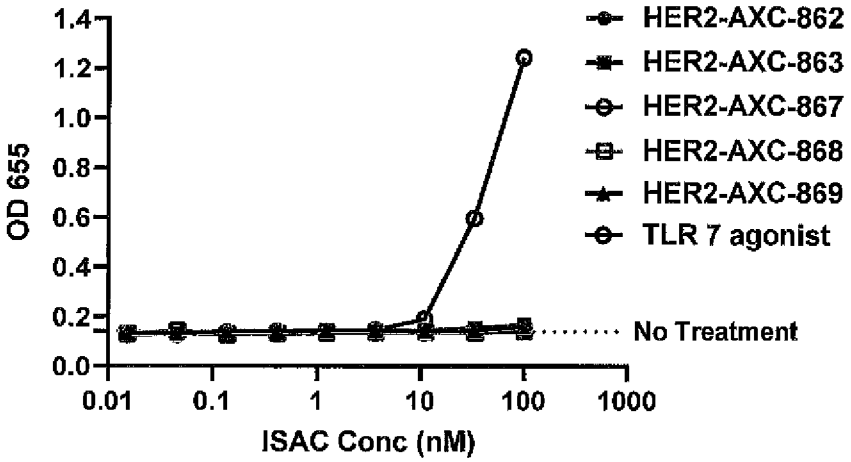
Figure 11C:
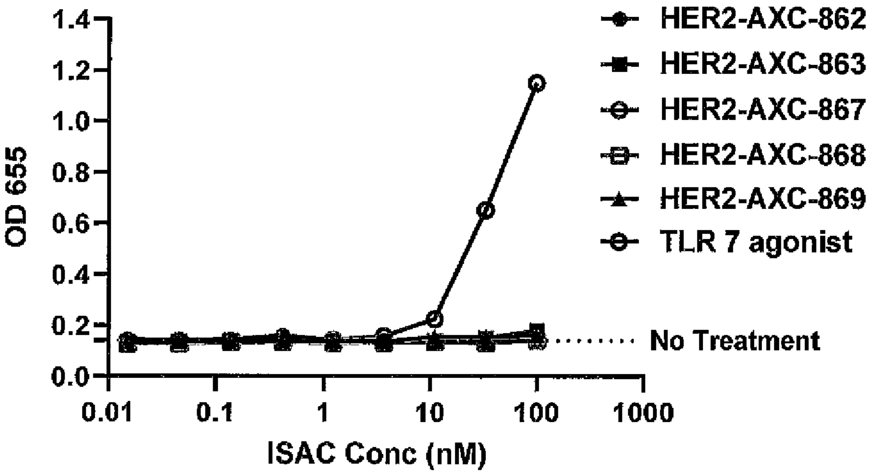

FIGS. 11A-11C compare tumor dependent ISAC activities of selected payload linkers when conjugated to the anti-HER2 antibody. SKOV3 is a HER2 high expressing tumor cell line (FIG. 11A); JIMT-1 is a HER2 medium/low expressing tumor cell line (FIG. 11B); and A431 is a HER2 low expressing tumor cell line (FIG. 11C). Small molecule TLR7 agonists show potent TLR7 activity in the presence of all tumor cell lines. All TLR7 ISACS show no activities in the presence of HER2 low or medium expressing tumor cell lines. ISAC with payload drug linker AXC-863 show potent dose dependent activities only in the presence of HER2 high expressing tumor cell lines.

Figure 12A:
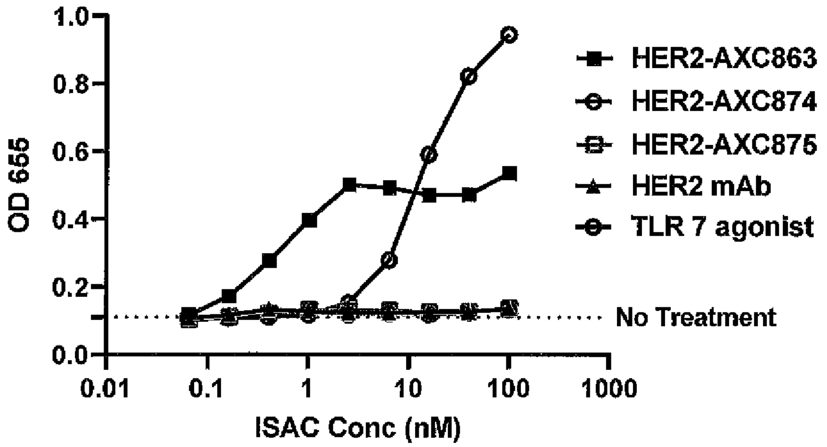
FIGS. 12A and 12B compare tumor dependent ISAC activities of additional payload linkers conjugated to anti-HER2 antibody in SKBR3 HER2 high expressing tumor cell line, (FIG. 12A), and HCC1806 HER2 very low expressing tumor cell line (FIG. 12B).
Figure 12B:
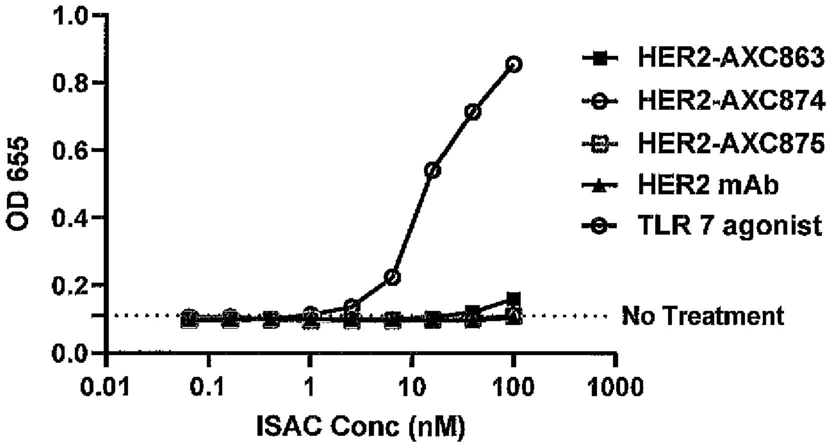

FIGS. 12A and 12B compare tumor dependent ISAC activities of additional payload linkers when conjugated to the anti-HER2 antibody. SKBR3 is a HER2 high expressing tumor cell line, (FIG. 12A), and HCC1806 is a HER2 very low expressing tumor cell line (FIG. 12B), Small molecule TLR7 agonists show potent TLR7 activity in the presence of all tumor cell lines. While all TLR7 ISACS and unconjugated anti HER2 antibody show no activities in the presence of HER2 very low expressing tumor cell lines. ISAC with payload drug linker AXC-863 show potent dose dependent activities only in the presence of HER2 high expressing tumor cell lines.

Figure 13A:
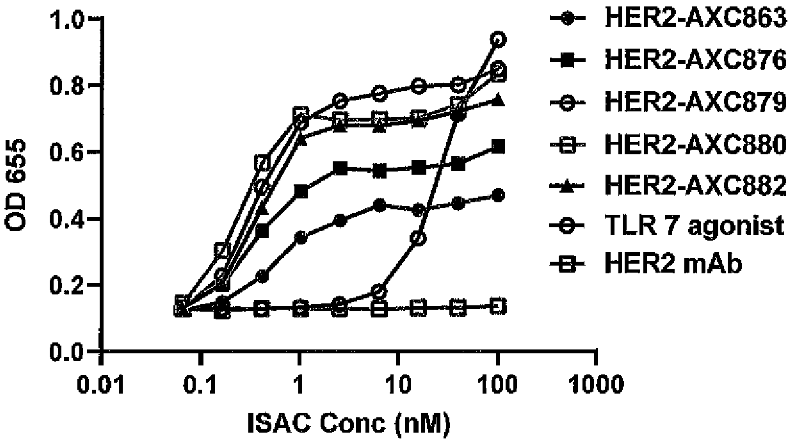
FIGS. 13A and 13B compare tumor dependent ISAC activities of additional payload linkers conjugated to anti-HER2 antibody in SKBR3 HER2 high expressing tumor cell line, (FIG. 13A), and HCC1806 HER2 very low expressing tumor cell line, (FIG. 13B).
Figure 13B:
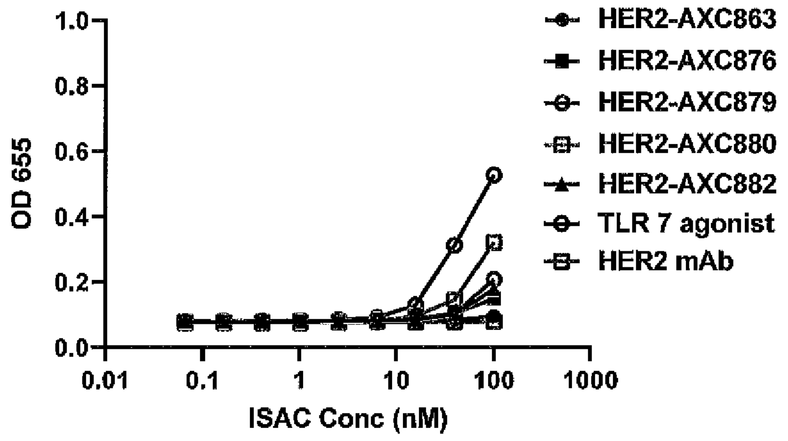
Figure 14A:
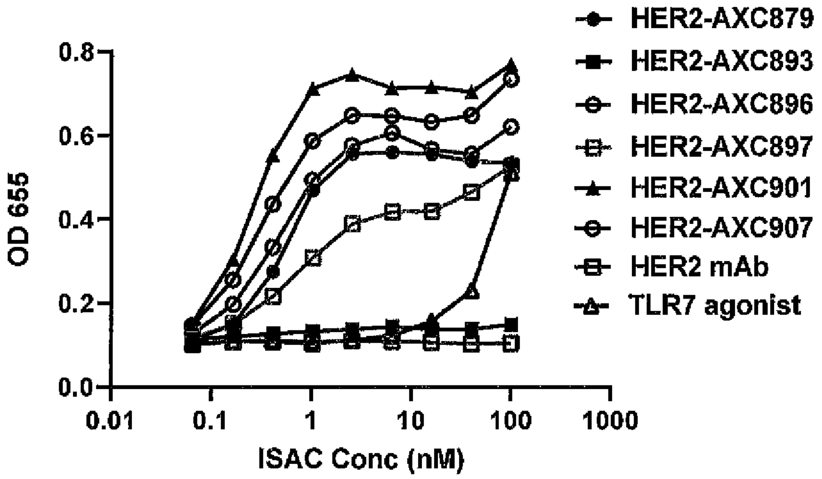
FIGS. 14A and 14B compare tumor-dependent ISAC activities of additional payload linkers conjugated to anti-HER2 antibody in SKBR3 HER2 high expressing tumor cell line (FIG. 14A), and HCC1806 HER2 very low expressing tumor cell line, (FIG. 14B).
Figure 14B:
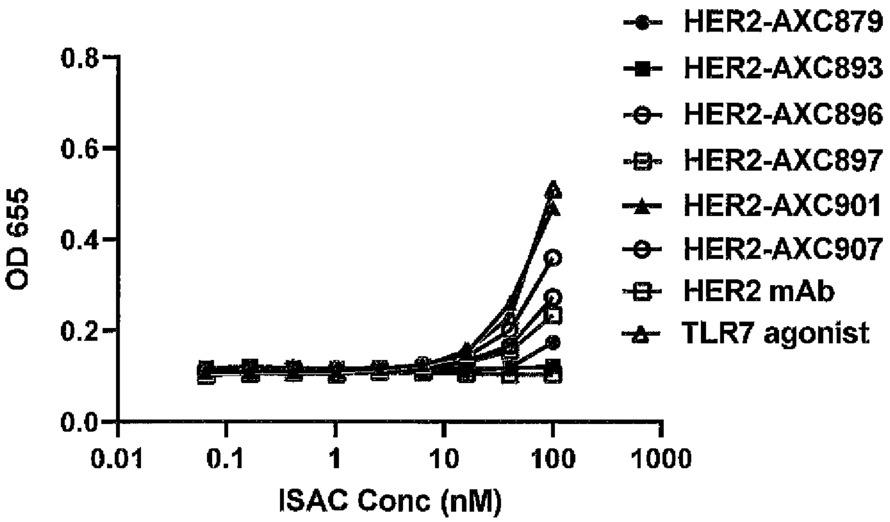

FIGS. 13A and 13B compare tumor dependent ISAC activities of additional payload linkers when conjugated to the anti-HER2 antibody. SKBR3 is a HER2 high expressing tumor cell line, (FIG. 13A), and HCC1806 is a HER2 very low expressing tumor cell line, (FIG. 13B). Small molecule TLR7 agonists show potent TLR7 activity in the presence of all tumor cell lines. All TLR7 ISACS and unconjugated anti-HER2 antibody show no activities in the presence of HER2 very low expressing tumor cell lines. All ISACs show potent dose dependent activities only in the presence of HER2 high expressing tumor cell lines (FIG. 13A). ISACS with payload drug linker AXC-879 demonstrated the highest HER2 dependent TLR7 activities FIGS. 14A and 14B compare tumor-dependent ISAC activities of additional payload linkers when conjugated to the anti-HER2 antibody. SKBR3 is a HER2 high expressing tumor cell line (FIG. 14A), and HCC1806 is a HER2 very low expressing tumor cell line, (FIG. 14B). Small molecule TLR7 agonists show potent TLR7 activity in the presence of all tumor cell lines. TLR7 ISACS and unconjugated anti HER2 antibody showed no activities in the presence of HER2 very low expressing tumor cell lines. All ISACs show potent dose dependent activities only in the presence of HER2 high tumor cell lines. ISACs with payload drug linker AXC-901 demonstrated the highest HER2 dependent TLR7 activities.

Figure 15A:
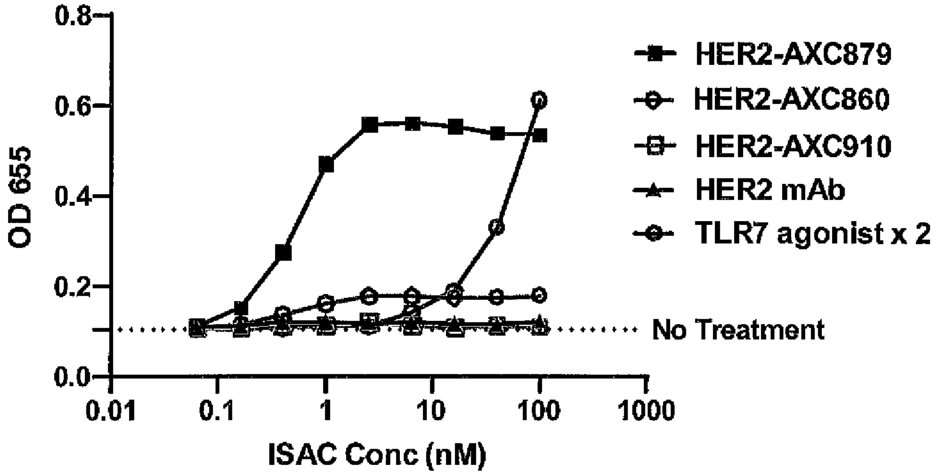
FIGS. 15A and 15B compare tumor-dependent ISAC activities of three (3) payload linkers conjugated to anti-HER2 antibody in SKBR3 HER2 high expressing tumor cell line (FIG. 15A), and HCC1806 HER2 very low expressing tumor cell line, (FIG. 15B) showing HER2-AXC-879 has the best ISAC activity.
Figure 15B:
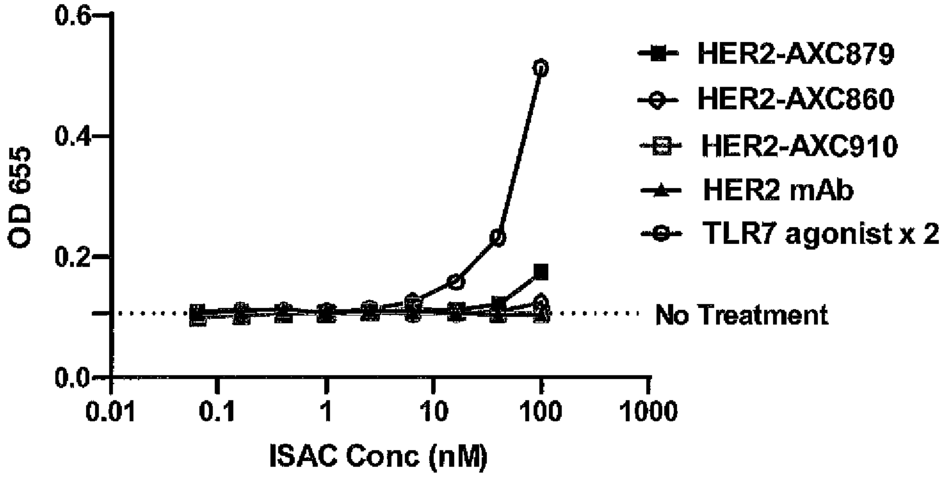

FIGS. 15A and 15B compare tumor-dependent ISAC activities of three (3) payload linkers conjugated to anti-HER2 antibody in SKBR3 HER2 high expressing tumor cell line (FIG. 15A), and HCC1806 HER2 very low expressing tumor cell line, (FIG. 15B) showing HER2-AXC-879 has the best ISAC activity compared to HER2-AXC-860 and HER2-AXC-910 representative of known ISACs. Table 17 depicts the TLR-agonist-linker structures used in generating the HER2-AXC ISACs compared.

TABLE 17

| Compound Name | Structure |
|---|---|
| TLR-agonist structures related to FIGS. 15A-15B | |
| AXC-860 | 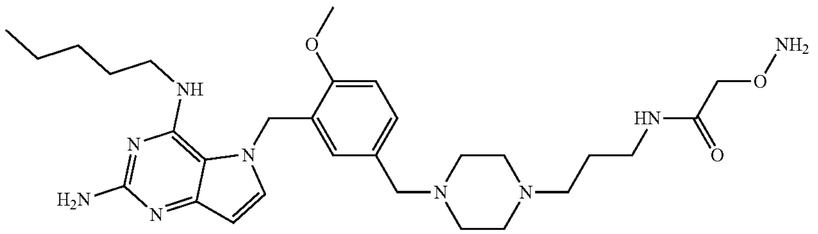 [SMILES: CCCCCNc1nc(N)nc2ccn(Cc3cc(CN4CCN(CCCNC(=O)CON)CC4)ccc3OC)c12] |
| AXC-879 | 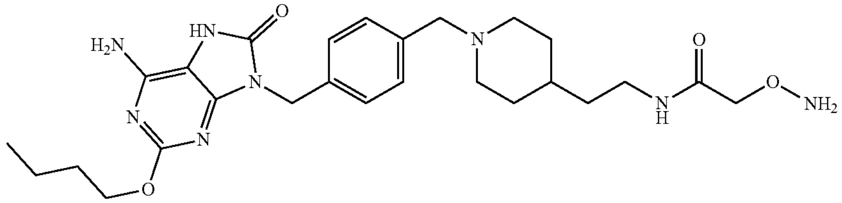 [SMILES: CCCCOc1nc(N)c2[nH]c(=O)n(Cc3ccc(CN4CCC(CCNC(=O)CON)CC4)cc3)c2n1] Exact Mass: 526.3 |
| AXC-910 | 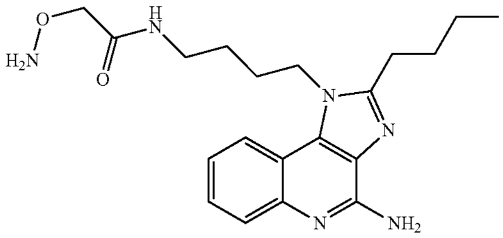 [SMILES: CCCCc1nc2c(N)nc3ccccc3c2n1CCCCNC(=O)CON] Molecular Weight: 384.5 |

Example 11: Treatment for Breast Cancer

Human Clinical Trial of the Safety and/or Efficacy of Trastuzumab-Linked TLR-Agonist Derivative for Breast Cancer Therapy Objective: To compare the safety and pharmacokinetics of administered composition comprising trastuzumab-linked TLR-agonist derivative.

Study Design: This study will be a Phase 1, single-center, open-label, randomized dose escalation study followed by a Phase II study in breast cancer patients. Patients should not have had exposure to trastuzumab-linked TLR-agonist derivative prior to the study entry. Patients must not have received treatment for their cancer within 2 weeks of beginning the trial. Treatments include the use of chemotherapy, hematopoietic growth factors, and biologic therapy such as monoclonal antibodies, Patients must have recovered from all toxicities (to grade 0 or 1) associated with previous treatment. All subjects are evaluated for safety and all blood collections for pharmacokinetic analysis are collected as scheduled. All studies are performed with institutional ethics committee approval and patient consent.

Phase I: Patients receive i.v, trastuzumab-linked TLR-agonist derivative on days 1, 8, and 15 of each 28-day cycle. Doses of trastuzumab-linked TLR-agonist derivative may be held or modified for toxicity based on assessments as outlined below. Treatment repeats every 28 days in the absence of unacceptable toxicity. Cohorts of 3-6 patients receive escalating doses of trastuzumab-linked TLR-agonist derivative until the maximum tolerated dose (MTD) for trastuzumab-linked TLR-agonist derivative is determined. The MTD is defined as the dose preceding that at which 2 of 3 or 2 of 6 patients experience dose-limiting toxicity. Dose limiting toxicities are determined according to the definitions and standards set by the National Cancer Institute (NCI) Common Terminology for Adverse Events (CTCAE) Version 3.0 (Aug. 9, 2006).

Phase II: Patients receive trastuzumab-linked TLR-agonist derivative as in phase I at the MTD determined in phase I. Treatment repeats every 4 weeks for 2-6 courses in the absence of disease progression or unacceptable toxicity. After completion of 2 courses of study therapy, patients who achieve a complete or partial response may receive an additional 4 courses. Patients who maintain stable disease for more than 2 months after completion of 6 courses of study therapy may receive an additional 6 courses at the time of disease progression, provided they meet original eligibility criteria.

Blood Sampling Serial blood is drawn by direct vein puncture before and after administration of trastuzumab-linked TLR-agonist derivative. Venous blood samples (5 mL) for determination of serum concentrations are obtained at about 10 minutes prior to dosing and at approximately the following times after dosing: days 1, 8, and 15. Each serum sample is divided into two aliquots. All serum samples are stored at −20° C. Serum samples are shipped on dry ice.

Pharmacokinetics: Patients undergo plasma/serum sample collection for pharmacokinetic evaluation before beginning treatment and at days 1, 8, and 15. Pharmacokinetic parameters are calculated by model independent methods on a Digital Equipment Corporation VAX 8600 computer system using the latest version of the BIOAVL software. The following pharmacokinetics parameters are determined: peak serum concentration ($C_{max}$); time to peak serum concentration ($t_{max}$); area under the concentration-time curve (AUC) from time zero to the last blood sampling time ($AUC_{0-72}$) calculated with the use of the linear trapezoidal rule; and terminal elimination half-life ($t_{1/2}$), computed from the elimination rate constant. The elimination rate constant is estimated by linear regression of consecutive data points in the terminal linear region of the log-linear concentration-time plot. The mean, standard deviation (SD), and coefficient of variation (CV) of the pharmacokinetic parameters are calculated for each treatment. The ratio of the parameter means (preserved formulation/non-preserved formulation) is calculated.

Patient Response to combination therapy: Patient response is assessed via imaging with X-ray, CT scans, and MRI, and imaging is performed prior to beginning the study and at the end of the first cycle; with additional imaging performed every four weeks or at the end of subsequent cycles. Imaging modalities are chosen based upon the cancer type and feasibility/availability, and the same imaging modality is utilized for similar cancer types as well as throughout each patient's study course. Response rates are determined using the RECIST criteria. (Therasse et al, J. Natl. Cancer Inst. 2000 Feb. 2; 92(3):205-16). Patients also undergo cancer/tumor biopsy to assess changes in progenitor cancer cell phenotype and clonogenic growth by flow cytometry, Western blotting, and IHC, and for changes in cytogenetics by FISH. After completion of study treatment, patients are followed periodically for 4 weeks.

Example 12: Treatment for Breast Cancer

Human Clinical Trial of the Safety and Efficacy of Trastuzumab-Linked TLR-Agonist Derivative for Breast Cancer Therapy Objective: Compare the efficacy and toxicity of trastuzumab-linked TLR-agonist derivative alone followed at disease progression by combination trastuzumab and paclitaxel vs first-line combination trastuzumab and paclitaxel in women with HER2-overexpressing metastatic breast cancer.

Study Design: This study is a randomized, multicenter study. Patients are stratified according to degree of HER2/neu-overexpression (2+ vs 3+), prior anthracycline-containing adjuvant treatment (no prior treatment vs prior treatment without radiotherapy to left chest wall vs prior treatment with radiotherapy to left chest wall), estrogen-receptor status (positive vs negative vs unknown), prior therapy (first-line vs second/third-line), and center. Patients are randomized to one of two treatment arms. Arm 1: Patients receive trastuzumab-linked TLR-agonist derivative IV over 30-90 minutes weekly. At time of disease progression, patients receive combination trastuzumab-linked TLR-agonist derivative IV and paclitaxel IV as in arm II. Arm H: Patients receive trastuzumab-linked TLR-agonist derivative IV over 30-90 minutes weekly. Paclitaxel is administered IV over 1 hour weekly for 3 weeks followed by 1 week of rest.

Treatment continues in both arms in the absence of disease progression or unacceptable toxicity. Quality of life is assessed at baseline and day 1 of courses 2, 3, 4, 5, 6, 8, 10, and 12. Patients are followed at 1, 3, and 6 months and then every 6 months thereafter.

Example 13: Treatment for Bladder Cancer

Objective: Determine the acute toxicity of paclitaxel and radiotherapy with or without a TLR-agonist derivative described herein in patients who have undergone prior transurethral bladder resection for muscle-invasive transitional cell carcinoma of the bladder.

Disease Characteristics: Histologically or cytologically is confirmed primary transitional cell carcinoma (TCC) of the bladder; histologic evidence of muscularis propria invasion; meets 1 of the following stage criteria: stage T2-4a; NX, N0, or N1; and M0 disease or clinical stage T1, grade 3/3 disease AND requires definitive local therapy; tumor involvement of the prostatic urethra allowed provided the following criteria are met: tumor is visibly completely resected; no evidence of stromal invasion of the prostate, no evidence of distant metastases by chest x-ray or CT scan AND abdominal/pelvic CT scan; has undergone transurethral bladder resection (as thorough as is judged safely possible) within the past 3-8 weeks, including bimanual examination with tumor mapping; sufficient tumor tissue available for HER2/neu analysis; not a candidate for radical cystectomy.

Study Design: This study is a non-randomized, multicenter study. Patients are assigned to 1 of 2 treatment groups according to HER2/neu status (HER2/neu 2+ or 3+ staining [group 1] vs HER2/neu 0 or 1+ staining [group 2]).

Group 1: Patients receive paclitaxel IV over 1 hour on days 1, 8, 15, 22, 29, 36, and 43 and a Trastuzumab-linked TLR-agonist derivative described herein via IV over 90 minutes on day 1 and then over 30 minutes on days 8, 15, 22, 29, 36, and 43. Patients also undergo radiotherapy once daily on days 1-5, 8-12, 15-19, 22-26, 29-33, 36-40, 43-47, and 50. Treatment continues in the absence of disease progression or unacceptable toxicity.

Group 2: Patients receive paclitaxel and undergo radiotherapy as in group 1. After completion of study treatment, patients are followed at 4-5 weeks, every 3 months for 1 year, every 4 months for 1 year, every 6 months for 3 years, and then annually thereafter.

Example 14: Treatment for Ovarian Cancer

Human Clinical Trial of the Safety and Efficacy of a Trastuzumab-linked TLR-agonist derivative described herein for Ovarian Cancer Therapy Objective: Evaluate the safety and efficacy of a four week once weekly IV dosage of composition comprising a Trastuzumab-linked TLR-agonist derivative described herein in women with HER2-overexpressing ovarian cancer.

Study Design: This study is a non-randomized, open-label, 11 week, multicenter study. This study will evaluate the safety profile of four once weekly IV dosage, the MTD, PK and immunogenicity of trastuzumab-linked TLR-agonist derivative. Patients are assigned to a single group. Patients receive one dose of trastuzumab-linked TLR-agonist derivative once a week for 4 weeks. Trastuzumab-linked TLR-agonist derivative will be administered by IV infusion on Study Days 1, 8, 15, and 22, Urine samples will be taken on days 1 and 22.

Blood Sampling Serial blood is drawn by direct vein puncture before and after administration of the Trastuzumab-linked TLR-agonist derivative. Venous blood samples (5 mL) for determination of serum concentrations are obtained at about 10 minutes prior to dosing and at approximately the following times after dosing: days 1, 2, 4, 5, 8, 15, 22, 36, 43 and 50. Each serum sample is divided into two aliquots. All serum samples are stored at −20° C. Serum samples are shipped on dry ice.

Treatment continues in the absence of disease progression or unacceptable toxicity. Quality of life is assessed at baseline and day 1 of courses 2, 3, 4, 5, 6, 8, 10, and 12. Patients are followed on days 29, 36, 43, and 50. Patients will be asked about adverse events. Patients will have an imaging scan and ECG to evaluate tumor size and heart function (day 43). At the termination of the study patients will have a physical exam day 50). Patients with evidence of disease regression may receive continued therapy until evidence of progression of disease is documented.

The present invention is further described by the following numbered embodiments.

1. A composition comprising one or more tumor-targeting polypeptides having one or more non-naturally encoded amino acids incorporated therein, wherein said polypeptides are linked to a TLR agonist molecule via a linker covalently bonded to the non-natural amino acid of the tumor-targeting polypeptide.

2. The composition of embodiment 1, wherein the tumor-targeting polypeptide an antibody that binds to HER2.

3. The composition of embodiment 1, wherein the tumor-targeting polypeptide is Trastuzumab.

4. The composition of embodiment 1, 2, or 3 wherein the TLR agonist is a TLR7 or TLR8 agonist.

5. The composition of embodiment 1, 2 or 3, wherein the TLR agonist is the TLR7 or TLR8 agonist of FIG. 4.

6. The composition of embodiment 1, wherein the tumor-targeting polypeptide is conjugated to one or more water soluble polymers.

7. The composition of embodiment 6, wherein at least one of the water soluble polymers is linked to at least one of the non-naturally encoded amino acids.

8. The composition of embodiment 7, wherein the water soluble polymer is PEG.

9. The composition of embodiment 1, wherein the linker is a PEG with a molecular weight between 10 and 50.

10. The composition of embodiment 1, wherein the composition comprises one or more amino acid substitution, addition or deletion that increases the stability or solubility of the composition.

13. The composition of embodiment 1, wherein the composition comprises one or more amino acid substitution, addition or deletion that increases the expression of the tumor-targeting polypeptide in a recombinant host cell or synthesized in vitro.

14. The composition of embodiment 1, wherein the non-naturally encoded amino acid is reactive toward a linker, polymer, or biologically active molecule that is otherwise unreactive toward any of the 20 common amino acids in the polypeptide.

15. The composition of embodiment 14, wherein the non-naturally encoded amino acid comprises a carbonyl group, an aminooxy group, a hydrazine group, a hydrazide group, a semicarbazide group, an azide group, or an alkyne group.

16. The composition of embodiment 14, wherein the non-naturally encoded amino acid comprises a carbonyl group.

17. The composition of embodiment 1, wherein the tumor-targeting polypeptide is linked to a biologically active molecule, a cytotoxic agent, a water soluble polymer, or an immunostimulatory agent.

What is claimed is:

1. A composition comprising:

an anti-HER2 antibody, or antigen-binding fragment thereof, comprising a heavy chain and a light chain, wherein the heavy chain and the light chain, respectively, comprise the amino acid sequences selected from the group consisting of:

(a) SEQ ID NOs: 1 and 7, wherein SEQ ID NO: 7 has a para-acetyl phenylalanine at amino acid position 121 according to Kabat numbering;

(b) SEQ ID NOs: 2 and 3, wherein SEQ ID NO: 2 has a para-acetyl phenylalanine at amino acid position 114 according to Kabat numbering;

(c) SEQ ID NOs: 2 and 4, wherein SEQ ID NO: 2 has a para-acetyl phenylalanine at amino acid position 114 according to Kabat numbering and SEQ ID NO: 4 has a para-acetyl phenylalanine at amino acid position 110 according to Kabat numbering;

(d) SEQ ID NOs: 2 and 5, wherein SEQ ID NO: 2 has a para-acetyl phenylalanine at amino acid position 114 according to Kabat numbering and SEQ ID NO: 5 has a para-acetyl phenylalanine at amino acid position 112 according to Kabat numbering;

(e) SEQ ID NOs: 2 and 7, wherein SEQ ID NO: 2 has a para-acetyl phenylalanine at amino acid position 114 according to Kabat numbering and SEQ ID NO: 7 has a para-acetyl phenylalanine at amino acid position 121 according to Kabat numbering; and (f) SEQ ID NOs: 2 and 8, wherein SEQ ID NO: 2 has a para-acetyl phenylalanine at amino acid position 114 according to Kabat numbering and SEQ ID NO: 8 has a para-acetyl phenylalanine at amino acid position 127 according to Kabat numbering, wherein:

each para-acetyl phenylalanine is covalently linked to a toll-like receptor (TLR) agonist via an oxime bond, and the TLR agonist has the following structure:

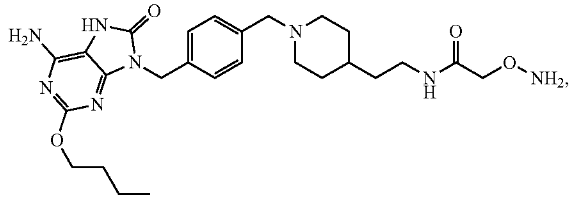 [SMILES: CCCCOc1nc(N)c2[nH]c(=O)n(Cc3ccc(CN4CCC(CCNC(=O)CON)CC4)cc3)c2n1]

or a salt thereof.

2. The composition of claim 1 wherein the anti-HER2 antibody comprises an IgG.

3. A method of treating a subject or patient having a HER2 positive cancer, comprising administering to the subject or patient a therapeutically-effective amount of a composition of claim 1.

4. A pharmaceutical composition comprising a therapeutically-effective amount of a composition of claim 1, and a pharmaceutically acceptable carrier or excipient.

5. A composition comprising:

an anti-HER2 antibody, or antigen-binding fragment thereof, comprising a heavy chain and a light chain, wherein the heavy chain and the light chain, respectively, comprise the amino acid sequence of SEQ ID NO: 1 and SEQ ID NO: 7, wherein SEQ ID NO: 7 has a para-acetyl phenylalanine at position 121 according to Kabat numbering wherein:

the para-acetyl phenylalanine is covalently linked to a toll-like receptor (TLR) agonist via an oxime bond, and the TLR agonist has the following structure:

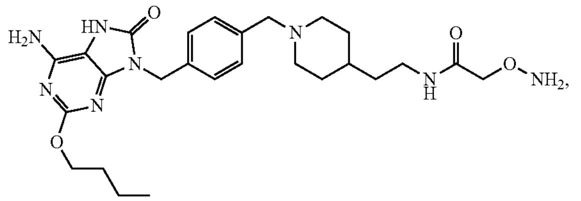 [SMILES: CCCCOc1nc(N)c2[nH]c(=O)n(Cc3ccc(CN4CCC(CCNC(=O)CON)CC4)cc3)c2n1]

or a salt thereof.

6. A composition comprising:

an anti-HER2 antibody, or antigen-binding fragment thereof, comprising a heavy chain and a light chain, wherein the heavy chain and the light chain, respectively, comprise the amino acid sequence of SEQ ID NO: 2 and SEQ ID NO: 3, wherein SEQ ID NO: 2 has a para-acetyl phenylalanine at position 114 according to Kabat numbering wherein:

the para-acetyl phenylalanine is covalently linked to a toll-like receptor (TLR) agonist via an oxime bond, and the TLR agonist has the following structure:

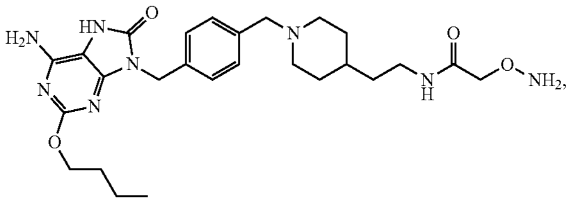 [SMILES: CCCCOc1nc(N)c2[nH]c(=O)n(Cc3ccc(CN4CCC(CCNC(=O)CON)CC4)cc3)c2n1]

or a salt thereof.

7. The composition of claim 1, wherein the heavy chain and the light chain, respectively, comprise the amino acid sequences of SEQ ID NO: 2 and SEQ ID NO: 4, wherein SEQ ID NO: 2 has a para-acetyl phenylalanine at amino acid position 114 according to Kabat numbering and SEQ ID NO: 4 has a para-acetyl phenylalanine at amino acid position 110 according to Kabat numbering.

8. The composition of claim 1, wherein the heavy chain and the light chain, respectively, comprise the amino acid sequences of SEQ ID NO: 2 and SEQ ID NO: 5, wherein SEQ ID NO: 2 has a para-acetyl phenylalanine at amino acid position 114 according to Kabat numbering and SEQ ID NO: 5 has a para-acetyl phenylalanine at amino acid position 112 according to Kabat numbering.

9. The composition of claim 1, wherein the heavy chain and the light chain, respectively, comprise the amino acid sequences of SEQ ID NO: 2 and SEQ ID NO: 7, wherein SEQ ID NO: 2 has a para-acetyl phenylalanine at amino acid position 114 according to Kabat numbering and SEQ ID NO: 7 has a para-acetyl phenylalanine at amino acid position 121 according to Kabat numbering.

10. The composition of claim 1, wherein the heavy chain and the light chain, respectively, comprise the amino acid sequences of SEQ ID NO: 2 and SEQ ID NO: 8, wherein SEQ ID NO: 2 has a para-acetyl phenylalanine at amino acid position 114 according to Kabat numbering and SEQ ID NO: 8 has a para-acetyl phenylalanine at amino acid position 127 according to Kabat numbering.

11. The method of claim 3, wherein the HER2 positive cancer is breast cancer, ovarian cancer, bladder cancer, gastric carcinoma, head and neck cancer, esophageal carcinoma, brain cancer or lung cancer.

12. The method of claim 11, wherein the HER2 positive cancer is breast cancer.

13. The method of claim 12, wherein the breast cancer is metastatic breast cancer.

14. The method of claim 11, wherein the HER2 positive cancer is ovarian cancer.

15. The method of claim 11, wherein the HER2 positive cancer is bladder cancer.

16. The composition of claim 1, wherein the anti-HER2 antibody fragment thereof comprises: (i) Fab, (Fab')2, Fv, or single chain Fv (scFv); (ii) one or more Fab, (Fab')2, Fv or single chain Fv (scFv) mutations; or (iii) one or more Fc mutations.

17. The composition of claim 1, wherein the TLR agonist is

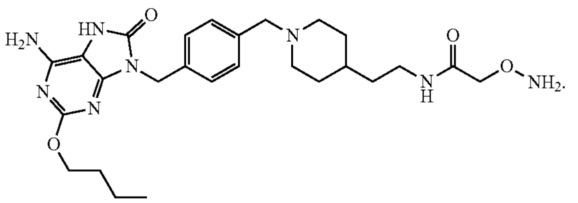 [SMILES: CCCCOc1nc(N)c2[nH]c(=O)n(Cc3ccc(CN4CCC(CCNC(=O)CON)CC4)cc3)c2n1]

18. The composition of claim 1, wherein the TLR agonist is a salt of:

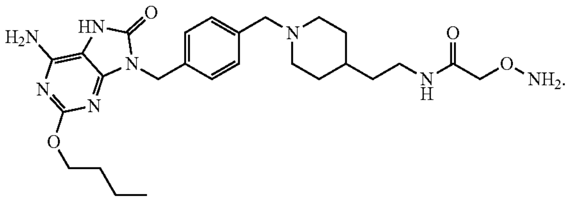 [SMILES: CCCCOc1nc(N)c2[nH]c(=O)n(Cc3ccc(CN4CCC(CCNC(=O)CON)CC4)cc3)c2n1]

position 121 according to Kabat numbering, a TLR agonist having the following structure:

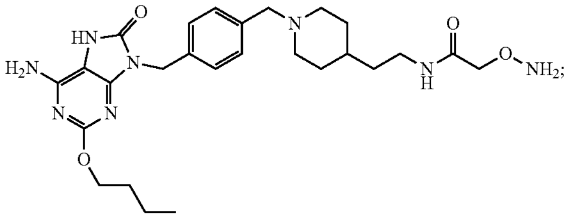 [SMILES: CCCCOc1nc(N)c2[nH]c(=O)n(Cc3ccc(CN4CCC(CCNC(=O)CON)CC4)cc3)c2n1]

wherein the para-acetyl phenylalanine is covalently linked to a TLR agonist via an oxime bond, wherein the anti-Her2 ADC has the following structure:

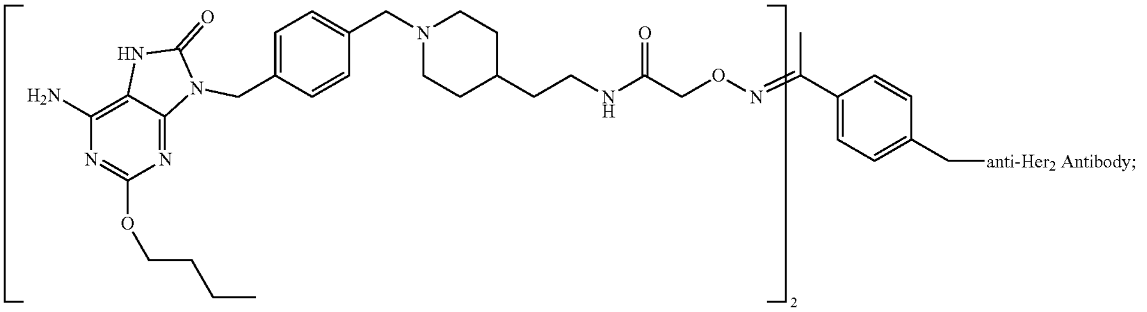

19. The composition of any one of the claims selected from 1, 4, 5 and 6, wherein the anti-Her2 antibody, or antigen binding fragment thereof, comprising a para-acetyl phenylalanine covalently linked to a TLR agonist via an oxime bond wherein the TLR agonist has the structure:

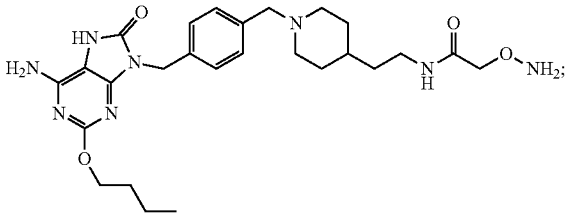 [SMILES: CCCCOc1nc(N)c2[nH]c(=O)n(Cc3ccc(CN4CCC(CCNC(=O)CON)CC4)cc3)c2n1]

comprises a drug-antibody ratio (DAR) of 1 or 2.

20. The composition of claim 19, wherein the DAR is 2.

21. An anti-Her2 antibody drug conjugate (ADC) comprising an anti-HER2 antibody, or antigen-binding fragment thereof, comprising a heavy chain and a light chain, wherein the heavy chain and the light chain, respectively, comprise the amino acid sequence of SEQ ID NO: 1 and SEQ ID NO: 7, wherein SEQ ID NO: 7 has a para-acetyl phenylalanine at comprising a DAR of 2.

22. An anti-Her2 antibody drug conjugate (ADC) comprising an anti-HER2 antibody, or antigen-binding fragment thereof, comprising a heavy chain and a light chain, wherein the heavy chain and the light chain, respectively, comprise the amino acid sequence of SEQ ID NO: 2 and SEQ ID NO: 3, wherein SEQ ID NO: 2 has a para-acetyl phenylalanine at position 114 according to Kabat numbering, a TLR agonist having the following structure:

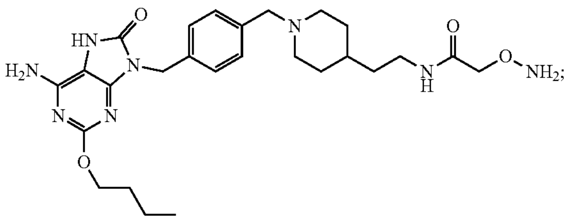

wherein the para-acetyl phenylalanine is covalently linked to a TLR agonist via an oxime bond, wherein the anti-Her2 ADC has the following structure:

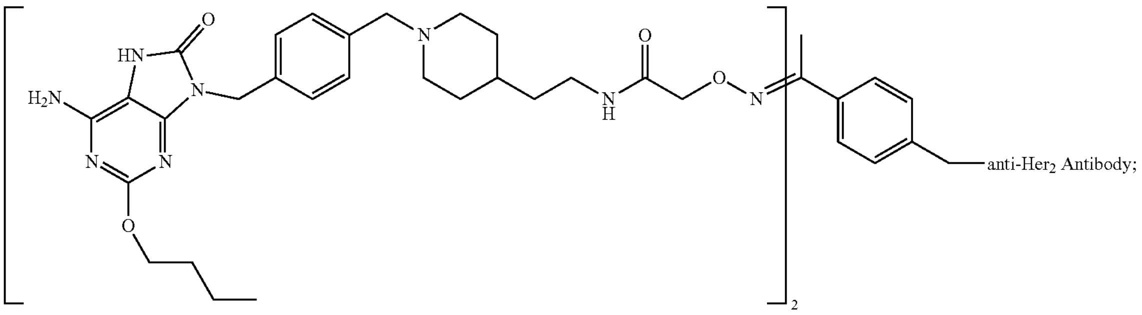
comprising a DAR of 2.
* * * * *